United States Patent
Nakagawa et al.

(10) Patent No.: US 11,871,728 B2
(45) Date of Patent: Jan. 16, 2024

(54) FEEDING MANAGEMENT SYSTEM AND FEEDING MANAGEMENT METHOD

(71) Applicant: AJINOMOTO CO., INC., Tokyo (JP)

(72) Inventors: Kazuki Nakagawa, Kanagawa (JP); Takeshi Fujieda, Kanagawa (JP); Takashi Mikami, Kanagawa (JP); Kazuhiro Sato, Kanagawa (JP); Ai Onishi, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 599 days.

(21) Appl. No.: 16/910,324

(22) Filed: Jun. 24, 2020

(65) Prior Publication Data

US 2020/0352140 A1    Nov. 12, 2020

Related U.S. Application Data

(63) Continuation of application No. PCT/JP2018/043077, filed on Nov. 21, 2018.

(30) Foreign Application Priority Data

Dec. 28, 2017   (JP) ................. 2017-254602

(51) Int. Cl.
*A01K 29/00*    (2006.01)
*A01K 5/02*    (2006.01)
*G01N 33/68*    (2006.01)

(52) U.S. Cl.
CPC .......... *A01K 29/005* (2013.01); *A01K 5/02* (2013.01); *G01N 33/6812* (2013.01); *G01N 2800/50* (2013.01)

(58) Field of Classification Search
CPC ...... A01K 29/005; A01K 5/02; A01K 11/006; A01K 11/004; A01K 5/0275; G01N 33/6812; G01N 2800/50; G01N 33/6806
See application file for complete search history.

(56) References Cited

U.S. PATENT DOCUMENTS

| | | | |
|---|---|---|---|
| 7,494,815 | B2 | 2/2009 | Shimbo et al. |
| 9,924,699 | B2 | 3/2018 | Wisse et al. |
| 2005/0079624 | A1 | 4/2005 | Miyano et al. |
| 2006/0286673 | A1 | 12/2006 | Miyano et al. |
| 2007/0137584 | A1 | 6/2007 | Travis |
| 2007/0269899 | A1 | 11/2007 | Shimbo et al. |

(Continued)

FOREIGN PATENT DOCUMENTS

| | | |
|---|---|---|
| EP | 0 801 524 A1 | 10/1997 |
| JP | 07-087860 A | 4/1995 |

(Continued)

OTHER PUBLICATIONS

Supplementary European Search Report dated Feb. 28, 2022 in EP 18896104.

(Continued)

*Primary Examiner* — Trinh T Nguyen
(74) *Attorney, Agent, or Firm* — Foley & Lardner LLP

(57) ABSTRACT

A feeding management system for a free stall cow barn includes an evaluation-related information storage unit, an association information storage unit, an evaluating unit, a selecting unit, a transmission unit, a reading unit, a feed information acquiring unit, a device information acquiring unit, and a control information transmitting unit.

2 Claims, 7 Drawing Sheets

(56) References Cited

U.S. PATENT DOCUMENTS

| | | | | |
|---|---|---|---|---|
| 2010/0154714 A1* | 6/2010 | DeVilliers | ............... | A01K 5/02 |
| | | | | 119/14.08 |
| 2016/0139134 A1 | 5/2016 | Miyano et al. | | |
| 2017/0013802 A1* | 1/2017 | Zimmerman | ...... | G06K 7/10366 |
| 2017/0303505 A1* | 10/2017 | Karsijns | ................ | B25J 9/1697 |
| 2018/0160649 A1* | 6/2018 | Hicks | ................. | A01K 11/006 |
| 2019/0082654 A1* | 3/2019 | Robbins | ............... | A01K 11/006 |
| 2020/0125849 A1* | 4/2020 | Labrecque | ............. | H04N 23/57 |
| 2020/0178505 A1* | 6/2020 | Womble | ................ | G08C 17/02 |

FOREIGN PATENT DOCUMENTS

| | | |
|---|---|---|
| JP | 2009-112207 A | 5/2009 |
| JP | 2010-506589 A | 3/2010 |
| WO | WO-96/19916 A1 | 7/1996 |
| WO | WO-03/069328 A1 | 8/2003 |
| WO | WO-2005/116629 A1 | 12/2005 |
| WO | WO-2010/071414 A2 | 6/2010 |
| WO | WO-2014/038932 A1 | 3/2014 |
| WO | WO-2016/053104 A1 | 4/2016 |
| WO | WO-2018/003638 A1 | 1/2018 |

OTHER PUBLICATIONS

Akamatsu et al., "Difference of Serum Total Cholesterol Concentration before Parturition in Dairy Cows affects Preventative Effects of Glycerite and By-pass type Amino Acids against Ketosis," Jul. 2009, 2:10-13, with English translation.

Duffield et al., "Impact of hyperketonemia in early lactation dairy cows on health and production," J. Dairy Sci., 2009, 92:571-580.

International Search Report dated Jan. 15, 2019 in PCT/JP2018/043077.

Ospina et al., "Association between the proportion of sampled transition cows with increased nonesterified fatty acids and B-hydroxybutyrate and disease incidence, pregnancy rate, and milk production at the herd level," J. Dairy Sci., Aug. 2010, 93(8):3595-3601.

Ospina et al., "Evaluation of nonesterified fatty acids and B-hydroxybutyrate in transition dairy cattle in the northeastern United States: Critical thresholds for prediction of clinical diseases," J. Dairy Sci., 2010, 93:546-554.

* cited by examiner

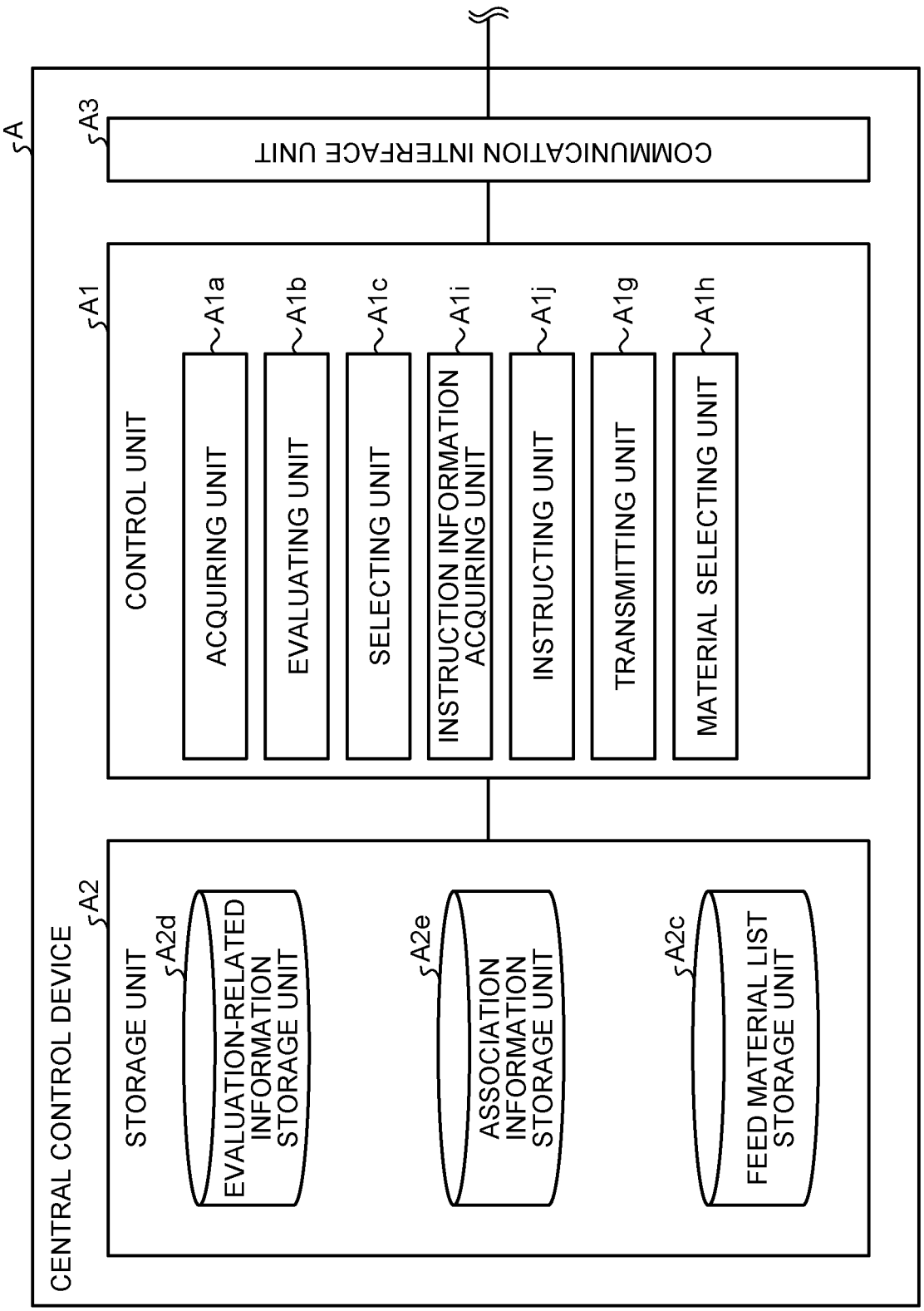

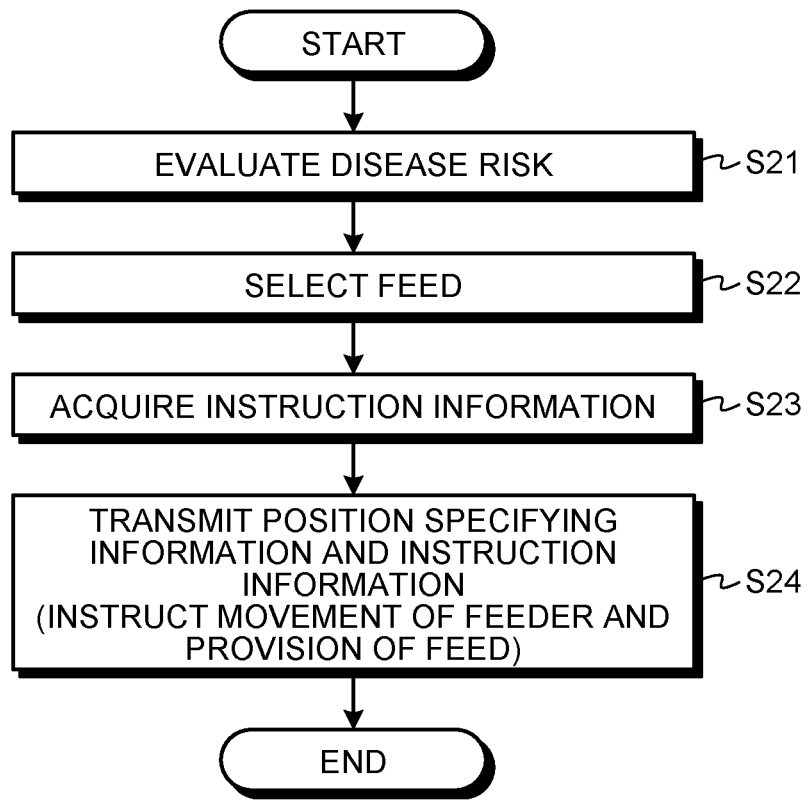

FEEDING MANAGEMENT SYSTEM AND FEEDING MANAGEMENT METHOD

CROSS-REFERENCE TO RELATED APPLICATION

This application is based upon and claims the benefit of priority from PCT Application PCT/JP2018/043077, filed Nov. 21, 2018, which claims priority from Japanese Patent Application No. 2017-254602, filed Dec. 28, 2017, the entire contents of which are incorporated herein by reference.

BACKGROUND OF THE INVENTION

1. Field of the Invention

The present invention relates to a feeding management system and a feeding management method.

2. Description of the Related Art

The period called the perinatal period of three weeks after parturition is a critical period for a dairy cow. In this period, diseases, for example, ketosis, milk fever, placental retention, and abomasum displacement, are often developed. Of these diseases, ketosis is a critical disease for which relevance to the reduction of reproductive performance and milk production has been reported ("T. F. Duffield, K. D. Lissemore, B. W. McBride, and K. E. Leslie, Impact of hyperketonemia in early lactation dairy cows on health and production. J. Dairy. Sci. 92: 571-580 (2009)").

Examples of techniques for animal husbandry management include techniques described in WO 2016/053104, WO 2014/038932, and WO 2010/071414. WO 2016/053104 discloses a system that communicatively connects livestock animals and apparatuses in a cow barn through a network and is capable of controlling the apparatus through the network. WO 2014/038932 discloses an animal husbandry system including a self-propelled feeding vehicle, a feed silo that supplies a feed to the feeding vehicle, and a central control device. WO 2010/071414 discloses an automatic feeding system including a computer and a feeding machine.

If it is possible that the risk of developing a perinatal disease (for example, ketosis) after parturition can be diagnosed in advance before parturition, for example, preventive nutrition intervention before parturition is considered to be able to reduce the development of a perinatal disease (for example, ketosis) and thereby contribute to efficient production for dairy farmers. Furthermore, giving a preventive treatment, such as recuperation, medication, or the additional feeding of a highly nutritious feed, to a cow (a cow before parturition) having a high risk of developing a perinatal disease (for example, ketosis) after parturition is considered to achieve efficient production without reducing the productivity of dairy cows.

However, there is the problem that no technique capable of providing a prophylactic feed to a dairy cow (a dairy cow before parturition) having a high risk of developing a perinatal disease (for example, ketosis) after parturition, without isolating the dairy cow, is present. Note that the systems disclosed in WO 2016/053104, WO 2014/038932, and WO 2010/071414 do not include a unit that implements the technique.

SUMMARY OF THE INVENTION

It is an object of the present invention to at least partially solve the problems in the conventional technology.

The present invention has been made in view of the problem above, and an object of the present invention is to provide a feeding management system and a feeding management method that are capable of providing a prophylactic feed to a dairy cow (a dairy cow before parturition) having a high risk of developing a perinatal disease (for example, ketosis) after parturition, without isolating the dairy cow.

To solve the problem and achieve the object described above, a feeding management system according to one aspect of the present invention is a feeding management system for a free stall cow barn, wherein the free stall cow barn is provided with a plurality of feeding places and is provided with an intrusion control device provided in each of the feeding places to control the intrusion of a dairy cow to the feeding place. The feeding management system includes: an evaluation-related information storage unit that stores evaluation-related information, wherein the evaluation-related information stores (I) cow specifying information for specifying a dairy cow, (II) transmission-unit specifying information for specifying a transmission unit attached to the dairy cow, and (III) evaluation information including (i) at least one value of a concentration value of an amino acid and a measurement value of a blood chemistry parameter in blood of the dairy cow before parturition, or (ii) a value of a formula including an explanatory variable to be substituted with the at least one value calculated using the formula and the at least one value, and is capable of further storing (IV) an evaluation result about a risk of developing a perinatal disease after parturition of the dairy cow and (V) feed specifying information for specifying a feed effective in preventing the perinatal disease after parturition; an association information storage unit that stores a plurality of pieces of association information including (I) device specifying information for specifying an intrusion control device and (II) feed specifying information on a feed provided in a feeding place; an evaluating unit that evaluates the risk of developing the perinatal disease after parturition of the dairy cow by using the evaluation information included in the evaluation-related information stored in the evaluation-related information storage unit, and stores an obtained evaluation result in the evaluation-related information; a selecting unit that, when the evaluation result obtained by the evaluating unit indicates a presence of the risk of disease development, selects a feed effective in preventing the perinatal disease after parturition, based on the evaluation result, and stores feed specifying information on the selected feed in the evaluation-related information; a transmission unit that transmits the cow specifying information or the transmission-unit specifying information; a reading unit that is provided at a predetermined position in the cow barn and reads the information transmitted from the transmission unit; a feed information acquiring unit that acquires, from the evaluation-related information storage unit, the feed specifying information included in the evaluation-related information including the information read by the reading unit; a device information acquiring unit that acquires, from the association information storage unit, the device specifying information included in the association information including the feed specifying information acquired by the feed information acquiring unit; and a control information transmitting unit that, when determining that the dairy cow having the risk of disease development is in the vicinity of the intrusion control device, transmits control information for controlling the intrusion control device to allow intrusion, the intrusion control device being specified based on the device specifying information acquired by the device information acquiring unit, to a controller that controls the operation of the intrusion control device.

A feeding management system according to one aspect of the present invention is a feeding management system for a stall cow barn, wherein the stall cow barn is provided with a plurality of feeders that stores one kind of feed and provides the feed or stores a plurality of kinds of raw materials and mixes the raw materials to provide one kind of feed, or a feeder that stores a plurality of kinds of feeds and provides the feeds. The feeding management system includes: an evaluation-related information storage unit that stores evaluation-related information, wherein the evaluation-related information stores (I) cow specifying information for specifying a dairy cow, (II) position specifying information for specifying a position of the dairy cow present in the cow barn, and (III) evaluation information including (i) at least one value of a concentration value of an amino acid and a measurement value of a blood chemistry parameter in blood of the dairy cow before parturition, or (ii) a value of a formula including an explanatory variable to be substituted with the at least one value calculated using the formula and the at least one value, and is capable of further storing (IV) an evaluation result about a risk of developing a perinatal disease after parturition of the dairy cow and (V) feed specifying information for specifying a feed effective in preventing the perinatal disease after parturition; an association information storage unit that stores a plurality of pieces of association information including (I) instruction information for instructing the feeder to provide one kind of feed and (II) the feed specifying information for specifying the feed; an evaluating unit that evaluates the risk of developing the perinatal disease after parturition of the dairy cow by using the evaluation information included in the evaluation-related information stored in the evaluation-related information storage unit, and stores an obtained evaluation result in the evaluation-related information; a selecting unit that, when the evaluation result obtained by the evaluating unit indicates a presence of the risk of disease development, selects a feed effective in preventing the perinatal disease after parturition, based on the evaluation result, and stores feed specifying information on the selected feed in the evaluation-related information; an instruction information acquiring unit that acquires, from the association information storage unit, the instruction information included in the association information including the feed specifying information on the feed selected by the selecting unit; and an instructing unit that instructs movement of a feeder and provision of a feed by transmitting the position specifying information included in the evaluation-related information including the feed specifying information on the selected feed and the instruction information acquired by the instruction information acquiring unit to a controller that controls the movement of the feeder and the provision of the feed.

The feeding management system according to another aspect of the present invention further includes: a transmitting unit that transmits information stored in the evaluation-related information storage unit to a mobile communication terminal belonging to a person involved in the cow barn; and a receiving unit that is installed in the mobile communication terminal and receives the information transmitted by the transmitting unit.

The feeding management system according to still another aspect of the present invention further includes an ordering unit that is installed in the mobile communication terminal and transmits order instruction information for placing an order with a supplier for a raw material of a feed.

The feeding management system according to still another aspect of the present invention further includes a material selecting unit that, based on an amino acid recommended for the prevention or amelioration of the risk of disease development and a feed material list of feed materials for a concentrate feed and a roughage, the feed material list including the amino acid content of a feed usually given to a dairy cow, selects a feed material from the feed material list.

The feeding management system according to still another aspect of the present invention is a feeding management system, wherein the formula further includes an explanatory variable to be substituted with a value that indicates a parous cow having an experience of parturition before the parturition or a value that indicates a nulliparous cow having no experience of parturition other than the parturition.

The feeding management system according to still another aspect of the present invention is a feeding management system, wherein the at least one value is at least one value of concentration values of 25 kinds of amino acids (Ala, Arg, Asn, Asp, BCAA, Cit, Cys, Glu, Gln, Gly, His, Ile, Leu, Lys, Met, 3MeHis, Orn, Phe, Pro, Ser, Tau, Thr, Trp, Tyr, and Val) and measurement values of 13 kinds of blood chemistry parameters (ALB, ALT, AST, BHBA, BUN, Ca, gGTP, Glc, NEFA, T-Bil, TCHO, TG, and TP) in blood of the dairy cow before parturition, and the perinatal disease is ketosis.

A feeding management method according to one aspect of the present invention is a feeding management method executed by a feeding management system for a free stall cow barn, wherein the feeding management system includes an evaluation-related information storage unit, an evaluating unit, a selecting unit, a transmission unit, a reading unit, a feed information acquiring unit, an association information storage unit, a device information acquiring unit, and a control information transmitting unit, and the free stall cow barn is provided with a plurality of feeding places, and an intrusion control device is provided in each of the feeding places to control the intrusion of a dairy cow to the feeding place. The feeding management method includes: a step executed by the evaluating unit of evaluating a risk of developing a perinatal disease after parturition of a dairy cow by using evaluation information included in evaluation-related information stored in the evaluation-related information storage unit that stores the evaluation-related information, and storing an obtained evaluation result in the evaluation-related information, wherein the evaluation-related information stores (I) cow specifying information for specifying a dairy cow, (II) transmission-unit specifying information for specifying a transmission unit attached to the dairy cow, and (III) the evaluation information including (i) at least one value of a concentration value of an amino acid and a measurement value of a blood chemistry parameter in blood of the dairy cow before parturition, or (ii) a value of a formula including an explanatory variable to be substituted with the at least one value calculated using the formula and the at least one value, and is capable of further storing (IV) an evaluation result about a risk of developing a perinatal disease after parturition of the dairy cow and (V) feed specifying information for specifying a feed effective in preventing the perinatal disease after parturition; a step executed by the selecting unit of, when an obtained evaluation result indicates a presence of the risk of disease development, selecting a feed effective in preventing the perinatal disease after parturition, based on the evaluation result, and storing feed specifying information on the selected feed in the evaluation-related information; a step executed by the transmission unit of transmitting the cow specifying information or the transmission-unit specifying information; a step executed by the reading unit provided at a predetermined position in the cow barn of reading the transmitted information; a step executed by the feed information acquiring unit of acquiring, from the evaluation-related information storage unit, the feed specifying information included in the evaluation-related information including the read information; a step executed by the device information acquiring unit of acquiring, from the association information storage unit that stores a plurality of pieces of association information including (I) device specifying information for specifying the intrusion control device and (II) feed specifying information on a feed to be provided in the feeding place, the device specifying information included in the association information including the acquired feed specifying information; and a step executed by the control information transmitting unit of, when determining that the dairy cow having the risk of disease development is in the vicinity of the intrusion control device, transmitting control information for controlling the intrusion control device to allow intrusion, the intrusion control device being specified based on the acquired device specifying information, to a controller that controls the operation of the intrusion control device.

A feeding management method according to one aspect of the present invention is a feeding management method executed by a feeding management system for a stall cow barn, wherein the feeding management system includes an evaluation-related information storage unit, an evaluating unit, a selecting unit, an association information storage unit, an instruction information acquiring unit, and an instructing unit, and the stall cow barn is provided with a plurality of feeders that stores one kind of feed and provides the feed or stores a plurality of kinds of raw materials and mixes the raw materials to provide one kind of feed, or a feeder that stores a plurality of kinds of feeds and provides the feeds. The feeding management method includes: a step executed by the evaluating unit of evaluating a risk of developing a perinatal disease after parturition of a dairy cow by using evaluation information included in evaluation-related information stored in the evaluation-related information storage unit that stores the evaluation-related information, and storing an obtained evaluation result in the evaluation-related information, wherein the evaluation-related information stores (I) cow specifying information for specifying a dairy cow, (II) position specifying information for specifying a position of the dairy cow present in the cow barn, and (III) evaluation information including (i) at least one value of a concentration value of an amino acid and a measurement value of a blood chemistry parameter in blood of the dairy cow before parturition, or (ii) a value of a formula including an explanatory variable to be substituted with the at least one value calculated using the formula and the at least one value, and is capable of further storing (IV) an evaluation result about a risk of developing a perinatal disease after parturition of the dairy cow and (V) feed specifying information for specifying a feed effective in preventing the perinatal disease after parturition; a step executed by the selecting unit of, when the obtained evaluation result indicates a presence of the risk of disease development, selecting a feed effective in preventing the perinatal disease after parturition, based on the evaluation result, and storing feed specifying information on the selected feed in the evaluation-related information; a step executed by the instruction information acquiring unit of acquiring, from the association information storage unit that stores a plurality of pieces of association information including (I) instruction information for instructing the feeder to provide one kind of feed and (II) feed specifying information for specifying a feed, the instruction information included in the association information including the feed specifying information on the selected feed; and a step executed by the instructing unit of instructing movement of a feeder and provision of a feed by transmitting the position specifying information included in the evaluation-related information including the feed specifying information on the selected feed and the acquired instruction information to a controller that controls the movement of the feeder and the provision of the feed.

The feeding management method according to another aspect of the present invention is a feeding management method, wherein the at least one value is at least one value of concentration values of the 25 kinds of amino acids and measurement values of the 13 kinds of blood chemistry parameters in blood of the dairy cow before parturition, and the perinatal disease is ketosis.

In the present description, various amino acids and blood chemistry parameters are mainly written in abbreviations, the formal names of these are as follows.

(Abbreviation for Amino Acid) (Formal Name)

Ala Alanine
Arg Arginine
Asn Asparagine
Asp Aspartic acid
BCAA Branched chain amino acids
Cit Citrulline
Cys Cystine
Gln Glutamine
Glu Glutamic acid
Gly Glycine
His Histidine
Ile Isoleucine
Leu Leucine
Lys Lysine
Met Methionine
3MeHis 3-Methyl histidine
Orn Ornithine
Phe Phenylalanine
Pro Proline
Ser Serine
Tau Taurine
Thr Threonine
Trp Tryptophan
Tyr Tyrosine
Val Valine (Abbreviation for Blood Biochemistry) (Formal Name)

ALB Albumin
ALT Alanine transaminase
AST Aspartate Aminotransferase
BHBA β-Hydroxybutyric acid
BUN Blood urea nitrogen
Ca Calcium
gGTP γ-glutamyltransferase
Glc Glucose
NEFA Non esterified fatty acid
T-Bil Total bilirubin
TCHO Total cholesterol TG Triglyceride
TP Total protein The feeding management system for the free stall cow barn according to one aspect of the present invention may include, for example, a transmitter (for example, a radio frequency (RF) tag) equivalent to the transmission unit, a reader (for example, a reader-writer for RF tags) equivalent to the reading unit, and an information processor (for example, a server) including a control unit and a storage unit and being capable of communicating with the reader, the controller, and the like. When the feeding management system for the free stall cow barn according to the present invention is configured as described above, the control unit may include, for example, the evaluating unit, the selecting unit, the feed information acquiring unit, the device information acquiring unit, and the control information transmitting unit, and the storage unit may include, for example, the evaluation-related information storage unit and the association information storage unit. When the feeding management system for the free stall cow barn according to the present invention is configured as described above, there may be provided a computer program that causes the control unit to function as, for example, the evaluating unit, the selecting unit, the feed information acquiring unit, the device information acquiring unit, and the control information transmitting unit, or a non-transitory tangible computer-readable recording medium that stores the computer program.

The feeding management system for the stall cow barn according to one aspect of the present invention may include, for example, an information processor (for example, a server) including a control unit and a storage unit and being capable of communicating with the controller and the like. When the feeding management system for the stall cow barn according to the present invention is configured as described above, the control unit may include, for example, the evaluating unit, the selecting unit, the instruction information acquiring unit, and the instructing unit, and the storage unit may include, for example, the evaluation-related information storage unit and the association information storage unit. When the feeding management system for the stall cow barn according to the present invention is configured as described above, there may be provided a computer program that causes the control unit to function as, for example, the evaluating unit, the selecting unit, the instruction information acquiring unit, and the instructing unit, or a non-transitory tangible computer-readable recording medium that stores the computer program.

The present invention is capable of providing a prophylactic feed to a dairy cow (a dairy cow before parturition) having a high risk of developing a perinatal disease (for example, ketosis) after parturition, without isolating the dairy cow.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a block diagram of another configuration example of the central control device A;
and
FIG. 7 is a diagram of another example of a flowchart of the feeding management processing.

DETAILED DESCRIPTION OF THE PREFERRED EMBODIMENTS

Hereinafter, exemplary embodiments of the feeding management system and the feeding management method according to the present invention will be described in detail with reference to the drawings. The present invention is not limited to these embodiments.

1. First Embodiment

A feeding system for a free stall cow barn according to a first embodiment will be described in detail with reference to FIG. 1 to FIG. 4.

1-1. Configuration

Figure 1:
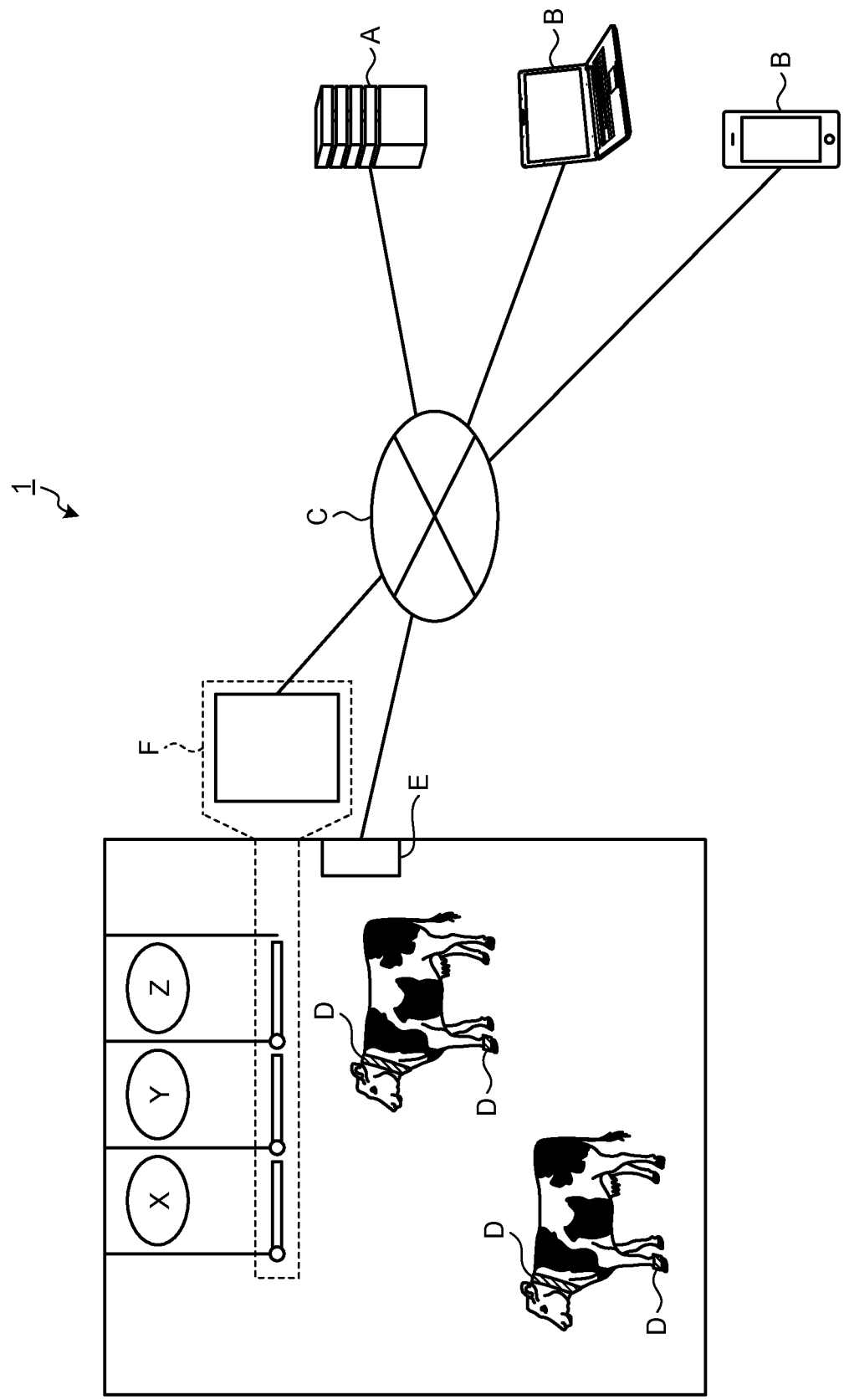
FIG. 1 is a diagram of an entire configuration example of a feeding system 1 for a free stall cow barn.

FIG. 1 is a diagram of an entire configuration example of the feeding system 1 for the free stall cow barn. As shown in FIG. 1, the free stall cow barn is provided with a plurality of feeding places, for example, a feeding place in which a standard feed X to be usually given to a dairy cow is placed, a feeding place in which a special-purpose feed Y effective in preventing a perinatal disease (for example, ketosis) after parturition is placed, and a feeding place in which a special-purpose feed Z more effective in the prevention than the special-purpose feed Y is placed. Furthermore, as shown in FIG. 1, in the free stall cow barn, an intrusion control device that controls the intrusion of a dairy cow to a feeding place is provided in each of the feeding places. In the free stall cow barn, a dairy cow can move freely without being tied in the cow barn. The intrusion control device may be, for example, a device such as a gate, or a device such as a cover for a feeding place.

The feeding system 1 for the free stall cow barn includes the central control device A, one or a plurality of mobile communication terminals B belonging to a person involved in the cow barn (for example, a person involved in dairy farming, such as an owner of a stock farm, a person in charge of feeding, or a veterinary), a network C, one or a plurality of transmitters D, a reader E, and an intrusion control system F.

The network C has the function of connecting the central control device A, the mobile communication terminals B, the reader E, and the intrusion control system F communicatively to one another, and is, for example, the Internet, an intranet, or a local area network (LAN) (including both wired and wireless).

The transmitter D is to be attached to a dairy cow (in particular, a dairy cow before parturition), and is a transmission unit such as an RF tag. Into the transmitter D, cow specifying information for specifying a dairy cow (for example, individual identification information (for example, an identification code or an identification ID)) or transmitter specifying information for specifying the transmitter D (for example, transmitter identification information (for example, an identification code or an identification ID)) is written in advance. The number of the transmitters D to be attached to a dairy cow may be two or more as shown in FIG. 1, or may be one.

The reader E is a reading unit, such as a reader/writer for RF tags, that reads information transmitted from the transmitter D. The reader E is disposed at a predetermined position in the cow barn (specifically, a position at which whether a dairy cow is in the vicinity of the intrusion control device can be determined). Information read by the reader E is automatically transmitted to the central control device A. The reader E may be disposed at a plurality of positions in the cow barn. When the reader E is disposed at a plurality of positions in the cow barn, for example, reader management information that stores "reader specifying information for specifying the reader (for example, reader identification information (for example, an identification code or an identification ID))", "positional information on a disposal position (place) of the reader in the cow barn", and "distance information on the distance from the reader to an intrusion control device (for example, an intrusion control device disposed nearest to the reader)" is registered, for every reader, in the central control device A, and a log recording unit (information processing unit) that records a reading history (a combination of a read time and reader specifying information) of a reader as reading history information is provided in the central control device A, whereby, based on the aforementioned information, a positional information history of a dairy cow can be traced, or the distance from a dairy cow to an intrusion control device can be grasped.

The intrusion control system F is an existing system for cow barns that includes, for example, a plurality of intrusion control devices such as a gate, and a controller having a built-in communication functions that controls the operation of the intrusion control devices (for example, an operation to allow intrusion (for example, an operation to open a gate) and an operation to inhibit intrusion (for example, an operation to close a gate)). When the readers E are disposed at a plurality of positions in the cow barn, for example, the reader management information further stores device specifying information of an intrusion control device corresponding to a feeding place that is the navigating destination of a dairy cow, whereby, when the reader disposed at a place distant from the feeding place that is the navigating destination reads information, the intrusion control device corresponding to the feeding place can be operated, and thus, the dairy cow can be navigated to the feeding place. In other words, by operating a plurality of intrusion control devices and a plurality of readers in combination, navigation to a predetermined feeding place can be performed at a place distant from the feeding place.

Figure 2:
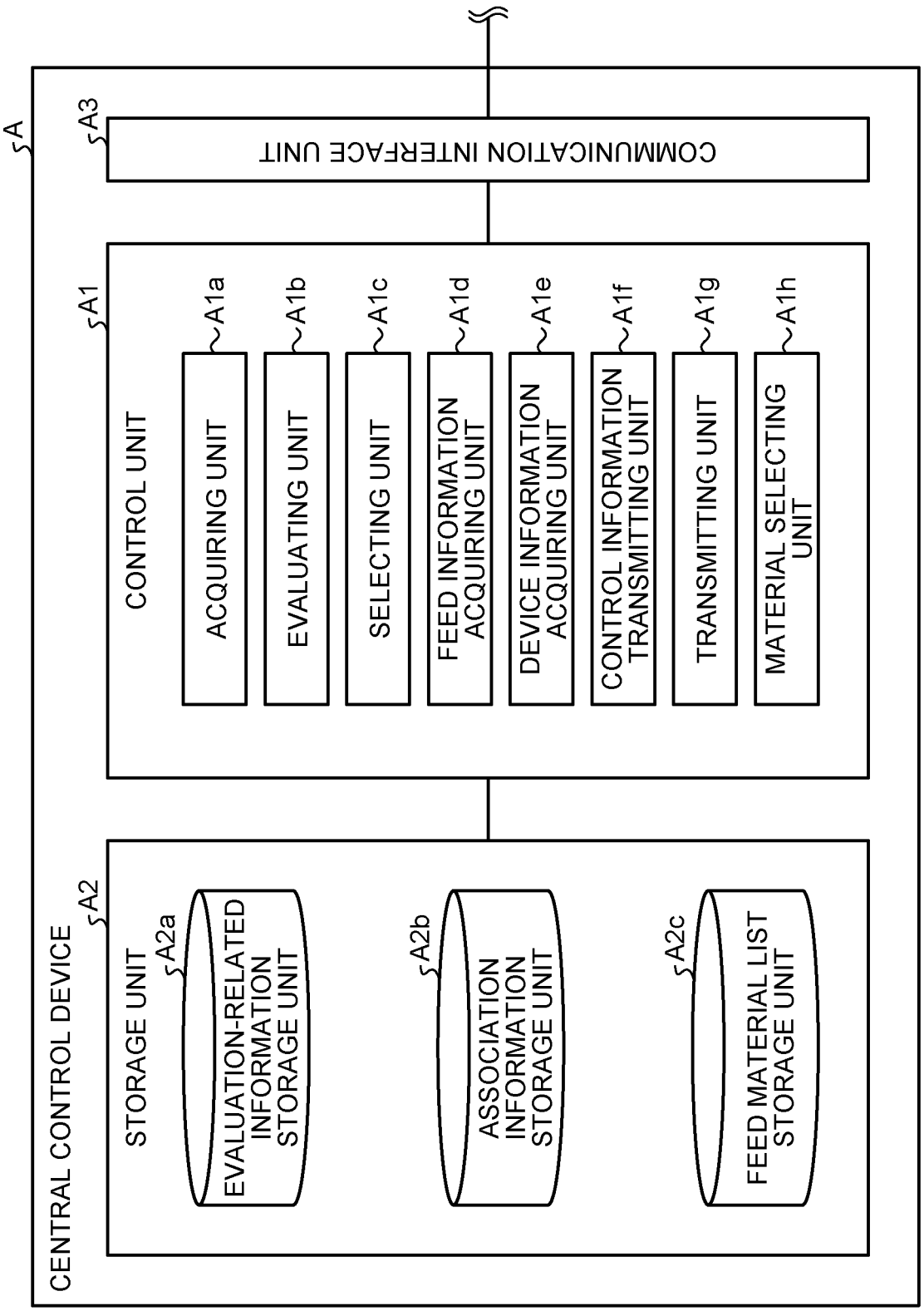
FIG. 2 is a block diagram of a configuration example of a central control device A.

FIG. 2 is a block diagram of a configuration example of the central control device A. The central control device A is equivalent to a server. The central control device A includes a control unit A1, such as a central processing unit (CPU), that integrally controls the central control device A, a storage unit A2 that stores various databases, tables, files, or the likes, and a communication interface unit A3 that connects the central control device A to the network C communicatively via a communication device such as a router and a wired or wireless communication line such as a private line. The units provided in the central control device A are connected to one another communicatively via any communication channel.

The communication interface unit A3 allows communications between the central control device A and the network C (or a communication device such as a router). In other words, the communication interface unit A3 has the function of performing data communications with other terminals via a communication line.

The storage unit A2 is a storage. Examples of the storage unit A2 include a memory such as a random access memory (RAM) or a read only memory (ROM), a fixed disk drive such as a hard disk, a flexible disk, and an optical disk. The storage unit A2 may store computer programs giving instructions to the CPU for various types of processing, in cooperation with an operating system (OS).

The storage unit A2 includes an evaluation-related information storage unit A2a, an association information storage unit A2b, and a feed material list storage unit A2c.

The evaluation-related information storage unit A2a is an information storage unit that stores a plurality of pieces of evaluation-related information. The evaluation-related information stores cow specifying information, transmitter specifying information, and evaluation information, and is capable of further storing (I) an evaluation result about the risk of developing a perinatal disease (for example, ketosis) after parturition of a dairy cow and (II) feed specifying information for specifying a feed effective in preventing a perinatal disease (for example, ketosis) after parturition. The evaluation information includes (I) at least one value of concentration values of amino acids and measurement values of blood chemistry parameters in blood of the dairy cow before parturition, or (II) a value of a formula including an explanatory variable to be substituted with the at least one value calculated using the formula and the at least one value.

The association information storage unit A2b is an information storage unit that stores a plurality of pieces of association information. The association information includes device specifying information for specifying an intrusion control device (for example, device identification information (for example, an identification code or an identification ID)), and feed specifying information for specifying a feed provided in a feeding place (for example, feed identification information (for example, an identification code or an identification ID)). The association information storage unit A2b may store, for example, association information on the standard feed X, association information on the special-purpose feed Y, and association information on the special-purpose feed Z.

The feed material list storage unit A2c is an information storage unit that stores a feed material list of feed materials for a concentrate feed and a roughage, the feed material list including the amino acid content of a feed usually given to a dairy cow. The feed material list includes, for example, the total digestible nutrients (TDN), the crude protein (CP) content, crude fat, sugar, starch, organic acids, neutral detergent fiber (NDF), and the amino acid composition of a roughage, such as straw, alfalfa, or perennial ryegrass, and of a concentrate feed, such as corn, barley, or soybean cake. The feed material list further includes the information on other components contained in the feeds other than the roughage and the concentrate feed, such as cottonseed, soybean cake, cornstarch, amino acids with a simple structure, mineral, and vitamins. The feed material list further includes not only materials, such as amino acids with a simple substance and vitamins, but also a lumen protection tablet that enhances the small-intestinal nutrient absorption of such biologically active materials. The feed material list further includes the information on, for example, a commercial mixed feed. Examples of the list including such information include "National Agriculture and Food Research Organization (ed.), Standard Tables of Feed Composition in Japan, Japan Livestock Industry Association, 2009", and "National Research Council, Nutrient Requirements of Dairy Cattle, 7th Revised Edition, National Academy Press, Washington, DC, USA, 2001". Furthermore, based on independent analysis results, a material may be added to the feed material list at any time.

The control unit A1 has an internal memory that stores, for example, a control program such as an OS, programs for various processing procedures, and needed data, and performs various types of information processing according to these programs. The control unit A1 functionally conceptually includes an acquiring unit A1a, an evaluating unit A1b, a selecting unit A1c, a feed information acquiring unit A1d, a device information acquiring unit A1e, a control information transmitting unit A1f, a transmitting unit A1g, and a material selecting unit A1h.

The acquiring unit A1a is an information processing unit that acquires evaluation information from an information processor (not illustrated) connected to the central control device A communicatively. The acquiring unit A1a may store the acquired evaluation information in the evaluation-related information, together with the cow specifying information and the transmitter specifying information.

The evaluating unit A1b is an information processing unit that evaluates the risk of developing a perinatal disease (for example, ketosis) after parturition of a dairy cow by using the evaluation information, and stores an acquired evaluation result in the evaluation-related information.

The formula may further include an explanatory variable to be substituted with a value that indicates a parous cow having an experience of parturition before a coming parturition or a value that indicates a nulliparous cow having no experience of parturition other than the coming parturition. Using the formula, a highly accurate evaluation result can be obtained in the evaluating unit A1b. For example, when (I) at least one value of concentration values of the 25 kinds of amino acids and measurement values of the 13 kinds of blood chemistry parameters, or (II) a value of a formula including an explanatory variable to be substituted with the at least one value calculated using the formula and the at least one value are included in the evaluation information, the evaluating unit A1b may evaluate the risk of developing ketosis after parturition of a dairy cow (a state of ketosis after parturition of a dairy cow) by using the evaluation information.

Embodiments of the acquiring unit A1a and the evaluating unit A1b will be described in detail in the following "Embodiments of Acquiring unit A1a and Evaluating unit A1b".

The selecting unit A1c is an information processing unit that, when an evaluation result obtained in the evaluating unit A1b indicates a presence of the risk of disease development, selects a feed effective in preventing a perinatal disease (for example, ketosis) after parturition, based on the evaluation result, and stores feed specifying information on the selected feed in the evaluation-related information. For example, when the evaluation result indicates that the risk of disease development is critically high (a high risk), the selecting unit A1c may select the special-purpose feed Z and store feed specifying information on the selected special-purpose feed Z in the evaluation-related information. For example, when the evaluation result indicates that the risk of disease development is high, but not critically high (a moderate risk), the selecting unit A1c may select the special-purpose feed Y and store feed specifying information on the selected special-purpose feed Y in the evaluation-related information.

The feed information acquiring unit A1d is an information processing unit that acquires, from the evaluation-related information storage unit A2a, feed specifying information included in the evaluation-related information including information read by the reader E.

The device information acquiring unit A1e is an information processing unit that acquires, from the association information storage unit A2b, device specifying information included in the association information including the feed specifying information acquired by the feed information acquiring unit A1d.

The control information transmitting unit A1f is an information processing unit that, when determining that a dairy cow having the risk of disease development is in the vicinity of an intrusion control device, transmits, to the controller, control information for controlling the intrusion control device to allow intrusion, the intrusion control device being specified based on the device specifying information acquired by the device information acquiring unit A1e. The controller that has received the control information controls the intrusion control device to allow intrusion, according to the control information.

The transmitting unit A1g is an information processing unit that transmits information stored in the evaluation-related information storage unit A2a to the mobile communication terminal B. Since the transmitting unit A1g and the receiving unit B1a described later are provided, the evaluation-related information can be shared with a person involved in the cow barn.

The material selecting unit A1h is an information processing unit that selects a feed material from the feed material list, based on (information on) an amino acid recommended for the prevention or amelioration of the risk of disease development and the feed material list. Since the material selecting unit A1h is provided, the feed material recommended for the prevention or amelioration of a disease risk can be selected easily.

For example, when an evaluation result indicates a presence of the risk of disease development in a dairy cow, the material selecting unit A1h may calculate the amino acid composition of the standard feed regularly given, based on the feed material list, and determine the kind and amount of an amino acid preparation to be added to the standard feed, based on the calculation result and information on the recommended amino acid. The material selecting unit A1h may select, from the special-purpose feeds prepared in advance, a feed having a composition most similar to the composition of the standard feed to which the determined amino acid preparation is added.

Here, in consideration of the number of times of parturition and the experience of parturition of a dairy cow evaluated to have a risk of disease development, the kind and amount of an amino acid preparation may be determined.

When a disease risk can be ranked in risk level on a scale of one to two or more, the kind and amount of an amino acid preparation to be recommended can be changed according to the level of the risk. In this case, there are determined the kind and amount of the amino acid preparation to be added to the standard feed calculated based on an amino acid composition calculated from information on an amino acid recommended for the prevention or amelioration and the standard feed. A feed having a composition most similar to the composition of the calculated standard feed to which the amino acid preparation is added is selected from the special-purpose feeds prepared in advance.

Alternatively, when the readers E are disposed at a plurality of positions in the cow barn, variations in the active mass of a daily cow are evaluated from a positional information history of the dairy cow, the positional information history being obtained based on the reading history information and the reader management information, and, a feed material can be selected, based on the evaluation result and an evaluation result about the risk of disease development. Besides the addition of the amino acid preparation, it is proposed that the standard feed has a high amino acid content (protein content) in the composition. When the amino acid content is significantly higher compared with the composition of the special-purpose feed prepared in advance, alarm information (alert information) for proposing the improvement of the special-purpose feed can be notified to the mobile communication terminals B belonging to persons involved in the cow barn (for example, an owner of a stock farm and a person involved in the stock farm).

Figure 3:
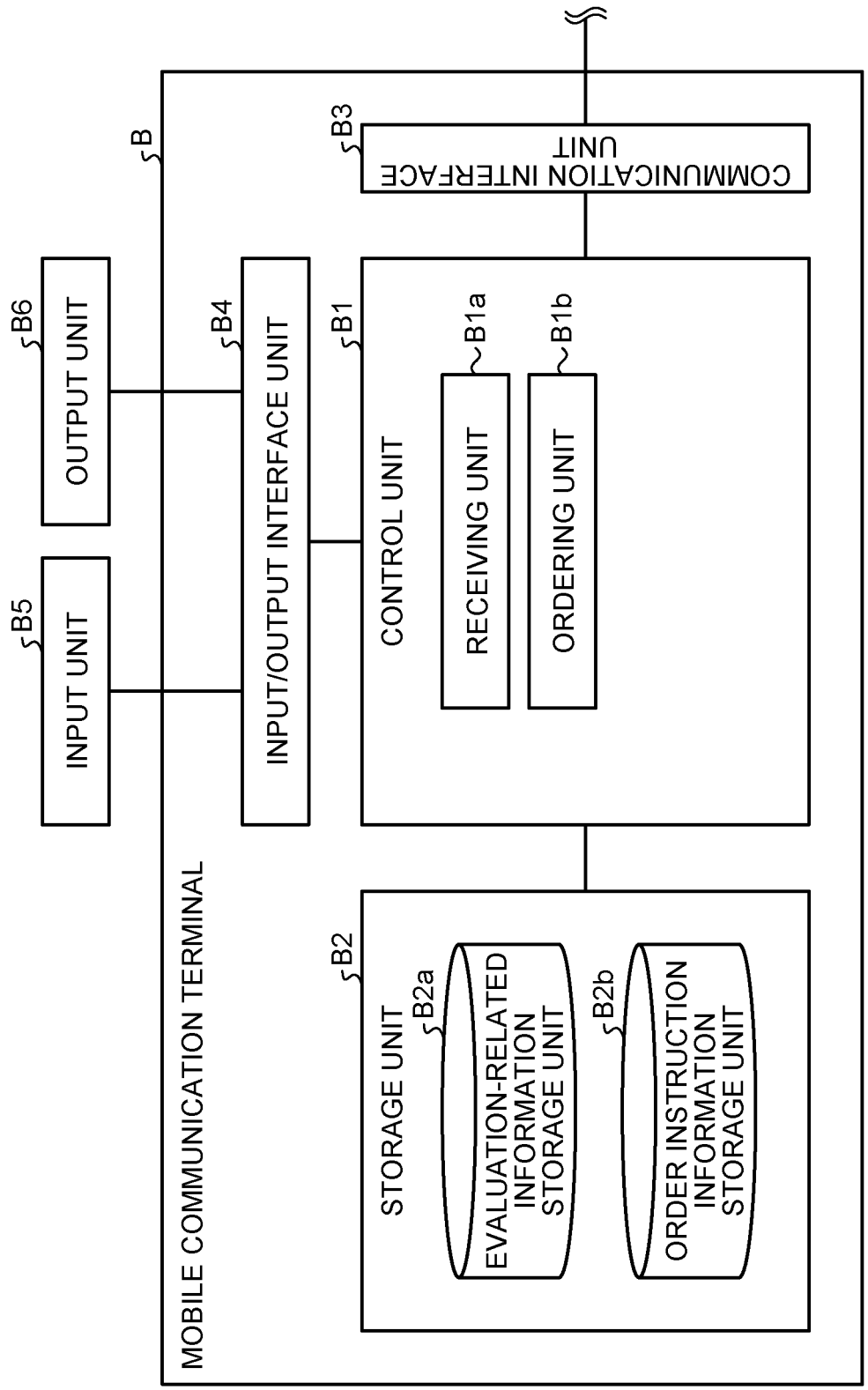
FIG. 3 is a block diagram of a configuration example of a mobile communication terminal B.

FIG. 3 is a block diagram of a configuration example of the mobile communication terminal B. The mobile communication terminal B is equivalent to a mobile information processor, such as a notebook personal computer, a personal digital assistant (PDA), a smartphone, or a tablet personal computer. A stationary information processor such as a desktop personal computer may be substituted for the mobile communication terminal B. The mobile communication terminal B includes a control unit B1, such as a CPU, that integrally controls the mobile communication terminal B, a storage unit B2 that stores various databases, tables, files, or the likes, a communication interface unit B3 that connects the mobile communication terminal B to the network C communicatively, an input/output interface unit B4 connected to an input unit B5 and an output unit B6, the input unit B5, and the output unit B6. The units provided in the mobile communication terminal B are connected to one another communicatively via any communication channel.

The communication interface unit B3 allows communications between the mobile communication terminal B and the network C (or a communication device such as a router). In other words, the communication interface unit B3 has a function to communicate data to other terminals via a communication line.

The input/output interface unit B4 is connected to the input unit B5 and the output unit B6. A monitor, a speaker, or a printer may be used as the output unit B6. A keyboard, a mouse, a microphone, a monitor that functions as a pointing device in cooperation with a mouse, or a touch panel may be used as the input unit B5.

The storage unit B2 is a storage. Examples of the storage unit B2 include a memory such as a RAM and a ROM, a fixed disk drive such as a hard disk, a flexible disk, and an optical disk. The storage unit B2 may store computer programs that give instructions to the CPU to perform various types of processing, in cooperation with an OS.

The storage unit B2 includes an evaluation-related information storage unit B2a and an order instruction information storage unit B2b. The evaluation-related information storage unit B2a is an information storage unit that stores the evaluation-related information. The order instruction information storage unit B2b is an information storage unit that stores order instruction information for placing an order with a supplier for a raw material for a feed.

The control unit B1 has an internal memory that stores, for example, a control program such as an OS, programs that define various processing procedures and the likes, and needed data, and performs various types of information processing according to these programs. The control unit B1 functionally conceptually includes the receiving unit B1a and an ordering unit B1b.

The receiving unit B1a is an information processing unit that receives information transmitted from the transmitting unit A1g. The receiving unit B1a may store the received information in the evaluation-related information storage unit B2a. Since the transmitting unit A1g and the receiving unit B1a are provided, the evaluation-related information can be shared with a person involved in the cow barn.

The ordering unit B1b is an information processing unit that transmits order instruction information, for example, to an information processor of a supplier (a receiver of an order). The ordering unit B1b may store the transmitted order instruction information in the order instruction information storage unit B2b. The order instruction information may be created using the mobile communication terminal B, for example, based on the result of an inventory check of a feed material necessary for feeding, the inventory check being made by a person involved in the cow barn based on information provided to the mobile communication terminal B. Since the ordering unit B1b is provided, the person involved in the cow barn can place an order easily.

1-2. Processing

Figure 4:
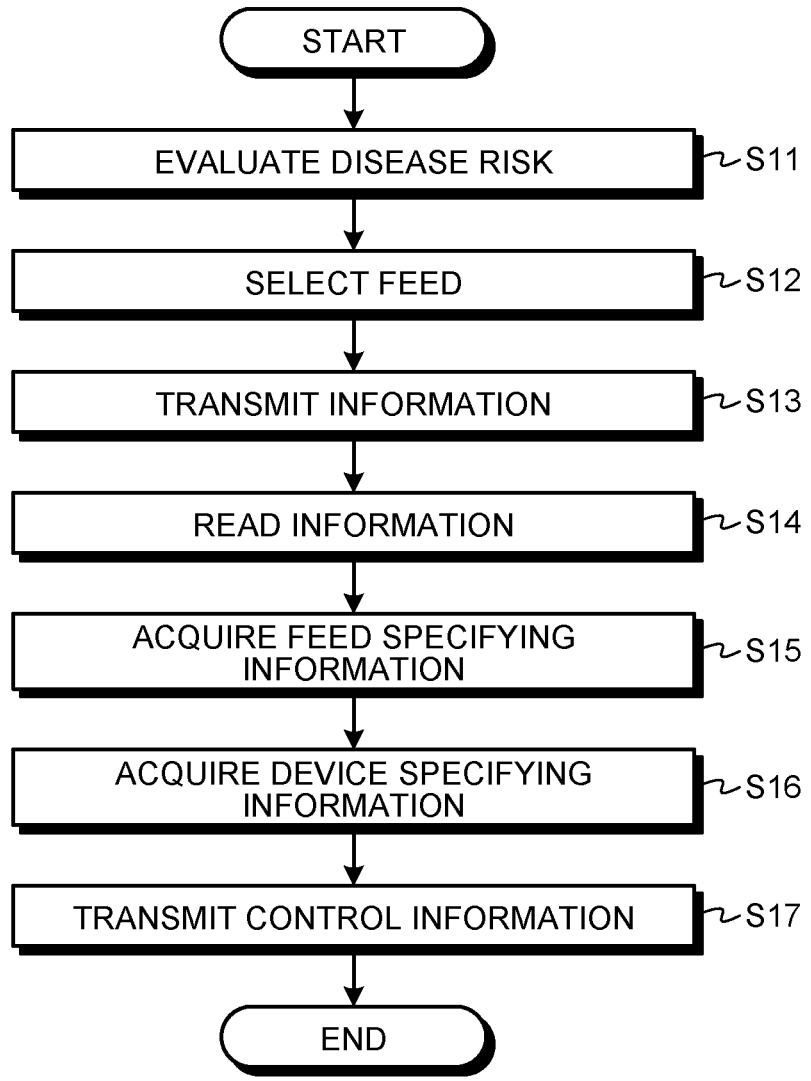
FIG. 4 is a diagram of an example of a flowchart of feeding management processing.

FIG. 4 is a diagram of an example of a flowchart of feeding management processing. The following explanations about the flowchart are given on the precondition that a plurality of pieces of evaluation-related information are stored in the evaluation-related information storage unit A2a. Furthermore, the following explanations are given on the precondition that the evaluation-related information includes at least the cow specifying information, the transmitter specifying information, and the evaluation information.

First, using the evaluation information included in the evaluation-related information stored in the evaluation-related information storage unit A2a, the evaluating unit A1b evaluates the risk of developing a perinatal disease (for example, ketosis) after parturition of a dairy cow specified based on the cow specifying information included in the evaluation-related information, and stores an obtained evaluation result (for example, any one of an evaluation result indicating that a disease risk is low (a low risk), an evaluation result indicating a moderate risk, and an evaluation result indicating a high risk) in the evaluation-related information (step S11).

Next, when the evaluation result obtained at step S1 indicates a moderate risk or a high risk, the selecting unit A1c selects a feed effective in preventing a perinatal disease (for example, ketosis) after parturition, based on the evaluation result, and stores feed specifying information on the selected feed in the evaluation-related information including the evaluation result (step S12). Specifically, when the evaluation result indicates a high risk, the selecting unit A1c selects the special-purpose feed Z, and stores feed specifying information on the selected special-purpose feed Z in the evaluation-related information. When the evaluation result indicates a moderate risk, the selecting unit A1c selects the special-purpose feed Y, and stores feed specifying information on the selected special-purpose feed Y in the evaluation-related information.

When the processing at step S1 and step S12 is executed to each piece of the evaluation-related information stored in the evaluation-related information storage unit A2a, each piece of the evaluation-related information is updated to either a state in which the evaluation result indicating a low risk is further stored, or a state in which either the evaluation result indicating a moderate risk or the evaluation result indicating a high risk and the feed specifying information are further stored.

On the other hand, processing at step S13 and subsequent steps is executed concurrently with the execution of the processing at step S1 and step S12.

The transmitter D transmits the cow specifying information or the transmitter specifying information (step S13).

The reader E reads the information transmitted from the transmitter D (step S14). The read information is automatically transmitted to the central control device A.

The feed information acquiring unit A1d acquires, from the evaluation-related information storage unit A2a, the feed specifying information included in the evaluation-related information including the information read at step S14 (Step S15). When the feed specifying information is acquired at step S15, it is determined that a dairy cow evaluated to have a moderate risk or a high risk is in the vicinity of the intrusion control device, and accordingly, the processing is shifted to the following step S16. In contrast, when the feed specifying information is not acquired at step S15, it is determined that a dairy cow evaluated to have a low risk or a dairy cow not subjected to risk evaluation and feed selection processing is in the vicinity of the intrusion control device, and accordingly, the processing is ended without being shifted to the following step S16.

The device information acquiring unit A1e acquires, from the association information storage unit A2b, device specifying information included in association information including the feed specifying information acquired at step S15 (step S16).

When determining that a dairy cow having the risk of disease development is in the vicinity of the intrusion control device, the control information transmitting unit A1f transmits, to the controller, control information for controlling the intrusion control device to allow intrusion, the intrusion control device being specified using the device specifying information acquired at step S16 (step S17). The controller that has received the control information controls the intrusion control device to allow intrusion, according to the control information.

Through the processing described above, a dairy cow evaluated to have a moderate risk can be navigated to a feeding place in which the special-purpose feed Y is placed, and a dairy cow evaluated to have a high risk can be navigated to a feeding place in which the special-purpose feed Z is placed, and thus the dairy cows can be given the special-purpose feed Y or the special-purpose feed Z.

The feed management processing according to the present embodiment may include the following processing steps (1) to (6). In other words, there may be provided a processing flow for performing a risk evaluation every time information is read by the reader E.

(1) The transmitter D transmits the transmitter specifying information or the cow specifying information.
(2) The reader E reads the information transmitted from the transmitter D.
(3) Using the evaluation information included in the evaluation-related information stored in the evaluation-related information storage unit A2a and including information read by the reader E, the evaluating unit A1b evaluates the risk of developing a perinatal disease (for example, ketosis) after parturition of a dairy cow specified based on the cow specifying information included in the evaluation-related information.
(4) When an evaluation result obtained by the evaluating unit A1b indicates a moderate risk or a high risk, the selecting unit A1c selects a feed effective in preventing a perinatal disease (for example, ketosis) after parturition, based on the evaluation result. For example, when the evaluation result indicates a high risk, feed specifying information on the special-purpose feed Z is outputted. When the evaluation result indicates a moderate risk, feed specifying information on the special-purpose feed Y is outputted.
(5) The device information acquiring unit A1e acquires, from the association information storage unit A2b, device specifying information included in association information including the feed specifying information of the feed selected by the selecting unit A1c.
(6) When determining that the dairy cow having the risk of disease development is in the vicinity of an intrusion control device, the control information transmitting unit A1f transmits, to the controller, control information for controlling the intrusion control device to allow intrusion, the intrusion control device being specified using the device specifying information acquired by the device information acquiring unit A1e.

2. Second Embodiment

A feeding system for a stall cow barn according to a second embodiment will be described in detail with reference to FIG. 5 to FIG. 7. In the description of the second embodiment, a description duplicating that of the first embodiment is sometimes omitted.

2-1. Configuration

Figure 5:
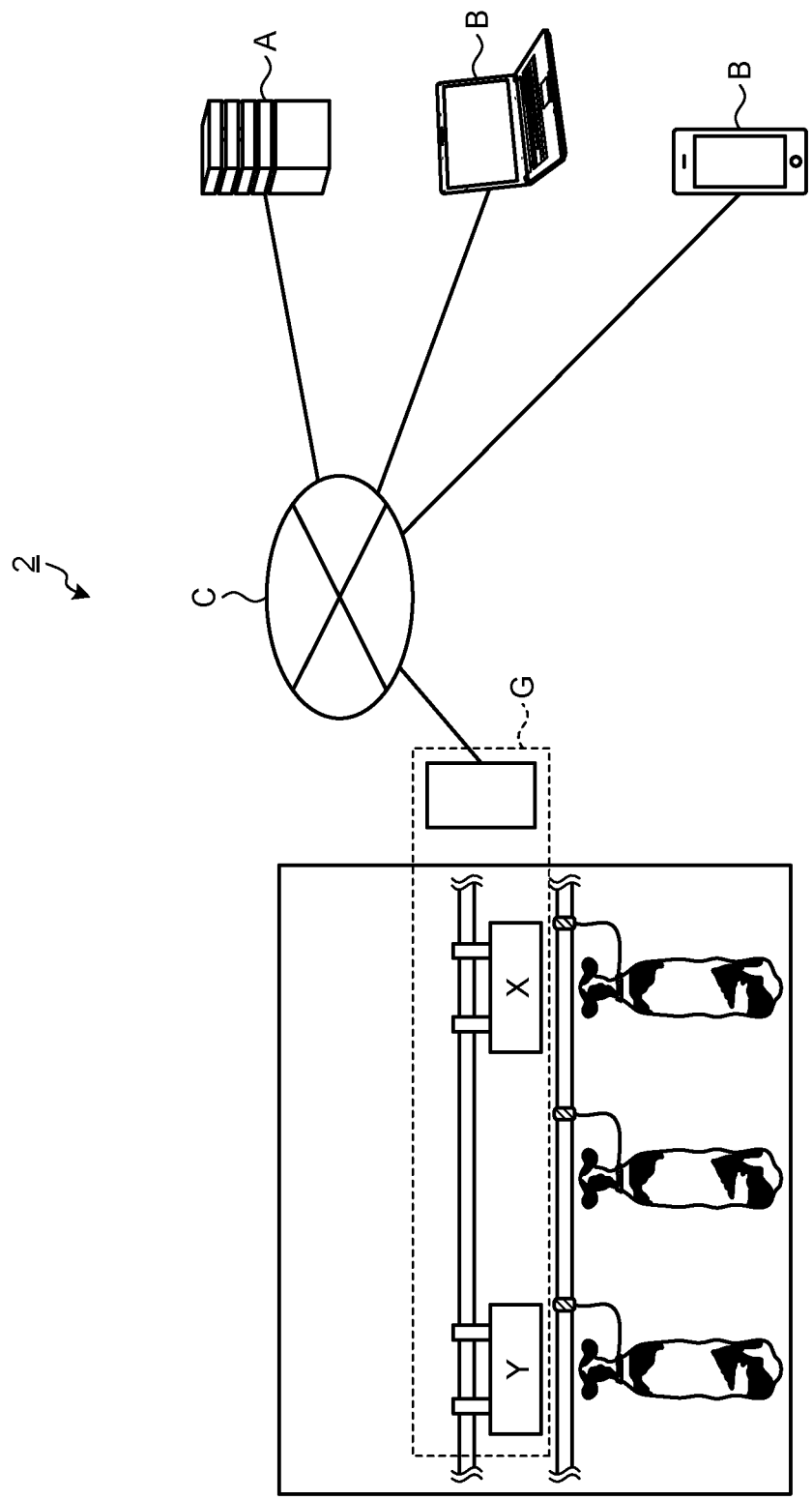
FIG. 5 is a diagram of an entire configuration example of a feeding system 2 for a stall cow barn.

FIG. 5 is a diagram of an entire configuration diagram of a feeding system 2 for a stall cow barn. As illustrated in FIG. 5, one or a plurality of feeders that provide a feed are placed in the stall cow barn. The feeder may be a special-purpose feeder that stores one kind of feed (for example, the standard feed X or the special-purpose feed Y) and provide the feed. The feeder may be a special-purpose feeder that stores a plurality of kinds of raw materials (for example, a plurality of kinds of raw materials for the standard feed X or a plurality of kinds of raw materials for the special-purpose feed Y) and mixes the raw materials to provide one kind of feed (for example, the standard feed X or the special-purpose feed Y). The feeder may be a complex feeder that stores a plurality of kinds of feeds (for example, the standard feed X or the special-purpose feed Y) and provides the feeds. As shown in FIG. 1, dairy cows are approximately fixed at a predetermined position in the stall cow barn.

The feeding system 2 for the stall cow barn includes the central control device A, one or a plurality of mobile communication terminals B belonging to persons involved in the cow barn, the network C, and a feeding system G.

The network C has the function of connecting the central control device A, the mobile communication terminal B, and the feeding system G communicatively to one another, and is, for example, the Internet, an intranet, or a LAN (including both wired and wireless).

The feeding system G is an existing system for cow barns, the system including, for example, a feeder, a moving mechanism that moves the feeder to the front of a dairy cow (for example, including a rail), and a controller that has a built-in communication function and controls the feeder. The feeding system G may be an existing system for cow barns, the system including, for example, a self-propelled feeder and a controller that has a built-in communication function and controls the self-propelled feeder.

FIG. 6 is a block diagram of a configuration example of the central control device A.

The storage unit A2 includes an evaluation-related information storage unit A2d, an association information storage unit A2e, and the feed material list storage unit A2c.

The evaluation-related information storage unit A2d is an information storage unit that stores a plurality of pieces of evaluation-related information. The evaluation-related information stores the cow specifying information, position specifying information for specifying a position of a dairy cow present in the cow barn, and evaluation information, and is capable of further storing (I) an evaluation result about the risk of developing a perinatal disease (for example, ketosis) after parturition of the dairy cow and (II) feed specifying information for specifying a feed effective in preventing a perinatal disease (for example, ketosis) after parturition.

The association information storage unit A2e is an information storage unit that stores a plurality of pieces of association information. The association information includes instruction information for instructing the feeder to provide one kind of feed and feed specifying information. The association information storage unit A2e may store, for example, association information on the standard feed X and association information on the special-purpose feed Y.

The control unit A1 functionally conceptually includes the acquiring unit A1a, the evaluating unit A1b, the selecting unit A1c, an instruction information acquiring unit A1i, an instructing unit A1j, the transmitting unit A1g, and the material selecting unit A1h.

The acquiring unit A1a may store the acquired evaluation information in the evaluation-related information, together with the cow specifying information and the position specifying information.

For example, when an evaluation result indicates that the risk of disease development is critically high (a high risk) or indicates that the risk of disease development is high, but not critically high, (a moderate risk), the selecting unit A1c may select the special-purpose feed Y and store feed specifying information on the selected special-purpose feed Y in the evaluation-related information.

The instruction information acquiring unit A1i is an information processing unit that acquires, from the association information storage unit A2e, instruction information included in the association information including the feed specifying information on the feed selected by the selecting unit A1c.

The instructing unit A1j is an information processing unit that instructs the movement of a feeder and the provision of a feed by transmitting, to the controller, position specifying information included in the evaluation-related information including the feed specifying information of the feed selected by the selecting unit A1c and the instruction information acquired by the instruction information acquiring unit A1i. Upon receiving the position specifying information and the instruction information, according to the information, the controller moves the feeder to a place in which a dairy cow having the risk of disease development is present, and causes the feeder to start the provision of the feed.

2-2. Processing

FIG. 7 is a diagram of an example of a flowchart of feeding management processing. The following explanations about the flowchart are given on the precondition that a plurality of pieces of evaluation-related information are stored in the evaluation-related information storage unit A2d. Furthermore, the following explanations are given on the precondition that the evaluation-related information includes at least the cow specifying information, the position specifying information, and the evaluation information.

First, using the evaluation information included in the evaluation-related information stored in the evaluation-related information storage unit A2d, the evaluating unit A1b evaluates the risk of developing a perinatal disease (for example, ketosis) after parturition of a dairy cow specified based on the cow specifying information included in the evaluation-related information, and stores an obtained evaluation result (for example, any one of an evaluation result indicating that the risk of disease development is low (a low risk), an evaluation result indicating a moderate risk, and an evaluation result indicating a high risk) in the evaluation-related information (step S21).

Next, when the evaluation result obtained at step S21 indicates a moderate risk or a high risk, the selecting unit A1c selects a feed effective in preventing a perinatal disease (for example, ketosis) after parturition, based on the evaluation result, and stores feed specifying information on the selected feed in the evaluation-related information including the evaluation result (step S22).

Specifically, when the evaluation result indicates a moderate risk or a high risk, the selecting unit A1c selects the special-purpose feed Y, and stores feed specifying information on the selected special-purpose feed Y in the evaluation-related information.

Next, the instruction information acquiring unit A1i acquires, from the association information storage unit A2e, instruction information included in the association information including the feed specifying information on the feed selected at step S22 (step S23).

Next, the instructing unit A1j instructs the movement of the feeder and the provision of the feed by transmitting, to the controller, the position specifying information included in the evaluation-related information including the feed specifying information on the feed selected at step S22 and the instruction information acquired at step S23 (step S24). Upon receiving the position specifying information and the instruction information, according to the information, the controller moves the feeder to a place in which a dairy cow having the risk of disease development is present, and causes the feeder to start the provision of the feed.

Through the processing described above, a feeder that provides the special-purpose feed Y can be moved to the front of a dairy cow evaluated to have a moderate risk or a high risk to start the provision of the feed, and the dairy cow can be given the special-purpose feed Y.

3. Other Embodiments

In addition to the embodiments described above, the feeding management system and the feeding management method according to the present invention can be practiced in various different embodiments within the technological scope of the claims.

Of the processings described in the embodiments, all or a part of the processings described as automatically performed ones may be manually performed, or all or a part of the processings described as manually performed ones may be also automatically performed by known methods.

In addition, the processing procedures, the control procedures, the specific names, the information including registered data of various processings and parameters such as retrieval conditions, the screen examples, and the database configuration shown in the description and the drawings may be arbitrarily modified unless otherwise specified.

The components of the central control device A and the mobile communication terminal B shown in the figures are functionally conceptual and therefore not be physically configured as shown in the figures.

For example, for the operational functions provided in each device, in particular, for the operational functions performed in the control unit, all or part thereof may be implemented by the CPU (Central Processing Unit) and programs interpreted and executed in the CPU, or may be implemented by wired-logic hardware. The program is recorded in a non-transitory tangible computer-readable recording medium including programmed instructions for making an information processing apparatus execute the feeding management method according to the present invention, and is mechanically read as needed by the central control device A. More specifically, computer programs to give instructions to the CPU in cooperation with the OS (operating system) to perform various processes are recorded in the storage unit A2 and the storage unit B2 such as ROM or a HDD (hard disk drive). The computer programs are executed by being loaded to RAM, and form the control unit in cooperation with the CPU.

The computer programs may be stored in an application program server connected to the central control device A via an arbitrary network, and all or part thereof can be downloaded as necessary.

The program (feeding management program) according to the present invention may be stored in the non-transitory tangible computer-readable recording medium, or can be configured as a program product. The "recording medium" mentioned here includes any "portable physical medium" such as a memory card, a USB (universal serial bus) memory, an SD (secure digital) card, a flexible disk, a magneto-optical disc, ROM, EPROM (erasable programmable read only memory), EEPROM (registered trademark) (electronically erasable and programmable read only memory), CD-ROM (compact disk read only memory), MO (magneto-optical disk), DVD (digital versatile disk), and Blu-ray (registered trademark) Disc.

The "program" mentioned here is a data processing method described in an arbitrary language or description method, and therefore any form such as a source code and a binary code is acceptable. The "program" is not necessarily limited to a program configured as a single unit, and, therefore, includes those dispersively configured as a plurality of modules and libraries and those in which the function of the program is achieved in cooperation with separate programs represented as OS (operating system). Any known configuration and procedures can be used as a specific configuration and reading procedure to read a recording medium by each apparatus shown in the embodiments, an installation procedure after the reading, and the like.

The various databases and the like stored in the storage unit A2 and the storage unit B2 are storage units such as a memory device such as RAM and ROM, a fixed disk drive such as a hard disk, a flexible disk, or an optical disc. The storage unit A2 and the storage unit B2 store therein various programs, tables, databases, files for Web (World Wide Web) pages, and the like used to perform various processes and to provide Web sites.

The central control device A may be configured as an information processing apparatus such as known personal computer and work station, or may be configured as the information processing apparatus connected to an arbitrary peripheral device. The central control device A may be provided by installing software (including the programs and the data, etc.) to cause the information processing apparatus to implement the feeding management method according to the present invention.

Furthermore, a specific configuration of dispersion or integration of the apparatuses is not limited to the shown one. The apparatuses can be configured by functionally or physically dispersing or integrating all or part of the apparatuses in arbitrary units according to various types of additions or the like or according to functional loads. In other words, the embodiments may be implemented in arbitrary combinations thereof or an embodiment may be selectively implemented.

Embodiments of Acquiring Unit A1a and Evaluating Unit A1b.

The acquiring unit A1a may acquire blood data including at least one value of concentration values of the 25 kinds of amino acids and measurement values of the 13 kinds of blood chemistry parameters (one or two or more values arbitrarily selected from concentration values of the 25 kinds of amino acids and measurement values of the 13 kinds of blood chemistry parameters) contained in blood (for example, including plasma and serum) extracted from a dairy cow that is an evaluation target before parturition (for example, a certain period earlier, before an expected date of parturition).

For example, the blood data may be measured by a company or other organization that performs measurements for the concentration values and the measurement values. The blood data may be obtained, for example, by performing measurements for the concentration values and the measurement values from the blood extracted from an evaluation target before parturition through the use of the following measuring method of (A), (B), or (C). Here, the unit of concentration value may be molar concentration, weight concentration, enzyme activity, or one obtained by addition, subtraction, multiplication, and division of any constant with these concentrations.

(A) Plasma is separated from blood by centrifuging the collected blood sample. All plasma samples are frozen and stored at −80° C. until the concentration value is measured. At the time of measuring the concentration value, acetonitrile is added to perform a protein removal treatment, pre-column derivatization is then performed using a labeled reagent (3-aminopyridyl-N-hydroxysuccinimidyl carbamate), and the concentration value is analyzed by liquid chromatograph mass spectrometer (LC/MS) (see International Publication WO 2003/069328 and International Publication WO 2005/116629).

(B) Plasma is separated from blood by centrifuging the collected blood sample. All plasma samples are frozen and stored at −80° C. until the concentration value is measured. At the time of measuring the concentration value, sulfosalicylic acid is added to perform a protein removal treatment, and the concentration value is analyzed by an amino acid analyzer based on post-column derivatization using a ninhydrin reagent.

(C) Blood cell separation is performed on the collected blood sample by using a membrane, MEMS (Micro Electro Mechanical Systems) technology, or the principle of centrifugation, whereby plasma or serum is separated from the blood. A plasma or serum sample the concentration value of which is not measured immediately after obtaining the plasma or the serum is frozen and stored at −80° C. until the concentration value is measured. At the time of measuring the concentration value, a molecule that reacts with or binds to a target amino acid or biochemistry, such as an enzyme or an aptamer, and the like are used to perform quantitative analysis and the like on an increasing or decreasing substance or a spectroscopic value by substrate recognition, whereby the concentration value is analyzed.

The evaluating unit A1b may evaluate (predict/estimate) the state of ketosis in postpartum dairy cows to be evaluated (for example, after the passage of a certain period following the date of parturition) by using (i) at least one value of the concentration values of the 25 kinds of amino acids and the measurement values of the 13 kinds of blood chemistry parameters included in the blood data, or (ii) a value of a formula calculated using the at least one value of the concentration values of the 25 kinds of amino acids and the measurement values of the 13 kinds of blood chemistry parameters and the formula including an explanatory variable to be substituted with the at least one value. Before this evaluation is performed, data such as missing values and outliers may be removed from the blood data. Thus, highly reliable information on the state of ketosis in postpartum dairy cows can be provided before parturition.

The state of ketosis in postpartum dairy cows for the subject to be evaluated may be evaluated by calculating a value of a formula using (i) the at least one value of the concentration values of the 25 kinds of amino acids and the measurement values of the 13 kinds of blood chemistry parameters and (ii) the formula including an explanatory variable to be substituted with the at least one value. The explanatory variable to be substituted with the concentration value or the measurement value may be substituted with a value obtained by converting the concentration value or the measurement value by the later-described method.

When the state of ketosis in postpartum dairy cows is evaluated, for example, a value related to the factors listed below having an impact on the development of ketosis may further be used in addition to the at least one value of the concentration values of the 25 kinds of amino acids and the measurement values of the 13 kinds of blood chemistry parameters. For example, an explanatory variable to be substituted with a value related to the factors listed below having an impact on the development of ketosis may further be included in the formula in addition to the explanatory variable to be substituted with the at least one value of the concentration values of the 25 kinds of amino acids and the measurement values of the 13 kinds of blood chemistry parameters.

parity term for indicating parous cow or nulliparous cow (binary variable); and body weight, food intake, body condition score (BCS), air temperature, humidity, breeding density, and season The concentration value or the value of the formula may be converted, for example, by the methods listed below, and the state of ketosis in postpartum dairy cows for the subject to be evaluated may be evaluated using the converted value.

The concentration value or the value of the formula may be converted such that a possible range of the concentration value or the value of the formula falls within a predetermined range (for example, the range from 0.0 to 1.0, the range from 0.0 to 10.0, the range from 0.0 to 100.0, or the range from −10.0 to 10.0), for example, by addition, subtraction, multiplication, and division of any given value with the concentration value or the value of the formula, by conversion of the concentration value or the value of the formula by a predetermined conversion method (for example, exponential transformation, logarithm transformation, angular transformation, square root transformation, probit transformation, reciprocal transformation, Box-Cox transformation, or power transformation), or by performing a combination of these computations on the concentration value or the value of the formula. For example, a value of an exponential function with the concentration value or the value of the formula as an exponent and Napier constant as the base may be further calculated (specifically, a value of $p/(1-p)$ where a natural logarithm $\ln(p/(1-p))$ is equal to the concentration value or the value of the formula when the probability p that the state of ketosis in postpartum dairy cows has the predetermined state (for example, the state where the blood concentration of BHBA exceeds the criterion value) is defined), and the value (specifically, the value of the probability p) may be further calculated by dividing the calculated value of the exponential function by the sum of 1 and the value of the exponential function.

The concentration value or the value of the formula may be converted such that the converted value is a particular value when a particular condition is met. For example, the concentration value or the value of the formula may be converted such that the converted value is 5.0 when the sensitivity is 95% and the converted value is 8.0 when the sensitivity is 80%.

As for the concentration value, for each amino acid, after normally distributing the concentration distribution, the concentration value may be standardized with a mean of 50 and a standard deviation of 10. As for the value of the formula, the value of the formula may be standardized with a mean of 50 and a standard deviation of 10.

These conversions may be applied to the measurement value.

If the at least one value of the concentration values of the 25 kinds of amino acids and the measurement values of the 13 kinds of blood chemistry parameters or the value of the formula is lower than a predetermined value (e.g., mean±1SD, 2SD, 3SD, N quantile, N percentile, or a cutoff value the clinical significance of which is recognized) or is equal to or lower than the predetermined value or is equal to or higher than the predetermined value or is higher than the predetermined value, the state of ketosis in postpartum dairy cows for the subject to be evaluated may be evaluated. In this case, instead of the concentration value or the value of the formula itself, a standard score may be used. For example, if the standard score is lower than the mean −2SD (when the standard score<30) or if the standard score is higher than the mean+2SD (when the standard score>70), the state of ketosis in postpartum dairy cows for the subject to be evaluated may be evaluated.

The risk (possibility) that the subject to be evaluated develops ketosis after parturition may be qualitatively evaluated. Specifically, the subject may be classified into any one of a plurality of categories defined at least considering the risk of developing ketosis after parturition using (i) the at least one value of the concentration values of the 25 kinds of amino acids and the measurement values of the 13 kinds of blood chemistry parameters and (ii) one or more preset thresholds or using (i) the at least one value, (ii) the formula including the explanatory variable to be substituted with the at least one value, and (iii) one or more preset thresholds. The categories may include (i) a category to which a subject with a high risk of developing ketosis after parturition (for example, a subject having the blood concentration of BHBA after parturition equal to or higher than the criterion value (for example, 1200 μmol/l)) belongs and (ii) a category to which a subject with a low risk of developing ketosis after parturition (for example, a subject having the blood concentration of BHBA after parturition lower than the criterion value (for example, 1200 μmol/l)) belongs. The categories may include (i) the category to which a subject with a high risk of developing ketosis after parturition belongs, (ii) the category to which a subject with a low risk of developing ketosis after parturition belongs, and (iii) a category to which a subject with an intermediate risk of developing ketosis after parturition belongs.

For example, a blood concentration value of BHBA in blood of the subject to be evaluated after parturition may be estimated using (i) the at least one value of the concentration values of the 25 kinds of amino acids and the measurement values of the 13 kinds of blood chemistry parameters and (ii) the one or more preset thresholds or using (i) the at least one value, (ii) the formula including the explanatory variable to be substituted with the at least one value, and (iii) the one or more preset thresholds.

The concentration value, the measurement value, or the value of the formula may be converted by the predetermined method, and the subject to be evaluated may be classified into any one of the categories using the converted value.

As for the formula used for the evaluation, the form of the formula is not specifically designated, however, for example, may be the following forms.

- linear model such as multiple regression equation, linear discriminant, principal component analysis, and canonical discriminant analysis that are based on the least-squares method;
- generalized linear model such as logistic regression and Cox regression that are based on the maximum likelihood method;
- generalized linear mixed model considering random effects due to individual differences, facility differences, and other factors in addition to the generalized linear model
- expression generated by cluster analysis, such as the K-means method and hierarchical cluster analysis;
- expression generated on the basis of the Bayesian statistics such as the Markov chain Monte Carlo (MCMC), the Bayesian network, and the hierarchical Bayesian method;
- expression generated by class classification such as support vector machine and decision tree;
- expression generated by a method such as fractional expression that does not belong to the above-cited categories; and
- expression represented as, for example, the summation of expressions of different forms Example 1

In an ordinary dairy firm, a total of 686 blood samples were collected from a total of 343 Holstein cows on the 21st day before the expected date of the parturition and on the 7th day after parturition. The 343 cows include parous cow having an experience of parturition in addition to the present one (282) and nulliparous cow having no experience of parturition other than the present parturition (61).

The blood samples collected on the 21st day before the expected date of the parturition were measured to determine the blood concentrations of the 25 kinds of amino acids (Ala, Arg, Asn, Asp, BCAA, Cit, Cys, Glu, Gln, Gly, His, Ile, Leu, Lys, Met, 3MeHis, Orn, Phe, Pro, Ser, Tau, Thr, Trp, Tyr, and Val). The blood samples collected on the 7th day after parturition were measured to determine the blood concentration of BHBA. The blood concentrations of the amino acids were measured by the above-mentioned measuring method (A).

First, on the basis of the BHBA value on the 7th day after parturition, the 343 cows were classified into the following two groups: a healthy group (BHBA<1200 μmol/l, including 238 parous cows and 56 nulliparouscows); and a ketosis group (BHBA≥1200 μmol/l, including 44 parous cows and 5 nulliparous cows). Then, an index that maximizes the discrimination ability for discriminating between the two groups was searched for by the logistic analysis (explanatory variable coverage method according to the minimum AIC) using two amino acids in the blood collected on the 21st day before the expected date of the parturition, and the searched formulae were evaluated using the AUC of the ROC curve.

The index formulae having an ROC_AUC of 0.67 or higher are listed in [11. Formula with two amino acid variables] detailed later. In [11. Formula with two amino acid variables], an ROC_AUC value, a value obtained by logit converting the value of an index formula, and the index formula are enumerated in this order (the same applies hereafter). The coefficients and the constants enumerated in [11. Formula with two amino acid variables] may be any values (the same applies hereafter).

Furthermore, index formulae were searched and evaluated in the same way using three to six amino acids in the blood collected on the 21st day before the expected date of the parturition. Index formulae having a high goodness-of-fit are listed in [12. Formula with three amino acid variables], [13. Formula with four amino acid variables], [14. Formula with five amino acid variables], and [15. Formula with six amino acid variables] detailed later.

It was proved that the index formulae in [11. Formula with two amino acid variables] to [15. Formula with six amino acid variables] have a higher ROC_AUC than that in the case reported by the non-patent literature (P. A. Ospina, D. V. Nydam, T. Stokol, and T. R. Overton, Evaluation of nonesterigied fatty acids and β-hydroxybutyrate in transition dairy cattle in the northeastern United States: Clinicalthresholds for prediction of clinical diseases. J. Dairy. Sci. 93: 546-554 (2010)) where only NEFA is used as the explanatory variable (ROC_AUC=0.665), and therefore the index formulae are valuable for evaluating the state of postpartum disease in the perinatal period (ketosis) (more specifically, the index formulae are valuable for evaluating whether the blood concentration of BHBA after parturition is lower than 1200 μmol/l or is equal to 1200 μmol/l or higher.)

Example 2

The blood samples used in Example 1 were used. The blood samples collected on the 21st day before the expected date of the parturition were measured to determine the concentration values of the 13 kinds of blood chemistry parameters (ALB (g/dl), ALT (IU/l), AST (IU/l), BHBA (μmol/l), BUN (mg/dl), Ca (mg/dl), gGTP (IU/l), Glc (mg/dl), NEFA (μEq/l), T-Bil (mg/dl), TCHO (mg/dl), TG (mg/dl), TP (g/dl)). The blood samples collected on the 7th day after parturition were measured to determine the blood concentration of BHBA. The concentration values of the blood chemistry parameters were measured by the abovementioned measuring method (C).

Similarly to Example 1, the 343 cows were classified into the following two groups: a healthy group (BHBA<1200 μmol/l, including 238 parous cows and 56 nulliparous cows); and a ketosis group (BHBA≥1200 μmol/l, including 44 parous cows and 5 nulliparous cows). Then, an index that maximizes the discrimination ability for discriminating between the two groups was searched for by the logistic analysis (explanatory variable coverage method according to the minimum AIC) using two blood chemistry parameters in the blood collected on the 21st day before the expected date of the parturition, and the searched formulae were evaluated using the AUC of the ROC curve.

The index formulae having an ROC_AUC of 0.7 or higher are listed in [21. Formula with two biochemistry variables] detailed later. Furthermore, index formulae were searched and evaluated in the same way using three to six blood chemistry parameters in the blood collected on the 21st day before the expected date of the parturition. Index formulae having a high goodness-of-fit are listed in [22. Formula with three biochemistry variables], [23. Formula with four biochemistry variables], [24. Formula with five biochemistry variables], and [25. Formula with six biochemistry variables] detailed later.

It was proved that the index formulae in [21. Formula with two biochemistry variables] to [25. Formula with six biochemistry variables] have a higher ROC_AUC than that in the case reported by the above-mentioned non-patent literature where only NEFA is used as the explanatory variable (ROC_AUC=0.665), and therefore the index formulae are valuable for evaluating the state of postpartum disease in the perinatal period (ketosis) (more specifically, the index formulae are valuable for evaluating whether the blood concentration of BHBA after parturition is lower than 1200 μmol/l or is equal to 1200 μmol/l or higher.)

Example 3

The blood samples used in Example 1 were used. The blood samples collected on the 21st day before the expected date of the parturition were measured to determine the blood concentrations of the 25 kinds of amino acids and the concentration values of the 13 kinds of blood chemistry parameters. The blood samples collected on the 7th day after parturition were measured to determine the blood concentration of BHBA. The blood concentrations of the amino acids were measured by the above-mentioned measuring method (A). The concentration values of the blood chemistry parameters were measured by the above-mentioned measuring method (C).

Similarly to Example 1, the 343 cows were classified into the following two groups: a healthy group; and a ketosis group. Then, an index that maximizes the discrimination ability for discriminating between the two groups was searched for by the logistic analysis (explanatory variable coverage method according to the minimum AIC) using a combination of amino acid and biochemistry (arbitrarily selected two substances from the 38 substances including the 25 kinds of amino acids and the 13 kinds of blood chemistry parameters) in the blood collected on the 21st day before the expected date of the parturition, and the searched formulae were evaluated using the AUC of the ROC curve.

The index formulae having an ROC_AUC of 0.7 or higher are listed in [31. Formula with two amino acid+biochemistry variables] detailed later. Furthermore, index formulae were searched and evaluated in the same way using combinations of amino acids and blood chemistry parameters (arbitrarily selected three to six substances from the 38 variables including the 25 kinds of amino acids and the 13 kinds of blood chemistry parameters) in the blood collected on the 21st day before the expected date of the parturition. Index formulae having a high goodness-of-fit are listed in [32. Formula with three amino acid+biochemistry variables], [33. Formula with four amino acid+biochemistry variables], [34. Formula with five amino acid+biochemistry variables], and [35. Formula with six amino acid+biochemistry variables] detailed later.

It was proved that the index formulae in [31. Formula with two amino acid+biochemistry variables] to [35. Formula with six amino acid+biochemistry variables] have a higher ROC_AUC than that in the case reported by the above-mentioned non-patent literature where only NEFA is used as the explanatory variable (ROC_AUC=0.665), and therefore the index formulae are valuable for evaluating the state of postpartum disease in the perinatal period (ketosis) (more specifically, the index formulae are valuable for evaluating whether the blood concentration of BHBA after parturition is lower than 1200 μmol/l or is equal to 1200 μmol/l or higher.)

Example 4

Similarly, index formulae were searched and evaluated in the same way further using a parity term for indicating parous cow or nulliparous cow (a binary variable (for example, it is an explanatory variable to be substituted with 1 or 0, 1 indicating parous cow, 0 indicating nulliparous cow)) in addition to amino acids and blood chemistry parameters in the blood collected on the 21st day before the expected date of the parturition.

Index formulae with an improved ROC_AUC by an added parity term to two to six amino acid variables are listed in [401. Formula (with two amino acid variables) with improved diagnostic accuracy by added parity term] to [405. Formula (with six amino acid variables) with improved diagnostic accuracy by added parity term] detailed later. Note that [401. Formula (with two amino acid variables) with improved diagnostic accuracy by added parity term] omits a parity term (Birth variable) (the same applies hereafter).

Index formulae with an improved ROC_AUC by an added parity term to two to six biochemistry variables are listed in [406. Formula (with two biochemistry variables) with improved diagnostic accuracy by added parity term] to [410. Formula (with six biochemistry variables) with improved diagnostic accuracy by added parity term] detailed later.

Index formulae with an improved ROC_AUC by an added combination of amino acids and blood chemistry parameters (arbitrarily selected two to six substances from the 38 substances including the 25 kinds of amino acids and the 13 kinds of blood chemistry parameters) with a parity term are listed in [411. Formula (with two amino acid+biochemistry variables) with improved diagnostic accuracy by added parity term] to [415. Formula (with six amino acid+biochemistry variables) with improved diagnostic accuracy by added parity term] detailed later.

Example 5

The blood samples used in Example 1 were used. The blood samples collected on the 21st day before the expected date of the parturition were measured to determine the blood concentrations of the 25 kinds of amino acids and the concentration values of the 13 kinds of blood chemistry parameters. The blood samples collected on the 7th day after parturition were measured to determine the blood concentration of BHBA. The blood concentrations of the amino acids were measured by the above-mentioned measuring method (A). The concentration values of the blood chemistry parameters were measured by the above-mentioned measuring method (C).

Similarly to Example 1, the 343 cows were classified into the following two groups: a healthy group; and a ketosis group. Then, an index that maximizes the discrimination ability for discriminating between the two groups was searched for by the logistic analysis (explanatory variable coverage method according to the minimum AIC) using a combination of amino acid and biochemistry (arbitrarily selected one substance from the 38 substances including the 25 kinds of amino acids and the 13 kinds of blood chemistry parameters) in the blood collected on the 21st day before the expected date of the parturition, and the searched formulae were evaluated using the AUC of the ROC curve.

It was proved that the index formula including only ALB as an explanatory variable (more specifically, "ALB+1" (the coefficients and the constants may be any values)) has a ROC_AUC of 0.697 higher than that in the case reported by the above-mentioned non-patent literature where only NEFA is used as explanatory variable (ROC_AUC=0.665), and therefore the index formula is valuable for evaluating the state of postpartum disease in the perinatal period (ketosis) (more specifically, the index formula is valuable for evaluating whether the blood concentration of BHBA after parturition is lower than 1200 μmol/l or is equal to 1200 μmol/l or higher.) The value obtained by logit converting the value of the index formula was 261.935.

[11. Formula with Two Amino Acid Variables]
0.687, 269.675, 1+His+Orn; 0.672, 270.428, 1+His+Asn

[12. Formula with Three Amino Acid Variables]
0.723, 264.542, 1+His+Asn+Orn; 0.705, 270.498, 1+His+Ala+Orn; 0.7 03, 267.279, 1+His+Orn+Phe; 0.702, 269.285, 1+His+Orn+Cys

[13. Formula with Four Amino Acid Variables]
0.735, 264.504, 1+His+Asn+Orn+Ile; 0.732, 263.944, 1+His+Asn+Thr+Orn; 0.732, 265.541, 1+His+Asn+Orn+Leu; 0.730, 265.947, 1+His+As n+Orn+BCAA; 0.728, 264.813, 1+His+Asn+Ser+Orn; 0.728, 264.782, 1+His+Asn+Gly+Orn; 0.728, 264.931, 1+His+Asn+Orn+Cys; 0.726, 266.3 07, 1+His+Asn+Pro+Orn; 0.726, 263.377, 1+His+Asn+Asp+Orn; 0.724, 266.291, 1+His+Asn+3MeHis+Orn; 0.724, 266.277, 1+His+Asn+Gln+Or n; 0.724, 266.300, 1+His+Asn+Orn+Met; 0.724, 265.906, 1+His+Asn+C it+Orn; 0.723, 266.489, 1+His+Asn+Orn+Val; 0.723, 266.272, 1+His+Asn+Tau+Orn; 0.722, 266.541, 1+His+Asn+Ala+Orn; 0.722, 266.542, 1+His+Asn+Orn+Lys; 0.722, 266.122, 1+His+Asn+Arg+Orn; 0.722, 266. 536, 1+His+Asn+Orn+Tyr; 0.721, 266.378, 1+His+Asn+Orn+Trp; 0.721, 266.490, 1+His+Asn+Glu+Orn; 0.721, 265.091, 1+His+Asn+Orn+Phe; 0. 719, 265.976, 1+His+Asn+Ser+Arg; 0.716, 262.212, 1+His+Asn+Gly+A sp; 0.716, 267.350, 1+His+Orn+Leu+Phe; 0.715, 260.861, 1+His+Asn+Ser+Asp; 0.714, 271.453, 1+His+Gly+Ala+Orn; 0.714, 271.120, 1+His+3MeHis+Ala+Orn; 0.713, 266.685, 1+His+Asn+Arg+Gly; 0.712, 268.0 02, 1+His+Orn+Ile+Phe; 0.712, 268.333, 1+His+Ser+Orn+Phe; 0.710, 270.200, 1+His+Gln+Orn+Cys; 0.710, 266.501, 1+His+Orn+Cys+Phe; 0. 710, 268.430, 1+His+Gly+Orn+Phe; 0.710, 267.764, 1+His+Tau+Orn+P he; 0.709, 268.397, 1+His+Gln+Orn+Phe; 0.709, 267.492, 1+His+Asp+Orn+Phe; 0.709, 268.445, 1+His+Orn+Phe+BCAA; 0.709, 268.741, 1+Hi s+Ala+Orn+Phe; 0.709, 268.248, 1+His+Asp+Orn+Cys; 0.709, 270.176, 1+His+Ala+Orn+Cys; 0.708, 269.420, 1+His+Arg+Orn+Cys; 0.707, 269. 469, 1+His+Orn+Cys+Tyr; 0.707, 271.883, 1+His+Tau+Ala+Orn; 0.707, 267.914, 1+His+3MeHis+Orn+Phe; 0.707, 272.015, 1+His+Ser+Ala+Or n; 0.707, 264.324, 1+Asn+Ser+Asp+Thr; 0.706, 268.898, 1+His+Orn+M et+Phe; 0.706, 268.156, 1+His+Asn+Arg+Ile; 0.706, 270.155, 1+Asn+Thr+Orn+Ile; 0.705, 270.958, 1+His+Tau+Orn+Cys; 0.705, 272.396, 1+His+Ala+Orn+Ile; 0.705, 272.314, 1+His+Cit+Ala+Orn; 0.705, 268. 762, 1+His+Asn+3MeHis+Arg; 0.705, 272.462, 1+His+Ala+Orn+Leu; 0. 705, 272.498, 1+His+Ala+Orn+Met; 0.705, 269.197, 1+His+Thr+Orn+P he; 0.705, 272.494, 1+His+Glu+Ala+Orn; 0.705, 272.493, 1+His+Ala+Orn+BCAA; 0.705, 271.636, 1+His+Arg+Ala+Orn; 0.705, 269.106, 1+Hi s+Cit+Orn+Phe; 0.705, 270.492, 1+His+Asn+Lys+Ile; 0.704, 267.405, 1+His+Asn+Gly+Cit; 0.704, 272.451, 1+His+Thr+Ala+Orn; 0.704, 270. 789, 1+His+3MeHis+Orn+Cys; 0.704, 269.210, 1+His+Glu+Orn+Phe; 0. 704, 271.060, 1+His+Cit+Orn+Cys; 0.704, 270.992, 1+His+Gly+Orn+C ys; 0.704, 272.011, 1+His+Gln+Ala+Orn; 0.704, 266.672, 1+His+Asn+Arg+Asp; 0.704, 271.027, 1+His+Glu+Orn+Cys; 0.704, 271.444, 1+His+Ala+Orn+Tyr; 0.704, 272.326, 1+His+Ala+Orn+Val; 0.704, 269.149, 1+His+Orn+Val+Phe; 0.703, 270.942, 1+His+Orn+Cys+Met; 0.703, 269. 203, 1+His+Pro+Orn+Phe; 0.703, 265.711, 1+His+Asn+3MeHis+Asp; 0. 703, 269.572, 1+His+Asn+Gly+Lys; 0.703, 272.725, 1+Asn+Orn+Cys+I le; 0.703, 269.279, 1+His+Orn+Tyr+Phe; 0.703, 272.332, 1+His+Ala+Pro+Orn; 0.703, 269.277, 1+His+Orn+Lys+Phe; 0.702, 271.252, 1+His+Ser+Orn+Cys; 0.702, 270.495, 1+His+Pro+Orn+Cys; 0.702, 269.249, 1+His+Asn+Arg+Met; 0.702, 271.025, 1+His+Orn+Cys+Val; 0.702, 271. 703, 1+His+Gln+Gly+Orn; 0.702, 266.722, 1+His+Asn+Asp+Thr; 0.702, 271.284, 1+His+Orn+Cys+Leu; 0.702, 271.280, 1+His+Orn+Cys+Ile; 0. 701, 269.319, 1+His+Asn+Val+BCAA; 0.701, 268.037, 1+His+Asn+Arg+Cys; 0.701, 271.226, 1+His+Orn+Tyr+Leu; 0.701, 269.884, 1+His+Orn+Cys+Lys; 0.701, 269.040, 1+His+Asn+Thr+Lys; 0.701, 266.860, 1+Hi s+Asn+Asp+Lys; 0.701, 268.655, 1+His+3MeHis+Asp+Orn; 0.701, 268. 216, 1+His+Asn+Arg+Thr; 0.701, 271.330, 1+His+Ala+Orn+Trp; 0.701, 269.160, 1+His+Arg+Orn+Phe; 0.701, 270.912, 1+His+Thr+Orn+Cys; 0. 701, 271.209, 1+His+Orn+Cys+BCAA; 0.701, 272.252, 1+Asn+Asp+Orn+Ile; 0.701, 268.848, 1+His+Orn+Phe+Trp; 0.701, 271.956, 1+Asn+Ser+Arg+Ile; 0.701, 272.447, 1+Asn+Ser+Orn+Ile; 0.701, 269.827, 1+Hi s+Tau+Asp+Orn; 0.700, 270.470, 1+His+Asp+Ala+Orn; 0.700, 270.716, 1+Asn+3MeHis+Thr+Orn; 0.700, 270.363, 1+His+Asn+Thr+Trp; 0.700, 272.229, 1+His+Gly+Pro+Orn

[14. Formula with Five Amino Acid Variables]
0.746, 262.572, 1+His+Asn+Orn+Ile+Phe; 0.743, 264.174, 1+His+Asn+Orn+Val+BCAA; 0.741, 263.058, 1+His+Asn+Gly+Thr+Orn; 0.741, 264. 488, 1+His+Asn+Gly+Orn+Ile; 0.741, 264.806, 1+His+Asn+Orn+Cys+I le; 0.741, 258.537, 1+His+Asn+Ser+Arg+Asp; 0.741, 262.801, 1+His+Asn+Asp+Orn+Ile; 0.741, 264.092, 1+His+Asn+Arg+Val+BCAA; 0.740, 263.924, 1+His+Asn+Orn+Leu+Phe; 0.739, 263.622, 1+His+Asn+Thr+O rn+Phe; 0.739, 262.902, 1+His+Asn+Asp+Thr+Orn; 0.739, 264.814, 1+His+Asn+Thr+Orn+Ile; 0.739, 264.995, 1+His+Asn+Thr+Orn+Trp; 0.7 39, 264.923, 1+His+Asn+Thr+Orn+Cys; 0.739, 259.042, 1+His+Asn+Se r+Asp+Orn; 0.738, 263.969, 1+His+Asn+Arg+Val+Ile; 0.738, 264.035, 1+His+Asn+Ser+Thr+Orn; 0.738, 266.053, 1+His+Asn+Orn+Cys+Leu; 0. 737, 265.999, 1+His+Asn+Orn+Val+Leu; 0.737, 264.916, 1+His+Asn+G ly+Orn+Leu; 0.737, 265.282, 1+His+Asn+Ser+Orn+Ile; 0.737, 265.39 8, 1+His+Asn+Arg+Orn+Ile; 0.737, 264.717, 1+His+Asn+Orn+Val+Il e; 0.737, 265.937, 1+His+Asn+Orn+Ile+Trp; 0.737, 266.494, 1+His+A sn+Pro+Orn+Ile; 0.736, 265.326, 1+His+Asn+Gly+Orn+BCAA; 0.736, 2 65.925, 1+His+Asn+Ser+Orn+Leu; 0.736, 265.408, 1+His+Asn+3MeHis+Thr+Orn; 0.736, 266.391, 1+His+Asn+Ala+Orn+Ile; 0.736, 267.042, 1+His+Asn+3MeHis+Orn+Leu; 0.736, 266.258, 1+His+Asn+3MeHis+Orn+Ile; 0.736, 266.504, 1+His+Asn+Orn+Met+Ile; 0.736, 265.064, 1+His+Asn+Orn+Phe+BCAA; 0.735, 265.781, 1+His+Asn+Orn+Tyr+Ile; 0.735, 261.542, 1+His+Asn+Gly+Asp+Orn; 0.735, 266.504, 1+His+Asn+Glu+Orn+Ile; 0.735, 265.740, 1+His+Asn+Gln+Thr+Orn; 0.735, 265.519, 1+His+Asn+Ser+Orn+Cys; 0.735, 266.443, 1+His+Asn+Gln+Orn+Ile; 0.735, 265.726, 1+His+Asn+Thr+Orn+Leu; 0.734, 265.735, 1+His+Asn+Thr+Orn+Val; 0.734, 266.209, 1+His+Asn+Ser+Gln+Orn; 0.734, 266.464, 1+His+Asn+Tau+Orn+Ile; 0.734, 265.585, 1+His+Asn+Gln+Gly+Orn; 0.734, 266.189, 1+His+Asn+Ser+Orn+BCAA; 0.734, 266.329, 1+His+Asn+Orn+Cys+BCAA; 0.734, 265.828, 1+His+Asn+Thr+Orn+Met; 0.734, 266.156, 1+His+Asn+Orn+Lys+Ile; 0.734, 267.149, 1+His+Asn+Orn+Leu+Trp; 0.734, 266.954, 1+His+Asn+Arg+Orn+Leu; 0.734, 260.995, 1+His+Asn+Gly+Asp+Thr; 0.734, 267.226, 1+His+Asn+Orn+Leu+BCAA; 0.734, 266.463, 1+His+Asn+Orn+Ile+Leu; 0.734, 264.475, 1+His+Asn+Asp+Orn+Leu; 0.734, 267.483, 1+His+Asn+3MeHis+Orn+BCAA; 0.733, 266.155, 1+His+Asn+Gly+Orn+Val; 0.733, 267.486, 1+His+Asn+Gln+Orn+Leu; 0.733, 265.812, 1+His+Asn+Thr+Orn+Tyr; 0.733, 265.944, 1+His+Asn+Glu+Thr+Orn; 0.733, 265.854, 1+His+Asn+Thr+Pro+Orn; 0.732, 265.912, 1+His+Asn+Thr+Orn+BCAA; 0.732, 267.214, 1+His+Asn+Orn+Tyr+Leu; 0.732, 267.518, 1+His+Asn+Pro+Orn+Leu; 0.732, 265.943, 1+His+Asn+Tau+Thr+Orn; 0.732, 265.944, 1+His+Asn+Thr+Ala+Orn; 0.732, 267.541, 1+His+Asn+Ala+Orn+Leu; 0.732, 267.515, 1+His+Asn+Tau+Orn+Leu; 0.732, 264.028, 1+His+Asn+3MeHis+Asp+Orn; 0.732, 265.610, 1+His+Asn+Cit+Thr+Orn; 0.732, 265.522, 1+His+Asn+Gly+Orn+Cys; 0.732, 265.568, 1+His+Asn+Orn+Ile+BCAA; 0.732, 265.729, 1+His+Asn+Cit+Orn+Ile; 0.732, 267.486, 1+His+Asn+Orn+Met+Leu; 0.732, 266.267, 1+His+Asn+Cit+Orn+Cys; 0.732, 265.775, 1+His+Asn+Thr+Orn+Lys; 0.732, 267.536, 1+His+Asn+Glu+Orn+Leu; 0.732, 264.507, 1+His+Asn+Ser+Orn+Phe; 0.732, 267.392, 1+His+Asn+Orn+Lys+Leu; 0.732, 266.758, 1+His+Asn+Cit+Orn+Leu; 0.731, 266.516, 1+His+Asn+Tau+Gly+Orn; 0.731, 266.789, 1+His+Asn+Pro+Orn+Cys; 0.731, 265.163, 1+His+Asn+Ser+Arg+Orn; 0.731, 265.583, 1+His+Asn+Arg+Thr+Orn; 0.731, 267.848, 1+His+Asn+Orn+Met+BCAA; 0.731, 264.683, 1+His+Asn+Asp+Pro+Orn; 0.731, 266.707, 1+His+Asn+Ser+Ala+Orn; 0.731, 263.240, 1+His+Asn+Asp+Orn+Cys; 0.731, 266.539, 1+His+Asn+Tau+Ser+Orn; 0.731, 267.872, 1+His+Asn+Pro+Orn+BCAA; 0.731, 267.421, 1+His+Asn+Arg+Orn+BCAA; 0.731, 264.869, 1+His+Asn+Asp+Orn+BCAA; 0.731, 258.875, 1+His+Asn+Ser+Asp+Cit; 0.730, 266.517, 1+His+Asn+Gln+Orn+Cys; 0.730, 267.543, 1+His+Asn+Orn+Trp+BCAA; 0.730, 266.654, 1+His+Asn+Ser+Orn+Val; 0.730, 266.641, 1+His+Asn+Gly+Pro+Orn; 0.730, 262.744, 1+His+Asn+Asp+Val+Ile; 0.730, 266.842, 1+His+Asn+Tau+Orn+Cys; 0.730, 267.850, 1+His+Asn+Gln+Orn+BCAA; 0.730, 266.792, 1+His+Asn+Ser+Pro+Orn; 0.730, 265.738, 1+His+Asn+Gly+Cit+Orn; 0.730, 267.946, 1+His+Asn+Ala+Orn+BCAA; 0.729, 266.858, 1+His+Asn+Orn+Cys+Val; 0.729, 265.404, 1+His+Asn+Ser+Cit+Orn; 0.729, 266.225, 1+His+Asn+Arg+Gly+Ile; 0.729, 267.947, 1+His+Asn+Glu+Orn+BCAA; 0.729, 266.693, 1+His+Asn+Gly+Ala+Orn; 0.729, 266.774, 1+His+Asn+Gly+Orn+Lys; 0.729, 267.885, 1+His+Asn+Tau+Orn+BCAA; 0.729, 265.117, 1+His+Asn+Gly+Orn+Phe; 0.729, 266.181, 1+His+Asn+Arg+Orn+Cys; 0.729, 267.253, 1+His+Asn+Cit+Orn+BCAA; 0.729, 266.329, 1+His+Asn+Gly+Glu+Orn; 0.729, 266.797, 1+His+Asn+Ser+Orn+Met; 0.729, 266.256, 1+His+Asn+Ser+Arg+Ile; 0.729, 268.004, 1+His+Asn+Gln+Pro+Orn; 0.729, 267.745, 1+His+Asn+Orn+Tyr+BCAA; 0.728, 266.566, 1+His+Asn+Gly+Orn+Met; 0.728, 266.849, 1+His+Asn+3MeHis+Orn+Cys; 0.728, 266.812, 1+His+Asn+Ser+Orn+Lys; 0.728, 267.861, 1+His+Asn+3MeHis+Gln+Orn; 0.728, 267.753, 1+His+Asn+Arg+Pro+Orn; 0.728, 266.735, 1+His+Asn+Ser+Orn+Trp; 0.728, 266.762, 1+His+Asn+Gly+Orn+Trp; 0.728, 266.301, 1+His+Asn+Ser+Gly+Orn; 0.728, 266.809, 1+His+Asn+3MeHis+Ser+Orn; 0.728, 266.772, 1+His+Asn+Gly+Orn+Tyr; 0.728, 266.623, 1+His+Asn+Ser+Orn+Tyr; 0.728, 268.134, 1+His+Asn+3MeHis+Orn+Val; 0.728, 263.367, 1+His+Asn+Asp+Val+BCAA; 0.728, 267.654, 1+His+Gly+Orn+Leu+Phe; 0.728, 266.130, 1+His+Asn+Arg+Gly+Orn; 0.728, 266.931, 1+His+Asn+Ala+Orn+Cys; 0.728, 267.844, 1+His+Asn+Orn+Lys+BCAA; 0.728, 266.896, 1+His+Asn+Orn+Cys+Met; 0.728, 264.747, 1+His+Asn+Asp+Glu+Orn; 0.727, 268.291, 1+His+Asn+Pro+Orn+Val; 0.727, 265.139, 1+His+Asn+Orn+Cys+Phe; 0.727, 268.078, 1+His+Asn+3MeHis+Pro+Orn; 0.727, 266.671, 1+His+Asn+Glu+Orn+Cys; 0.727, 266.145, 1+His+3MeHis+Orn+Leu+Phe; 0.727, 264.949, 1+His+Asn+Asp+Orn+Met; 0.727, 265.910, 1+His+Asn+Arg+Ile+BCAA; 0.727, 267.973, 1+His+Asn+Tau+3MeHis+Orn; 0.727, 266.738, 1+His+Asn+3MeHis+Gly+Orn; 0.727, 266.888, 1+His+Ser+Asp+Orn+Phe; 0.727, 266.720, 1+His+Asn+Ser+Glu+Orn; 0.727, 268.108, 1+His+Asn+Tau+Pro+Orn; 0.727, 264.806, 1+His+Asn+Tau+Asp+Orn; 0.727, 266.308, 1+His+Asn+Orn+Met+Phe; 0.727, 266.612, 1+His+Asn+Orn+Tyr+Phe; 0.727, 267.531, 1+His+Asn+Arg+Orn+Met; 0.727, 266.896, 1+His+Asn+Orn+Cys+Tyr; 0.727, 266.615, 1+His+Asn+Orn+Val+Phe; 0.727, 267.990, 1+His+Asn+Gln+Orn+Met; 0.727, 264.981, 1+His+Asn+Asp+Cit+Orn; 0.727, 268.286, 1+His+Asn+Ala+Pro+Orn; 0.727, 268.041, 1+His+Asn+Tau+Orn+Met; 0.727, 268.300, 1+His+Asn+Pro+Orn+Lys; 0.727, 264.579, 1+His+Asn+Asp+Orn+Phe; 0.727, 266.687, 1+His+Asn+Pro+Orn+Phe; 0.726, 268.274, 1+His+Asn+Glu+Pro+Orn; 0.726, 268.011, 1+His+Asn+Tau+Gln+Orn; 0.726, 260.874, 1+His+Asn+Ser+Asp+Thr; 0.726, 268.137, 1+His+Asn+Pro+Orn+Trp; 0.726, 265.358, 1+His+Asn+Arg+Asp+Orn; 0.726, 267.234, 1+His+Orn+Val+Leu+Phe; 0.726, 266.896, 1+His+Asn+Orn+Cys+Lys; 0.726, 268.137, 1+His+Asn+Pro+Orn+Met; 0.726, 267.701, 1+His+Asn+3MeHis+Arg+Orn; 0.726, 263.032, 1+His+Asn+Arg+Gly+Asp; 0.726, 265.372, 1+His+Asn+Asp+Orn+Val; 0.726, 267.060, 1+His+Orn+Val+Phe+BCAA; 0.726, 267.416, 1+His+Asn+Cit+Pro+Orn; 0.726, 265.377, 1+His+Asn+Asp+Orn+Lys; 0.726, 265.184, 1+His+Asn+Asp+Orn+Tyr; 0.726, 266.759, 1+His+Asn+Orn+Cys+Trp; 0.726, 267.839, 1+His+Asn+Tau+Arg+Orn; 0.725, 268.112, 1+His+Asn+3MeHis+Orn+Met; 0.725, 261.976, 1+His+Asn+Gly+Asp+Cit; 0.725, 261.496, 1+His+Asn+Ser+Asp+Lys; 0.725, 266.389, 1+His+Asn+Ser+Arg+Thr; 0.725, 267.496, 1+His+Asn+3MeHis+Cit+Orn; 0.725, 260.778, 1+His+Asn+Ser+Asp+Phe; 0.725, 268.068, 1+His+Asn+Arg+Orn+Val; 0.725, 265.375, 1+His+Asn+Gln+Asp+Orn

[15. Formula with Six Amino Acid Variables]
0.758, 260.134, 1+His+Asn+Asp+Thr+Val+Ile; 0.758, 262.965, 1+His+Asn+Thr+Orn+Val+BCAA; 0.757, 260.870, 1+His+Asn+Orn+Val+Phe+BCAA; 0.755, 261.881, 1+His+Asn+Gly+Orn+Ile+Phe; 0.753, 260.987, 1+His+Asn+Arg+Asp+Val+Ile; 0.753, 257.843, 1+His+Asn+Ser+Asp+Thr+Orn; 0.753, 262.474, 1+His+Asn+Ser+Orn+Ile+Phe; 0.752, 260.302, 1+His+Asn+Gly+Asp+Orn+

Ile; 0.752, 261.350, 1+His+Asn+Asp+Orn+Val+BCAA; 0.752, 261.692, 1+His+Asn+Gly+Orn+Leu+Phe; 0.752, 263.083, 1+His+Asn+Thr+Orn+Val+Ile; 0.752, 263.546, 1+His+Asn+Gln+Gly+Thr+Orn; 0.752, 262.034, 1+His+Asn+Arg+Thr+Val+Ile; 0.752, 261.912, 1+His+Asn+Asp+Orn+Ile+Phe; 0.751, 263.997, 1+His+Asn+Arg+Orn+Val+BCAA; 0.751, 261.898, 1+His+Asn+Arg+Asp+Val+BCAA; 0.751, 259.640, 1+His+Asn+Gly+Asp+Thr+Orn; 0.751, 263.059, 1+His+Asn+Orn+Val+Ile+Phe; 0.751, 262.228, 1+His+Asn+Orn+Cys+Ile+Phe; 0.751, 262.417, 1+His+Asn+Thr+Orn+Ile+Phe; 0.750, 262.708, 1+His+Asn+Arg+Thr+Val+BCAA; 0.750, 261.282, 1+His+Asn+Asp+Thr+Val+BCAA; 0.750, 265.277, 1+His+Asn+Thr+Orn+Val+Leu; 0.750, 257.983, 1+His+Asn+Ser+Arg+Asp+Thr; 0.750, 262.552, 1+His+Asn+Asp+Orn+Cys+Ile; 0.750, 263.046, 1+His+Asn+Ser+Orn+Leu+Phe; 0.749, 264.293, 1+His+Asn+Ala+Orn+Ile+Phe; 0.749, 265.126, 1+His+Asn+Orn+Cys+Val+BCAA; 0.749, 261.296, 1+His+Asn+Asp+Orn+Val+Ile; 0.749, 265.170, 1+His+Asn+Gly+Orn+Cys+Ile; 0.749, 259.007, 1+His+Asn+Ser+Asp+Glu+Orn; 0.749, 262.924, 1+His+Asn+Gly+Orn+Phe+BCAA; 0.748, 264.236, 1+His+Asn+Orn+Ile+Phe+Trp; 0.748, 265.959, 1+His+Asn+Gly+Ala+Orn+Ile; 0.748, 264.377, 1+His+Asn+Orn+Met+Ile+Phe; 0.748, 262.460, 1+His+Asn+Ser+Thr+Orn+Phe; 0.748, 263.692, 1+His+Asn+Orn+Val+Leu+Phe; 0.748, 263.923, 1+His+Asn+Ser+Orn+Phe+BCAA; 0.748, 265.974, 1+His+Asn+Ala+Orn+Val+BCAA; 0.748, 263.956, 1+His+Asn+3MeHis+Orn+Leu+Phe; 0.748, 259.515, 1+His+Asn+Ser+Asp+Orn+Ile; 0.748, 258.828, 1+His+Asn+Ser+Arg+Asp+Ile; 0.748, 263.806, 1+His+Asn+Gly+Thr+Orn+Ile; 0.747, 263.011, 1+His+Asn+3MeHis+Asp+Thr+Orn; 0.747, 261.433, 1+His+Asn+Gly+Asp+Orn+Leu; 0.747, 262.593, 1+His+Asn+Asp+Thr+Ile+BCAA; 0.747, 264.112, 1+His+Asn+Orn+Ile+Phe+BCAA; 0.747, 263.870, 1+His+Asn+Cit+Orn+Ile+Phe; 0.747, 263.344, 1+His+Asn+3MeHis+Asp+Orn+Ile; 0.747, 263.724, 1+His+Asn+3MeHis+Orn+Ile+Phe; 0.747, 264.525, 1+His+Asn+Thr+Orn+Ile+BCAA; 0.747, 263.251, 1+His+Asn+Asp+Glu+Orn+Ile; 0.747, 265.248, 1+His+Asn+Orn+Tyr+Val+BCAA; 0.747, 263.831, 1+His+Asn+Arg+Cys+Val+Ile; 0.747, 264.508, 1+His+Asn+Gln+Orn+Ile+Phe; 0.746, 262.199, 1+His+Asn+Gly+Thr+Orn+Phe; 0.746, 263.375, 1+His+Asn+Asp+Thr+Orn+Ile; 0.746, 264.571, 1+His+Asn+Orn+Lys+Ile+Phe; 0.746, 265.380, 1+His+Asn+Gly+Orn+Val+BCAA; 0.746, 265.862, 1+His+Asn+Gly+Orn+Cys+Leu; 0.746, 264.559, 1+His+Asn+Pro+Orn+Ile+Phe; 0.746, 264.570, 1+His+Asn+Orn+Tyr+Ile+Phe; 0.746, 259.022, 1+His+Asn+Ser+Arg+Asp+Glu; 0.746, 265.388, 1+His+Asn+Thr+Orn+Ile+Trp; 0.746, 264.558, 1+His+Asn+Glu+Orn+Ile+Phe; 0.746, 264.232, 1+His+Asn+Arg+Orn+Ile+Phe; 0.746, 264.265, 1+His+Asn+Tau+Orn+Ile+Phe; 0.746, 264.471, 1+His+Asn+Orn+Ile+Leu+Phe; 0.745, 264.760, 1+His+Asn+Arg+Cys+Val+BCAA; 0.745, 264.661, 1+His+Asn+3MeHis+Asp+Orn+Leu; 0.745, 261.802, 1+His+Asn+Gly+Asp+Orn+BCAA; 0.745, 265.290, 1+His+Asn+Ser+Thr+Orn+Ile; 0.745, 265.195, 1+His+Asn+Orn+Cys+Val+Ile; 0.745, 263.985, 1+His+Asn+Thr+Orn+Leu+Phe; 0.745, 265.324, 1+His+Asn+Arg+Gly+Val+BCAA; 0.745, 265.605, 1+His+Asn+Arg+Glu+Val+BCAA; 0.745, 264.500, 1+His+Asn+Gly+Thr+Orn+Cys; 0.745, 265.315, 1+His+Asn+Tau+Arg+Val+Ile; 0.745, 264.926, 1+His+Asn+Arg+Gly+Orn+Ile; 0.745, 265.085, 1+His+Asn+Arg+Orn+Cys+Ile; 0.745, 266.722, 1+His+Asn+3MeHis+Ala+Orn+Leu+Phe; 0.745, 262.030, 1+His+Asn+Arg+Gly+Asp+Ile; 0.745, 265.924, 1+His+Asn+Orn+Lys+Val+BCAA; 0.745, 259.910, 1+His+Asn+3MeHis+Ser+Arg+Asp; 0.745, 265.888, 1+His+Asn+Ser+Orn+Val+BCAA; 0.745, 265.615, 1+His+Asn+Thr+Orn+Cys+Ile; 0.745, 259.531, 1+His+Asn+Ser+Asp+Orn+Phe; 0.744, 265.919, 1+His+Asn+Thr+Orn+Tyr+Ile; 0.744, 259.713, 1+His+Asn+Ser+Arg+Asp+Orn; 0.744, 266.729, 1+His+Asn+3MeHis+Orn+Cys+Ile; 0.744, 264.613, 1+His+Asn+Asp+Pro+Orn+Ile; 0.744, 264.681, 1+His+Asn+Gly+Thr+Orn+BCAA; 0.744, 261.285, 1+His+Asn+Gly+Asp+Thr+Lys; 0.744, 264.551, 1+His+Asn+Ser+Arg+Val+Ile; 0.744, 260.327, 1+His+Asn+Ser+Arg+Asp+Leu; 0.744, 265.038, 1+His+Asn+Arg+Val+Leu+BCAA; 0.744, 265.038, 1+His+Asn+Arg+Val+Ile+BCAA; 0.744, 265.038, 1+His+Asn+Arg+Val+Ile+Leu; 0.744, 265.038, 1+His+Asn+Arg+Ile+Leu+BCAA; 0.744, 262.602, 1+His+Asn+Asp+Orn+Ile+BCAA; 0.744, 265.049, 1+His+Asn+Thr+Orn+Phe+Trp; 0.744, 264.870, 1+His+Asn+Cit+Orn+Val+BCAA; 0.744, 266.066, 1+His+Asn+Orn+Val+Trp+BCAA; 0.744, 265.910, 1+His+Asn+Tau+Orn+Val+BCAA; 0.744, 264.871, 1+His+Asn+Gly+Thr+Ala+Orn; 0.744, 265.877, 1+His+Asn+Orn+Cys+Tyr+Ile; 0.744, 261.631, 1+His+Asn+Arg+Gly+Asp+Thr; 0.744, 260.418, 1+His+Asn+Ser+Arg+Asp+Pro; 0.744, 264.903, 1+His+Asn+Thr+Orn+Phe+BCAA; 0.744, 264.039, 1+His+Asn+Orn+Cys+Leu+Phe; 0.744, 265.840, 1+His+Asn+Orn+Cys+Ile+BCAA; 0.744, 265.487, 1+His+Asn+Ser+Gln+Thr+Orn; 0.744, 265.447, 1+His+Asn+Arg+Gly+Val+Ile; 0.744, 265.776, 1+His+Asn+Gln+Gly+Orn+Ile; 0.744, 263.389, 1+His+Asn+Arg+Val+Phe+BCAA; 0.744, 264.373, 1+His+Asn+Gly+Thr+Orn+Leu; 0.744, 265.544, 1+His+Asn+Arg+Ala+Val+Ile; 0.744, 259.773, 1+His+Asn+Ser+Arg+Asp+Phe; 0.743, 266.118, 1+His+Asn+Gly+Orn+Cys+BCAA; 0.743, 263.400, 1+His+Asn+Asp+Thr+Orn+Cys; 0.743, 259.444, 1+His+Asn+Ser+Asp+Orn+Cys; 0.743, 265.930, 1+His+Asn+Orn+Val+Leu+BCAA; 0.743, 265.930, 1+His+Asn+Orn+Val+Ile+BCAA; 0.743, 265.930, 1+His+Asn+Orn+Val+Ile+Leu; 0.743, 265.930, 1+His+Asn+Orn+Ile+Leu+BCAA; 0.743, 260.600, 1+His+Asn+Ser+Asp+Orn+BCAA; 0.743, 266.123, 1+His+Asn+Orn+Met+Val+BCAA; 0.743, 265.843, 1+His+Asn+Tau+Arg+Val+BCAA; 0.743, 266.060, 1+His+Asn+Glu+Orn+Val+BCAA; 0.743, 264.035, 1+His+Asn+Asp+Thr+Orn+Trp; 0.743, 260.473, 1+His+Asn+Ser+Asp+Orn+Leu; 0.743, 263.884, 1+His+Asn+Asp+Glu+Thr+Orn; 0.743, 266.036, 1+His+Asn+Gln+Orn+Val+BCAA; 0.743, 266.150, 1+His+Asn+Pro+Orn+Val+BCAA; 0.743, 266.936, 1+His+Asn+Orn+Cys+Val+Leu; 0.743, 264.312, 1+His+Asn+Asp+Orn+Val+Leu; 0.743, 259.193, 1+His+Asn+Ser+Asp+Cit+Orn; 0.743, 265.285, 1+His+Asn+Ser+Thr+Orn+Cys; 0.743, 260.126, 1+His+Asn+Tau+Ser+Arg+Asp; 0.743, 260.241, 1+His+Asn+Ser+Arg+Asp+Tyr; 0.743, 266.943, 1+His+Asn+Arg+Orn+Val+Leu; 0.743, 261.867, 1+His+Asn+Gly+Asp+Orn+Cys; 0.743, 266.232, 1+His+Asn+Gly+Orn+Lys+Ile; 0.743, 266.644, 1+His+Asn+Thr+Orn+Leu+Trp; 0.743, 266.255, 1+His+Asn+Gln+Gly+Orn+Leu; 0.743, 264.324, 1+His+Asn+Arg+Orn+Val+Ile; 0.743, 265.239, 1+His+Asn+Arg+Cit+Val+BCAA; 0.743, 266.047, 1+His+Asn+Thr+Orn+Cys+Trp; 0.743, 266.314, 1+His+Asn+3MeHis+Thr+Orn+Ile; 0.743, 265.397, 1+His+Asn+3MeHis+Orn+Phe+BCAA; 0.743, 261.167, 1+His+Asn+Gly+Asp+Thr+Phe; 0.743, 266.174, 1+His+Asn+3MeHis+Orn+Val+BCAA; 0.743, 260.379, 1+His+Asn+Ser+Arg+Asp+BCAA; 0.743, 267.003, 1+His+Asn+3MeHis+Gln+Thr+Orn; 0.743, 258.560, 1+His+Asn+Ser+Arg+Asp+Cys; 0.743, 266.667, 1+His+Asn+Gln+Orn+Cys+Ile; 0.743, 266.405, 1+His+Asn+Gly+Orn+Val+Leu; 0.743, 263.166, 1+His+Asn+Asp+Lys+Val+Ile; 0.743, 265.477, 1+His+Asn+Orn+Met+Leu+Phe; 0.743, 265.159, 1+His+Asn+Arg+

Glu+Val+Ile; 0.743, 264.223, 1+His+Asn+Asp+Orn+Ile+Trp; 0.743, 264.061, 1+His+Asn+Asp+Orn+Leu+Phe; 0.742, 266.443, 1+His+Asn+Tau+Gly+Orn+Ile; 0.742, 266.725, 1+His+Asn+Ser+Orn+Cys+Leu; 0.742, 265.138, 1+His+Asn+Asp+Glu+Orn+Leu; 0.742, 266.668, 1+His+Asn+Ala+Orn+Cys+Ile; 0.742, 265.998, 1+His+Asn+Arg+Tyr+Val+BCAA; 0.742, 267.133, 1+His+Asn+Thr+Orn+Leu+BCAA; 0.742, 266.755, 1+His+Asn+Gly+Ala+Orn+Leu; 0.742, 263.129, 1+His+Asn+Arg+Asp+Ile+BCAA; 0.742, 266.141, 1+His+Asn+Gln+Gly+Orn+Cys; 0.742, 265.885, 1+His+Asn+Ser+Orn+Cys+Ile; 0.742, 266.600, 1+His+Asn+Gln+Thr+Orn+Cys; 0.742, 264.486, 1+His+Asn+Asp+Thr+Pro+Orn; 0.742, 266.021, 1+His+Asn+Gly+Orn+Tyr+Ile; 0.742, 265.901, 1+His+Asn+Arg+Gly+Orn+Leu; 0.742, 265.440, 1+His+Asn+Orn+Leu+Phe+BCAA; 0.742, 266.123, 1+His+Asn+Ala+Orn+Val+Ile; 0.742, 266.063, 1+His+Asn+Gln+Arg+Val+BCAA; 0.742, 264.913, 1+His+Asn+Orn+Cys+Phe+BCAA; 0.742, 262.636, 1+His+Asn+Gly+Asp+Cit+Orn; 0.742, 265.267, 1+His+Asn+Ser+Thr+Orn+Trp; 0.742, 266.053, 1+His+Asn+3MeHis+Arg+Val+BCAA; 0.742, 264.812, 1+His+Asn+Ser+Arg+Val+BCAA; 0.742, 266.067, 1+His+Asn+Arg+Orn+Trp+BCAA; 0.742, 266.418, 1+His+Asn+Gly+Orn+Ile+Leu; 0.742, 264.514, 1+His+Asn+Asp+Orn+Cys+Leu; 0.742, 264.686, 1+His+Asn+Asp+Orn+Tyr+Ile; 0.742, 260.144, 1+His+Asn+Ser+Arg+Gly+Asp; 0.742, 264.420, 1+His+Asn+Gly+Cit+Thr+Orn; 0.742, 265.977, 1+His+Asn+Arg+Met+Val+BCAA; 0.742, 264.485, 1+His+Asn+Gly+Thr+Orn+Trp; 0.742, 266.806, 1+His+Asn+Tau+Orn+Cys+Ile; 0.742, 266.008, 1+His+Asn+Cit+Orn+Cys+Ile; 0.742, 266.711, 1+His+Asn+Orn+Cys+Met+Ile; 0.742, 264.692, 1+His+Asn+Gln+Asp+Orn+Ile; 0.742, 268.009, 1+His+Asn+3MeHis+Ala+Orn+Ile; 0.742, 260.536, 1+His+Asn+Ser+Arg+Asp+Trp; 0.742, 265.045, 1+His+Asn+3MeHis+Gly+Thr+Orn; 0.742, 267.153, 1+His+Ala+Orn+Val+Phe+BCAA; 0.741, 266.089, 1+His+Asn+Arg+Pro+Val+BCAA; 0.741, 267.054, 1+His+Asn+3MeHis+Thr+Orn+Leu; 0.741, 260.532, 1+His+Asn+Ser+Arg+Asp+Lys; 0.741, 260.434, 1+His+Asn+Ser+Arg+Asp+Met; 0.741, 265.038, 1+His+Asn+Gly+Thr+Pro+Orn; 0.741, 258.973, 1+His+Asn+Ser+Arg+Asp+Cit; 0.741, 263.096, 1+His+Asn+Gln+Gly+Asp+Orn; 0.741, 266.723, 1+His+Asn+Glu+Orn+Cys+Ile; 0.741, 260.916, 1+His+Asn+Ser+Asp+Pro+Orn; 0.741, 266.487, 1+His+Asn+Gly+Pro+Orn+Ile; 0.741, 266.216, 1+His+Asn+Orn+Cys+Ile+Trp; 0.741, 266.895, 1+His+Asn+Ser+Ala+Orn+Ile; 0.741, 260.535, 1+His+Asn+Ser+Arg+Asp+Val; 0.741, 265.043, 1+His+Asn+Gly+Thr+Orn+Val; 0.741, 266.840, 1+His+Asn+Gln+Thr+Orn+Trp; 0.741, 266.262, 1+His+Asn+Gly+Glu+Orn+Ile; 0.741, 265.879, 1+His+Asn+Ser+Thr+Orn+Leu; 0.741, 265.026, 1+His+Asn+Gly+Thr+Orn+Tyr; 0.741, 263.441, 1+His+Asn+Asp+Thr+Orn+Phe; 0.741, 262.920, 1+His+Asn+Tau+Gly+Asp+Orn; 0.741, 264.338, 1+His+Asn+Asp+Cit+Orn+Ile; 0.741, 267.114, 1+His+Asn+Gly+Ala+Orn+BCAA; 0.741, 266.272, 1+His+Asn+Gly+Orn+Ile+Trp; 0.741, 265.050, 1+His+Asn+Tau+Gly+Thr+Orn; 0.741, 266.806, 1+His+Asn+Pro+Orn+Cys+Ile; 0.741, 264.766, 1+His+Asn+Asp+Orn+Met+Ile; 0.741, 267.845, 1+His+Gly+Ala+Orn+Leu+Phe; 0.741, 266.487, 1+His+Asn+Gly+Orn+Met+Ile; 0.741, 264.741, 1+His+Asn+Ser+Gly+Thr+Orn; 0.741, 264.324, 1+His+Asn+Thr+Orn+Cys+Phe; 0.741, 264.625, 1+His+Asn+Tau+Asp+Orn+Ile; 0.741, 264.996, 1+His+Asn+Gly+Thr+Orn+Met; 0.741, 267.757, 1+His+Asn+Ala+Orn+Ile+Trp; 0.741, 266.079, 1+His+Asn+Arg+Ala+Val+BCAA; 0.741, 266.379, 1+His+Asn+Arg+Gly+Orn+BCAA; 0.741, 265.939, 1+His+Asn+3MeHis+Ser+Thr+Orn; 0.741, 266.863, 1+His+Asn+3MeHis+Arg+Orn+Ile; 0.741, 260.921, 1+His+Asn+Ser+Gln+Asp+Orn; 0.741, 262.956, 1+His+Asn+Asp+Val+Ile+Phe; 0.741, 266.563, 1+His+Asn+Gln+Gly+Orn+BCAA; 0.741, 265.329, 1+His+Asn+Gln+Thr+Orn+Phe; 0.741, 266.694, 1+His+Asn+Thr+Orn+Cys+Leu; 0.741, 265.415, 1+His+Asn+Ser+Orn+Val+Phe; 0.741, 265.853, 1+His+Asn+Arg+Lys+Val+BCAA; 0.741, 260.218, 1+His+Asn+Tau+Ser+Asp+Orn; 0.741, 265.878, 1+His+Asn+Orn+Lys+Leu+Phe; 0.741, 262.531, 1+His+Asn+Asp+Val+Phe+BCAA; 0.741, 266.643, 1+His+Asn+3MeHis+Thr+Orn+Cys; 0.741, 260.223, 1+His+Asn+Ser+Asp+Thr+Lys; 0.741, 264.911, 1+His+Asn+Gly+Thr+Orn+Lys; 0.741, 265.095, 1+His+Asn+3MeHis+Asp+Orn+BCAA; 0.741, 264.207, 1+His+Asn+Thr+Val+Phe+BCAA; 0.741, 264.622, 1+His+Asn+Asp+Thr+Orn+Met; 0.741, 259.759, 1+His+Asn+Ser+Asp+Thr+Phe; 0.740, 264.613, 1+His+Asn+Ser+Arg+Orn+Ile; 0.740, 265.697, 1+His+Asn+Orn+Leu+Phe+Trp; 0.740, 266.013, 1+His+Asn+Gly+Orn+Val+Ile; 0.740, 266.613, 1+His+Asn+3MeHis+Thr+Orn+Trp; 0.740, 267.808, 1+His+Asn+3MeHis+Orn+Cys+Leu; 0.740, 264.419, 1+His+Asn+Arg+Gly+Thr+Orn; 0.740, 265.147, 1+His+Asn+Cit+Orn+Leu+Phe; 0.740, 265.091, 1+His+Asn+Thr+Val+Ile+Phe; 0.740, 266.862, 1+His+Asn+Thr+Orn+Trp+BCAA; 0.740, 266.368, 1+His+Asn+Ser+Gly+Orn+Ile; 0.740, 266.737, 1+His+Asn+Gly+Orn+Lys+Leu; 0.740, 260.717, 1+His+Asn+Ser+Asp+Thr+Val; 0.740, 262.971, 1+His+Asn+Gly+Asp+Pro+Orn; 0.740, 267.306, 1+His+Asn+3MeHis+Thr+Orn+BCAA; 0.740, 266.857, 1+His+Asn+Thr+Orn+Cys+BCAA; 0.740, 266.892, 1+His+Asn+Cit+Orn+Val+Leu; 0.740, 266.691, 1+His+Asn+Orn+Cys+Ile+Leu; 0.740, 265.817, 1+His+Asn+Tau+Orn+Leu+Phe; 0.740, 264.720, 1+His+Asn+Asp+Thr+Orn+Leu; 0.740, 260.481, 1+His+Asn+Ser+Gln+Arg+Asp; 0.740, 266.387, 1+His+Asn+Gly+Orn+Ile+BCAA; 0.740, 265.401, 1+His+Asn+Thr+Pro+Orn+Phe; 0.740, 266.183, 1+His+Asn+Orn+Cys+Lys+Ile; 0.740, 262.850, 1+His+Asn+Gly+Asp+Orn+Val; 0.740, 260.727, 1+His+Asn+3MeHis+Ser+Asp+Orn; 0.740, 260.495, 1+His+Asn+Ser+Gly+Asp+Orn; 0.740, 264.525, 1+His+Asn+Arg+Asp+Orn+Ile; 0.740, 264.791, 1+His+Asn+Gly+Glu+Thr+Orn; 0.740, 266.735, 1+His+Asn+Thr+Ala+Orn+Ile; 0.740, 264.887, 1+His+Asn+Asp+Thr+Orn+BCAA; 0.740, 266.299, 1+His+Asn+Arg+Thr+Orn+Cys; 0.740, 264.501, 1+His+Asn+3MeHis+Thr+Orn+Phe; 0.740, 265.272, 1+His+Asn+Gly+Cit+Orn+Ile; 0.740, 266.870, 1+His+Asn+Thr+Pro+Orn+Cys; 0.740, 265.863, 1+His+Asn+Orn+Tyr+Leu+Phe; 0.740, 267.867, 1+His+Asn+Tau+Orn+Val+Leu; 0.740, 263.833, 1+His+Asn+Asp+Lys+Val+BCAA; 0.740, 265.910, 1+His+Asn+Gln+Orn+Leu+Phe; 0.740, 265.919, 1+His+Asn+Ala+Orn+Leu+Phe; 0.740, 266.407, 1+His+Asn+3MeHis+Gly+Orn+Ile; 0.740, 266.794, 1+His+Asn+Glu+Thr+Orn+Ile; 0.740, 264.923, 1+His+Asn+Thr+Orn+Met+Phe; 0.740, 260.463, 1+His+Asn+Ser+Arg+Asp+Ala; 0.740, 264.490, 1+His+Asn+Asp+Orn+Ile+Leu; 0.740, 267.658, 1+His+Asn+Ser+Gln+Orn+Leu; 0.740, 265.622, 1+His+Asn+Thr+Orn+Val+Phe; 0.740, 266.887, 1+His+Asn+Ser+Orn+Cys+BCAA; 0.740, 265.901, 1+His+Asn+Ser+Thr+Ala+Orn; 0.739, 265.963, 1+His+Asn+Orn+Tyr+Val+Ile; 0.739, 264.893, 1+His+Asn+Arg+Asp+Thr+Orn; 0.739, 264.899, 1+His+Asn+Gln+Asp+Thr+Orn; 0.739, 261.093, 1+His+Asn+Gly+Asp+Cit+Thr; 0.739, 262.921, 1+His+Asn+Asp+Cit+Val+Ile; 0.739, 262.358, 1+His+Asn+Gly+Asp+Val+Ile; 0.739, 265.920, 1+His+Asn+Pro+Orn+Leu+Phe; 0.739, 264.370, 1+His+Asn+Asp+Orn+Lys+Ile; 0.739, 267.503, 1+His+Asn+3MeHis+Orn+Tyr+Ile; 0.739, 267.908, 1+His+Asn+Gln+Orn+Cys+Leu; 0.739, 267.256, 1+His+Asn+Cit+Orn+Cys+Leu; 0.739, 265.892, 1+His+Asn+Arg+Orn+Leu+Phe;

0.739, 263.018, 1+His+Asn+Asp+Cit+Val+BCAA; 0.739, 266.193, 1+His+Asn+Tau+Orn+Val+Ile; 0.739, 267.167, 1+His+Asn+Ser+Orn+Val+Leu; 0.739, 264.402, 1+His+Asn+Arg+Val+Ile+Phe; 0.739, 260.963, 1+His+Asn+Ser+Asp+Orn+Val; 0.739, 265.998, 1+His+Asn+Ser+Thr+Orn+BCAA; 0.739, 266.045, 1+His+Asn+Ser+Orn+Tyr+Ile; 0.739, 265.621, 1+His+Asn+Glu+Thr+Orn+Phe; 0.739, 264.735, 1+His+Asn+Asp+Thr+Orn+Lys; 0.739, 264.878, 1+His+Asn+Asp+Thr+Orn+Tyr; 0.739, 265.781, 1+His+Asn+Glu+Orn+Leu+Phe; 0.739, 264.711, 1+His+Asn+Asp+Pro+Orn+Cys; 0.739, 267.057, 1+His+Asn+Ser+Orn+Tyr+Leu; 0.739, 266.813, 1+His+Asn+Thr+Pro+Orn+Ile; 0.739, 265.858, 1+His+Asn+Arg+Val+Ile+Trp; 0.739, 264.782, 1+His+Asn+Asp+Ala+Orn+Ile; 0.739, 267.399, 1+His+Asn+Gln+Gly+Pro+Orn; 0.739, 265.622, 1+His+Asn+Thr+Ala+Orn+Phe; 0.739, 266.993, 1+His+Asn+Thr+Ala+Orn+Trp; 0.739, 266.814, 1+His+Asn+Thr+Orn+Met+Ile; 0.739, 267.690, 1+His+Asn+Ala+Orn+Tyr+Ile; 0.739, 262.595, 1+His+Asn+Gly+Asp+Val+BCAA; 0.739, 267.087, 1+His+Asn+Ala+Orn+Ile+BCAA; 0.739, 267.594, 1+His+Asn+Orn+Tyr+Val+Leu; 0.739, 265.093, 1+His+Asn+Gly+Orn+Val+Phe; 0.739, 266.760, 1+His+Asn+Ser+Gln+Orn+Cys; 0.739, 267.272, 1+His+3MeHis+Ala+Orn+Ile+Phe; 0.739, 262.366, 1+His+Asn+Gly+Asp+Lys+Ile; 0.739, 267.924, 1+His+Asn+Orn+Cys+Leu+BCAA; 0.739, 266.537, 1+His+Asn+Orn+Met+Phe+BCAA; 0.739, 267.203, 1+His+Asn+Gln+Gly+Orn+Val; 0.739, 266.923, 1+His+Asn+Thr+Orn+Val+Trp; 0.739, 266.499, 1+His+Asn+Thr+Orn+Ile+Leu; 0.739, 265.613, 1+His+Asn+Arg+Thr+Orn+Phe; 0.739, 264.682, 1+His+Asn+Asp+Thr+Ala+Orn; 0.739, 265.415, 1+His+Asn+Ser+Thr+Orn+Tyr; 0.739, 266.843, 1+His+Asn+Thr+Orn+Met+Trp; 0.739, 267.849, 1+His+Asn+3MeHis+Orn+Val+Leu; 0.739, 267.977, 1+His+Asn+Glu+Orn+Val+Leu; 0.739, 265.589, 1+His+Asn+Thr+Orn+Lys+Phe; 0.739, 265.680, 1+His+Asn+Asp+Glu+Orn+BCAA; 0.739, 265.336, 1+His+Asn+Thr+Orn+Tyr+Phe; 0.739, 265.404, 1+His+Asn+Cit+Thr+Orn+Phe; 0.739, 261.039, 1+His+Asn+Ser+Asp+Orn+Trp; 0.739, 268.301, 1+His+Gly+Ala+Orn+Ile+Phe; 0.739, 267.344, 1+His+Asn+Tau+Gln+Gly+Orn; 0.739, 264.484, 1+His+Asn+Ser+Arg+Thr+Orn; 0.739, 266.754, 1+His+Asn+Gln+Thr+Orn+Ile; 0.739, 266.784, 1+His+Asn+Gly+Glu+Orn+Leu; 0.739, 265.543, 1+His+Asn+Gly+Cit+Orn+Leu; 0.739, 266.893, 1+His+Asn+Gly+Orn+Cys+Val; 0.739, 267.146, 1+His+Asn+Arg+Orn+Tyr+Ile; 0.739, 268.003, 1+His+Asn+Glu+Orn+Cys+Leu; 0.739, 261.041, 1+His+Asn+Ser+Asp+Orn+Met; 0.739, 262.742, 1+His+Asn+Gly+Asp+Glu+Thr; 0.739, 266.248, 1+His+Asn+Thr+Lys+Val+BCAA; 0.739, 267.356, 1+His+Asn+3MeHis+Thr+Ala+Orn; 0.739, 265.799, 1+His+Asn+Ser+Arg+Ile+BCAA; 0.739, 265.804, 1+His+Asn+Arg+Lys+Val+Ile; 0.739, 265.921, 1+His+Asn+Arg+Tyr+Val+Ile; 0.739, 266.756, 1+His+Asn+Thr+Orn+Cys+Tyr; 0.739, 264.838, 1+His+Asn+Tau+Asp+Thr+Orn; 0.739, 268.348, 1+His+Asn+Ala+Pro+Orn+Ile; 0.738, 264.795, 1+His+Asn+Arg+Thr+Ile+BCAA; 0.738, 266.910, 1+His+Asn+Thr+Pro+Orn+Trp; 0.738, 266.188, 1+His+Asn+Asp+Pro+Orn+Leu; 0.738, 265.986, 1+His+Asn+Thr+Lys+Val+Ile; 0.738, 265.954, 1+His+Asn+Ser+Thr+Orn+Val; 0.738, 266.994, 1+His+Asn+Glu+Thr+Orn+Trp; 0.738, 268.047, 1+His+Asn+Pro+Orn+Cys+Leu; 0.738, 267.335, 1+His+Asn+Arg+Ala+Orn+Ile; 0.738, 264.514, 1+His+Asn+Asp+Thr+Orn+Val; 0.738, 261.036, 1+His+Asn+Ser+Asp+Orn+Lys; 0.738, 266.396, 1+His+Asn+Gln+Orn+Val+Ile; 0.738, 267.287, 1+His+Asn+3MeHis+Glu+Thr+Orn; 0.738, 265.439, 1+His+Asn+Ser+Arg+Orn+Cys; 0.738, 266.921, 1+His+Asn+Thr+Ala+Orn+Cys; 0.738, 267.481, 1+His+Asn+Orn+Lys+Tyr+Ile; 0.738, 265.683, 1+His+Asn+Arg+Orn+Ile+BCAA; 0.738, 267.906, 1+His+Asn+Orn+Lys+Val+Leu; 0.738, 262.321, 1+His+Asn+Gly+Asp+Thr+Trp; 0.738, 262.633, 1+His+Asn+Gly+Asp+Thr+Val; 0.738, 266.326, 1+His+Asn+Ser+Orn+Val+Ile; 0.738, 268.118, 1+His+Asn+3MeHis+Gln+Orn+Ile; 0.738, 266.787, 1+His+Asn+Tau+Thr+Orn+Ile; 0.738, 266.856, 1+His+Asn+Glu+Thr+Orn+Cys; 0.738, 268.197, 1+His+Asn+Tau+3MeHis+Orn+Ile; 0.738, 265.976, 1+His+Asn+Arg+Thr+Orn+Ile; 0.738, 266.959, 1+His+Asn+Tau+Thr+Orn+Trp; 0.738, 265.618, 1+His+Asn+Ser+Gln+Orn+Phe; 0.738, 266.851, 1+His+Asn+Gly+Orn+Leu+BCAA; 0.738, 266.870, 1+His+Asn+Arg+Orn+Ile+Trp; 0.738, 266.035, 1+His+Asn+Tau+Ser+Thr+Orn; 0.738, 267.005, 1+His+Asn+Ser+Gln+Orn+Ile; 0.738, 267.902, 1+His+Asn+Gln+Orn+Val+Leu; 0.738, 266.791, 1+His+Asn+Gly+Orn+Leu+Trp; 0.738, 265.729, 1+His+Asn+Cit+Orn+Val+Ile; 0.738, 267.803, 1+His+Asn+Tau+Orn+Ile+Trp; 0.738, 267.814, 1+His+Asn+Ser+Orn+Leu+BCAA; 0.738, 268.051, 1+His+Asn+Orn+Cys+Met+Leu; 0.738, 264.759, 1+His+Asn+Asp+Orn+Cys+BCAA; 0.738, 267.335, 1+His+Asn+Thr+Val+Ile+Trp; 0.738, 265.147, 1+His+Asn+Ser+Cit+Thr+Orn; 0.738, 266.803, 1+His+Asn+Thr+Orn+Cys+Val; 0.738, 261.033, 1+His+Asn+Ser+Asp+Orn+Tyr; 0.738, 262.168, 1+His+Asn+Gln+Gly+Asp+Thr; 0.738, 266.912, 1+His+Asn+Thr+Orn+Cys+Met; 0.738, 266.909, 1+His+Asn+Tau+Thr+Orn+Cys; 0.738, 266.547, 1+His+Asn+Cit+Thr+Orn+Cys; 0.738, 265.513, 1+His+Asn+Tau+Thr+Orn+Phe; 0.738, 267.812, 1+His+Asn+3MeHis+Orn+Ile+Trp; 0.738, 261.034, 1+His+Asn+Ser+Asp+Ala+Orn; 0.738, 260.049, 1+His+Asn+Ser+Asp+Cit+Lys; 0.738, 266.491, 1+His+Asn+Orn+Val+Ile+Trp; 0.738, 267.266, 1+His+Asn+3MeHis+Ser+Orn+Ile; 0.738, 265.802, 1+His+Asn+Arg+Pro+Val+Ile; 0.738, 265.423, 1+His+Asn+Arg+Cys+Ile+BCAA; 0.738, 266.963, 1+His+Asn+Thr+Orn+Tyr+Trp; 0.738, 267.093, 1+His+Asn+Arg+Orn+Cys+Leu; 0.738, 268.053, 1+His+Asn+Ala+Orn+Cys+Leu; 0.738, 267.998, 1+His+Asn+Ala+Orn+Val+Leu; 0.738, 266.929, 1+His+Asn+Thr+Orn+Lys+Trp; 0.738, 265.967, 1+His+Asn+3MeHis+Arg+Val+Ile; 0.738, 265.858, 1+His+Asn+Ser+Thr+Orn+Lys; 0.738, 266.353, 1+His+Asn+Cit+Thr+Orn+Ile; 0.738, 267.812, 1+His+Asn+Ser+Ala+Orn+Leu; 0.738, 267.321, 1+His+Asn+3MeHis+Cit+Orn+Ile; 0.738, 267.997, 1+His+Asn+Pro+Orn+Val+Leu; 0.738, 267.253, 1+His+Asn+Arg+Orn+Met+Ile; 0.738, 264.736, 1+His+Asn+Asp+Cit+Thr+Orn; 0.738, 263.304, 1+His+Asn+Gly+Asp+Glu+Orn; 0.738, 265.051, 1+His+Asn+Asp+Orn+Phe+BCAA; 0.738, 267.148, 1+His+Asn+Ser+Gln+Gly+Orn; 0.738, 266.028, 1+His+Asn+Ser+Glu+Thr+Orn; 0.738, 269.002, 1+His+Asn+3MeHis+Ala+Orn+Leu; 0.738, 266.763, 1+His+Asn+Ser+Gly+Orn+Leu; 0.738, 266.654, 1+His+Asn+Gly+Orn+Tyr+Leu; 0.738, 268.104, 1+His+3MeHis+Ala+Orn+Phe+BCAA; 0.738, 258.896, 1+His+Asn+Ser+Asp+Cit+Phe; 0.738, 266.028, 1+His+Asn+Ser+Thr+Orn+Met; 0.738, 266.147, 1+His+Asn+Thr+Orn+Lys+Ile; 0.738, 266.746, 1+His+Asn+Arg+Thr+Orn+Trp; 0.737, 268.902, 1+His+Asn+3MeHis+Gln+Orn+Leu; 0.737, 265.802, 1+His+Asn+Ser+Cit+Orn+Ile; 0.737, 266.861, 1+His+Asn+Cit+Orn+Ile+Trp; 0.737, 267.686, 1+His+Asn+Orn+Tyr+Met+Ile; 0.737, 267.353, 1+His+Asn+Arg+Pro+Orn+Ile; 0.737, 267.220, 1+His+Asn+Tau+Ser+Orn+Ile; 0.737, 266.513, 1+His+Asn+Cit+Thr+Orn+Trp; 0.737, 268.050, 1+His+Asn+Ala+Orn+Lys+Ile; 0.737, 262.757, 1+His+Asn+Gly+Asp+Orn+Phe; 0.737, 266.993, 1+His+Asn+Pro+Orn+Phe+BCAA; 0.737, 268.041, 1+His+Asn+Ser+Ala+Orn+BCAA; 0.737, 268.052, 1+His+Asn+Tau+Orn+Cys+Leu; 0.737, 268.128,

1+His+Asn+3Me His+Arg+Orn+Leu; 0.737, 267.397, 1+His+Asn+Gln+Arg+Orn+Ile; 0.7 37, 267.269, 1+His+Asn+Ser+Glu+Orn+Ile; 0.737, 261.664, 1+His+As n+Gly+Asp+Ile+Phe; 0.737, 267.932, 1+His+Asn+Pro+Orn+Ile+Trp; 0. 737, 266.115, 1+His+Asn+Asp+Orn+Leu+BCAA; 0.737, 262.592, 1+His+Asn+3MeHis+Gly+Asp+Thr; 0.737, 265.675, 1+His+Asn+Asp+Glu+Pro+Orn; 0.737, 267.743, 1+His+Asn+Pro+Orn+Tyr+Ile; 0.737, 268.595, 1+His+Asn+3MeHis+Orn+Tyr+Leu; 0.737, 266.033, 1+His+Asn+Ser+Thr+Pro+Orn; 0.737, 266.821, 1+His+Asn+3MeHis+Arg+Thr+Orn; 0.737, 2 68.801, 1+His+Asn+3MeHis+Orn+Leu+BCAA; 0.737, 268.134, 1+His+As n+Gln+Orn+Cys+BCAA; 0.737, 265.194, 1+His+Asn+Asp+Thr+Val+Leu; 0.737, 267.279, 1+His+Asn+Ser+Orn+Ile+Leu; 0.737, 266.915, 1+His+Asn+Tau+Gly+Orn+Leu; 0.737, 266.949, 1+His+Asn+3MeHis+Cit+Thr+Orn; 0.737, 268.108, 1+His+Asn+3MeHis+Orn+Cys+BCAA; 0.737, 267. 993, 1+His+Asn+Orn+Met+Val+Leu; 0.737, 265.364, 1+His+3MeHis+As p+Orn+Leu+Phe; 0.737, 267.125, 1+His+Asn+Gln+Arg+Gly+Orn; 0.737, 259.319, 1+His+Asn+Ser+Asp+Cit+Thr; 0.737, 266.996, 1+His+Asn+S er+Orn+Lys+Ile; 0.737, 267.176, 1+His+Asn+Gly+Orn+Lys+BCAA; 0.7 37, 267.909, 1+His+Asn+Gln+Orn+Ile+Trp; 0.737, 267.611, 1+His+As n+Cit+Orn+Cys+BCAA; 0.737, 265.518, 1+His+Asn+Arg+Cit+Val+Ile; 0.737, 267.335, 1+His+Asn+3Me-His+Thr+Orn+Val; 0.737, 267.165, 1+His+Asn+Gly+Glu+Orn+BCAA; 0.737, 266.909, 1+His+Asn+Gly+Orn+Me t+Leu; 0.737, 267.354, 1+His+Asn+Thr+Orn+Tyr+Leu; 0.737, 266.957, 1+His+Asn+Orn+Tyr+Phe+BCAA; 0.737, 267.090, 1+His+Asn+Arg+Cit+Orn+Ile; 0.737, 262.255, 1+His+Asn+Gly+Asp+Thr+Ile; 0.737, 267.3 61, 1+His+Asn+3MeHis+Thr+Orn+Met; 0.737, 267.337, 1+His+Asn+Ser+Orn+Cys+Val; 0.737, 267.889, 1+His+Asn+Orn+Val+Leu+Trp; 0.737, 267.525, 1+His+Asn+Gln+Gly+Orn+Tyr; 0.737, 268.986, 1+His+Asn+3 MeHis+Glu+Orn+Leu; 0.737, 266.463, 1+His+Asn+Glu+Orn+Val+Ile; 0. 737, 267.101, 1+His+Asn+Ser+Gly+Orn+BCAA; 0.737, 269.010, 1+His+Asn+Tau+3MeHis+Orn+Leu; 0.737, 268.361, 1+His+Asn+Tau+Ala+Orn+Ile; 0.737, 266.905, 1+His+Asn+3MeHis+Gly+Orn+Leu; 0.737, 268.00 3, 1+His+Asn+3MeHis+Cit+Orn+Leu; 0.737, 267.937, 1+His+Asn+Glu+Orn+Ile+Trp; 0.737, 267.421, 1+His+Asn+Arg+Orn+Cys+BCAA; 0.737, 265.817, 1+His+Asn+Arg+Met+Val+Ile; 0.737, 263.030, 1+His+Asn+T au+Asp+Val+Ile; 0.737, 267.393, 1+His+Asn+Arg+Glu+Orn+Ile; 0.73 7, 268.156, 1+His+Asn+Ser+Gln+Ala+Orn; 0.737, 267.345, 1+His+Asn+3MeHis+Thr+Pro+Orn; 0.737, 267.851, 1+His+Asn+Ser+Gln+Orn+BCA A; 0.737, 265.909, 1+His+Asn+Ser+Arg+Orn+Leu; 0.737, 267.320, 1+H is+Asn+Tau+Gly+Orn+BCAA; 0.737, 266.601, 1+His+Asn+Arg+Gly+Cys+Ile; 0.737, 263.119, 1+His+Asn+Gly+Asp+Orn+Met; 0.737, 266.692, 1+His+Asn+3MeHis+Orn+Val+Ile; 0.737, 268.015, 1+His+Asn+Gly+Al a+Orn+Val; 0.737, 266.899, 1+His+Asn+Gly+Pro+Orn+Leu; 0.737, 268. 494, 1+His+Asn+Pro+Orn+Met+Ile; 0.737, 266.098, 1+His+Asn+Gly+C it+Orn+BCAA; 0.737, 263.424, 1+His+Asn+3MeHis+Gly+Asp+Orn; 0.73 6, 266.908, 1+His+Asn+Orn+Tyr+Ile+BCAA; 0.736, 267.304, 1+His+As n+Gly+Orn+Met+BCAA; 0.736, 267.155, 1+His+Asn+Gly+Orn+Trp+BCAA; 0.736, 267.315, 1+His+Asn+3MeHis+Gly+Orn+BCAA; 0.736, 267.936, 1+His+Asn+Orn+Met+Ile+Trp; 0.736, 263.483, 1+His+Asn+Arg+Gly+A sp+Orn; 0.736, 266.205, 1+His+Asn+Arg+Orn+BCAA; 0.736, 267.2 39, 1+His+Asn+3MeHis+Thr+Orn+Tyr; 0.736, 266.698, 1+His+Asn+Pro+Orn+Val+Ile; 0.736, 267.205, 1+His+Asn+Ser+Orn+Met+Ile; 0.736, 266.922, 1+His+Asn+Ser+Orn+Ile+Trp; 0.736, 267.924, 1+His+Asn+S er+Glu+Orn+Leu; 0.736, 266.752, 1+His+Asn+Cit+Orn+Ile+BCAA; 0.7 36, 268.287, 1+His+Asn+Ala+Orn+Ile+Leu; 0.736, 267.145, 1+His+As n+Gly+Orn+Tyr+BCAA; 0.736, 268.494, 1+His+Asn+Glu+Pro+Orn+Ile; 0.736, 265.620, 1+His+Asn+Gln+Gly+Orn+Phe; 0.736, 267.392, 1+His+Asn+Orn+Tyr+Ile+Trp; 0.736, 267.591, 1+His+Asn+Gln+Thr+Orn+Me t; 0.736, 267.619, 1+His+Asn+Gln+Thr+Orn+Leu; 0.736, 267.326, 1+H is+Asn+Gly+Pro+Orn+BCAA; 0.736, 265.553, 1+His+Asn+Arg+Gly+Ile+Phe; 0.736, 267.377, 1+His+Asn+Tau+Arg+Orn+Ile; 0.736, 267.000, 1+His+Asn+Glu+Orn+Phe+BCAA; 0.736, 267.646, 1+His+Asn+Orn+Cys+Tyr+Leu; 0.736, 263.539, 1+His+Asn+Gly+Asp+Orn+Trp; 0.736, 267.9 50, 1+His+Asn+Tau+Ser+Gln+Orn; 0.736, 269.429, 1+His+Asn+3MeHis+Ala+Orn+BCAA; 0.736, 267.214, 1+His+Asn+Ser+Glu+Orn+Cys; 0.736, 264.184, 1+His+Asn+Asp+Pro+Val+Ile; 0.736, 268.386, 1+His+Asn+A la+Orn+Met+Ile; 0.736, 259.911, 1+His+Asn+3MeHis+Ser+Asp+Cit; 0. 736, 266.698, 1+His+Asn+Orn+Met+Val+Ile; 0.736, 267.365, 1+His+A sn+Gln+Thr+Orn+Val; 0.736, 266.714, 1+His+Asn+Gly+Glu+Orn+Cys; 0.736, 267.405, 1+His+Asn+Tau+3MeHis+Thr+Orn; 0.736, 268.360, 1+His+Asn+Gln+Ala+Orn+Ile; 0.736, 266.735, 1+His+Asn+Arg+Gly+Ile+BCAA; 0.736, 266.551, 1+His+Asn+Arg+Gly+Orn+Cys; 0.736, 267.255, 1+His+Asn+Arg+Orn+Ile+Leu; 0.736, 268.978, 1+His+Gly+Ala+Orn+P he+BCAA; 0.736, 267.630, 1+His+Asn+Gln+Thr+Pro+Orn; 0.736, 267.7 76, 1+His+Asn+Orn+Cys+Lys+Leu; 0.736, 260.354, 1+His+Asn+Ser+As p+Glu+Thr; 0.736, 263.535, 1+His+Asn+Gly+Asp+Orn+Lys; 0.736, 267. 018, 1+His+Asn+Orn+Lys+Phe+BCAA; 0.736, 267.414, 1+His+Asn+Tau+Ser+Orn+Cys; 0.736, 268.197, 1+His+Asn+3MeHis+Glu+Orn+Ile; 0.73 6, 267.239, 1+His+Asn+Arg+Orn+Lys+Ile; 0.736, 267.076, 1+His+Asn+Cit+Orn+Tyr+Ile; 0.736, 267.629, 1+His+Asn+Gln+Thr+Orn+Tyr; 0. 736, 267.769, 1+His+Asn+Gln+Orn+Tyr+Ile; 0.736, 269.035, 1+His+A sn+3Me-His+Orn+Met+Leu; 0.736, 267.411, 1+His+Asn+Ser+Ala+Orn+C ys; 0.736, 267.775, 1+His+Asn+Ser+Orn+Lys+Leu; 0.736, 268.969, 1+His+Asn+Orn+Leu+Trp+BCAA; 0.736, 267.744, 1+His+Asn+Tau+Orn+Ty r+Ile; 0.736, 267.083, 1+His+Asn+3MeHis+Thr+Orn+Lys; 0.736, 267. 371, 1+His+Asn+Gln+Gly+Glu+Orn; 0.736, 267.843, 1+His+Asn+3MeHi s+Ser+Orn+Leu; 0.736, 267.198, 1+His+Asn+Tau+Orn+Ile+BCAA; 0.73 6, 265.841, 1+His+Asn+Gln+Arg+Val+Ile; 0.736, 268.249, 1+His+Asn+Glu+Orn+Cys+BCAA; 0.736, 266.440, 1+His+Asn+Cit+Orn+Phe+BCAA; 0.736, 267.794, 1+His+Asn+3MeHis+Orn+Lys+Ile; 0.736, 266.149, 1+His+Asn+Ser+Cit+Orn+Cys; 0.736, 268.385, 1+His+Asn+Glu+Ala+Orn+Ile; 0.736, 267.063, 1+His+Asn+Ala+Orn+Phe+BCAA; 0.736, 267.682, 1+His+Asn+Orn+Lys+Ile+Trp; 0.736, 265.691, 1+His+Asn+Ser+Arg+O rn+Phe; 0.736, 265.657, 1+His+Asn+Tau+Ser+Orn+Phe; 0.736, 268.29 9, 1+His+Asn+Pro+Orn+Cys+BCAA; 0.736, 267.201, 1+His+Asn+Orn+Il e+Trp+BCAA; 0.736, 268.345, 1+His+Asn+Gln+Pro+Orn+Cys; 0.736, 26 8.504, 1+His+Asn+Glu+Orn+Met+Ile; 0.736, 264.909, 1+His+Asn+Ser+Orn+Cys+Phe; 0.736, 261.677, 1+His+Asn+Ser+Asp+Thr+Trp; 0.736, 268.252, 1+His+Asn+3MeHis+Pro+Orn+Ile; 0.736, 265.180, 1+His+As n+Tau+3MeHis+Asp+Orn; 0.735, 267.903, 1+His+Asn+Ser+Orn+Met+Le u; 0.735, 267.710, 1+His+Asn+Tau+Thr+Orn+Leu; 0.735, 269.183, 1+H is+Asn+Tau+Orn+Leu+BCAA; 0.735, 267.572, 1+His+Asn+Thr+Orn+Met+Val; 0.735, 267.910, 1+His+Asn+Orn+Ile+Leu+Trp; 0.735, 261.442, 1+His+Asn+3MeHis+Ser+Asp+Thr; 0.735, 263.315, 1+His+Asn+Arg+Gl y+Asp+Cys; 0.735, 264.288, 1+His+Asn+3MeHis+Asp+Orn+Cys; 0.735, 268.109, 1+His+Asn+Tau+Gly+

Orn+Val; 0.735, 267.738, 1+His+Asn+Gln+Thr+Orn+BCAA; 0.735, 266.880, 1+His+Asn+Tau+Orn+Phe+BCAA; 0.735, 268.261, 1+Asn+3MeHis+Asp+Thr+Orn+Ile; 0.735, 268.771, 1+His+Asn+3MeHis+Orn+Leu+Trp; 0.735, 267.261, 1+His+Asn+Ser+Pro+Orn+Ile; 0.735, 269.286, 1+His+Asn+3MeHis+Gln+Orn+BCAA; 0.735, 268.127, 1+His+Asn+Tau+Ser+Orn+BCAA; 0.735, 268.925, 1+His+Asn+Orn+Tyr+Leu+Trp; 0.735, 265.983, 1+His+Asn+Asp+Cit+Orn+Leu; 0.735, 266.500, 1+His+Asn+Orn+Lys+Val+Ile; 0.735, 267.528, 1+His+Asn+Gln+Thr+Orn+Lys; 0.735, 269.037, 1+His+Asn+3MeHis+Pro+Orn+Leu; 0.735, 265.519, 1+His+Asn+Ser+Arg+Ile+Phe; 0.735, 267.672, 1+His+Asn+Orn+Cys+Leu+Trp; 0.735, 266.785, 1+His+Asn+Orn+Phe+Trp+BCAA; 0.735, 263.519, 1+His+Asn+Gly+Asp+Ala+Orn; 0.735, 262.576, 1+His+Asn+Gly+Asp+Orn+Tyr; 0.735, 267.727, 1+His+Asn+Gln+Glu+Thr+Orn; 0.735, 268.438, 1+His+Asn+Gln+Orn+Met+Ile; 0.735, 267.673, 1+His+Asn+Thr+Orn+Met+Leu; 0.735, 264.118, 1+His+Asn+3MeHis+Asp+Thr+Lys; 0.735, 267.026, 1+His+Asn+Arg+Orn+Phe+BCAA; 0.735, 267.549, 1+His+Asn+Gln+Gly+Ala+Orn; 0.735, 268.458, 1+His+Asn+Tau+Pro+Orn+Ile; 0.735, 268.425, 1+His+Asn+Gln+Pro+Orn+Ile; 0.735, 267.703, 1+His+Asn+Thr+Pro+Orn+Leu; 0.735, 267.552, 1+His+Asn+Arg+Gly+Lys+Ile; 0.735, 268.256, 1+His+Asn+3MeHis+Orn+Ile+Leu; 0.735, 267.009, 1+His+Asn+Gln+Orn+Phe+BCAA; 0.735, 262.779, 1+His+Asn+Gly+Asp+Thr+Pro; 0.735, 267.889, 1+His+Asn+Tau+Ser+Orn+Leu; 0.735, 267.681, 1+His+Asn+Ser+Orn+Leu+Trp; 0.735, 267.780, 1+His+Asn+Glu+Orn+Tyr+Ile; 0.735, 267.447, 1+His+Asn+Gln+Cit+Thr+Orn; 0.735, 269.165, 1+His+Asn+Gln+Orn+Leu+BCAA; 0.735, 267.584, 1+His+Asn+Gln+Gly+Orn+Trp; 0.735, 267.505, 1+His+Asn+Ser+Orn+Cys+Met; 0.735, 268.081, 1+His+Asn+Gln+Orn+Lys+Ile; 0.735, 267.740, 1+His+Asn+Tau+Gln+Thr+Orn; 0.735, 266.448, 1+His+Asn+Ser+Pro+Orn+Phe; 0.735, 268.018, 1+His+Asn+Orn+Cys+Tyr+BCAA; 0.735, 265.750, 1+His+Asn+3MeHis+Asp+Orn+Met; 0.735, 268.256, 1+His+Asn+3MeHis+Orn+Met+Ile; 0.735, 266.426, 1+His+Asn+Gln+Asp+Orn+Leu; 0.735, 267.572, 1+His+Asn+3MeHis+Gln+Gly+Orn; 0.735, 261.433, 1+His+Asn+Ser+Asp+Val+Ile; 0.735, 269.090, 1+His+Asn+Orn+Met+Leu+Trp; 0.735, 267.726, 1+His+Asn+Thr+Ala+Orn+Leu; 0.735, 266.171, 1+His+Asn+Gly+Orn+Tyr+Phe; 0.735, 268.441, 1+His+Asn+Pro+Orn+Ile+Leu; 0.735, 268.093, 1+His+Asn+Tau+Orn+Lys+Ile; 0.735, 267.514, 1+His+Asn+Ser+Pro+Orn+Cys; 0.735, 267.422, 1+His+Asn+Tau+Gly+Orn+Cys; 0.735, 269.218, 1+His+Asn+Ala+Orn+Leu+BCAA; 0.735, 264.571, 1+His+Asn+Cit+Val+Phe+BCAA; 0.735, 264.986, 1+His+Asn+Tau+Asp+Orn+Cys; 0.735, 262.431, 1+His+Asn+Gly+Asp+Thr+Cys; 0.735, 268.183, 1+His+Asn+Ser+Glu+Orn+BCAA; 0.735, 268.180, 1+His+Asn+Ser+Orn+Met+BCAA; 0.735, 268.463, 1+His+Asn+Tau+Orn+Met+Ile; 0.735, 268.659, 1+His+Asn+3MeHis+Arg+Orn+BCAA; 0.735, 268.127, 1+His+Asn+Cit+Orn+Leu+Trp; 0.735, 268.186, 1+His+Asn+Ser+Gln+Pro+Orn; 0.735, 267.770, 1+His+Asn+Orn+Tyr+Ile+Leu; 0.735, 266.647, 1+His+Asn+Thr+Orn+Cys+Lys; 0.735, 268.945, 1+His+Asn+Gln+Arg+Orn+Leu; 0.735, 269.220, 1+His+Asn+Pro+Orn+Leu+BCAA; 0.735, 269.178, 1+His+Asn+Orn+Met+Leu+BCAA; 0.735, 268.326, 1+His+Asn+Ala+Orn+Cys+BCAA; 0.735, 265.343, 1+His+Asn+3MeHis+Asp+Pro+Orn; 0.735, 268.464, 1+His+Asn+Tau+Glu+Orn+Ile; 0.735, 267.734, 1+His+Asn+Gln+Thr+Ala+Orn; 0.735, 267.430, 1+His+Asn+Gly+Ala+Orn+Cys; 0.735, 262.842, 1+His+Asn+Gly+Asp+Thr+Ala; 0.735, 266.286, 1+His+Asn+Asp+Orn+Met+Leu; 0.735, 267.891, 1+His+Asn+Ser+Pro+Orn+Leu; 0.735, 269.407, 1+His+Asn+Gln+Orn+Met+Leu; 0.735, 268.926, 1+His+Asn+Orn+Tyr+Leu+BCAA; 0.735, 268.440, 1+His+Asn+Gln+Glu+Orn+Ile; 0.735, 268.599, 1+His+Asn+Arg+Orn+Leu+BCAA; 0.735, 268.459, 1+His+Asn+Glu+Orn+Ile+Leu; 0.735, 263.358, 1+Asn+Ser+Asp+Glu+Thr+Orn; 0.735, 265.674, 1+His+Asn+3MeHis+Arg+Asp+Ile; 0.735, 260.525, 1+His+Asn+Ser+Asp+Cit+Trp; 0.735, 266.515, 1+His+Asn+Orn+Cys+Val+Phe; 0.734, 267.584, 1+His+Asn+Gln+Gly+Orn+Lys; 0.734, 267.265, 1+His+Asn+Gln+Gly+Orn+Met; 0.734, 267.841, 1+His+Asn+Thr+Ala+Pro+Orn; 0.734, 267.433, 1+His+Asn+Ser+Orn+Tyr+BCAA; 0.734, 263.812, 1+His+Asn+Arg+Gly+Asp+Leu; 0.734, 267.709, 1+His+Asn+Glu+Thr+Orn+Leu; 0.734, 265.353, 1+His+Asn+3MeHis+Asp+Cit+Orn; 0.734, 267.280, 1+His+Asn+Arg+Thr+Orn+Leu; 0.734, 267.272, 1+His+Asn+Cit+Orn+Lys+Ile; 0.734, 267.536, 1+His+Gly+Asp+Orn+Leu+Phe; 0.734, 268.167, 1+His+Asn+Ser+Gln+Orn+Val; 0.734, 267.303, 1+His+Asn+Gln+Orn+Ile+BCAA; 0.734, 267.824, 1+His+Asn+Thr+Ala+Orn+Met; 0.734, 267.734, 1+His+Asn+Thr+Ala+Orn+Val; 0.734, 268.124, 1+His+Asn+Gly+Pro+Orn+Val; 0.734, 267.448, 1+His+Asn+Gln+Arg+Thr+Orn; 0.734, 266.446, 1+His+Asn+Asp+Pro+Orn+BCAA; 0.734, 267.011, 1+His+Asn+Asp+Orn+Val+Phe+BCAA; 0.734, 268.200, 1+His+Asn+Ser+Gln+Glu+Orn; 0.734, 267.769, 1+His+Asn+Thr+Pro+Orn+Met; 0.734, 268.884, 1+His+Asn+Arg+Pro+Orn+Leu; 0.734, 266.591, 1+His+Asn+Gln+Gly+Cit+Orn; 0.734, 268.156, 1+His+Asn+Glu+Orn+Lys+Ile; 0.734, 266.417, 1+His+Asn+Arg+Asp+Orn+Leu; 0.734, 268.159, 1+His+Asn+3MeHis+Ser+Gln+Orn; 0.734, 268.401, 1+His+Asn+Tau+Gln+Orn+Ile; 0.734, 269.399, 1+His+Asn+3MeHis+Glu+Orn+BCAA; 0.734, 267.041, 1+His+Asn+Gly+Cit+Orn+Val; 0.734, 269.453, 1+His+Asn+3MeHis+Orn+Met+BCAA; 0.734, 264.723, 1+His+Asn+Asp+Lys+Ile+BCAA; 0.734, 267.828, 1+His+Asn+Tau+Thr+Orn+Met; 0.734, 269.417, 1+His+Asn+Tau+3MeHis+Orn+BCAA; 0.734, 269.067, 1+His+Asn+Tau+Orn+Leu+Trp; 0.734, 266.861, 1+His+Asn+Ser+Orn+Ile+BCAA; 0.734, 267.509, 1+His+Asn+3MeHis+Ser+Orn+Cys; 0.734, 269.443, 1+His+Asn+3MeHis+Pro+Orn+BCAA; 0.734, 269.149, 1+His+Asn+Ala+Orn+Leu+Trp; 0.734, 266.463, 1+His+Asn+Gly+Cit+Orn+Cys; 0.734, 267.631, 1+His+Asn+Cit+Ala+Orn+Ile; 0.734, 268.329, 1+His+Asn+Orn+Cys+Met+BCAA; 0.734, 265.065, 1+His+Asn+Ser+Cit+Orn+Phe; 0.734, 266.963, 1+His+Tau+Orn+Val+Phe+BCAA; 0.734, 268.385, 1+His+Asn+Gln+Gly+Orn+Leu+Phe; 0.734, 268.328, 1+His+Asn+Tau+Orn+Cys+BCAA; 0.734, 268.664, 1+His+Asn+Arg+Orn+Met+Leu; 0.734, 268.138, 1+His+Asn+Pro+Orn+Lys+Ile; 0.734, 268.940, 1+His+Asn+Arg+Glu+Orn+Leu; 0.734, 268.440, 1+His+Asn+Gly+Ala+Pro+Orn; 0.734, 268.696, 1+His+Asn+3MeHis+Orn+Lys+Leu; 0.734, 267.574, 1+His+Asn+Thr+Pro+Orn+Val; 0.734, 268.626, 1+His+Asn+Cit+Pro+Orn+Leu; 0.734, 268.195, 1+His+Asn+Cit+Orn+Cys+Val; 0.734, 268.087, 1+His+Asn+3MeHis+Cit+Orn+Cys; 0.734, 269.012, 1+His+Asn+Orn+Tyr+Met+Leu; 0.734, 267.828, 1+His+Asn+Glu+Thr+Orn+Met; 0.734, 267.436, 1+His+Asn+Gly+Pro+Orn+Cys; 0.734, 268.384, 1+His+Asn+Tau+Orn+Ile+Leu; 0.734, 269.226, 1+His+Asn+Glu+Orn+Leu+BCAA; 0.734, 268.144, 1+His+Asn+Orn+Lys+Met+Ile; 0.734, 269.126, 1+His+Asn+Orn+Lys+Leu+BCAA; 0.734, 266.149, 1+His+Asn+Asp+Orn+Leu+Trp; 0.734, 262.967, 1+His+Asn+Tau+Gly+Asp+Thr; 0.734, 269.123, 1+His+Asn+Orn+Leu+Trp; 0.734, 267.715, 1+His+Asn+Glu+Thr+Orn+Val; 0.734, 268.434, 1+His+Asn+Tau+Gln+Orn+Cys; 0.734, 269.469, 1+His+Asn+Pro+Orn+Met+Leu; 0.734, 269.134, 1+His+Asn+Pro+Orn+Leu+Trp; 0.734, 266.400, 1+His+Asn+Ser+Ala+Orn+Phe; 0.734, 268. 184, 1+His+Asn+Ser+Gln+Orn+Met; 0.734, 267.333, 1+His+Asn+Orn+L ys+Ile+BCAA; 0.734, 266.336, 1+His+Asn+Ser+Cit+Orn+Leu; 0.734, 2 68.462, 1+His+Asn+Orn+Met+Ile+Leu; 0.734, 266.475, 1+His+Asn+As p+Orn+Tyr+Leu; 0.734, 267.563, 1+His+3MeHis+Gly+Orn+Leu+Phe; 0. 734, 267.811, 1+His+Asn+Thr+Ala+Orn+Tyr; 0.734, 268.368, 1+His+A sn+Gln+Orn+Ile+Leu; 0.734, 265.865, 1+His+Asn+3MeHis+Asp+Orn+V al; 0.734, 268.136, 1+His+Asn+Orn+Lys+Ile+Leu; 0.734, 266.407, 1+His+Asn+Asp+Pro+Orn+Met; 0.734, 265.559, 1+His+Asn+Gly+Orn+Cys+Phe; 0.734, 266.820, 1+His+Asn+Tau+Ser+Arg+Orn; 0.734, 267.401, 1+His+Asn+Thr+Orn+Lys+Leu; 0.734, 267.688, 1+His+Asn+Thr+Orn+T yr+BCAA; 0.734, 267.910, 1+His+Asn+Orn+Cys+Trp+BCAA; 0.734, 267. 938, 1+His+Asn+Gln+Cit+Orn+Cys; 0.734, 268.935, 1+His+Asn+Tau+A rg+Orn+Leu; 0.734, 265.819, 1+His+Asn+3MeHis+Asp+Glu+Orn; 0.734, 267.916, 1+His+Asn+Cit+Pro+Orn+Cys; 0.734, 266.357, 1+His+Asn+A sp+Orn+Lys+Leu; 0.734, 266.307, 1+His+3MeHis+Orn+Cys+Leu+Phe; 0. 734, 267.786, 1+His+Asn+Ser+Gly+Orn+Val; 0.734, 269.201, 1+His+A sn+Gln+Orn+Tyr+Leu; 0.734, 268.882, 1+His+Asn+Arg+Orn+Tyr+Leu; 0.734, 266.864, 1+His+Asn+Pro+Orn+Cys+Phe; 0.734, 267.707, 1+His+Ser+Asp+Orn+Leu+Phe; 0.734, 268.180, 1+His+Asn+Ser+Pro+Orn+BC AA; 0.734, 268.317, 1+His+Asn+3MeHis+Gln+Orn+Cys; 0.734, 267.817, 1+His+Asn+Thr+Orn+Met+BCAA; 0.734, 267.486, 1+His+Asn+Ser+Orn+Cys+Lys; 0.734, 264.454, 1+His+Asn+Tau+Asp+Val+BCAA; 0.734, 261. 869, 1+His+Asn+Gly+Asp+Cit+Ile; 0.733, 268.198, 1+His+Asn+Ser+G ln+Orn+Lys; 0.733, 268.125, 1+His+Asn+3MeHis+Ser+Orn+BCAA; 0.73 3, 261.567, 1+His+Asn+Ser+Asp+Glu+Lys; 0.733, 268.328, 1+His+Asn+Cit+Orn+Leu+BCAA; 0.733, 265.970, 1+His+Asn+Asp+Cit+Pro+Orn; 0. 733, 265.744, 1+His+Asn+Asp+Pro+Orn+Phe; 0.733, 267.797, 1+His+S er+Asp+Ala+Orn+Phe; 0.733, 266.691, 1+His+Asn+Ser+Cit+Orn+BCA A; 0.733, 267.458, 1+His+Asn+Cit+Thr+Orn+Met; 0.733, 267.299, 1+H is+Asn+Cit+Thr+Orn+Leu; 0.733, 259.836, 1+His+Asn+Ser+Asp+Glu+Cit; 0.733, 259.762, 1+His+Asn+Ser+Gly+Asp+Cit; 0.733, 262.994, 1+His+Asn+Gly+Asp+Thr+BCAA; 0.733, 266.587, 1+His+Asn+Asp+Pro+O rn+Tyr; 0.733, 268.053, 1+His+Asn+Gly+Orn+Met+Val; 0.733, 267.42 7, 1+His+Asn+Glu+Orn+Ile+BCAA; 0.733, 267.107, 1+His+Asn+Ser+Gl y+Orn+Cys; 0.733, 269.472, 1+His+Asn+Gln+Glu+Orn+Leu; 0.733, 267. 442, 1+His+Asn+Arg+Gly+Orn+Val; 0.733, 267.664, 1+His+Asn+Thr+P ro+Orn+Tyr; 0.733, 265.111, 1+His+Asn+Asp+Orn+Cys+Tyr; 0.733, 26 7.469, 1+His+3MeHis+Cit+Orn+Leu+Phe; 0.733, 267.984, 1+His+Asn+3MeHis+Arg+Orn+Cys; 0.733, 269.176, 1+His+Asn+Pro+Orn+Tyr+Leu; 0.733, 263.183, 1+His+Asn+Gly+Asp+Ile+BCAA; 0.733, 267.383, 1+Hi s+Asn+Cit+Thr+Pro+Orn; 0.733, 268.939, 1+His+Asn+Arg+Ala+Orn+L eu; 0.733, 266.290, 1+His+Asn+Tau+Asp+Orn+Leu; 0.733, 264.826, 1+His+Asn+Asp+Cit+Orn+Cys; 0.733, 268.044, 1+His+Asn+Ser+Gln+Orn+Tyr; 0.733, 269.184, 1+His+Asn+3MeHis+Orn+Trp+BCAA; 0.733, 267. 534, 1+His+Asn+Thr+Orn+Tyr+Met; 0.733, 269.177, 1+His+Asn+3MeHi s+Orn+Tyr+BCAA; 0.733, 267.902, 1+His+Asn+Arg+Pro+Orn+Cys; 0.73 3, 267.680, 1+His+Asn+Thr+Orn+Tyr+Val; 0.733, 269.453, 1+His+Asn+Tau+Orn+Met+Leu; 0.733, 269.446, 1+His+Asn+Gln+Pro+Orn+Leu; 0. 733, 268.564, 1+His+Asn+3MeHis+Cit+Orn+BCAA; 0.733, 262.961, 1+H is+Asn+Gly+Asp+Thr+Met; 0.733, 260.253, 1+His+Asn+Ser+Gly+Asp+Thr; 0.733, 267.099, 1+His+Asn+Ser+Arg+Pro+Orn; 0.733, 268.039, 1+His+Asn+Arg+Gly+Val+Leu; 0.733, 267.517, 1+His+Asn+Cit+Thr+Or n+Tyr; 0.733, 267.434, 1+His+Asn+Cit+Thr+Orn+Val; 0.733, 269.270, 1+His+Asn+Arg+Pro+Orn+BCAA; 0.733, 267.415, 1+His+Asn+3MeHis+O rn+Val+Phe; 0.733, 268.523, 1+His+Ser+Asp+Cit+Orn+Phe; 0.733, 26 7.124, 1+His+Gly+Orn+Cys+Leu+Phe; 0.733, 268.165, 1+His+Asn+Ser+Gln+Orn+Trp; 0.733, 268.537, 1+His+Asn+Ser+Ala+Orn+Val; 0.733, 267.523, 1+His+Asn+Pro+Orn+Ile+BCAA; 0.733, 267.754, 1+His+Asn+Gln+Arg+Gly+Ile; 0.733, 267.413, 1+His+Asn+Arg+Thr+Pro+Orn; 0.7 33, 268.914, 1+His+Asn+Arg+Orn+Lys+Leu; 0.733, 267.623, 1+His+As n+Cit+Pro+Orn+Ile; 0.733, 266.245, 1+His+Asn+Asp+Ala+Orn+Leu; 0. 733, 263.656, 1+Asn+3MeHis+Ser+Asp+Thr+Phe; 0.733, 268.436, 1+Hi s+Asn+Tau+Ser+Ala+Orn; 0.733, 267.923, 1+His+Asn+Ser+Orn+Trp+B CAA; 0.733, 267.853, 1+His+Asn+Tau+Thr+Pro+Orn; 0.733, 268.119, 1+His+Asn+Gly+Orn+Lys+Val; 0.733, 267.702, 1+His+Asn+Gln+Cit+Or n+Ile; 0.733, 264.615, 1+His+Asn+Asp+Tyr+Val+Ile; 0.733, 266.992, 1+His+Asn+Ser+Arg+Orn+Lys; 0.733, 267.585, 1+His+Asn+Thr+Orn+L ys+Met; 0.733, 268.146, 1+His+Asn+3MeHis+Gly+Orn+Val; 0.733, 268. 130, 1+His+Asn+Gly+Orn+Tyr+Val; 0.733, 267.853, 1+His+Asn+Glu+T hr+Pro+Orn; 0.733, 269.200, 1+His+Asn+Tau+Orn+Tyr+Leu; 0.733, 26 8.710, 1+His+Asn+3MeHis+Orn+Cys+Val; 0.733, 267.482, 1+His+Asn+Gly+Orn+Cys+Met; 0.733, 267.844, 1+His+Asn+Thr+Pro+Orn+BCAA; 0. 733, 268.619, 1+His+Asn+Arg+Orn+Leu+Trp; 0.733, 266.907, 1+His+A sn+Ser+Arg+Orn+Val; 0.733, 267.811, 1+His+Asn+Tau+Thr+Orn+Tyr; 0.733, 267.275, 1+His+Asn+Thr+Tyr+Val+BCAA; 0.733, 269.451, 1+Hi s+Asn+Tau+Gln+Orn+Leu; 0.733, 264.949, 1+His+Asn+Asp+Glu+Orn+C ys; 0.733, 268.443, 1+His+Orn+Tyr+Val+Phe+BCAA; 0.733, 267.706, 1+His+Asn+Tau+Thr+Orn+Val; 0.733, 266.895, 1+His+Asn+Ser+Arg+Gl y+Orn; 0.733, 267.621, 1+His+Asn+Arg+Gly+Glu+Ile; 0.733, 267.687, 1+His+Asn+Thr+Orn+Lys+Tyr; 0.733, 267.337, 1+His+Asn+Tau+Gly+C it+Orn; 0.733, 267.378, 1+His+Asn+Arg+Thr+Orn+Val; 0.733, 269.49 4, 1+His+Asn+Tau+Pro+Orn+Leu; 0.733, 269.513, 1+His+Asn+Glu+Pro+Orn+Leu; 0.733, 269.517, 1+His+Asn+Ala+Pro+Orn+Leu; 0.733, 268. 076, 1+His+Asn+Orn+Cys+Lys+BCAA; 0.733, 260.731, 1+His+Asn+Ser+Asp+Cit+Val; 0.733, 267.984, 1+His+Ser+Gln+Asp+Orn+Phe; 0.733, 2 68.494, 1+His+Asn+Tau+Ser+Orn+Val; 0.733, 267.944, 1+His+Asn+Gl u+Thr+Ala+Orn; 0.733, 267.909, 1+His+Asn+Glu+Thr+Orn+BCAA; 0.73 3, 267.645, 1+His+Asn+Tau+Cit+Orn+Ile; 0.733, 260.445, 1+His+Asn+Ser+Asp+Cit+Pro; 0.733, 267.709, 1+His+Asn+Glu+Cit+Orn+Ile; 0. 733, 267.237, 1+His+3MeHis+Pro+Orn+Leu+Phe; 0.733, 267.914, 1+Hi s+Asn+Gly+Glu+Orn+Val; 0.733, 266.836, 1+His+Asn+Ser+Gln+Cit+O rn; 0.733, 267.266, 1+His+Asn+Ser+Orn+Cys+Tyr; 0.733, 269.203, 1+His+Asn+Glu+Orn+Tyr+Leu; 0.733, 267.564, 1+His+Asn+3MeHis+Orn+Ile+BCAA; 0.733, 267.596, 1+His+Asn+Tau+Cit+Thr+Orn; 0.733, 268. 727, 1+His+Asn+Tau+Pro+Orn+Cys; 0.733, 264.282, 1+His+Asn+Asp+V al+Leu+BCAA; 0.733, 264.282, 1+His+Asn+Asp+Val+Ile+BCAA; 0.733, 264.282, 1+His+Asn+Asp+Val+Ile+Leu; 0.733, 264.282, 1+His+Asn+A sp+Ile+Leu+BCAA; 0.733, 267.812, 1+His+Asn+Glu+Thr+Orn+Tyr; 0.7 33, 269.741, 1+His+Asn+Gln+Pro+Orn+BCAA; 0.733, 268.116, 1+His+A sn+Tau+Cit+Orn+Cys; 0.733, 269.515, 1+His+Asn+Tau+Ala+Orn+Leu; 0.733, 266.012, 1+His+Asn+3MeHis+Asp+Orn+Trp; 0.732, 268.356, 1+His+Asn+Tau+Ser+Orn+Trp; 0.732, 267.081, 1+His+Asn+Ser+Arg+Glu+Orn; 0.732, 268.068, 1+His+Asn+Ser+Orn+Lys+BCAA; 0.732, 267.644, 1+His+Asn+Thr+Orn+Lys+Val; 0.732, 267.943, 1+His+Asn+Tau+Glu+T hr+Orn; 0.732, 268.702, 1+His+Asn+Tau+Cit+Orn+Leu; 0.732, 269.481, 1+His+Asn+Glu+Orn+Met+Leu; 0.732, 266.281, 1+His+Asn+Tau+Asp+Pro+Orn; 0.732, 267.948, 1+His+Asn+Thr+Lys+Ile+BCAA; 0.732, 264.483, 1+His+Asn+Asp+Val+Ile+Trp; 0.732, 267.707, 1+His+Asn+Cit+Orn+Ile+Leu; 0.732, 266.136, 1+His+Asn+Ser+Gly+Orn+Phe; 0.732, 266.545, 1+His+Asn+Asp+Pro+Orn+Trp; 0.732, 262.962, 1+His+Asn+Gly+Asp+Thr+Leu; 0.732, 265.153, 1+His+Asn+Asp+Orn+Cys+Met; 0.732, 267.771, 1+His+Asn+Tau+Thr+Orn+Lys; 0.732, 267.095, 1+His+Asn+Ser+Arg+Ala+Orn; 0.732, 266.880, 1+His+Asn+Ser+Arg+Orn+Met; 0.732, 266.401, 1+His+Asn+Ser+Glu+Orn+Phe; 0.732, 267.911, 1+His+Asn+Thr+Ala+Orn+BCAA; 0.732, 267.665, 1+Asn+Asp+Thr+Orn+Val+Ile; 0.732, 268.463, 1+His+Asn+Cit+Orn+Tyr+Leu; 0.732, 267.724, 1+His+Asn+Cit+Orn+Met+Ile; 0.732, 263.616, 1+His+Asn+3MeHis+Gly+Asp+Cit; 0.732, 265.218, 1+His+Asn+Gln+Asp+Orn+Cys; 0.732, 267.067, 1+His+3MeHis+Orn+Val+Leu+Phe; 0.732, 268.111, 1+His+Asn+Thr+Val+Trp+BCAA; 0.732, 266.463, 1+His+Asn+Ser+Arg+Cit+Orn; 0.732, 269.483, 1+His+Asn+Gln+Ala+Orn+Leu; 0.732, 267.869, 1+His+Asn+Arg+Gly+Pro+Orn; 0.732, 267.601, 1+His+Asn+Glu+Cit+Thr+Orn; 0.732, 269.140, 1+His+Asn+Glu+Orn+Leu+Trp; 0.732, 267.392, 1+His+Asn+3MeHis+Gly+Orn+Cys; 0.732, 268.683, 1+His+Asn+Cit+Orn+Met+Leu; 0.732, 269.485, 1+His+Asn+Ala+Orn+Met+Leu; 0.732, 269.607, 1+His+Asn+3MeHis+Gln+Pro+Orn; 0.732, 267.943, 1+His+Asn+Tau+Thr+Ala+Orn; 0.732, 267.428, 1+His+Asn+Ser+Orn+Cys+Trp; 0.732, 269.513, 1+His+Asn+Tau+Glu+Orn+Leu; 0.732, 267.717, 1+Asn+3MeHis+Thr+Orn+Ile+Phe; 0.732, 267.472, 1+His+Asn+Tau+Arg+Ile+BCAA; 0.732, 267.159, 1+His+Asn+Ser+Arg+Orn+Tyr; 0.732, 267.647, 1+His+Asn+Thr+Pro+Orn+Lys; 0.732, 267.864, 1+His+Asn+Arg+Gly+Orn+Tyr; 0.732, 268.764, 1+His+Asn+Ala+Pro+Orn+Cys; 0.732, 267.522, 1+His+Asn+Gly+Orn+Cys+Tyr; 0.732, 266.207, 1+His+Tau+Ser+Asp+Orn+Phe; 0.732, 268.535, 1+His+Asn+Tau+Ser+Pro+Orn; 0.732, 266.683, 1+His+Asn+Ser+Gln+Arg+Orn; 0.732, 268.645, 1+His+Asn+Ser+Ala+Pro+Orn; 0.732, 268.157, 1+His+Asn+Arg+Gly+Ala+Ile; 0.732, 267.610, 1+His+Asn+Cit+Thr+Ala+Orn; 0.732, 269.054, 1+His+Asn+Orn+Lys+Leu+Trp; 0.732, 267.944, 1+His+Asn+Arg+Orn+Cys+Met; 0.732, 267.665, 1+His+Pro+Orn+Val+Phe+BCAA; 0.732, 268.025, 1+His+Asn+Tau+Ser+Gly+Orn; 0.732, 269.800, 1+His+Asn+3MeHis+Gln+Orn+Val; 0.732, 268.304, 1+His+Asn+Tau+Gly+Orn+Met; 0.732, 265.941, 1+His+Asn+3MeHis+Arg+Asp+Orn; 0.732, 268.385, 1+His+Asn+Gln+Glu+Orn+Cys; 0.732, 269.052, 1+His+Asn+Arg+Orn+Met+BCAA; 0.732, 267.552, 1+His+Asn+Cit+Thr+Orn+BCAA; 0.732, 261.831, 1+His+Asn+Ser+Asp+Thr+BCAA; 0.732, 259.723, 1+His+Asn+Ser+Asp+Cit+Cys; 0.732, 268.434, 1+His+Asn+Tau+Gly+Ala+Orn; 0.732, 268.039, 1+His+Asn+Gly+Orn+Val+Trp; 0.732, 268.773, 1+His+Asn+Pro+Orn+Cys+Met; 0.732, 265.990, 1+His+Asn+3MeHis+Gln+Asp+Orn; 0.732, 268.740, 1+His+Asn+Gln+Cit+Orn+Leu; 0.732, 263.187, 1+His+Asn+Asp+Cys+Val+Ile; 0.732, 268.796, 1+His+Gly+Orn+Leu+Phe+BCAA; 0.732, 268.526, 1+His+Asn+Tau+3MeHis+Ser+Orn; 0.732, 267.567, 1+His+Asn+Orn+Met+Ile+BCAA; 0.732, 268.738, 1+His+Asn+Tau+3MeHis+Orn+Cys; 0.732, 268.465, 1+His+Asn+Gln+Orn+Cys+Met; 0.732, 269.859, 1+His+Asn+Ala+Pro+Orn+BCAA; 0.732, 268.751, 1+His+Asn+Pro+Orn+Cys+Val; 0.732, 269.364, 1+His+Asn+Pro+Orn+Lys+Leu; 0.732, 264.891, 1+His+Asn+3MeHis+Asp+Lys+Ile; 0.732, 267.917, 1+His+Asn+Arg+Gly+Ile+Trp; 0.732, 267.841, 1+His+Asn+Glu+Cit+Orn+Cys; 0.732, 268.387, 1+His+Gly+Orn+Val+Leu+Phe; 0.732, 268.437, 1+His+Asn+Tau+Gly+Orn+Trp; 0.732, 267.911, 1+His+Asn+Tau+Thr+Orn+BCAA; 0.732, 269.302, 1+His+Asn+Orn+Lys+Met+Leu; 0.732, 266.029, 1+His+Asn+Ser+Orn+Lys+Phe; 0.732, 268.267, 1+His+Asn+Cit+Ala+Orn+Cys; 0.732, 266.857, 1+His+3MeHis+Ser+Asp+Orn+Phe; 0.732, 268.620, 1+His+Asn+3MeHis+Ser+Orn+Val; 0.732, 266.970, 1+His+Asn+Tau+Ser+Cit+Orn; 0.732, 267.849, 1+His+Asn+Tau+Arg+Gly+Orn; 0.732, 267.581, 1+His+Asn+Tau+Arg+Thr+Orn; 0.732, 269.493, 1+His+Asn+Gln+Orn+Trp+BCAA; 0.732, 267.571, 1+His+Asn+Arg+Thr+Orn+Tyr; 0.732, 266.506, 1+His+Asn+Ser+Orn+Phe+Trp; 0.732, 267.348, 1+His+Asn+Gly+Cit+Pro+Orn; 0.732, 267.516, 1+His+Asn+Gly+Orn+Cys+Lys; 0.732, 266.423, 1+His+Asn+Tau+Gly+Orn+Phe; 0.732, 269.536, 1+His+Asn+Glu+Ala+Orn+Leu; 0.732, 268.337, 1+His+Asn+Pro+Orn+Tyr+Phe; 0.732, 262.137, 1+His+Asn+Ser+Asp+Thr+Leu; 0.732, 267.775, 1+His+Asn+Glu+Thr+Orn+Lys; 0.732, 267.215, 1+His+Asn+Ser+Arg+Gly+Ile; 0.732, 266.342, 1+His+Asn+Ser+Orn+Tyr+Phe; 0.732, 262.852, 1+His+Asn+Gly+Asp+Cit+Pro; 0.732, 269.362, 1+His+Asn+Tau+Orn+Lys+Leu; 0.732, 264.509, 1+His+Asn+Asp+Glu+Val+Ile; 0.732, 269.443, 1+His+Asn+Orn+Met+Trp+BCAA; 0.732, 266.665, 1+His+Asn+Asp+Pro+Orn+Lys; 0.732, 266.131, 1+His+Asn+Gly+Cit+Orn+Phe; 0.732, 268.876, 1+His+Tau+Gly+Orn+Leu+Phe; 0.732, 269.210, 1+His+Asn+3MeHis+Orn+Lys+BCAA; 0.732, 267.154, 1+His+Asn+Ser+Arg+Orn+Trp; 0.732, 268.512, 1+His+Asn+Arg+Cit+Orn+Leu; 0.732, 269.095, 1+His+Asn+Orn+Lys+Tyr+Leu; 0.732, 266.574, 1+His+Asn+Cit+Orn+Cys+Phe; 0.732, 266.788, 1+His+3MeHis+Asp+Orn+Phe+BCAA; 0.732, 268.526, 1+His+Asn+Tau+Ser+Orn+Met; 0.732, 266.489, 1+His+Asn+Ser+Arg+Cys+Ile; 0.732, 268.515, 1+His+Asn+Tau+Gly+Orn+Lys; 0.732, 267.774, 1+His+Asn+Thr+Ala+Orn+Lys; 0.732, 267.915, 1+His+Asn+3MeHis+Ser+Arg+Ile; 0.732, 267.431, 1+His+Asn+Cit+Thr+Orn+Lys; 0.732, 269.843, 1+His+Asn+Ala+Orn+Met+BCAA; 0.732, 267.285, 1+His+Asn+Ser+Cit+Ala+Orn; 0.732, 269.791, 1+His+Asn+Pro+Orn+Met+BCAA; 0.732, 266.853, 1+His+Asn+Gly+Pro+Orn+Phe; 0.732, 268.755, 1+His+Asn+Glu+Cit+Orn+Leu; 0.732, 266.165, 1+His+Asn+Asp+Glu+Orn+Met; 0.732, 262.606, 1+His+Asn+Gly+Asp+Cit+Cys; 0.731, 268.512, 1+His+Asn+Tau+Gly+Orn+Tyr; 0.731, 267.784, 1+His+Asn+Gln+Thr+Val+Ile; 0.731, 267.672, 1+His+Asn+Thr+Orn+Lys+BCAA; 0.731, 267.220, 1+His+Asn+Ser+Cit+Orn+Tyr; 0.731, 268.509, 1+His+Asn+Gln+Ala+Orn+Cys; 0.731, 269.537, 1+His+Asn+Tau+3MeHis+Gln+Orn; 0.731, 265.712, 1+His+Asn+Asp+Orn+Met+Phe; 0.731, 266.676, 1+His+Asn+Gln+Asp+Pro+Orn; 0.731, 266.611, 1+His+Asn+Asp+Orn+Met+BCAA; 0.731, 265.755, 1+His+Asn+3MeHis+Asp+Orn+Tyr; 0.731, 266.629, 1+His+Asn+Arg+Asp+Pro+Orn; 0.731, 267.660, 1+His+Asn+Gly+Cit+Ala+Orn; 0.731, 260.775, 1+His+Asn+Ser+Asp+Cit+Ala; 0.731, 266.595, 1+His+Asn+Tau+Asp+Orn+BCAA; 0.731, 260.767, 1+His+Asn+Ser+Asp+Cit+Met; 0.731, 261.243, 1+His+Asn+Ser+Asp+Glu+Phe; 0.731, 268.670, 1+His+Asn+Gly+Ala+Orn+Tyr; 0.731, 267.136, 1+His+Asn+3MeHis+Ser+Arg+Orn; 0.731, 267.578, 1+His+Asn+Arg+Thr+Ala+Orn; 0.731, 269.712, 1+His+Asn+Gln+Orn+Met+BCAA; 0.731, 267.434, 1+His+Asn+Arg+Cit+Thr+Orn; 0.731, 267.523, 1+His+Asn+Arg+Thr+Orn+BCAA; 0.731, 269.202, 1+His+Asn+Ala+Orn+Tyr+Leu; 0.731, 266.199, 1+His+Asn+Ser+Orn+Met+Phe; 0.731, 268.755, 1+His+Asn+Cit+Ala+Orn+Leu; 0.731, 268.250, 1+His+Asn+Cit+Orn+Cys+Tyr; 0.731, 268.924, 1+His+Ser+Ala+Orn+Leu+Phe; 0.731, 266.828, 1+His+Asn+Arg+Asp+Orn+BCAA; 0.

731, 269.502, 1+His+Asn+3MeHis+Arg+Orn+Val; 0.731, 268.365, 1+His+Asn+3MeHis+Glu+Orn+Cys; 0.731, 269.335, 1+His+Asn+Gln+Orn+Lys+Leu; 0.731, 268.568, 1+His+Asn+Glu+Pro+Orn+Cys; 0.731, 267.208, 1+His+Asn+Tau+3MeHis+Orn+Leu+Phe; 0.731, 266.837, 1+His+Asn+Glu+Orn+Cys+Phe; 0.731, 265.105, 1+His+Asn+Arg+Asp+Orn+Cys; 0.731, 268.713, 1+His+Asn+3MeHis+Pro+Orn+Cys; 0.731, 267.215, 1+His+Asn+Arg+Thr+Orn+Met; 0.731, 268.815, 1+His+Asn+Tau+Orn+Cys+Val; 0.731, 264.372, 1+His+Asn+Arg+Gly+Asp+Pro; 0.731, 264.126, 1+His+Asn+Arg+Gly+Asp+BCAA; 0.731, 265.964, 1+His+Asn+3MeHis+Asp+Orn+Lys; 0.731, 266.441, 1+His+Asn+Asp+Cit+Orn+BCAA; 0.731, 266.535, 1+His+Asn+Asp+Orn+Trp+BCAA; 0.731, 267.606, 1+His+Asp+Orn+Val+Leu+Phe; 0.731, 268.424, 1+His+Asn+Tau+Gly+Pro+Orn; 0.731, 268.508, 1+His+Asn+Gln+Orn+Cys+Val; 0.731, 269.848, 1+His+Asn+Glu+Orn+Met+BCAA; 0.731, 264.701, 1+His+Asn+Asp+Met+Val+Ile; 0.731, 263.382, 1+Asn+Ser+Arg+Asp+Glu+Thr; 0.731, 265.104, 1+His+Asn+Asp+Ile+Phe+BCAA; 0.731, 266.506, 1+Asn+Ser+Thr+Orn+Ile+Phe; 0.731, 268.624, 1+His+Asn+Ser+Orn+Lys+Val; 0.731, 266.566, 1+His+Asn+Arg+Asp+Val+Leu; 0.731, 268.103, 1+His+Asn+Arg+Gly+Ile+Leu; 0.731, 269.419, 1+His+Asn+Arg+Glu+Orn+BCAA; 0.731, 269.071, 1+His+Asn+Arg+Orn+Trp+BCAA; 0.731, 267.047, 1+His+Asn+Gly+Ala+Orn+Phe; 0.731, 266.040, 1+His+Asn+Tau+Asp+Glu+Orn; 0.731, 265.380, 1+His+Asn+Asp+Orn+Tyr+Phe; 0.731, 268.690, 1+His+Asn+3MeHis+Ser+Ala+Orn; 0.731, 269.036, 1+His+Asn+Tau+3MeHis+Cit+Orn; 0.731, 269.387, 1+His+Asn+Gln+Arg+Orn+BCAA; 0.731, 268.534, 1+His+Asn+Cit+Orn+Lys+Leu; 0.731, 266.814, 1+His+Asn+Orn+Cys+Met+Phe; 0.731, 262.771, 1+His+Asn+Gly+Asp+Thr+Tyr; 0.731, 267.887, 1+His+3MeHis+Glu+Orn+Leu+Phe; 0.731, 267.527, 1+His+3MeHis+Orn+Val+Phe+BCAA; 0.731, 266.887, 1+His+Asn+Ser+Gly+Cit+Orn; 0.731, 269.401, 1+His+Asn+Arg+Orn+Lys+BCAA; 0.731, 269.400, 1+His+Asn+Arg+Orn+Tyr+BCAA; 0.731, 268.210, 1+His+Asn+Cit+Orn+Cys+Met; 0.731, 268.301, 1+His+Asn+Tau+Ser+Orn+Tyr; 0.731, 268.620, 1+His+Asn+Ser+Glu+Orn+Val; 0.731, 268.707, 1+His+Asn+Ser+Ala+Orn+Lys; 0.731, 268.428, 1+His+Asn+Gly+Ala+Orn+Met; 0.731, 269.412, 1+His+Asn+Tau+Orn+Trp+BCAA; 0.731, 262.064, 1+His+Asn+Ser+Asp+Val+BCAA; 0.731, 264.800, 1+His+Asn+3MeHis+Asp+Val+BCAA; 0.731, 268.020, 1+His+Asn+Arg+Gly+Orn+Lys; 0.731, 267.520, 1+His+Asn+Arg+Thr+Orn+Lys; 0.731, 269.541, 1+His+Asn+Glu+Orn+Trp+BCAA; 0.731, 262.584, 1+His+Asn+3MeHis+Ser+Asp+Lys; 0.731, 268.652, 1+His+Asn+Ser+Pro+Orn+Val; 0.731, 269.414, 1+His+Asn+Arg+Ala+Orn+BCAA; 0.731, 269.378, 1+His+Asn+Glu+Orn+Lys+Leu; 0.731, 264.369, 1+His+Asn+Arg+Gly+Asp+Met; 0.731, 268.208, 1+His+Asn+Cit+Orn+Cys+Lys; 0.731, 266.785, 1+His+Asn+Asp+Orn+Lys+BCAA; 0.731, 265.232, 1+His+Asn+Asp+Orn+Cys+Val; 0.731, 268.527, 1+His+Asn+Tau+Ser+Orn+Lys; 0.731, 268.482, 1+His+Asn+Ser+Orn+Val+Trp; 0.731, 267.583, 1+His+Asn+Arg+Glu+Thr+Orn; 0.731, 268.477, 1+His+Asn+Gly+Pro+Orn+Met; 0.731, 269.540, 1+His+Asn+Ala+Orn+Trp+BCAA; 0.731, 267.275, 1+His+Asn+Arg+Glu+Ile+BCAA; 0.731, 266.391, 1+His+Asn+Tau+Asp+Orn+Met; 0.731, 266.618, 1+His+Asn+Asp+Ala+Pro+Orn; 0.731, 266.846, 1+His+Asn+Gln+Asp+Orn+BCAA; 0.731, 265.116, 1+His+Asn+Asp+Orn+Cys+Trp; 0.731, 268.342, 1+His+Ser+Asp+Glu+Orn+Phe; 0.731, 267.757, 1+His+Asn+Ser+Arg+Val+Leu; 0.731, 267.895, 1+His+Asn+Gln+Arg+Orn+Cys; 0.731, 269.872, 1+His+Asn+Glu+Pro+Orn+BCAA; 0.731, 267.700, 1+His+Asn+Ser+Arg+Lys+Ile; 0.731, 262.111, 1+His+Asn+Ser+Asp+Ile+BCAA; 0.731, 266.837, 1+His+Asn+Cit+Val+Ile+Phe; 0.731, 263.460, 1+His+Asn+Tau+Gly+Asp+Cit; 0.731, 263.620, 1+His+Asn+Gly+Asp+Cit+Lys; 0.731, 267.951, 1+His+Asn+Cit+Orn+Cys+Trp; 0.731, 265.902, 1+Asn+Gly+Thr+Orn+Ile+Phe; 0.731, 260.875, 1+His+Asn+Ser+Asp+Cit+BCAA; 0.731, 267.458, 1+His+3MeHis+Orn+Leu+Phe+BCAA; 0.731, 269.657, 1+His+Asn+3MeHis+Gln+Orn+Met; 0.731, 264.933, 1+His+Asn+Asp+Cit+Ile+BCAA; 0.731, 269.486, 1+His+Asn+Pro+Orn+Trp+BCAA; 0.731, 267.137, 1+His+Asn+Ser+Glu+Cit+Orn; 0.731, 268.355, 1+His+Asn+Pro+Orn+Val+Phe; 0.731, 266.742, 1+His+Asn+Orn+Cys+Tyr+Phe; 0.731, 265.543, 1+His+Asn+3MeHis+Asp+Cit+Thr; 0.731, 264.936, 1+His+Asn+3MeHis+Asp+Orn+Phe; 0.731, 267.959, 1+His+3MeHis+Orn+Tyr+Leu+Phe; 0.730, 266.966, 1+His+Asn+Thr+Tyr+Val+Ile; 0.730, 267.788, 1+His+Asn+Ser+Arg+Tyr+Ile; 0.730, 268.640, 1+His+Asn+Gly+Pro+Orn+Lys; 0.730, 267.685, 1+His+Asn+Ser+Arg+Ile+Leu; 0.730, 267.801, 1+His+Asn+Gln+Orn+Met+Phe; 0.730, 267.490, 1+His+Asn+Gly+Orn+Cys+Trp; 0.730, 265.159, 1+His+Asn+Asp+Tyr+Val+BCAA; 0.730, 269.388, 1+His+Asn+Ala+Orn+Lys+Leu; 0.730, 261.598, 1+His+Asn+Ser+Gly+Asp+Phe; 0.730, 263.384, 1+His+Asn+Arg+Gly+Asp+Tyr; 0.730, 267.836, 1+His+3MeHis+Ser+Orn+Leu+Phe; 0.730, 268.236, 1+His+Asn+3MeHis+Ser+Gly+Orn; 0.730, 268.097, 1+His+Asn+Tau+Arg+Orn+Cys; 0.730, 268.624, 1+His+Asn+Cit+Orn+Trp+BCAA; 0.730, 267.220, 1+His+Asn+Ser+Cit+Orn+Val; 0.730, 266.291, 1+Asn+Gly+Asp+Thr+Val+Ile; 0.730, 267.892, 1+His+Asn+Orn+Met+Val+Phe; 0.730, 266.621, 1+His+Asn+Asp+Glu+Orn+Val; 0.730, 268.439, 1+His+Asn+Tau+Ser+Glu+Orn; 0.730, 268.492, 1+His+Asn+Tau+3MeHis+Gly+Orn; 0.730, 267.970, 1+His+Asn+Ser+Gly+Glu+Orn; 0.730, 268.248, 1+His+Asn+Ser+Orn+Tyr+Val; 0.730, 268.375, 1+His+Asn+Gln+Orn+Cys+Trp; 0.730, 267.377, 1+His+Asn+3MeHis+Ser+Cit+Orn; 0.730, 269.366, 1+His+Asn+Tau+Arg+Orn+BCAA; 0.730, 269.201, 1+His+Asn+Gln+Cit+Orn+BCAA; 0.730, 269.263, 1+His+Asn+Arg+Pro+Orn+Met; 0.730, 266.354, 1+His+Asn+Gly+Orn+Met+Phe; 0.730, 268.292, 1+His+Asn+Orn+Tyr+Val+Phe; 0.730, 269.270, 1+His+Gly+Cit+Orn+Leu+Phe; 0.730, 268.681, 1+His+Asn+Ser+Ala+Orn+Met; 0.730, 269.772, 1+His+Asn+Tau+Orn+Met+BCAA; 0.730, 268.205, 1+His+Asn+3MeHis+Arg+Gly+Ile; 0.730, 267.508, 1+His+Asn+Arg+Gly+Orn+Met; 0.730, 260.797, 1+His+Asn+Ser+Asp+Cit+Tyr; 0.730, 262.822, 1+His+Asn+Gly+Asp+Cit+Leu; 0.730, 264.744, 1+His+Asn+Asp+Ala+Val+Ile; 0.730, 260.167, 1+His+Asn+Tau+Ser+Asp+Cit; 0.730, 267.871, 1+His+Tau+Orn+Val+Leu+Phe; 0.730, 264.985, 1+His+Asn+Asp+Ala+Orn+Cys; 0.730, 268.135, 1+His+Asn+Ser+Gly+Ala+Orn; 0.730, 268.652, 1+His+Asn+Ser+Orn+Met+Val; 0.730, 268.597, 1+His+Asn+3MeHis+Gly+Pro+Orn; 0.730, 268.216, 1+His+Asn+Ser+Arg+Ala+Ile; 0.730, 266.455, 1+His+Asn+3MeHis+Ser+Orn+Phe; 0.730, 268.216, 1+His+Asn+Arg+Gly+Tyr+Ile; 0.730, 266.628, 1+His+Asn+Gly+Glu+Orn+Phe; 0.730, 269.410, 1+His+Asn+Orn+Tyr+Trp+BCAA; 0.730, 267.848, 1+Asn+Thr+Orn+Val+Ile+Phe; 0.730, 260.430, 1+His+Asn+Ser+Asp+Cit+Ile; 0.730, 266.666, 1+His+Asn+Asp+Pro+Orn+Val; 0.730, 268.234, 1+His+Asn+Ser+Gly+Orn+Met; 0.730, 268.154, 1+His+Asn+Gly+Glu+Orn+Met; 0.730, 268.446, 1+His+Asn+Gln+Orn+Cys+Lys; 0.730, 269.122, 1+His+Asn+Cit+Orn+Met+BCAA; 0.730, 268.748, 1+Asn+Asp+Thr+Orn+Ile+BCAA; 0.730, 264.187, 1+Asn+Ser+Asp+Thr+Orn+Ile; 0.730, 266.554, 1+His+Asn+Asp+Glu+Cit+Orn; 0.730, 268.260, 1+His+Asn+Ser+Gly+Pro+Orn; 0.730, 267.204,

1+His+Asn+Ser+Cit+Orn+Trp; 0.730, 268.068, 1+His+Asn+Arg+Orn+Cys+Trp; 0. 730, 264.385, 1+His+Asn+3MeHis+Asp+Val+Ile; 0.730, 264.743, 1+His+Asn+Gln+Asp+Val+Ile; 0.730, 269.012, 1+His+Asn+Cit+Pro+Orn+BCAA; 0.730, 268.044, 1+His+Asn+Pro+Orn+Met+Phe; 0.730, 266.646, 1+His+Asn+Arg+Ile+Phe+BCAA; 0.730, 260.846, 1+His+Asn+Ser+Gln+Asp+Cit; 0.730, 266.662, 1+His+Asn+Asp+Ala+Orn+BCAA; 0.730, 269.9 91, 1+His+Asn+3MeHis+Ala+Pro+Orn; 0.730, 269.770, 1+His+Asn+Tau+Gln+Orn+BCAA; 0.730, 268.199, 1+His+Asn+Tau+Arg+Gly+Ile; 0.730, 268.842, 1+His+Asn+Tau+Ala+Orn+Cys; 0.730, 269.817, 1+His+Asn+Tau+Pro+Orn+BCAA; 0.730, 267.586, 1+His+Asn+Arg+Ile+Trp+BCAA; 0. 730, 268.858, 1+His+Asn+Ala+Orn+Cys+Val; 0.730, 265.650, 1+His+Asn+Asp+Pro+Ile+BCAA; 0.730, 266.949, 1+His+Asn+Arg+Gly+Orn+Phe; 0.730, 265.204, 1+His+Asn+Asp+Orn+Cys+Lys; 0.730, 265.739, 1+Asn+Gly+Asp+Thr+Orn+Ile; 0.730, 268.677, 1+His+Asn+Gly+Ala+Orn+Lys; 0.730, 269.848, 1+His+Asn+Gln+Ala+Orn+BCAA; 0.730, 268.720, 1+His+Asn+Pro+Orn+Cys+Tyr; 0.730, 267.088, 1+Asn+Asp+Thr+Lys+Val+Ile; 0.730, 269.035, 1+His+Asn+Arg+Cit+Orn+BCAA; 0.730, 265.2 48, 1+His+Asn+Asp+Val+Trp+BCAA; 0.730, 268.737, 1+Asn+Asp+Thr+Val+Ile+Trp; 0.730, 265.087, 1+His+Asn+Asp+Glu+Val+BCAA; 0.730, 2 66.381, 1+His+Asn+Arg+Gly+Thr+Ile; 0.730, 267.592, 1+His+Asn+Arg+Ala+Ile+BCAA; 0.730, 261.512, 1+His+Asn+Ser+Asp+Ile+Phe; 0.73 0, 263.774, 1+His+Asn+Arg+Gly+Asp+Cit; 0.730, 264.074, 1+Asn+3MeHis+Ser+Asp+Thr+Orn; 0.730, 266.875, 1+His+Asn+3MeHis+Orn+Cys+Phe; 0.730, 268.804, 1+His+Asn+Tau+Orn+Cys+Met; 0.730, 268.641, 1+His+Asn+Gly+Pro+Orn+Tyr; 0.730, 268.216, 1+His+Asn+Cit+Lys+Val+Ile; 0.730, 268.799, 1+His+Asn+Tau+Orn+Cys+Tyr; 0.730, 267.885, 1+His+Asn+Arg+Cit+Orn+Cys; 0.730, 267.655, 1+His+Asn+Gly+Cit+Orn+Trp; 0.730, 264.032, 1+His+Asn+Gly+Asp+Lys+Leu; 0.730, 267.02 9, 1+His+Asn+Asp+Thr+Val+Trp; 0.730, 268.592, 1+His+Ala+Orn+Val+Leu+Phe; 0.730, 262.212, 1+His+Asn+Ser+Asp+Thr+Tyr; 0.730, 268. 277, 1+His+Gln+Orn+Val+Phe+BCAA; 0.730, 269.623, 1+His+Gly+Orn+Ile+Leu+Phe; 0.730, 268.139, 1+His+Asn+Arg+Orn+Cys+Tyr; 0.730, 2 67.663, 1+His+Asn+Arg+Gly+Glu+Orn; 0.730, 265.023, 1+His+Asn+Tau+Asp+Ile+BCAA; 0.730, 260.854, 1+His+Asn+Ser+Asp+Cit+Leu; 0.73 0, 267.436, 1+His+3MeHis+Gln+Orn+Leu+Phe; 0.730, 268.642, 1+His+Asn+Ser+Glu+Ala+Orn; 0.730, 269.123, 1+His+Asn+3MeHis+Gln+Cit+Orn; 0.730, 269.179, 1+His+Asn+3MeHis+Arg+Orn+Met; 0.730, 269.84 5, 1+His+Asn+Gln+Glu+Orn+BCAA; 0.730, 268.838, 1+His+Asn+Orn+Cys+Met+Val; 0.730, 269.307, 1+His+Asn+3MeHis+Cit+Orn+Val; 0.730, 269.475, 1+His+Gly+Orn+Tyr+Leu+Phe; 0.730, 268.917, 1+His+Asn+Thr+Ile+Trp+BCAA; 0.730, 268.788, 1+His+Asn+3MeHis+Ser+Pro+Orn; 0.730, 266.467, 1+His+Asn+Ser+Arg+Thr+Phe; 0.730, 270.110, 1+His+Asn+3MeHis+Ala+Orn+Val; 0.730, 268.240, 1+His+Asn+Gly+Glu+Pro+Orn; 0.730, 268.673, 1+His+Asn+Gly+Ala+Orn+Trp; 0.730, 267.736, 1+His+Asn+Gly+Cit+Orn+Lys; 0.730, 269.946, 1+His+Asn+Glu+Ala+Orn+BCAA; 0.730, 269.478, 1+His+Asn+Orn+Lys+Trp+BCAA; 0.730, 267. 500, 1+His+Asn+Arg+Gly+Cit+Orn; 0.730, 268.772, 1+His+Asn+Orn+Cys+Tyr+Val; 0.730, 268.594, 1+His+Asn+Tau+Glu+Orn+Cys; 0.730, 26 8.884, 1+His+Ser+Ala+Orn+Ile+Phe; 0.730, 266.281, 1+His+Asn+Asp+Glu+Orn+Tyr; 0.730, 267.937, 1+His+Gly+Pro+Orn+Leu+Phe; 0.729, 268.790, 1+His+Asn+Ser+Pro+Orn+Lys; 0.729, 269.799, 1+His+Asn+Gln+Pro+Orn+Met; 0.729, 268.496, 1+His+Asn+Gln+Orn+Cys+Tyr; 0.72 9, 269.641, 1+His+Asn+Pro+Orn+Tyr+BCAA; 0.729, 269.707, 1+His+Asn+Orn+Lys+Met+BCAA; 0.729, 269.545, 1+His+Asn+Gln+Arg+Pro+Orn; 0.729, 269.142, 1+His+Asn+Tau+Cit+Orn+BCAA; 0.729, 268.113, 1+His+Asn+Gln+Orn+Tyr+Phe; 0.729, 266.690, 1+His+3MeHis+Asp+Orn+Ile+Phe; 0.729, 268.735, 1+His+Gly+Orn+Val+Phe+BCAA; 0.729, 268.71 1, 1+His+Asn+Ser+Pro+Orn+Trp; 0.729, 268.275, 1+His+Asn+Gly+Glu+Ala+Orn; 0.729, 269.815, 1+His+Asn+Tau+Gln+Pro+Orn; 0.729, 267. 598, 1+His+Asn+Arg+Pro+Ile+BCAA; 0.729, 267.109, 1+His+Asn+Gly+Orn+Phe+Trp; 0.729, 266.596, 1+His+Asn+Gln+Orn+Cys+Phe; 0.729, 2 68.624, 1+His+Asn+Ser+Ala+Orn+Trp; 0.729, 267.265, 1+His+Asn+Ser+Cit+Pro+Orn; 0.729, 268.179, 1+His+Asn+Arg+Orn+Cys+Lys; 0.729, 266.900, 1+His+Asn+Gly+Glu+Cit+Orn; 0.729, 270.355, 1+His+Gly+Ala+Orn+Val+Phe; 0.729, 268.619, 1+His+Asn+Gly+Pro+Orn+Trp; 0.72 9, 269.885, 1+His+Asn+Tau+Ala+Orn+BCAA; 0.729, 269.698, 1+His+Asn+Tau+Orn+Tyr+BCAA; 0.729, 269.342, 1+His+Asn+3MeHis+Arg+Pro+Orn; 0.729, 263.254, 1+Asn+3MeHis+Ser+Arg+Asp+Thr; 0.729, 261.850, 1+His+Asn+3MeHis+Ser+Asp+Phe; 0.729, 267.865, 1+His+3MeHis+Arg+Orn+Leu+Phe; 0.729, 267.869, 1+His+3MeHis+Orn+Lys+Leu+Phe; 0.7 29, 267.632, 1+His+Asn+Ser+Arg+Thr+Trp; 0.729, 267.242, 1+His+Asn+Arg+Thr+Val+Leu; 0.729, 268.059, 1+His+Asn+Tau+Gly+Glu+Orn; 0. 729, 268.172, 1+His+Asn+Arg+Ala+Orn+Cys; 0.729, 266.801, 1+His+Asn+Arg+Asp+Orn+Met; 0.729, 271.755, 1+His+Arg+Gly+Ala+Orn+Cys; 0.729, 266.851, 1+His+Asn+Asp+Orn+Tyr+BCAA; 0.729, 268.791, 1+His+Asn+Tau+Orn+Cys+Lys; 0.729, 267.397, 1+His+Asn+Ser+Cit+Orn+Lys; 0.729, 268.089, 1+His+Asn+Arg+Gly+Ala+Orn; 0.729, 269.744, 1+His+Asn+Arg+Pro+Orn+Val; 0.729, 263.668, 1+Asn+Ser+Arg+Asp+Thr+Ile; 0.729, 265.961, 1+His+Asn+3MeHis+Asp+Ala+Orn; 0.729, 266.0 16, 1+His+Asn+3MeHis+Asp+Thr+Val; 0.729, 265.897, 1+His+Ser+Asp+Orn+Cys+Phe; 0.729, 268.811, 1+His+Ser+Asp+Orn+Val+Phe; 0.729, 268.780, 1+His+Asn+Ser+Pro+Orn+Met; 0.729, 269.992, 1+His+Asn+3 MeHis+Pro+Orn+Val; 0.729, 268.152, 1+His+Asn+Ser+Gln+Arg+Ile; 0. 729, 267.709, 1+His+Asn+Gly+Cit+Orn+Tyr; 0.729, 268.117, 1+His+Asn+Gly+Cit+Lys+Ile; 0.729, 266.604, 1+His+Asn+Cit+Thr+Val+Ile; 0.729, 269.737, 1+His+Asn+Tau+Gln+Orn+Met; 0.729, 269.746, 1+His+Asn+Gln+Orn+Lys+BCAA; 0.729, 269.695, 1+His+Asn+Gln+Orn+Tyr+BCAA; 0.729, 267.626, 1+His+Asn+Arg+Lys+Ile+BCAA; 0.729, 265.180, 1+His+Asn+Asp+Ala+Val+BCAA; 0.729, 268.102, 1+His+Asn+Arg+Orn+Cys+Val; 0.729, 266.500, 1+His+Asn+Asp+Cit+Orn+Met; 0.729, 269.1 00, 1+His+Asn+Cit+Orn+Lys+BCAA; 0.729, 268.112, 1+His+Asn+Orn+Lys+Met+Phe; 0.729, 266.992, 1+His+Asn+Orn+Cys+Lys+Phe; 0.729, 26 8.149, 1+His+Pro+Orn+Val+Leu+Phe; 0.729, 268.542, 1+His+Asn+Ser+Ala+Orn+Tyr; 0.729, 269.833, 1+His+Asn+Tau+3MeHis+Pro+Orn; 0.7 29, 269.884, 1+His+Asn+Tau+Glu+Orn+BCAA; 0.729, 268.660, 1+His+Asn+Glu+Orn+Cys+Val; 0.729, 262.336, 1+His+Asn+Ser+Asp+Lys+Phe; 0.729, 269.635, 1+His+Gly+Glu+Orn+Leu+Phe; 0.729, 268.794, 1+His+Asn+3MeHis+Ser+Orn+Met; 0.729, 269.858, 1+His+Asn+Gln+Pro+Orn+Trp; 0.729, 268.587, 1+His+Asn+Tau+Orn+Cys+Trp; 0.729, 268.319, 1+His+Asn+Gly+Glu+Orn+Lys; 0.729, 268.591, 1+His+Asn+Orn+Cys+Val+Trp; 0.729, 269.501, 1+His+Asn+Orn+Tyr+Met+BCAA; 0.729, 269.8 09, 1+His+Asn+Tau+3MeHis+Orn+Met; 0.729, 268.200, 1+His+Asn+Arg+Gly+Pro+Ile; 0.729, 269.090, 1+His+Asn+Cit+Orn+Tyr+BCAA; 0.729, 268.086, 1+His+Asn+Orn+Tyr+Met+Phe; 0.729, 263.767, 1+Asn+Ser+Asp+Thr+Orn+Phe; 0.729, 267.116, 1+His+

Asn+3MeHis+Gly+Orn+Phe; 0. 729, 262.243, 1+His+Asn+ Ser+Asp+Lys+Ile; 0.729, 266.753, 1+His+A sn+Tau+Orn+ Cys+Phe; 0.729, 268.329, 1+His+Arg+Orn+Val+Phe+BCA A; 0.729, 270.003, 1+His+Asn+Gln+Glu+Pro+Orn; 0.729, 268.768, 1+H is+Asn+Gly+Orn+Lys+Tyr; 0.729, 267.582, 1+H is+Asn+Arg+Asp+Thr+Val+Ile; 0.729, 269.501, 1+His+ Asn+Lys+Tyr+Val+BCAA; 0.729, 267.388, 1+His+Asn+ Ser+Cit+Orn+Met; 0.729, 269.253, 1+His+Asn+Cit+Ala+O rn+BCAA; 0.729, 269.201, 1+His+Asn+Arg+Cit+Pro+Orn; 0.729, 264.2 47, 1+His+Asn+Asp+Orn+Cys+Phe; 0.729, 267.186, 1+Asn+Asp+Thr+Va 1+Ile+Phe; 0.729, 266.443, 1+His+Asn+Cit+Thr+Val+BCAA; 0.729, 26 8.732, 1+His+ Asn+Pro+Orn+Cys+Lys; 0.729, 269.760, 1+His+Asn+Pro+ Orn+Lys+BCAA; 0.729, 269.935, 1+His+Asn+Tau+3Me-His+Orn+Val; 0. 729, 269.238, 1+His+Asn+Glu+Cit+Orn+ BCAA; 0.729, 266.311, 1+His+Asn+Tau+Asp+Cit+Orn; 0.729, 268.855, 1+His+Cit+Orn+Val+Leu+Ph e; 0.729, 268.488, 1+His+Asn+3MeHis+Gly+Orn+Met; 0.729, 268.299, 1+His+Asn+Ser+Gly+Orn+Lys; 0.729, 268.556, 1+His+Asn+Gly+Orn+T yr+Met; 0.729, 268.252, 1+His+ Asn+Tau+Ser+Arg+Ile; 0.729, 269.25 9, 1+His+Asn+Tau+ Arg+Orn+Met; 0.729, 267.787, 1+His+Asn+Ser+Arg+Ile+ Trp; 0.729, 264.613, 1+Asn+Ser+Asp+Thr+Val+Ile; 0.729, 269. 369, 1+His+Asn+3MeHis+Gln+Arg+Orn; 0.729, 267.727, 1+His+Asn+3M eHis+Gly+Cit+Orn; 0.729, 268.252, 1+His+Asn+Ser+Arg+Pro+Ile; 0. 729, 265.173, 1+His+Asn+Asp+Pro+Val+BCAA; 0.729, 268.656, 1+His+ Asn+Glu+Orn+Cys+Met; 0.729, 264.795, 1+His+Asn+ Tau+Arg+Gly+As p; 0.729, 268.247, 1+His+Asn+Gln+Pro+ Orn+Phe; 0.729, 269.717, 1+H is+Asn+3MeHis+Gln+Glu+ Orn; 0.729, 268.218, 1+His+Asn+Ser+Arg+M et+Ile; 0.729, 265.321, 1+His+Asn+Asp+Met+Val+BCAA; 0.729, 264.4 24, 1+Asn+Ser+Asp+Glu+Thr+Phe; 0.729, 268.494, 1+His+Ser+Arg+As p+Orn+Phe; 0.729, 269.961, 1+His+ Asn+3MeHis+Glu+Orn+Val; 0.729, 270.015, 1+His+Asn+ 3MeHis+Orn+Met+Val; 0.729, 268.565, 1+His+As n+Gly+ Orn+Lys+Met; 0.729, 270.101, 1+His+Asn+Ala+Pro+Orn+ Met; 0. 729, 263.328, 1+His+Asn+Ser+Asp+Pro+Lys; 0.729, 269.329, 1+His+A sn+Gln+Arg+Orn+Met; 0.729, 267.462, 1+His+Asn+Gly+Cit+Orn+Met; 0.729, 268.772, 1+His+Asn+Orn+Cys+Lys+Val; 0.729, 266.214, 1+His+ Asn+3MeHis+Asp+Cit+Ile; 0.729, 266.502, 1+His+Asn+ Tau+Asp+Orn+Trp; 0.729, 263.962, 1+Asn+3MeHis+Ser+ Asp+Thr+Lys; 0.728, 268.7 49, 1+His+Asn+Gly+Orn+Lys+ Trp; 0.728, 265.478, 1+His+Asn+3MeHis+Arg+Asp+Thr; 0.728, 268.670, 1+His+Asn+3MeHis+Gly+Ala+Orn; 0.7 28, 270.001, 1+His+Asn+Gln+Ala+Pro+Orn; 0.728, 267.298, 1+His+As n+Cit+Lys+Val+BCAA; 0.728, 269.730, 1+His+Asn+Arg+Glu+Pro+Orn; 0.728, 268.325, 1+His+Ser+Asp+Orn+Ile+Phe; 0.728, 268.793, 1+His+ Asn+Ser+Orn+Lys+Met; 0.728, 268.823, 1+His+Asn+3Me-His+Orn+Cys+Met; 0.728, 264.355, 1+His+Asn+Gly+Asp+ Ile+Leu; 0.728, 267.798, 1+His+Asn+3MeHis+Cit+Orn+ Phe; 0.728, 268.615, 1+His+Gly+Asp+Or n+Ile+Phe; 0.728, 268.926, 1+His+Ser+Orn+Val+Leu+Phe; 0.728, 269. 549, 1+His+Gly+Orn+Lys+Leu+Phe; 0.728, 269.619, 1+His+ Ser+Gly+O rn+Leu+Phe; 0.728, 268.734, 1+His+Asn+Ser+ Orn+Lys+Trp; 0.728, 26 8.746, 1+His+Asn+Gly+Orn+Tyr+ Trp; 0.728, 268.722, 1+His+Asn+3Me His+Gly+Orn+Tyr; 0.728, 268.506, 1+His+Asn+Ser+Glu+Orn+Tyr; 0.7 28, 268.322, 1+His+Asn+Gly+Glu+Orn+Tyr; 0.728, 269.019, 1+His+As n+3MeHis+Cit+Pro+Orn; 0.728, 269.115, 1+Asn+Thr+Orn+Ile+Phe+BC AA; 0.728, 267.834, 1+His+ Asn+Cit+Pro+Orn+Phe; 0.728, 268.670, 1+His+Asn+3Me-His+Ser+Glu+Orn; 0.728, 269.859, 1+His+Asn+3MeHis+G ln+Ala+Orn; 0.728, 268.260, 1+His+Asn+Ser+Gly+Orn+ Tyr; 0.728, 26 8.424, 1+His+Asn+Thr+Met+Val+Ile; 0.728, 269.957, 1+His+Asn+3Me His+Pro+Orn+Met; 0.728, 269.560, 1+His+Asn+Tau+Arg+Pro+Orn; 0.7 28, 264.645, 1+His+Asn+Gln+Arg+Gly+Asp; 0.728, 269.744, 1+His+As n+Glu+Orn+Tyr+BCAA; 0.728, 266.647, 1+His+Asn+Tau+ Asp+Orn+Tyr; 0.728, 268.398, 1+His+Ser+Asp+Pro+Orn+ Phe; 0.728, 268.061, 1+His+Asn+Ser+Gln+Arg+Thr; 0.728, 269.778, 1+His+Asn+Tau+Orn+Lys+BC AA; 0.728, 268.838, 1+His+Asn+3MeHis+Ala+Orn+Cys; 0.728, 267.845, 1+His+Asn+3MeHis+Arg+Ile+BCAA; 0.728, 267.899, 1+His+Asn+Arg+G lu+Orn+Cys; 0.728, 269.747, 1+His+Asn+Arg+Ala+Pro+Orn; 0.728, 26 9.736, 1+His+ Asn+Arg+Pro+Orn+Tyr; 0.728, 266.899, 1+His+Asn+Asp+ Orn+Tyr+Met; 0.728, 265.630, 1+His+Asn+Tau+Asp+Orn+ Phe; 0.728, 266.617, 1+His+Asn+Gly+Orn+Lys+Phe; 0.728, 269.731, 1+His+Ser+A la+Orn+Phe+BCAA; 0.728, 267.678, 1+His+Tau+Gly+Asp+Orn+Phe; 0.7 28, 269.604, 1+His+Gly+Thr+Orn+Leu+Phe; 0.728, 268.883, 1+His+Se r+Asp+Orn+Tyr+Phe; 0.728, 268.710, 1+His+Asn+Ser+ Orn+Met+Trp; 0. 728, 268.708, 1+His+Asn+Ser+Glu+Pro+ Orn; 0.728, 269.350, 1+His+A sn+Tau+3MeHis+Arg+Orn; 0.728, 268.327, 1+His+Asn+3MeHis+Gly+Gl u+Orn; 0.728, 267.568, 1+His+Asn+Ser+Arg+Leu+Phe; 0.728, 266.205, 1+His+Asn+Asp+Cit+Orn+Phe; 0.728, 269.661, 1+His+Asn+Orn+Lys+T yr+BCAA; 0.728, 266.886, 1+Asn+Gly+Asp+Thr+Ile+BCAA; 0.728, 268. 633, 1+Asn+Asp+Thr+Orn+Ile+Phe; 0.728, 268.186, 1+His+ Asn+Ser+A rg+Glu+Ile; 0.728, 269.842, 1+His+Asn+Glu+ Orn+Lys+BCAA; 0.728, 2 67.511, 1+His+Asn+Tau+Orn+ Met+Phe; 0.728, 264.383, 1+His+Asn+As p+Cys+Val+ BCAA; 0.728, 270.002, 1+His+Asn+Gln+Pro+Orn+Val; 0.72 8, 268.314, 1+His+Asn+Gly+Glu+Orn+Trp; 0.728, 270.269, 1+His+Asn+Glu+Pro+Orn+Val; 0.728, 273.086, 1+His+3MeHis+Ala+Orn+Tyr+Le u; 0.728, 268.462, 1+His+Asn+Orn+Lys+Val+Phe; 0.728, 268.827, 1+H is+Orn+Ile+Leu+Phe+BCAA; 0.728, 268.827, 1+His+Orn+ Val+Leu+Phe+BCAA; 0.728, 268.827, 1+His+Orn+Val+ Ile+Phe+BCAA; 0.728, 268.82 7, 1+His+Orn+Val+Ile+ Leu+Phe; 0.728, 268.705, 1+His+Ser+Gly+Asp+Orn+Phe; 0.728, 269.736, 1+His+Asn+Tau+Gln+Orn+Trp; 0.728, 268. 523, 1+His+Asn+Ser+Orn+Tyr+Met; 0.728, 269.278, 1+His+Asn+3MeHi s+Cit+Orn+Met; 0.728, 262.389, 1+His+Asn+Ser+Asp+Thr+Met; 0.728, 265.365, 1+His+ Asn+Gln+Asp+Val+BCAA; 0.728, 266.783, 1+His+Asn+ Asp+Orn+Met+Trp; 0.728, 267.671, 1+His+Asn+Cit+Orn+ Met+Phe; 0.7 28, 268.921, 1+His+Asn+3MeHis+Glu+Cit+ Orn; 0.728, 262.664, 1+His+Asn+Ser+Asp+Pro+Phe; 0.728, 269.842, 1+His+3MeHis+Ala+Orn+Val+Phe; 0.728, 270.104, 1+His+3MeHis+Thr+Ala+Orn+Phe; 0.728, 269.5 56, 1+His+Gly+Orn+Met+Leu+Phe; 0.728, 269.956, 1+His+Asn+Tau+3M eHis+Ala+Orn; 0.728, 268.616, 1+His+Asn+Ser+Orn+Lys+Tyr; 0.728, 268.616, 1+His+ Asn+Pro+Orn+Cys+Trp; 0.728, 269.519, 1+His+Asn+A rg+Orn+Met+Val; 0.728, 269.743, 1+His+Asn+Ala+Orn+ Tyr+BCAA; 0.7 28, 267.840, 1+His+Asn+Tau+Orn+Tyr+ Phe; 0.728, 268.272, 1+His+As n+Glu+Orn+Met+Phe; 0.728, 266.752, 1+His+Asn+Asp+Cit+Orn+Trp; 0. 728, 268.735, 1+His+Asn+3MeHis+Ser+Orn+Trp; 0.728, 268.621, 1+Hi s+Asn+3MeHis+Ser+Orn+Tyr; 0.728, 268.278, 1+His+Asn+Ser+Gly+Or n+Trp; 0.728, 264.198, 1+His+Asn+Gly+Asp+Glu+Ile; 0.728, 269.113, 1+His+ Asn+Lys+Val+Ile+Phe; 0.728, 269.692, 1+His+Asn+3Me-His+Ar g+Orn+Lys; 0.728, 269.844, 1+His+Asn+Ala+Orn+ Lys+BCAA; 0.728, 26 4.714, 1+His+Asn+3MeHis+Arg+ Gly+Asp; 0.728, 266.747, 1+His+Asn+Arg+Asp+Glu+Orn; 0.728, 266.951, 1+His+Asn+Asp+Orn+Tyr+Trp; 0.7 28, 268.580, 1+His+Asn+Ser+Pro+Orn+Tyr; 0.728, 270.064, 1+His+As n+3MeHis+Orn+Tyr+Val; 0.728, 269.978,

1+His+Asn+Gln+Pro+Orn+Tyr; 0.728, 268.536, 1+His+Asn+Gly+Orn+Met+Trp; 0.728, 268.127, 1+His+Asn+Arg+Gly+Orn+Trp; 0.728, 266.440, 1+His+Asn+Asp+Orn+Lys+Phe; 0.728, 269.741, 1+His+Asn+Arg+Pro+Orn+Lys; 0.728, 268.578, 1+His+Asn+Glu+Orn+Tyr+Phe; 0.728, 267.137, 1+His+Asn+Ala+Orn+Cys+Phe; 0.728, 267.106, 1+His+Asn+Orn+Cys+Phe+Trp; 0.728, 270.052, 1+His+Asn+3MeHis+Pro+Orn+Lys; 0.728, 269.980, 1+His+Asn+Gln+Pro+Orn+Lys; 0.728, 267.149, 1+His+Asn+Arg+Gly+Cit+Ile; 0.728, 268.125, 1+His+Asn+3MeHis+Arg+Gly+Orn; 0.728, 266.922, 1+His+Asn+Asp+Orn+Lys+Met; 0.728, 265.594, 1+His+Asn+3MeHis+Asp+Ile+Phe; 0.728, 266.388, 1+His+Asn+Asp+Orn+Val+Phe; 0.728, 266.798, 1+His+Asn+Tau+Arg+Asp+Orn; 0.728, 267.172, 1+His+Orn+Cys+Val+Leu+Phe; 0.728, 268.991, 1+His+Gly+Asp+Ala+Orn+Phe; 0.728, 269.879, 1+His+Asn+3MeHis+Glu+Pro+Orn; 0.728, 269.917, 1+His+Asn+3MeHis+Glu+Orn+Met; 0.728, 270.131, 1+His+Asn+Pro+Orn+Met+Val; 0.728, 269.465, 1+His+Asn+3MeHis+Cit+Orn+Lys; 0.728, 266.731, 1+His+Asn+Gln+Asp+Glu+Orn; 0.728, 264.493, 1+His+Asn+Gly+Asp+Val+Leu; 0.728, 264.364, 1+Asn+Ser+Asp+Cit+Thr+Phe; 0.727, 267.384, 1+His+Asn+Glu+Thr+Val+Ile; 0.727, 270.068, 1+His+Asn+Pro+Orn+Val+Trp; 0.727, 269.145, 1+His+Asn+Tau+Cit+Pro+Orn; 0.727, 268.114, 1+His+Asn+Tau+Pro+Orn+Phe; 0.727, 268.559, 1+His+Asn+Arg+Pro+Orn+Phe; 0.727, 264.310, 1+His+Asn+Gly+Asp+Ile+Trp; 0.727, 268.305, 1+His+Asn+Ala+Orn+Met+Phe; 0.727, 266.646, 1+His+Asn+Asp+Glu+Orn+Trp; 0.727, 266.927, 1+His+Asn+Arg+Orn+Cys+Phe; 0.727, 269.434, 1+His+Gln+Gly+Orn+Ile+Phe; 0.727, 268.706, 1+His+Gly+Asp+Orn+Phe+BCAA; 0.727, 269.857, 1+His+Asn+3MeHis+Gln+Orn+Tyr; 0.727, 268.594, 1+His+Asn+Ser+Orn+Tyr+Trp; 0.727, 270.273, 1+His+Asn+Ala+Pro+Orn+Val; 0.727, 266.940, 1+His+Asn+Gln+Asp+Orn+Met; 0.727, 262.150, 1+His+Asn+Tau+Ser+Asp+Phe; 0.727, 264.908, 1+His+Asn+3MeHis+Asp+Thr+Phe; 0.727, 265.898, 1+His+Asn+Gly+Cit+Ile+Phe; 0.727, 269.178, 1+His+Asn+Gln+Cit+Pro+Orn; 0.727, 263.116, 1+His+Asn+Gly+Asp+Leu+Phe; 0.727, 267.071, 1+His+Asn+Arg+Asp+Orn+Tyr; 0.727, 266.112, 1+His+Asn+Asp+Glu+Orn+Phe; 0.727, 264.236, 1+Asn+Ser+Asp+Glu+Thr+Lys; 0.727, 268.431, 1+His+Ser+Asp+Orn+Phe+BCAA; 0.727, 269.439, 1+His+Gln+Gly+Orn+Phe+BCAA; 0.727, 268.141, 1+His+3MeHis+Orn+Ile+Leu+Phe; 0.727, 269.223, 1+His+Thr+Orn+Val+Leu+Phe; 0.727, 268.808, 1+His+Asn+3MeHis+Ser+Orn+Lys; 0.727, 268.719, 1+His+Asn+Ser+Glu+Orn+Lys; 0.727, 269.048, 1+His+Asn+Arg+Cit+Val+Leu; 0.727, 270.274, 1+His+Asn+Pro+Orn+Lys+Val; 0.727, 269.634, 1+His+Asn+3MeHis+Arg+Orn+Tyr; 0.727, 267.701, 1+His+Asn+Lys+Val+Phe+BCAA; 0.727, 268.486, 1+His+Asn+Glu+Orn+Cys+Trp; 0.727, 266.747, 1+His+Asn+Asp+Glu+Orn+Lys; 0.727, 268.129, 1+His+3MeHis+Thr+Orn+Leu+Phe; 0.727, 268.711, 1+His+Asn+3MeHis+Gly+Orn+Trp; 0.727, 270.081, 1+His+Asn+3MeHis+Ala+Orn+Met; 0.727, 267.390, 1+His+Asn+Ser+Arg+Thr+Ile; 0.727, 268.894, 1+His+Asn+Ala+Orn+Cys+Met; 0.727, 269.387, 1+His+Asn+Arg+Orn+Met+Trp; 0.727, 262.578, 1+His+Asn+Ser+Asp+Thr+Ala; 0.727, 267.999, 1+His+Asn+Arg+Gly+Met+Ile; 0.727, 266.948, 1+His+Asn+Asp+Orn+Met+Val; 0.727, 262.785, 1+His+Asn+Ser+Gln+Asp+Thr; 0.727, 266.805, 1+His+Asn+Tau+Gln+Asp+Orn; 0.727, 266.791, 1+His+Asn+Tau+Asp+Orn+Lys; 0.727, 268.757, 1+His+Gln+Orn+Val+Leu+Phe; 0.727, 268.781, 1+His+Ser+Asp+Orn+Lys+Phe; 0.727, 268.639, 1+His+Asn+Ser+Glu+Orn+Trp; 0.727, 269.821, 1+His+Asn+3MeHis+Gln+Orn+Lys; 0.727, 269.948, 1+His+Asn+3MeHis+Orn+Val+Trp; 0.727, 263.041, 1+His+Asn+Gly+Asp+Cit+Phe; 0.727, 268.043, 1+His+Asn+3MeHis+Orn+Tyr+Phe; 0.727, 268.467, 1+His+Asn+Pro+Orn+Lys+Phe; 0.727, 269.212, 1+His+3MeHis+Gly+Orn+Phe+BCAA; 0.727, 268.758, 1+His+Cit+Orn+Val+Phe+BCAA; 0.727, 267.812, 1+His+3MeHis+Orn+Leu+Phe+Trp; 0.727, 268.796, 1+His+Asn+3MeHis+Orn+Cys+Lys; 0.727, 269.481, 1+His+Asn+3MeHis+Cit+Ala+Orn; 0.727, 267.675, 1+His+Asn+Arg+Met+Ile+BCAA; 0.727, 269.088, 1+His+Asn+Cit+Pro+Orn+Trp; 0.727, 266.563, 1+His+Asn+Arg+Asp+Orn+Phe; 0.727, 268.036, 1+His+Asn+Arg+Orn+Met+Phe; 0.727, 264.909, 1+His+Asn+Gly+Asp+Pro+Lys; 0.727, 267.994, 1+His+Asn+Cit+Orn+Tyr+Phe; 0.727, 268.316, 1+His+Asn+Orn+Lys+Tyr+Phe; 0.727, 269.836, 1+His+Ala+Orn+Leu+Phe+BCAA; 0.727, 269.733, 1+His+Gln+Gly+Ala+Orn+Phe; 0.727, 268.818, 1+Asn+Thr+Orn+Cys+Ile+Phe; 0.727, 268.713, 1+His+Asn+3MeHis+Orn+Cys+Trp; 0.727, 269.526, 1+His+Asn+Arg+Orn+Lys+Met; 0.727, 268.193, 1+His+Asn+Tau+Orn+Val+Phe; 0.727, 266.221, 1+His+Asn+3MeHis+Asp+Cit+Lys; 0.727, 269.511, 1+His+Ser+Orn+Leu+Phe+BCAA; 0.727, 268.136, 1+His+3MeHis+Orn+Met+Leu+Phe; 0.727, 268.888, 1+His+Ser+Asp+Thr+Orn+Phe; 0.727, 266.916, 1+His+Gly+Asp+Orn+Cys+Phe; 0.727, 269.970, 1+His+Asn+3MeHis+Pro+Orn+Trp; 0.727, 269.530, 1+His+Asn+Arg+Orn+Tyr+Met; 0.727, 267.161, 1+His+Asn+Arg+Gly+Leu+Phe; 0.727, 269.631, 1+His+Asn+Arg+Pro+Orn+Trp; 0.727, 268.666, 1+His+Asn+Glu+Ala+Orn+Cys; 0.727, 267.573, 1+His+Asn+Ser+Cit+Ile+Phe; 0.727, 263.691, 1+His+Asn+Gly+Asp+Cit+Met; 0.727, 264.879, 1+His+Asn+Arg+Gly+Asp+Val; 0.727, 264.516, 1+His+Asn+Arg+Gly+Asp+Phe; 0.727, 268.467, 1+His+Asn+Orn+Val+Phe+Trp; 0.727, 268.829, 1+His+Asp+Orn+Leu+Phe+BCAA; 0.727, 269.694, 1+His+Asn+Tau+3MeHis+Glu+Orn; 0.727, 270.057, 1+His+Asn+3MeHis+Orn+Lys+Val; 0.727, 270.281, 1+His+Asn+Ala+Pro+Orn+Lys; 0.727, 267.895, 1+His+Asn+3MeHis+Orn+Met+Phe; 0.727, 266.976, 1+His+Asn+Asp+Cit+Orn+Val; 0.727, 268.165, 1+His+Gly+Orn+Cys+Phe+BCAA; 0.727, 268.709, 1+His+Asn+Ser+Glu+Orn+Met; 0.727, 267.837, 1+His+Asn+Cit+Tyr+Val+BCAA; 0.727, 266.975, 1+His+Asn+Arg+Asp+Cit+Orn; 0.727, 267.782, 1+His+Asn+Arg+Asp+Ile+Trp; 0.727, 268.925, 1+His+Orn+Lys+Val+Phe+BCAA; 0.727, 268.408, 1+His+Asn+Gly+Thr+Val+BCAA; 0.727, 270.095, 1+His+Asn+Tau+Ala+Pro+Orn; 0.727, 269.990, 1+His+Asn+Gln+Orn+Met+Val; 0.727, 269.698, 1+His+Asn+3MeHis+Arg+Ala+Orn; 0.727, 268.810, 1+His+Asn+3MeHis+Orn+Cys+Tyr; 0.727, 268.896, 1+His+Asn+Ala+Orn+Cys+Tyr; 0.727, 267.881, 1+His+Asn+Arg+Tyr+Ile+BCAA; 0.727, 268.617, 1+His+Asn+Glu+Orn+Cys+Tyr; 0.727, 267.639, 1+His+Asn+Tau+3MeHis+Orn+Phe; 0.727, 268.665, 1+His+Asn+Ala+Pro+Orn+Phe; 0.727, 266.981, 1+His+Asn+Gln+Asp+Cit+Orn; 0.727, 268.421, 1+His+Asn+Gln+Orn+Val+Phe; 0.727, 268.615, 1+His+Asn+Glu+Orn+Val+Phe; 0.727, 267.570, 1+His+3MeHis+Orn+Cys+Phe+BCAA; 0.727, 270.068, 1+Asn+Asp+Glu+Thr+Orn+Ile; 0.727, 270.000, 1+His+Asn+Tau+Gln+Glu+Orn; 0.727, 269.799, 1+His+Asn+3MeHis+Gln+Orn+Trp; 0.727, 269.664, 1+His+Asn+Tau+Gln+Arg+Orn; 0.727, 270.037, 1+His+Asn+3MeHis+Pro+Orn+Tyr; 0.727, 269.943, 1+His+Asn+Pro+Orn+Met+Trp; 0.727, 268.844, 1+His+Asn+Orn+Cys+Lys+Met; 0.727, 268.655, 1+His+Asn+Glu+Pro+Orn+Phe; 0.727, 263.874, 1+His+Asn+Gly+Asp+Cit+Trp; 0.727, 268.896, 1+His+Asn+Gly+Ile+Phe; 0.727, 266.716, 1+His+Asn+Asp+Cit+Ala+Orn; 0.727, 266.975, 1+His+Asn+Asp+Cit+Orn+Lys; 0.727, 270.855, 1+His+Gly+Thr+Ala+Orn+Phe; 0.727, 267.583, 1+His+

3MeHis+Orn+Cys+Ile+Phe; 0.727, 269.702, 1+His+Asn+Tau+Orn+Met+Trp; 0.727, 270.061, 1+His+Asn+Lys+Tyr+Val+Ile; 0.727, 268.718, 1+His+Asn+3MeHis+Gly+Orn+Lys; 0.727, 270.062, 1+His+Asn+Tau+Pro+Orn+Tyr; 0.727, 270.848, 1+His+Asn+Thr+Ile+Phe+Trp; 0.727, 269.653, 1+His+Asn+3MeHis+Arg+Orn+Trp; 0.727, 267.180, 1+His+Asn+Asp+Cit+Thr+Trp; 0.727, 268.820, 1+His+Asn+Orn+Cys+Tyr+Met; 0.727, 264.145, 1+Asn+3MeHis+Ser+Asp+Cit+Thr; 0.727, 269.229, 1+His+Glu+Orn+Val+Leu+Phe; 0.727, 269.988, 1+His+Asn+Gln+Ala+Orn+Met; 0.727, 263.011, 1+His+Asn+Tau+Ser+Asp+Lys; 0.727, 269.385, 1+His+Asn+Cit+Ala+Pro+Orn; 0.727, 262.874, 1+His+Asn+Tau+Ser+Asp+Thr; 0.727, 264.394, 1+His+Asn+Gly+Asp+Pro+Ile; 0.727, 268.630, 1+His+Asn+Glu+Orn+Cys+Lys; 0.727, 267.097, 1+His+Asn+Ser+Arg+Cit+Ile; 0.727, 268.346, 1+His+Asn+Arg+Orn+Tyr+Phe; 0.727, 267.627, 1+His+Asn+Asp+Thr+Phe+Trp; 0.727, 268.181, 1+His+Asn+3MeHis+Pro+Orn+Phe; 0.727, 264.353, 1+His+Asn+Gln+Gly+Asp+Ile; 0.727, 262.817, 1+His+Asn+3MeHis+Ser+Asp+Glu; 0.726, 267.316, 1+His+Asn+Ser+Arg+Thr+Cys; 0.726, 270.085, 1+His+Asn+Tau+Pro+Orn+Lys; 0.726, 267.802, 1+His+Asn+Gln+Arg+Ile+BCAA; 0.726, 268.266, 1+His+Asn+Orn+Met+Phe+Trp; 0.726, 264.265, 1+Asn+Ser+Arg+Asp+Thr+Phe; 0.726, 263.597, 1+His+Asn+Gln+Gly+Asp+Cit; 0.726, 266.531, 1+His+Asn+Asp+Orn+Phe+Trp; 0.726, 266.800, 1+Asn+3MeHis+Asp+Thr+Lys+Ile; 0.726, 266.765, 1+His+Asn+Asp+Cit+Orn+Tyr; 0.726, 266.676, 1+His+Orn+Cys+Val+Phe+BCAA; 0.726, 268.948, 1+His+Arg+Orn+Val+Leu+Phe; 0.726, 270.110, 1+His+Asn+Glu+Pro+Orn+Met; 0.726, 269.530, 1+His+Asn+Arg+Ala+Orn+Met; 0.726, 268.758, 1+His+Asn+Ala+Orn+Cys+Trp; 0.726, 273.428, 1+His+3MeHis+Gln+Gly+Ala+Orn; 0.726, 264.329, 1+His+Asn+3MeHis+Gly+Asp+Ile; 0.726, 264.592, 1+His+Asn+Gly+Asp+Pro+Phe; 0.726, 266.547, 1+His+Asn+Gln+Asp+Orn+Phe; 0.726, 265.345, 1+Asn+Gly+Asp+Thr+Ile+Phe; 0.726, 270.039, 1+His+Asn+Tau+Ala+Orn+Met; 0.726, 263.468, 1+His+Asn+Ser+Asp+Lys+Trp; 0.726, 262.873, 1+His+Asn+Ser+Asp+Thr+Ile; 0.726, 268.610, 1+His+Asn+Ala+Orn+Tyr+Phe; 0.726, 267.371, 1+His+Asn+Gln+Asp+Orn+Val; 0.726, 268.610, 1+His+Asn+Ala+Orn+Val+Phe; 0.726, 269.247, 1+His+Asn+Tau+Cit+Orn+Met; 0.726, 270.262, 1+His+Asn+Glu+Ala+Pro+Orn; 0.726, 262.868, 1+His+Asn+Ser+Asp+Thr+Pro; 0.726, 263.481, 1+His+Asn+Ser+Asp+Lys+Val; 0.726, 269.054, 1+His+Ala+Orn+Val+Ile+Phe; 0.726, 267.357, 1+His+Asn+Gln+Arg+Asp+Orn; 0.726, 267.352, 1+His+Asn+Arg+Asp+Orn+Val; 0.726, 267.183, 1+His+Asn+Gln+Asp+Orn+Tyr; 0.726, 269.990, 1+His+Tau+Gly+Orn+Phe+BCAA; 0.726, 268.787, 1+His+Ser+Pro+Orn+Leu+Phe; 0.726, 269.922, 1+His+Asn+Tau+Orn+Tyr+Met; 0.726, 270.039, 1+His+Asn+Tau+Orn+Met+Val; 0.726, 263.502, 1+His+Asn+Gly+Asp+Cys+Ile; 0.726, 270.137, 1+His+Asn+Pro+Orn+Lys+Trp; 0.726, 269.494, 1+His+Asn+3MeHis+Cit+Orn+Tyr; 0.726, 269.224, 1+His+Asn+Cit+Pro+Orn+Met; 0.726, 264.983, 1+Asn+Ser+Asp+Thr+Ile+BCAA; 0.726, 266.740, 1+His+Asn+Tau+Asp+Orn+Val; 0.726, 268.072, 1+His+Asn+Cit+Orn+Val+Phe; 0.726, 268.971, 1+His+Glu+Orn+Val+Phe+BCAA; 0.726, 268.837, 1+His+Ser+Asp+Orn+Met+Phe; 0.726, 268.484, 1+His+Asn+Gln+Thr+Val+BCAA; 0.726, 269.913, 1+His+Asn+Gln+Orn+Tyr+Met; 0.726, 270.108, 1+His+Asn+Ala+Pro+Orn+Trp; 0.726, 269.935, 1+His+Asn+Tau+3MeHis+Orn+Lys; 0.726, 269.809, 1+His+Asn+Tau+Arg+Orn+Tyr; 0.726, 269.839, 1+His+Asn+Tau+Arg+Orn+Val; 0.726, 269.935, 1+His+Asn+Tau+Pro+Orn+Met; 0.726, 270.266, 1+His+Asn+Glu+Pro+Orn+Lys; 0.726, 268.896, 1+His+Asn+Ala+Orn+Cys+Lys; 0.726, 270.046, 1+His+Asn+Arg+Orn+Tyr+Val; 0.726, 269.410, 1+His+Asn+Cit+Pro+Orn+Val; 0.726, 269.247, 1+His+Asn+3MeHis+Arg+Cit+Orn; 0.726, 269.209, 1+His+Orn+Lys+Val+Leu+Phe; 0.726, 270.106, 1+His+Asn+Pro+Orn+Lys+Met; 0.726, 269.505, 1+His+Asn+Arg+Glu+Orn+Met; 0.726, 269.906, 1+His+Asn+Arg+Orn+Tyr+Trp; 0.726, 266.209, 1+His+Asn+3MeHis+Asp+Thr+Trp; 0.726, 268.873, 1+His+Asn+Orn+Cys+Lys+Tyr; 0.726, 267.207, 1+His+Asn+Asp+Orn+Val+Trp; 0.726, 268.650, 1+His+Asn+Pro+Orn+Phe+Trp; 0.726, 264.989, 1+His+Asn+Arg+Gly+Asp+Glu; 0.726, 262.532, 1+His+Asn+Ser+Asp+Leu+Phe; 0.726, 268.493, 1+His+Asn+Gln+Orn+Lys+Phe; 0.726, 267.358, 1+His+Asn+Arg+Asp+Orn+Lys; 0.726, 269.430, 1+His+Arg+Gly+Orn+Leu+Phe; 0.726, 269.003, 1+His+Ser+Orn+Val+Phe+BCAA; 0.726, 267.863, 1+His+Asn+3MeHis+Ser+Arg+Thr; 0.726, 268.383, 1+His+Asn+Ser+Arg+Thr+Pro; 0.726, 270.001, 1+His+Asn+Tau+Gln+Orn+Tyr; 0.726, 269.823, 1+His+Asn+Gln+Orn+Met+Trp; 0.726, 269.831, 1+His+Asn+Tau+Arg+Orn+Lys; 0.726, 270.106, 1+His+Asn+Tau+Pro+Orn+Val; 0.726, 266.039, 1+His+Asn+Arg+Gly+Thr+Phe; 0.726, 268.712, 1+His+Asn+Orn+Cys+Met+Trp; 0.726, 267.369, 1+His+Asn+Asp+Orn+Lys+Val; 0.726, 268.311, 1+His+Tau+3MeHis+Orn+Ile+Phe; 0.726, 269.154, 1+His+Orn+Met+Val+Leu+Phe; 0.726, 269.997, 1+His+Asn+Tau+Orn+Lys+Met; 0.726, 269.988, 1+His+Asn+Tau+Gln+Orn+Lys; 0.726, 267.530, 1+His+Asn+Ser+Arg+Cit+Thr; 0.726, 269.987, 1+His+Asn+Gln+Glu+Orn+Met; 0.726, 273.064, 1+His+3MeHis+Ser+Arg+Ala+Orn; 0.726, 262.674, 1+His+Asn+Ser+Asp+Phe+BCAA; 0.726, 263.357, 1+His+Asn+Ser+Asp+Lys+Leu; 0.726, 267.912, 1+Asn+3MeHis+Asp+Thr+Val+Ile; 0.726, 269.365, 1+His+Asn+Gln+Cit+Orn+Met; 0.726, 268.345, 1+His+Asn+Arg+Gly+Cys+Leu; 0.726, 270.235, 1+His+Asn+Pro+Orn+Tyr+Val; 0.726, 271.954, 1+His+Gln+Gly+Ala+Orn+Cys; 0.726, 266.509, 1+His+Asn+Tau+Asp+Ala+Orn; 0.726, 264.938, 1+His+Asn+Arg+Gly+Asp+Lys; 0.726, 268.582, 1+His+Asn+Arg+Orn+Val+Phe; 0.726, 269.248, 1+His+3MeHis+Cit+Orn+Phe+BCAA; 0.726, 269.058, 1+His+Thr+Orn+Val+Phe+BCAA; 0.726, 268.943, 1+His+Gly+Orn+Leu+Phe+Trp; 0.726, 268.382, 1+His+Asn+Ser+Arg+Thr+Leu; 0.726, 270.024, 1+His+Asn+Orn+Met+Val+Trp; 0.726, 269.948, 1+His+Asn+Tau+3MeHis+Orn+Tyr; 0.726, 270.070, 1+His+Asn+Tau+Glu+Pro+Orn; 0.726, 267.838, 1+His+Asn+Thr+Ile+Phe+BCAA; 0.726, 264.547, 1+His+Asn+Tau+Gly+Asp+Ile; 0.726, 263.490, 1+His+Asn+Ser+Asp+Lys+Tyr; 0.726, 263.363, 1+His+Asn+Ser+Gln+Asp+Lys; 0.726, 265.030, 1+His+Asn+Arg+Gly+Asp+Trp; 0.726, 264.322, 1+His+Asn+Gly+Asp+Lys+BCAA; 0.726, 266.773, 1+His+Asn+Asp+Ala+Orn+Met; 0.726, 266.517, 1+His+Asn+Asp+Glu+Ala+Orn; 0.726, 266.335, 1+His+Asn+Arg+Asp+Cys+Ile; 0.726, 269.044, 1+His+Tau+Gln+Gly+Orn+Phe; 0.726, 267.170, 1+His+Asn+Asp+Orn+Lys+Tyr; 0.726, 269.330, 1+His+3MeHis+Ser+Orn+Phe+BCAA; 0.726, 269.837, 1+His+Asn+Arg+Lys+Val+Leu; 0.726, 270.001, 1+His+Asn+Tau+Glu+Orn+Met; 0.726, 269.382, 1+His+Asn+3MeHis+Arg+Glu+Orn; 0.726, 268.749, 1+His+Asn+Orn+Cys+Lys+Trp; 0.726, 263.198, 1+His+Asn+Gly+Asp+Cit+BCAA; 0.726, 269.374, 1+His+Asp+Glu+Orn+Leu+Phe; 0.726, 268.427, 1+His+Asn+Ser+Gln+Arg+Gly; 0.726, 270.086, 1+His+Asn+Gln+Orn+Val+Trp; 0.726, 270.099, 1+His+Asn+Glu+Pro+Orn+Trp; 0.726, 270.274, 1+His+Asn+Ala+Orn+Met+Val; 0.726, 262.232, 1+His+Asn+Ser+Asp+Thr+Cys; 0.726, 263.976, 1+His+Asn+Gly+Asp+Glu+Cit; 0.726, 266.312, 1+His+Asn+3MeHis+Asp+Cit+Pro; 0.726, 269.046, 1+His+Orn+Tyr+Val+Leu+Phe; 0.726, 269.056, 1+His+Orn+Met+Val+Phe+

BCAA; 0.726, 268.257, 1+His+Asn+S er+Arg+Thr+Met; 0.726, 269.812, 1+His+Asn+Tau+Pro+Orn+Trp; 0.72 6, 270.032, 1+His+Asn+3MeHis+Glu+Ala+Orn; 0.726, 269.932, 1+His+Asn+Gln+Arg+Orn+Lys; 0.726, 269.593, 1+His+Asn+Gln+Arg+Cit+Or n; 0.726, 269.585, 1+His+Asn+Cit+Orn+Met+Val; 0.726, 269.823, 1+A sn+Asp+Thr+Ile+Trp+BCAA; 0.726, 267.533, 1+His+Asn+Arg+Cit+Ile+BCAA; 0.726, 269.673, 1+His+Ser+Gln+Orn+Leu+Phe; 0.725, 268.956, 1+His+Asn+Gln+Arg+Gly+Leu; 0.725, 267.927, 1+His+Asn+Ser+Arg+G ly+Cys; 0.725, 269.315, 1+His+Asn+Glu+Cit+Pro+Orn; 0.725, 269.26 4, 1+His+Asn+Cit+Orn+Met+Trp; 0.725, 266.779, 1+Asn+3MeHis+Ser+Arg+Asp+Ile; 0.725, 262.774, 1+His+Asn+Ser+Asp+Met+Phe; 0.725, 2 70.252, 1+His+Tau+3MeHis+Asp+Ala+Orn; 0.725, 268.516, 1+His+Ser+Asp+Orn+Phe+Trp; 0.725, 267.719, 1+His+Asn+Ser+Arg+Thr+Val; 0. 725, 268.157, 1+His+Asn+Ser+Arg+Cys+Leu; 0.725, 268.995, 1+His+A sn+Tau+Cit+Orn+Trp; 0.725, 262.670, 1+His+Asn+Ser+Asp+Glu+Pro; 0.725, 266.355, 1+His+Asn+Asp+Ala+Orn+Phe; 0.725, 268.140, 1+His+Asn+Tau+Orn+Lys+Phe; 0.725, 266.866, 1+His+Asn+Ser+Arg+Gly+Th r; 0.725, 269.296, 1+His+Asn+3MeHis+Cit+Orn+Trp; 0.725, 267.243, 1+His+Asn+Gln+Asp+Orn+Trp; 0.725, 268.335, 1+His+Asn+3MeHis+Or n+Lys+Phe; 0.725, 263.246, 1+His+Asn+Gly+Asp+Cit+Tyr; 0.725, 270. 033, 1+His+Ser+Cit+Orn+Leu+Phe; 0.725, 269.993, 1+His+Asn+Tau+G ln+Orn+Val; 0.725, 269.929, 1+His+Asn+Gln+Arg+Orn+Val; 0.725, 26 2.636, 1+His+Asn+Ser+Asp+Tyr+Phe; 0.725, 268.242, 1+His+Asn+Gln+Cit+Orn+Phe; 0.725, 269.441, 1+His+Tau+Ser+Orn+Leu+Phe; 0.725, 270.092, 1+His+Asn+Ser+Thr+Phe+Trp; 0.725, 270.575, 1+His+Asn+G ly+Lys+Val+Ile; 0.725, 270.128, 1+His+Asn+Pro+Orn+Tyr+Trp; 0.72 5, 268.049, 1+His+Asn+Asp+Glu+Thr+Trp; 0.725, 268.241, 1+His+Asn+Asp+Thr+Ile+Trp; 0.725, 267.998, 1+His+Asn+Tau+Gln+Orn+Phe; 0. 725, 268.655, 1+His+Ser+Ala+Orn+Cys+Phe; 0.725, 268.923, 1+His+G ly+Ala+Orn+Cys+Phe; 0.725, 268.309, 1+His+Asn+Ser+Arg+Glu+Thr; 0.725, 268.225, 1+His+Asn+Gly+Thr+Val+Ile; 0.725, 263.484, 1+His+Asn+Ser+Asp+Lys+Met; 0.725, 269.947, 1+His+Asn+Gln+Orn+Lys+Me t; 0.725, 269.452, 1+His+Asn+Cit+Orn+Val+Trp; 0.725, 267.683, 1+H is+Asn+Tau+Cit+Orn+Phe; 0.725, 264.490, 1+Asn+Ser+Asp+Thr+Ile+Phe; 0.725, 267.797, 1+His+Ser+Orn+Cys+Leu+Phe; 0.725, 268.560, 1+His+Gln+Gly+Asp+Orn+Phe; 0.725, 269.088, 1+His+Asp+Thr+Tyr+Va l+Ile; 0.725, 269.396, 1+His+Asn+Tau+Glu+Cit+Orn; 0.725, 269.832, 1+His+Asn+Gln+Arg+Orn+Trp; 0.725, 270.059, 1+His+Asn+Arg+Orn+L ys+Val; 0.725, 268.749, 1+His+Asn+Orn+Cys+Tyr+Trp; 0.725, 267.61 6, 1+His+Asn+Arg+Orn+Asp+Thr+Trp; 0.725, 267.296, 1+His+Asn+Gly+Thr+Ile+Phe; 0.725, 265.346, 1+Asn+Ser+Asp+Thr+Pro+Orn; 0.725, 266. 565, 1+His+Asn+Asp+Cit+Val+Leu; 0.725, 269.930, 1+His+Ser+Orn+T yr+Leu+Phe; 0.725, 270.703, 1+His+Gly+Cit+Orn+Phe+BCAA

[21. Formula with Two Biochemistry Variables]
0.723, 255.038, 1+ALB+ALT; 0.720, 261.158, 1+ALB+AST; 0.716, 260.0 41, 1+ALB+NEFA; 0.715, 258.893, 1+ALB+BUN; 0.706, 261.403, 1+ALB+T-BIL; 0.704, 263.905, 1+ALB+Glc; 0.704, 263.684, 1+ALB+gGT; 0.700, 263.426, 1+ALB+Ca; 0.700, 263.479, 1+ALB+BHBA

[22. Formula with Three Biochemistry Variables]
0.735, 253.211, 1+ALB+BUN+ALT; 0.734, 258.533, 1+ALB+AST+NEFA; 0. 728, 256.521, 1+ALB+AST+ALT; 0.728, 259.757, 1+ALB+AST+T-BIL; 0.7 27, 256.324, 1+ALB+ALT+T-BIL; 0.727, 255.913, 1+ALB+ALT+NEFA; 0.7 25, 256.962, 1+ALB+ALT+Glc; 0.725, 258.863, 1+ALB+BUN+AST; 0.725, 256.900, 1+TP+ALB+ALT; 0.724, 258.078, 1+ALB+BUN+T-BIL; 0.724, 25 6.915, 1+ALB+ALT+TG; 0.724, 256.456, 1+ALB+ALT+TCHO; 0.723, 257.0 22, 1+ALB+ALT+gGT; 0.723, 262.537, 1+ALB+AST+BHBA; 0.723, 262.767, 1+TP+ALB+AST; 0.723, 256.757, 1+ALB+ALT+BHBA; 0.723, 256.552, 1+A LB+Ca+ALT; 0.722, 258.215, 1+ALB+BUN+NEFA; 0.721, 262.733, 1+ALB+Ca+AST; 0.720, 263.100, 1+ALB+AST+Glc; 0.718, 263.152, 1+ALB+AST+gGT; 0.718, 262.730, 1+ALB+AST+TG; 0.717, 262.659, 1+ALB+AST+TCH O; 0.717, 260.265, 1+ALB+BUN+BHBA; 0.717, 260.771, 1+ALB+BUN+Glc; 0.717, 262.036, 1+ALB+NEFA+TG; 0.716, 262.040, 1+ALB+NEFA+Glc; 0. 716, 261.623, 1+TP+ALB+NEFA; 0.716, 262.038, 1+ALB+NEFA+T-BIL; 0. 716, 262.022, 1+ALB+NEFA+BHBA; 0.716, 260.406, 1+TP+ALB+BUN; 0.71 5, 261.977, 1+ALB+gGT+NEFA; 0.715, 261.777, 1+ALB+Ca+NEFA; 0.714, 260.256, 1+ALB+BUN+Ca; 0.714, 260.795, 1+ALB+BUN+gGT; 0.712, 260. 311, 1+ALB+BUN+TCHO; 0.710, 260.586, 1+ALB+BUN+TG; 0.710, 263.196, 1+ALB+gGT+T-BIL; 0.709, 263.250, 1+ALB+T-BIL+BHBA; 0.708, 263.02 9, 1+TP+ALB+T-BIL; 0.708, 263.072, 1+ALB+Ca+T-BIL; 0.708, 260.737, 1+ALB+NEFA+TCHO; 0.705, 265.284, 1+TP+ALB+gGT; 0.705, 263.334, 1+ALB+T-BIL+TG; 0.705, 265.661, 1+ALB+gGT+Glc; 0.705, 263.372, 1+AL B+T-BIL+Glc; 0.704, 262.427, 1+ALB+T-BIL+TCHO; 0.704, 265.225, 1+ALB+Ca+gGT; 0.704, 265.269, 1+ALB+gGT+BHBA; 0.700, 265.135, 1+TP+ALB+BHBA; 0.700, 265.163, 1+ALB+gGT+TG

[23. Formula with Four Biochemistry Variables]
0.739, 254.351, 1+ALB+BUN+ALT+T-BIL; 0.739, 254.641, 1+ALB+BUN+A LT+NEFA; 0.737, 254.938, 1+ALB+BUN+AST+ALT; 0.737, 254.677, 1+ALB+BUN+Ca+ALT; 0.737, 254.892, 1+TP+ALB+BUN+ALT; 0.736, 255.038, 1+ALB+BUN+ALT+Glc; 0.736, 254.733, 1+ALB+BUN+ALT+BHBA; 0.736, 255. 206, 1+ALB+BUN+ALT+gGT; 0.736, 257.734, 1+ALB+BUN+AST+NEFA; 0.73 5, 255.202, 1+ALB+BUN+ALT+TG; 0.735, 254.733, 1+ALB+BUN+ALT+TCH O; 0.735, 259.856, 1+TP+ALB+AST+NEFA; 0.734, 260.519, 1+ALB+AST+N EFA+Glc; 0.734, 260.436, 1+ALB+AST+NEFA+TG; 0.734, 257.484, 1+ALB+BUN+AST+T-BIL; 0.734, 260.531, 1+ALB+AST+NEFA+BHBA; 0.733, 256. 921, 1+ALB+AST+ALT+NEFA; 0.733, 260.356, 1+ALB+Ca+AST+NEFA; 0.73 3, 260.499, 1+ALB+AST+NEFA+T-BIL; 0.732, 260.305, 1+ALB+AST+gGT+NEFA; 0.730, 259.904, 1+ALB+AST+NEFA+TCHO; 0.730, 257.387, 1+ALB+AST+ALT+T-BIL; 0.730, 260.174, 1+ALB+BUN+AST+BHBA; 0.730, 257.65 6, 1+TP+ALB+ALT+NEFA; 0.729, 261.129, 1+TP+ALB+AST+T-BIL; 0.729, 258.134, 1+ALB+AST+ALT+BHBA; 0.729, 260.723, 1+ALB+BUN+AST+Glc; 0.729, 257.883, 1+ALB+AST+ALT+TCHO; 0.729, 261.657, 1+ALB+AST+T-BIL+BHBA; 0.728, 258.430, 1+ALB+AST+ALT+Glc; 0.728, 258.068, 1+AL B+Ca+AST+ALT; 0.728, 257.895, 1+ALB+ALT+NEFA+Glc; 0.728, 258.329, 1+TP+ALB+AST+ALT; 0.728, 261.748, 1+ALB+AST+T-BIL+Glc; 0.728, 26 1.534, 1+ALB+Ca+AST+T-BIL; 0.728, 258.509, 1+ALB+AST+ALT+gGT; 0. 728, 258.109, 1+TP+ALB+ALT+T-BIL; 0.727, 261.756, 1+ALB+AST+T-BI L+TG; 0.727, 257.332, 1+ALB+ALT+NEFA+TCHO; 0.727, 258.307, 1+ALB+ALT+gGT+T-BIL; 0.727, 261.700, 1+ALB+AST+gGT+T-BIL; 0.727, 258.3 20, 1+ALB+ALT+T-BIL+TG; 0.727, 258.320, 1+ALB+ALT+T-BIL+Glc; 0.7 27, 258.324, 1+ALB+AST+T-BIL+BHBA; 0.727, 260.357, 1+ALB+BUN+Ca+AST; 0.727, 258.748, 1+TP+ALB+ALT+TG; 0.727, 257.913, 1+ALB+ALT+N EFA+T-BIL; 0.727, 258.407, 1+ALB+AST+ALT+TG; 0.727, 257.894, 1+AL B+ALT+NEFA+TG; 0.727, 257.913, 1+ALB+ALT+gGT+ NEFA; 0.726, 257.90 7, 1+ALB+ALT+NEFA+BHBA; 0.726, 258.844, 1+TP+ALB+ALT+gGT; 0.726, 257.780, 1+ALB+ALT+T-BIL+TCHO; 0.726, 261.320, 1+ALB+ AST+T-BIL+TCHO; 0.726, 263.947, 1+TP+ALB+AST+ BHBA; 0.726, 257.579, 1+ALB+Ca+ALT+NEFA; 0.726, 257.948, 1+ALB+Ca+ALT+T-BIL; 0.726, 258.522, 1+TP+ ALB+ALT+BHBA; 0.726, 258.677, 1+ALB+ALT+BHBA+ TG; 0.725, 258.2 79, 1+ALB+ALT+TG+TCHO; 0.725, 258.372, 1+TP+ALB+Ca+ALT; 0.725, 26 0.202, 1+TP+ ALB+BUN+AST; 0.725, 258.393, 1+ALB+ALT+Glc+ TCHO; 0.7 25, 258.834, 1+ALB+ALT+Glc+TG; 0.725, 258.366, 1+TP+ALB+ALT+TCH O; 0.725, 258.824, 1+TP+ ALB+ALT+Glc

[24. Formula with Five Biochemistry Variables]
0.740, 255.932, 1+TP+ALB+BUN+ALT+T-BIL; 0.740, 256.577, 1+ALB+BU N+ALT+NEFA+TG; 0.740, 256.293, 1+ALB+BUN+ALT+T-BIL+TG; 0.740, 25 5.934, 1+ALB+ BUN+Ca+ALT+T-BIL; 0.740, 256.622, 1+ALB+BUN+ ALT+gG T+NEFA; 0.740, 255.931, 1+ALB+BUN+ALT+ T-BIL+TCHO; 0.740, 256.125, 1+ALB+BUN+AST+ALT+ NEFA; 0.739, 255.778, 1+ALB+BUN+AST+ALT+T-BI L; 0.739, 256.201, 1+ALB+BUN+ALT+NEFA+TCHO; 0.739, 256.351, 1+ALB+BUN+ALT+NEFA+T-BIL; 0.739, 256.244, 1+TP+ALB+BUN+ALT+NEFA; 0.7 39, 256.213, 1+ALB+BUN+Ca+ALT+NEFA; 0.739, 256.316, 1+ALB+ BUN+AL T+T-BIL+BHBA; 0.738, 256.346, 1+ALB+ BUN+ALT+gGT+T-BIL; 0.738, 25 6.293, 1+TP+ALB+ BUN+Ca+ALT; 0.738, 256.293, 1+ALB+BUN+ALT+T- BIL+Glc; 0.738, 256.517, 1+ALB+BUN+ALT+NEFA+Glc; 0.738, 256.442, 1+A LB+BUN+Ca+AST+ALT; 0.737, 256.247, 1+TP+ALB+BUN+ALT+BHBA; 0.737, 256.389, 1+ALB+BUN+AST+ALT+TCHO; 0.737, 256.406, 1+ALB+BUN+AST+ALT+BHBA; 0.737, 256.447, 1+ALB+BUN+ALT+NEFA+BHBA; 0.737, 256.76 2, 1+ALB+BUN+AST+ALT+Glc; 0.737, 256.662, 1+ALB+ BUN+Ca+ALT+gGT; 0.737, 256.563, 1+TP+ALB+BUN+ AST+ALT; 0.737, 256.492, 1+TP+ALB+B UN+ALT+ TCHO; 0.737, 259.597, 1+ALB+BUN+AST+NEFA+TG; 0.737, 259.6 37, 1+ALB+BUN+AST+NEFA+Glc; 0.737, 256.186, 1+ALB+BUN+Ca+ALT+TC HO; 0.737, 256.665, 1+ALB+BUN+Ca+ALT+TG; 0.737, 256.232, 1+ALB+BU N+ALT+BHBA+TCHO; 0.737, 256.563, 1+ALB+BUN+ ALT+Glc+TCHO; 0.736, 256.870, 1+TP+ALB+BUN+ ALT+TG; 0.736, 256.930, 1+ALB+BUN+AST+ALT+TG; 0.736, 256.620, 1+ALB+BUN+Ca+ALT+Glc; 0.736, 257.029, 1+ALB+BUN+ALT+gGT+Glc; 0.736, 256.714, 1+ALB+BUN+ALT+gGT+BHBA; 0.736, 256.887, 1+TP+ ALB+BUN+ALT+gGT; 0.736, 256.726, 1+TP+ALB+ BUN+ALT+Glc; 0.736, 259.465, 1+ALB+BUN+Ca+AST+ NEFA; 0.736, 258.528, 1+TP+ALB+AST+ALT+NEFA; 0.736, 256.673, 1+ALB+BUN+ALT+BHBA+Glc; 0.73 6, 259.456, 1+ALB+BUN+AST+gGT+NEFA; 0.736, 256.377, 1+ALB+BUN+Ca+ALT+BHBA; 0.735, 256.733, 1+ALB+ BUN+ALT+BHBA+TG; 0.735, 257.194, 1+ALB+BUN+ ALT+gGT+TG; 0.735, 262.402, 1+ALB+AST+NEFA+T- BIL+TG; 0.735, 261.776, 1+TP+ALB+AST+NEFA+TG; 0.735, 259.472, 1+ALB+BUN+AST+T-BIL+Glc; 0.735, 256.733, 1+ALB+BUN+ALT+gGT+TCHO; 0.735, 25 9.423, 1+ALB+BUN+AST+T-BIL+TG; 0.735, 258.916, 1+TP+ALB+BUN+AST+NEFA; 0.735, 257.023, 1+ALB+ BUN+ALT+Glc+TG; 0.735, 256.866, 1+AL B+BUN+ AST+ALT+gGT; 0.735, 261.843, 1+TP+ALB+AST+ NEFA+Glc; 0.735, 261.809, 1+TP+ALB+AST+NEFA+T- BIL; 0.734, 262.436, 1+ALB+AST+NEF A+BHBA+TG; 0.734, 259.623, 1+ALB+BUN+AST+NEFA+BHBA; 0.734, 261.8 21, 1+TP+ALB+AST+NEFA+BHBA; 0.734, 259.273, 1+ALB+BUN+AST+NEFA+T-BIL; 0.734, 256.709, 1+ALB+BUN+ALT+TG+TCHO; 0.734, 258.892, 1+A LB+AST+ALT+NEFA+Glc; 0.734, 259.306, 1+ALB+ BUN+AST+NEFA+TCHO; 0. 734, 262.268, 1+ALB+Ca+ AST+NEFA+TG; 0.734, 262.519, 1+ALB+AST+NE FA+BHBA+Glc; 0.734, 258.903, 1+ALB+AST+ALT+ NEFA+BHBA; 0.734, 259. 338, 1+ALB+BUN+AST+ gGT+T-BIL; 0.734, 258.852, 1+ALB+AST+ALT+NEF A+TG; 0.734, 261.636, 1+TP+ALB+Ca+AST+NEFA; 0.734, 262.494, 1+ALB+AST+NEFA+T-BIL+Glc; 0.734, 259.199, 1+ALB+BUN+Ca+AST+T-BIL; 0. 734, 262.426, 1+ALB+AST+NEFA+Glc+TG; 0.734, 258.333, 1+ALB+ AST+A LT+NEFA+TCHO; 0.733, 262.229, 1+ALB+AST+ gGT+NEFA+TG; 0.733, 258. 909, 1+ALB+AST+ALT+ NEFA+T-BIL; 0.733, 262.356, 1+ALB+Ca+AST+NEF A+Glc; 0.733, 259.053, 1+TP+ALB+AST+ALT+T-BIL; 0.733, 258.655, 1+ALB+Ca+AST+ALT+NEFA; 0.733, 259.472, 1+ALB+BUN+AST+T-BIL+BHBA; 0.733, 262.355, 1+ALB+Ca+AST+NEFA+BHBA; 0.733, 262.326, 1+ALB+Ca+AST+NEFA+T-BIL; 0.733, 262.289, 1+ALB+ AST+gGT+NEFA+Glc; 0.733, 261.814, 1+ALB+AST+ NEFA+TG+TCHO; 0.733, 261.175, 1+TP+ALB+AST+N EFA+TCHO; 0.733, 258.596, 1+TP+ALB+BUN+AST+T- BIL; 0.733, 262.493, 1+ALB+AST+NEFA+T-BIL+BHBA; 0.733, 259.200, 1+ALB+BUN+AST+T-BIL+TCHO; 0.732, 262.287, 1+ALB+AST+gGT+NEFA+T-BIL; 0.732, 262.302, 1+ALB+AST+gGT+NEFA+BHBA; 0.732, 262.121, 1+ALB+BUN+AST+BHBA+Gl c; 0.732, 261.780, 1+TP+ALB+AST+gGT+NEFA; 0.732, 258.790, 1+ALB+A ST+ALT+gGT+NEFA; 0.732, 258.795, 1+ALB+ AST+ALT+T-BIL+TCHO; 0.73 1, 262.118, 1+ALB+Ca+ AST+gGT+NEFA; 0.731, 259.109, 1+TP+ALB+ALT+ NEFA+TCHO; 0.731, 261.894, 1+ALB+AST+NEFA+T- BIL+TCHO; 0.731, 261. 903, 1+ALB+AST+NEFA+Glc+ TCHO; 0.731, 259.831, 1+ALB+Ca+AST+ALT+BHBA; 0.731, 259.282, 1+TP+ALB+Ca+ALT+NEFA; 0.731, 259.420, 1+ALB+Ca+AST+ALT+TCHO; 0.731, 259.464, 1+ALB+AST+ALT+BHBA+TCHO; 0.73 0, 261.904, 1+ALB+AST+NEFA+BHBA+TCHO; 0.730, 259.081, 1+ALB+Ca+A ST+ALT+T-BIL; 0.730, 259.386, 1+ALB+ AST+ALT+T-BIL+TG; 0.730, 259. 383, 1+ALB+AST+ ALT+T-BIL+Glc; 0.730, 259.385, 1+ALB+AST+ALT+T-B IL+BHBA; 0.730, 259.631, 1+TP+ALB+ALT+gGT+ NEFA; 0.730, 259.643, 1+TP+ALB+ALT+NEFA+TG; 0.730, 259.628, 1+TP+ALB+ALT+NEFA+BHBA; 0. 730, 259.655, 1+TP+ALB+ALT+NEFA+T-BIL; 0.730, 259.713, 1+ALB+AST+ALT+TG+TCHO; 0.730, 259.638, 1+TP+ ALB+ALT+NEFA+Glc; 0.730, 263. 126, 1+TP+ALB+ AST+T-BIL+TG; 0.729, 260.065, 1+ALB+AST+ALT+ BHBA+TG; 0.729, 260.117, 1+ALB+AST+ALT+BHBA+ Glc; 0.729, 263.118, 1+TP+ALB+AST+T-BIL+Glc; 0.729, 263.128, 1+TP+ALB+AST+gGT+T-BIL; 0.72 9, 259.802, 1+TP+ALB+AST+ALT+BHBA; 0.729, 262.856, 1+TP+ ALB+Ca+A ST+T-BIL; 0.729, 261.277, 1+TP+ALB+ BUN+AST+BHBA; 0.729, 260.036, 1+TP+ALB+ALT+ gGT+T-BIL; 0.729, 259.881, 1+ALB+AST+ALT+gGT+ TCH O; 0.729, 262.070, 1+ALB+BUN+AST+gGT+BHBA; 0.729, 261.735, 1+ALB+Ca+AST+NEFA+TCHO; 0.729, 259.798, 1+ALB+AST+ALT+Glc+TCHO; 0.729, 259.347, 1+ALB+AST+ALT+gGT+T-BIL; 0.729, 263.657, 1+ALB+ AST+T-B IL+BHBA+Glc; 0.729, 263.102, 1+TP+ALB+ AST+T-BIL+BHBA; 0.729, 261. 873, 1+ALB+BUN+AST+ BHBA+TCHO; 0.729, 261.869, 1+ALB+BUN+Ca+AST+ BHBA; 0.729, 260.240, 1+TP+ALB+AST+ALT+Glc; 0.729, 260.183, 1+TP+ALB+AST+ALT+TG; 0.729, 259.953, 1+ALB+Ca+AST+ALT+TG; 0.728, 263. 657, 1+ALB+AST+T-BIL+BHBA+TG; 0.728, 259.691, 1+TP+

ALB+Ca+ALT+T-BIL;0.728, 260.329, 1+TP+ALB+AST+ ALT+gGT; 0.728, 260.052, 1+ALB+Ca+AST+ALT+Glc; 0.728, 262.082, 1+TP+ALB+BUN+AST+Glc; 0.728, 259.766, 1+TP+ALB+AST+ALT+TCHO; 0.728, 260.100, 1+TP+ALB+ALT+T-BI L+TG; 0.728, 263.747, 1+ALB+ AST+T-BIL+Glc+TG; 0.728, 263.491, 1+A LB+Ca+AST+ T-BIL+Glc; 0.728, 260.415, 1+ALB+AST+ALT+gGT+Glc; 0.7 28, 260.308, 1+ALB+AST+ALT+Glc+TG; 0.728, 262.666, 1+ALB+BUN+AST+gGT+Glc; 0.728, 262.308, 1+ALB+BUN+Ca+AST+Glc; 0.728, 259.892, 1+ALB+ ALT+NEFA+T-BIL+Glc; 0.728, 259.895, 1+ALB+ALT+ gGT+NEFA+Gl c; 0.728, 260.099, 1+ALB+AST+ALT+ gGT+BHBA; 0.728, 259.325, 1+ALB+ALT+NEFA+Glc+ TCHO; 0.728, 259.831, 1+TP+ALB+Ca+AST+ALT; 0.728, 2 61.621, 1+TP+ALB+BUN+Ca+AST; 0.728, 260.047, 1+ALB+Ca+AST+ALT+g GT; 0.728, 259.894, 1+ALB+ ALT+NEFA+BHBA+Glc; 0.728, 261.656, 1+AL B+AST+ gGT+NEFA+TCHO; 0.728, 260.305, 1+ALB+ALT+gGT+ T-BIL+TG; 0. 727, 260.167, 1+TP+ALB+ALT+TG+ TCHO; 0.727, 260.712, 1+TP+ALB+ALT+gGT+TG; 0.727, 259.750, 1+ALB+ALT+gGT+T-BIL+TCHO; 0.727, 263.53 3, 1+ALB+Ca+AST+T-BIL+TG; 0.727, 262.688, 1+TP+ALB+AST+T-BIL+TC HO; 0.727, 260.298, 1+TP+ ALB+ALT+gGT+TCHO; 0.727, 260.105, 1+TP+A LB+ALT+T-BIL+BHBA; 0.727, 260.306, 1+ALB+ALT+ gGT+T-BIL+BHBA; 0. 727, 259.326, 1+ALB+ALT+ NEFA+TG+TCHO; 0.727, 259.331, 1+ALB+ALT+gGT+ NEFA+TCHO; 0.727, 260.106, 1+TP+ALB+ALT+T-BIL+ Glc; 0.727, 26 2.037, 1+ALB+BUN+AST+BHBA+TG; 0.727, 260.381, 1+ALB+AST+ALT+gGT+TG; 0.727, 260.320, 1+ALB+ALT+T-BIL+BHBA+TG; 0.727, 259.879, 1+A LB+ALT+NEFA+Glc+TG; 0.727, 260.319, 1+ALB+ALT+T-BIL+BHBA+Glc; 0. 727, 259.761, 1+ALB+ALT+T-BIL+TG+TCHO; 0.727, 262.435, 1+ALB+BUN+AST+Glc+TCHO; 0.727, 260.303, 1+ALB+ ALT+gGT+T-BIL+Glc; 0.727, 2 59.567, 1+ALB+Ca+ALT+ NEFA+TG; 0.727, 259.893, 1+ALB+ALT+gGT+NEF A+TG; 0.727, 263.376, 1+ALB+Ca+AST+T-BIL+BHBA; 0.727, 262.289, 1+ALB+BUN+Ca+AST+gGT; 0.727, 259.912, 1+ALB+ALT+gGT+NEFA+T-BIL; 0. 727, 263.612, 1+ALB+AST+gGT+T-BIL+BHBA; 0.727, 260.471, 1+TP+ALB+ALT+gGT+BHBA; 0.727, 259.327, 1+ALB+ALT+NEFA+BHBA+TCHO; 0.727, 259.329, 1+ALB+ALT+NEFA+T-BIL+TCHO; 0.727, 259.617, 1+TP+ALB+AL T+T-BIL+TCHO; 0.727, 260.315, 1+ALB+ALT+T-BIL+Glc+TG; 0.727, 259. 894, 1+ALB+ ALT+NEFA+T-BIL+TG; 0.727, 263.692, 1+ALB+AST+ gGT+T-B IL+Glc; 0.726, 259.780, 1+ALB+ALT+T-BIL+ BHBA+TCHO; 0.726, 259.93 1, 1+ALB+Ca+ALT+T-BIL+ BHBA; 0.726, 259.940, 1+ALB+Ca+ALT+gGT+T-BIL; 0.726, 259.779, 1+ALB+ALT+T-BIL+Glc+TCHO; 0.726, 265.672, 1+TP+ALB+Ca+AST+BHBA; 0.726, 259.400, 1+ALB+Ca+ALT+T-BIL+TCHO; 0. 726, 265.946, 1+TP+ ALB+AST+BHBA+Glc; 0.726, 263.099, 1+ALB+Ca+AS T+T-BIL+TCHO; 0.726, 259.907, 1+ALB+ALT+gGT+ NEFA+BHBA; 0.726, 26 3.697, 1+ALB+AST+gGT+T-BIL+TG; 0.726, 259.579, 1+ALB+Ca+ALT+gGT+NEFA; 0.726, 263.315, 1+ALB+AST+T-BIL+TG+TCHO; 0.726, 259.890, 1+ALB+ALT+NEFA+BHBA+TG; 0.726, 259.578, 1+ALB+Ca+ALT+NEFA+BHBA; 0.726, 259.996, 1+TP+ALB+ALT+BHBA+TCHO; 0.726, 265.946, 1+TP+ ALB+AST+gGT+BHBA; 0.726, 259.004, 1+ALB+Ca+ ALT+NEFA+TCHO; 0.726, 25 9.941, 1+ALB+Ca+ALT+T-BIL+TG; 0.726, 259.901, 1+ALB+ALT+NEFA+T-BIL+ BHBA; 0.726, 263.300, 1+ALB+AST+T-BIL+Glc+TCHO; 0.726, 260.4 18, 1+TP+ALB+ALT+BHBA+TG; 0.726, 262.516, 1+ALB+BUN+AST+Glc+TG; 0.726, 260.674, 1+ALB+ALT+gGT+BHBA+TG; 0.726, 260.773, 1+TP+ ALB+ALT+gGT+Glc; 0.726, 259.579, 1+ALB+Ca+ALT+ NEFA+Glc; 0.726, 259.5 78, 1+ALB+Ca+ALT+NEFA+T-BIL; 0.726, 263.467, 1+ALB+Ca+AST+gGT+T-BIL;0.726, 260.666, 1+TP+ALB+ALT+Glc+TG; 0.726, 260.143, 1+ALB+ALT+gGT+BHBA+TCHO; 0.726, 263.214, 1+ALB+AST+T-BIL+BHBA+TCHO; 0. 726, 260.829, 1+ALB+ALT+gGT+Glc+TG; 0.725, 260.363, 1+ALB+ ALT+gG T+Glc+TCHO; 0.725, 262.202, 1+TP+ALB+ BUN+AST+gGT; 0.725, 260.332, 1+TP+ALB+Ca+ALT+ gGT; 0.725, 259.844, 1+TP+ALB+Ca+ALT+TCHO; 0.72 5, 260.213, 1+ALB+ALT+Glc+TG+TCHO; 0.725, 259.940, 1+ALB+Ca+ALT+T-BIL+Glc; 0.725, 260.041, 1+ALB+ ALT+BHBA+TG+TCHO; 0.725, 260.30 6, 1+TP+ALB+ ALT+Glc+TCHO; 0.725, 260.264, 1+ALB+ALT+gGT+ TG+TCHO

[25. Formula with Six Biochemistry Variables]

0.743, 257.619, 1+TP+ALB+BUN+AST+ALT+NEFA; 0.742, 257.680, 1+ALB+BUN+AST+ALT+T-BIL+TG; 0.741, 258.010, 1+ALB+BUN+AST+ALT+NEFA+TG; 0.741, 257.432, 1+ALB+BUN+Ca+AST+ALT+T-BIL; 0.741, 257.757, 1+TP+ALB+BUN+Ca+ALT+NEFA; 0.740, 257.900, 1+ALB+BUN+ALT+T-BIL+T G+TCHO; 0.740, 257.768, 1+ALB+BUN+Ca+AST+ALT+NEFA; 0.740, 257.72 6, 1+ALB+BUN+AST+ALT+T-BIL+Glc; 0.740, 257.283, 1+ALB+BUN+AST+A LT+T-BIL+TCHO; 0.740, 257.504, 1+ALB+BUN+Ca+ALT+T-BIL+TCHO; 0.7 40, 257.637, 1+ALB+BUN+AST+ALT+NEFA+TCHO; 0.740, 257.876, 1+TP+A LB+BUN+ALT+T-BIL+Glc; 0.740, 257.931, 1+TP+ALB+BUN+ALT+NEFA+T-BIL;0.740, 257.754, 1+ALB+BUN+AST+ALT+T-BIL+BHBA; 0.740, 257.77 2, 1+ALB+BUN+AST+ALT+NEFA+T-BIL; 0.740, 257.931, 1+ALB+BUN+ALT+gGT+T-BIL+TCHO; 0.740, 257.892, 1+TP+ALB+BUN+ALT+T-BIL+TG; 0.74 0, 258.288, 1+ALB+BUN+ALT+NEFA+T-BIL+TG; 0.740, 257.651, 1+ALB+B UN+AST+ALT+gGT+T-BIL; 0.740, 257.880, 1+ALB+BUN+Ca+AST+ALT+TCH O; 0.740, 257.922, 1+TP+ALB+BUN+ALT+gGT+T-BIL; 0.740, 257.243, 1+TP+ALB+BUN+AST+ALT+T-BIL; 0.740, 257.999, 1+ALB+BUN+AST+ALT+NE FA+Glc; 0.740, 258.380, 1+ALB+BUN+Ca+AST+ALT+Glc; 0.740, 257.453, 1+TP+ALB+BUN+Ca+ALT+T-BIL; 0.740, 258.565, 1+ALB+BUN+ALT+gGT+N EFA+TG; 0.740, 258.343, 1+ALB+BUN+AST+ALT+BHBA+Glc; 0.740, 258.1 82, 1+ALB+BUN+Ca+ALT+gGT+NEFA; 0.740, 257.931, 1+ALB+BUN+ALT+NE FA+T-BIL+TCHO; 0.740, 258.291, 1+ALB+BUN+ALT+gGT+T-BIL+TG; 0.74 0, 257.928, 1+ALB+BUN+AST+ALT+NEFA+BHBA; 0.740, 257.933, 1+ALB+B UN+Ca+ALT+NEFA+T-BIL; 0.740, 257.587, 1+TP+ALB+BUN+ALT+T-BIL+T CHO; 0.739, 258.266, 1+ALB+BUN+ALT+T-BIL+BHBA+TG; 0.739, 261.515, 1+ALB+BUN+AST+NEFA+Glc+TG; 0.739, 258.165, 1+ALB+BUN+ALT+NEFA+TG+TCHO; 0.739, 258.191, 1+ALB+BUN+ALT+gGT+NEFA+TCHO; 0.739, 257. 768, 1+ALB+BUN+Ca+ALT+NEFA+TCHO; 0.739, 257.925, 1+ALB+BUN+Ca+A LT+T-BIL+Glc; 0.739, 258.286, 1+ALB+BUN+ALT+gGT+T-BIL+Glc; 0.73 9, 258.248, 1+ALB+BUN+ALT+T-BIL+Glc+TG; 0.739, 258.247, 1+TP+ALB+BUN+Ca+ALT+Glc; 0.739, 257.809, 1+ALB+BUN+AST+ALT+BHBA+TCHO; 0. 739, 257.865, 1+TP+ALB+BUN+ALT+NEFA+TCHO; 0.739, 257.929, 1+ALB+BUN+Ca+ALT+T-BIL+BHBA; 0.739, 257.875, 1+ALB+BUN+ALT+T-BIL+Glc+TCHO; 0.739, 258.307, 1+ALB+BUN+ALT+gGT+T-BIL+BHBA; 0.739, 258. 123, 1+TP+ALB+BUN+ALT+NEFA+Glc; 0.739, 258.004, 1+TP+ALB+BUN+Ca+AST+ALT; 0.739, 257.882, 1+ALB+BUN+ALT+T-BIL+BHBA+TCHO;

0.739, 258.198, 1+TP+ALB+BUN+ALT+NEFA+TG; 0.739, 258.495, 1+ALB+BUN+ALT+gGT+NEFA+Glc; 0.739, 258.244, 1+TP+ALB+BUN+ALT+gGT+NEFA; 0.739, 258.172, 1+ALB+BUN+Ca+ALT+NEFA+Glc; 0.739, 258.315, 1+ALB+BUN+ALT+NEFA+T-BIL+BHBA; 0.739, 258.168, 1+ALB+BUN+Ca+ALT+NEFA+TG; 0.739, 257.837, 1+TP+ALB+BUN+ALT+T-BIL+BHBA; 0.739, 257.939, 1+ALB+BUN+AST+ALT+gGT+NEFA; 0.739, 258.089, 1+ALB+BUN+ALT+NEFA+Glc+TCHO; 0.738, 257.861, 1+TP+ALB+BUN+Ca+ALT+BHBA; 0.738, 258.346, 1+ALB+BUN+ALT+gGT+NEFA+T-BIL; 0.738, 258.292, 1+ALB+BUN+ALT+NEFA+T-BIL+Glc; 0.738, 257.920, 1+ALB+BUN+Ca+ALT+gGT+T-BIL; 0.738, 257.937, 1+TP+ALB+BUN+ALT+NEFA+BHBA; 0.738, 258.103, 1+ALB+BUN+Ca+ALT+NEFA+BHBA; 0.738, 258.203, 1+TP+ALB+BUN+ALT+BHBA+Glc; 0.738, 258.272, 1+ALB+BUN+AST+ALT+gGT+BHBA; 0.738, 257.892, 1+TP+ALB+BUN+Ca+ALT+TCHO; 0.738, 258.432, 1+ALB+BUN+Ca+AST+ALT+TG; 0.738, 257.890, 1+ALB+BUN+Ca+ALT+T-BIL+TG; 0.738, 258.275, 1+ALB+BUN+ALT+T-BIL+BHBA+Glc; 0.738, 258.469, 1+ALB+BUN+ALT+NEFA+Glc+TG; 0.738, 258.207, 1+ALB+BUN+AST+ALT+Glc+TCHO; 0.738, 258.405, 1+ALB+BUN+AST+ALT+BHBA+TG; 0.738, 257.834, 1+TP+ALB+BUN+AST+ALT+BHBA; 0.738, 258.292, 1+TP+ALB+BUN+Ca+ALT+gGT; 0.738, 261.422, 1+ALB+BUN+Ca+AST+NEFA+Glc; 0.738, 257.847, 1+TP+ALB+BUN+ALT+BHBA+TCHO; 0.738, 258.454, 1+TP+ALB+BUN+ALT+TG+TCHO; 0.738, 258.645, 1+ALB+BUN+Ca+ALT+gGT+TG; 0.738, 258.158, 1+ALB+BUN+Ca+ALT+TG+TCHO; 0.737, 258.351, 1+ALB+BUN+Ca+AST+ALT+gGT; 0.737, 257.992, 1+ALB+BUN+ALT+NEFA+BHBA+TCHO; 0.737, 258.115, 1+TP+ALB+BUN+AST+ALT+TCHO; 0.737, 258.264, 1+TP+ALB+BUN+Ca+ALT+TG; 0.737, 258.420, 1+ALB+BUN+ALT+gGT+NEFA+BHBA; 0.737, 258.183, 1+ALB+BUN+Ca+ALT+gGT+TCHO; 0.737, 258.227, 1+ALB+BUN+ALT+gGT+BHBA+TCHO; 0.737, 258.652, 1+ALB+BUN+ALT+gGT+BHBA+Glc; 0.737, 261.571, 1+ALB+BUN+AST+NEFA+BHBA+Glc; 0.737, 258.131, 1+ALB+BUN+Ca+ALT+Glc+TCHO; 0.737, 258.246, 1+TP+ALB+BUN+ALT+gGT+BHBA; 0.737, 258.749, 1+ALB+BUN+AST+ALT+Glc+TG; 0.737, 260.807, 1+TP+ALB+BUN+AST+NEFA+TG; 0.737, 258.393, 1+ALB+BUN+ALT+NEFA+BHBA+TG; 0.737, 261.495, 1+ALB+BUN+AST+NEFA+BHBA+TG; 0.737, 258.391, 1+ALB+BUN+ALT+NEFA+BHBA+Glc; 0.737, 258.227, 1+ALB+BUN+ALT+BHBA+TG+TCHO; 0.737, 258.095, 1+ALB+BUN+Ca+AST+ALT+BHBA; 0.737, 258.530, 1+ALB+BUN+ALT+Glc+TG+TCHO; 0.737, 258.542, 1+TP+ALB+BUN+AST+ALT+TG; 0.737, 258.682, 1+ALB+BUN+AST+ALT+gGT+Glc; 0.737, 258.562, 1+ALB+BUN+ALT+gGT+Glc+TCHO; 0.737, 258.867, 1+TP+ALB+BUN+ALT+gGT+TG; 0.737, 258.549, 1+TP+ALB+BUN+AST+ALT+gGT; 0.737, 258.348, 1+ALB+BUN+Ca+ALT+gGT+BHBA; 0.737, 261.344, 1+ALB+BUN+Ca+AST+NEFA+TG; 0.737, 258.605, 1+ALB+BUN+Ca+ALT+Glc+TG; 0.736, 261.350, 1+ALB+BUN+AST+gGT+NEFA+Glc; 0.736, 261.399, 1+ALB+BUN+Ca+AST+NEFA+BHBA; 0.736, 261.345, 1+ALB+BUN+AST+gGT+NEFA+TG; 0.736, 258.603, 1+ALB+BUN+Ca+ALT+gGT+Glc; 0.736, 258.481, 1+TP+ALB+BUN+ALT+gGT+TCHO; 0.736, 258.242, 1+TP+ALB+BUN+ALT+BHBA+TG; 0.736, 261.319, 1+ALB+BUN+AST+gGT+NEFA+BHBA; 0.736, 263.728, 1+TP+ALB+AST+NEFA+T-BIL+TG; 0.736, 258.360, 1+ALB+BUN+Ca+ALT+BHBA+Glc; 0.736, 258.694, 1+TP+ALB+BUN+ALT+Glc+TG; 0.736, 258.397, 1+TP+ALB+BUN+AST+ALT+Glc; 0.736, 258.176, 1+ALB+BUN+ALT+BHBA+Glc+TCHO; 0.736, 259.010, 1+ALB+BUN+ALT+gGT+Glc+TG; 0.736, 258.366, 1+ALB+BUN+AST+ALT+TG+TCHO; 0.736, 258.332, 1+TP+ALB+BUN+ALT+Glc+TCHO; 0.736, 261.175, 1+ALB+BUN+AST+NEFA+TG+TCHO; 0.736, 258.723, 1+TP+ALB+BUN+ALT+gGT+Glc; 0.736, 258.713, 1+ALB+BUN+ALT+gGT+BHBA+TG; 0.736, 263.746, 1+TP+ALB+AST+NEFA+BHBA+TG; 0.736, 258.672, 1+ALB+BUN+ALT+BHBA+Glc+TG; 0.736, 258.345, 1+ALB+BUN+AST+ALT+gGT+TCHO; 0.736, 258.375, 1+ALB+BUN+Ca+ALT+BHBA+TG; 0.736, 260.309, 1+ALB+AST+ALT+NEFA+BHBA+TCHO; 0.736, 260.586, 1+TP+ALB+BUN+Ca+AST+NEFA; 0.736, 260.825, 1+TP+ALB+BUN+AST+NEFA+Glc; 0.736, 260.021, 1+TP+ALB+AST+ALT+NEFA+TCHO; 0.736, 261.244, 1+ALB+BUN+AST+NEFA+T-BIL+Glc; 0.736, 260.223, 1+TP+ALB+Ca+AST+ALT+NEFA; 0.736, 264.399, 1+ALB+AST+NEFA+T-BIL+Glc+TG; 0.735, 257.866, 1+ALB+BUN+Ca+ALT+BHBA+TCHO; 0.735, 261.172, 1+ALB+BUN+Ca+AST+gGT+NEFA; 0.735, 261.127, 1+ALB+BUN+AST+NEFA+T-BIL+TG; 0.735, 260.470, 1+TP+ALB+AST+ALT+NEFA+TG; 0.735, 260.498, 1+TP+ALB+AST+ALT+NEFA+Glc; 0.735, 263.766, 1+TP+ALB+AST+NEFA+Glc+TG; 0.735, 261.242, 1+ALB+BUN+AST+NEFA+Glc+TCHO; 0.735, 261.405, 1+ALB+BUN+AST+T-BIL+BHBA+TG; 0.735, 260.671, 1+TP+ALB+BUN+AST+NEFA+BHBA; 0.735, 260.511, 1+TP+ALB+AST+ALT+NEFA+T-BIL; 0.735, 263.802, 1+TP+ALB+AST+NEFA+T-BIL+BHBA; 0.735, 261.298, 1+ALB+BUN+AST+gGT+T-BIL+TG; 0.735, 264.392, 1+ALB+AST+NEFA+T-BIL+BHBA+TG; 0.735, 261.054, 1+ALB+BUN+AST+gGT+NEFA+T-BIL; 0.735, 263.818, 1+TP+ALB+AST+NEFA+BHBA+Glc; 0.735, 263.805, 1+TP+ALB+AST+NEFA+T-BIL+Glc; 0.735, 260.311, 1+ALB+AST+ALT+NEFA+Glc+TCHO; 0.735, 263.566, 1+TP+ALB+Ca+AST+NEFA+TG; 0.735, 260.464, 1+TP+ALB+AST+ALT+NEFA+BHBA; 0.735, 260.480, 1+TP+ALB+AST+ALT+gGT+NEFA; 0.735, 261.417, 1+ALB+BUN+AST+T-BIL+Glc+TG; 0.735, 260.821, 1+TP+ALB+AST+gGT+NEFA; 0.735, 261.148, 1+ALB+BUN+Ca+AST+T-BIL+TG; 0.735, 261.221, 1+ALB+BUN+AST+NEFA+BHBA+TCHO; 0.735, 260.299, 1+ALB+AST+ALT+NEFA+TG+TCHO; 0.735, 258.707, 1+ALB+BUN+ALT+gGT+TG+TCHO; 0.734, 260.388, 1+TP+ALB+BUN+AST+NEFA+T-BIL; 0.734, 263.622, 1+TP+ALB+Ca+AST+NEFA+BHBA; 0.734, 258.850, 1+ALB+BUN+AST+ALT+gGT+TG; 0.734, 264.268, 1+ALB+Ca+AST+NEFA+Glc+TG; 0.734, 260.446, 1+TP+ALB+BUN+AST+NEFA+TCHO; 0.734, 261.162, 1+ALB+BUN+Ca+AST+T-BIL+BHBA; 0.734, 260.901, 1+ALB+AST+ALT+NEFA+T-BIL+BHBA; 0.734, 261.014, 1+ALB+AST+ALT+NEFA+T-BIL+BHBA; 0.734, 261.273, 1+ALB+BUN+AST+NEFA+T-BIL+BHBA; 0.734, 261.332, 1+ALB+BUN+AST+gGT+T-BIL+BHBA; 0.734, 260.887, 1+ALB+AST+ALT+NEFA+T-BIL+Glc; 0.734, 261.323, 1+ALB+BUN+AST+gGT+T-BIL+Glc; 0.734, 263.711, 1+TP+ALB+AST+gGT+NEFA+TG; 0.734, 264.237, 1+ALB+Ca+AST+NEFA+T-BIL+TG; 0.734, 263.594, 1+TP+ALB+Ca+AST+NEFA+T-BIL; 0.734, 263.092, 1+TP+ALB+AST+NEFA+TG+TCHO; 0.734, 260.552, 1+TP+ALB+BUN+AST+T-BIL+TG; 0.734, 263.636, 1+TP+ALB+Ca+AST+NEFA+Glc; 0.734, 260.245, 1+TP+ALB+BUN+Ca+AST+T-BIL; 0.734, 260.063, 1+ALB+Ca+AST+ALT+NEFA+TCHO; 0.734, 260.885, 1+ALB+AST+ALT+NEFA+BHBA+Glc; 0.734, 264.426, 1+ALB+AST+NEFA+BHBA+Glc+TG; 0.734, 261.015, 1+ALB+BUN+Ca+AST+NEFA+T-BIL; 0.734, 261.199, 1+ALB+BUN+Ca+AST+T-BIL+Glc; 0.734, 261.452, 1+ALB+BUN+AST+T-BIL+BHBA+Glc; 0.734, 264.48 5, 1+ALB+AST+NEFA+T-BIL+BHBA+Glc; 0.734, 261.158, 1+ALB+BUN+AST+T-BIL+TG+TCHO; 0.734, 261.195, 1+ALB+BUN+AST+T-BIL+Glc+TCHO; 0. 734, 260.324, 1+ALB+AST+ALT+NEFA+T-BIL+TCHO; 0.734, 260.829, 1+A LB+AST+ALT+NEFA+Glc+TG; 0.734, 260.838, 1+ALB+AST+ALT+NEFA+BHB A+TG; 0.734, 260.840, 1+ALB+AST+ALT+NEFA+T-BIL+TG; 0.734, 264.22 7, 1+ALB+AST+gGT+NEFA+BHBA+TG; 0.734, 261.046, 1+ALB+BUN+Ca+AST+NEFA+TCHO; 0.734, 260.591, 1+TP+ALB+BUN+AST+T-BIL+BHBA; 0.734, 260.934, 1+ALB+BUN+AST+NEFA+T-BIL+TCHO; 0.734, 264.266, 1+ALB+C a+AST+NEFA+BHBA+TG; 0.734, 263.159, 1+TP+ALB+AST+NEFA+BHBA+TCH O; 0.734, 260.585, 1+TP+ALB+BUN+AST+T-BIL+Glc; 0.733, 261.048, 1+TP+ALB+AST+ALT+T-BIL+BHBA; 0.733, 263.765, 1+TP+ALB+AST+gGT+NE FA+Glc; 0.733, 264.210, 1+ALB+AST+gGT+NEFA+T-BIL+TG; 0.733, 260. 918, 1+ALB+BUN+Ca+AST+T-BIL+TCHO; 0.733, 263.161, 1+TP+ALB+AST+NEFA+T-BIL+TCHO; 0.733, 260.653, 1+ALB+Ca+AST+ALT+NEFA+Glc; 0.7 33, 260.653, 1+ALB+Ca+AST+ALT+NEFA+BHBA; 0.733, 261.050, 1+TP+AL B+AST+ALT+T-BIL+Glc; 0.733, 264.354, 1+ALB+Ca+AST+NEFA+BHBA+Gl c; 0.733, 261.053, 1+TP+ALB+AST+ALT+T-BIL+TG; 0.733, 260.576, 1+T P+ALB+BUN+AST+gGT+T-BIL; 0.733, 263.744, 1+TP+ALB+AST+gGT+NEFA+BHBA; 0.733, 263.805, 1+ALB+AST+NEFA+T-BIL+TG+TCHO; 0.733, 260. 601, 1+ALB+Ca+AST+ALT+NEFA+TG; 0.733, 263.814, 1+ALB+AST+NEFA+G lc+TG+TCHO; 0.733, 261.037, 1+ALB+BUN+Ca+AST+gGT+T-BIL; 0.733, 2 64.326, 1+ALB+Ca+AST+NEFA+T-BIL+Glc; 0.733, 263.745, 1+TP+ALB+A ST+gGT+NEFA+T-BIL; 0.733, 261.187, 1+ALB+BUN+AST+T-BIL+BHBA+TC HO; 0.733, 263.174, 1+TP+ALB+AST+NEFA+Glc+TCHO; 0.733, 263.556, 1+TP+ALB+Ca+AST+gGT+NEFA; 0.733, 264.217, 1+ALB+AST+gGT+NEFA+Gl c+TG; 0.733, 260.734, 1+ALB+AST+ALT+gGT+NEFA+TG; 0.733, 264.289, 1+ALB+AST+gGT+NEFA+BHBA+Glc; 0.733, 264.278, 1+ALB+AST+gGT+NEF A+T-BIL+Glc; 0.733, 263.813, 1+ALB+AST+NEFA+BHBA+TG+TCHO; 0.733, 260.646, 1+ALB+Ca+AST+ALT+NEFA+T-BIL; 0.733, 260.758, 1+ALB+AST+ALT+gGT+NEFA+Glc; 0.733, 260.559, 1+TP+ALB+AST+ALT+T-BIL+TCH O; 0.732, 261.050, 1+TP+ALB+AST+ALT+gGT+T-BIL; 0.732, 262.963, 1+TP+ALB+Ca+AST+NEFA+TCHO; 0.732, 264.286, 1+ALB+AST+gGT+NEFA+T-BIL+BHBA; 0.732, 260.792, 1+ALB+AST+ALT+T-BIL+Glc+TCHO; 0.732, 2 60.231, 1+ALB+AST+ALT+gGT+NEFA+TCHO; 0.732, 260.480, 1+ALB+Ca+A ST+ALT+T-BIL+TCHO; 0.732, 261.060, 1+ALB+BUN+AST+gGT+T-BIL+TCH O; 0.732, 264.049, 1+ALB+Ca+AST+gGT+NEFA+TG; 0.732, 264.305, 1+AL B+Ca+AST+NEFA+T-BIL+BHBA; 0.732, 260.795, 1+ALB+AST+ALT+T-BIL+BHBA+TCHO; 0.732, 260.785, 1+ALB+AST+ALT+gGT+NEFA+T-BIL; 0.732, 263.653, 1+ALB+Ca+AST+NEFA+TG+TCHO; 0.732, 261.264, 1+TP+ALB+Ca+ALT+gGT+NEFA; 0.732, 260.794, 1+ALB+AST+ALT+T-BIL+TG+TCHO; 0.7 32, 260.705, 1+TP+ALB+Ca+AST+ALT+T-BIL; 0.731, 260.315, 1+TP+ALB+BUN+AST+T-BIL+TCHO; 0.731, 264.014, 1+ALB+BUN+AST+gGT+BHBA+Gl c; 0.731, 261.406, 1+ALB+Ca+AST+ALT+Glc+TCHO; 0.731, 260.767, 1+A LB+AST+ALT+gGT+NEFA+BHBA; 0.731, 264.117, 1+ALB+Ca+AST+gGT+NEF A+Glc; 0.731, 261.351, 1+ALB+AST+ALT+BHBA+TG+TCHO; 0.731, 263.24 4, 1+TP+ALB+BUN+AST+BHBA+Glc; 0.731, 260.514, 1+ALB+Ca+AST+ALT+gGT+NEFA; 0.731, 264.118, 1+ALB+Ca+AST+gGT+NEFA+BHBA; 0.731, 261. 602, 1+TP+ALB+ALT+gGT+NEFA+BHBA; 0.731, 261.614, 1+TP+ALB+ALT+g GT+NEFA+TG; 0.731, 261.087, 1+TP+ALB+ALT+gGT+NEFA+TCHO; 0.731, 2 60.775, 1+ALB+AST+ALT+gGT+T-BIL+TCHO; 0.731, 261.249, 1+ALB+Ca+AST+ALT+TG+TCHO; 0.731, 264.103, 1+ALB+Ca+AST+gGT+NEFA+T-BIL; 0. 731, 261.155, 1+ALB+Ca+AST+ALT+BHBA+TCHO; 0.731, 261.281, 1+TP+A LB+Ca+ALT+NEFA+T-BIL; 0.731, 264.794, 1+TP+ALB+Ca+AST+T-BIL+BH BA; 0.731, 263.902, 1+ALB+AST+NEFA+BHBA+Glc+TCHO; 0.731, 261.614, 1+TP+ALB+ALT+gGT+NEFA+Glc; 0.731, 261.830, 1+ALB+Ca+AST+ALT+BH BA+Glc; 0.731, 261.106, 1+TP+ALB+ALT+NEFA+T-BIL+TCHO; 0.731, 261. 281, 1+TP+ALB+Ca+ALT+NEFA+Glc; 0.731, 263.894, 1+ALB+AST+NEFA+T-BIL+Glc+TCHO; 0.731, 261.451, 1+ALB+AST+ALT+BHBA+Glc+TCHO; 0.7 31, 261.081, 1+ALB+Ca+AST+ALT+T-BIL+TG; 0.730, 261.104, 1+TP+ALB+ALT+NEFA+Glc+TCHO; 0.730, 261.752, 1+ALB+Ca+AST+ALT+BHBA+TG; 0. 730, 261.612, 1+TP+ALB+ALT+NEFA+T-BIL+BHBA; 0.730, 261.277, 1+TP+ALB+Ca+ALT+NEFA+BHBA; 0.730, 263.584, 1+ALB+AST+gGT+NEFA+TG+T CHO; 0.730, 261.075, 1+ALB+Ca+AST+ALT+T-BIL+Glc; 0.730, 261.643, 1+TP+ALB+ALT+NEFA+T-BIL+TG; 0.730, 260.751, 1+ALB+Ca+ALT+NE FA+TCHO; 0.730, 261.383, 1+ALB+AST+ALT+T-BIL+BHBA+TG; 0.730, 261. 380, 1+ALB+AST+ALT+T-BIL+BHBA+Glc; 0.730, 261.382, 1+ALB+AST+AL T+T-BIL+Glc+TG; 0.730, 261.089, 1+TP+ALB+ALT+NEFA+BHBA+TCHO; 0. 730, 263.083, 1+TP+ALB+AST+gGT+NEFA+TCHO; 0.730, 263.851, 1+ALB+BUN+Ca+AST+BHBA+Glc; 0.730, 261.630, 1+TP+ALB+ALT+gGT+NEFA+T-B IL; 0.730, 264.852, 1+TP+ALB+Ca+AST+T-BIL+TG; 0.730, 263.887, 1+A LB+AST+NEFA+T-BIL+BHBA+TCHO; 0.730, 261.412, 1+ALB+Ca+AST+ALT+gGT+TCHO; 0.730, 262.033, 1+TP+ALB+ALT+gGT+T-BIL+TG; 0.730, 261. 104, 1+TP+ALB+ALT+NEFA+TG+TCHO; 0.730, 263.834, 1+ALB+BUN+AST+B HBA+Glc+TCHO; 0.730, 261.481, 1+TP+ALB+Ca+AST+ALT+BHBA; 0.730, 2 62.033, 1+TP+ALB+ALT+gGT+T-BIL+BHBA; 0.730, 261.571, 1+TP+ALB+A ST+ALT+TG+TCHO; 0.730, 262.942, 1+TP+ALB+BUN+Ca+AST+BHBA; 0.730, 261.635, 1+TP+ALB+ALT+NEFA+T-BIL+Glc; 0.730, 261.236, 1+TP+ALB+AST+ALT+BHBA+TCHO; 0.730, 261.793, 1+TP+ALB+AST+ALT+BHBA+Glc; 0. 730, 261.707, 1+TP+ALB+AST+ALT+BHBA+TG; 0.730, 263.972, 1+ALB+BU N+AST+BHBA+Glc+TG; 0.730, 264.801, 1+TP+ALB+Ca+AST+T-BIL+Glc; 0. 729, 263.269, 1+TP+ALB+BUN+AST+gGT+BHBA; 0.729, 261.621, 1+TP+AL B+ALT+NEFA+BHBA+Glc; 0.729, 261.343, 1+ALB+AST+ALT+gGT+T-BIL+G lc; 0.729, 265.116, 1+TP+ALB+AST+T-BIL+Glc+TG; 0.729, 265.117, 1+TP+ALB+AST+gGT+T-BIL+Glc; 0.729, 261.618, 1+TP+ALB+ALT+NEFA+BH BA+TG; 0.729, 261.275, 1+TP+ALB+Ca+ALT+NEFA+TG; 0.729, 261.636, 1+TP+ALB+Ca+ALT+gGT+T-BIL; 0.729, 262.044, 1+ALB+AST+ALT+BHBA+G lc+TG; 0.729, 262.081, 1+ALB+AST+ALT+gGT+BHBA+Glc; 0.729, 261.53 7, 1+TP+ALB+ALT+gGT+T-BIL+TCHO; 0.729, 261.794, 1+ALB+AST+ALT+g GT+Glc+TCHO; 0.729, 261.347, 1+ALB+AST+ALT+gGT+T-BIL+TG; 0.729, 264.854, 1+TP+ALB+Ca+AST+gGT+T-BIL; 0.729, 261.031, 1+ALB+Ca+AS T+ALT+gGT+T-BIL; 0.729, 261.799, 1+TP+ALB+AST+ALT+gGT+BHBA; 0.7 29, 261.347, 1+ALB+AST+ALT+gGT+T-BIL+BHBA; 0.729, 265.125, 1+TP+ALB+AST+gGT+T-BIL+TG; 0.729, 261.627, 1+TP+ALB+ALT+NEFA+Glc+TG; 0.729, 261.061, 1+ALB+Ca+AST+ALT+T-BIL+BHBA; 0.729, 261.789, 1+ALB+Ca+AST+ALT+gGT+BHBA; 0.729, 262.034, 1+TP+ALB+ALT+gGT+T-BIL+Glc; 0.729, 261.448, 1+ALB+AST+ALT+gGT+BHBA+TCHO; 0.729, 262.014, 1+ALB+AST+ALT+gGT+BHBA+TG; 0.729, 263.732, 1+ALB+Ca+AST+NEFA+Glc+TCHO; 0.729, 263.757, 1+ALB+BUN+Ca+AST+gGT+BHBA; 0.729, 262.240, 1+TP+ALB+AST+ALT+gGT+Glc; 0.729, 261.269, 1+TP+ALB+Ca+AST+ALT+TCHO; 0.729, 265.098, 1+TP+ALB+AST+T-BIL+BHBA+Glc; 0.729, 265.102, 1+TP+ALB+AST+gGT+T-BIL+BHBA; 0.729, 265.101, 1+TP+ALB+AST+T-BIL+BHBA+TG; 0.729, 263.729, 1+ALB+Ca+AST+NEFA+BHBA+TCHO; 0.729, 263.727, 1+ALB+Ca+AST+NEFA+T-BIL+TCHO; 0.729, 263.654, 1+ALB+AST+gGT+NEFA+Glc+TCHO; 0.729, 261.619, 1+ALB+AST+ALT+Glc+TG+TCHO; 0.729, 265.656, 1+ALB+AST+T-BIL+BHBA+Glc+TG; 0.729, 264.416, 1+TP+ALB+Ca+AST+T-BIL+TCHO; 0.728, 262.094, 1+TP+ALB+ALT+T-BIL+BHBA+TG; 0.728, 261.689, 1+TP+ALB+Ca+ALT+T-BIL+BHBA; 0.728, 261.933, 1+ALB+Ca+AST+ALT+Glc+TG; 0.728, 261.819, 1+TP+ALB+Ca+AST+ALT+Glc; 0.728, 261.685, 1+TP+ALB+AST+ALT+Glc+TCHO; 0.728, 263.590, 1+TP+ALB+BUN+Ca+AST+Glc; 0.728, 263.773, 1+ALB+BUN+AST+gGT+BHBA+TCHO; 0.728, 262.181, 1+TP+ALB+AST+ALT+gGT+TG; 0.728, 261.205, 1+TP+ALB+Ca+ALT+T-BIL+TCHO; 0.728, 261.319, 1+ALB+ALT+NEFA+Glc+TG+TCHO; 0.728, 261.701, 1+ALB+AST+ALT+gGT+TG+TCHO; 0.728, 262.085, 1+TP+ALB+AST+ALT+Glc+TG; 0.728, 265.491, 1+ALB+Ca+AST+T-BIL+Glc+TG; 0.728, 264.081, 1+TP+ALB+BUN+AST+gGT+Glc; 0.728, 261.679, 1+TP+ALB+Ca+AST+ALT+TG; 0.728, 261.737, 1+ALB+ALT+gGT+T-BIL+TG+TCHO; 0.728, 261.323, 1+ALB+ALT+gGT+NEFA+Glc+TCHO; 0.728, 264.238, 1+ALB+BUN+Ca+AST+gGT+Glc; 0.728, 261.677, 1+TP+ALB+Ca+ALT+T-BIL+TG; 0.728, 261.680, 1+TP+ALB+Ca+ALT+T-BIL+Glc; 0.728, 263.654, 1+ALB+AST+gGT+NEFA+T-BIL+TCHO; 0.728, 261.765, 1+TP+ALB+AST+ALT+gGT+TCHO; 0.728, 261.894, 1+ALB+ALT+gGT+NEFA+BHBA+Glc; 0.728, 261.892, 1+ALB+gGT+NEFA+T-BIL+Glc; 0.728, 261.749, 1+ALB+ALT+gGT+T-BIL+Glc+TCHO; 0.728, 261.593, 1+TP+ALB+ALT+T-BIL+TG+TCHO; 0.728, 262.124, 1+TP+ALB+ALT+gGT+TG+TCHO; 0.728, 264.686, 1+TP+ALB+AST+gGT+T-BIL+TCHO; 0.728, 261.914, 1+ALB+Ca+AST+ALT+gGT+TG; 0.728, 261.831, 1+TP+ALB+Ca+AST+ALT+gGT; 0.728, 262.095, 1+TP+ALB+ALT+T-BIL+Glc+TG; 0.727, 261.750, 1+ALB+ALT+gGT+T-BIL+BHBA+TCHO; 0.727, 263.656, 1+ALB+AST+gGT+NEFA+BHBA+TCHO; 0.727, 262.030, 1+ALB+Ca+AST+ALT+gGT+Glc; 0.727, 261.382, 1+ALB+Ca+ALT+gGT+T-BIL+TCHO; 0.727, 263.475, 1+ALB+Ca+AST+gGT+NEFA+TCHO; 0.727, 263.571, 1+ALB+BUN+Ca+AST+BHBA+TCHO; 0.727, 261.934, 1+TP+ALB+ALT+gGT+BHBA+TCHO; 0.727, 262.304, 1+ALB+ALT+gGT+T-BIL+BHBA+TG; 0.727, 261.612, 1+TP+ALB+ALT+T-BIL+BHBA+TCHO; 0.727, 261.566, 1+ALB+Ca+ALT+NEFA+Glc+TG; 0.727, 261.317, 1+ALB+ALT+NEFA+T-BIL+Glc+TCHO; 0.727, 264.679, 1+TP+ALB+AST+T-BIL+TG+TCHO; 0.727, 261.323, 1+ALB+ALT+gGT+NEFA+TG+TCHO; 0.727, 262.301, 1+ALB+ALT+gGT+T-BIL+Glc+TG; 0.727, 263.619, 1+TP+ALB+BUN+Ca+AST+gGT; 0.727, 262.103, 1+TP+ALB+ALT+T-BIL+BHBA+Glc; 0.727, 261.878, 1+ALB+ALT+NEFA+BHBA+Glc+TG; 0.727, 261.761, 1+ALB+ALT+T-BIL+BHBA+TG+TCHO; 0.727, 261.323, 1+ALB+ALT+NEFA+BHBA+Glc+TCHO; 0.727, 262.241, 1+TP+ALB+ALT+gGT+Glc+TCHO; 0.727, 261.878, 1+ALB+ALT+gGT+NEFA+Glc+TCHO; 0.727, 261.878, 1+ALB+ALT+gGT+NEFA+Glc+TG; 0.727, 262.301, 1+ALB+ALT+gGT+T-BIL+BHBA+Glc; 0.727, 261.853, 1+TP+ALB+ALT+BHBA+TG+TCHO; 0.727, 261.322, 1+ALB+ALT+NEFA+T-BIL+TG+TCHO; 0.727, 261.328, 1+ALB+ALT+gGT+NEFA+T-BIL+TCHO; 0.727, 261.567, 1+ALB+Ca+ALT+gGT+NEFA+TG; 0.727, 261.566, 1+ALB+Ca+ALT+NEFA+BHBA+TG; 0.727, 264.654, 1+TP+ALB+AST+T-BIL+BHBA+TCHO; 0.727, 261.875, 1+ALB+ALT+NEFA+T-BIL+Glc+TG; 0.727, 265.612, 1+ALB+AST+gGT+T-BIL+BHBA+TG; 0.727, 261.389, 1+ALB+Ca+ALT+T-BIL+BHBA+TCHO; 0.727, 262.983, 1+TP+ALB+BUN+AST+BHBA+TCHO; 0.727, 265.376, 1+ALB+Ca+AST+T-BIL+BHBA+TG; 0.727, 264.380, 1+ALB+BUN+AST+gGT+Glc+TCHO; 0.727, 261.892, 1+ALB+ALT+gGT+NEFA+T-BIL+TG; 0.727, 262.277, 1+ALB+AST+ALT+gGT+Glc+TG; 0.727, 265.612, 1+ALB+AST+gGT+T-BIL+BHBA+Glc; 0.727, 261.758, 1+ALB+ALT+T-BIL+Glc+TG+TCHO; 0.727, 262.383, 1+TP+ALB+ALT+gGT+BHBA+TG; 0.727, 262.314, 1+ALB+ALT+T-BIL+BHBA+Glc+TG; 0.727, 263.899, 1+ALB+BUN+AST+gGT+BHBA+TG; 0.727, 261.886, 1+ALB+ALT+NEFA+T-BIL+BHBA+Glc; 0.727, 261.326, 1+ALB+ALT+gGT+NEFA+BHBA+TCHO; 0.727, 261.616, 1+TP+ALB+ALT+T-BIL+Glc+TCHO; 0.727, 261.565, 1+ALB+Ca+ALT+NEFA+T-BIL+TG; 0.727, 264.661, 1+TP+ALB+AST+T-BIL+Glc+TCHO; 0.727, 267.945, 1+TP+ALB+AST+gGT+BHBA+Glc; 0.726, 261.002, 1+ALB+Ca+ALT+NEFA+TG+TCHO; 0.726, 264.016, 1+ALB+BUN+Ca+AST+Glc+TCHO; 0.726, 265.362, 1+ALB+Ca+AST+T-BIL+BHBA+Glc; 0.726, 263.095, 1+TP+ALB+BUN+AST+BHBA+TG; 0.726, 261.779, 1+ALB+ALT+T-BIL+BHBA+Glc+TCHO; 0.726, 263.215, 1+TP+ALB+BUN+NEFA+T-BIL+TG; 0.726, 262.326, 1+TP+ALB+Ca+ALT+gGT+Glc; 0.726, 261.375, 1+ALB+Ca+ALT+T-BIL+TG+TCHO; 0.726, 261.322, 1+ALB+ALT+NEFA+BHBA+TG+TCHO; 0.726, 261.312, 1+ALB+ALT+NEFA+T-BIL+BHBA+TCHO; 0.726, 264.109, 1+ALB+BUN+Ca+AST+Glc+TG; 0.726, 267.672, 1+TP+ALB+Ca+AST+gGT+BHBA; 0.726, 261.001, 1+ALB+Ca+ALT+NEFA+Glc+TCHO; 0.726, 262.031, 1+ALB+ALT+gGT+BHBA+TG+TCHO; 0.726, 262.408, 1+TP+ALB+ALT+BHBA+Glc+TG; 0.726, 261.884, 1+ALB+ALT+NEFA+T-BIL+BHBA+TG; 0.726, 261.888, 1+ALB+ALT+gGT+NEFA+BHBA+TG; 0.726, 261.935, 1+ALB+Ca+ALT+gGT+T-BIL+TG; 0.726, 262.465, 1+TP+ALB+ALT+gGT+BHBA+Glc; 0.726, 265.092, 1+ALB+Ca+AST+T-BIL+TG+TCHO; 0.726, 261.004, 1+ALB+Ca+ALT+NEFA+BHBA+TCHO; 0.726, 261.577, 1+ALB+Ca+ALT+gGT+NEFA+T-BIL; 0.726, 261.578, 1+ALB+Ca+ALT+gGT+NEFA+BHBA; 0.726, 262.635, 1+TP+ALB+ALT+gGT+Glc+TG; 0.726, 261.932, 1+ALB+Ca+ALT+gGT+T-BIL+Glc; 0.726, 261.901, 1+ALB+ALT+gGT+NEFA+T-BIL+BHBA; 0.726, 265.690, 1+ALB+AST+gGT+T-BIL+Glc+TG; 0.726, 261.926, 1+ALB+Ca+ALT+T-BIL+BHBA+TG; 0.726, 261.578, 1+ALB+Ca+ALT+NEFA+BHBA+Glc; 0.726, 261.579, 1+ALB+Ca+ALT+gGT+NEFA+Glc; 0.726, 263.705, 1+ALB+BUN+AST+BHBA+TG+TCHO; 0.726, 261.793, 1+TP+ALB+Ca+ALT+gGT+TCHO; 0.726, 261.004, 1+ALB+Ca+ALT+gGT+NEFA+TCHO; 0.726, 261.578, 1+ALB+Ca+ALT+NEFA+T-BIL+Glc; 0.726, 261.578, 1+ALB+Ca+ALT+NEFA+T-BIL+BHBA; 0.726, 265.296, 1+ALB+AST+T-BIL+Glc+TG+TCHO; 0.726, 262.105, 1+TP+ALB+Ca+ALT+gGT+BHBA; 0.726, 263.306,

1+TP+ALB+BUN+Ca+AST+TCHO; 0.726, 261.921, 1+ALB+Ca+ALT+gGT+T-BIL+BHBA; 0.726, 263.842, 1+ALB+BUN+NEFA+T-BIL+Glc+TG; 0.726, 260.999, 1+ALB+Ca+ALT+NEFA+T-BIL+TC HO; 0.726, 265.462, 1+ALB+Ca+AST+gGT+T-BIL+TG; 0.726, 265.033, 1+ALB+Ca+AST+T-BIL+Glc+TCHO; 0.726, 262.136, 1+ALB+ALT+gGT+BHBA+Glc+TCHO; 0.726, 261.993, 1+TP+ALB+ALT+BHBA+Glc+TCHO; 0.726, 263. 725, 1+ALB+BUN+Ca+AST+BHBA+TG; 0.726, 263.788, 1+TP+ALB+BUN+AST+Glc+TCHO; 0.725, 262.101, 1+TP+ALB+ALT+Glc+TG+TCHO; 0.725, 261. 927, 1+ALB+Ca+ALT+T-BIL+BHBA+Glc; 0.725, 267.665, 1+TP+ALB+Ca+A ST+BHBA+Glc; 0.725, 263.853, 1+ALB+BUN+NEFA+T-BIL+BHBA+TG; 0.72 5, 265.212, 1+ALB+AST+T-BIL+BHBA+TG+TCHO; 0.725, 265.425, 1+ALB+Ca+AST+gGT+T-BIL+Glc; 0.725, 265.210, 1+ALB+AST+T-BIL+BHBA+Glc+TCHO; 0.725, 265.324, 1+ALB+Ca+AST+gGT+T-BIL+BHBA; 0.725, 261.7 83, 1+ALB+Ca+ALT+gGT+TG+TCHO; 0.725, 262.418, 1+ALB+Ca+ALT+gGT+Glc+TG; 0.725, 261.387, 1+ALB+Ca+ALT+T-BIL+Glc+TCHO; 0.725, 261. 640, 1+TP+ALB+Ca+ALT+TG+TCHO; 0.725, 262.199, 1+ALB+ALT+gGT+Glc+TG+TCHO; 0.725, 263.815, 1+ALB+BUN+gGT+NEFA+T-BIL+TG; 0.725, 26 2.031, 1+ALB+ALT+BHBA+Glc+TG+TCHO

[31. Formula with Two Amino Acid+Biochemistry Variables]
0.763, 248.642, 1+ALB+Asn; 0.744, 253.061, 1+Lys+ALB; 0.738, 253.7 92, 1+ALB+Orn; 0.734, 252.872, 1+Trp+ALB; 0.731, 254.350, 1+Arg+AL B; 0.726, 256.225, 1+ALB+Val; 0.726, 257.113, 1+Phe+ALB; 0.723, 255. 038, 1+ALB+ALT; 0.723, 257.733, 1+ALB+Pro; 0.722, 257.587, 1+Thr+A LB; 0.721, 257.548, 1+BCAA+ALB; 0.720, 261.158, 1+ALB+AST; 0.716, 2 60.041, 1+ALB+NEFA; 0.716, 257.824, 1+Tyr+ALB; 0.716, 259.283, 1+A LB+Ile; 0.715, 260.567, 1+ALB+Met; 0.715, 258.893, 1+ALB+BUN; 0.71 4, 258.964, 1+ALB+Leu; 0.713, 261.403, 1+ALB+Gln; 0.712, 260.027, 1+Ala+ALB; 0.710, 259.796, 1+ALB+Cit; 0.709, 260.990, 1+ALB+3MeHi s; 0.707, 257.951, 1+ALB+Asp; 0.705, 262.900, 1+His+ALB; 0.703, 262. 874, 1+ALB+Ser; 0.703, 262.337, 1+Gly+ALB

[32. Formula with Three Amino Acid+Biochemistry Variables]
0.777, 247.271, 1+ALB+Asn+Gly; 0.773, 248.921, 1+ALB+Asn+Ser; 0.7 73, 244.352, 1+ALB+ALT+Asn; 0.773, 245.149, 1+ALB+BUN+Asn; 0.769, 250.185, 1+ALB+Asn+Cys; 0.768, 249.593, 1+ALB+Asn+Ile; 0.768, 248. 672, 1+ALB+Asn+Trp; 0.767, 249.804, 1+ALB+Asn+Thr; 0.767, 248.957, 1+ALB+His+Asn; 0.767, 249.625, 1+ALB+NEFA+Asn; 0.767, 249.682, 1+ALB+Asn+Lys; 0.766, 249.352, 1+ALB+Asn+3MeHis; 0.766, 249.150, 1+ALB+Asn+Orn; 0.765, 247.500, 1+ALB+Asn+Cit; 0.765, 250.485, 1+ALB+Asn+Leu; 0.764, 250.583, 1+ALB+Asn+Phe; 0.764, 250.396, 1+ALB+As n+Met; 0.764, 250.565, 1+ALB+Asn+Tyr; 0.764, 249.300, 1+ALB+Asn+A rg; 0.764, 250.624, 1+ALB+Asn+BCAA; 0.763, 250.570, 1+ALB+Asn+Gl u; 0.763, 250.525, 1+ALB+T-BIL+Asn; 0.763, 250.640, 1+ALB+Asn+Pr o; 0.763, 250.638, 1+ALB+BHBA+Asn; 0.763, 250.542, 1+ALB+Asn+Tau; 0.763, 249.786, 1+ALB+TCHO+Asn; 0.763, 250.577, 1+TP+ALB+Asn; 0.7 63, 249.387, 1+ALB+Glc+Asn; 0.763, 250.591, 1+ALB+Asn+Gln; 0.762, 250.594, 1+ALB+TG+Asn; 0.762, 250.616, 1+ALB+Asn+Ala; 0.762, 250. 469, 1+ALB+Asn+Val; 0.761, 247.695, 1+ALB+Asn+Asp; 0.761, 250.443, 1+ALB+Ca+Asn; 0.761, 248.073, 1+ALB+AST+Asn; 0.759, 250.463, 1+AL B+gGT+Asn; 0.755, 250.530, 1+Lys+ALB+BUN; 0.754, 253.542, 1+ALB+C ys+Lys; 0.753, 248.182, 1+Lys+ALT+ALB; 0.752, 249.196, 1+Phe+ALT+ALB; 0.752, 250.326, 1+Trp+ALB+BUN; 0.751, 252.852, 1+ALB+AST+Or n; 0.751, 248.364, 1+Arg+ALT+ALB; 0.750, 252.721, 1+Lys+AST+ALB; 0. 750, 251.803, 1+ALB+Cit+Trp; 0.750, 252.205, 1+ALB+3MeHis+Lys; 0. 750, 254.610, 1+Ala+Lys+ALB; 0.749, 249.708, 1+Trp+ALT+ALB; 0.749, 252.295, 1+Trp+Lys+ALB; 0.749, 249.606, 1+ALB+ALT+Orn; 0.748, 253. 998, 1+Lys+ALB+TP; 0.748, 253.750, 1+Gly+Lys+ALB; 0.747, 252.887, 1+Lys+ALB+NEFA; 0.747, 252.457, 1+ALB+Orn+Trp; 0.747, 251.166, 1+ALB+ALT+Pro; 0.747, 252.432, 1+Phe+ALB+BUN; 0.746, 253.509, 1+Ala+Trp+ALB; 0.745, 254.117, 1+ALB+T-BIL+Lys; 0.745, 254.557, 1+ALB+Orn+Cys; 0.745, 254.993, 1+ALB+Tau+Lys; 0.745, 253.492, 1+ALB+Cit+Lys; 0.745, 254.000, 1+ALB+Orn+Lys; 0.745, 254.823, 1+ALB+Ser+Ly s; 0.744, 254.919, 1+ALB+Lys+Leu; 0.744, 253.135, 1+ALB+BUN+Orn; 0. 744, 251.960, 1+Trp+AST+ALB; 0.744, 254.524, 1+ALB+Pro+Lys; 0.744, 254.625, 1+ALB+Ala+Orn; 0.744, 254.232, 1+Lys+His+ALB; 0.744, 254. 593, 1+ALB+Gln+Lys; 0.743, 255.060, 1+BCAA+Lys+ALB; 0.743, 254.94 5, 1+Lys+Thr+ALB; 0.743, 255.050, 1+Lys+Glc+ALB; 0.743, 254.767, 1+ALB+Lys+Ile; 0.743, 251.293, 1+ALB+ALT+Val; 0.743, 254.893, 1+Ly s+TG+ALB; 0.743, 254.361, 1+ALB+His+Orn; 0.743, 255.027, 1+Lys+gG T+ALB; 0.743, 253.476, 1+ALB+Pro+Trp; 0.743, 254.875, 1+ALB+Lys+M et; 0.743, 254.917, 1+Lys+Tyr+ALB; 0.743, 254.848, 1+Lys+Phe+ALB; 0.742, 252.540, 1+ALB+Asp+Lys; 0.742, 254.818, 1+ALB+Gly+Orn; 0.7 42, 254.102, 1+ALB+Cys+Trp; 0.742, 255.002, 1+ALB+Glu+Lys; 0.742, 253.499, 1+Arg+AST+ALB; 0.742, 254.318, 1+Lys+TCHO+ALB; 0.742, 25 4.849, 1+ALB+Lys+Val; 0.742, 254.605, 1+ALB+Orn+Phe; 0.742, 251.5 29, 1+Thr+ALT+ALB; 0.742, 254.875, 1+Lys+ALB+BHBA; 0.741, 253.922, 1+Arg+Lys+ALB; 0.741, 253.981, 1+Trp+Phe+ALB; 0.741, 254.982, 1+L ys+ALB+Ca; 0.741, 254.650, 1+ALB+Pro+Orn; 0.741, 254.444, 1+Thr+A LB+BUN; 0.741, 254.643, 1+ALB+Arg+Cys; 0.741, 253.839, 1+ALB+3MeH is+Orn; 0.741, 252.460, 1+Trp+Arg+ALB; 0.741, 255.141, 1+ALB+Thr+Orn; 0.741, 254.817, 1+ALB+NEFA+Orn; 0.740, 255.481, 1+ALB+T-BIL+Orn; 0.740, 251.854, 1+BCAA+ALT+ALB; 0.740, 252.816, 1+ALB+3MeHis+Arg; 0.740, 254.038, 1+Gly+Trp+ALB; 0.740, 255.517, 1+ALB+Gln+Or n; 0.740, 254.849, 1+TP+ALB+Orn; 0.739, 255.279, 1+ALB+Cit+Orn; 0. 739, 253.805, 1+Trp+ALB+TP; 0.739, 255.061, 1+ALB+TCHO+Orn; 0.739, 255.836, 1+Phe+ALB+NEFA; 0.739, 254.250, 1+ALB+Val+Trp; 0.739, 25 4.972, 1+ALB+BUN+Pro; 0.739, 255.668, 1+ALB+Ser+Orn; 0.739, 255.7 25, 1+ALB+gGT+Orn; 0.739, 254.645, 1+ALB+Arg+Orn; 0.739, 255.788, 1+ALB+Orn+Leu; 0.739, 253.400, 1+Arg+ALB+BUN; 0.739, 256.967, 1+G ly+Phe+ALB; 0.738, 255.789, 1+ALB+BHBA+Orn; 0.738, 255.791, 1+ALB+Orn+Ile; 0.738, 255.782, 1+ALB+Orn+Met; 0.738, 255.790, 1+ALB+Gl c+Orn; 0.738, 255.301, 1+ALB+Ser+Arg; 0.738, 253.444, 1+ALB+ALT+M et; 0.738, 255.726, 1+ALB+Tau+Orn; 0.738, 253.925, 1+ALB+3MeHis+T rp; 0.738, 254.575, 1+ALB+Tau+Trp; 0.738, 255.742, 1+ALB+Glu+Orn; 0.738, 251.937, 1+ALB+Asp+Trp; 0.738, 255.521, 1+ALB+3MeHis+Phe; 0.738, 255.582, 1+ALB+Ca+Orn; 0.738, 251.632, 1+Tyr+ALT+ALB; 0.73 8, 254.336, 1+ALB+Gln+Trp; 0.737, 254.595, 1+Trp+Thr+ALB; 0.737, 2 54.199, 1+Gly+Arg+ALB; 0.737, 255.725, 1+ALB+Orn+BCAA; 0.737, 255. 747, 1+ALB+TG+Orn; 0.737, 252.229, 1+ALB+ALT+Leu; 0.737, 255.738, 1+ALB+AST+Val; 0.737, 254.444, 1+Arg+ALB+NEFA;

0.736, 254.682, 1+BCAA+Trp+ALB; 0.736, 254.578, 1+Trp+Tyr+ALB; 0.736, 255.403, 1+ALB+Orn+Tyr; 0.736, 254.791, 1+ALB+Met+Trp; 0.736, 256.807, 1+ALB+Gly+Pro; 0.736, 253.933, 1+ALB+Asp+Orn; 0.736, 253.436, 1+ALB+ALT+Ile; 0.735, 254.482, 1+Trp+ALB+NEFA; 0.735, 253.531, 1+ALB+ALT+Cit; 0.735, 255.417, 1+ALB+Orn+Val; 0.735, 254.255, 1+Ala+ALT+ALB; 0.735, 253.211, 1+ALB+BUN+ALT; 0.735, 255.338, 1+Ala+ALB+BUN; 0.735, 254.754, 1+ALB+T-BIL+Trp; 0.734, 254.312, 1+ALB+ALT+Gln; 0.734, 255.496, 1+ALB+Arg+Pro; 0.734, 255.949, 1+ALB+Cit+Thr; 0.734, 257.200, 1+ALB+Ala+Val; 0.734, 258.129, 1+ALB+Cys+Phe; 0.734, 256.784, 1+Thr+AST+ALB; 0.734, 254.871, 1+ALB+Glu+Trp; 0.734, 256.789, 1+ALB+NEFA+Pro; 0.734, 254.537, 1+Trp+His+ALB; 0.734, 257.371, 1+ALB+Cys+Val; 0.734, 258.533, 1+ALB+AST+NEFA; 0.734, 254.871, 1+ALB+Ile+Trp; 0.734, 254.869, 1+ALB+Ser+Trp; 0.734, 256.786, 1+ALB+3MeHis+Pro; 0.734, 257.635, 1+ALB+3MeHis+Ala; 0.734, 258.338, 1+Ala+Gly+ALB; 0.734, 254.664, 1+ALB+BUN+Val; 0.734, 259.444, 1+ALB+AST+Met; 0.734, 255.218, 1+Arg+Thr+ALB; 0.733, 254.825, 1+Trp+TG+ALB; 0.733, 254.835, 1+ALB+Leu+Trp; 0.733, 254.834, 1+Trp+Glc+ALB; 0.733, 254.859, 1+Trp+ALB+BHBA; 0.733, 255.711, 1+ALB+T-BIL+Arg; 0.733, 254.855, 1+Trp+gGT+ALB; 0.733, 255.614, 1+Ala+Arg+ALB; 0.733, 255.674, 1+Arg+Phe+ALB; 0.733, 257.047, 1+ALB+AST+Pro; 0.733, 258.362, 1+ALB+Gln+Phe; 0.733, 257.170, 1+ALB+T-BIL+Phe; 0.733, 255.037, 1+ALB+Asp+Val; 0.733, 256.482, 1+Phe+AST+ALB; 0.733, 254.349, 1+Trp+TCHO+ALB; 0.733, 256.133, 1+ALB+Arg+Met; 0.732, 256.156, 1+ALB+Gln+Arg; 0.732, 257.047, 1+ALB+Pro+Val; 0.732, 255.996, 1+Arg+gGT+ALB; 0.732, 258.519, 1+ALB+Thr+Cys; 0.732, 256.801, 1+ALB+Val+BCAA; 0.732, 255.779, 1+His+ALT+ALB; 0.732, 256.954, 1+BCAA+AST+ALB; 0.732, 255.561, 1+BCAA+ALB+BUN; 0.732, 257.606, 1+ALB+Pro+Phe; 0.732, 254.791, 1+Trp+ALB+Ca; 0.732, 256.316, 1+ALB+Tau+Arg; 0.732, 257.972, 1+Gly+Thr+ALB; 0.731, 256.319, 1+Arg+Glc+ALB; 0.731, 257.379, 1+ALB+Val+Phe; 0.731, 258.221, 1+Ala+Phe+ALB; 0.731, 257.096, 1+ALB+NEFA+Val; 0.731, 255.379, 1+Arg+TCHO+ALB; 0.731, 251.171, 1+ALB+ALT+Asp; 0.731, 255.206, 1+ALB+Arg+Val; 0.731, 256.332, 1+Arg+TG+ALB; 0.731, 256.028, 1+Arg+ALB+TP; 0.731, 258.466, 1+Ala+ALB+NEFA; 0.730, 256.321, 1+Arg+ALB+BHBA; 0.730, 255.046, 1+Tyr+ALB+BUN; 0.730, 255.673, 1+Arg+His+ALB; 0.730, 255.998, 1+Arg+ALB+Ca; 0.730, 254.856, 1+ALB+Arg+Asp; 0.730, 257.057, 1+Tyr+AST+ALB; 0.729, 258.861, 1+Phe+ALB+TP; 0.729, 257.528, 1+Thr+ALB+NEFA; 0.729, 255.988, 1+BCAA+Arg+ALB; 0.729, 258.012, 1+Thr+Phe+ALB; 0.729, 257.059, 1+ALB+3MeHis+Val; 0.728, 258.523, 1+Ala+BCAA+ALB; 0.728, 256.521, 1+ALB+AST+ALT; 0.728, 256.222, 1+Arg+Tyr+ALB; 0.728, 258.749, 1+Ala+Thr+ALB; 0.727, 257.901, 1+BCAA+ALB+NEFA; 0.727, 255.913, 1+ALB+ALT+NEFA; 0.726, 261.364, 1+Gly+AST+ALB; 0.726, 254.428, 1+ALB+BUN+Asp; 0.726, 258.393, 1+BCAA+Phe+ALB; 0.726, 259.204, 1+Ala+AST+ALB; 0.726, 257.107, 1+ALB+AST+Asp; 0.725, 259.112, 1+Phe+Glc+ALB; 0.725, 258.619, 1+Phe+Tyr+ALB; 0.725, 258.707, 1+Phe+His+ALB; 0.725, 261.495, 1+His+AST+ALB; 0.725, 258.898, 1+Phe+TG+ALB; 0.725, 258.863, 1+ALB+BUN+AST; 0.725, 258.720, 1+Gly+BCAA+ALB; 0.724, 258.961, 1+Phe+ALB+Ca; 0.724, 259.114, 1+BCAA+ALB+TP; 0.724, 257.919, 1+Phe+TCHO+ALB; 0.724, 258.811, 1+Phe+ALB+BHBA; 0.724, 255.937, 1+ALB+ALT+3MeHis; 0.724, 259.381, 1+Thr+ALB+TP; 0.724, 257.861, 1+ALB+Tyr+Val; 0.724, 258.977, 1+Phe+gGT+ALB; 0.724, 256.690, 1+ALB+NEFA+Asp; 0.723, 259.377, 1+Thr+Glc+ALB; 0.723, 259.515, 1+Thr+ALB+BHBA; 0.723, 257.204, 1+ALB+3MeHis+Tyr; 0.723, 258.661, 1+BCAA+Thr+ALB; 0.723, 256.310, 1+ALB+Asp+Phe; 0.723, 259.271, 1+Thr+His+ALB; 0.723, 256.443, 1+Gly+ALT+ALB; 0.723, 259.363, 1+Thr+gGT+ALB; 0.722, 258.289, 1+Tyr+ALB+NEFA; 0.722, 258.616, 1+Gly+Tyr+ALB; 0.722, 260.388, 1+ALB+AST+3MeHis; 0.722, 258.215, 1+ALB+BUN+NEFA; 0.722, 258.879, 1+BCAA+His+ALB; 0.722, 259.054, 1+Ala+Tyr+ALB; 0.722, 258.492, 1+Thr+Tyr+ALB; 0.721, 254.090, 1+ALB+3MeHis+Asp; 0.721, 258.911, 1+Thr+TCHO+ALB; 0.721, 259.494, 1+Thr+ALB+Ca; 0.720, 259.548, 1+BCAA+Glc+ALB; 0.720, 259.402, 1+BCAA+ALB+Ca; 0.720, 259.159, 1+BCAA+ALB+BHBA; 0.720, 259.459, 1+BCAA+gGT+ALB; 0.720, 258.956, 1+BCAA+Tyr+ALB; 0.720, 258.471, 1+BCAA+TCHO+ALB; 0.719, 260.032, 1+His+ALB+BUN; 0.719, 259.206, 1+Thr+TG+ALB; 0.718, 259.423, 1+BCAA+TG+ALB; 0.718, 259.025, 1+ALB+BUN+3MeHis; 0.717, 259.803, 1+Tyr+Glc+ALB; 0.716, 257.278, 1+ALB+Asp+Tyr; 0.716, 261.513, 1+Ala+gGT+ALB; 0.716, 259.659, 1+Tyr+ALB+Ca; 0.716, 259.686, 1+Tyr+gGT+ALB; 0.716, 259.585, 1+Tyr+ALB+TP; 0.715, 259.791, 1+Tyr+TG+ALB; 0.715, 260.298, 1+Gly+ALB+BUN; 0.715, 261.135, 1+ALB+NEFA+3MeHis; 0.714, 259.675, 1+Tyr+ALB+BHBA; 0.714, 259.593, 1+Tyr+His+ALB; 0.714, 262.014, 1+Gly+ALB+NEFA; 0.714, 261.729, 1+His+ALB+NEFA; 0.713, 258.324, 1+Tyr+TCHO+ALB; 0.712, 261.677, 1+Ala+TG+ALB; 0.712, 261.988, 1+Ala+His+ALB; 0.712, 262.021, 1+Ala+Glc+ALB; 0.712, 262.023, 1+Ala+ALB+TP; 0.711, 263.250, 1+Gly+His+ALB; 0.711, 261.830, 1+Ala+ALB+Ca; 0.711, 260.810, 1+Ala+TCHO+ALB; 0.711, 261.651, 1+Ala+ALB+BHBA; 0.709, 264.620, 1+His+gGT+ALB; 0.707, 264.722, 1+His+ALB+TP; 0.705, 264.509, 1+His+ALB+Ca; 0.705, 268.177, 1+Phe+His+ALT; 0.705, 264.873, 1+His+Glc+ALB; 0.704, 263.960, 1+Gly+ALB+BHBA; 0.704, 264.637, 1+His+ALB+BHBA; 0.703, 264.226, 1+Gly+gGT+ALB; 0.703, 264.470, 1+His+TG+ALB; 0.703, 263.895, 1+Gly+ALB+TP; 0.702, 263.751, 1+His+TCHO+ALB; 0.702, 264.299, 1+Gly+Glc+ALB; 0.702, 264.083, 1+Gly+TG+ALB; 0.702, 263.875, 1+Gly+ALB+Ca; 0.701, 263.247, 1+Gly+TCHO+ALB; 0.700, 268.528, 1+BUN+ALT+Asn

[33. Formula with Four Amino Acid+Biochemistry Variables]

0.785, 242.136, 1+ALB+BUN+ALT+Asn; 0.780, 245.877, 1+ALB+BUN+Asn+Ile; 0.780, 247.807, 1+ALB+Asn+Orn+Ile; 0.780, 245.448, 1+ALB+BUN+Asn+Trp; 0.779, 248.189, 1+ALB+Asn+Lys+Ile; 0.779, 245.198, 1+ALB+ALT+Asn+Ile; 0.778, 245.741, 1+ALB+ALT+Asn+Thr; 0.778, 247.779, 1+ALB+Asn+Arg+Ile; 0.778, 245.488, 1+ALB+ALT+Asn+Trp; 0.777, 249.815, 1+ALB+Asn+Tyr+Trp; 0.777, 247.010, 1+ALB+His+Asn+Orn; 0.777, 245.155, 1+ALB+ALT+His+Asn; 0.776, 245.415, 1+ALB+ALT+Glc+Asn; 0.776, 245.353, 1+ALB+BUN+His+Asn; 0.776, 246.620, 1+ALB+BUN+NEFA+Asn; 0.776, 246.436, 1+ALB+BUN+Asn+Thr; 0.776, 246.576, 1+ALB+BUN+Asn+3MeHis; 0.775, 246.386, 1+ALB+BUN+Asn+Lys; 0.775, 244.982, 1+ALB+ALT+Asn+Arg; 0.775, 246.381, 1+ALB+BUN+Glc+Asn; 0.775, 246.083, 1+ALB+ALT+Asn+3MeHis; 0.775, 245.552, 1+ALB+ALT+Asn+Orn; 0.775, 247.021, 1+ALB+BUN+Asn+Tyr; 0.774, 246.913, 1+ALB+BUN+T-BIL+Asn; 0.774, 248.976, 1+ALB+His+Asn+Lys; 0.774, 243.764, 1+ALB+BUN+Asn+Asp; 0.774, 246.311, 1+ALB+ALT+Asn+Tyr; 0.774, 246.301, 1+ALB+ALT+NEFA+Asn; 0.774, 246.800,

1+ALB+BUN+Asn+Phe; 0.774, 245.857, 1+ALB+ALT+Asn+Phe; 0.774, 250.456, 1+ALB+NEFA+Asn+Ile; 0.774, 243.147, 1+ALB+ALT+Asn+Asp; 0.773, 249.483, 1+ALB+NEFA+His+Asn; 0.773, 251.166, 1+ALB+Asn+Lys+Tyr; 0.773, 245.569, 1+ALB+ALT+Asn+Lys; 0.773, 246.721, 1+ALB+BUN+Asn+Orn; 0.773, 246.656, 1+ALB+BUN+Asn+Arg; 0.773, 246.345, 1+ALB+ALT+BHBA+Asn; 0.773, 246.313, 1+ALB+ALT+Asn+Val; 0.773, 247.149, 1+ALB+BUN+Asn+Val; 0.773, 246.262, 1+ALB+Ca+ALT+Asn; 0.772, 245.478, 1+ALB+BUN+AST+Asn; 0.772, 250.750, 1+ALB+NEFA+Asn+Thr; 0.772, 247.047, 1+ALB+BUN+gGT+Asn; 0.772, 246.952, 1+ALB+BUN+Ca+Asn; 0.772, 246.343, 1+ALB+ALT+gGT+Asn; 0.772, 246.255, 1+ALB+ALT+T-BIL+Asn; 0.772, 250.455, 1+ALB+Asn+Orn+Tyr; 0.772, 250.623, 1+ALB+His+Asn+Ile; 0.772, 247.054, 1+ALB+BUN+BHBA+Asn; 0.771, 245.698, 1+ALB+AST+ALT+Asn; 0.771, 249.051, 1+ALB+Glc+His+Asn; 0.771, 248.008, 1+ALB+His+Asn+Arg; 0.771, 250.066, 1+ALB+Asn+Arg+Tyr; 0.770, 247.955, 1+ALB+AST+Asn+Trp; 0.770, 249.804, 1+ALB+Asn+Thr+Lys; 0.770, 249.402, 1+ALB+Glc+Asn+Ile; 0.770, 250.047, 1+ALB+Asn+3MeHis+Lys; 0.770, 251.257, 1+ALB+Asn+Thr+Ile; 0.770, 252.317, 1+ALB+Asn+Tyr+Phe; 0.770, 249.358, 1+ALB+Asn+Thr+Orn; 0.770, 251.384, 1+ALB+NEFA+Asn+Tyr; 0.770, 249.833, 1+ALB+Asn+3MeHis+Trp; 0.770, 248.904, 1+ALB+AST+Asn+Ile; 0.769, 250.808, 1+ALB+NEFA+T-BIL+Asn; 0.769, 250.147, 1+ALB+Asn+Orn+Trp; 0.769, 250.566, 1+ALB+NEFA+Asn+Lys; 0.769, 249.970, 1+ALB+Asn+3MeHis+Orn; 0.769, 251.485, 1+ALB+T-BIL+Asn+Ile; 0.769, 250.372, 1+ALB+NEFA+Asn+Trp; 0.769, 250.599, 1+ALB+Asn+Val+Trp; 0.768, 251.417, 1+ALB+NEFA+BHBA+Asn; 0.768, 246.270, 1+Phe+ALT+ALB+BUN; 0.768, 250.571, 1+ALB+NEFA+Asn+Orn; 0.768, 250.454, 1+ALB+Asn+Lys+Trp; 0.768, 251.576, 1+ALB+BHBA+Asn+Ile; 0.768, 250.604, 1+ALB+T-BIL+His+Asn; 0.768, 251.530, 1+ALB+T-BIL+Asn+Lys; 0.768, 251.641, 1+ALB+T-BIL+Asn+Thr; 0.768, 251.443, 1+ALB+NEFA+Asn+Phe; 0.768, 250.630, 1+ALB+Asn+Phe+Trp; 0.768, 251.002, 1+ALB+NEFA+Asn+3MeHis; 0.768, 246.659, 1+ALB+Asn+3MeHis+Asp; 0.767, 250.690, 1+ALB+His+Asn+Thr; 0.767, 250.994, 1+ALB+Asn+Orn+Val; 0.767, 251.780, 1+ALB+BHBA+Asn+Thr; 0.767, 250.157, 1+ALB+Asn+Arg+Trp; 0.767, 251.612, 1+ALB+Asn+Lys+Phe; 0.767, 251.068, 1+ALB+Asn+Orn+Lys; 0.767, 249.504, 1+ALB+Asn+3MeHis+Arg; 0.767, 251.650, 1+ALB+Asn+Lys+Val; 0.767, 250.899, 1+ALB+BHBA+His+Asn; 0.767, 248.515, 1+ALB+AST+Asn+Orn; 0.767, 250.757, 1+ALB+Glc+Asn+Lys; 0.767, 250.523, 1+ALB+Glc+Asn+Thr; 0.767, 251.673, 1+ALB+BHBA+Asn+Lys; 0.767, 251.418, 1+ALB+gGT+Asn+Ile; 0.766, 251.586, 1+ALB+NEFA+Asn+Val; 0.766, 249.367, 1+ALB+AST+Asn+Lys; 0.766, 251.330, 1+ALB+Ca+Asn+Ile; 0.766, 251.129, 1+ALB+BHBA+Asn+Orn; 0.766, 250.238, 1+ALB+NEFA+Glc+Asn; 0.766, 248.768, 1+ALB+NEFA+Asn+Asp; 0.766, 250.445, 1+ALB+NEFA+Asn+Arg; 0.766, 251.323, 1+ALB+Asn+3MeHis+Tyr; 0.766, 251.147, 1+ALB+Asn+Orn+Phe; 0.766, 248.651, 1+ALB+Asn+Asp+Tyr; 0.766, 252.115, 1+ALB+Asn+Tyr+Val; 0.766, 249.614, 1+Ala+Trp+ALB+BUN; 0.766, 249.223, 1+ALB+AST+Asn+Thr; 0.766, 250.024, 1+ALB+Asn+Arg+Thr; 0.766, 250.794, 1+ALB+gGT+His+Asn; 0.766, 250.712, 1+ALB+Ca+His+Asn; 0.766, 248.353, 1+ALB+Asn+Asp+Trp; 0.766, 251.139, 1+ALB+T-BIL+Asn+Orn; 0.766, 251.310, 1+ALB+Asn+3MeHis+Val; 0.765, 252.478, 1+ALB+T-BIL+BHBA+Asn; 0.765, 249.280, 1+ALB+Asn+Asp+Lys; 0.765, 248.937, 1+ALB+AST+His+Asn; 0.765, 251.639, 1+ALB+gGT+Asn+Thr; 0.765, 250.904, 1+ALB+Asn+Arg+Orn; 0.765, 251.088, 1+ALB+Asn+3MeHis+Phe; 0.765, 251.626, 1+ALB+Ca+Asn+Thr; 0.765, 251.532, 1+ALB+gGT+NEFA+Asn; 0.765, 251.509, 1+ALB+Ca+Asn+Lys; 0.764, 250.209, 1+ALB+Glc+Asn+Orn; 0.764, 248.587, 1+ALB+AST+NEFA+Asn; 0.764, 251.592, 1+ALB+gGT+Asn+Lys; 0.764, 251.017, 1+ALB+Ca+Asn+Orn; 0.764, 249.194, 1+ALB+Asn+Asp+Orn; 0.764, 251.137, 1+ALB+Asn+Arg+Lys; 0.764, 251.035, 1+ALB+gGT+Asn+Orn; 0.764, 251.256, 1+ALB+T-BIL+Asn+Arg; 0.763, 251.292, 1+ALB+BHBA+Asn+Arg; 0.763, 251.296, 1+ALB+Asn+Arg+Val; 0.763, 251.392, 1+ALB+Ca+NEFA+Asn; 0.763, 251.113, 1+ALB+T-BIL+Glc+Asn; 0.763, 250.490, 1+ALB+Glc+Asn+Arg; 0.763, 251.223, 1+ALB+Asn+Arg+Phe; 0.763, 248.839, 1+ALB+AST+Asn+3MeHis; 0.763, 249.984, 1+ALB+AST+Asn+Tyr; 0.762, 248.975, 1+ALB+AST+Glc+Asn; 0.762, 249.461, 1+ALB+Asn+Arg+Asp; 0.762, 246.875, 1+Lys+ALT+ALB+BUN; 0.762, 252.467, 1+ALB+Asn+Val+Phe; 0.762, 248.753, 1+ALB+AST+Asn+Arg; 0.762, 251.080, 1+ALB+gGT+Asn+Arg; 0.762, 249.641, 1+ALB+Asn+Asp+Phe; 0.761, 251.112, 1+ALB+gGT+Glc+Asn; 0.761, 249.680, 1+ALB+Asn+Asp+Val; 0.761, 249.995, 1+ALB+AST+BHBA+Asn; 0.761, 250.056, 1+ALB+AST+Asn+Phe; 0.761, 249.704, 1+ALB+AST+T-BIL+Asn; 0.761, 251.321, 1+ALB+Ca+Glc+Asn; 0.761, 247.033, 1+ALB+AST+Asn+Asp; 0.761, 252.357, 1+ALB+gGT+T-BIL+Asn; 0.761, 252.326, 1+ALB+Ca+T-BIL+Asn; 0.760, 251.177, 1+ALB+BHBA+Glc+Asn; 0.760, 251.196, 1+ALB+Ca+Asn+Arg; 0.760, 251.182, 1+Ala+Lys+ALB+BUN; 0.760, 249.933, 1+Trp+Lys+ALB+BUN; 0.760, 252.427, 1+ALB+Ca+BHBA+Asn; 0.760, 254.427, 1+Ala+Gly+Lys+ALB; 0.760, 249.969, 1+ALB+AST+Asn+Val; 0.760, 252.461, 1+ALB+gGT+BHBA+Asn; 0.760, 249.867, 1+ALB+Ca+AST+Asn; 0.760, 249.244, 1+Trp+Phe+ALT+ALB; 0.759, 248.130, 1+Trp+ALT+ALB+BUN; 0.759, 250.045, 1+ALB+AST+gGT+Asn; 0.759, 250.657, 1+Trp+Phe+ALB+BUN; 0.759, 250.662, 1+ALB+BUN+3MeHis+Lys; 0.759, 253.121, 1+Gly+Lys+AST+ALB; 0.759, 253.536, 1+Ala+Gly+Trp+ALB; 0.758, 248.590, 1+Trp+Arg+ALT+ALB; 0.758, 248.377, 1+Arg+ALT+ALB+BUN; 0.758, 249.048, 1+ALB+ALT+3MeHis+Lys; 0.758, 249.102, 1+ALB+ALT+Orn+Phe; 0.758, 248.941, 1+ALB+ALT+Arg+Phe; 0.758, 251.684, 1+Lys+Phe+ALB+BUN; 0.758, 249.427, 1+ALB+BUN+Asp+Lys; 0.758, 250.478, 1+Ala+Trp+ALT+ALB; 0.758, 251.642, 1+Lys+His+ALB+BUN; 0.757, 250.887, 1+Lys+ALB+BUN+TP; 0.757, 250.761, 1+Trp+ALB+BUN+TP; 0.757, 249.183, 1+Lys+Phe+ALT+ALB; 0.757, 249.370, 1+Lys+ALT+ALB+TP; 0.757, 252.245, 1+ALB+Ca+gGT+Asn; 0.757, 252.127, 1+Gly+Lys+ALB+BUN; 0.757, 251.203, 1+Lys+ALB+BUN+NEFA; 0.757, 250.303, 1+Gly+Phe+ALT+ALB; 0.756, 249.842, 1+ALB+ALT+3MeHis+Phe; 0.756, 249.599, 1+ALB+ALT+Orn+Trp; 0.756, 250.916, 1+Ala+ALT+ALB+BUN; 0.756, 247.453, 1+ALB+ALT+Asp+Lys; 0.756, 252.024, 1+Lys+AST+ALB+NEFA; 0.756, 249.862, 1+Ala+Lys+ALT+ALB; 0.756, 250.498, 1+Phe+ALT+ALB+NEFA; 0.756, 251.016, 1+Lys+AST+ALB+BUN; 0.756, 249.556, 1+Lys+ALT+AST+ALB; 0.756, 249.731, 1+Gly+Lys+ALT+ALB; 0.756, 249.753, 1+Thr+ALT+ALB+BUN; 0.756, 249.597, 1+ALB+BUN+ALT+Orn; 0.755, 253.249, 1+Lys+AST+ALB+TP; 0.755, 252.320, 1+ALB+BUN+Lys+Ile; 0.755, 252.326, 1+Lys+Thr+ALB+BUN; 0.755, 248.880, 1+Trp+Lys+ALT+ALB; 0.755, 251.409, 1+ALB+BUN+T-BIL+Lys; 0.755, 249.596, 1+Arg+ALT+AST+ALB; 0.755, 252.386, 1+Lys+Tyr+

ALB+BUN; 0.755, 249.600, 1+Gly+Arg+ALT+ALB; 0.755, 250.002, 1+Ala+Arg+ALT+ALB; 0.755, 252.506, 1+ALB+BUN+Lys+Val; 0.755, 252.518, 1+Lys+Glc+ALB+BUN; 0.755, 249.862, 1+ALB+ALT+Lys+Ile; 0.755, 254.388, 1+Ala+Gly+Arg+ALB; 0.754, 252.143, 1+Arg+Lys+ALB+BUN; 0.754, 249.801, 1+Lys+ALT+ALB+NEFA; 0.754, 249.703, 1+ALB+ALT+Orn+Lys; 0.754, 249.553, 1+Arg+Thr+ALT+ALB; 0.754, 251.503, 1+ALB+AST+Orn+Trp; 0.754, 248.808, 1+Arg+Lys+ALT+ALB; 0.754, 254.700, 1+Lys+His+ALB+TP; 0.754, 251.150, 1+ALB+BUN+Orn+Trp; 0.754, 252.530, 1+Lys+gGT+ALB+BUN; 0.754, 248.911, 1+ALB+BUN+Asp+Trp; 0.754, 251.823, 1+Trp+Lys+AST+ALB; 0.754, 252.476, 1+BCAA+Lys+ALB+BUN; 0.754, 250.018, 1+Lys+Thr+ALT+ALB; 0.754, 250.089, 1+ALB+ALT+T-BIL+Lys; 0.754, 252.315, 1+ALB+BUN+Orn+Lys; 0.754, 253.450, 1+ALB+AST+Orn+Lys; 0.754, 252.451, 1+Ala+Trp+AST+ALB; 0.754, 252.399, 1+Lys+ALB+BUN+Ca; 0.754, 250.996, 1+Phe+ALT+ALB+BHBA; 0.754, 252.132, 1+ALB+AST+3MeHis+Lys; 0.754, 250.123, 1+Arg+ALT+ALB+TP; 0.754, 250.126, 1+ALB+ALT+Lys+Val; 0.754, 252.120, 1+ALB+BUN+3MeHis+Phe; 0.754, 253.381, 1+ALB+AST+NEFA+Orn; 0.754, 254.010, 1+ALB+AST+His+Orn; 0.753, 249.602, 1+Lys+TCHO+ALT+ALB; 0.753, 250.180, 1+BCAA+Lys+ALT+ALB; 0.753, 252.513, 1+Lys+TG+ALB+BUN; 0.753, 250.063, 1+Lys+ALT+ALB+BHBA; 0.753, 250.754, 1+Phe+His+ALT+ALB; 0.753, 250.975, 1+Trp+Arg+ALB+BUN; 0.753, 250.179, 1+Lys+Glc+ALT+ALB; 0.753, 250.181, 1+Lys+TG+ALT+ALB; 0.753, 252.973, 1+Gly+Arg+AST+ALB; 0.753, 249.044, 1+ALB+ALT+3MeHis+Arg; 0.753, 249.776, 1+ALB+ALT+Arg+Orn; 0.753, 249.745, 1+Lys+His+ALT+ALB; 0.753, 252.773, 1+Ala+Phe+ALB+BUN; 0.753, 250.959, 1+Ala+Phe+ALT+ALB; 0.753, 254.251, 1+Gly+Lys+ALB+TP; 0.753, 252.200, 1+Lys+ALB+BUN+BHBA; 0.753, 250.232, 1+Arg+TG+ALT+ALB; 0.753, 251.074, 1+Phe+ALT+ALB+TP; 0.753, 250.294, 1+ALB+ALT+Arg+Ile; 0.753, 252.597, 1+ALB+BUN+Orn+Phe; 0.753, 255.257, 1+Ala+Lys+His+ALB; 0.753, 250.172, 1+Lys+ALT+gGT+ALB; 0.753, 254.111, 1+ALB+AST+T-BIL+Orn; 0.753, 256.931, 1+Ala+Gly+Phe+ALB; 0.752, 252.914, 1+Trp+Lys+ALB+TP; 0.752, 252.134, 1+Lys+TCHO+ALB+BUN; 0.752, 252.696, 1+Trp+Lys+His+ALB; 0.752, 249.969, 1+Lys+Tyr+ALT+ALB; 0.752, 253.857, 1+ALB+AST+Orn+Phe; 0.752, 253.867, 1+Ala+Trp+Lys+ALB; 0.752, 251.036, 1+ALB+ALT+His+Orn; 0.752, 254.206, 1+Ala+Lys+AST+ALB; 0.752, 254.796, 1+ALB+AST+BHBA+Orn; 0.752, 254.844, 1+ALB+AST+Orn+Ile; 0.752, 250.127, 1+Lys+ALT+ALB+Ca; 0.752, 250.854, 1+ALB+ALT+Thr+Orn; 0.752, 251.194, 1+Phe+TG+ALT+ALB; 0.752, 253.296, 1+Gly+Trp+Lys+ALB; 0.752, 250.761, 1+Phe+TCHO+ALT+ALB; 0.752, 250.318, 1+Arg+ALT+gGT+ALB; 0.752, 252.320, 1+Trp+TG+ALB+BUN; 0.752, 251.980, 1+Trp+Thr+ALB+BUN; 0.752, 252.646, 1+ALB+3MeHis+Lys+Trp; 0.752, 250.072, 1+Arg+ALT+ALB+Ca; 0.752, 249.901, 1+ALB+ALT+Arg+Val; 0.752, 250.186, 1+Arg+ALT+ALB+NEFA; 0.752, 254.358, 1+Ala+Lys+ALB+NEFA; 0.752, 251.191, 1+Phe+ALT+gGT+ALB; 0.752, 248.294, 1+ALB+ALT+Asp+Trp; 0.752, 250.604, 1+ALB+AST+ALT+Orn; 0.752, 252.461, 1+Trp+AST+ALB+TP; 0.752, 252.130, 1+Gly+Trp+ALB+BUN; 0.752, 254.697, 1+ALB+Ca+AST+Orn; 0.752, 254.725, 1+ALB+AST+gGT+Orn; 0.752, 250.875, 1+ALB+ALT+Val+Phe; 0.752, 250.340, 1+Arg+Glc+ALT+ALB; 0.752, 252.543, 1+Phe+ALB+BUN+NEFA; 0.752, 254.312, 1+Lys+His+AST+ALB; 0.752, 251.129, 1+Phe+Tyr+ALT+ALB; 0.752, 251.137, 1+BCAA+Phe+ALT+ALB; 0.752, 250.797, 1+Phe+ALT+AST+ALB; 0.752, 250.883, 1+Trp+ALT+ALB+TP; 0.751, 250.998, 1+ALB+ALT+Val+Trp; 0.751, 248.703, 1+ALB+ALT+Arg+Asp; 0.751, 253.548, 1+Lys+ALB+TP+NEFA; 0.751, 252.061, 1+Trp+Tyr+ALB+BUN; 0.751, 252.325, 1+Trp+gGT+ALB+BUN; 0.751, 251.191, 1+Phe+Glc+ALT+ALB; 0.751, 249.606, 1+ALB+3MeHis+Asp+Lys; 0.751, 253.764, 1+BCAA+Trp+Lys+ALB; 0.751, 250.381, 1+Trp+AST+ALB+BUN; 0.751, 254.219, 1+ALB+AST+Thr+Orn; 0.751, 254.849, 1+ALB+AST+Glc+Orn; 0.751, 253.423, 1+Arg+Lys+AST+ALB; 0.751, 249.266, 1+ALB+ALT+Asp+Orn; 0.751, 252.301, 1+BCAA+Trp+ALB+BUN; 0.751, 250.770, 1+Thr+Phe+ALT+ALB; 0.751, 254.495, 1+ALB+AST+Lys+Ile; 0.751, 252.961, 1+ALB+BUN+AST+Orn; 0.751, 253.127, 1+ALB+AST+3MeHis+Orn; 0.751, 249.916, 1+Arg+His+ALT+ALB; 0.751, 254.444, 1+Lys+AST+ALB+BHBA; 0.751, 251.133, 1+Phe+ALT+ALB+Ca; 0.751, 250.364, 1+Arg+ALT+ALB+BHBA; 0.751, 252.324, 1+Trp+Glc+ALB+BUN; 0.751, 251.593, 1+Trp+Arg+AST+ALB; 0.751, 250.363, 1+ALB+ALT+T-BIL+Arg; 0.751, 253.741, 1+ALB+AST+Arg+Orn; 0.751, 253.253, 1+ALB+AST+T-BIL+Lys; 0.751, 249.958, 1+Arg+TCHO+ALT+ALB; 0.751, 253.575, 1+ALB+3Me His+Orn+Lys; 0.751, 250.975, 1+ALB+ALT+3MeHis+Orn; 0.751, 253.768, 1+ALB+3MeHis+Lys+Phe; 0.751, 252.148, 1+ALB+BUN+Val+Trp; 0.751, 252.029, 1+ALB+AST+Asp+Lys; 0.751, 252.710, 1+ALB+3MeHis+Arg+Lys; 0.751, 253.579, 1+Gly+Phe+ALB+BUN; 0.751, 253.779, 1+Thr+Phe+ALB+BUN; 0.751, 254.499, 1+Lys+Phe+AST+ALB; 0.751, 255.345, 1+Gly+Lys+Phe+ALB; 0.751, 250.675, 1+ALB+BUN+ALT+Val; 0.750, 251.833, 1+ALB+BUN+3MeHis+Trp; 0.750, 250.303, 1+Arg+Tyr+ALT+ALB; 0.750, 251.396, 1+Gly+Trp+ALT+ALB; 0.750, 251.173, 1+Trp+TCHO+ALT+ALB; 0.750, 255.704, 1+Gly+BCAA+Lys+ALB; 0.750, 254.532, 1+ALB+AST+Lys+Val; 0.750, 251.925, 1+Trp+His+ALB+BUN; 0.750, 254.252, 1+Gly+Arg+Lys+ALB; 0.750, 254.720, 1+BCAA+Lys+AST+ALB; 0.750, 252.209, 1+Trp+ALB+BUN+BHBA; 0.750, 255.204, 1+Ala+Trp+Phe+ALB; 0.750, 251.694, 1+Trp+ALT+gGT+ALB; 0.750, 254.300, 1+Lys+TCHO+AST+ALB; 0.750, 252.027, 1+Trp+TCHO+ALB+BUN; 0.750, 254.716, 1+Lys+Glc+AST+ALB; 0.750, 252.216, 1+Trp+ALB+BUN+NEFA; 0.750, 251.101, 1+Trp+Thr+ALT+ALB; 0.750, 256.601, 1+Ala+Lys+Glc+ALB; 0.750, 250.222, 1+BCAA+Arg+ALT+ALB; 0.750, 251.688, 1+Trp+Glc+ALT+ALB; 0.749, 250.633, 1+Trp+ALT+AST+ALB; 0.749, 256.589, 1+Ala+BCAA+Lys+ALB; 0.749, 254.243, 1+Trp+Lys+Tyr+ALB; 0.749, 254.573, 1+Lys+Thr+AST+ALB; 0.749, 251.707, 1+Trp+ALT+ALB+BHBA; 0.749, 251.277, 1+BCAA+Trp+ALT+ALB; 0.749, 254.580, 1+Lys+AST+gGT+ALB; 0.749, 255.001, 1+Ala+Trp+ALB+NEFA; 0.749, 254.631, 1+Lys+TG+AST+ALB; 0.749, 251.691, 1+Trp+TG+ALT+ALB; 0.749, 251.708, 1+Trp+ALT+ALB+NEFA; 0.749, 254.672, 1+Lys+AST+ALB+Ca; 0.749, 254.260, 1+Trp+Lys+ALB+BHBA; 0.749, 256.584, 1+Ala+Lys+Thr+ALB; 0.749, 255.905, 1+Lys+Phe+ALB+TP; 0.749, 253.513, 1+Phe+His+ALB+BUN; 0.749, 252.921, 1+Gly+Trp+AST+ALB; 0.749, 256.522, 1+Ala+Lys+gGT+ALB; 0.749, 253.535, 1+Trp+Lys+ALB+NEFA; 0.749, 255.976, 1+Lys+Thr+ALB+TP; 0.749, 250.973, 1+BCAA+ALT+ALB+BUN; 0.749, 255.895, 1+Ala+Lys+ALB+TP; 0.749, 253.756, 1+Trp+Lys+TCHO+ALB; 0.749, 252.176, 1+Trp+ALB+BUN+Ca; 0.749, 254.286, 1+Trp+Lys+Phe+ALB; 0.749, 255.984, 1+BCAA+Lys+ALB+TP; 0.749, 254.559, 1+Lys+Tyr+AST+ALB; 0.749, 254.204, 1+Trp+Lys+Thr+ALB;

0.749, 256.507, 1+Ala+Lys+Phe+ALB; 0.749, 253.504, 1+Lys+His+ALB+NEFA; 0.749, 251.656, 1+Trp+His+ALT+ALB; 0.748, 253.550, 1+Ala+Arg+ALB+BUN; 0.748, 252.912, 1+Arg+AST+ALB+NEFA; 0.748, 253.959, 1+Ala+Trp+Arg+ALB; 0.748, 254.293, 1+Trp+Lys+gGT+ALB; 0.748, 254.253, 1+Trp+Lys+Glc+ALB; 0.748, 255.525, 1+Lys+Phe+His+ALB; 0.748, 253.698, 1+Trp+Arg+Lys+ALB; 0.748, 255.625, 1+Lys+ALB+TP+BHBA; 0.748, 256.579, 1+Ala+Lys+Tyr+ALB; 0.748, 255.741, 1+Gly+Lys+Glc+ALB; 0.748, 253.357, 1+Arg+Phe+ALB+BUN; 0.748, 255.604, 1+Gly+Lys+ALB+BHBA; 0.748, 250.242, 1+Tyr+ALT+ALB+BUN; 0.748, 256.547, 1+Ala+Lys+ALB+Ca; 0.748, 255.597, 1+Gly+Lys+Thr+ALB; 0.748, 254.713, 1+BCAA+Lys+ALB+NEFA; 0.748, 255.451, 1+Ala+Trp+Glc+ALB; 0.748, 255.046, 1+Gly+Lys+His+ALB; 0.748, 255.973, 1+Lys+Glc+ALB+TP; 0.748, 253.795, 1+Phe+ALB+BUN+TP; 0.748, 255.785, 1+Lys+gGT+ALB+TP; 0.748, 255.949, 1+Lys+Tyr+ALB+TP; 0.748, 254.832, 1+Lys+Glc+ALB+NEFA; 0.748, 255.748, 1+Gly+Lys+gGT+ALB; 0.748, 254.870, 1+Lys+Thr+ALB+NEFA; 0.748, 254.248, 1+Trp+Lys+TG+ALB; 0.748, 254.839, 1+Lys+TG+ALB+NEFA; 0.748, 251.008, 1+Trp+Tyr+ALT+ALB; 0.747, 255.906, 1+Lys+ALB+TP+Ca; 0.747, 254.242, 1+Trp+Lys+ALB+Ca; 0.747, 254.932, 1+Gly+Lys+TCHO+ALB; 0.747, 254.792, 1+Gly+Trp+Phe+ALB; 0.747, 254.189, 1+Ala+Trp+His+ALB; 0.747, 254.385, 1+Phe+Glc+ALB+BUN; 0.747, 253.269, 1+Trp+Phe+AST+ALB; 0.747, 255.506, 1+Ala+Trp+Thr+ALB; 0.747, 256.423, 1+Ala+Lys+ALB+BHBA; 0.747, 254.859, 1+Lys+ALB+NEFA+BHBA; 0.747, 255.772, 1+Lys+TG+ALB+TP; 0.747, 252.741, 1+Phe+AST+ALB+BUN; 0.747, 251.626, 1+Trp+ALT+ALB+Ca; 0.747, 254.748, 1+Gly+Lys+ALB+NEFA; 0.747, 255.731, 1+Gly+Lys+TG+ALB; 0.747, 254.887, 1+Lys+gGT+ALB+NEFA; 0.747, 254.526, 1+Ala+Thr+ALB+BUN; 0.747, 255.113, 1+Lys+TCHO+ALB+TP; 0.747, 255.506, 1+Ala+Trp+ALB+BHBA; 0.747, 254.877, 1+Ala+Trp+TCHO+ALB; 0.746, 254.419, 1+BCAA+Phe+ALB+BUN; 0.746, 255.508, 1+Ala+BCAA+Trp+ALB; 0.746, 255.790, 1+Ala+Lys+TCHO+ALB; 0.746, 255.642, 1+Gly+Lys+Tyr+ALB; 0.746, 255.116, 1+Arg+Lys+ALB+TP; 0.746, 253.112, 1+Gly+Trp+Arg+ALB; 0.746, 253.712, 1+Arg+Thr+ALB+BUN; 0.746, 255.508, 1+Ala+Trp+Tyr+ALB; 0.746, 254.963, 1+Ala+Trp+ALB+TP; 0.746, 255.682, 1+Gly+Lys+ALB+Ca; 0.746, 253.804, 1+Phe+TCHO+ALB+BUN; 0.746, 253.945, 1+Lys+TCHO+ALB+NEFA; 0.746, 255.742, 1+Lys+Thr+His+ALB; 0.746, 255.485, 1+Ala+Trp+TG+ALB; 0.746, 254.323, 1+Arg+Lys+His+ALB; 0.746, 253.691, 1+Trp+Thr+AST+ALB; 0.745, 254.423, 1+Phe+TG+ALB+BUN; 0.745, 256.469, 1+Ala+Lys+TG+ALB; 0.745, 254.384, 1+Phe+gGT+ALB+BUN; 0.745, 255.984, 1+Gly+Phe+AST+ALB; 0.745, 254.839, 1+Lys+ALB+Ca+NEFA; 0.745, 257.955, 1+Ala+Gly+Thr+ALB; 0.745, 254.375, 1+Phe+Tyr+ALB+BUN; 0.745, 254.107, 1+Arg+Lys+ALB+NEFA; 0.745, 252.995, 1+Ala+Thr+ALT+ALB; 0.745, 256.059, 1+BCAA+Lys+His+ALB; 0.745, 254.404, 1+Arg+Thr+AST+ALB; 0.745, 254.730, 1+Ala+ALB+BUN+NEFA; 0.745, 255.140, 1+Ala+Gly+ALB+BUN; 0.745, 255.425, 1+Ala+Trp+gGT+ALB; 0.745, 253.863, 1+Trp+AST+ALB+BHBA; 0.745, 253.119, 1+Ala+BCAA+ALT+ALB; 0.745, 252.988, 1+Gly+Thr+ALT+ALB; 0.745, 253.840, 1+BCAA+Trp+AST+ALB; 0.745, 254.727, 1+Ala+Arg+AST+ALB; 0.744, 256.899, 1+BCAA+Lys+Thr+ALB; 0.744, 256.706, 1+Ala+AST+ALB+NEFA; 0.744, 253.676, 1+Trp+Tyr+AST+ALB; 0.744, 256.206, 1+Lys+His+Glc+ALB; 0.744, 253.706, 1+Trp+AST+gGT+ALB; 0.744, 253.569, 1+Trp+Arg+ALB+TP; 0.744, 254.997, 1+Arg+AST+ALB+TP; 0.744, 253.945, 1+Trp+Glc+AST+ALB; 0.744, 255.448, 1+Ala+Trp+ALB+Ca; 0.744, 253.593, 1+Trp+TCHO+AST+ALB; 0.744, 254.712, 1+Gly+Trp+ALB+TP; 0.744, 252.929, 1+BCAA+Thr+ALT+ALB; 0.744, 253.241, 1+Trp+AST+ALB+NEFA; 0.744, 255.273, 1+Ala+BCAA+ALB+BUN; 0.744, 253.958, 1+Trp+TG+AST+ALB; 0.744, 252.668, 1+Trp+Arg+His+ALB; 0.744, 256.768, 1+BCAA+Lys+Phe+ALB; 0.744, 253.309, 1+Arg+AST+ALB+BUN; 0.744, 255.182, 1+Thr+ALB+BUN+NEFA; 0.744, 255.636, 1+Ala+Arg+Lys+ALB; 0.744, 256.901, 1+Lys+Thr+gGT+ALB; 0.744, 255.376, 1+Arg+AST+ALB+BHBA; 0.744, 256.907, 1+Lys+Thr+Glc+ALB; 0.744, 256.216, 1+Lys+His+gGT+ALB; 0.744, 253.854, 1+Trp+His+AST+ALB; 0.743, 258.494, 1+Ala+Gly+BCAA+ALB; 0.743, 255.431, 1+Arg+Glc+AST+ALB; 0.743, 256.877, 1+Lys+TG+gGT+ALB; 0.743, 255.382, 1+Gly+Arg+Phe+ALB; 0.743, 255.810, 1+BCAA+Arg+Lys+ALB; 0.743, 257.050, 1+BCAA+Lys+Glc+ALB; 0.743, 253.907, 1+Trp+AST+ALB+Ca; 0.743, 256.886, 1+Lys+Glc+TG+ALB; 0.743, 253.852, 1+Trp+Arg+TCHO+ALB; 0.743, 257.014, 1+Lys+Glc+gGT+ALB; 0.743, 256.887, 1+BCAA+Lys+TG+ALB; 0.743, 257.026, 1+BCAA+Lys+gGT+ALB; 0.743, 255.498, 1+Arg+TG+AST+ALB; 0.743, 256.280, 1+Lys+Glc+TCHO+ALB; 0.742, 254.379, 1+Ala+Gly+ALT+ALB; 0.742, 255.889, 1+Gly+Thr+ALB+BUN; 0.742, 253.641, 1+Gly+BCAA+ALT+ALB; 0.742, 257.084, 1+Ala+Gly+AST+ALB; 0.742, 256.240, 1+Lys+Thr+TCHO+ALB; 0.742, 254.560, 1+Thr+AST+ALB+BUN; 0.742, 256.888, 1+Gly+Thr+AST+ALB; 0.742, 256.771, 1+Lys+Thr+TG+ALB; 0.742, 255.497, 1+Arg+AST+gGT+ALB; 0.742, 253.347, 1+Thr+Glc+ALT+ALB; 0.742, 255.078, 1+Arg+TCHO+AST+ALB; 0.742, 256.312, 1+Lys+TCHO+gGT+ALB; 0.742, 255.119, 1+Ala+ALT+ALB+NEFA; 0.742, 253.687, 1+BCAA+ALT+ALB+NEFA; 0.742, 255.253, 1+BCAA+Arg+AST+ALB; 0.742, 256.318, 1+BCAA+Lys+TCHO+ALB; 0.742, 253.638, 1+BCAA+ALT+ALB+BHBA; 0.741, 255.922, 1+Arg+Lys+Glc+ALB; 0.741, 255.922, 1+Gly+BCAA+Trp+ALB; 0.741, 255.663, 1+Gly+Trp+Thr+ALB; 0.741, 254.454, 1+Trp+Arg+Thr+ALB; 0.741, 253.521, 1+Thr+ALT+gGT+ALB; 0.741, 255.642, 1+BCAA+Trp+ALB+TP; 0.741, 255.190, 1+Gly+Arg+Thr+ALB; 0.741, 254.313, 1+BCAA+Trp+Arg+ALB; 0.741, 254.452, 1+Trp+Arg+Glc+ALB; 0.741, 253.181, 1+Thr+TCHO+ALT+ALB; 0.741, 253.509, 1+Thr+TG+ALT+ALB; 0.741, 253.280, 1+BCAA+ALT+AST+ALB; 0.741, 252.831, 1+Thr+ALT+AST+ALB; 0.741, 253.203, 1+BCAA+TCHO+ALT+ALB; 0.741, 253.841, 1+BCAA+TG+ALT+ALB; 0.741, 254.460, 1+Trp+Arg+TG+ALB; 0.741, 256.378, 1+Thr+Glc+ALB+BUN; 0.740, 256.132, 1+Lys+TCHO+TG+ALB; 0.740, 255.874, 1+Arg+Lys+TG+ALB; 0.740, 255.850, 1+Arg+Lys+Thr+ALB; 0.740, 253.852, 1+BCAA+ALT+gGT+ALB; 0.740, 256.038, 1+Gly+Trp+TG+ALB; 0.740, 253.854, 1+BCAA+Glc+ALT+ALB; 0.740, 256.088, 1+BCAA+Thr+ALB+BUN; 0.740, 254.256, 1+Gly+Arg+ALB+BUN; 0.740, 255.366, 1+Trp+ALB+TP+NEFA; 0.740, 254.378, 1+Trp+Arg+gGT+ALB; 0.740, 256.034, 1+Gly+Trp+ALB+BHBA; 0.740, 255.813, 1+Arg+Lys+gGT+ALB; 0.740, 253.544, 1+BCAA+ALT+ALB+TP; 0.740, 255.122, 1+Arg+Lys+TCHO+ALB; 0.739, 256.001, 1+Gly+Trp+Glc+ALB; 0.739, 256.302, 1+Thr+TG+ALB+BUN; 0.739, 256.038, 1+Gly+Trp+gGT+ALB; 0.739, 255.762, 1+Trp+Glc+ALB+TP; 0.739, 254.812, 1+Arg+TCHO+ALB+BUN; 0.739, 256.352, 1+Thr+gGT+ALB+BUN; 0.739, 256.129, 1+Gly+Arg+TG+ALB; 0.739, 255.192, 1+Trp+TCHO+ALB+TP; 0.739, 253.739, 1+BCAA+

ALT+ALB+Ca; 0.739, 255.254, 1+Arg+Glc+ALB+BUN; 0.739, 255.400, 1+Arg+TG+ALB+BUN; 0.739, 257.881, 1+Ala+Thr+AST+ALB; 0.739, 256.481, 1+Trp+Thr+Glc+ALB; 0.739, 255.206, 1+Arg+gGT+ALB+BUN; 0.738, 256.026, 1+Gly+Trp+ALB+NEFA; 0.738, 255.723, 1+Trp+ALB+TP+BHBA; 0.738, 256.176, 1+Gly+Arg+Glc+ALB; 0.738, 255.719, 1+Trp+TG+ALB+TP; 0.738, 255.458, 1+Ala+AST+ALB+BUN; 0.738, 255.657, 1+Trp+gGT+ALB+TP; 0.738, 255.168, 1+Gly+Arg+TCHO+ALB; 0.738, 256.787, 1+BCAA+AST+ALB+NEFA; 0.738, 257.877, 1+Gly+BCAA+AST+ALB; 0.738, 256.301, 1+BCAA+Trp+ALB+NEFA; 0.737, 256.137, 1+Gly+BCAA+Arg+ALB; 0.737, 256.081, 1+Thr+TCHO+ALB+BUN; 0.737, 255.602, 1+Ala+ALT+AST+ALB; 0.737, 256.037, 1+Gly+Arg+gGT+ALB; 0.737, 256.567, 1+BCAA+Trp+Thr+ALB; 0.737, 255.965, 1+Gly+Trp+ALB+Ca; 0.737, 255.443, 1+Gly+Trp+TCHO+ALB; 0.737, 259.470, 1+Ala+Gly+ALB+NEFA; 0.737, 256.205, 1+Ala+TG+ALT+ALB; 0.737, 258.569, 1+Ala+BCAA+ALB+NEFA; 0.737, 255.707, 1+Trp+ALB+TP+Ca; 0.736, 256.413, 1+Trp+Glc+ALB+NEFA; 0.736, 257.855, 1+Ala+BCAA+AST+ALB; 0.736, 256.142, 1+Ala+ALT+gGT+ALB; 0.736, 256.451, 1+Trp+ALB+NEFA+BHBA; 0.736, 256.480, 1+Trp+TG+ALB+NEFA; 0.736, 257.211, 1+Ala+Glc+ALB+BUN; 0.736, 256.647, 1+BCAA+Trp+Glc+ALB; 0.736, 255.689, 1+BCAA+AST+ALB+BUN; 0.735, 256.063, 1+Ala+ALT+ALB+BHBA; 0.735, 256.091, 1+BCAA+Trp+TCHO+ALB; 0.735, 256.253, 1+Ala+ALT+ALB+TP; 0.735, 256.654, 1+BCAA+Trp+ALB+BHBA; 0.735, 256.669, 1+BCAA+Trp+gGT+ALB; 0.735, 256.475, 1+Trp+gGT+ALB+NEFA; 0.735, 255.768, 1+Ala+TCHO+ALT+ALB; 0.735, 256.609, 1+BCAA+Trp+ALB+Ca; 0.735, 256.043, 1+Ala+ALT+ALB+Ca; 0.735, 256.589, 1+Ala+ALB+BUN+BHBA; 0.735, 255.120, 1+Gly+ALT+ALB+BUN; 0.735, 256.650, 1+BCAA+Trp+TG+ALB; 0.735, 257.332, 1+Ala+ALB+BUN+TP; 0.734, 257.103, 1+Ala+ALB+BUN+Ca; 0.734, 260.336, 1+Ala+Gly+Glc+ALB; 0.734, 258.269, 1+BCAA+AST+ALB+TP; 0.734, 260.061, 1+Ala+Gly+gGT+ALB; 0.734, 256.796, 1+Trp+Glc+ALB+BHBA; 0.734, 256.610, 1+Ala+TCHO+ALB+BUN; 0.734, 256.413, 1+Trp+ALB+Ca+NEFA; 0.734, 258.421, 1+BCAA+AST+ALB+BHBA; 0.734, 256.787, 1+Trp+Glc+TG+ALB; 0.734, 256.279, 1+Trp+Glc+TCHO+ALB; 0.733, 260.334, 1+Ala+Gly+TG+ALB; 0.733, 256.554, 1+BCAA+ALB+BUN+NEFA; 0.733, 255.846, 1+Trp+TCHO+ALB+NEFA; 0.733, 256.232, 1+Ala+Glc+ALT+ALB; 0.733, 260.155, 1+Ala+Gly+ALB+BHBA; 0.733, 260.322, 1+Ala+Gly+ALB+TP; 0.733, 256.815, 1+Trp+TG+gGT+ALB; 0.733, 256.813, 1+Trp+Glc+gGT+ALB; 0.733, 256.731, 1+Trp+Glc+ALB+Ca; 0.733, 256.817, 1+Trp+TG+ALB+BHBA; 0.733, 256.843, 1+Trp+gGT+ALB+BHBA; 0.733, 257.207, 1+Ala+TG+ALB+BUN; 0.732, 260.513, 1+Gly+AST+ALB+NEFA; 0.732, 256.344, 1+Trp+TCHO+gGT+ALB; 0.732, 256.337, 1+Trp+TCHO+ALB+BHBA; 0.732, 260.410, 1+Ala+TG+ALB+NEFA; 0.732, 256.992, 1+BCAA+ALB+BUN+BHBA; 0.732, 256.300, 1+Trp+TCHO+TG+ALB; 0.732, 258.924, 1+Ala+TCHO+ALB+NEFA; 0.732, 260.354, 1+Ala+ALB+NEFA+BHBA; 0.732, 260.237, 1+Ala+Gly+ALB+Ca; 0.732, 256.746, 1+Trp+TG+ALB+Ca; 0.732, 258.793, 1+Ala+Gly+TCHO+ALB; 0.732, 257.013, 1+Ala+gGT+ALB+BUN; 0.732, 257.323, 1+Gly+BCAA+ALB+BUN; 0.732, 256.837, 1+BCAA+ALB+BUN+TP; 0.732, 258.953, 1+BCAA+Glc+AST+ALB; 0.732, 256.783, 1+Trp+ALB+Ca+BHBA; 0.731, 260.416, 1+Ala+ALB+TP+NEFA; 0.731, 260.428, 1+Ala+Glc+ALB+NEFA; 0.731, 260.237, 1+Ala+gGT+ALB+NEFA; 0.731, 257.541, 1+BCAA+Glc+ALB+BUN; 0.731, 256.269, 1+Trp+TCHO+ALB+Ca; 0.731, 258.851, 1+BCAA+AST+ALB+Ca; 0.731, 256.776, 1+Trp+gGT+ALB+Ca; 0.731, 258.872, 1+BCAA+AST+gGT+ALB; 0.730, 257.530, 1+BCAA+gGT+ALB+BUN; 0.730, 259.356, 1+BCAA+ALB+TP+NEFA; 0.730, 257.546, 1+BCAA+TG+ALB+BUN; 0.730, 258.380, 1+BCAA+TCHO+AST+ALB; 0.730, 258.914, 1+BCAA+TG+AST+ALB; 0.729, 260.388, 1+Ala+BCAA+ALB+TP; 0.729, 257.330, 1+BCAA+ALB+BUN+Ca; 0.729, 260.124, 1+Gly+AST+ALB+BUN; 0.729, 260.382, 1+Ala+ALB+Ca+NEFA; 0.729, 257.772, 1+Gly+ALT+AST+ALB; 0.729, 259.868, 1+BCAA+TG+ALB+NEFA; 0.728, 263.294, 1+Gly+Glc+AST+ALB; 0.728, 260.523, 1+Ala+BCAA+Glc+ALB; 0.728, 260.162, 1+Ala+BCAA+ALB+BHBA; 0.728, 259.856, 1+Gly+BCAA+ALB+NEFA; 0.728, 256.893, 1+BCAA+TCHO+ALB+BUN; 0.728, 260.414, 1+Ala+BCAA+TG+ALB; 0.728, 262.841, 1+Gly+AST+ALB+BHBA; 0.728, 259.890, 1+BCAA+Glc+ALB+NEFA; 0.727, 260.105, 1+Gly+BCAA+ALB+TP; 0.727, 259.876, 1+BCAA+gGT+ALB+NEFA; 0.727, 257.868, 1+Gly+ALT+ALB+NEFA; 0.727, 259.367, 1+Ala+BCAA+TCHO+ALB; 0.727, 258.576, 1+BCAA+TCHO+ALB+NEFA; 0.727, 259.889, 1+BCAA+ALB+NEFA+BHBA; 0.727, 260.541, 1+Ala+AST+ALB+BHBA; 0.727, 261.182, 1+Ala+AST+gGT+ALB; 0.727, 260.424, 1+Ala+BCAA+ALB+Ca; 0.726, 261.179, 1+Ala+Glc+AST+ALB; 0.726, 260.987, 1+Ala+TG+AST+ALB; 0.726, 261.199, 1+Ala+AST+ALB+TP; 0.726, 258.200, 1+Gly+ALT+ALB+TP; 0.725, 259.805, 1+BCAA+ALB+Ca+NEFA; 0.725, 262.656, 1+Gly+AST+ALB+TP; 0.725, 260.318, 1+Ala+BCAA+gGT+ALB; 0.725, 260.719, 1+Gly+BCAA+Glc+ALB; 0.725, 261.110, 1+BCAA+Glc+ALB+TP; 0.724, 261.078, 1+Ala+AST+ALB+Ca; 0.724, 263.232, 1+Gly+TG+AST+ALB; 0.724, 262.863, 1+Gly+TCHO+AST+ALB; 0.724, 258.208, 1+Gly+ALT+ALB+BHBA; 0.724, 260.697, 1+Gly+BCAA+TG+ALB; 0.724, 263.280, 1+Gly+AST+gGT+ALB; 0.724, 258.417, 1+Gly+TG+ALT+ALB; 0.723, 257.884, 1+Gly+TCHO+ALT+ALB; 0.723, 260.681, 1+Gly+BCAA+gGT+ALB; 0.723, 258.369, 1+Gly+Glc+ALT+ALB; 0.723, 258.441, 1+Gly+ALT+gGT+ALB; 0.723, 260.616, 1+Ala+TCHO+AST+ALB; 0.722, 259.529, 1+Gly+BCAA+TCHO+ALB; 0.720, 261.457, 1+BCAA+Glc+gGT+ALB; 0.719, 260.450, 1+BCAA+Glc+TCHO+ALB; 0.718, 261.422, 1+BCAA+Glc+TG+ALB; 0.718, 260.350, 1+BCAA+TCHO+TG+ALB; 0.718, 261.361, 1+BCAA+TG+gGT+ALB; 0.718, 260.444, 1+BCAA+TCHO+gGT+ALB; 0.717, 262.182, 1+Gly+Glc+ALB+BUN; 0.716, 263.511, 1+Ala+Glc+gGT+ALB; 0.716, 263.282, 1+Ala+TG+gGT+ALB; 0.714, 262.508, 1+Ala+TCHO+gGT+ALB; 0.714, 262.250, 1+Gly+gGT+ALB+BUN; 0.713, 261.654, 1+Gly+TCHO+ALB+BUN; 0.712, 263.670, 1+Ala+Glc+TG+ALB; 0.711, 262.808, 1+Ala+Glc+TCHO+ALB; 0.711, 262.453, 1+Ala+TCHO+TG+ALB; 0.711, 262.155, 1+Gly+TG+ALB+BUN; 0.704, 266.192, 1+Gly+Glc+gGT+ALB; 0.703, 266.013, 1+Gly+TG+gGT+ALB; 0.703, 266.043, 1+Gly+Glc+TG+ALB; 0.701, 265.213, 1+Gly+TCHO+gGT+ALB; 0.701, 265.238, 1+Gly+Glc+TCHO+ALB

[34. Formula with Five Amino Acid+Biochemistry Variables]

0.793, 244.793, 1+ALB+BUN+Asn+Lys+Ile; 0.791, 242.674, 1+ALB+BUN+ALT+Asn+Ile; 0.788, 243.255, 1+ALB+ALT+Asn+Arg+Ile; 0.788, 246.467, 1+ALB+BUN+Asn+Tyr+Trp; 0.788, 245.925, 1+ALB+BUN+Asn+Orn+Ile; 0.788, 244.645, 1+ALB+ALT+Asn+Orn+Ile; 0.788, 244.026, 1+ALB+BUN+ALT+Asn+Tyr; 0.788, 243.397, 1+ALB+BUN+ALT+Asn+Trp; 0.787, 243.528,

1+ALB+BUN+ALT+Asn+Thr; 0.787, 243.564, 1+ALB+BUN+ALT+Glc+Asn; 0.786, 242.822, 1+ALB+BUN+ALT+His+Asn; 0.786, 245.522, 1+ALB+BUN+Asn+Arg+Ile; 0.786, 248.696, 1+ALB+NEFA+Asn+Lys+Ile; 0.786, 243.593, 1+ALB+BUN+ALT+Asn+Arg; 0.785, 245.463, 1+ALB+ALT+Glc+Asn+Ile; 0.785, 240.471, 1+ALB+BUN+ALT+Asn+Asp; 0.785, 244.078, 1+ALB+BUN+ALT+Asn+3MeHis; 0.785, 244.097, 1+ALB+BUN+ALT+Asn+Val; 0.785, 248.892, 1+ALB+His+Asn+Lys+Ile; 0.785, 246.776, 1+ALB+AST+Asn+Orn+Ile; 0.785, 243.275, 1+ALB+BUN+ALT+Asn+Phe; 0.785, 244.135, 1+ALB+BUN+ALT+gGT+Asn; 0.785, 246.979, 1+ALB+His+Asn+Orn+Ile; 0.785, 244.111, 1+ALB+BUN+ALT+T-BIL+Asn; 0.785, 244.136, 1+ALB+BUN+ALT+NEFA+Asn; 0.785, 243.984, 1+ALB+BUN+ALT+Asn+Orn; 0.785, 244.135, 1+ALB+ALT+Asn+Lys+Ile; 0.784, 243.561, 1+ALB+BUN+ALT+Asn+Lys; 0.784, 244.100, 1+ALB+BUN+ALT+BHBA+Asn; 0.784, 245.878, 1+ALB+ALT+Asn+Arg+Tyr; 0.784, 249.968, 1+ALB+Asn+Arg+Tyr+Trp; 0.784, 244.829, 1+ALB+ALT+His+Asn+Orn; 0.784, 245.578, 1+ALB+BUN+His+Asn+Lys; 0.783, 248.076, 1+ALB+AST+Asn+Lys+Ile; 0.783, 247.206, 1+ALB+BUN+NEFA+Asn+Ile; 0.783, 249.226, 1+ALB+Asn+Thr+Lys+Ile; 0.783, 248.902, 1+ALB+NEFA+Asn+Arg+Ile; 0.783, 247.312, 1+ALB+ALT+Asn+Tyr+Phe; 0.783, 246.349, 1+ALB+BUN+Glc+Asn+Ile; 0.783, 244.029, 1+ALB+BUN+Ca+ALT+Asn; 0.783, 245.421, 1+ALB+BUN+His+Asn+Orn; 0.783, 249.203, 1+ALB+BHBA+Asn+Orn+Ile; 0.782, 247.085, 1+ALB+ALT+Asn+Tyr+Trp; 0.782, 247.850, 1+ALB+His+Asn+Arg+Ile; 0.782, 248.316, 1+ALB+Asn+Arg+Lys+Ile; 0.782, 248.610, 1+ALB+Asn+Arg+Orn+Ile; 0.782, 249.416, 1+ALB+NEFA+Asn+Orn+Ile; 0.782, 247.414, 1+ALB+Glc+Asn+Orn+Ile; 0.782, 245.861, 1+ALB+ALT+Glc+His+Asn; 0.782, 244.434, 1+ALB+BUN+Asn+Asp+Tyr; 0.782, 246.914, 1+ALB+BUN+Asn+Val+Trp; 0.782, 244.383, 1+ALB+ALT+His+Asn+Arg; 0.782, 248.706, 1+ALB+Asn+Orn+Lys+Ile; 0.782, 243.821, 1+ALB+BUN+AST+ALT+Asn; 0.782, 246.108, 1+ALB+BUN+Glc+His+Asn; 0.782, 247.618, 1+ALB+BUN+T-BIL+Asn+Ile; 0.782, 246.088, 1+ALB+BUN+AST+Asn+Ile; 0.781, 247.672, 1+ALB+BUN+Asn+Thr+Ile; 0.781, 248.087, 1+ALB+Glc+Asn+Lys+Ile; 0.781, 247.123, 1+ALB+ALT+NEFA+Asn+Ile; 0.781, 247.311, 1+ALB+BUN+Asn+Lys+Trp; 0.781, 251.249, 1+ALB+Asn+Lys+Tyr+Trp; 0.781, 249.061, 1+ALB+Asn+Thr+Orn+Ile; 0.781, 247.905, 1+ALB+Glc+Asn+Arg+Ile; 0.781, 246.271, 1+ALB+ALT+Asn+Thr+Orn; 0.781, 250.755, 1+ALB+Asn+Orn+Tyr+Trp; 0.781, 246.998, 1+ALB+ALT+Asn+Thr+Ile; 0.781, 247.781, 1+ALB+BUN+Asn+Lys+Tyr; 0.781, 244.690, 1+ALB+BUN+Asn+Asp+Trp; 0.780, 247.104, 1+ALB+ALT+BHBA+Asn+Ile; 0.780, 247.775, 1+ALB+BUN+gGT+Asn+Ile; 0.780, 247.545, 1+ALB+Glc+His+Asn+Orn; 0.780, 250.028, 1+ALB+T-BIL+Asn+Lys+Ile; 0.780, 245.774, 1+ALB+BUN+His+Asn+Arg; 0.780, 246.608, 1+ALB+ALT+His+Asn+Ile; 0.780, 249.418, 1+ALB+NEFA+Glc+His+Asn; 0.780, 250.115, 1+ALB+BHBA+Asn+Lys+Ile; 0.780, 248.221, 1+ALB+NEFA+His+Asn+Orn; 0.780, 246.850, 1+ALB+ALT+Glc+Asn+Thr; 0.780, 247.153, 1+ALB+ALT+Asn+Orn+Tyr; 0.780, 246.544, 1+ALB+BUN+NEFA+His+Asn; 0.780, 247.370, 1+ALB+BUN+NEFA+Asn+Trp; 0.780, 246.891, 1+ALB+AST+Asn+Arg+Ile; 0.780, 249.628, 1+ALB+Ca+Asn+Orn+Ile; 0.780, 247.432, 1+ALB+BUN+Asn+Orn+Trp; 0.780, 246.884, 1+ALB+BUN+His+Asn+Ile; 0.780, 247.860, 1+ALB+BUN+BHBA+Asn+Ile; 0.780, 247.111, 1+ALB+BUN+Asn+3MeHis+Trp; 0.780, 247.082, 1+ALB+ALT+T-BIL+Asn+Ile; 0.780, 249.779, 1+ALB+T-BIL+Asn+Orn+Ile; 0.780, 250.007, 1+ALB+His+Asn+Thr+Lys; 0.779, 247.995, 1+ALB+BUN+Asn+Tyr+Phe; 0.779, 250.174, 1+ALB+gGT+Asn+Lys+Ile; 0.779, 251.443, 1+ALB+NEFA+Asn+Tyr+Trp; 0.779, 246.539, 1+ALB+AST+ALT+Asn+Ile; 0.779, 247.590, 1+ALB+BUN+Ca+Asn+Ile; 0.779, 247.813, 1+ALB+BUN+Asn+Arg+Tyr; 0.779, 248.254, 1+ALB+His+Asn+Thr+Orn; 0.779, 243.753, 1+ALB+BUN+Asn+3MeHis+Asp; 0.779, 246.169, 1+ALB+ALT+Asn+Thr+Lys; 0.779, 247.424, 1+ALB+BUN+Asn+Phe+Trp; 0.779, 246.770, 1+ALB+BUN+Asn+Thr+Lys; 0.779, 247.872, 1+ALB+BUN+NEFA+Asn+Thr; 0.779, 246.985, 1+ALB+ALT+NEFA+His+Asn; 0.779, 249.937, 1+ALB+NEFA+Glc+Asn+Ile; 0.779, 247.817, 1+ALB+BUN+NEFA+Asn+Lys; 0.779, 249.745, 1+ALB+gGT+Asn+Orn+Ile; 0.778, 251.713, 1+ALB+Asn+Tyr+Phe+Trp; 0.778, 247.192, 1+ALB+ALT+gGT+Asn+Ile; 0.778, 247.381, 1+ALB+BUN+Asn+Arg+Trp; 0.778, 249.303, 1+ALB+BHBA+Asn+Arg+Ile; 0.778, 248.252, 1+ALB+BUN+Asn+Orn+Tyr; 0.778, 247.424, 1+ALB+ALT+Asn+Val+Trp; 0.778, 249.930, 1+ALB+Ca+Asn+Lys+Ile; 0.778, 244.034, 1+ALB+ALT+Asn+3MeHis+Asp; 0.778, 247.816, 1+ALB+Asn+Asp+Tyr+Trp; 0.778, 249.035, 1+ALB+AST+Asn+Tyr+Trp; 0.778, 251.890, 1+ALB+NEFA+BHBA+Asn+Ile; 0.778, 247.663, 1+ALB+ALT+NEFA+Asn+Thr; 0.778, 247.741, 1+ALB+ALT+BHBA+Asn+Thr; 0.778, 244.216, 1+ALB+ALT+Asn+Asp+Tyr; 0.778, 247.069, 1+ALB+Ca+ALT+Asn+Ile; 0.778, 245.959, 1+ALB+ALT+Asn+Arg+Thr; 0.778, 247.364, 1+ALB+ALT+Asn+Orn+Val; 0.778, 246.867, 1+ALB+BUN+T-BIL+His+Asn; 0.778, 247.316, 1+ALB+ALT+NEFA+Glc+Asn; 0.778, 249.779, 1+ALB+T-BIL+Asn+Arg+Ile; 0.778, 252.443, 1+ALB+NEFA+Asn+Tyr+Phe; 0.778, 248.036, 1+ALB+BUN+Asn+Lys+Val; 0.778, 246.754, 1+ALB+ALT+Glc+Asn+Orn; 0.778, 247.334, 1+ALB+ALT+Asn+3MeHis+Trp; 0.778, 247.319, 1+ALB+AST+His+Asn+Orn; 0.778, 246.960, 1+ALB+ALT+His+Asn+Thr; 0.778, 249.183, 1+ALB+NEFA+His+Asn+Lys; 0.778, 248.365, 1+ALB+BUN+NEFA+Asn+Tyr; 0.778, 245.754, 1+ALB+BUN+AST+Asn+Trp; 0.777, 247.686, 1+ALB+ALT+T-BIL+Asn+Thr; 0.777, 251.795, 1+ALB+Asn+Tyr+Val+Trp; 0.777, 245.307, 1+ALB+BUN+NEFA+Asn+Asp; 0.777, 247.732, 1+ALB+ALT+gGT+Asn+Thr; 0.777, 247.216, 1+ALB+ALT+Asn+Lys+Tyr; 0.777, 245.568, 1+ALB+ALT+His+Asn+Lys; 0.777, 247.595, 1+ALB+BUN+Asn+3MeHis+Lys; 0.777, 247.482, 1+ALB+ALT+NEFA+Asn+Trp; 0.777, 248.147, 1+ALB+BUN+T-BIL+Asn+Thr; 0.777, 248.494, 1+ALB+BUN+Asn+Orn+Val; 0.777, 247.462, 1+ALB+BUN+Asn+Thr+Orn; 0.777, 251.568, 1+ALB+NEFA+Asn+Lys+Tyr; 0.777, 250.743, 1+ALB+NEFA+Asn+Arg+Tyr; 0.777, 247.664, 1+ALB+BUN+Asn+Arg+Thr; 0.777, 248.944, 1+ALB+gGT+His+Asn+Orn; 0.777, 247.827, 1+ALB+BUN+NEFA+Glc+Asn; 0.777, 246.391, 1+ALB+ALT+Glc+Asn+Arg; 0.777, 248.142, 1+ALB+BUN+NEFA+Asn+Phe; 0.777, 245.481, 1+ALB+BUN+Asn+Asp+Lys; 0.777, 247.415, 1+ALB+ALT+Asn+3MeHis+Phe; 0.777, 247.551, 1+ALB+ALT+NEFA+T-BIL+Asn; 0.777, 247.175, 1+ALB+BUN+His+Asn+Thr; 0.777, 246.060, 1+ALB+BUN+AST+His+Asn; 0.777, 249.538, 1+ALB+gGT+Asn+Arg+Ile; 0.777, 244.700, 1+ALB+ALT+Asn+Asp+Trp; 0.777, 247.109, 1+ALB+AST+ALT+Asn+Thr; 0.777, 247.146, 1+ALB+ALT+gGT+His+Asn; 0.777, 247.843, 1+ALB+BUN+Glc+Asn+Lys; 0.777, 249.468, 1+ALB+Glc+His+Asn+Lys; 0.776, 247.147, 1+ALB+ALT+BHBA+His+Asn; 0.776, 248.899, 1+ALB+T-BIL+His+Asn+Orn; 0.776, 248.894, 1+ALB+His+Asn+Orn+

Lys; 0.776, 247.321, 1+ALB+BUN+AST+Asn+Tyr; 0.776, 247.665, 1+ALB+BUN+Glc+Asn+Thr; 0.776, 248.499, 1+ALB+BUN+Asn+3MeHis+Tyr; 0.776, 249.009, 1+ALB+BHBA+His+Asn+Orn; 0.776, 250.580, 1+ALB+NEFA+Asn+Thr+Lys; 0.776, 247.144, 1+ALB+ALT+T-BIL+His+Asn; 0.776, 249.515, 1+ALB+Asn+Arg+Thr+Ile; 0.776, 246.612, 1+ALB+AST+ALT+Asn+Trp; 0.776, 247.306, 1+ALB+ALT+Asn+3MeHis+Orn; 0.776, 248.054, 1+ALB+ALT+Asn+3MeHis+Tyr; 0.776, 248.563, 1+ALB+BUN+NEFA+T-BIL+Asn; 0.776, 247.146, 1+ALB+ALT+Asn+Orn+Trp; 0.776, 244.910, 1+ALB+ALT+Asn+Arg+Asp; 0.776, 251.143, 1+ALB+NEFA+His+Asn+Ile; 0.776, 246.671, 1+ALB+BUN+AST+Asn+Thr; 0.776, 247.995, 1+ALB+BUN+Asn+3MeHis+Phe; 0.776, 248.234, 1+ALB+ALT+NEFA+Asn+Tyr; 0.776, 246.500, 1+ALB+ALT+Asn+3MeHis+Arg; 0.776, 248.359, 1+ALB+BUN+NEFA+Asn+3MeHis; 0.776, 247.301, 1+ALB+ALT+Asn+Phe+Trp; 0.776, 246.909, 1+ALB+BUN+AST+Asn+3MeHis; 0.776, 247.668, 1+ALB+Ca+ALT+Asn+Thr; 0.776, 248.130, 1+ALB+BUN+T-BIL+Asn+Lys; 0.776, 246.664, 1+ALB+ALT+Asn+Arg+Trp; 0.776, 248.671, 1+ALB+BUN+Asn+Val+Phe; 0.776, 248.335, 1+ALB+BUN+NEFA+Asn+Orn; 0.776, 248.561, 1+ALB+BUN+Asn+3MeHis+Val; 0.776, 247.397, 1+ALB+ALT+T-BIL+Glc+Asn; 0.776, 248.055, 1+ALB+BUN+T-BIL+Glc+Asn; 0.776, 251.238, 1+ALB+Asn+3MeHis+Tyr+Trp; 0.776, 248.620, 1+ALB+BUN+NEFA+BHBA+Asn; 0.776, 247.137, 1+ALB+BUN+Ca+His+Asn; 0.776, 247.386, 1+ALB+ALT+gGT+Glc+Asn; 0.776, 248.160, 1+ALB+BUN+NEFA+Asn+Arg; 0.776, 251.376, 1+ALB+NEFA+T-BIL+Asn+Ile; 0.776, 247.332, 1+ALB+ALT+BHBA+Glc+Asn; 0.776, 251.696, 1+ALB+NEFA+Asn+Orn+Tyr; 0.776, 249.264, 1+ALB+AST+NEFA+Asn+Ile; 0.775, 252.118, 1+ALB+NEFA+Asn+Thr+Ile; 0.775, 246.884, 1+ALB+ALT+Asn+Arg+Val; 0.775, 247.748, 1+ALB+ALT+NEFA+Asn+Phe; 0.775, 248.128, 1+ALB+BUN+Asn+3MeHis+Orn; 0.775, 248.569, 1+ALB+NEFA+His+Asn+Arg; 0.775, 245.758, 1+ALB+BUN+Asn+Asp+Phe; 0.775, 247.171, 1+ALB+ALT+Asn+Lys+Trp; 0.775, 246.939, 1+ALB+BUN+AST+Asn+Lys; 0.775, 248.591, 1+ALB+BUN+NEFA+Asn+Val; 0.775, 248.857, 1+ALB+Ca+His+Asn+Orn; 0.775, 252.228, 1+ALB+Asn+Orn+Tyr+Phe; 0.775, 247.502, 1+ALB+ALT+BHBA+Asn+Orn; 0.775, 248.253, 1+ALB+ALT+NEFA+BHBA+Asn; 0.775, 246.715, 1+ALB+BUN+AST+Glc+Asn; 0.775, 251.772, 1+ALB+Asn+Arg+Lys+Tyr; 0.775, 246.970, 1+ALB+ALT+NEFA+Asn+Arg; 0.775, 247.243, 1+ALB+BUN+gGT+His+Asn; 0.775, 248.483, 1+ALB+His+Asn+Arg+Orn; 0.775, 246.931, 1+ALB+ALT+BHBA+Asn+Arg; 0.775, 250.450, 1+ALB+T-BIL+His+Asn+Lys; 0.775, 248.283, 1+ALB+BUN+BHBA+Asn+Lys; 0.775, 247.784, 1+ALB+BUN+Asn+3MeHis+Arg; 0.775, 249.678, 1+ALB+Ca+Asn+Arg+Ile; 0.775, 248.348, 1+ALB+BUN+gGT+Asn+Lys; 0.775, 251.382, 1+ALB+NEFA+BHBA+His+Asn; 0.775, 247.549, 1+ALB+ALT+gGT+Asn+Orn; 0.775, 248.568, 1+ALB+BUN+gGT+NEFA+Asn; 0.775, 247.683, 1+Ala+Trp+ALT+ALB+BUN; 0.775, 248.179, 1+ALB+ALT+Asn+Tyr+Val; 0.775, 248.332, 1+ALB+BUN+gGT+Asn+Thr; 0.775, 244.881, 1+ALB+ALT+Asn+Asp+Lys; 0.775, 246.944, 1+ALB+ALT+Asn+Arg+Orn; 0.775, 245.753, 1+ALB+BUN+Asn+Arg+Asp; 0.775, 247.390, 1+ALB+Ca+ALT+Glc+Asn; 0.775, 248.405, 1+ALB+BUN+Ca+NEFA+Asn; 0.775, 253.156, 1+ALB+Asn+Lys+Tyr+Phe; 0.775, 247.550, 1+ALB+ALT+NEFA+Asn+Orn; 0.775, 248.077, 1+ALB+BUN+Glc+Asn+Orn; 0.775, 248.369, 1+ALB+BUN+Asn+Orn+Lys; 0.775, 248.082, 1+ALB+ALT+NEFA+Asn+3MeHis; 0.775, 246.737, 1+ALB+AST+ALT+His+Asn; 0.775, 246.867, 1+ALB+ALT+Glc+Asn+Lys; 0.775, 246.961, 1+ALB+ALT+gGT+Asn+Arg; 0.775, 245.649, 1+ALB+BUN+Asn+Asp+Val; 0.774, 248.073, 1+ALB+ALT+Asn+3MeHis+Val; 0.774, 248.354, 1+ALB+BUN+Asn+Lys+Phe; 0.774, 247.327, 1+ALB+ALT+T-BIL+Asn+Orn; 0.774, 246.774, 1+ALB+ALT+T-BIL+Asn+Arg; 0.774, 247.107, 1+ALB+BUN+BHBA+His+Asn; 0.774, 245.035, 1+ALB+ALT+Asn+Asp+Orn; 0.774, 246.279, 1+ALB+AST+ALT+Asn+Arg; 0.774, 246.734, 1+ALB+BUN+AST+NEFA+Asn; 0.774, 247.046, 1+ALB+Ca+ALT+His+Asn; 0.774, 247.141, 1+ALB+ALT+Asn+3MeHis+Lys; 0.774, 249.610, 1+ALB+His+Asn+Arg+Lys; 0.774, 245.764, 1+ALB+BUN+Asn+Asp+Orn; 0.774, 248.265, 1+ALB+BUN+Ca+Asn+Thr; 0.774, 245.119, 1+ALB+ALT+NEFA+Asn+Asp; 0.774, 248.591, 1+ALB+BUN+T-BIL+Asn+Orn; 0.774, 247.311, 1+ALB+ALT+Asn+Orn+Phe; 0.774, 248.101, 1+ALB+BUN+Glc+Asn+Arg; 0.774, 248.913, 1+ALB+BUN+T-BIL+BHBA+Asn; 0.774, 247.824, 1+ALB+ALT+Asn+Val+Phe; 0.774, 247.495, 1+ALB+AST+ALT+NEFA+Asn; 0.774, 248.192, 1+ALB+BUN+gGT+Glc+Asn; 0.774, 248.275, 1+ALB+BUN+BHBA+Asn+Thr; 0.774, 248.487, 1+ALB+BUN+T-BIL+Asn+Arg; 0.774, 249.458, 1+ALB+AST+His+Asn+Lys; 0.774, 248.963, 1+ALB+BUN+Asn+Tyr+Val; 0.774, 247.476, 1+ALB+ALT+Asn+Lys+Phe; 0.774, 250.204, 1+ALB+Glc+His+Asn+Ile; 0.774, 250.372, 1+ALB+T-BIL+Glc+His+Asn; 0.774, 247.376, 1+ALB+ALT+Asn+Orn+Lys; 0.774, 250.251, 1+ALB+Asn+3MeHis+Arg+Tyr; 0.774, 251.247, 1+ALB+NEFA+His+Asn+Thr; 0.774, 246.930, 1+ALB+ALT+Asn+Arg+Phe; 0.774, 248.565, 1+ALB+BUN+Asn+Arg+Val; 0.774, 247.021, 1+ALB+BUN+AST+Asn+Orn; 0.774, 246.903, 1+ALB+ALT+Asn+Arg+Lys; 0.774, 251.597, 1+ALB+Asn+Orn+Val+Trp; 0.774, 244.469, 1+ALB+AST+ALT+Asn+Asp; 0.774, 249.487, 1+ALB+Asn+Asp+Orn+Tyr; 0.774, 248.955, 1+ALB+AST+Glc+Asn+Ile; 0.774, 249.659, 1+ALB+AST+Asn+Thr+Lys; 0.774, 248.288, 1+ALB+BUN+Ca+Glc+Asn; 0.774, 245.089, 1+ALB+ALT+Asn+Asp+Phe; 0.774, 248.277, 1+ALB+ALT+NEFA+Asn+Val; 0.774, 249.208, 1+ALB+NEFA+Asn+Asp+Tyr; 0.773, 247.322, 1+ALB+AST+ALT+Asn+Phe; 0.773, 250.872, 1+ALB+NEFA+Asn+Thr+Orn; 0.773, 252.372, 1+ALB+gGT+NEFA+Asn+Ile; 0.773, 247.421, 1+Ala+Phe+ALT+ALB+BUN; 0.773, 244.073, 1+ALB+BUN+AST+Asn+Asp; 0.773, 246.945, 1+ALB+Ca+ALT+Asn+Arg; 0.773, 252.620, 1+ALB+NEFA+BHBA+Asn+Thr; 0.773, 247.500, 1+ALB+ALT+NEFA+Asn+Lys; 0.773, 248.295, 1+ALB+ALT+gGT+NEFA+Asn; 0.773, 248.650, 1+ALB+BUN+gGT+Asn+Orn; 0.773, 251.617, 1+ALB+Asn+3MeHis+Lys+Tyr; 0.773, 247.569, 1+ALB+ALT+gGT+Asn+Lys; 0.773, 248.324, 1+ALB+BUN+Asn+Arg+Lys; 0.773, 247.503, 1+ALB+ALT+T-BIL+Asn+Lys; 0.773, 248.681, 1+ALB+BUN+BHBA+Asn+Orn; 0.773, 248.577, 1+ALB+BUN+Asn+Arg+Orn; 0.773, 251.459, 1+ALB+Asn+3MeHis+Orn+Tyr; 0.773, 247.484, 1+ALB+Ca+ALT+Asn+Orn; 0.773, 251.582, 1+ALB+Asn+3MeHis+Orn+Val; 0.773, 246.817, 1+ALB+AST+ALT+Glc+Asn; 0.773, 245.135, 1+ALB+ALT+Asn+Asp+Val; 0.773, 248.744, 1+ALB+Glc+His+Asn+Arg; 0.773, 247.385, 1+ALB+Asn+3MeHis+Asp+Tyr; 0.773, 247.569, 1+ALB+ALT+BHBA+Asn+Lys; 0.773, 248.829, 1+ALB+BUN+gGT+T-BIL+Asn; 0.773, 247.431, 1+ALB+BUN+AST+gGT+Asn; 0.773, 253.147, 1+ALB+Asn+Lys+Tyr+Val; 0.773, 250.959, 1+ALB+NEFA+T-BIL+His+Asn; 0.773, 251.547, 1+ALB+Asn+Arg+Orn+Tyr; 0.773, 247.425, 1+ALB+ALT+Asn+Lys+Val; 0.773, 248.203, 1+ALB+Ca+ALT+NEFA+Asn; 0.773, 248.260, 1+ALB+

Ca+ALT+BHBA+Asn; 0.773, 248.606, 1+ALB+BUN+BHBA+Asn+Arg; 0.773, 249.371, 1+ALB+AST+NEFA+Asn+Trp; 0.773, 251.538, 1+ALB+T-BIL+Asn+Thr+Lys; 0.773, 247.657, 1+ALB+AST+ALT+Asn+Tyr; 0.773, 250.926, 1+ALB+gGT+His+Asn+Lys; 0.773, 246.902, 1+Trp+Phe+ALT+ALB+BUN; 0.773, 251.872, 1+ALB+Asn+Arg+Tyr+Val; 0.773, 248.335, 1+ALB+ALT+gGT+BHBA+Asn; 0.773, 248.557, 1+ALB+BUN+Asn+Orn+Phe; 0.773, 247.474, 1+ALB+BUN+AST+Asn+Val; 0.773, 248.724, 1+ALB+AST+Asn+Thr+Orn; 0.773, 248.217, 1+ALB+BUN+Ca+Asn+Lys; 0.773, 250.873, 1+ALB+BHBA+His+Asn+Lys; 0.773, 246.969, 1+ALB+AST+ALT+Asn+Lys; 0.773, 247.075, 1+ALB+BUN+AST+T-BIL+Asn; 0.773, 247.002, 1+ALB+BUN+AST+Asn+Arg; 0.773, 248.717, 1+ALB+BUN+Ca+T-BIL+Asn; 0.773, 251.656, 1+ALB+Asn+3MeHis+Lys+Val; 0.773, 252.067, 1+ALB+NEFA+T-BIL+Asn+Thr; 0.773, 247.238, 1+ALB+BUN+AST+Asn+Phe; 0.772, 250.747, 1+ALB+Ca+His+Asn+Lys; 0.772, 248.566, 1+ALB+BUN+Ca+Asn+Orn; 0.772, 251.379, 1+ALB+NEFA+Glc+Asn+Thr; 0.772, 248.576, 1+ALB+BUN+Asn+Arg+Phe; 0.772, 249.752, 1+ALB+T-BIL+His+Asn+Arg; 0.772, 247.378, 1+ALB+AST+ALT+Asn+3MeHis; 0.772, 249.465, 1+ALB+AST+Asn+Arg+Tyr; 0.772, 252.237, 1+ALB+Asn+Orn+Lys+Tyr; 0.772, 252.292, 1+ALB+NEFA+Asn+Lys+Val; 0.772, 246.741, 1+ALB+AST+ALT+Asn+Orn; 0.772, 249.725, 1+ALB+AST+NEFA+Asn+Thr; 0.772, 249.745, 1+ALB+AST+Asn+Orn+Tyr; 0.772, 248.034, 1+ALB+BUN+BHBA+Glc+Asn; 0.772, 251.418, 1+ALB+gGT+NEFA+His+Asn; 0.772, 251.995, 1+ALB+Asn+Arg+Tyr+Phe; 0.772, 251.022, 1+ALB+Glc+Asn+Thr+Lys; 0.772, 249.136, 1+ALB+AST+NEFA+His+Asn; 0.772, 249.262, 1+ALB+AST+Glc+His+Asn; 0.772, 248.168, 1+ALB+Ca+ALT+T-BIL+Asn; 0.772, 251.197, 1+ALB+Ca+NEFA+His+Asn; 0.772, 252.344, 1+ALB+NEFA+Asn+Orn+Val; 0.772, 249.467, 1+ALB+Asn+Arg+Asp+Tyr; 0.772, 247.298, 1+ALB+BUN+AST+BHBA+Asn; 0.772, 251.022, 1+ALB+T-BIL+Glc+Asn+Ile; 0.772, 248.249, 1+ALB+AST+His+Asn+Arg; 0.772, 250.541, 1+ALB+AST+T-BIL+Asn+Ile; 0.772, 248.834, 1+ALB+BUN+Ca+gGT+Asn; 0.772, 248.249, 1+ALB+Ca+ALT+gGT+Asn; 0.772, 247.662, 1+ALB+AST+ALT+gGT+Asn; 0.772, 248.539, 1+ALB+BUN+gGT+Asn+Arg; 0.771, 250.851, 1+ALB+Glc+His+Asn+Thr; 0.771, 252.452, 1+ALB+Asn+Orn+Tyr+Val; 0.771, 252.150, 1+ALB+Ca+NEFA+Asn+Ile; 0.771, 252.667, 1+ALB+gGT+NEFA+Asn+Thr; 0.771, 247.693, 1+ALB+AST+ALT+BHBA+Asn; 0.771, 248.127, 1+BCAA+Phe+ALT+ALB+BUN; 0.771, 249.782, 1+ALB+AST+Asn+Val+Trp; 0.771, 250.511, 1+ALB+Glc+Asn+Thr+Orn; 0.771, 249.625, 1+ALB+His+Asn+Arg+Thr; 0.771, 247.690, 1+ALB+AST+ALT+T-BIL+Asn; 0.771, 249.996, 1+ALB+BHBA+His+Asn+Arg; 0.771, 247.479, 1+ALB+BUN+ALT+3MeHis+Phe; 0.771, 248.527, 1+ALB+BUN+Ca+Asn+Arg; 0.771, 251.227, 1+ALB+Glc+Asn+Thr+Ile; 0.771, 248.246, 1+ALB+ALT+gGT+T-BIL+Asn; 0.771, 248.804, 1+ALB+BUN+Ca+BHBA+Asn; 0.771, 248.045, 1+ALB+Asn+3MeHis+Asp+Lys; 0.771, 250.569, 1+ALB+AST+Asn+Thr+Ile; 0.771, 253.115, 1+ALB+T-BIL+Asn+Thr+Ile; 0.771, 251.360, 1+ALB+Asn+3MeHis+Lys+Trp; 0.771, 250.595, 1+Ala+Gly+Trp+ALB+BUN; 0.771, 249.415, 1+ALB+AST+Asn+Orn+Trp; 0.771, 250.945, 1+ALB+Asn+Thr+Orn+Lys; 0.771, 252.485, 1+ALB+His+Asn+Thr+Ile; 0.771, 252.773, 1+ALB+Asn+3MeHis+Tyr+Phe; 0.771, 251.695, 1+ALB+NEFA+T-BIL+Asn+Orn; 0.771, 247.269, 1+ALB+BUN+Ca+AST+Asn; 0.771, 247.485, 1+ALB+Ca+ALT+Asn+Lys; 0.771, 252.129, 1+ALB+Asn+Lys+Val+Trp; 0.771, 248.963, 1+ALB+BUN+gGT+BHBA+Asn; 0.771, 251.681, 1+ALB+Asn+3MeHis+Val+Trp; 0.771, 251.276, 1+ALB+Asn+3MeHis+Orn+Trp; 0.771, 251.028, 1+Ala+Trp+Phe+ALB+BUN; 0.771, 251.816, 1+ALB+NEFA+T-BIL+Glc+Asn; 0.771, 252.276, 1+ALB+NEFA+Asn+Val+Trp; 0.770, 248.227, 1+ALB+ALT+T-BIL+BHBA+Asn; 0.770, 249.886, 1+ALB+AST+Asn+Lys+Trp; 0.770, 251.138, 1+ALB+NEFA+Asn+Arg+Thr; 0.770, 248.086, 1+Gly+Phe+ALT+ALB+BUN; 0.770, 249.809, 1+ALB+AST+NEFA+Asn+Lys; 0.770, 251.352, 1+ALB+BHBA+Asn+Thr+Orn; 0.770, 252.613, 1+ALB+BHBA+His+Asn+Ile; 0.770, 251.792, 1+ALB+NEFA+Asn+3MeHis+Trp; 0.770, 250.410, 1+ALB+AST+His+Asn+Ile; 0.770, 247.566, 1+Trp+Lys+ALT+ALB+BUN; 0.770, 251.088, 1+ALB+gGT+Glc+Asn+Ile; 0.770, 248.244, 1+Phe+Tyr+ALT+ALB+BUN; 0.770, 248.219, 1+Phe+ALT+gGT+ALB+BUN; 0.770, 251.686, 1+ALB+NEFA+Asn+3MeHis+Lys; 0.770, 253.256, 1+ALB+T-BIL+BHBA+Asn+Ile; 0.770, 252.046, 1+ALB+Asn+3MeHis+Lys+Phe; 0.770, 252.885, 1+ALB+NEFA+Asn+3MeHis+Tyr; 0.770, 247.663, 1+ALB+AST+ALT+Asn+Val; 0.770, 250.869, 1+ALB+AST+gGT+Asn+Ile; 0.770, 253.257, 1+ALB+BHBA+Asn+Thr+Ile; 0.770, 252.263, 1+ALB+Asn+Lys+Phe+Trp; 0.770, 252.392, 1+ALB+NEFA+BHBA+Asn+Lys; 0.770, 252.558, 1+ALB+NEFA+Asn+Lys+Phe; 0.770, 251.827, 1+ALB+Asn+3MeHis+Phe+Trp; 0.770, 250.751, 1+ALB+gGT+Glc+His+Asn; 0.770, 251.541, 1+ALB+NEFA+Glc+Asn+Lys; 0.770, 252.574, 1+ALB+T-BIL+BHBA+His+Asn; 0.770, 249.781, 1+ALB+gGT+His+Asn+Arg; 0.770, 251.898, 1+ALB+Asn+Arg+Val+Trp; 0.770, 247.078, 1+ALB+BUN+ALT+Lys+Phe; 0.770, 249.483, 1+ALB+AST+Asn+Arg+Trp; 0.770, 251.346, 1+ALB+T-BIL+Asn+Thr+Orn; 0.770, 252.320, 1+ALB+T-BIL+His+Asn+Ile; 0.770, 251.467, 1+ALB+NEFA+Glc+Asn+Arg; 0.770, 248.076, 1+ALB+Asn+3MeHis+Asp+Trp; 0.770, 250.893, 1+ALB+AST+BHBA+Asn+Ile; 0.770, 250.904, 1+ALB+AST+Asn+Lys+Tyr; 0.770, 247.657, 1+ALB+BUN+ALT+Orn+Phe; 0.770, 248.547, 1+ALB+Asn+3MeHis+Asp+Val; 0.769, 252.329, 1+ALB+T-BIL+His+Asn+Thr; 0.769, 251.738, 1+ALB+BHBA+Asn+Thr+Lys; 0.769, 249.865, 1+ALB+AST+Asn+3MeHis+Lys; 0.769, 250.197, 1+ALB+AST+Asn+Orn+Val; 0.769, 251.845, 1+ALB+NEFA+Asn+3MeHis+Orn; 0.769, 250.487, 1+ALB+Asn+Asp+Tyr+Phe; 0.769, 252.008, 1+ALB+NEFA+Asn+Lys+Trp; 0.769, 253.105, 1+ALB+NEFA+Asn+Tyr+Val; 0.769, 249.549, 1+ALB+AST+NEFA+Asn+Orn; 0.769, 251.812, 1+ALB+NEFA+T-BIL+Asn+Lys; 0.769, 248.229, 1+Phe+Glc+ALT+ALB+BUN; 0.769, 250.914, 1+ALB+Asn+3MeHis+Arg+Trp; 0.769, 250.113, 1+ALB+AST+NEFA+T-BIL+Asn; 0.769, 247.565, 1+ALB+AST+Asn+Asp+Trp; 0.769, 252.460, 1+ALB+gGT+His+Asn+Ile; 0.769, 251.270, 1+ALB+Ca+Asn+Thr+Orn; 0.769, 252.139, 1+ALB+Asn+Orn+Lys+Trp; 0.769, 252.283, 1+ALB+NEFA+BHBA+Asn+Orn; 0.769, 250.530, 1+Ala+Trp+Lys+ALB+BUN; 0.769, 251.913, 1+ALB+NEFA+Asn+Orn+Trp; 0.769, 249.900, 1+ALB+Ca+His+Asn+Arg; 0.769, 250.977, 1+ALB+Ca+Glc+His+Asn; 0.769, 251.118, 1+ALB+Asn+Arg+Thr+Orn; 0.769, 253.090, 1+ALB+gGT+Asn+Thr+Ile; 0.769, 247.627, 1+Arg+Phe+ALT+ALB+BUN; 0.769, 248.070, 1+Phe+ALT+ALB+BUN+NEFA; 0.769, 252.800, 1+ALB+Asn+Orn+Lys+Val; 0.769, 251.281, 1+ALB+BHBA+Glc+Asn+Ile; 0.769, 251.457, 1+ALB+NEFA+Glc+Asn+Orn; 0.769, 253.490, 1+ALB+T-BIL+BHBA+Asn+Lys; 0.769, 248.263, 1+ALB+BUN+ALT+Val+Phe; 0.769, 249.757, 1+Ala+Trp+His+ALB+BUN; 0.769, 251.700, 1+ALB+Asn+3MeHis+Orn+Lys; 0.769, 252.060, 1+ALB+Asn+Orn+Phe+Trp; 0.769, 248.377, 1+ALB+Asn+

3MeHis+Arg+Asp; 0.769, 251.285, 1+ALB+gGT+Asn+Thr+Or n; 0.769, 251.767, 1+ALB+gGT+Asn+Thr+Lys; 0.769, 252.589, 1+ALB+A sn+Val+Phe+Trp; 0.769, 248.093, 1+Phe+TG+ALT+ALB+BUN; 0.769, 249. 816, 1+ALB+AST+Asn+Phe+Trp; 0.769, 251.327, 1+ALB+Ca+Glc+Asn+Il e; 0.769, 250.353, 1+ALB+AST+T-BIL+His+Asn; 0.769, 251.362, 1+ALB+Asn+3MeHis+Arg+Orn; 0.769, 252.803, 1+ALB+NEFA+T-BIL+BHBA+As n; 0.769, 245.539, 1+ALB+BUN+ALT+Asp+Phe; 0.769, 249.151, 1+ALB+A ST+Asn+3MeHis+Trp; 0.769, 247.970, 1+Phe+TCHO+ALT+ALB+BUN; 0.76 9, 250.487, 1+ALB+BHBA+Glc+His+Asn; 0.769, 250.302, 1+ALB+NEFA+A sn+Asp+Lys; 0.769, 249.491, 1+ALB+AST+Asn+Arg+Thr; 0.769, 252.00 8, 1+Ala+Gly+Lys+ALB+BUN; 0.769, 252.768, 1+ALB+gGT+NEFA+T-BIL+Asn; 0.769, 247.592, 1+ALB+Ca+AST+ALT+Asn; 0.768, 252.615, 1+ALB+BHBA+His+Asn+Thr; 0.768, 247.922, 1+Phe+ALT+ALB+BUN+TP; 0.768, 2 52.371, 1+ALB+NEFA+Asn+Phe+Trp; 0.768, 252.344, 1+ALB+Ca+His+As n+Ile; 0.768, 252.470, 1+ALB+T-BIL+Glc+Asn+Lys; 0.768, 252.975, 1+ALB+Asn+Orn+Val+Phe; 0.768, 251.352, 1+ALB+NEFA+Asn+3MeHis+Ar g; 0.768, 247.395, 1+Phe+His+ALT+ALB+BUN; 0.768, 251.326, 1+ALB+A sn+Arg+Thr+Lys; 0.768, 252.196, 1+ALB+T-BIL+Glc+Asn+Thr; 0.768, 253.024, 1+ALB+Ca+Asn+Thr+Ile; 0.768, 253.440, 1+ALB+NEFA+Asn+V al+Phe; 0.768, 253.621, 1+ALB+T-BIL+BHBA+Asn+Thr; 0.768, 250.111, 1+ALB+AST+Glc+Asn+Thr; 0.768, 249.413, 1+ALB+AST+Asn+3MeHis+Or n; 0.768, 252.540, 1+ALB+Ca+NEFA+Asn+Thr; 0.768, 251.921, 1+ALB+A sn+3MeHis+Orn+Phe; 0.768, 248.611, 1+ALB+NEFA+Asn+3MeHis+Asp; 0. 768, 251.274, 1+ALB+Asn+3Me-His+Arg+Lys; 0.768, 248.194, 1+Phe+AL T+ALB+BUN+Ca; 0.768, 250.614, 1+ALB+Ca+AST+Asn+Ile; 0.768, 251.4 18, 1+ALB+NEFA+T-BIL+Asn+Arg; 0.768, 247.955, 1+Phe+ALT+ALB+BUN+BHBA; 0.768, 248.058, 1+Thr+Phe+ALT+ALB+BUN; 0.768, 250.306, 1+A LB+AST+NEFA+Asn+Tyr; 0.768, 252.466, 1+ALB+Ca+His+Asn+Thr; 0.76 8, 251.672, 1+ALB+Ca+Asn+Thr+Lys; 0.768, 252.377, 1+ALB+NEFA+Asn+Arg+Val; 0.768, 248.493, 1+ALB+Asn+3MeHis+Asp+Orn; 0.768, 251.9 23, 1+ALB+Asn+Arg+Phe+Trp; 0.768, 254.003, 1+ALB+Asn+Tyr+Val+Ph e; 0.768, 248.657, 1+ALB+Asn+3MeHis+Asp+Phe; 0.768, 252.553, 1+AL B+NEFA+Asn+Orn+Phe; 0.768, 251.250, 1+Ala+Trp+Arg+ALB+BUN; 0.76 8, 250.521, 1+ALB+NEFA+Asn+Asp+Orn; 0.768, 251.811, 1+ALB+NEFA+A sn+Arg+Trp; 0.768, 250.565, 1+ALB+AST+His+Asn+Thr; 0.768, 251.25 8, 1+ALB+Glc+Asn+Arg+Thr; 0.768, 251.297, 1+ALB+Asn+3MeHis+Arg+Val; 0.768, 252.340, 1+ALB+NEFA+Asn+Orn+Lys; 0.768, 252.011, 1+AL B+Asn+Arg+Orn+Trp; 0.768, 245.550, 1+ALB+BUN+ALT+Asp+Lys; 0.768, 249.459, 1+ALB+AST+NEFA+Glc+Asn; 0.768, 252.730, 1+ALB+Asn+Arg+Orn+Val; 0.768, 248.187, 1+Trp+Arg+ALT+ALB+BUN; 0.767, 252.138, 1+ALB+Asn+Arg+Lys+Trp; 0.767, 252.193, 1+ALB+NEFA+Asn+Arg+Lys; 0. 767, 250.259, 1+ALB+Asn+Asp+Orn+Trp; 0.767, 250.297, 1+ALB+Asn+A sp+Lys+Trp; 0.767, 252.356, 1+ALB+Ca+T-BIL+His+Asn; 0.767, 253.2 23, 1+ALB+Ca+T-BIL+Asn+Ile; 0.767, 250.157, 1+ALB+Asn+Asp+Val+T rp; 0.767, 252.538, 1+ALB+gGT+NEFA+Asn+Lys; 0.767, 247.885, 1+ALB+AST+Asn+Asp+Tyr; 0.767, 253.397, 1+ALB+gGT+BHBA+Asn+Ile; 0.767, 252.259, 1+ALB+NEFA+Asn+Arg+Orn; 0.767, 252.463, 1+ALB+gGT+T-BI L+His+Asn; 0.767, 253.188, 1+ALB+Asn+3MeHis+Tyr+Val; 0.767, 251. 331, 1+ALB+AST+Asn+Lys+Val; 0.767, 251.344, 1+Ala+BCAA+Trp+ALB+BUN; 0.767, 253.602, 1+ALB+Asn+Lys+Val+Phe; 0.767, 251.408, 1+Ala+Lys+His+ALB+BUN; 0.767, 252.531, 1+ALB+gGT+His+Asn+Thr; 0.767, 250.990, 1+BCAA+Trp+Lys+ALB+BUN; 0.767, 253.025, 1+ALB+Asn+Orn+Lys+Phe; 0.767, 253.321, 1+ALB+gGT+T-BIL+Asn+Ile; 0.767, 252.990, 1+ALB+NEFA+Asn+3MeHis+Val; 0.767, 250.507, 1+ALB+AST+BHBA+Asn+Orn; 0.767, 251.608, 1+Ala+Trp+Thr+ALB+BUN; 0.767, 250.360, 1+ALB+AST+T-BIL+Asn+Orn; 0.767, 250.595, 1+ALB+NEFA+Asn+Arg+Asp; 0.7 67, 250.910, 1+Ala+Trp+ALB+BUN+TP; 0.767, 250.509, 1+ALB+AST+Asn+Orn+Lys; 0.767, 253.038, 1+ALB+T-BIL+Asn+Orn+Lys; 0.767, 251.50 3, 1+ALB+Asn+3MeHis+Arg+Phe; 0.767, 250.006, 1+ALB+NEFA+Asn+Asp+Trp; 0.767, 251.382, 1+Ala+Trp+ALB+BUN+NEFA; 0.767, 248.112, 1+P he+ALT+AST+ALB+BUN; 0.767, 251.836, 1+ALB+AST+Asn+Tyr+Phe; 0.76 6, 253.327, 1+ALB+Ca+BHBA+Asn+Ile; 0.766, 252.361, 1+ALB+Ca+NEFA+Asn+Lys; 0.766, 253.059, 1+ALB+BHBA+Asn+Orn+Lys; 0.766, 252.083, 1+ALB+gGT+NEFA+Glc+Asn; 0.766, 253.062, 1+ALB+T-BIL+BHBA+Asn+O rn; 0.766, 250.033, 1+ALB+Asn+Asp+Phe+Trp; 0.766, 252.238, 1+ALB+NEFA+BHBA+Glc+Asn; 0.766, 251.590, 1+Ala+Trp+TG+ALB+BUN; 0.766, 250.758, 1+ALB+NEFA+Asn+Asp+Val; 0.766, 250.794, 1+ALB+AST+T-BI L+Asn+Thr; 0.766, 246.203, 1+ALB+BUN+ALT+Asp+Trp; 0.766, 251.950, 1+ALB+T-BIL+Asn+Arg+Thr; 0.766, 252.264, 1+ALB+gGT+Glc+Asn+Th r; 0.766, 251.198, 1+ALB+Asn+Asp+Lys+Val; 0.766, 253.331, 1+ALB+g GT+NEFA+BHBA+Asn; 0.766, 251.281, 1+ALB+AST+Asn+Lys+Phe; 0.766, 248.776, 1+ALB+AST+Asn+Asp+Lys; 0.766, 252.504, 1+ALB+gGT+NEFA+Asn+Orn; 0.766, 251.556, 1+Ala+Trp+Tyr+ALB+BUN; 0.766, 252.442, 1+ALB+NEFA+Asn+Arg+Phe; 0.766, 251.487, 1+Ala+Trp+ALB+BUN+BHBA; 0.766, 249.422, 1+ALB+AST+NEFA+Asn+Arg; 0.766, 252.670, 1+ALB+NE FA+Asn+3MeHis+Phe; 0.766, 250.068, 1+ALB+Asn+Asp+Tyr+Val; 0.766, 253.488, 1+ALB+gGT+T-BIL+Asn+Thr; 0.766, 250.776, 1+ALB+AST+BHB A+His+Asn; 0.766, 249.184, 1+Ala+Arg+ALT+ALB+BUN; 0.766, 250.333, 1+ALB+Asn+Arg+Asp+Trp; 0.766, 250.918, 1+ALB+AST+gGT+His+Asn; 0. 766, 252.537, 1+ALB+Ca+NEFA+T-BIL+Asn; 0.766, 252.409, 1+ALB+Ca+NEFA+Asn+Orn; 0.766, 250.765, 1+ALB+NEFA+Asn+Asp+Phe; 0.766, 249. 718, 1+Ala+Trp+AST+ALB+BUN; 0.766, 247.607, 1+ALB+AST+NEFA+Asn+Asp; 0.766, 252.879, 1+ALB+Asn+Arg+Orn+Lys; 0.766, 249.761, 1+ALB+AST+Glc+Asn+Orn; 0.766, 249.043, 1+ALB+AST+Asn+3MeHis+Arg; 0.7 66, 251.286, 1+ALB+AST+BHBA+Asn+Lys; 0.766, 253.240, 1+ALB+Ca+NE FA+BHBA+Asn; 0.766, 252.024, 1+ALB+BHBA+Asn+Arg+Thr; 0.766, 250. 477, 1+ALB+AST+Asn+Orn+Phe; 0.766, 253.079, 1+ALB+Asn+3MeHis+Va l+Phe; 0.766, 250.448, 1+ALB+AST+gGT+Asn+Orn; 0.766, 250.469, 1+A LB+AST+NEFA+Asn+Phe; 0.766, 251.258, 1+Ala+Trp+TCHO+ALB+BUN; 0. 766, 252.108, 1+ALB+NEFA+BHBA+Asn+Arg; 0.766, 252.317, 1+ALB+gGT+NEFA+Asn+Arg; 0.765, 252.745, 1+ALB+gGT+BHBA+His+Asn; 0.765, 24 8.640, 1+Lys+Thr+ALT+ALB+BUN; 0.765, 253.356, 1+ALB+Ca+T-BIL+As n+Lys; 0.765, 251.301, 1+ALB+AST+gGT+Asn+Lys; 0.765, 250.955, 1+A LB+AST+T-BIL+Asn+Lys; 0.765, 247.781, 1+Ala+Lys+ALT+ALB+BUN; 0. 765, 248.266, 1+ALB+BUN+ALT+Arg+Lys; 0.765, 248.266, 1+Arg+Lys+A LT+ALB+BUN; 0.765, 251.063, 1+ALB+Asn+Asp+Orn+Val; 0.765, 248.38 6, 1+Lys+His+ALT+ALB+BUN; 0.765, 246.081, 1+ALB+AST+Asn+3MeHis+Asp; 0.765, 247.689, 1+Lys+ALT+ALB+BUN+TP; 0.765, 252.602, 1+ALB+Ca+BHBA+His+Asn; 0.765, 252.892, 1+ALB+T-BIL+Asn+

Arg+Orn; 0.765, 251.584, 1+Ala+Trp+gGT+ALB+BUN; 0.765, 251.610, 1+Ala+Trp+Glc+ALB+BUN; 0.765, 250.151, 1+ALB+AST+NEFA+Asn+3MeHis; 0.765, 253.462, 1+ALB+Ca+T-BIL+Asn+Thr; 0.765, 252.112, 1+ALB+T-BIL+Glc+Asn+Orn; 0.765, 252.206, 1+ALB+BHBA+Glc+Asn+Thr; 0.765, 248.168, 1+ALB+BUN+ALT+3MeHis+Lys; 0.765, 251.288, 1+Trp+Phe+ALB+BUN+TP; 0.765, 250.526, 1+ALB+AST+NEFA+BHBA+Asn; 0.765, 248.945, 1+Trp+ALT+ALB+BUN+TP; 0.765, 253.449, 1+ALB+gGT+T-BIL+Asn+Lys; 0.765, 251.119, 1+ALB+Asn+Asp+Orn+Lys; 0.765, 251.080, 1+ALB+AST+BHBA+Asn+Thr; 0.765, 253.131, 1+ALB+Ca+gGT+Asn+Ile; 0.765, 252.972, 1+ALB+gGT+Asn+Orn+Lys; 0.765, 248.751, 1+Lys+ALT+ALB+BUN+NEFA; 0.765, 253.009, 1+ALB+Ca+BHBA+Asn+Orn; 0.765, 253.058, 1+ALB+Asn+Arg+Lys+Val; 0.765, 252.878, 1+ALB+BHBA+Asn+Arg+Orn; 0.765, 250.694, 1+ALB+AST+Asn+Arg+Lys; 0.765, 253.483, 1+ALB+Ca+BHBA+Asn+Lys; 0.765, 252.093, 1+ALB+Glc+Asn+Arg+Orn; 0.765, 252.590, 1+ALB+gGT+Glc+Asn+Lys; 0.765, 251.250, 1+ALB+Asn+Arg+Asp+Lys; 0.765, 250.299, 1+ALB+AST+Asn+Arg+Orn; 0.765, 252.070, 1+Ala+Gly+Trp+AST+ALB; 0.765, 252.465, 1+ALB+Ca+Glc+Asn+Thr; 0.765, 249.945, 1+Trp+Lys+ALB+BUN+TP; 0.765, 251.528, 1+Ala+Trp+ALB+BUN+Ca; 0.764, 251.188, 1+ALB+Asn+Arg+Asp+Orn; 0.764, 252.185, 1+ALB+Glc+Asn+Orn+Lys; 0.764, 247.592, 1+ALB+BUN+3MeHis+Asp+Lys; 0.764, 248.713, 1+ALB+BUN+ALT+T-BIL+Lys; 0.764, 251.820, 1+ALB+gGT+Asn+Arg+Thr; 0.764, 252.840, 1+ALB+Asn+Arg+Orn+Phe; 0.764, 250.940, 1+ALB+Asn+Asp+Lys+Phe; 0.764, 250.704, 1+ALB+Ca+AST+His+Asn; 0.764, 253.620, 1+ALB+gGT+BHBA+Asn+Thr; 0.764, 252.569, 1+ALB+BHBA+Glc+Asn+Lys; 0.764, 248.613, 1+ALB+BUN+ALT+Lys+Ile; 0.764, 250.301, 1+Trp+Lys+His+ALB+BUN; 0.764, 251.187, 1+ALB+AST+gGT+Asn+Thr; 0.764, 252.161, 1+ALB+Ca+NEFA+Glc+Asn; 0.764, 253.555, 1+Ala+Gly+Lys+AST+ALB; 0.764, 253.065, 1+ALB+T-BIL+Asn+Arg+Lys; 0.764, 248.805, 1+Lys+ALT+gGT+ALB+BUN; 0.764, 250.523, 1+ALB+AST+Glc+Asn+Lys; 0.764, 250.798, 1+ALB+AST+Asn+3MeHis+Tyr; 0.764, 252.148, 1+ALB+BHBA+Glc+Asn+Orn; 0.764, 250.585, 1+ALB+AST+NEFA+Asn+Val; 0.764, 252.382, 1+ALB+Glc+Asn+Arg+Lys; 0.764, 248.797, 1+ALB+AST+Asn+Arg+Asp; 0.764, 251.291, 1+Lys+His+ALB+BUN+TP; 0.764, 253.026, 1+ALB+gGT+T-BIL+Asn+Orn; 0.764, 248.515, 1+ALB+AST+Asn+Asp+Orn; 0.764, 253.005, 1+ALB+Ca+T-BIL+Asn+Orn; 0.764, 252.326, 1+ALB+T-BIL+Glc+Asn+Arg; 0.764, 253.136, 1+ALB+BHBA+Asn+Arg+Lys; 0.764, 251.067, 1+ALB+Asn+Asp+Orn+Phe; 0.764, 250.379, 1+ALB+Ca+AST+Asn+Orn; 0.764, 251.041, 1+ALB+Ca+AST+Asn+Thr; 0.764, 253.576, 1+ALB+Ca+BHBA+Asn+Thr; 0.764, 252.800, 1+ALB+Ca+Asn+Arg+Orn; 0.764, 253.585, 1+ALB+gGT+BHBA+Asn+Lys; 0.764, 251.948, 1+ALB+Ca+Asn+Arg+Thr; 0.764, 252.692, 1+ALB+Ca+Glc+Asn+Lys; 0.764, 252.932, 1+ALB+Ca+Asn+Orn+Lys; 0.764, 253.011, 1+ALB+gGT+BHBA+Asn+Orn; 0.764, 251.661, 1+Ala+Lys+ALB+BUN+NEFA; 0.764, 252.749, 1+ALB+gGT+Asn+Arg+Orn; 0.764, 251.629, 1+ALB+BUN+Lys+Val+Trp; 0.763, 251.973, 1+BCAA+Trp+Phe+ALB+BUN; 0.763, 248.825, 1+Lys+TG+ALT+ALB+BUN; 0.763, 251.188, 1+ALB+Ca+AST+Asn+Lys; 0.763, 253.043, 1+Gly+Lys+AST+ALB+TP; 0.763, 252.949, 1+ALB+Asn+Arg+Lys+Phe; 0.763, 252.998, 1+Ala+Gly+Phe+ALB+BUN; 0.763, 248.693, 1+Lys+Tyr+ALT+ALB+BUN; 0.763, 249.163, 1+Arg+Thr+ALT+ALB+BUN; 0.763, 248.830, 1+ALB+BUN+ALT+Orn+Lys; 0.763, 253.221, 1+ALB+Asn+Arg+Val+Phe; 0.763, 248.828, 1+Gly+Lys+ALT+ALB+BUN; 0.763, 252.317, 1+ALB+Ca+NEFA+Asn+Arg; 0.763, 250.047, 1+Trp+ALT+gGT+ALB+BUN; 0.763, 250.098, 1+ALB+AST+Glc+Asn+Arg; 0.763, 252.530, 1+ALB+Ca+gGT+His+Asn; 0.763, 252.160, 1+ALB+Ca+Glc+Asn+Orn; 0.763, 250.428, 1+ALB+AST+gGT+NEFA+Asn; 0.763, 252.413, 1+ALB+BHBA+Glc+Asn+Arg; 0.763, 253.023, 1+BCAA+Lys+Phe+ALB+BUN; 0.763, 252.671, 1+Ala+Lys+Phe+ALB+BUN; 0.763, 251.636, 1+Trp+Lys+Phe+ALB+BUN; 0.763, 248.861, 1+Lys+Glc+ALT+ALB+BUN; 0.763, 249.278, 1+ALB+BUN+Asp+Lys+Trp; 0.763, 250.724, 1+ALB+AST+Asn+Arg+Val; 0.763, 253.165, 1+ALB+T-BIL+BHBA+Asn+Arg; 0.763, 254.122, 1+Ala+Gly+Trp+Lys+ALB; 0.763, 256.142, 1+Ala+Gly+BCAA+Lys+ALB; 0.763, 248.593, 1+Lys+ALT+ALB+BUN+BHBA; 0.763, 250.594, 1+ALB+AST+Asn+Arg+Phe; 0.762, 252.022, 1+ALB+gGT+Glc+Asn+Orn; 0.762, 248.874, 1+ALB+BUN+ALT+Lys+Val; 0.762, 249.064, 1+ALB+BUN+ALT+Orn+Trp; 0.762, 251.968, 1+Trp+Lys+AST+ALB+TP; 0.762, 253.442, 1+ALB+Ca+gGT+Asn+Thr; 0.762, 250.238, 1+Trp+Phe+His+ALT+ALB; 0.762, 254.848, 1+Ala+Gly+Lys+His+ALB; 0.762, 250.969, 1+ALB+AST+gGT+Glc+Asn; 0.762, 253.043, 1+ALB+gGT+T-BIL+Asn+Arg; 0.762, 248.817, 1+BCAA+Lys+ALT+ALB+BUN; 0.762, 250.658, 1+Gly+Trp+Phe+ALT+ALB; 0.762, 253.406, 1+ALB+Ca+gGT+Asn+Lys; 0.762, 252.859, 1+ALB+gGT+T-BIL+Glc+Asn; 0.762, 251.919, 1+Trp+Lys+gGT+ALB+BUN; 0.762, 255.139, 1+Ala+Gly+Trp+Phe+ALB; 0.762, 253.807, 1+Ala+Gly+Trp+Arg+ALB; 0.762, 250.052, 1+Gly+Arg+Phe+ALT+ALB; 0.762, 251.659, 1+ALB+AST+Asn+Tyr+Val; 0.762, 251.457, 1+ALB+Asn+Arg+Asp+Val; 0.762, 251.821, 1+Lys+Phe+His+ALB+BUN; 0.762, 249.487, 1+Trp+Thr+ALT+ALB+BUN; 0.762, 250.502, 1+ALB+AST+T-BIL+Asn+Arg; 0.762, 254.308, 1+ALB+Ca+T-BIL+BHBA+Asn; 0.762, 250.952, 1+ALB+BUN+3MeHis+Lys+Trp; 0.762, 250.731, 1+ALB+AST+BHBA+Asn+Arg; 0.762, 248.365, 1+Lys+TCHO+ALT+ALB+BUN; 0.762, 251.673, 1+Gly+Trp+Lys+ALB+BUN; 0.762, 252.180, 1+Lys+AST+ALB+TP+NEFA; 0.762, 253.025, 1+ALB+Ca+Asn+Arg+Lys; 0.762, 250.960, 1+Ala+Gly+Lys+ALT+ALB; 0.762, 251.574, 1+ALB+BUN+3MeHis+Lys+Phe; 0.762, 251.618, 1+Trp+Lys+ALB+BUN+NEFA; 0.762, 251.618, 1+ALB+BUN+NEFA+Lys+Trp; 0.762, 252.955, 1+Ala+Gly+Arg+AST+ALB; 0.762, 250.330, 1+ALB+Ca+AST+NEFA+Asn; 0.762, 250.828, 1+BCAA+Lys+Phe+ALT+ALB; 0.762, 252.975, 1+ALB+gGT+Asn+Arg+Lys; 0.762, 250.695, 1+ALB+AST+Asn+3MeHis+Phe; 0.762, 253.285, 1+ALB+Ca+gGT+NEFA+Asn; 0.762, 254.307, 1+ALB+gGT+T-BIL+BHBA+Asn; 0.762, 248.560, 1+Lys+ALT+AST+ALB+BUN; 0.762, 250.353, 1+ALB+BUN+AST+Lys+Trp; 0.762, 250.353, 1+Trp+Lys+AST+ALB+BUN; 0.762, 253.079, 1+ALB+T-BIL+BHBA+Glc+Asn; 0.762, 250.966, 1+ALB+ALT+Orn+Tyr+Phe; 0.762, 250.828, 1+ALB+AST+Asn+3MeHis+Val; 0.762, 249.655, 1+Trp+TCHO+ALT+ALB+BUN; 0.761, 251.691, 1+ALB+AST+T-BIL+BHBA+Asn; 0.761, 253.150, 1+ALB+Ca+T-BIL+Asn+Arg; 0.761, 252.889, 1+ALB+Ca+gGT+Asn+Orn; 0.761, 253.069, 1+ALB+gGT+BHBA+Asn+Arg; 0.761, 251.468, 1+Ala+Gly+Trp+ALT+ALB; 0.761, 250.694, 1+Ala+Gly+Arg+ALT+ALB; 0.761, 249.907, 1+Trp+Arg+Phe+ALT+ALB; 0.761, 250.239, 1+ALB+ALT+Orn+Phe+Trp; 0.761, 250.454, 1+ALB+AST+T-BIL+Glc+Asn; 0.761, 250.539, 1+Gly+Lys+Phe+ALT+ALB; 0.761, 252.948, 1+Ala+BCAA+Lys+ALB+BUN; 0.761, 256.425, 1+Ala+Gly+Lys+TG+ALB; 0.761, 252.473,

1+Trp+Phe+Tyr+ALB+BUN; 0.761, 249.909, 1+ALB+ALT+3MeHis+Lys+Phe; 0.761, 251.888, 1+Trp+Lys+Tyr+ALB+BUN; 0.761, 249.968, 1+Trp+TG+ALT+ALB+BUN; 0.761, 248.788, 1+Lys+ALT+ALB+BU N+Ca; 0.761, 251.819, 1+Trp+Arg+Lys+ALB+BUN; 0.761, 251.926, 1+Tr p+Lys+TG+ALB+BUN; 0.761, 252.443, 1+ALB+Ca+Glc+Asn+Arg; 0.761, 2 53.052, 1+ALB+Ca+T-BIL+Glc+Asn; 0.761, 250.271, 1+Ala+Trp+Arg+A LT+ALB; 0.761, 251.976, 1+Lys+His+ALB+BUN+NEFA; 0.761, 253.154, 1+Ala+Lys+Thr+ALB+BUN; 0.761, 251.275, 1+ALB+Asn+Arg+Asp+Phe; 0. 761, 250.883, 1+Trp+Phe+His+ALB+BUN; 0.761, 250.301, 1+Trp+Lys+P he+ALT+ALB; 0.761, 250.737, 1+ALB+AST+gGT+Asn+Arg; 0.761, 252.65 7, 1+Ala+Phe+ALB+BUN+NEFA; 0.761, 252.567, 1+ALB+BUN+3MeHis+Lys+Val; 0.761, 251.572, 1+ALB+Asn+Asp+Val+Phe; 0.761, 247.995, 1+AL B+BUN+ALT+Arg+Asp; 0.761, 251.291, 1+ALB+BUN+AST+3MeHis+Lys; 0. 761, 253.194, 1+ALB+Ca+BHBA+Asn+Arg; 0.761, 250.958, 1+Ala+Trp+P he+ALT+ALB; 0.761, 251.076, 1+BCAA+Trp+Phe+ALT+ALB; 0.761, 250.6 84, 1+Gly+Lys+ALT+ALB+TP; 0.761, 256.419, 1+Ala+Gly+Lys+Tyr+AL B; 0.761, 250.915, 1+ALB+ALT+Orn+Val+Phe; 0.761, 252.230, 1+Gly+L ys+ALB+BUN+TP; 0.761, 249.033, 1+ALB+AST+Asn+Asp+Val; 0.760, 256. 418, 1+Ala+Gly+Lys+Glc+ALB; 0.760, 256.421, 1+Ala+Gly+Lys+Thr+A LB; 0.760, 252.263, 1+Gly+Trp+Phe+ALB+BUN; 0.760, 250.127, 1+ALB+ALT+3MeHis+Orn+Phe; 0.760, 252.162, 1+ALB+BUN+NEFA+3MeHis+Lys; 0.760, 252.644, 1+Trp+Phe+TG+ALB+BUN; 0.760, 249.991, 1+BCAA+Trp+ALT+ALB+BUN; 0.760, 253.147, 1+Ala+Lys+Glc+ALB+BUN; 0.760, 249. 394, 1+ALB+BUN+ALT+3Me-His+Arg; 0.760, 250.036, 1+ALB+BUN+ALT+3M eHis+Trp; 0.760, 249.887, 1+ALB+BUN+ALT+Val+Trp; 0.760, 250.058, 1+Trp+ALT+ALB+BUN+BHBA; 0.760, 250.161, 1+ALB+BUN+Asp+Phe+Trp; 0.760, 250.925, 1+Gly+Lys+ALT+AST+ALB; 0.760, 255.071, 1+Gly+BCA A+Lys+AST+ALB; 0.760, 251.494, 1+ALB+Ca+AST+T-BIL+Asn; 0.760, 25 1.919, 1+ALB+BUN+Orn+Lys+Trp; 0.760, 249.589, 1+Trp+Arg+ALT+AST+ALB; 0.760, 250.045, 1+Lys+Phe+His+ALT+ALB; 0.760, 253.182, 1+Al a+Lys+Tyr+ALB+BUN; 0.760, 250.273, 1+Ala+Thr+ALT+ALB+BUN; 0.760, 250.662, 1+Arg+Phe+Tyr+ALT+ALB; 0.760, 255.606, 1+Ala+Gly+Lys+A LB+TP; 0.760, 250.934, 1+ALB+ALT+NEFA+Orn+Phe; 0.760, 253.432, 1+Ala+Trp+Lys+His+ALB; 0.760, 250.736, 1+Trp+Phe+ALT+ALB+TP; 0.76 0, 251.968, 1+ALB+AST+Asn+Val+Phe; 0.760, 252.977, 1+Lys+Thr+His+ALB+BUN; 0.760, 250.805, 1+Trp+Phe+TCHO+ALT+ALB; 0.760, 256.248, 1+Ala+Gly+Lys+Phe+ALB; 0.760, 251.902, 1+Trp+Lys+Thr+ALB+BUN; 0. 760, 251.932, 1+Trp+Lys+Glc+ALB+BUN; 0.760, 250.501, 1+Trp+Arg+T yr+ALT+ALB; 0.760, 251.211, 1+Trp+Phe+ALT+gGT+ALB; 0.760, 253.36 8, 1+Gly+Arg+Lys+AST+ALB; 0.760, 251.652, 1+ALB+AST+gGT+T-BIL+A sn; 0.760, 252.728, 1+Ala+Lys+TCHO+ALB+BUN; 0.760, 252.292, 1+Lys+Phe+ALB+BUN+NEFA; 0.760, 251.188, 1+Trp+Phe+Tyr+ALT+ALB; 0.760, 251.210, 1+Trp+Phe+TG+ALT+ALB; 0.760, 249.642, 1+ALB+ALT+Arg+Ly s+Ile; 0.760, 253.763, 1+ALB+BUN+Thr+Lys+Ile; 0.760, 251.591, 1+A la+Gly+Phe+ALT+ALB; 0.760, 252.287, 1+Trp+Phe+ALB+BUN+NEFA; 0.7 60, 249.959, 1+ALB+BUN+ALT+Arg+Orn; 0.760, 250.124, 1+Trp+Glc+AL T+ALB+BUN; 0.760, 253.124, 1+Gly+Lys+Phe+ALB+BUN; 0.760, 251.633, 1+Trp+Lys+TCHO+ALB+BUN; 0.760, 250.574, 1+ALB+ALT+Arg+Thr+Ile; 0.760, 248.914, 1+ALB+ALT+Asp+Phe+Trp; 0.760, 255.475, 1+Ala+Gly+Trp+TG+ALB; 0.760, 252.081, 1+ALB+BUN+T-BIL+His+Lys; 0.760, 254. 840, 1+Gly+Lys+His+AST+ALB; 0.760, 251.844, 1+Trp+Lys+ALB+BUN+C a; 0.760, 252.305, 1+Ala+Lys+ALB+BUN+TP; 0.760, 252.905, 1+ALB+gG T+BHBA+Glc+Asn; 0.760, 256.386, 1+Ala+Gly+Lys+gGT+ALB; 0.760, 25 1.778, 1+Trp+Lys+ALB+BUN+BHBA; 0.760, 248.913, 1+ALB+AST+Asn+As p+Phe; 0.760, 254.436, 1+Lys+His+AST+ALB+TP; 0.760, 252.869, 1+AL B+BUN+His+Orn+Lys; 0.760, 252.554, 1+Trp+Lys+His+ALB+TP; 0.760, 251.090, 1+Lys+AST+ALB+BUN+TP; 0.760, 253.175, 1+Ala+Lys+TG+ALB+BUN; 0.760, 251.620, 1+ALB+BUN+3MeHis+Phe+Trp; 0.760, 254.052, 1+Ala+Lys+His+ALB+NEFA; 0.760, 251.207, 1+Trp+Phe+ALT+ALB+BHBA; 0.760, 251.236, 1+Trp+Phe+Glc+ALT+ALB; 0.759, 249.579, 1+Arg+Phe+His+ALT+ALB; 0.759, 255.457, 1+Ala+Gly+Trp+Glc+ALB; 0.759, 251. 462, 1+Lys+ALB+BUN+TP+NEFA; 0.759, 251.686, 1+Ala+Lys+AST+ALB+B UN; 0.759, 251.956, 1+ALB+AST+gGT+BHBA+Asn; 0.759, 251.795, 1+Gly+Phe+His+ALT+ALB; 0.759, 252.422, 1+Gly+Lys+AST+ALB+BUN; 0.759, 253.014, 1+Ala+Arg+Lys+ALB+BUN; 0.759, 252.536, 1+ALB+BUN+Val+P he+Trp; 0.759, 252.540, 1+ALB+BUN+3MeHis+Orn+Lys; 0.759, 250.542, 1+Ala+Trp+Lys+ALT+ALB; 0.759, 250.851, 1+Ala+Arg+Phe+ALT+ALB; 0. 759, 252.657, 1+Trp+Phe+gGT+ALB+BUN; 0.759, 250.314, 1+Arg+Lys+P he+ALT+ALB; 0.759, 251.243, 1+Trp+Thr+Phe+ALT+ALB; 0.759, 253.25 5, 1+Ala+Trp+Lys+AST+ALB; 0.759, 250.072, 1+Trp+ALT+ALB+BUN+NEF A; 0.759, 250.514, 1+BCAA+Trp+Arg+ALT+ALB; 0.759, 250.060, 1+ALB+AST+ALT+Lys+Trp; 0.759, 250.060, 1+Trp+Lys+ALT+AST+ALB; 0.759, 2 50.582, 1+Trp+Phe+ALT+AST+ALB; 0.759, 250.905, 1+ALB+Ca+AST+Glc+Asn; 0.759, 250.643, 1+ALB+ALT+NEFA+Arg+Phe; 0.759, 250.643, 1+A rg+Phe+ALT+ALB+NEFA; 0.759, 250.263, 1+Arg+Glc+ALT+ALB+BUN; 0.7 59, 251.242, 1+ALB+ALT+Val+Phe+Trp; 0.759, 253.041, 1+ALB+Ca+gGT+Glc+Asn; 0.759, 255.191, 1+Ala+Gly+Arg+Lys+ALB; 0.759, 249.932, 1+Trp+Arg+Lys+ALT+ALB; 0.759, 253.019, 1+Phe+His+ALB+BUN+NEFA; 0.759, 251.631, 1+Trp+Arg+ALB+BUN+TP; 0.759, 249.466, 1+Trp+Arg+His+ALT+ALB; 0.759, 250.163, 1+Arg+Tyr+ALT+ALB+BUN; 0.759, 250.6 49, 1+ALB+Ca+AST+Asn+Arg; 0.759, 250.004, 1+Arg+ALT+ALB+BUN+TP; 0.759, 250.567, 1+ALB+ALT+3MeHis+Phe+Trp; 0.759, 250.000, 1+Trp+ALT+ALB+BUN+Ca; 0.759, 251.150, 1+ALB+ALT+Lys+Val+Phe; 0.759, 25 1.155, 1+Trp+Phe+ALT+ALB+NEFA; 0.759, 250.658, 1+Lys+Phe+ALT+AL B+TP; 0.759, 253.535, 1+Gly+Trp+Lys+ALB+TP; 0.759, 252.539, 1+ALB+BUN+3MeHis+Lys+Tyr; 0.759, 252.651, 1+Trp+Phe+Glc+ALB+BUN; 0.7 59, 252.656, 1+Trp+Thr+Phe+ALB+BUN; 0.759, 250.128, 1+Arg+TG+ALT+ALB+BUN; 0.759, 251.078, 1+Ala+Lys+Phe+ALT+ALB; 0.759, 250.751, 1+Lys+Phe+ALT+ALB+NEFA; 0.759, 251.372, 1+Lys+AST+ALB+BUN+NEF A; 0.759, 255.117, 1+Gly+Lys+Glc+AST+ALB; 0.759, 256.315, 1+Ala+G ly+Lys+ALB+BHBA; 0.759, 255.531, 1+Ala+Gly+Trp+ALB+BHBA; 0.759, 250.036, 1+Trp+His+ALT+ALB+BUN; 0.759, 250.373, 1+Arg+ALT+gGT+A LB+BUN; 0.759, 253.294, 1+BCAA+Trp+Lys+AST+ALB; 0.759, 254.896, 1+Gly+Lys+AST+ALB+BHBA; 0.759, 251.845, 1+ALB+Ca+AST+gGT+Asn; 0. 759, 252.965, 1+ALB+Ca+gGT+Asn+Arg; 0.759, 252.191, 1+ALB+gGT+Gl c+Asn+Arg; 0.759, 253.646, 1+Lys+Phe+Tyr+ALB+BUN; 0.759, 250.807, 1+BCAA+Arg+Phe+ALT+ALB; 0.759, 253.867, 1+Ala+Gly+Trp+His+ALB; 0.759, 250.113, 1+Gly+Trp+ALT+ALB+BUN; 0.759, 254.702, 1+Gly+Lys+TCHO+AST+ALB; 0.759, 250.709, 1+ALB+ALT+Orn+Lys+Phe; 0.759, 255. 121, 1+Gly+Lys+

TG+AST+ALB; 0.759, 256.376, 1+Ala+Gly+Lys+ALB+Ca; 0.759, 252.762, 1+Ala+Lys+ALB+BUN+BHBA; 0.759, 250.308, 1+ALB+BUN+NEFA+Asp+Lys; 0.759, 250.523, 1+ALB+ALT+Arg+Orn+Phe; 0.759, 252.734, 1+ALB+BUN+NEFA+Lys+Ile; 0.759, 249.963, 1+Trp+Arg+ALT+ALB+TP; 0.759, 253.142, 1+Ala+Lys+gGT+ALB+BUN; 0.759, 255.534, 1+Ala+Gly+Trp+Thr+ALB; 0.759, 248.110, 1+ALB+ALT+3MeHis+Asp+Phe; 0.759, 250.606, 1+ALB+AST+BHBA+Glc+Asn; 0.759, 250.472, 1+Trp+AS T+ALB+BUN+TP; 0.759, 252.239, 1+Ala+ALT+ALB+BUN+NEFA; 0.759, 250. 218, 1+BCAA+Arg+ALT+ALB+BUN; 0.759, 255.514, 1+Ala+Gly+Trp+ALB+NEFA; 0.759, 249.015, 1+ALB+ALT+Arg+Asp+Lys; 0.759, 249.426, 1+AL B+BUN+3MeHis+Asp+Phe; 0.759, 253.330, 1+Gly+Lys+His+ALB+BUN; 0. 759, 249.998, 1+Trp+Lys+His+ALT+ALB; 0.759, 250.048, 1+Gly+Trp+Arg+ALT+ALB; 0.759, 251.166, 1+Lys+Phe+Tyr+ALT+ALB; 0.759, 250.41 8, 1+ALB+AST+ALT+3MeHis+Lys; 0.758, 253.092, 1+Ala+Lys+ALB+BUN+Ca; 0.758, 250.585, 1+ALB+ALT+Arg+Val+Trp; 0.758, 250.588, 1+Trp+Arg+ALT+gGT+ALB; 0.758, 249.804, 1+Trp+Lys+ALT+ALB+TP; 0.758, 25 2.585, 1+Gly+Trp+Lys+AST+ALB; 0.758, 254.835, 1+ALB+AST+Orn+Lys+Ile; 0.758, 253.610, 1+ALB+BUN+Lys+Val+Phe; 0.758, 252.190, 1+AL B+BUN+Orn+Phe+Trp; 0.758, 253.188, 1+Lys+gGT+ALB+BUN+NEFA; 0.75 8, 250.095, 1+Gly+Arg+ALT+ALB+BUN; 0.758, 250.323, 1+ALB+BUN+ALT+T-BIL+Arg; 0.758, 250.980, 1+ALB+ALT+NEFA+3MeHis+Lys; 0.758, 25 0.434, 1+ALB+AST+ALT+Orn+Phe; 0.758, 253.933, 1+ALB+BUN+Orn+Lys+Ile; 0.758, 252.074, 1+Ala+Trp+ALT+ALB+TP; 0.758, 248.517, 1+ALB+BUN+ALT+Asp+Orn; 0.758, 250.305, 1+Arg+ALT+ALB+BUN+BHBA; 0.758, 250.587, 1+Trp+Arg+Glc+ALT+ALB; 0.758, 250.829, 1+Arg+Phe+TG+AL T+ALB; 0.758, 248.900, 1+ALB+ALT+Arg+Asp+Trp; 0.758, 251.296, 1+A la+Trp+ALT+AST+ALB; 0.758, 253.090, 1+ALB+Ca+BHBA+Glc+Asn; 0.75 8, 251.117, 1+ALB+BUN+Asp+Lys+Phe; 0.758, 252.751, 1+BCAA+Lys+AL B+BUN+TP; 0.758, 254.050, 1+BCAA+Lys+Thr+ALB+BUN; 0.758, 249.568, 1+Trp+Tyr+ALT+ALB+BUN; 0.758, 250.563, 1+Trp+Arg+ALT+ALB+BHBA; 0.758, 250.589, 1+Trp+Arg+ALT+ALB+NEFA; 0.758, 250.807, 1+Arg+Th r+Phe+ALT+ALB; 0.758, 251.025, 1+ALB+ALT+3MeHis+Lys+Val; 0.758, 252.273, 1+Gly+Phe+ALT+gGT+ALB; 0.758, 249.812, 1+ALB+BUN+AST+A sp+Lys; 0.758, 249.923, 1+Arg+ALT+AST+ALB+BUN; 0.758, 255.809, 1+Ala+Gly+Lys+ALB+NEFA; 0.758, 250.558, 1+Gly+Arg+ALT+AST+ALB; 0. 758, 252.751, 1+BCAA+Trp+ALB+BUN+TP; 0.758, 250.177, 1+Trp+Arg+T CHO+ALT+ALB; 0.758, 251.735, 1+ALB+Ca+AST+BHBA+Asn; 0.758, 254.1 38, 1+ALB+Ca+gGT+T-BIL+Asn; 0.758, 252.446, 1+Ala+Trp+TG+ALT+AL B; 0.758, 253.631, 1+ALB+BUN+His+Lys+Ile; 0.758, 251.165, 1+Lys+P he+ALT+gGT+ALB; 0.758, 249.543, 1+ALB+ALT+3MeHis+Arg+Lys; 0.758, 250.662, 1+Lys+Phe+ALT+AST+ALB; 0.758, 254.922, 1+Gly+Lys+Thr+A ST+ALB; 0.758, 252.344, 1+Ala+Trp+Thr+ALT+ALB; 0.758, 250.275, 1+Arg+ALT+ALB+BUN+NEFA; 0.758, 252.466, 1+Ala+Trp+ALT+ALB+NEFA; 0. 758, 255.490, 1+Ala+Gly+Trp+Tyr+ALB; 0.758, 249.506, 1+ALB+ALT+3 MeHis+Arg+Phe; 0.758, 252.195, 1+Lys+Phe+AST+ALB+BUN; 0.758, 250. 553, 1+Lys+ALT+AST+ALB+TP; 0.758, 252.032, 1+Ala+Trp+TCHO+ALT+A LB; 0.758, 251.427, 1+ALB+BUN+Asp+Lys+Val; 0.758, 252.438, 1+Ala+Trp+Glc+ALT+ALB; 0.758, 252.477, 1+Ala+Trp+ALT+gGT+ALB; 0.758, 2 50.936, 1+Arg+Phe+ALT+gGT+ALB; 0.758, 250.373, 1+ALB+BUN+ALT+Ar g+Ile; 0.758, 247.111, 1+ALB+ALT+3Me His+Asp+Lys; 0.758, 251.417, 1+ALB+BUN+Asp+Orn+Lys; 0.758, 251.962, 1+ALB+BUN+3MeHis+Arg+Ly s; 0.758, 252.906, 1+BCAA+Lys+ALB+BUN+NEFA; 0.758, 250.936, 1+ALB+ALT+Arg+Val+Phe; 0.758, 248.401, 1+ALB+ALT+Asp+Lys+Trp; 0.758, 250.089, 1+Arg+His+ALT+ALB+BUN; 0.758, 250.690, 1+Lys+Phe+TCHO+ALT+ALB; 0.758, 251.426, 1+ALB+BUN+Arg+Asp+Lys; 0.758, 253.024, 1+ALB+BUN+T-BIL+Lys+Ile; 0.758, 248.974, 1+ALB+BUN+3MeHis+Asp+T rp; 0.758, 252.761, 1+Trp+TG+ALB+BUN+TP; 0.758, 249.721, 1+Arg+Ly s+His+ALT+ALB; 0.758, 250.894, 1+ALB+ALT+3MeHis+Lys+Tyr; 0.758, 251.554, 1+ALB+BUN+AST+T-BIL+Lys; 0.758, 250.031, 1+Arg+TCHO+AL T+ALB+BUN; 0.758, 253.670, 1+Lys+Phe+Glc+ALB+BUN; 0.758, 252.386, 1+Ala+BCAA+Trp+ALT+ALB; 0.758, 249.366, 1+ALB+ALT+Asp+Orn+Trp; 0.758, 249.974, 1+ALB+BUN+ALT+Arg+Val; 0.758, 250.649, 1+ALB+ALT+Orn+Lys+Trp; 0.758, 254.912, 1+Ala+Gly+Trp+ALB+TP; 0.758, 250.5 05, 1+Gly+Trp+Lys+ALT+ALB; 0.758, 253.560, 1+ALB+AST+NEFA+Orn+L ys; 0.758, 249.997, 1+Arg+ALT+ALB+BUN+Ca; 0.758, 251.422, 1+Ala+L ys+ALT+ALB+NEFA; 0.758, 250.423, 1+ALB+ALT+Arg+Orn+Trp; 0.758, 2 49.503, 1+Trp+ALT+AST+ALB+BUN; 0.758, 250.404, 1+Trp+Arg+TG+ALT+ALB; 0.758, 251.112, 1+ALB+BUN+AST+Orn+Trp; 0.758, 252.850, 1+AL B+BUN+AST+Lys+Ile; 0.758, 253.385, 1+ALB+AST+Orn+Val+Trp; 0.758, 248.970, 1+ALB+BUN+AST+Asp+Trp; 0.758, 251.135, 1+Ala+BCAA+ALT+ALB+BUN; 0.758, 252.847, 1+Lys+TG+ALB+BUN+TP; 0.758, 253.397, 1+A la+Gly+Arg+ALB+BUN; 0.758, 253.064, 1+Lys+TG+ALB+BUN+NEFA; 0.75 8, 249.497, 1+ALB+ALT+Arg+Asp+Phe; 0.758, 249.166, 1+ALB+ALT+NEF A+Asp+Lys; 0.758, 250.607, 1+BCAA+Trp+Lys+ALT+ALB; 0.758, 253.48 3, 1+ALB+AST+NEFA+Lys+Ile; 0.757, 252.476, 1+Ala+Trp+ALT+ALB+BH BA; 0.757, 252.841, 1+Lys+Thr+ALB+BUN+TP; 0.757, 255.503, 1+Ala+G ly+Trp+gGT+ALB; 0.757, 249.422, 1+ALB+ALT+Asp+Orn+Phe; 0.757, 25 0.377, 1+ALB+BUN+ALT+Thr+Orn; 0.757, 251.188, 1+Ala+Arg+ALT+AST+ALB; 0.757, 251.114, 1+ALB+ALT+Orn+Lys+Ile; 0.757, 249.396, 1+AL B+AST+3MeHis+Asp+Lys; 0.757, 253.858, 1+Gly+Lys+AST+ALB+NEFA; 0. 757, 253.638, 1+ALB+BUN+Glc+His+Lys; 0.757, 252.576, 1+Trp+Thr+A LB+BUN+TP; 0.757, 250.988, 1+ALB+BUN+AST+Phe+Trp; 0.757, 251.013, 1+Trp+Arg+AST+ALB+BUN; 0.757, 254.674, 1+Ala+Gly+Trp+TCHO+ALB; 0.757, 253.535, 1+ALB+BUN+Orn+Lys+Phe; 0.757, 253.201, 1+Lys+Glc+ALB+BUN+NEFA; 0.757, 252.430, 1+Gly+Trp+ALB+BUN+TP; 0.757, 253. 641, 1+ALB+BUN+gGT+His+Lys; 0.757, 250.396, 1+ALB+AST+ALT+Orn+T rp; 0.757, 252.788, 1+ALB+BUN+His+Arg+Lys; 0.757, 253.316, 1+Ala+Lys+AST+ALB+NEFA; 0.757, 253.627, 1+Ala+Trp+AST+ALB+TP; 0.757, 2 52.631, 1+ALB+BUN+3MeHis+Orn+Phe; 0.757, 252.760, 1+Trp+Glc+ALB+BUN+TP; 0.757, 251.353, 1+Lys+ALT+gGT+ALB+TP; 0.757, 252.970, 1+BCAA+Lys+AST+ALB+BUN; 0.757, 252.884, 1+Lys+Glc+ALB+BUN+TP; 0.7 57, 252.787, 1+ALB+BUN+AST+Orn+Phe; 0.757, 252.943, 1+ALB+AST+NE FA+3MeHis+Lys; 0.757, 255.473, 1+Ala+Gly+Trp+ALB+Ca; 0.757, 250. 467, 1+Trp+Arg+ALT+ALB+Ca; 0.757, 254.124, 1+Gly+Lys+gGT+ALB+BU N; 0.757, 251.407, 1+ALB+BUN+Asp+Lys+Tyr; 0.757, 253.904, 1+Gly+L ys+Thr+ALB+BUN; 0.757, 252.323, 1+ALB+BUN+Arg+Phe+Trp; 0.757, 25 3.106, 1+Lys+Thr+ALB+BUN+NEFA; 0.757, 250.831, 1+Lys+ALT+ALB+TP+NEFA; 0.757, 250.930, 1+ALB+AST+ALT+Orn+Lys; 0.757, 252.795, 1+L ys+Thr+AST+ALB+BUN; 0.757, 251.939, 1+Gly+Trp+Arg+AST+ALB; 0.75 7, 253.514, 1+Ala+Trp+AST+ALB+NEFA; 0.757, 252.296, 1+Lys+ALB+BU N+TP+BHBA; 0.757, 251.354, 1+BCAA+Lys+ALT+ALB+TP; 0.757, 251.508, 1+ALB+AST+NEFA+Asp+Lys; 0.757, 253.198, 1+ALB+BUN+NEFA+Lys+Ty r; 0.757, 250.755, 1+ALB+ALT+3MeHis+Orn+Lys; 0.757, 251.200, 1+Al a+Lys+ALT+AST+ALB; 0.757, 253.027, 1+ALB+AST+NEFA+Orn+Trp; 0.75 7, 254.803, 1+Gly+Lys+AST+gGT+ALB; 0.757, 254.126, 1+Gly+Lys+TG+ALB+BUN; 0.757, 253.171, 1+ALB+BUN+NEFA+Orn+Lys; 0.757, 251.569, 1+ALB+BUN+ALT+gGT+Orn; 0.757, 252.660, 1+Trp+ALB+BUN+TP+NEFA; 0. 757, 250.525, 1+Trp+Arg+Thr+ALT+ALB; 0.757, 253.054, 1+Gly+Trp+A ST+ALB+TP; 0.757, 252.473, 1+Trp+ALB+BUN+TP+BHBA; 0.757, 255.428, 1+Ala+Gly+BCAA+Trp+ALB; 0.757, 249.912, 1+ALB+ALT+3MeHis+Arg+T rp; 0.757, 250.724, 1+ALB+ALT+His+Arg+Orn; 0.757, 250.844, 1+Gly+Arg+Thr+ALT+ALB; 0.757, 254.195, 1+ALB+AST+His+Orn+Lys; 0.757, 2 48.940, 1+ALB+ALT+Asp+Lys+Phe; 0.757, 250.230, 1+ALB+ALT+3Me-His+Lys+Trp; 0.757, 250.365, 1+ALB+AST+ALT+Arg+Phe; 0.757, 252.799, 1+Lys+AST+gGT+ALB+BUN; 0.757, 250.094, 1+Arg+Lys+ALT+AST+ALB; 0. 757, 251.320, 1+ALB+ALT+Thr+Lys+Ile; 0.757, 253.154, 1+ALB+AST+O rn+Lys+Trp; 0.757, 253.691, 1+Gly+Lys+TCHO+ALB+BUN; 0.757, 250.3 18, 1+Trp+Lys+TCHO+ALT+ALB; 0.757, 253.389, 1+ALB+BUN+NEFA+3MeH is+Phe; 0.757, 250.979, 1+ALB+BUN+AST+ALT+Orn; 0.757, 252.438, 1+Ala+Trp+ALT+ALB+Ca; 0.757, 251.994, 1+Ala+Gly+ALT+ALB+BUN; 0.75 7, 250.833, 1+ALB+ALT+NEFA+Lys+Trp; 0.757, 252.682, 1+ALB+BUN+AS T+Orn+Lys; 0.757, 251.530, 1+ALB+AST+Asp+Lys+Trp; 0.756, 254.231, 1+ALB+Ca+gGT+BHBA+Asn; 0.756, 254.026, 1+Gly+BCAA+Lys+ALB+BUN; 0.756, 249.371, 1+ALB+ALT+Asp+Orn+Lys; 0.756, 253.053, 1+ALB+AST+NEFA+Arg+Lys; 0.756, 252.396, 1+Trp+TCHO+ALB+BUN+TP; 0.756, 254. 118, 1+Gly+Lys+Glc+ALB+BUN; 0.756, 256.211, 1+Ala+Gly+Arg+TG+AL B; 0.756, 253.140, 1+ALB+BUN+NEFA+Lys+Val; 0.756, 253.547, 1+ALB+BUN+Arg+Lys+Ile; 0.756, 250.656, 1+Ala+Arg+Lys+ALT+ALB; 0.756, 2 51.658, 1+ALB+ALT+NEFA+3MeHis+Phe; 0.756, 250.886, 1+ALB+AST+AL T+NEFA+Lys; 0.756, 253.286, 1+ALB+AST+NEFA+His+Lys; 0.756, 253.5 85, 1+ALB+BUN+Arg+Lys+Phe; 0.756, 251.561, 1+Trp+ALT+AST+ALB+T P; 0.756, 251.596, 1+ALB+ALT+Orn+Val+Trp; 0.756, 250.840, 1+ALB+A LT+Lys+Val+Trp; 0.756, 251.248, 1+ALB+BUN+ALT+His+Orn; 0.756, 25 1.713, 1+Gly+Lys+TG+ALT+ALB; 0.756, 251.556, 1+Gly+Lys+Thr+ALT+ALB; 0.756, 252.655, 1+ALB+BUN+AST+BHBA+Lys; 0.756, 252.864, 1+AL B+BUN+AST+Lys+Tyr; 0.756, 253.476, 1+ALB+AST+Orn+Tyr+Trp; 0.756, 252.712, 1+ALB+AST+NEFA+Lys+Trp; 0.756, 253.152, 1+ALB+BUN+NEFA+BHBA+Lys; 0.756, 251.537, 1+ALB+BUN+ALT+Orn+Ile; 0.756, 251.580, 1+ALB+BUN+ALT+Glc+Orn; 0.756, 251.222, 1+Gly+Arg+TG+ALT+ALB; 0. 756, 251.266, 1+ALB+AST+ALT+Lys+Ile; 0.756, 253.170, 1+ALB+BUN+B HBA+His+Lys; 0.756, 250.745, 1+ALB+ALT+His+Orn+Lys; 0.756, 250.8 53, 1+Trp+Lys+Glc+ALT+ALB; 0.756, 252.515, 1+Arg+Lys+AST+ALB+BU N; 0.756, 251.552, 1+BCAA+Lys+ALT+AST+ALB; 0.756, 252.915, 1+Ala+TG+ALT+ALB+BUN; 0.756, 253.092, 1+ALB+BUN+Orn+Val+Trp; 0.756, 25 3.162, 1+ALB+BUN+NEFA+T-BIL+Lys; 0.756, 249.453, 1+ALB+ALT+Asp+Lys+Tyr; 0.756, 253.013, 1+Lys+TG+AST+ALB+BUN; 0.756, 251.924, 1+Ala+Arg+ALT+gGT+ALB; 0.756, 253.458, 1+ALB+BUN+NEFA+Orn+Phe; 0. 756, 250.628, 1+ALB+BUN+Asp+Orn+Trp; 0.756, 251.844, 1+Ala+BCAA+Lys+ALT+ALB; 0.756, 250.140, 1+ALB+ALT+His+Arg+Thr; 0.756, 251.7 46, 1+Thr+TG+ALT+ALB+BUN; 0.756, 251.288, 1+ALB+AST+ALT+T-BIL+L ys; 0.756, 253.543, 1+Gly+Arg+Lys+ALB+BUN; 0.756, 250.873, 1+ALB+AST+ALT+Arg+Orn; 0.756, 251.353, 1+ALB+ALT+NEFA+Lys+Ile; 0.756, 251.721, 1+ALB+BUN+ALT+Thr+Ile; 0.756, 251.727, 1+Gly+Lys+Glc+A LT+ALB; 0.756, 252.472, 1+ALB+AST+3MeHis+Arg+Lys; 0.756, 253.008, 1+ALB+AST+Arg+Orn+Trp; 0.756, 252.472, 1+ALB+BUN+AST+His+Lys; 0. 756, 254.024, 1+ALB+AST+NEFA+Lys+Tyr; 0.756, 251.179, 1+Gly+Lys+TCHO+ALT+ALB; 0.756, 252.415, 1+Ala+ALT+ALB+BUN+BHBA; 0.756, 253. 341, 1+ALB+BUN+T-BIL+Thr+Lys; 0.756, 253.371, 1+ALB+BUN+T-BIL+O rn+Lys; 0.756, 248.452, 1+ALB+BUN+ALT+Asp+Val; 0.756, 252.490, 1+ALB+ALT+NEFA+Tyr+Phe; 0.756, 254.455, 1+ALB+AST+Arg+Lys+Ile; 0. 756, 252.992, 1+ALB+BUN+AST+Lys+Val; 0.756, 251.265, 1+ALB+AST+A LT+His+Lys; 0.756, 254.319, 1+ALB+BUN+gGT+Lys+Ile; 0.756, 251.52 4, 1+ALB+ALT+NEFA+Orn+Lys; 0.756, 251.747, 1+Thr+ALT+gGT+ALB+BU N; 0.756, 251.747, 1+ALB+BUN+ALT+gGT+Thr; 0.756, 251.824, 1+ALB+A LT+3MeHis+Tyr+Phe; 0.756, 253.006, 1+Lys+Glc+AST+ALB+BUN; 0.756, 253.360, 1+ALB+AST+Orn+Phe+Trp; 0.756, 254.023, 1+ALB+AST+NEFA+BHBA+Lys; 0.756, 252.730, 1+Lys+TCHO+AST+ALB+BUN; 0.756, 252.713, 1+Ala+ALT+ALB+BUN+Ca; 0.756, 250.655, 1+ALB+BUN+Arg+Asp+Trp; 0. 756, 251.862, 1+Ala+Lys+ALT+gGT+ALB; 0.756, 250.778, 1+ALB+ALT+A rg+Orn+Lys; 0.756, 250.844, 1+Trp+Lys+ALT+gGT+ALB; 0.756, 253.11 9, 1+ALB+BUN+Ca+NEFA+Lys; 0.756, 252.915, 1+Ala+ALT+ALB+BUN+TP; 0.756, 251.161, 1+ALB+BUN+ALT+3MeHis+Orn; 0.756, 252.506, 1+Gly+Trp+Arg+ALB+BUN; 0.756, 251.862, 1+Ala+Lys+TG+ALT+ALB; 0.756, 25 0.208, 1+Gly+Arg+Lys+ALT+ALB; 0.756, 250.791, 1+ALB+ALT+Arg+Lys+Tyr; 0.756, 251.708, 1+Gly+BCAA+Lys+ALT+ALB; 0.756, 251.825, 1+A LB+ALT+3MeHis+Val+Phe; 0.756, 251.169, 1+ALB+ALT+NEFA+His+Lys; 0.756, 251.516, 1+ALB+AST+ALT+Arg+Ile; 0.756, 251.583, 1+ALB+BUN+ALT+NEFA+Orn; 0.756, 251.331, 1+Ala+Lys+TCHO+ALT+ALB; 0.756, 25 2.697, 1+Trp+gGT+ALB+BUN+TP; 0.756, 252.895, 1+ALB+BUN+NEFA+Arg+Lys; 0.756, 249.432, 1+ALB+ALT+Asp+Lys+Val; 0.756, 252.993, 1+Al a+Trp+Arg+AST+ALB; 0.756, 253.962, 1+ALB+AST+NEFA+Orn+Phe; 0.75 6, 253.791, 1+ALB+AST+Lys+Tyr+Trp; 0.756, 253.999, 1+ALB+AST+NEF A+T-BIL+Lys; 0.756, 255.386, 1+Ala+Gly+Lys+TCHO+ALB; 0.756, 251. 347, 1+ALB+BUN+Ca+ALT+Orn; 0.756, 251.618, 1+ALB+ALT+Thr+Orn+Ly s; 0.755, 248.473, 1+ALB+ALT+3Me-His+Arg+Asp; 0.755, 251.858, 1+Al a+Lys+Glc+ALT+ALB; 0.755, 250.650, 1+BCAA+Arg+Lys+ALT+ALB; 0.75 5, 251.703, 1+Gly+Lys+ALT+gGT+ALB; 0.755, 251.788, 1+Ala+Lys+Thr+ALT+ALB; 0.755, 251.555, 1+Lys+TG+ALT+AST+ALB; 0.755, 254.004, 1+ALB+AST+NEFA+Lys+Val; 0.755, 253.487, 1+ALB+BUN+Ca+His+Lys; 0. 755, 253.408, 1+ALB+BUN+T-BIL+BHBA+Lys; 0.755, 251.564, 1+ALB+BU N+ALT+T-BIL+Orn; 0.755, 248.774, 1+ALB+AST+ALT+Asp+Lys; 0.755, 2 50.622, 1+ALB+ALT+NEFA+Arg+Lys; 0.755, 250.878, 1+Trp+Lys+Thr+A LT+ALB; 0.755, 251.695, 1+ALB+BUN+ALT+NEFA+Thr; 0.755, 253.346, 1+ALB+AST+Arg+Tyr+Trp; 0.755, 253.408, 1+ALB+BUN+gGT+T-BIL+Lys; 0.755, 252.534, 1+ALB+BUN+3MeHis+Orn+Trp; 0.755, 255.123, 1+Ala+BCAA+Trp+Lys+ALB; 0.755, 250.741, 1+ALB+BUN+ALT+Orn+Tyr; 0.755, 251.302, 1+ALB+BUN+ALT+Orn+

Val; 0.755, 251.145, 1+ALB+AST+ALT+NEFA+Arg; 0.755, 251.340, 1+ALB+ALT+Arg+Thr+Orn; 0.755, 251.367, 1+ALB+AST+ALT+BHBA+Lys; 0.755, 252.771, 1+Ala+Glc+ALT+ALB+BUN; 0. 755, 254.169, 1+ALB+BUN+Thr+Orn+Lys; 0.755, 251.566, 1+ALB+ALT+NEFA+Orn+Trp; 0.755, 253.962, 1+BCAA+Arg+Lys+ALB+BUN; 0.755, 250. 885, 1+ALB+BUN+Asp+Val+Trp; 0.755, 251.556, 1+BCAA+Thr+ALT+ALB+BUN; 0.755, 251.531, 1+ALB+ALT+BHBA+His+Lys; 0.755, 251.554, 1+Lys+Glc+ALT+AST+ALB; 0.755, 253.984, 1+ALB+AST+NEFA+Thr+Lys; 0.75 5, 252.928, 1+ALB+BUN+Ca+AST+Lys; 0.755, 252.576, 1+Ala+TCHO+ALT+ALB+BUN; 0.755, 250.747, 1+Arg+Thr+ALT+AST+ALB; 0.755, 251.571, 1+ALB+AST+ALT+BHBA+Arg; 0.755, 254.326, 1+Lys+Thr+Glc+ALB+BUN; 0.755, 251.480, 1+ALB+ALT+Arg+Orn+Ile; 0.755, 251.426, 1+Ala+Arg+Thr+ALT+ALB; 0.755, 251.714, 1+ALB+ALT+T-BIL+Lys+Ile; 0.755, 25 4.843, 1+ALB+AST+T-BIL+Lys+Ile; 0.755, 250.879, 1+Lys+TCHO+ALT+AST+ALB; 0.755, 251.924, 1+ALB+BUN+3MeHis+Arg+Trp; 0.755, 250.80 4, 1+ALB+ALT+T-BIL+Arg+Lys; 0.755, 251.513, 1+ALB+ALT+T-BIL+His+Lys; 0.755, 254.002, 1+ALB+AST+NEFA+Glc+Lys; 0.755, 254.770, 1+Gly+Arg+TG+AST+ALB; 0.755, 251.927, 1+Ala+BCAA+Arg+ALT+ALB; 0.75 5, 252.749, 1+ALB+BUN+Arg+Orn+Trp; 0.755, 250.723, 1+Arg+Lys+Thr+ALT+ALB; 0.755, 251.656, 1+ALB+BUN+ALT+BHBA+Thr; 0.755, 251.726, 1+ALB+AST+Asp+Orn+Trp; 0.755, 251.602, 1+Ala+Arg+TCHO+ALT+ALB; 0.755, 252.886, 1+Ala+ALT+gGT+ALB+BUN; 0.755, 254.051, 1+ALB+BUN+BHBA+Thr+Lys; 0.755, 254.303, 1+ALB+BUN+Glc+Orn+Lys; 0.755, 251. 987, 1+Ala+Arg+Glc+ALT+ALB; 0.755, 252.933, 1+Trp+Arg+TG+ALB+BUN; 0.755, 251.688, 1+ALB+ALT+T-BIL+Orn+Lys; 0.755, 250.867, 1+Trp+Lys+TG+ALT+ALB; 0.755, 253.853, 1+Ala+Gly+Thr+ALT+ALB; 0.755, 2 51.500, 1+BCAA+Arg+Thr+ALT+ALB; 0.755, 255.339, 1+ALB+AST+BHBA+Orn+Lys; 0.755, 253.407, 1+ALB+BUN+T-BIL+Glc+Lys; 0.755, 254.518, 1+Lys+Glc+gGT+ALB+BUN; 0.755, 254.538, 1+ALB+BUN+Orn+Tyr+Phe; 0. 755, 254.307, 1+ALB+BUN+Glc+Lys+Ile; 0.755, 250.733, 1+ALB+ALT+3MeHis+Arg+Orn; 0.755, 250.272, 1+ALB+ALT+Arg+Asp+Orn; 0.755, 251. 794, 1+ALB+ALT+NEFA+BHBA+Lys; 0.755, 250.808, 1+Arg+Lys+Glc+ALT+ALB; 0.755, 251.709, 1+ALB+ALT+NEFA+Thr+Lys; 0.755, 254.502, 1+ALB+AST+NEFA+His+Orn; 0.755, 252.576, 1+Trp+ALB+BUN+TP+Ca; 0.755, 250.231, 1+ALB+AST+ALT+3MeHis+Arg; 0.755, 254.048, 1+ALB+BUN+BHBA+Lys+Ile; 0.755, 251.696, 1+Thr+Glc+ALT+ALB+BUN; 0.755, 251.68 8, 1+ALB+BUN+ALT+T-BIL+Thr; 0.755, 252.338, 1+ALB+AST+3MeHis+Lys+Trp; 0.755, 251.517, 1+ALB+AST+ALT+T-BIL+Arg; 0.755, 251.588, 1+Arg+ALT+AST+gGT+ALB; 0.755, 254.482, 1+Gly+BCAA+Trp+Lys+ALB; 0. 755, 251.873, 1+Ala+Arg+TG+ALT+ALB; 0.755, 251.582, 1+Gly+Arg+Glc+ALT+ALB; 0.755, 253.767, 1+Trp+Lys+Thr+AST+ALB; 0.755, 251.331, 1+ALB+Ca+AST+ALT+Arg; 0.755, 250.069, 1+ALB+ALT+NEFA+Asp+Phe; 0. 755, 251.558, 1+ALB+ALT+Orn+Tyr+Trp; 0.755, 250.877, 1+ALB+ALT+Lys+Tyr+Trp; 0.755, 251.518, 1+Arg+Thr+ALT+gGT+ALB; 0.755, 251.51 8, 1+ALB+ALT+gGT+Arg+Thr; 0.755, 254.527, 1+ALB+AST+T-BIL+Orn+Lys; 0.755, 251.511, 1+ALB+Ca+AST+ALT+Lys; 0.755, 254.142, 1+Arg+Lys+TG+ALB+BUN; 0.755, 251.694, 1+ALB+ALT+gGT+Orn+Lys; 0.755, 251. 585, 1+Gly+Arg+ALT+gGT+ALB; 0.755, 255.449, 1+ALB+AST+Orn+Lys+Val; 0.755, 254.070, 1+ALB+AST+NEFA+Arg+Orn; 0.755, 251.171, 1+Arg+TCHO+ALT+AST+ALB; 0.755, 254.304, 1+Lys+Thr+TG+ALB+BUN; 0.755, 254.524, 1+ALB+BUN+Orn+Val+Phe; 0.755, 253.977, 1+ALB+BUN+Arg+Thr+Lys; 0.755, 251.858, 1+ALB+ALT+Glc+Lys+Ile; 0.755, 251.543, 1+ALB+ALT+BHBA+Arg+Thr; 0.755, 255.105, 1+ALB+AST+T-BIL+His+Orn; 0.754, 256.886, 1+ALB+NEFA+Orn+Tyr+Phe; 0.754, 254.067, 1+ALB+BUN+BHBA+Orn+Lys; 0.754, 252.926, 1+ALB+BUN+Arg+Tyr+Trp; 0.754, 25 1.799, 1+ALB+ALT+NEFA+Lys+Val; 0.754, 250.807, 1+ALB+ALT+gGT+Arg+Lys; 0.754, 251.473, 1+ALB+ALT+NEFA+Arg+Thr; 0.754, 251.533, 1+ALB+ALT+Glc+Arg+Thr; 0.754, 251.944, 1+ALB+ALT+BHBA+Thr+Lys; 0. 754, 252.536, 1+ALB+AST+3MeHis+Orn+Trp; 0.754, 253.774, 1+ALB+AST+Lys+Val+Trp; 0.754, 253.818, 1+ALB+AST+Lys+Phe+Trp; 0.754, 251. 409, 1+ALB+AST+ALT+gGT+Lys; 0.754, 252.737, 1+ALB+AST+NEFA+Arg+Trp; 0.754, 254.365, 1+Ala+Trp+AST+ALB+BHBA; 0.754, 254.811, 1+ALB+AST+NEFA+Thr+Orn; 0.754, 253.996, 1+ALB+Ca+AST+NEFA+Lys; 0.75 4, 254.091, 1+ALB+BUN+Arg+Orn+Lys; 0.754, 251.309, 1+ALB+ALT+3MeHis+Orn+Trp; 0.754, 254.142, 1+ALB+BUN+Arg+Lys+Val; 0.754, 251.6 68, 1+ALB+ALT+BHBA+Orn+Lys; 0.754, 250.765, 1+ALB+BUN+NEFA+Asp+Trp; 0.754, 250.790, 1+ALB+ALT+BHBA+Arg+Lys; 0.754, 251.838, 1+ALB+ALT+gGT+Lys+Ile; 0.754, 251.503, 1+ALB+AST+ALT+Lys+Val; 0.754, 253.344, 1+ALB+AST+NEFA+Asp+Orn; 0.754, 251.550, 1+ALB+AST+ALT+Glc+Arg; 0.754, 254.314, 1+ALB+BUN+Orn+Lys+Val; 0.754, 253.673, 1+ALB+AST+NEFA+Lys+Phe; 0.754, 251.633, 1+ALB+ALT+His+Lys+Ile; 0. 754, 251.973, 1+ALB+ALT+T-BIL+Thr+Lys; 0.754, 254.441, 1+Ala+BCAA+Trp+AST+ALB; 0.754, 253.192, 1+ALB+BUN+T-BIL+Arg+Lys; 0.754, 2 51.783, 1+ALB+ALT+NEFA+Glc+Lys; 0.754, 250.808, 1+ALB+ALT+Arg+Lys+Val; 0.754, 254.316, 1+ALB+AST+T-BIL+Arg+Lys; 0.754, 251.532, 1+ALB+BUN+ALT+His+Thr; 0.754, 251.372, 1+ALB+AST+ALT+Thr+Lys; 0. 754, 255.371, 1+ALB+AST+NEFA+Orn+Ile; 0.754, 255.774, 1+ALB+AST+Thr+Orn+Ile; 0.754, 251.636, 1+ALB+Ca+ALT+Orn+Lys; 0.754, 251.70 1, 1+ALB+ALT+Orn+Lys+Val; 0.754, 253.331, 1+ALB+AST+3MeHis+Orn+Lys; 0.754, 251.777, 1+ALB+ALT+BHBA+Lys+Ile; 0.754, 252.562, 1+ALB+ALT+Thr+Orn+Ile; 0.754, 253.094, 1+ALB+AST+Arg+Lys+Trp; 0.754, 253.314, 1+ALB+BUN+Ca+T-BIL+Lys; 0.754, 251.686, 1+ALB+BUN+Ca+ALT+Thr; 0.754, 250.851, 1+ALB+3MeHis+Asp+Lys+Trp; 0.754, 251.376, 1+ALB+3MeHis+Arg+Asp+Lys; 0.754, 251.043, 1+ALB+ALT+NEFA+3MeHis+Arg; 0.754, 251.535, 1+ALB+BUN+ALT+BHBA+Orn; 0.754, 251.697, 1+ALB+ALT+Glc+Orn+Lys; 0.754, 249.916, 1+ALB+AST+ALT+Arg+Asp; 0.7 54, 251.528, 1+ALB+ALT+T-BIL+Arg+Thr; 0.754, 252.611, 1+ALB+BUN+AST+3MeHis+Phe; 0.754, 255.248, 1+ALB+AST+Orn+Lys+Phe; 0.754, 25 2.512, 1+ALB+BUN+AST+NEFA+Phe; 0.754, 251.943, 1+ALB+Ca+ALT+Arg+Ile; 0.754, 251.760, 1+ALB+Ca+ALT+NEFA+Lys; 0.754, 254.223, 1+ALB+BUN+Ca+Thr+Lys; 0.754, 254.323, 1+ALB+BUN+gGT+Thr+Lys; 0.754, 254.384, 1+ALB+BUN+Lys+Tyr+Val; 0.754, 254.468, 1+ALB+BUN+NEFA+Tyr+Phe; 0.754, 254.315, 1+ALB+BUN+gGT+Orn+Lys; 0.754, 250.174, 1+ALB+ALT+Arg+Asp+Val; 0.754, 254.323, 1+ALB+3MeHis+Lys+Val+Trp; 0.754, 251.622, 1+ALB+ALT+Orn+Lys+Tyr; 0.754, 251.984, 1+ALB+ALT+Glc+Thr+Lys; 0.754, 254.451, 1+Ala+Trp+TG+AST+ALB; 0.754, 250. 699, 1+ALB+Ca+ALT+Arg+Lys; 0.754, 251.547, 1+ALB+Ca+ALT+Arg+Orn; 0.754, 254.399, 1+ALB+BUN+Ca+gGT+Lys; 0.754, 254.241, 1+ALB+BUN+Orn+Lys+Tyr; 0.754, 251.740, 1+ALB+

ALT+Glc+His+Lys; 0.754, 251.962, 1+ALB+AST+ALT+ 3MeHis+Orn; 0.754, 255.449, 1+ALB+AST+Glc+Orn+Lys; 0.754, 252.095, 1+ALB+ALT+NEFA+Arg+Ile; 0.754, 256.009, 1+ALB+AST+Glc+His+Orn; 0.754, 255.793, 1+ALB+Ca+AST+His+Orn; 0.754, 252.683, 1+ALB+BUN+3MeHis+Arg+Phe; 0.754, 249.268, 1+ALB+AST+ALT+Asp+Trp; 0.754, 252.788, 1+ALB+BUN+NEFA+Arg+Trp; 0.754, 252.973, 1+ALB+BUN+Arg+Val+Trp; 0.754, 253.079, 1+ALB+BUN+NEFA+Orn+Trp; 0.754, 251.774, 1+ALB+ALT+gGT+NEFA+Lys; 0.754, 254.120, 1+ALB+BUN+3MeHis+Val+Phe; 0.754, 254.752, 1+ALB+NEFA+Arg+Lys+Ile; 0.754, 253.719, 1+ALB+AST+3MeHis+Lys+Phe; 0.754, 254.396, 1+ALB+BUN+Ca+Glc+Lys; 0.754, 251.292, 1+ALB+AST+ALT+His+Arg; 0.754, 251.786, 1+ALB+AST+ALT+NEFA+Phe; 0.754, 252.437, 1+ALB+ALT+NEFA+Val+Phe; 0.754, 252.202, 1+ALB+AST+ALT+His+Orn; 0.754, 253.146, 1+ALB+BUN+Orn+Tyr+Trp; 0.754, 251.719, 1+ALB+ALT+NEFA+Arg+Orn; 0.754, 255.426, 1+ALB+AST+Arg+Orn+Ile; 0.754, 251.981, 1+ALB+Ca+ALT+Thr+Lys; 0.754, 250.900, 1+ALB+BUN+Asp+Tyr+Trp; 0.754, 251.773, 1+ALB+ALT+Glc+Arg+Orn; 0.754, 252.071, 1+ALB+ALT+T-BIL+Glc+Lys; 0.754, 252.079, 1+ALB+ALT+gGT+T-BIL+Lys; 0.754, 254.112, 1+ALB+BUN+Glc+Arg+Lys; 0.754, 254.488, 1+ALB+AST+T-BIL+His+Lys; 0.753, 251.542, 1+ALB+AST+ALT+Arg+Tyr; 0.753, 254.135, 1+ALB+BUN+Arg+Lys+Tyr; 0.753, 250.506, 1+ALB+ALT+NEFA+Arg+Asp; 0.753, 251.708, 1+ALB+ALT+NEFA+T-BIL+Lys; 0.753, 252.048, 1+ALB+ALT+gGT+BHBA+Lys; 0.753, 251.716, 1+ALB+ALT+NEFA+Lys+Tyr; 0.753, 255.430, 1+ALB+AST+Orn+Lys+Tyr; 0.753, 254.332, 1+Ala+Trp+AST+gGT+ALB; 0.753, 252.714, 1+ALB+BUN+Asp+Orn+Phe; 0.753, 251.672, 1+ALB+ALT+Arg+Orn+Val; 0.753, 251.865, 1+ALB+AST+ALT+Thr+Orn; 0.753, 254.116, 1+ALB+AST+3MeHis+Lys+Val; 0.753, 255.350, 1+ALB+AST+NEFA+T-BIL+Orn; 0.753, 255.377, 1+ALB+AST+NEFA+Glc+Orn; 0.753, 254.177, 1+ALB+BUN+Ca+Orn+Lys; 0.753, 251.771, 1+ALB+ALT+BHBA+Arg+Orn; 0.753, 251.032, 1+ALB+ALT+3MeHis+Arg+Tyr; 0.753, 251.919, 1+ALB+AST+3MeHis+Arg+Trp; 0.753, 254.103, 1+ALB+BUN+3MeHis+Tyr+Phe; 0.753, 251.450, 1+ALB+AST+ALT+3MeHis+Phe; 0.753, 255.251, 1+ALB+ALT+His+Thr+Lys; 0.753, 251.796, 1+ALB+Ca+ALT+Lys+Ile; 0.753, 252.012, 1+ALB+ALT+gGT+Thr+Lys; 0.753, 252.425, 1+Gly+Trp+ALT+ALB+TP; 0.753, 254.946, 1+ALB+AST+Arg+Orn+Lys; 0.753, 256.100, 1+ALB+AST+T-BIL+Orn+Ile; 0.753, 254.174, 1+Trp+AST+ALB+TP+BHBA; 0.753, 252.039, 1+ALB+Ca+ALT+gGT+Arg; 0.753, 256.678, 1+ALB+Ca+AST+Orn+Ile; 0.753, 255.293, 1+ALB+Ca+AST+NEFA+Orn; 0.753, 254.179, 1+ALB+BUN+Ca+Lys+Ile; 0.753, 252.051, 1+ALB+ALT+T-BIL+BHBA+Lys; 0.753, 249.923, 1+ALB+ALT+Asp+Val+Trp; 0.753, 251.980, 1+ALB+AST+Arg+Asp+Trp; 0.753, 254.131, 1+ALB+BUN+gGT+Arg+Lys; 0.753, 252.333, 1+Trp+TG+AST+ALB+BUN; 0.753, 256.256, 1+ALB+AST+His+Lys+Ile; 0.753, 252.292, 1+ALB+ALT+BHBA+Arg+Ile; 0.753, 254.491, 1+ALB+BUN+Arg+Orn+Phe; 0.753, 250.351, 1+ALB+AST+ALT+Asp+Orn; 0.753, 254.570, 1+ALB+AST+NEFA+3MeHis+Orn; 0.753, 255.920, 1+ALB+AST+BHBA+His+Orn; 0.753, 254.429, 1+Ala+Trp+Glc+AST+ALB; 0.753, 254.438, 1+Trp+Glc+AST+ALB+TP; 0.753, 251.545, 1+ALB+Ca+ALT+His+Arg; 0.753, 253.451, 1+ALB+BUN+3MeHis+Tyr+Trp; 0.753, 251.447, 1+ALB+3MeHis+Asp+Lys+Tyr; 0.753, 251.767, 1+ALB+ALT+Arg+Orn+Tyr; 0.753, 249.105, 1+ALB+ALT+3MeHis+Asp+Trp; 0.753, 252.019, 1+Trp+AST+gGT+ALB+BUN; 0.753, 250.942, 1+ALB+ALT+3MeHis+Arg+Val; 0.753, 251.755, 1+ALB+BUN+ALT+Tyr+Val; 0.753, 250.364, 1+ALB+ALT+Asp+Val+Phe; 0.753, 251.762, 1+ALB+ALT+gGT+Arg+Orn; 0.753, 255.293, 1+ALB+AST+gGT+Orn+Lys; 0.753, 251.935, 1+ALB+Ca+ALT+NEFA+Arg; 0.753, 254.119, 1+Ala+Trp+TCHO+AST+ALB; 0.753, 251.683, 1+ALB+Ca+ALT+His+Lys; 0.753, 252.243, 1+ALB+ALT+gGT+Arg+Ile; 0.753, 253.893, 1+ALB+BUN+BHBA+Arg+Lys; 0.753, 254.200, 1+ALB+BUN+gGT+BHBA+Lys; 0.753, 248.980, 1+ALB+BUN+ALT+Asp+Tyr; 0.753, 252.831, 1+ALB+ALT+NEFA+Thr+Orn; 0.753, 253.851, 1+ALB+BUN+AST+NEFA+Orn; 0.753, 255.336, 1+ALB+AST+NEFA+BHBA+Orn; 0.753, 255.379, 1+ALB+AST+Thr+Orn+Lys; 0.753, 251.602, 1+ALB+ALT+NEFA+His+Arg; 0.753, 251.831, 1+ALB+ALT+NEFA+Arg+Val; 0.753, 250.917, 1+ALB+ALT+Asp+Orn+Val; 0.753, 252.028, 1+ALB+ALT+BHBA+Glc+Lys; 0.753, 252.169, 1+ALB+ALT+gGT+Glc+Lys; 0.753, 252.195, 1+Trp+AST+ALB+BUN+BHBA; 0.753, 253.640, 1+ALB+AST+Arg+Asp+Lys; 0.753, 251.870, 1+ALB+BUN+AST+3MeHis+Trp; 0.753, 252.051, 1+Gly+Trp+AST+ALB+BUN; 0.753, 255.632, 1+ALB+AST+T-BIL+Thr+Orn; 0.753, 253.973, 1+ALB+BUN+Ca+Arg+Lys; 0.753, 251.521, 1+ALB+3MeHis+Asp+Lys+Phe; 0.753, 252.958, 1+ALB+ALT+NEFA+His+Orn; 0.753, 251.729, 1+ALB+ALT+gGT+His+Lys; 0.753, 254.381, 1+ALB+NEFA+His+Orn+Lys; 0.753, 252.394, 1+ALB+AST+ALT+NEFA+Orn; 0.753, 253.663, 1+ALB+AST+3MeHis+Orn+Phe; 0.753, 252.262, 1+ALB+ALT+Glc+Arg+Ile; 0.753, 252.292, 1+ALB+ALT+T-BIL+Arg+Ile; 0.753, 254.200, 1+ALB+BUN+BHBA+Glc+Lys; 0.753, 251.764, 1+ALB+ALT+T-BIL+Arg+Orn; 0.753, 251.179, 1+ALB+AST+ALT+Arg+Val; 0.753, 253.984, 1+ALB+BUN+AST+T-BIL+Orn; 0.753, 256.002, 1+ALB+AST+T-BIL+BHBA+Orn; 0.753, 251.966, 1+ALB+BUN+NEFA+Asp+Phe; 0.753, 251.969, 1+ALB+ALT+Lys+Tyr+Val; 0.753, 254.365, 1+BCAA+Trp+AST+ALB+TP; 0.753, 255.387, 1+ALB+Ca+AST+Orn+Lys; 0.753, 254.410, 1+Ala+Trp+AST+ALB+Ca; 0.752, 251.328, 1+ALB+3MeHis+Asp+Lys+Val; 0.752, 251.390, 1+ALB+BUN+AST+ALT+Thr; 0.752, 253.657, 1+Trp+AST+ALB+TP+NEFA; 0.752, 252.040, 1+ALB+Ca+ALT+T-BIL+Lys; 0.752, 252.114, 1+ALB+Ca+ALT+Glc+Lys; 0.752, 251.912, 1+ALB+ALT+NEFA+T-BIL+Arg; 0.752, 250.293, 1+ALB+ALT+NEFA+Asp+Trp; 0.752, 252.137, 1+ALB+BUN+AST+Tyr+Trp; 0.752, 255.846, 1+ALB+AST+Orn+Val+Phe; 0.752, 256.841, 1+ALB+AST+Glc+Orn+Ile; 0.752, 251.883, 1+ALB+ALT+Arg+Tyr+Val; 0.752, 250.234, 1+ALB+ALT+Asp+Tyr+Trp; 0.752, 254.337, 1+ALB+BUN+AST+His+Orn; 0.752, 255.030, 1+ALB+AST+T-BIL+Arg+Orn; 0.752, 256.093, 1+ALB+AST+T-BIL+Glc+Orn; 0.752, 256.795, 1+ALB+AST+BHBA+Orn+Ile; 0.752, 252.115, 1+ALB+Ca+ALT+gGT+Lys; 0.752, 252.180, 1+ALB+ALT+NEFA+Glc+Arg; 0.752, 252.145, 1+ALB+ALT+NEFA+BHBA+Arg; 0.752, 252.854, 1+ALB+ALT+gGT+Thr+Orn; 0.752, 255.842, 1+ALB+AST+Orn+Tyr+Phe; 0.752, 256.039, 1+ALB+AST+Thr+Lys+Ile; 0.752, 256.004, 1+ALB+Ca+AST+T-BIL+Orn; 0.752, 251.946, 1+Trp+TCHO+ALT+AST+ALB; 0.752, 252.611, 1+Ala+ALT+AST+ALB+BUN; 0.752, 252.317, 1+ALB+ALT+gGT+BHBA+Arg; 0.752, 249.646, 1+ALB+ALT+3MeHis+Asp+Orn; 0.752, 253.029, 1+ALB+ALT+BHBA+His+Orn; 0.752, 255.930, 1+ALB+AST+gGT+T-BIL+Orn; 0.752, 254.413, 1+ALB+AST+His+Arg+Orn; 0.752, 252.026, 1+ALB+Ca+ALT+BHBA+Lys; 0.752, 252.163, 1+ALB+ALT+NEFA+Arg+Tyr; 0.752, 252.317, 1+ALB+

ALT+gGT+T-BIL+Arg; 0.752, 254.292, 1+BCAA+Trp+TG+ALB+BUN; 0.752, 255.234, 1+ALB+T-BIL+His+Orn+Lys; 0.752, 252.550, 1+ALB+AST+ALT+T-BIL+Orn; 0.752, 253.520, 1+ALB+AST+Asp+Orn+Lys; 0.752, 255.961, 1+ALB+AST+BHBA+His+Lys; 0.752, 256.796, 1+ALB+AST+BHBA+Glc+Orn; 0.752, 253.569, 1+ALB+AST+gGT+NEFA+Lys; 0.752, 252.072, 1+ALB+Ca+ALT+T-BIL+Arg; 0.752, 256.669, 1+ALB+Ca+AST+BHBA+Orn; 0.752, 254.042, 1+ALB+BUN+3MeHis+Arg+Orn; 0.752, 254.300, 1+BCAA+Trp+gGT+ALB+BUN; 0.752, 254.629, 1+ALB+3MeHis+Lys+Tyr+Trp; 0.752, 251.862, 1+ALB+ALT+gGT+His+Arg; 0.752, 254.433, 1+ALB+NEFA+3MeHis+Lys+Trp; 0.752, 252.244, 1+ALB+BUN+AST+Val+Trp; 0.752, 256.185, 1+ALB+AST+BHBA+Thr+Orn; 0.752, 251.433, 1+ALB+Ca+ALT+Arg+Thr; 0.752, 253.727, 1+ALB+3MeHis+Arg+Lys+Trp; 0.752, 254.093, 1+Gly+Trp+TG+ALB+BUN; 0.752, 253.032, 1+ALB+ALT+gGT+His+Orn; 0.752, 251.339, 1+ALB+AST+ALT+Lys+Tyr; 0.752, 251.884, 1+ALB+ALT+T-BIL+His+Arg; 0.752, 251.364, 1+ALB+NEFA+3MeHis+Asp+Lys; 0.752, 252.156, 1+ALB+ALT+gGT+NEFA+Arg; 0.752, 252.419, 1+ALB+AST+ALT+Orn+Val; 0.752, 256.297, 1+ALB+AST+Glc+His+Lys; 0.752, 256.711, 1+ALB+AST+gGT+Orn+Ile; 0.752, 254.337, 1+Ala+Gly+BCAA+ALT+ALB; 0.752, 248.631, 1+ALB+BUN+ALT+3MeHis+Asp; 0.752, 253.714, 1+ALB+BUN+3MeHis+Val+Trp; 0.752, 252.846, 1+ALB+ALT+BHBA+Thr+Orn; 0.752, 252.863, 1+Trp+Glc+ALT+ALB+TP; 0.752, 252.604, 1+ALB+AST+ALT+Glc+Orn; 0.752, 252.878, 1+Trp+ALT+ALB+TP+NEFA; 0.752, 252.509, 1+BCAA+Trp+ALT+ALB+TP; 0.752, 255.943, 1+ALB+AST+His+Orn+Ile; 0.752, 252.072, 1+ALB+Ca+ALT+Glc+Arg; 0.752, 252.340, 1+ALB+ALT+T-BIL+Glc+Arg; 0.752, 254.507, 1+ALB+3MeHis+Arg+Lys+Val; 0.752, 251.876, 1+ALB+ALT+Glc+His+Arg; 0.752, 254.523, 1+ALB+3MeHis+Lys+Phe+Trp; 0.752, 250.697, 1+ALB+ALT+Arg+Asp+Tyr; 0.752, 252.948, 1+ALB+ALT+His+Orn+Ile; 0.752, 253.045, 1+Gly+BCAA+Trp+ALT+ALB; 0.752, 252.604, 1+ALB+AST+ALT+Orn+Ile; 0.752, 253.650, 1+ALB+BUN+AST+3MeHis+Orn; 0.752, 254.929, 1+ALB+BUN+AST+Glc+Orn; 0.752, 254.390, 1+ALB+AST+His+Arg+Lys; 0.752, 255.355, 1+ALB+AST+Arg+Thr+Orn; 0.752, 255.230, 1+ALB+AST+T-BIL+Thr+Lys; 0.752, 254.448, 1+Trp+TG+AST+ALB+TP; 0.752, 256.562, 1+ALB+Ca+AST+gGT+Orn; 0.752, 254.110, 1+ALB+BUN+Ca+BHBA+Lys; 0.752, 254.543, 1+ALB+BUN+NEFA+Val+Phe; 0.752, 254.319, 1+Trp+TG+gGT+ALB+BUN; 0.752, 251.604, 1+ALB+3MeHis+Asp+Orn+Lys; 0.752, 254.123, 1+Gly+Trp+gGT+ALB+BUN; 0.752, 253.938, 1+ALB+BUN+His+Thr+Orn; 0.752, 252.367, 1+BCAA+Trp+AST+ALB+BUN; 0.752, 255.875, 1+ALB+AST+gGT+His+Orn; 0.752, 250.434, 1+ALB+AST+3MeHis+Asp+Trp; 0.752, 252.466, 1+ALB+BUN+AST+Asp+Orn; 0.752, 254.547, 1+ALB+AST+His+Thr+Orn; 0.752, 255.547, 1+ALB+AST+Arg+Thr+Ile; 0.752, 252.338, 1+ALB+ALT+BHBA+Glc+Arg; 0.752, 253.026, 1+ALB+ALT+T-BIL+His+Orn; 0.752, 253.034, 1+ALB+ALT+Glc+His+Orn; 0.752, 252.875, 1+ALB+ALT+Tyr+Val+Phe; 0.752, 253.568, 1+ALB+BUN+AST+Arg+Phe; 0.752, 252.378, 1+Trp+Glc+AST+ALB+BUN; 0.752, 252.315, 1+BCAA+Trp+ALT+AST+ALB; 0.752, 252.444, 1+ALB+Ca+AST+ALT+Orn; 0.752, 254.334, 1+ALB+3MeHis+Orn+Lys+Trp; 0.752, 255.525, 1+ALB+3MeHis+Lys+Val+Phe; 0.752, 255.885, 1+ALB+Orn+Tyr+Phe+Trp; 0.752, 252.052, 1+ALB+AST+ALT+Val+Trp; 0.752, 255.314, 1+ALB+AST+NEFA+Orn+Val; 0.752, 256.491, 1+ALB+AST+Glc+Lys+Ile; 0.752, 254.173, 1+Trp+TCHO+AST+ALB+TP; 0.751, 252.297, 1+ALB+ALT+gGT+Glc+Arg; 0.751, 252.857, 1+ALB+ALT+3MeHis+Orn+Val; 0.751, 254.299, 1+BCAA+Trp+Glc+ALB+BUN; 0.751, 254.318, 1+Trp+Glc+TG+ALB+BUN; 0.751, 252.880, 1+Trp+TG+ALT+ALB+TP; 0.751, 255.399, 1+ALB+AST+Arg+Lys+Tyr; 0.751, 255.043, 1+ALB+AST+gGT+NEFA+Orn; 0.751, 254.128, 1+Gly+Trp+Glc+ALB+BUN; 0.751, 253.961, 1+ALB+BUN+AST+Arg+Orn; 0.751, 256.652, 1+ALB+AST+gGT+BHBA+Orn; 0.751, 256.720, 1+ALB+AST+gGT+Glc+Orn; 0.751, 252.065, 1+ALB+Ca+ALT+BHBA+Arg; 0.751, 256.694, 1+ALB+Ca+AST+Glc+Orn; 0.751, 255.558, 1+ALB+Ca+AST+Arg+Orn; 0.751, 255.366, 1+ALB+3MeHis+Orn+Lys+Val; 0.751, 251.901, 1+ALB+ALT+BHBA+His+Arg; 0.751, 253.704, 1+ALB+BUN+NEFA+Arg+Phe; 0.751, 254.034, 1+Gly+Trp+ALB+BUN+BHBA; 0.751, 254.035, 1+ALB+BUN+Tyr+Val+Trp; 0.751, 252.464, 1+ALB+AST+ALT+gGT+Orn; 0.751, 253.354, 1+ALB+AST+3MeHis+Arg+Orn; 0.751, 254.236, 1+ALB+AST+NEFA+Arg+Thr; 0.751, 253.150, 1+Trp+Glc+TCHO+ALT+ALB; 0.751, 254.659, 1+ALB+3MeHis+Arg+Orn+Lys; 0.751, 255.766, 1+ALB+3MeHis+Lys+Tyr+Phe; 0.751, 255.940, 1+ALB+His+Orn+Lys+Ile; 0.751, 251.203, 1+ALB+ALT+NEFA+Asp+Orn; 0.751, 253.926, 1+ALB+BUN+AST+Thr+Orn; 0.751, 256.190, 1+ALB+AST+Glc+Thr+Orn; 0.751, 254.408, 1+Trp+AST+gGT+ALB+TP; 0.751, 251.079, 1+ALB+ALT+Asp+Orn+Tyr; 0.751, 252.588, 1+ALB+AST+ALT+BHBA+Orn; 0.751, 255.213, 1+ALB+AST+NEFA+Orn+Tyr; 0.751, 255.325, 1+ALB+AST+Arg+Thr+Lys; 0.751, 256.274, 1+ALB+AST+BHBA+Lys+Ile; 0.751, 256.160, 1+ALB+Ca+AST+Thr+Orn; 0.751, 252.280, 1+Trp+AST+ALB+BUN+Ca; 0.751, 253.704, 1+ALB+Asp+Lys+Tyr+Trp; 0.751, 250.167, 1+ALB+AST+ALT+Asp+Phe; 0.751, 252.827, 1+ALB+ALT+T-BIL+Thr+Orn; 0.751, 251.495, 1+ALB+ALT+His+Thr+Orn; 0.751, 252.126, 1+Trp+AST+ALB+BUN+NEFA; 0.751, 254.806, 1+ALB+BUN+AST+BHBA+Orn; 0.751, 255.375, 1+ALB+AST+Arg+Orn+Phe; 0.751, 252.143, 1+ALB+AST+NEFA+Asp+Trp; 0.751, 255.638, 1+ALB+3MeHis+Orn+Val+Phe; 0.751, 255.673, 1+ALB+NEFA+Orn+Lys+Ile; 0.751, 254.065, 1+ALB+BUN+NEFA+Val+Trp; 0.751, 255.389, 1+ALB+NEFA+Lys+Tyr+Trp; 0.751, 252.442, 1+ALB+AST+ALT+Val+Phe; 0.751, 252.846, 1+Trp+ALT+ALB+TP+BHBA; 0.751, 253.931, 1+ALB+AST+Asp+Lys+Val; 0.751, 256.323, 1+ALB+AST+gGT+Lys+Ile; 0.751, 253.249, 1+ALB+AST+NEFA+Arg+Asp; 0.751, 254.023, 1+Trp+TCHO+gGT+ALB+BUN; 0.751, 254.619, 1+ALB+3MeHis+Arg+Lys+Tyr; 0.751, 256.062, 1+ALB+Glc+His+Orn+Lys; 0.751, 254.021, 1+ALB+AST+Asp+Lys+Tyr; 0.751, 257.105, 1+ALB+NEFA+Orn+Val+Phe; 0.751, 252.008, 1+ALB+AST+ALT+Tyr+Trp; 0.751, 254.323, 1+Trp+Glc+gGT+ALB+BUN; 0.751, 252.760, 1+ALB+ALT+Glc+Thr+Orn; 0.751, 255.168, 1+ALB+NEFA+His+Thr+Lys; 0.751, 255.420, 1+ALB+AST+Glc+Arg+Lys; 0.751, 252.766, 1+ALB+AST+Asp+Val+Trp; 0.751, 252.799, 1+ALB+Ca+ALT+His+Orn; 0.751, 252.480, 1+Trp+TCHO+ALT+ALB+TP; 0.751, 251.915, 1+ALB+ALT+His+Arg+Ile; 0.751, 252.989, 1+ALB+ALT+NEFA+Val+Trp; 0.751, 254.196, 1+Trp+TG+ALB+BUN+BHBA; 0.751, 256.006, 1+Ala+Gly+BCAA+ALB+BUN; 0.751, 252.873, 1+Trp+ALT+gGT+ALB+TP; 0.751, 253.257, 1+BCAA+Trp+ALT+gGT+ALB; 0.751, 253.873, 1+ALB+NEFA+His+Arg+Lys; 0.751, 253.593, 1+ALB+AST+Arg+Val+Trp; 0.751, 255.405, 1+ALB+AST+Arg+Lys+Phe; 0.751, 252.772, 1+ALB+AST+Asp+Phe+Trp; 0.751, 252.363, 1+ALB+ALT+T-BIL+BHBA+Arg; 0.751, 254.122, 1+Gly+Trp+ALB+BUN+

NEFA; 0.751, 251.101, 1+ALB+AST+3 MeHis+Arg+Asp; 0.751, 252.084, 1+Trp+TCHO+AST+ALB+BUN; 0.751, 254.206, 1+Trp+gGT+ALB+BUN+BHBA; 0.751, 253.693, 1+Trp+ALT+gGT+ALB+BHBA; 0.751, 255.268, 1+ALB+AST+BHBA+Arg+Lys; 0.751, 253.985, 1+BCAA+Trp+TCHO+ALB+BUN; 0.751, 254.115, 1+Gly+BCAA+Trp+ALB+BUN; 0.751, 256.743, 1+ALB+T-BIL+Orn+Lys+Ile; 0.751, 251.767, 1+ALB+BUN+ALT+3MeHis+Tyr; 0.751, 251.633, 1+ALB+AST+3MeHis+Asp+Orn; 0.751, 252.146, 1+Gly+Trp+ALT+AST+ALB; 0.751, 254.956, 1+ALB+NEFA+3MeHis+Lys+Phe; 0.751, 252.850, 1+ALB+ALT+3MeHis+Val+Trp; 0.751, 254.162, 1+Trp+TG+ALB+BUN+NEFA; 0.751, 252.812, 1+ALB+ALT+Tyr+Val+Trp; 0.751, 253.233, 1+BCAA+Trp+TG+ALT+ALB; 0.751, 257.370, 1+Ala+Gly+BCAA+AST+ALB; 0.751, 253.580, 1+ALB+AST+Arg+Phe+Trp; 0.750, 255.683, 1+ALB+Orn+Lys+Tyr+Trp; 0.750, 252.603, 1+Trp+TG+ALT+AST+ALB; 0.750, 252.101, 1+ALB+AST+ALT+Orn+Tyr; 0.750, 255.222, 1+ALB+AST+T-BIL+BHBA+Lys; 0.750, 252.969, 1+ALB+ALT+NEFA+3MeHis+Orn; 0.750, 253.618, 1+ALB+BUN+ALT+T-BIL+Ile; 0.750, 252.672, 1+ALB+BUN+ALT+NEFA+Val; 0.750, 254.002, 1+ALB+AST+3MeHis+Lys+Tyr; 0.750, 252.326, 1+ALB+BUN+AST+ALT+Val; 0.750, 253.693, 1+Trp+ALT+gGT+ALB+NEFA; 0.750, 256.337, 1+ALB+AST+BHBA+Thr+Lys; 0.750, 256.257, 1+ALB+Ca+AST+His+Lys; 0.750, 253.169, 1+Trp+TCHO+ALT+gGT+ALB; 0.750, 254.392, 1+Trp+AST+ALB+TP+Ca; 0.750, 252.410, 1+ALB+ALT+3MeHis+Orn+Tyr; 0.750, 253.828, 1+ALB+BUN+NEFA+3MeHis+Trp; 0.750, 254.212, 1+Trp+gGT+ALB+BUN+NEFA; 0.750, 253.396, 1+Gly+Trp+ALT+ALB+BHBA; 0.750, 253.759, 1+ALB+BUN+AST+Arg+Thr; 0.750, 255.180, 1+ALB+AST+T-BIL+Glc+Lys; 0.750, 253.628, 1+ALB+BUN+Asp+Tyr+Phe; 0.750, 252.600, 1+Trp+ALT+AST+ALB+BHBA; 0.750, 253.376, 1+Gly+Trp+Glc+ALT+ALB; 0.750, 256.177, 1+ALB+Lys+Tyr+Phe+Trp; 0.750, 256.632, 1+ALB+T-BIL+Glc+His+Lys; 0.750, 255.104, 1+ALB+AST+3MeHis+Orn+Val; 0.750, 256.125, 1+ALB+AST+gGT+Thr+Orn; 0.750, 252.782, 1+Trp+ALT+ALB+TP+Ca; 0.750, 252.720, 1+BCAA+Trp+TCHO+ALT+ALB; 0.750, 253.359, 1+ALB+BUN+Arg+Asp+Phe; 0.750, 252.567, 1+Trp+ALT+AST+ALB+NEFA; 0.750, 254.193, 1+BCAA+Trp+ALB+BUN+NEFA; 0.750, 255.368, 1+ALB+NEFA+His+Lys+Ile; 0.750, 253.328, 1+ALB+BUN+AST+NEFA+Arg; 0.750, 253.171, 1+Trp+TCHO+ALT+ALB+BHBA; 0.750, 253.172, 1+Trp+TCHO+ALT+ALB+NEFA; 0.750, 254.171, 1+BCAA+Trp+ALB+BUN+BHBA; 0.750, 250.602, 1+ALB+ALT+Asp+Tyr+Phe; 0.750, 254.206, 1+Trp+Glc+ALB+BUN+BHBA; 0.750, 253.680, 1+Trp+TG+ALT+gGT+ALB; 0.750, 255.966, 1+ALB+BHBA+His+Orn+Lys; 0.750, 255.493, 1+ALB+gGT+NEFA+His+Lys; 0.750, 255.701, 1+ALB+AST+BHBA+Arg+Orn; 0.750, 255.720, 1+ALB+AST+Glc+Arg+Orn; 0.750, 255.737, 1+ALB+AST+Arg+Orn+Tyr; 0.750, 252.785, 1+ALB+Ca+ALT+Thr+Orn; 0.750, 255.558, 1+ALB+3MeHis+Orn+Lys+Tyr; 0.750, 255.796, 1+ALB+BUN+Thr+Orn+Ile; 0.750, 254.883, 1+Gly+Trp+TG+AST+ALB; 0.750, 254.023, 1+Trp+TCHO+TG+ALB+BUN; 0.750, 252.476, 1+BCAA+ALT+ALB+BUN+TP; 0.750, 254.027, 1+Trp+Glc+TCHO+ALB+BUN; 0.750, 253.169, 1+Trp+TCHO+TG+ALT+ALB; 0.750, 253.259, 1+BCAA+Trp+Glc+ALT+ALB; 0.750, 252.889, 1+Gly+Trp+TCHO+ALT+ALB; 0.750, 255.757, 1+Ala+BCAA+ALB+BUN+NEFA; 0.750, 252.863, 1+BCAA+TG+ALT+ALB+BUN; 0.750, 256.977, 1+Ala+Trp+TG+ALB+NEFA; 0.750, 254.169, 1+Trp+TG+ALB+BUN+Ca; 0.750, 252.570, 1+Trp+ALT+AST+ALB+Ca; 0.750, 254.216, 1+Trp+Glc+ALB+BUN+NEFA; 0.750, 253.265, 1+BCAA+Trp+ALT+ALB+BHBA; 0.750, 253.675, 1+Trp+Glc+ALT+gGT+ALB; 0.750, 254.491, 1+Gly+Trp+AST+gGT+ALB; 0.750, 252.942, 1+BCAA+ALT+gGT+ALB+BUN; 0.750, 253.682, 1+Trp+Glc+ALT+ALB+BHBA; 0.749, 252.388, 1+Trp+ALT+AST+gGT+ALB; 0.749, 253.707, 1+Trp+ALT+ALB+NEFA+BHBA; 0.749, 254.173, 1+Trp+gGT+ALB+BUN+Ca; 0.749, 252.623, 1+Trp+Glc+ALT+AST+ALB; 0.749, 257.001, 1+Ala+BCAA+Trp+ALB+NEFA; 0.749, 253.320, 1+Gly+Trp+TG+ALT+ALB; 0.749, 253.687, 1+Trp+Glc+ALT+ALB+NEFA; 0.749, 253.689, 1+Trp+TG+ALT+ALB+BHBA; 0.749, 252.967, 1+Gly+BCAA+ALT+ALB+BUN; 0.749, 253.671, 1+Trp+Glc+TG+ALT+ALB; 0.749, 256.885, 1+Ala+Trp+Glc+ALB+NEFA; 0.749, 254.853, 1+Gly+Trp+AST+ALB+BHBA; 0.749, 254.158, 1+BCAA+Trp+ALB+BUN+Ca; 0.749, 253.321, 1+Gly+Trp+ALT+ALB+Ca; 0.749, 253.685, 1+Trp+TG+ALT+ALB+NEFA; 0.749, 253.277, 1+BCAA+Trp+ALT+ALB+NEFA; 0.749, 252.942, 1+BCAA+ALT+ALB+BUN+NEFA; 0.749, 254.161, 1+Trp+ALB+BUN+NEFA+BHBA; 0.749, 254.323, 1+Ala+AST+ALB+BUN+NEFA; 0.749, 253.878, 1+Trp+TCHO+ALB+BUN+NEFA; 0.749, 253.807, 1+Gly+Trp+TCHO+ALB+BUN; 0.749, 253.087, 1+Trp+TCHO+ALT+ALB+Ca; 0.749, 256.298, 1+Ala+Gly+ALB+BUN+NEFA; 0.749, 256.205, 1+Ala+Trp+TCHO+ALB+NEFA; 0.749, 254.822, 1+Gly+Trp+AST+ALB+NEFA; 0.749, 253.989, 1+Gly+Trp+ALB+BUN+Ca; 0.749, 253.917, 1+Trp+TCHO+ALB+BUN+BHBA; 0.749, 252.572, 1+BCAA+ALT+ALB+BUN+BHBA; 0.749, 253.258, 1+Gly+Trp+ALT+ALB+NEFA; 0.749, 253.216, 1+BCAA+Trp+ALT+ALB+Ca; 0.749, 252.945, 1+BCAA+Glc+ALT+ALB+BUN; 0.749, 254.176, 1+Trp+Glc+ALB+BUN+Ca; 0.749, 254.907, 1+Gly+Trp+Glc+AST+ALB; 0.749, 252.456, 1+BCAA+TCHO+ALT+ALB+BUN; 0.749, 254.080, 1+Trp+ALB+BUN+Ca+NEFA; 0.748, 254.556, 1+Gly+Trp+TCHO+AST+ALB; 0.748, 252.643, 1+BCAA+ALT+AST+ALB+BUN; 0.748, 254.857, 1+Gly+BCAA+Trp+AST+ALB; 0.748, 254.971, 1+Ala+Gly+AST+ALB+BUN; 0.748, 255.329, 1+Ala+Gly+ALT+AST+ALB; 0.748, 257.451, 1+Ala+BCAA+Trp+Glc+ALB; 0.747, 256.771, 1+Ala+Trp+Glc+TCHO+ALB; 0.747, 257.042, 1+Ala+Gly+Glc+ALB+BUN; 0.747, 257.426, 1+Ala+Trp+Glc+TG+ALB; 0.746, 256.868, 1+Ala+BCAA+Trp+TCHO+ALB; 0.746, 257.484, 1+Ala+BCAA+Trp+TG+ALB; 0.746, 256.855, 1+Ala+Trp+TCHO+TG+ALB; 0.746, 254.535, 1+Ala+BCAA+TCHO+ALT+ALB; 0.746, 257.358, 1+Ala+Trp+Glc+gGT+ALB; 0.745, 257.137, 1+Ala+Gly+TG+ALB+BUN; 0.745, 255.111, 1+Ala+BCAA+ALT+gGT+ALB; 0.745, 254.487, 1+Ala+BCAA+ALT+AST+ALB; 0.745, 255.107, 1+Ala+BCAA+TG+ALT+ALB; 0.745, 255.118, 1+Ala+BCAA+Glc+ALT+ALB; 0.745, 257.425, 1+Ala+BCAA+Trp+gGT+ALB; 0.745, 256.835, 1+Ala+Trp+TCHO+gGT+ALB; 0.745, 255.824, 1+BCAA+Trp+Glc+AST+ALB; 0.745, 255.840, 1+BCAA+Trp+TG+AST+ALB; 0.745, 255.695, 1+Trp+TG+AST+gGT+ALB; 0.744, 255.453, 1+Ala+BCAA+AST+ALB+BUN; 0.744, 257.412, 1+Ala+Trp+TG+gGT+ALB; 0.744, 255.462, 1+BCAA+Trp+TCHO+AST+ALB; 0.744, 255.581, 1+BCAA+Trp+AST+gGT+ALB; 0.744, 255.698, 1+Trp+Glc+AST+gGT+ALB; 0.744, 255.943, 1+Trp+Glc+TG+AST+ALB; 0.744, 255.584, 1+Trp+TCHO+TG+AST+ALB; 0.744, 257.216, 1+Ala+BCAA+Glc+ALB+BUN; 0.744, 255.366, 1+Trp+TCHO+AST+gGT+ALB; 0.744, 256.951, 1+Ala+Gly+gGT+ALB+BUN; 0.744, 257.260, 1+Ala+BCAA+TG+ALB+BUN; 0.744, 254.943, 1+Gly+BCAA+ALT+AST+A

LB; 0.744, 259.063, 1+Ala+Gly+Glc+AST+ALB; 0.743, 260.493, 1+Ala+Gly+BCAA+Glc+ALB; 0.743, 259.080, 1+Ala+Gly+TG+AST+ALB; 0.743, 2 56.208, 1+Ala+Gly+ TCHO+ALB+BUN; 0.743, 255.573, 1+Trp+Glc+TCHO+ AST+ALB; 0.743, 260.492, 1+Ala+Gly+BCAA+TG+ALB; 0.743, 256.348, 1+Ala+Gly+TG+ALT+ALB; 0.743, 257.886, 1+Gly+BCAA+Trp+Glc+ALB; 0. 743, 255.588, 1+Gly+BCAA+TG+ALT+ALB; 0.743, 256.560, 1+Ala+ BCAA+TCHO+ALB+BUN; 0.743, 255.004, 1+Gly+ BCAA+TCHO+ALT+ALB; 0.743, 25 6.370, 1+Ala+Gly+ Glc+ALT+ALB; 0.742, 255.641, 1+Gly+BCAA+Glc+AL T+ALB; 0.742, 255.633, 1+Gly+BCAA+ALT+gGT+ALB; 0.742, 259.075, 1+Ala+Gly+AST+gGT+ALB; 0.742, 256.325, 1+Ala+Gly+ALT+gGT+ALB; 0.7 42, 257.921, 1+Gly+BCAA+Trp+TG+ALB; 0.742, 257.116, 1+Ala+ BCAA+g GT+ALB+BUN; 0.741, 257.922, 1+Gly+BCAA+ Trp+gGT+ALB; 0.741, 254.5 91, 1+BCAA+TCHO+ALT+ AST+ALB; 0.741, 255.896, 1+Ala+Gly+TCHO+ALT+ ALB; 0.741, 255.184, 1+BCAA+ALT+AST+gGT+ALB; 0.741, 255.279, 1+B CAA+Glc+ALT+AST+ALB; 0.741, 255.840, 1+BCAA+TG+ALT+gGT+ALB; 0.7 41, 255.262, 1+BCAA+TG+ALT+AST+ALB; 0.741, 255.201, 1+BCAA+TCHO+TG+ALT+ALB; 0.741, 255.841, 1+BCAA+Glc+TG+ALT+ALB; 0.741, 255.20 3, 1+BCAA+TCHO+ALT+gGT+ALB; 0.741, 260.354, 1+Ala+Gly+BCAA+gGT+ALB; 0.740, 255.203, 1+BCAA+Glc+TCHO+ALT+ALB; 0.740, 255.851, 1+B CAA+Glc+ALT+gGT+ALB; 0.740, 257.322, 1+Ala+Glc+ AST+ALB+BUN; 0.7 40, 259.049, 1+Ala+Gly+BCAA+ TCHO+ALB; 0.740, 258.001, 1+Gly+Trp+Glc+TG+ALB; 0.739, 258.038, 1+Gly+Trp+TG+gGT+ALB; 0.739, 258.434, 1+Ala+Gly+TCHO+AST+ALB; 0.739, 258.000, 1+Gly+Trp+Glc+gGT+ALB; 0.738, 257.594, 1+Ala+ALT+ AST+gGT+ALB; 0.738, 259.684, 1+Gly+BCA A+AST+ gGT+ALB; 0.738, 259.876, 1+Gly+BCAA+TG+AST+ ALB; 0.738, 257. 266, 1+Gly+BCAA+Trp+TCHO+ALB; 0.738, 257.564, 1+Ala+Glc+ALT+AST+ALB; 0.738, 259.877, 1+Gly+BCAA+Glc+AST+ALB; 0.738, 257.455, 1+A la+AST+gGT+ALB+BUN; 0.738, 257.301, 1+Gly+ BCAA+AST+ALB+BUN; 0.7 38, 257.560, 1+BCAA+ AST+gGT+ALB+BUN; 0.738, 257.440, 1+Gly+Trp+T CHO+gGT+ALB; 0.738, 257.370, 1+Gly+Trp+Glc+ TCHO+ALB; 0.738, 257. 558, 1+Ala+TG+ALT+AST+ ALB; 0.737, 257.106, 1+Ala+TCHO+AST+ALB+B UN; 0.737, 258.542, 1+Ala+Glc+TCHO+ALB+BUN; 0.737, 257.443, 1+Gly+Trp+TCHO+TG+ALB; 0.737, 257.116, 1+Ala+TCHO+ALT+AST+ALB; 0.737, 258.112, 1+Ala+ TG+ALT+gGT+ALB; 0.737, 257.691, 1+Ala+TCHO+TG+ AL T+ALB; 0.736, 259.821, 1+Ala+BCAA+TG+AST+ ALB; 0.736, 259.855, 1+A la+BCAA+Glc+AST+ALB; 0.736, 257.644, 1+Ala+TCHO+ALT+gGT+ALB; 0. 736, 257.402, 1+Ala+TG+AST+ALB+BUN; 0.736, 258.022, 1+BCAA+Trp+G lc+TCHO+ALB; 0.736, 259.840, 1+Ala+ BCAA+AST+gGT+ALB; 0.736, 258. 181, 1+Ala+Glc+ TG+ALT+ALB; 0.736, 256.653, 1+Gly+TCHO+ALT+ ALB+B UN; 0.736, 257.689, 1+BCAA+TG+AST+ALB+ BUN; 0.735, 258.123, 1+Ala+Glc+ALT+gGT+ALB; 0.735, 259.289, 1+Gly+BCAA+TCHO+AST+ALB; 0.735, 257.673, 1+BCAA+Glc+AST+ALB+BUN; 0.735, 256.953, 1+Gly+Glc+ALT+ALB+BUN; 0.735, 258.060, 1+BCAA+ Trp+TCHO+TG+ALB; 0.735, 258.630, 1+BCAA+Trp+ Glc+gGT+ALB; 0.735, 257.109, 1+Gly+ALT+gGT+ALB+ BUN

[35. Formula with Six Amino Acid+Biochemistry Variables]

0.798, 245.367, 1+ALB+BUN+His+Asn+Lys+Ile; 0.797, 245.864, 1+ALB+BUN+NEFA+Asn+Lys+Ile; 0.797, 241.939, 1+ALB+BUN+ALT+Asn+Lys+I le; 0.796, 242.147, 1+ALB+BUN+ALT+Asn+Arg+Ile; 0.796, 244.074, 1+ALB+BUN+ALT+Asn+Tyr+Phe; 0.795, 246.402, 1+ALB+BUN+Asn+Orn+Lys+Ile; 0.795, 243.435, 1+ALB+BUN+ALT+Glc+Asn+Ile; 0.795, 245.378, 1+ALB+BUN+Glc+Asn+Lys+Ile; 0.795, 245.911, 1+ALB+ BUN+Asn+Arg+L ys+Ile; 0.794, 243.433, 1+ALB+BUN+ ALT+Asn+Orn+Ile; 0.794, 246.04 8, 1+ALB+BUN+Asn+ Thr+Lys+Ile; 0.794, 244.832, 1+ALB+BUN+ALT+Asn+ Tyr+Trp; 0.793, 246.792, 1+ALB+BUN+BHBA+Asn+Lys+ Ile; 0.793, 246. 473, 1+ALB+BUN+T-BIL+Asn+Lys+Ile; 0.793, 243.782, 1+ALB+ALT+His+Asn+Arg+Ile; 0.793, 244.761, 1+ALB+BUN+ALT+Asn+Arg+Tyr; 0.793, 246.793, 1+ALB+BUN+gGT+Asn+Lys+Ile; 0.793, 246.514, 1+ALB+BUN+C a+Asn+Lys+Ile; 0.793, 244.524, 1+ALB+BUN+ALT+Asn+Thr+Ile; 0.792, 246.409, 1+ALB+Glc+His+Asn+Orn+Ile; 0.792, 245.753, 1+ALB+ BUN+H is+Asn+Arg+Ile; 0.792, 245.599, 1+ALB+BUN+ His+Asn+Orn+Ile; 0.79 2, 243.756, 1+ALB+ALT+Glc+ Asn+Arg+Ile; 0.792, 244.065, 1+ALB+BUN+ALT+His+ Asn+Ile; 0.792, 243.750, 1+ALB+BUN+Asn+Asp+Tyr+ Trp; 0. 792, 247.825, 1+ALB+BUN+Asn+Tyr+Phe+Trp; 0.792, 244.925, 1+ALB+B UN+ALT+Asn+Val+Trp; 0.792, 245.917, 1+ALB+BUN+AST+Asn+Orn+Ile; 0.791, 244.667, 1+ALB+BUN+ALT+NEFA+Asn+Ile; 0.791, 244.672, 1+AL B+BUN+ALT+BHBA+Asn+Ile; 0.791, 246.246, 1+ALB+BUN+Glc+Asn+Orn+Ile; 0.791, 241.142, 1+ALB+BUN+ALT+Asn+Asp+Tyr; 0.791, 248.008, 1+ALB+BUN+Asn+Lys+Tyr+Trp; 0.791, 244.672, 1+ALB+BUN+ALT+gGT+As n+Ile; 0.791, 243.971, 1+ALB+BUN+ALT+Glc+His+Asn; 0.791, 244.827, 1+ALB+ALT+His+Asn+Orn+Ile; 0.790, 243.310, 1+ALB+ BUN+ALT+His+A sn+Arg; 0.790, 244.651, 1+ALB+BUN+ ALT+T-BIL+Asn+Ile; 0.790, 244. 438, 1+ALB+ALT+Glc+ Asn+Lys+Ile; 0.790, 244.609, 1+ALB+ALT+Glc+A sn+Orn+Ile; 0.790, 244.829, 1+ALB+ALT+Asn+Arg+Orn+ Ile; 0.790, 24 4.068, 1+ALB+ALT+Asn+Arg+Lys+Ile; 0.790, 246.992, 1+ALB+BUN+Asn+Arg+Orn+Ile; 0.790, 245.391, 1+ALB+ALT+Asn+Orn+Lys+Ile; 0.790, 247.812, 1+ALB+BUN+BHBA+Asn+Orn+Ile; 0.790, 244.254, 1+ALB+BUN+ALT+Asn+Thr+Lys; 0.790, 246.085, 1+ALB+ALT+Asn+Thr+Orn+Ile; 0.7 90, 244.604, 1+ALB+ BUN+ALT+Asn+Val+Phe; 0.790, 248.175, 1+ALB+NE FA+Glc+Asn+Lys+Ile; 0.790, 247.692, 1+ALB+BUN+ Asn+Arg+Tyr+Trp; 0.790, 247.626, 1+ALB+BUN+NEFA+ Asn+Orn+Ile; 0.790, 248.936, 1+AL B+NEFA+His+Asn+ Lys+Ile; 0.790, 248.530, 1+ALB+NEFA+His+Asn+Arg+ Ile; 0.789, 247.434, 1+ALB+BUN+Asn+Thr+Orn+Ile; 0.789, 244.503, 1+ALB+BUN+Ca+ALT+Asn+Ile; 0.789, 245.000, 1+ALB+BUN+ALT+Glc+As n+Thr; 0.789, 243.470, 1+ALB+BUN+ALT+His+Asn+Lys; 0.789, 249.675, 1+ALB+NEFA+BHBA+Asn+Lys+Ile; 0.789, 248.345, 1+ALB+His+Asn+Arg+Lys+Ile; 0.789, 245.213, 1+ALB+ALT+His+Asn+Lys+Ile; 0.789, 245. 534, 1+ALB+ BUN+AST+Asn+Lys+Ile; 0.789, 245.038, 1+ALB+BUN+ ALT+A sn+Thr+Orn; 0.789, 244.715, 1+ALB+BUN+ALT+ Asn+Arg+Thr; 0.789, 24 8.363, 1+ALB+BUN+NEFA+ Asn+Tyr+Trp; 0.789, 243.811, 1+ALB+BUN+AL T+His+ Asn+Orn; 0.789, 248.289, 1+ALB+BUN+Asn+Orn+Tyr+ Trp; 0.789, 247.263, 1+ALB+ALT+Asn+Arg+Tyr+Phe; 0.789, 246.228, 1+ALB+BUN+G lc+Asn+Arg+Ile; 0.789, 247.894, 1+ALB+BUN+gGT+Asn+Orn+Ile; 0.78 8, 245.689, 1+ALB+BUN+ALT+Asn+Orn+Tyr; 0.788, 242.143, 1+ALB+BUN+ALT+Asn+Asp+Trp; 0.788, 244.481, 1+ALB+ALT+BHBA+Asn+Arg+Ile; 0. 788, 244.747, 1+ALB+ALT+T-BIL+Asn+Arg+Ile; 0.788, 246.815, 1+ALB+AST+Glc+Asn+Orn+Ile; 0.788, 248.885,

1+ALB+ALT+NEFA+Asn+Tyr+Phe; 0.788, 249.197, 1+ALB+NEFA+Asn+Arg+Lys+Ile; 0.788, 245.249, 1+ALB+ALT+NEFA+Asn+Arg+Ile; 0.788, 248.518, 1+ALB+Glc+His+Asn+Lys+Ile; 0.788, 241.772, 1+ALB+BUN+ALT+Asn+3MeHis+Asp; 0.788, 245.089, 1+ALB+BUN+ALT+Asn+Lys+Tyr; 0.788, 247.613, 1+ALB+His+Asn+Arg+Orn+Ile; 0.788, 247.903, 1+ALB+BUN+T-BIL+Asn+Orn+Ile; 0.788, 247.431, 1+ALB+BUN+BHBA+Asn+Arg+Ile; 0.788, 244.367, 1+ALB+BUN+AST+ALT+Asn+Ile; 0.788, 249.946, 1+ALB+NEFA+Asn+Orn+Lys+Ile; 0.788, 246.021, 1+ALB+BUN+ALT+NEFA+Asn+Tyr; 0.788, 245.194, 1+ALB+BUN+ALT+Glc+Asn+Arg; 0.788, 245.614, 1+ALB+BUN+Asn+Asp+Tyr+Phe; 0.788, 245.065, 1+ALB+ALT+Asn+Arg+Thr+Ile; 0.788, 246.644, 1+ALB+ALT+gGT+Asn+Orn+Ile; 0.788, 245.981, 1+ALB+BUN+ALT+Asn+3MeHis+Tyr; 0.788, 244.943, 1+ALB+BUN+ALT+Asn+Phe+Trp; 0.788, 247.260, 1+ALB+ALT+NEFA+Glc+Asn+Ile; 0.788, 244.650, 1+ALB+BUN+ALT+His+Asn+Thr; 0.788, 249.682, 1+ALB+NEFA+Asn+Thr+Lys+Ile; 0.788, 245.394, 1+ALB+BUN+ALT+Asn+Orn+Trp; 0.788, 246.573, 1+ALB+BUN+AST+Glc+Asn+Ile; 0.788, 246.026, 1+ALB+BUN+ALT+Asn+Tyr+Val; 0.788, 245.311, 1+ALB+BUN+ALT+NEFA+Asn+Trp; 0.788, 248.155, 1+ALB+AST+NEFA+Asn+Lys+Ile; 0.788, 249.084, 1+ALB+NEFA+BHBA+Asn+Arg+Ile; 0.788, 245.956, 1+ALB+ALT+BHBA+Asn+Orn+Ile; 0.788, 247.347, 1+ALB+BUN+Asn+Arg+Thr+Ile; 0.788, 246.847, 1+ALB+AST+His+Asn+Orn+Ile; 0.788, 248.420, 1+ALB+NEFA+His+Asn+Orn+Ile; 0.788, 245.376, 1+ALB+BUN+ALT+Asn+3MeHis+Trp; 0.788, 245.179, 1+ALB+BUN+ALT+Asn+Arg+Trp; 0.787, 248.320, 1+ALB+ALT+Asn+Tyr+Phe+Trp; 0.787, 248.131, 1+ALB+His+Asn+Orn+Lys+Ile; 0.787, 247.712, 1+ALB+BUN+Ca+Asn+Orn+Ile; 0.787, 245.444, 1+ALB+BUN+ALT+BHBA+Asn+Thr; 0.787, 248.352, 1+ALB+BUN+Asn+Tyr+Val+Trp; 0.787, 246.940, 1+ALB+BUN+NEFA+Asn+Arg+Ile; 0.787, 246.253, 1+ALB+ALT+His+Asn+Thr+Orn; 0.787, 248.605, 1+ALB+BUN+NEFA+Asn+Tyr+Phe; 0.787, 248.731, 1+ALB+BHBA+His+Asn+Orn+Ile; 0.787, 246.638, 1+ALB+ALT+NEFA+Asn+Orn+Ile; 0.787, 248.762, 1+ALB+NEFA+Glc+Asn+Orn+Ile; 0.787, 248.149, 1+ALB+AST+Asn+Orn+Lys+Ile; 0.787, 245.310, 1+ALB+BUN+ALT+Asn+Arg+Val; 0.787, 245.528, 1+ALB+BUN+ALT+gGT+Asn+Thr; 0.787, 248.308, 1+ALB+BUN+Asn+3MeHis+Tyr+Trp; 0.787, 245.232, 1+ALB+ALT+gGT+Asn+Arg+Ile; 0.787, 248.024, 1+ALB+AST+Asn+Thr+Orn+Ile; 0.787, 245.525, 1+ALB+BUN+ALT+NEFA+Asn+Thr; 0.787, 247.787, 1+ALB+Glc+His+Asn+Arg+Ile; 0.787, 250.129, 1+ALB+NEFA+Asn+Arg+Orn+Ile; 0.787, 246.021, 1+ALB+BUN+ALT+Asn+3MeHis+Val; 0.787, 242.288, 1+ALB+BUN+ALT+Asn+Asp+Phe; 0.787, 246.392, 1+ALB+BUN+Glc+His+Asn+Orn; 0.787, 248.510, 1+ALB+AST+BHBA+Asn+Orn+Ile; 0.787, 245.521, 1+ALB+BUN+ALT+T-BIL+Asn+Thr; 0.787, 248.275, 1+ALB+BUN+Asn+Lys+Val+Trp; 0.787, 244.793, 1+ALB+BUN+ALT+NEFA+His+Asn; 0.787, 245.196, 1+ALB+BUN+ALT+Asn+Lys+Trp; 0.787, 245.611, 1+ALB+BUN+AST+Asn+Arg+Ile; 0.787, 247.065, 1+ALB+ALT+Asn+Arg+Tyr+Trp; 0.787, 245.142, 1+ALB+BUN+ALT+Glc+Asn+Lys; 0.787, 245.559, 1+ALB+BUN+ALT+gGT+Glc+Asn; 0.787, 245.559, 1+ALB+BUN+ALT+T-BIL+Glc+Asn; 0.787, 245.562, 1+ALB+BUN+ALT+NEFA+Glc+Asn; 0.787, 246.700, 1+ALB+BUN+AST+Asn+Tyr+Trp; 0.787, 245.353, 1+ALB+BUN+ALT+BHBA+Glc+Asn; 0.786, 247.393, 1+ALB+ALT+Glc+Asn+Thr+Ile; 0.786, 246.804, 1+ALB+BUN+His+Asn+Thr+Lys; 0.786, 244.459, 1+ALB+AST+ALT+Asn+Arg+Ile; 0.786, 246.643, 1+ALB+BUN+Glc+His+Asn+Lys; 0.786, 245.224, 1+ALB+Ca+ALT+Asn+Arg+Ile; 0.786, 247.184, 1+ALB+BUN+Glc+His+Asn+Ile; 0.786, 249.436, 1+ALB+NEFA+T-BIL+Asn+Lys+Ile; 0.786, 245.531, 1+ALB+BUN+ALT+T-BIL+Asn+Arg; 0.786, 248.659, 1+ALB+NEFA+Glc+Asn+Arg+Ile; 0.786, 245.455, 1+ALB+BUN+ALT+Glc+Asn+Orn; 0.786, 246.784, 1+ALB+ALT+Glc+His+Asn+Ile; 0.786, 245.977, 1+ALB+ALT+NEFA+Asn+Lys+Ile; 0.786, 250.694, 1+ALB+gGT+NEFA+Asn+Lys+Ile; 0.786, 245.700, 1+ALB+BUN+ALT+Asn+Orn+Val; 0.786, 249.721, 1+ALB+BHBA+Asn+Arg+Orn+Ile; 0.786, 244.821, 1+ALB+BUN+ALT+T-BIL+His+Asn; 0.786, 244.822, 1+ALB+BUN+ALT+gGT+His+Asn; 0.786, 245.165, 1+ALB+BUN+ALT+Asn+Arg+Phe; 0.786, 247.783, 1+ALB+ALT+NEFA+Asn+Arg+Tyr; 0.786, 246.114, 1+ALB+ALT+T-BIL+Asn+Orn+Ile; 0.786, 246.616, 1+ALB+BUN+NEFA+His+Asn+Lys; 0.786, 247.546, 1+ALB+AST+Asn+Arg+Orn+Ile; 0.786, 250.305, 1+ALB+His+Asn+Thr+Lys+Ile; 0.786, 245.702, 1+ALB+ALT+Glc+His+Asn+Orn; 0.786, 242.161, 1+ALB+BUN+ALT+Asn+Asp+Val; 0.786, 248.099, 1+ALB+AST+NEFA+Asn+Orn+Ile; 0.786, 247.361, 1+ALB+ALT+Asn+3MeHis+Arg+Tyr; 0.786, 248.970, 1+ALB+T-BIL+His+Asn+Orn+Ile; 0.786, 250.703, 1+ALB+NEFA+Asn+Thr+Orn+Ile; 0.786, 247.441, 1+ALB+ALT+BHBA+Glc+Asn+Ile; 0.786, 244.993, 1+ALB+BUN+ALT+Asn+Lys+Val; 0.786, 245.586, 1+ALB+BUN+ALT+Asn+Arg+Orn; 0.786, 242.330, 1+ALB+BUN+ALT+Asn+Asp+Lys; 0.786, 245.417, 1+ALB+ALT+Asn+Thr+Lys+Ile; 0.786, 245.591, 1+ALB+BUN+ALT+NEFA+Asn+Arg; 0.786, 245.593, 1+ALB+BUN+ALT+gGT+Asn+Arg; 0.786, 248.940, 1+ALB+gGT+His+Asn+Orn+Ile; 0.786, 247.011, 1+ALB+BUN+His+Asn+Orn+Lys; 0.786, 247.512, 1+ALB+BUN+NEFA+Glc+Asn+Ile; 0.786, 248.834, 1+ALB+ALT+Asn+3MeHis+Tyr+Phe; 0.786, 247.570, 1+ALB+AST+NEFA+Asn+Arg+Ile; 0.786, 246.070, 1+ALB+BUN+ALT+NEFA+Asn+3MeHis; 0.786, 245.265, 1+ALB+BUN+ALT+Asn+Orn+Phe; 0.786, 248.677, 1+ALB+His+Asn+Thr+Orn+Ile; 0.786, 248.473, 1+ALB+Glc+Asn+Orn+Lys+Ile; 0.785, 248.195, 1+ALB+ALT+Asn+Orn+Tyr+Phe; 0.785, 246.095, 1+ALB+BUN+ALT+NEFA+Asn+Val; 0.785, 244.682, 1+ALB+BUN+ALT+BHBA+His+Asn; 0.785, 245.266, 1+ALB+BUN+ALT+NEFA+Asn+Phe; 0.785, 245.427, 1+ALB+BUN+ALT+Asn+3MeHis+Lys; 0.785, 245.584, 1+ALB+BUN+ALT+BHBA+Asn+Arg; 0.785, 242.466, 1+ALB+BUN+ALT+NEFA+Asn+Asp; 0.785, 245.920, 1+ALB+BUN+ALT+Asn+3MeHis+Orn; 0.785, 245.436, 1+ALB+BUN+ALT+Asn+3MeHis+Arg; 0.785, 249.998, 1+ALB+NEFA+BHBA+Asn+Orn+Ile; 0.785, 247.452, 1+ALB+BUN+T-BIL+Asn+Arg+Ile; 0.785, 247.459, 1+ALB+ALT+T-BIL+Glc+Asn+Ile; 0.785, 242.463, 1+ALB+BUN+ALT+Asn+Arg+Asp; 0.785, 246.896, 1+ALB+BUN+His+Asn+Thr+Orn; 0.785, 251.941, 1+ALB+Asn+Arg+Tyr+Phe+Trp; 0.785, 245.549, 1+ALB+BUN+ALT+gGT+Asn+Lys; 0.785, 250.891, 1+ALB+BHBA+His+Asn+Lys+Ile; 0.785, 247.586, 1+ALB+ALT+NEFA+Glc+His+Asn; 0.785, 248.759, 1+ALB+AST+T-BIL+Asn+Orn+Ile; 0.785, 245.444, 1+ALB+BUN+Ca+ALT+Asn+Thr; 0.785, 251.817, 1+ALB+Asn+Arg+Orn+Tyr+Trp; 0.785, 245.103, 1+ALB+BUN+ALT+Asn+3MeHis+Phe; 0.785, 251.437, 1+ALB+NEFA+Asn+Arg+Tyr+Trp; 0.785, 250.227, 1+ALB+BHBA+Asn+Orn+Lys+Ile; 0.785, 246.545, 1+ALB+Ca+ALT+Asn+Orn+Ile; 0.785, 246.135, 1+ALB+BUN+ALT+gGT+NEFA+Asn; 0.785, 245.165, 1+ALB+BUN+ALT+

Asn+Lys+Phe; 0.785, 245.428, 1+ALB+BUN+Asn+Asp+Lys+Tyr; 0.785, 246.099, 1+ALB+BUN+ALT+gGT+BHBA+Asn; 0.785, 245.577, 1+ALB+BUN+NEFA+Asn+Asp+Tyr; 0.785, 247.390, 1+ALB+BUN+gGT+Asn+Arg+Ile; 0.785, 245.627, 1+ALB+AST+ALT+Asn+Orn+Ile; 0.785, 247.426, 1+ALB+ALT+gGT+Glc+Asn+Ile; 0.785, 245.520, 1+ALB+BUN+Ca+ALT+Glc+Asn; 0.785, 250.399, 1+ALB+Ca+NEFA+Asn+Lys+Ile; 0.785, 245.982, 1+ALB+BUN+ALT+gGT+Asn+Orn; 0.785, 246.110, 1+ALB+BUN+ALT+gGT+T-BIL+Asn; 0.785, 248.560, 1+ALB+NEFA+Glc+His+Asn+Orn; 0.785, 246.104, 1+ALB+ALT+gGT+Asn+Lys+Ile; 0.785, 248.613, 1+ALB+AST+gGT+Asn+Orn+Ile; 0.785, 245.930, 1+ALB+BUN+ALT+T-BIL+Asn+Orn; 0.785, 250.882, 1+ALB+gGT+His+Asn+Lys+Ile; 0.785, 244.943, 1+ALB+ALT+Asn+Asp+Tyr+Trp; 0.785, 245.209, 1+ALB+BUN+AST+ALT+Asn+Thr; 0.785, 245.561, 1+ALB+BUN+ALT+NEFA+Asn+Lys; 0.785, 246.055, 1+ALB+BUN+ALT+NEFA+T-BIL+Asn; 0.785, 245.961, 1+ALB+ALT+BHBA+Asn+Lys+Ile; 0.784, 246.895, 1+ALB+AST+ALT+Glc+Asn+Ile; 0.784, 248.255, 1+ALB+BUN+Glc+Asn+Thr+Ile; 0.784, 251.926, 1+ALB+Asn+Arg+Lys+Tyr+Trp; 0.784, 244.958, 1+ALB+BUN+AST+ALT+Asn+Trp; 0.784, 246.982, 1+ALB+BUN+T-BIL+His+Asn+Lys; 0.784, 244.708, 1+ALB+BUN+Ca+ALT+His+Asn; 0.784, 247.862, 1+ALB+ALT+Asn+Arg+Tyr+Val; 0.784, 245.979, 1+ALB+BUN+ALT+NEFA+Asn+Orn; 0.784, 249.304, 1+ALB+AST+His+Asn+Lys+Ile; 0.784, 246.092, 1+ALB+BUN+ALT+NEFA+BHBA+Asn; 0.784, 249.075, 1+ALB+BUN+NEFA+T-BIL+Asn+Ile; 0.784, 245.548, 1+ALB+BUN+ALT+Asn+Orn+Lys; 0.784, 247.739, 1+ALB+ALT+Glc+His+Asn+Thr; 0.784, 242.373, 1+ALB+BUN+ALT+Asn+Asp+Orn; 0.784, 245.545, 1+ALB+BUN+ALT+T-BIL+Asn+Lys; 0.784, 247.286, 1+ALB+BUN+BHBA+His+Asn+Lys; 0.784, 250.623, 1+ALB+NEFA+Asn+Arg+Thr+Ile; 0.784, 246.788, 1+ALB+ALT+NEFA+His+Asn+Orn; 0.784, 245.242, 1+ALB+BUN+AST+ALT+Glc+Asn; 0.784, 245.558, 1+ALB+ALT+Glc+His+Asn+Arg; 0.784, 247.476, 1+ALB+BUN+T-BIL+Glc+His+Asn; 0.784, 247.788, 1+ALB+ALT+Asn+Arg+Orn+Tyr; 0.784, 245.068, 1+ALB+BUN+AST+ALT+Asn+Phe; 0.784, 246.893, 1+ALB+BUN+NEFA+His+Asn+Orn; 0.784, 248.466, 1+ALB+Glc+Asn+Arg+Lys+Ile; 0.784, 247.135, 1+ALB+BUN+His+Asn+Arg+Lys; 0.784, 248.888, 1+ALB+NEFA+T-BIL+Asn+Arg+Ile; 0.784, 250.456, 1+ALB+T-BIL+His+Asn+Lys+Ile; 0.784, 249.763, 1+ALB+T-BIL+His+Asn+Arg+Ile; 0.784, 249.896, 1+ALB+BHBA+Asn+Arg+Lys+Ile; 0.784, 245.968, 1+ALB+BUN+ALT+BHBA+Asn+Orn; 0.784, 246.064, 1+ALB+ALT+T-BIL+Asn+Lys+Ile; 0.784, 249.355, 1+ALB+BHBA+Glc+Asn+Orn+Ile; 0.784, 248.516, 1+ALB+Glc+Asn+Arg+Orn+Ile; 0.784, 249.688, 1+ALB+BHBA+His+Asn+Arg+Ile; 0.784, 251.968, 1+ALB+Asn+Arg+Tyr+Val+Trp; 0.784, 247.872, 1+ALB+BUN+T-BIL+Glc+Asn+Ile; 0.784, 248.981, 1+ALB+Glc+Asn+Thr+Orn+Ile; 0.784, 244.220, 1+ALB+BUN+Asn+3MeHis+Asp+Tyr; 0.784, 247.161, 1+ALB+BUN+AST+NEFA+Asn+Ile; 0.784, 247.437, 1+ALB+Ca+ALT+Glc+Asn+Ile; 0.784, 248.414, 1+ALB+ALT+Asn+Orn+Tyr+Trp; 0.784, 247.169, 1+ALB+BUN+T-BIL+His+Asn+Orn; 0.784, 249.648, 1+ALB+AST+T-BIL+Asn+Lys+Ile; 0.784, 247.869, 1+ALB+AST+Asn+Arg+Lys+Ile; 0.784, 248.851, 1+ALB+ALT+NEFA+BHBA+Asn+Ile; 0.784, 246.825, 1+ALB+ALT+BHBA+His+Asn+Orn; 0.784, 246.829, 1+ALB+ALT+gGT+His+Asn+Orn; 0.784, 248.990, 1+ALB+ALT+Asn+3MeHis+Tyr+Trp; 0.784, 249.441, 1+ALB+Glc+Asn+Thr+Lys+Ile; 0.784, 245.512, 1+ALB+BUN+ALT+BHBA+Asn+Lys; 0.784, 250.043, 1+ALB+Asn+Arg+Thr+Orn+Ile; 0.784, 247.396, 1+ALB+BUN+Ca+Asn+Arg+Ile; 0.784, 251.475, 1+ALB+T-BIL+BHBA+Asn+Lys+Ile; 0.784, 245.710, 1+ALB+BUN+AST+ALT+Asn+Tyr; 0.784, 246.331, 1+ALB+BUN+Asn+Asp+Tyr+Val; 0.784, 249.184, 1+ALB+AST+Asn+Thr+Lys+Ile; 0.784, 250.599, 1+ALB+Ca+His+Asn+Lys+Ile; 0.784, 245.979, 1+ALB+BUN+ALT+T-BIL+BHBA+Asn; 0.784, 249.602, 1+ALB+T-BIL+Glc+Asn+Lys+Ile; 0.784, 245.054, 1+ALB+ALT+Asn+Arg+Asp+Tyr; 0.784, 248.791, 1+ALB+Ca+His+Asn+Orn+Ile; 0.784, 249.337, 1+ALB+BUN+Asn+Lys+Tyr+Phe; 0.784, 247.714, 1+ALB+ALT+Asn+Arg+Lys+Tyr; 0.784, 248.883, 1+ALB+BUN+NEFA+Asn+Lys+Tyr; 0.784, 249.130, 1+ALB+BUN+NEFA+BHBA+Asn+Ile; 0.784, 250.301, 1+ALB+T-BIL+Asn+Arg+Lys+Ile; 0.784, 250.071, 1+ALB+AST+BHBA+Asn+Lys+Ile; 0.783, 244.645, 1+ALB+BUN+AST+ALT+His+Asn; 0.783, 245.421, 1+ALB+BUN+ALT+Asn+Arg+Lys; 0.783, 253.020, 1+ALB+NEFA+Asn+Tyr+Phe+Trp; 0.783, 245.801, 1+ALB+BUN+Asn+Asp+Val+Trp; 0.783, 249.830, 1+ALB+Asn+Arg+Orn+Lys+Ile; 0.783, 248.214, 1+ALB+AST+Glc+Asn+Lys+Ile; 0.783, 249.210, 1+ALB+AST+Asn+Arg+Tyr+Trp; 0.783, 248.995, 1+ALB+BUN+NEFA+Asn+Thr+Ile; 0.783, 248.641, 1+ALB+BUN+Asn+Val+Phe+Trp; 0.783, 250.234, 1+ALB+NEFA+His+Asn+Thr+Lys; 0.783, 249.596, 1+ALB+NEFA+Glc+His+Asn+Lys; 0.783, 247.284, 1+ALB+BUN+NEFA+Glc+His+Asn; 0.783, 247.374, 1+ALB+BUN+gGT+His+Asn+Orn; 0.783, 247.557, 1+ALB+BUN+gGT+His+Asn+Lys; 0.783, 246.285, 1+ALB+BUN+AST+His+Asn+Orn; 0.783, 249.384, 1+ALB+T-BIL+Glc+Asn+Orn+Ile; 0.783, 247.636, 1+ALB+AST+His+Asn+Arg+Ile; 0.783, 245.533, 1+ALB+BUN+Ca+ALT+Asn+Arg; 0.783, 245.646, 1+ALB+AST+ALT+Asn+Lys+Ile; 0.783, 247.383, 1+ALB+AST+Glc+Asn+Arg+Ile; 0.783, 246.768, 1+ALB+ALT+T-BIL+His+Asn+Orn; 0.783, 248.468, 1+ALB+BUN+Asn+3MeHis+Val+Trp; 0.783, 246.559, 1+ALB+ALT+Glc+His+Asn+Lys; 0.783, 247.431, 1+ALB+BUN+AST+His+Asn+Ile; 0.783, 248.114, 1+ALB+ALT+NEFA+T-BIL+Asn+Ile; 0.783, 245.886, 1+ALB+ALT+His+Asn+Arg+Orn; 0.783, 246.281, 1+ALB+BUN+Asn+Asp+Orn+Tyr; 0.783, 248.570, 1+ALB+Ca+AST+Asn+Orn+Ile; 0.783, 249.595, 1+ALB+Asn+Thr+Orn+Lys+Ile; 0.783, 248.613, 1+ALB+BUN+Asn+Orn+Val+Trp; 0.783, 252.623, 1+ALB+Asn+Orn+Tyr+Phe+Trp; 0.783, 248.108, 1+ALB+BUN+gGT+Glc+Asn+Ile; 0.783, 251.213, 1+ALB+BHBA+Asn+Thr+Lys+Ile; 0.783, 248.233, 1+ALB+BUN+Ca+Glc+Asn+Ile; 0.783, 250.633, 1+ALB+BHBA+Asn+Thr+Orn+Ile; 0.783, 251.222, 1+ALB+gGT+Asn+Thr+Lys+Ile; 0.783, 242.177, 1+ALB+BUN+AST+ALT+Asn+Asp; 0.783, 248.012, 1+ALB+BUN+NEFA+His+Asn+Ile; 0.783, 249.558, 1+ALB+BUN+T-BIL+BHBA+Asn+Ile; 0.783, 249.810, 1+ALB+His+Asn+Arg+Thr+Ile; 0.783, 249.931, 1+ALB+NEFA+T-BIL+Asn+Orn+Ile; 0.783, 246.709, 1+ALB+BUN+AST+His+Asn+Lys; 0.783, 246.029, 1+ALB+BUN+Ca+ALT+gGT+Asn; 0.783, 246.080, 1+ALB+ALT+His+Asn+Arg+Thr; 0.783, 249.199, 1+ALB+BUN+Asn+3MeHis+Tyr+Phe; 0.783, 248.804, 1+ALB+BUN+NEFA+Asn+Val+Trp; 0.783, 249.159, 1+ALB+BUN+gGT+NEFA+Asn+Ile; 0.783, 249.621, 1+ALB+Asn+Arg+Thr+Lys+Ile; 0.783, 245.256, 1+ALB+BUN+AST+ALT+Asn+Arg; 0.783, 249.907, 1+ALB+AST+Asn+Orn+Tyr+Trp; 0.783, 245.992, 1+ALB+Ca+ALT+Asn+Lys+Ile; 0.783, 245.290, 1+ALB+BUN+AST+ALT+Asn+Lys; 0.783, 248.030, 1+ALB+BUN+AST+gGT+Asn+Ile; 0.783, 250.765, 1+ALB+gGT+NEFA+Asn+Arg+Ile; 0.782, 246.029, 1+ALB+BUN+Ca+ALT+NEFA+Asn; 0.782, 245.465, 1+ALB+BUN+Ca+ALT+Asn+Lys; 0.782, 250.420, 1+ALB+NEFA+Glc+His+Asn+Ile; 0.782, 246.606, 1+ALB+ALT+His+Asn+Orn+Lys; 0.782, 247.845, 1+ALB+ALT+T-BIL+Glc+His+Asn; 0.782, 245.743, 1+ALB+BUN+AST+ALT+Asn+3MeHis; 0.782, 246.006, 1+ALB+BUN+Ca+ALT+T-BIL+Asn; 0.782, 245.783, 1+ALB+BUN+AST+ALT+Asn+Val; 0.782, 248.448, 1+ALB+ALT+NEFA+His+Asn+Ile; 0.782, 249.084, 1+ALB+ALT+Asn+Tyr+Val+Trp; 0.782, 250.984, 1+ALB+T-BIL+BHBA+Asn+Orn+Ile; 0.782, 249.898, 1+ALB+AST+gGT+Asn+Lys+Ile; 0.782, 247.281, 1+ALB+BUN+Ca+His+Asn+Orn; 0.782, 249.084, 1+ALB+ALT+NEFA+Asn+Tyr+Trp; 0.782, 249.111, 1+ALB+AST+NEFA+Glc+Asn+Ile; 0.782, 248.725, 1+ALB+ALT+NEFA+Glc+Asn+Thr; 0.782, 249.381, 1+ALB+BUN+Asn+Orn+Tyr+Phe; 0.782, 246.176, 1+ALB+BUN+Asn+Arg+Asp+Tyr; 0.782, 246.252, 1+ALB+ALT+NEFA+His+Asn+Arg; 0.782, 246.885, 1+ALB+BUN+NEFA+His+Asn+Arg; 0.782, 247.640, 1+ALB+BUN+AST+T-BIL+Asn+Ile; 0.782, 252.571, 1+ALB+NEFA+Asn+Lys+Tyr+Trp; 0.782, 247.822, 1+ALB+ALT+gGT+Glc+His+Asn; 0.782, 248.784, 1+ALB+BUN+Asn+3MeHis+Lys+Val; 0.782, 248.280, 1+ALB+AST+NEFA+His+Asn+Orn; 0.782, 250.505, 1+ALB+Ca+Asn+Orn+Lys+Ile; 0.782, 249.305, 1+ALB+ALT+Asn+Tyr+Val+Phe; 0.782, 249.098, 1+ALB+BUN+NEFA+Glc+Asn+Thr; 0.782, 248.684, 1+ALB+BUN+Asn+Arg+Val+Trp; 0.782, 246.839, 1+ALB+BUN+AST+Glc+His+Asn; 0.782, 246.752, 1+ALB+Ca+ALT+His+Asn+Orn; 0.782, 248.893, 1+ALB+BUN+Ca+NEFA+Asn+Ile; 0.782, 246.382, 1+ALB+ALT+BHBA+His+Asn+Arg; 0.782, 246.862, 1+ALB+ALT+His+Asn+Thr+Lys; 0.782, 248.501, 1+ALB+ALT+Asn+Lys+Tyr+Trp; 0.782, 247.153, 1+ALB+AST+ALT+Asn+Arg+Tyr; 0.782, 245.891, 1+ALB+BUN+Ca+ALT+Asn+Orn; 0.782, 245.970, 1+ALB+BUN+Ca+ALT+BHBA+Asn; 0.782, 248.994, 1+ALB+BUN+NEFA+Asn+Arg+Tyr; 0.782, 245.618, 1+ALB+BUN+AST+ALT+Asn+Orn; 0.782, 247.059, 1+ALB+BUN+His+Asn+Arg+Orn; 0.782, 252.922, 1+ALB+NEFA+Asn+Orn+Tyr+Phe; 0.782, 247.556, 1+ALB+ALT+BHBA+Glc+His+Asn; 0.782, 250.705, 1+ALB+T-BIL+Asn+Orn+Lys+Ile; 0.782, 248.908, 1+ALB+ALT+NEFA+Asn+Thr+Ile; 0.782, 249.552, 1+ALB+NEFA+His+Asn+Thr+Orn; 0.782, 247.978, 1+ALB+BUN+Glc+His+Asn+Thr; 0.782, 248.140, 1+ALB+AST+ALT+Asn+Tyr+Trp; 0.782, 250.971, 1+ALB+T-BIL+Asn+Thr+Lys+Ile; 0.782, 252.168, 1+ALB+NEFA+Asn+Arg+Tyr+Phe; 0.782, 253.253, 1+ALB+NEFA+Asn+Lys+Tyr+Phe; 0.782, 249.002, 1+ALB+ALT+NEFA+T-BIL+Asn+Thr; 0.782, 253.243, 1+ALB+Asn+Lys+Tyr+Phe+Trp; 0.782, 245.800, 1+ALB+BUN+AST+ALT+NEFA+Asn; 0.782, 245.821, 1+ALB+BUN+AST+ALT+T-BIL+Asn; 0.782, 252.478, 1+ALB+NEFA+Asn+Orn+Tyr+Trp; 0.782, 252.633, 1+ALB+Asn+Orn+Tyr+Val+Trp; 0.782, 245.761, 1+ALB+BUN+AST+ALT+gGT+Asn; 0.782, 250.027, 1+ALB+gGT+Glc+Asn+Lys+Ile; 0.781, 253.213, 1+ALB+Asn+Lys+Tyr+Val+Trp; 0.781, 247.368, 1+ALB+BUN+AST+Asn+Thr+Lys; 0.781, 247.501, 1+ALB+BUN+His+Asn+Arg+Thr; 0.781, 251.015, 1+ALB+gGT+Asn+Thr+Orn+Ile; 0.781, 250.487, 1+ALB+gGT+Asn+Arg+Orn+Ile; 0.781, 248.126, 1+ALB+BUN+NEFA+Asn+Thr+Lys; 0.781, 246.345, 1+ALB+ALT+T-BIL+His+Asn+Arg; 0.781, 249.194, 1+ALB+BUN+Asn+Arg+Tyr+Phe; 0.781, 249.625, 1+ALB+BUN+BHBA+Asn+Thr+Ile; 0.781, 249.866, 1+ALB+BHBA+Glc+Asn+Arg+Ile; 0.781, 249.380, 1+ALB+Ca+Glc+Asn+Orn+Ile; 0.781, 247.610, 1+ALB+ALT+Glc+Asn+Thr+Orn; 0.781, 248.914, 1+ALB+ALT+T-BIL+Asn+Thr+Ile; 0.781, 245.393, 1+ALB+ALT+Asn+Asp+Tyr+Phe; 0.781, 249.334, 1+ALB+BUN+Asn+Arg+Lys+Tyr; 0.781, 249.416, 1+ALB+Asn+Asp+Orn+Tyr+Trp; 0.781, 249.036, 1+ALB+Asn+Arg+Asp+Tyr+Trp; 0.781, 250.694, 1+ALB+gGT+Asn+Orn+Lys+Ile; 0.781, 249.419, 1+ALB+BUN+Ca+Asn+Thr+Ile; 0.781, 251.113, 1+ALB+Ca+BHBA+Asn+Orn+Ile; 0.781, 250.192, 1+ALB+Ca+Asn+Arg+Lys+Ile; 0.781, 248.949, 1+ALB+Glc+His+Asn+Thr+Orn; 0.781, 249.534, 1+ALB+BUN+gGT+T-BIL+Asn+Ile; 0.781, 249.311, 1+ALB+BUN+Asn+Lys+Phe+Trp; 0.781, 251.384, 1+ALB+gGT+NEFA+Asn+Orn+Ile; 0.781, 245.203, 1+ALB+BUN+Asn+3MeHis+Asp+Trp; 0.781, 250.779, 1+ALB+Ca+NEFA+Asn+Arg+Ile; 0.781, 251.046, 1+ALB+T-BIL+Asn+Thr+Orn+Ile; 0.781, 245.747, 1+ALB+BUN+AST+ALT+BHBA+Asn; 0.781, 247.830, 1+ALB+BUN+AST+Asn+Thr+Ile; 0.781, 250.248, 1+ALB+gGT+Asn+Arg+Lys+Ile; 0.781, 250.854, 1+ALB+T-BIL+BHBA+Asn+Arg+Ile; 0.781, 248.032, 1+ALB+ALT+NEFA+Asn+Thr+Lys; 0.781, 249.380, 1+ALB+BUN+T-BIL+Asn+Thr+Ile; 0.781, 247.863, 1+ALB+BUN+gGT+Glc+His+Asn; 0.781, 246.921, 1+ALB+BUN+Glc+His+Asn+Arg; 0.781, 247.959, 1+BCAA+Lys+Phe+ALT+ALB+BUN; 0.781, 249.074, 1+ALB+BUN+Asn+3MeHis+Lys+Tyr; 0.781, 250.959, 1+ALB+Asn+3MeHis+Arg+Tyr+Trp; 0.781, 248.348, 1+ALB+AST+ALT+Asn+Thr+Ile; 0.781, 249.079, 1+ALB+NEFA+Glc+His+Asn+Arg; 0.781, 246.670, 1+ALB+BUN+Asn+Asp+Lys+Trp; 0.781, 249.607, 1+ALB+gGT+His+Asn+Arg+Ile; 0.781, 250.564, 1+ALB+T-BIL+Asn+Arg+Orn+Ile; 0.781, 249.119, 1+ALB+ALT+gGT+NEFA+Asn+Ile; 0.781, 251.270, 1+ALB+NEFA+Glc+His+Asn+Thr; 0.781, 249.688, 1+ALB+BUN+Asn+Orn+Lys+Tyr; 0.781, 249.301, 1+ALB+BUN+Asn+Orn+Lys+Trp; 0.781, 247.306, 1+ALB+BUN+BHBA+His+Asn+Orn; 0.781, 249.275, 1+ALB+gGT+Glc+Asn+Orn+Ile; 0.781, 248.713, 1+ALB+AST+BHBA+Asn+Arg+Ile; 0.781, 247.833, 1+ALB+Ca+ALT+Glc+His+Asn; 0.781, 245.756, 1+ALB+ALT+Asn+Asp+Orn+Tyr; 0.781, 250.739, 1+ALB+AST+Asn+Lys+Tyr+Trp; 0.781, 250.020, 1+ALB+Ca+Glc+Asn+Lys+Ile; 0.781, 252.681, 1+ALB+Asn+Orn+Lys+Tyr+Trp; 0.781, 248.269, 1+ALB+ALT+NEFA+Asn+Thr+Orn; 0.781, 244.931, 1+ALB+ALT+Asn+3MeHis+Asp+Tyr; 0.781, 248.117, 1+ALB+BUN+BHBA+Glc+Asn+Ile; 0.781, 248.069, 1+ALB+AST+Glc+His+Asn+Orn; 0.781, 248.414, 1+ALB+BUN+T-BIL+His+Asn+Ile; 0.781, 248.829, 1+ALB+BUN+His+Asn+Thr+Ile; 0.781, 246.347, 1+ALB+Ca+ALT+His+Asn+Arg; 0.781, 248.991, 1+ALB+ALT+gGT+Asn+Thr+Ile; 0.781, 248.795, 1+ALB+AST+T-BIL+Asn+Arg+Ile; 0.781, 248.270, 1+ALB+ALT+gGT+Asn+Thr+Orn; 0.781, 251.415, 1+ALB+T-BIL+His+Asn+Thr+Lys; 0.781, 249.175, 1+ALB+BUN+NEFA+Asn+Lys+Trp; 0.781, 247.099, 1+ALB+BUN+AST+Asn+Val+Trp; 0.781, 250.507, 1+ALB+Ca+Asn+Arg+Orn+Ile; 0.781, 246.355, 1+ALB+ALT+gGT+His+Asn+Arg; 0.781, 251.213, 1+ALB+Ca+NEFA+Asn+Orn+Ile; 0.781, 252.219, 1+ALB+Asn+3MeHis+Orn+Tyr+Trp; 0.781, 246.489, 1+ALB+BUN+Asn+Arg+Asp+Trp; 0.781, 248.083, 1+ALB+BUN+AST+Asn+Arg+Tyr; 0.780, 248.847, 1+ALB+BUN+Asn+3MeHis+Lys+Trp; 0.780, 250.056, 1+ALB+BHBA+Glc+Asn+Lys+Ile; 0.780, 249.445, 1+ALB+Asn+Asp+Lys+Tyr+Trp; 0.780, 248.369, 1+ALB+BUN+AST+Asn+Lys+Tyr; 0.780, 244.597, 1+ALB+BUN+AST+Asn+Asp+Tyr; 0.780, 250.716, 1+ALB+Glc+His+Asn+Thr+Lys; 0.780, 247.790, 1+ALB+ALT+Asn+Thr+Orn+Lys; 0.780, 249.135, 1+ALB+ALT+

NEFA+Asn+Orn+Tyr; 0.780, 246.585, 1+ALB+BUN+NEFA+Asn+Asp+Trp; 0.780, 246.630, 1+ALB+BUN+Asn+Asp+Phe+Trp; 0.780, 247.904, 1+ALB+BUN+AST+NEFA+Asn+Thr; 0. 780, 251.141, 1+ALB+gGT+BHBA+Asn+Orn+Ile; 0.780, 247.391, 1+ALB+BUN+Ca+His+Asn+Lys; 0.780, 251.272, 1+ALB+NEFA+T-BIL+Glc+His+A sn; 0.780, 249.304, 1+ALB+NEFA+Asn+Asp+Tyr+Trp; 0.780, 249.788, 1+ALB+T-BIL+Glc+Asn+Arg+Ile; 0.780, 248.286, 1+ALB+AST+ALT+NEFA+Asn+Ile; 0.780, 248.442, 1+ALB+AST+His+Asn+Thr+Orn; 0.780, 250. 377, 1+ALB+AST+NEFA+Asn+Tyr+Trp; 0.780, 249.096, 1+ALB+ALT+gGT+BHBA+Asn+Ile; 0.780, 249.762, 1+ALB+BUN+gGT+BHBA+Asn+Ile; 0.780, 247.370, 1+ALB+BUN+T-BIL+His+Asn+Arg; 0.780, 248.577, 1+ALB+ALT+T-BIL+His+Asn+Ile; 0.780, 248.860, 1+ALB+ALT+NEFA+T-BIL+Glc+A sn; 0.780, 248.950, 1+ALB+ALT+BHBA+Asn+Thr+Ile; 0.780, 248.249, 1+ALB+ALT+BHBA+Asn+Thr+Orn; 0.780, 249.303, 1+ALB+BUN+Asn+Arg+L ys+Trp; 0.780, 248.022, 1+ALB+BUN+AST+BHBA+Asn+Ile; 0.780, 248.5 36, 1+ALB+ALT+His+Asn+Thr+Ile; 0.780, 249.120, 1+ALB+BUN+NEFA+A sn+Thr+Orn; 0.780, 252.016, 1+ALB+gGT+T-BIL+Asn+Lys+Ile; 0.780, 248.372, 1+ALB+BUN+NEFA+His+Asn+Thr; 0.780, 249.217, 1+ALB+T-BI L+Glc+His+Asn+Orn; 0.780, 247.114, 1+ALB+BUN+AST+NEFA+His+Asn; 0.780, 249.466, 1+ALB+BUN+Ca+gGT+Asn+Ile; 0.780, 248.982, 1+ALB+Ca+ALT+NEFA+Asn+Ile; 0.780, 249.073, 1+ALB+ALT+T-BIL+BHBA+Asn+Ile; 0.780, 249.700, 1+ALB+BUN+Asn+Lys+Tyr+Val; 0.780, 248.439, 1+ALB+ALT+NEFA+T-BIL+His+Asn; 0.780, 249.919, 1+ALB+NEFA+His+As n+Orn+Lys; 0.780, 249.779, 1+ALB+Glc+Asn+Arg+Thr+Ile; 0.780, 249. 796, 1+ALB+Ca+AST+Asn+Lys+Ile; 0.780, 248.017, 1+ALB+BUN+Ca+Glc+His+Asn; 0.780, 248.956, 1+ALB+ALT+Asn+3MeHis+Orn+Tyr; 0.780, 2 49.398, 1+ALB+gGT+Glc+His+Asn+Orn; 0.780, 249.069, 1+ALB+BUN+NE FA+Asn+Lys+Val; 0.780, 249.002, 1+ALB+BUN+Asn+3MeHis+Phe+Trp; 0. 780, 245.324, 1+ALB+BUN+Asn+3MeHis+Asp+Lys; 0.780, 248.635, 1+AL B+AST+Asn+Arg+Thr+Ile; 0.780, 247.763, 1+ALB+BUN+Ca+AST+Asn+Il e; 0.780, 248.612, 1+ALB+BUN+Ca+His+Asn+Ile; 0.780, 248.708, 1+AL B+ALT+BHBA+Glc+Asn+Thr; 0.780, 248.785, 1+ALB+ALT+NEFA+His+Asn+Thr; 0.780, 249.992, 1+ALB+BUN+Asn+Tyr+Val+Phe; 0.780, 246.141, 1+ALB+ALT+His+Asn+Arg+Lys; 0.780, 249.740, 1+ALB+NEFA+T-BIL+Hi s+Asn+Orn; 0.780, 249.745, 1+ALB+Asn+Asp+Tyr+Phe+Trp; 0.780, 246. 922, 1+ALB+BUN+Asn+Asp+Lys+Val; 0.780, 247.290, 1+ALB+ALT+NEFA+His+Asn+Lys; 0.780, 248.889, 1+ALB+Ca+ALT+Asn+Thr+Ile; 0.780, 24 8.601, 1+ALB+ALT+gGT+His+Asn+Ile; 0.780, 248.409, 1+ALB+BUN+T-B IL+Asn+Thr+Lys; 0.780, 248.769, 1+ALB+ALT+Asn+Lys+Tyr+Phe; 0.78 0, 251.441, 1+ALB+NEFA+T-BIL+Glc+Asn+Ile; 0.780, 245.899, 1+ALB+ALT+Asn+3MeHis+Asp+Phe; 0.780, 248.852, 1+ALB+AST+ALT+Asn+Tyr+Phe; 0.780, 249.568, 1+ALB+BUN+gGT+Asn+Thr+Ile; 0.780, 249.675, 1+ALB+BUN+Asn+Arg+Orn+Tyr; 0.780, 250.066, 1+ALB+NEFA+BHBA+His+Asn+Orn; 0.780, 246.351, 1+ALB+AST+ALT+His+Asn+Orn; 0.780, 248.4 95, 1+ALB+AST+ALT+gGT+Asn+Ile; 0.780, 246.509, 1+ALB+BUN+Asn+As p+Orn+Trp; 0.780, 247.469, 1+ALB+ALT+Glc+Asn+Arg+Thr; 0.780, 247. 647, 1+ALB+ALT+Glc+Asn+Thr+Lys; 0.780, 248.086, 1+ALB+ALT+T-BIL+Asn+Thr+Orn; 0.780, 245.819, 1+ALB+ALT+Asn+3MeHis+Asp+Trp; 0.7 80, 247.960, 1+BCAA+Trp+Phe+ALT+ALB+BUN; 0.780, 249.435, 1+ALB+A ST+NEFA+Glc+His+Asn; 0.780, 246.622, 1+ALB+BUN+AST+His+Asn+Ar g; 0.780, 248.845, 1+ALB+ALT+T-BIL+Glc+Asn+Thr; 0.780, 246.061, 1+ALB+ALT+NEFA+Asn+Asp+Tyr; 0.780, 249.232, 1+ALB+Glc+His+Asn+A rg+Orn; 0.780, 249.496, 1+ALB+Glc+His+Asn+Orn+Lys; 0.780, 252.09 9, 1+ALB+gGT+BHBA+Asn+Lys+Ile; 0.780, 248.472, 1+ALB+BUN+AST+As n+Orn+Tyr; 0.780, 248.148, 1+ALB+ALT+BHBA+Asn+Thr+Lys; 0.780, 24 8.897, 1+ALB+BUN+Glc+Asn+Thr+Orn; 0.780, 248.455, 1+ALB+BUN+AST+Asn+Tyr+Phe; 0.780, 249.108, 1+ALB+BUN+NEFA+Asn+3MeHis+Trp; 0. 780, 249.357, 1+ALB+BUN+NEFA+Asn+Orn+Trp; 0.780, 248.526, 1+ALB+AST+ALT+T-BIL+Asn+Ile; 0.780, 249.744, 1+ALB+Ca+His+Asn+Arg+Il e; 0.780, 248.892, 1+ALB+BUN+Asn+3MeHis+Arg+Tyr; 0.780, 249.307, 1+ALB+BUN+NEFA+Asn+Phe+Trp; 0.780, 248.866, 1+ALB+AST+gGT+Asn+Arg+Ile; 0.779, 249.870, 1+ALB+Ca+Glc+Asn+Arg+Ile; 0.779, 250.15 1, 1+ALB+T-BIL+His+Asn+Thr+Orn; 0.779, 247.915, 1+ALB+BUN+AST+G lc+Asn+Thr; 0.779, 248.535, 1+ALB+BUN+NEFA+T-BIL+His+Asn; 0.779, 249.742, 1+ALB+BUN+NEFA+Asn+Orn+Tyr; 0.779, 248.518, 1+ALB+AST+ALT+BHBA+Asn+Ile; 0.779, 250.928, 1+ALB+Ca+Asn+Thr+Orn+Ile; 0.7 79, 249.334, 1+ALB+BUN+Ca+T-BIL+Asn+Ile; 0.779, 248.594, 1+ALB+A LT+BHBA+His+Asn+Ile; 0.779, 248.710, 1+ALB+ALT+Asn+Orn+Val+Tr p; 0.779, 247.606, 1+ALB+BUN+BHBA+His+Asn+Arg; 0.779, 248.775, 1+ALB+BUN+gGT+His+Asn+Ile; 0.779, 251.012, 1+ALB+AST+Asn+Tyr+Phe+Trp; 0.779, 249.437, 1+ALB+AST+NEFA+His+Asn+Lys; 0.779, 252.964, 1+ALB+Asn+3MeHis+Orn+Tyr+Phe; 0.779, 249.840, 1+ALB+BUN+NEFA+T-BIL+Asn+Thr; 0.779, 249.065, 1+ALB+ALT+Asn+Val+Phe+Trp; 0.779, 252.260, 1+ALB+NEFA+Asn+Arg+Lys+Tyr; 0.779, 249.082, 1+ALB+BUN+Asn+3MeHis+Orn+Trp; 0.779, 249.076, 1+ALB+ALT+gGT+T-BIL+Asn+Il e; 0.779, 250.367, 1+ALB+NEFA+Asn+Asp+Tyr+Phe; 0.779, 249.514, 1+ALB+gGT+Glc+Asn+Arg+Ile; 0.779, 251.771, 1+ALB+Ca+T-BIL+Asn+Ly s+Ile; 0.779, 248.166, 1+ALB+ALT+gGT+Asn+Thr+Lys; 0.779, 251.885, 1+ALB+NEFA+BHBA+Glc+Asn+Ile; 0.779, 250.200, 1+ALB+gGT+NEFA+Hi s+Asn+Orn; 0.779, 246.027, 1+ALB+AST+ALT+His+Asn+Arg; 0.779, 245. 702, 1+ALB+BUN+Ca+AST+ALT+Asn; 0.779, 251.019, 1+ALB+Ca+Asn+Thr+Lys+Ile; 0.779, 248.972, 1+ALB+ALT+NEFA+BHBA+His+Asn; 0.779, 24 9.754, 1+ALB+Asn+Asp+Tyr+Val+Trp; 0.779, 249.800, 1+ALB+NEFA+As n+Asp+Lys+Tyr; 0.779, 251.162, 1+ALB+BHBA+Asn+Arg+Thr+Ile; 0.77 9, 247.567, 1+ALB+BUN+AST+NEFA+Asn+Trp; 0.779, 249.295, 1+ALB+AS T+His+Asn+Orn+Lys; 0.779, 250.252, 1+ALB+BHBA+His+Asn+Thr+Orn; 0.779, 248.347, 1+ALB+ALT+Asn+Arg+Val+Trp; 0.779, 249.113, 1+ALB+ALT+Asn+Orn+Tyr+Val; 0.779, 247.962, 1+Ala+Trp+Phe+ALT+ALB+BU N; 0.779, 249.634, 1+ALB+BUN+NEFA+Asn+Val+Phe; 0.779, 250.460, 1+ALB+AST+His+Asn+Thr+Lys; 0.779, 247.010, 1+ALB+BUN+NEFA+Asn+As p+Lys; 0.779, 247.694, 1+ALB+BUN+AST+Asn+Arg+Trp; 0.779, 252.423, 1+ALB+Asn+3MeHis+Lys+Tyr+Trp; 0.779, 249.694, 1+ALB+BUN+Asn+3M eHis+Orn+Val; 0.779, 248.159, 1+ALB+ALT+T-BIL+Asn+Thr+Lys; 0.77 9, 249.292, 1+ALB+BUN+T-BIL+Glc+Asn+Thr; 0.779, 251.274, 1+ALB+g GT+NEFA+Glc+His+Asn; 0.779, 249.802, 1+ALB+BUN+Asn+Tyr+Va 1; 0.779, 248.917, 1+ALB+BUN+Asn+3MeHis+Arg+Trp; 0.779, 249.378, 1+ALB+BUN+Asn+Arg+Phe+Trp; 0.779, 246.805, 1+ALB+AST+Asn+Asp+T yr+Trp; 0.779, 251.330,

1+ALB+Ca+NEFA+Glc+His+Asn; 0.779, 249.81 9, 1+ALB+BUN+gGT+NEFA+Asn+Thr; 0.779, 251.981, 1+ALB+gGT+His+As n+Thr+Lys; 0.779, 247.651, 1+ALB+AST+ALT+Asn+Thr+Lys; 0.779, 249. 414, 1+ALB+BUN+Asn+Orn+Phe+Trp; 0.779, 247.040, 1+ALB+BUN+NEFA+Asn+Asp+Val; 0.779, 247.256, 1+ALB+BUN+Asn+Arg+Asp+Lys; 0.779, 2 47.369, 1+ALB+BUN+BHBA+Glc+His+Asn; 0.779, 245.753, 1+ALB+BUN+A sn+3MeHis+Arg+Asp; 0.779, 250.880, 1+ALB+AST+NEFA+Asn+Lys+Tyr; 0.779, 244.983, 1+ALB+BUN+AST+Asn+Asp+Trp; 0.779, 248.956, 1+ALB+Ca+ALT+T-BIL+Asn+Ile; 0.779, 247.700, 1+ALB+ALT+Asn+Arg+Thr+O rn; 0.779, 248.552, 1+ALB+BUN+BHBA+Asn+Thr+Lys; 0.779, 248.680, 1+ALB+BUN+Asn+Thr+Orn+Lys; 0.779, 247.944, 1+ALB+ALT+BHBA+Asn+A rg+Thr; 0.779, 250.205, 1+ALB+gGT+His+Asn+Thr+Orn; 0.779, 248.49 7, 1+ALB+BUN+gGT+NEFA+His+Asn; 0.779, 249.236, 1+ALB+ALT+Asn+3M eHis+Val+Trp; 0.779, 250.208, 1+ALB+BUN+Asn+Orn+Tyr+Val; 0.779, 245.446, 1+ALB+ALT+Asn+Asp+Lys+Tyr; 0.779, 245.770, 1+ALB+ALT+A sn+3MeHis+Arg+Asp; 0.779, 247.776, 1+ALB+BUN+AST+His+Asn+Thr; 0. 779, 245.746, 1+ALB+BUN+NEFA+Asn+3MeHis+Asp; 0.779, 249.004, 1+A LB+Ca+ALT+BHBA+Asn+Ile; 0.779, 248.821, 1+ALB+ALT+gGT+Glc+Asn+Thr; 0.779, 247.820, 1+ALB+ALT+T-BIL+Asn+Arg+Thr; 0.779, 252.869, 1+ALB+NEFA+BHBA+His+Asn+Ile; 0.779, 246.002, 1+ALB+ALT+Asn+3Me His+Asp+Orn; 0.779, 248.854, 1+ALB+ALT+Asn+Orn+Lys+Tyr; 0.779, 2 49.813, 1+ALB+BUN+NEFA+Asn+Orn+Lys; 0.779, 249.892, 1+ALB+BUN+A sn+Orn+Lys+Val; 0.779, 251.804, 1+ALB+NEFA+Glc+Asn+Thr+Ile; 0.7 79, 248.224, 1+ALB+ALT+Asn+3MeHis+Arg+Val; 0.779, 253.867, 1+ALB+NEFA+Asn+3MeHis+Tyr+Phe; 0.779, 247.455, 1+ALB+AST+ALT+Asn+Th r+Orn; 0.779, 247.626, 1+ALB+BUN+gGT+His+Asn+Arg; 0.779, 249.381, 1+ALB+BUN+Asn+Arg+Orn+Trp; 0.779, 248.165, 1+ALB+BUN+AST+NEFA+Asn+Lys; 0.779, 245.689, 1+ALB+BUN+Asn+3MeHis+Asp+Phe; 0.778, 24 9.868, 1+ALB+BUN+Asn+Lys+Val+Phe; 0.778, 252.972, 1+ALB+Asn+3Me His+Tyr+Phe+Trp; 0.778, 249.286, 1+ALB+BUN+NEFA+Asn+Arg+Trp; 0. 778, 250.015, 1+ALB+BUN+Asn+Orn+Val+Phe; 0.778, 251.336, 1+ALB+N EFA+BHBA+Glc+His+Asn; 0.778, 247.646, 1+ALB+BUN+AST+Asn+Thr+Or n; 0.778, 248.475, 1+ALB+Ca+ALT+His+Asn+Ile; 0.778, 251.894, 1+AL B+Ca+BHBA+Asn+Lys+Ile; 0.778, 249.492, 1+ALB+Ca+Glc+His+Asn+Or n; 0.778, 249.911, 1+ALB+His+Asn+Thr+Orn+Lys; 0.778, 248.754, 1+A LB+ALT+Asn+Orn+Val+Phe; 0.778, 248.983, 1+ALB+ALT+gGT+NEFA+His+Asn; 0.778, 247.276, 1+ALB+BUN+NEFA+Asn+Asp+Phe; 0.778, 249.259, 1+ALB+BUN+NEFA+Glc+Asn+Lys; 0.778, 249.057, 1+ALB+AST+T-BIL+Hi s+Asn+Orn; 0.778, 248.757, 1+ALB+BUN+gGT+Asn+Thr+Lys; 0.778, 253. 429, 1+ALB+NEFA+Asn+Tyr+Val+Trp; 0.778, 249.860, 1+ALB+BUN+NEFA+BHBA+Asn+Thr; 0.778, 247.668, 1+ALB+BUN+Ca+His+Asn+Arg; 0.778, 249.336, 1+ALB+BUN+T-BIL+Asn+Thr+Orn; 0.778, 247.929, 1+ALB+ALT+NEFA+Asn+Arg+Thr; 0.778, 248.800, 1+ALB+ALT+Asn+3MeHis+Lys+Ty r; 0.778, 249.807, 1+ALB+BUN+gGT+NEFA+Asn+Lys; 0.778, 251.035, 1+ALB+AST+Asn+Tyr+Val+Trp; 0.778, 253.709, 1+ALB+Asn+Tyr+Val+Phe+Trp; 0.778, 248.352, 1+ALB+BUN+Glc+Asn+Thr+Lys; 0.778, 250.665, 1+ALB+T-BIL+Glc+His+Asn+Lys; 0.778, 245.884, 1+ALB+ALT+Asn+3Me His+Asp+Val; 0.778, 249.815, 1+ALB+BUN+NEFA+BHBA+Asn+Lys; 0.778, 248.757, 1+ALB+BUN+BHBA+His+Asn+Ile; 0.778, 248.724, 1+ALB+BUN+Asn+Arg+Thr+Lys; 0.778, 251.850, 1+ALB+BHBA+His+Asn+Thr+Lys; 0. 778, 246.012, 1+ALB+ALT+Asn+Asp+Tyr+Val; 0.778, 246.609, 1+ALB+A LT+Asn+Arg+Asp+Trp; 0.778, 248.514, 1+ALB+BUN+NEFA+BHBA+His+As n; 0.778, 247.566, 1+ALB+ALT+gGT+His+Asn+Lys; 0.778, 248.828, 1+A LB+Ca+ALT+Glc+Asn+Thr; 0.778, 248.308, 1+ALB+BUN+Ca+NEFA+His+A sn; 0.778, 249.644, 1+ALB+ALT+NEFA+BHBA+Asn+Thr; 0.778, 248.862, 1+ALB+AST+ALT+NEFA+Asn+Thr; 0.778, 248.952, 1+ALB+ALT+gGT+His+Asn+Thr; 0.778, 249.357, 1+ALB+ALT+NEFA+Asn+Orn+Val; 0.778, 250. 840, 1+ALB+T-BIL+BHBA+His+Asn+Orn; 0.778, 245.653, 1+ALB+ALT+As n+3MeHis+Asp+Lys; 0.778, 247.290, 1+ALB+AST+ALT+His+Asn+Lys; 0. 778, 248.128, 1+ALB+AST+ALT+His+Asn+Ile; 0.778, 247.405, 1+ALB+B UN+AST+Asn+3MeHis+Trp; 0.778, 251.600, 1+ALB+Ca+T-BIL+Asn+Orn+Ile; 0.778, 248.731, 1+ALB+ALT+NEFA+Glc+Asn+Orn; 0.778, 249.420, 1+ALB+ALT+NEFA+Asn+Val+Trp; 0.778, 247.730, 1+ALB+BUN+AST+Asn+Orn+Trp; 0.778, 249.129, 1+ALB+BUN+NEFA+Asn+Arg+Thr; 0.778, 247. 498, 1+ALB+AST+ALT+Glc+His+Asn; 0.778, 251.126, 1+ALB+NEFA+BHBA+His+Asn+Lys; 0.778, 250.456, 1+ALB+NEFA+Asn+Asp+Orn+Tyr; 0.778, 247.715, 1+ALB+BUN+AST+Asn+Lys+Trp; 0.778, 250.524, 1+ALB+AST+A sn+Orn+Val+Trp; 0.778, 248.233, 1+ALB+Ca+ALT+Asn+Thr+Orn; 0.778, 249.657, 1+ALB+ALT+gGT+NEFA+Asn+Thr; 0.778, 249.002, 1+ALB+ALT+Asn+3MeHis+Orn+Val; 0.778, 249.516, 1+ALB+BUN+T-BIL+Glc+Asn+Ly s; 0.778, 249.760, 1+ALB+BUN+Asn+3MeHis+Orn+Tyr; 0.778, 249.283, 1+ALB+BHBA+Glc+His+Asn+Orn; 0.778, 252.514, 1+ALB+NEFA+Asn+Arg+Orn+Tyr; 0.778, 249.633, 1+ALB+BUN+NEFA+Glc+Asn+Orn; 0.778, 249. 285, 1+ALB+AST+BHBA+His+Asn+Orn; 0.778, 249.542, 1+ALB+BUN+Ca+B HBA+Asn+Ile; 0.778, 247.535, 1+ALB+ALT+Asn+Arg+Thr+Lys; 0.778, 2 49.034, 1+ALB+ALT+NEFA+Asn+Lys+Tyr; 0.778, 249.635, 1+ALB+ALT+T-BIL+BHBA+Asn+Thr; 0.778, 251.775, 1+ALB+NEFA+Glc+Asn+Thr+Lys; 0.778, 249.149, 1+Ala+BCAA+Phe+ALT+ALB+BUN; 0.778, 248.406, 1+AL B+AST+ALT+NEFA+His+Asn; 0.778, 249.763, 1+ALB+BUN+NEFA+T-BIL+A sn+Lys; 0.778, 247.290, 1+ALB+BUN+NEFA+Asn+Asp+Orn; 0.778, 245.2 44, 1+ALB+BUN+Asn+3MeHis+Asp+Val; 0.778, 248.485, 1+ALB+AST+NEF A+His+Asn+Arg; 0.778, 248.424, 1+ALB+BUN+AST+NEFA+Asn+Tyr; 0.77 8, 250.593, 1+ALB+AST+NEFA+T-BIL+Asn+Ile; 0.778, 247.886, 1+ALB+Asn+3MeHis+Asp+Lys+Tyr; 0.778, 248.345, 1+ALB+ALT+NEFA+Glc+Asn+Arg; 0.778, 249.227, 1+ALB+ALT+Asn+3MeHis+Val+Phe; 0.778, 245.9 61, 1+ALB+ALT+NEFA+Asn+3MeHis+Asp; 0.778, 248.208, 1+ALB+BUN+AS T+T-BIL+Asn+Thr; 0.778, 248.678, 1+ALB+BUN+T-BIL+His+Asn+Thr; 0. 778, 249.553, 1+ALB+NEFA+His+Asn+Arg+Orn; 0.778, 247.452, 1+ALB+BUN+AST+T-BIL+His+Asn; 0.778, 249.962, 1+ALB+NEFA+Asn+Arg+Asp+Tyr; 0.778, 251.503, 1+ALB+AST+NEFA+Asn+Tyr+Phe; 0.778, 251.044, 1+ALB+gGT+BHBA+Asn+Arg+Ile; 0.778, 251.825, 1+ALB+Ca+His+Asn+T hr+Lys; 0.778, 249.677, 1+ALB+ALT+gGT+T-BIL+Asn+Thr; 0.778, 253. 134, 1+ALB+NEFA+Asn+3MeHis+Tyr+Trp; 0.778, 251.715, 1+ALB+gGT+T-BIL+Asn+Orn+Ile; 0.778, 247.527, 1+ALB+ALT+BHBA+His+Asn+Lys; 0. 778, 247.754, 1+ALB+BUN+AST+Asn+Phe+Trp; 0.778, 251.554, 1+ALB+C a+gGT+Asn+Orn+Ile; 0.778, 253.546, 1+ALB+

NEFA+Asn+Lys+Tyr+Val; 0.778, 249.289, 1+ALB+ALT+ NEFA+BHBA+Glc+Asn; 0.778, 250.213, 1+ALB+NEFA+ His+Asn+Arg+Thr; 0.778, 246.697, 1+ALB+ALT+Asn+ Asp+Phe+Trp; 0.778, 249.405, 1+ALB+ALT+NEFA+Asn+ 3MeHis+Phe; 0.777, 250. 048, 1+ALB+Ca+NEFA+His+ Asn+Orn; 0.777, 247.938, 1+ALB+ALT+gGT+A sn+Arg+ Thr; 0.777, 251.851, 1+ALB+NEFA+Asn+3MeHis+Arg+ Tyr; 0.77 7, 247.567, 1+ALB+ALT+T-BIL+His+Asn+Lys; 0.777, 248.497, 1+ALB+A ST+ALT+Asn+Val+Trp; 0.777, 251.910, 1+ALB+Ca+gGT+Asn+Lys+Ile; 0. 777, 248.788, 1+ALB+ALT+NEFA+T-BIL+Asn+Orn; 0.777, 249.295, 1+AL B+ALT+gGT+NEFA+Glc+Asn; 0.777, 249.593, 1+ALB+BUN+Asn+3MeHis+O rn+Lys; 0.777, 252.659, 1+ALB+NEFA+Asn+Arg+Tyr+Val; 0.777, 249.7 40, 1+ALB+BUN+NEFA+Asn+Lys+Phe; 0.777, 253.706, 1+ALB+NEFA+BHBA+Asn+Thr+Ile; 0.777, 250.840, 1+ALB+gGT+T-BIL+His+Asn+Orn; 0.77 7, 249.489, 1+ALB+BUN+Asn+3MeHis+Lys+Phe; 0.777, 250.007, 1+ALB+BUN+NEFA+Asn+Orn+Val; 0.777, 250.352, 1+ALB+BUN+NEFA+Asn+Tyr+V al; 0.777, 248.033, 1+ALB+BUN+AST+gGT+His+Asn; 0.777, 248.834, 1+ALB+AST+His+Asn+Arg+Orn; 0.777, 248.650, 1+ALB+BUN+Ca+Asn+Thr+Lys; 0.777, 249.059, 1+ALB+ Ca+ALT+gGT+Asn+Ile; 0.777, 248.772, 1+ALB+Asn+ 3MeHis+Asp+Tyr+Phe; 0.777, 251.767, 1+ALB+gGT+ NEFA+Glc+Asn+Ile; 0.777, 253.340, 1+ALB+NEFA+T-BIL+BHBA+Asn+Ile; 0.777, 250.065, 1+ALB+AST+ NEFA+Asn+Thr+Lys; 0.777, 250.979, 1+ALB+AST+ NEFA+BHBA+Asn+Ile; 0.777, 249.732, 1+ALB+ALT+ gGT+BHBA+Asn+Thr; 0.777, 251.503, 1+ALB+T-BIL+ Glc+His+Asn+Ile; 0.777, 247.748, 1+A LB+Asn+3MeHis+ Asp+Tyr+Trp; 0.777, 248.735, 1+ALB+ALT+BHBA+Glc+ Asn+Orn; 0.777, 248.946, 1+ALB+ALT+BHBA+His+ Asn+Thr; 0.777, 249. 409, 1+ALB+BUN+gGT+Asn+Thr+ Orn; 0.777, 249.931, 1+ALB+BUN+NEFA+Asn+Arg+Val; 0.777, 247.292, 1+ALB+BUN+NEFA+Asn+Arg+Asp; 0.777, 249.728, 1+ALB+BUN+NEFA+Asn+3MeHis+Phe; 0.777, 250.791, 1+ALB+N EFA+T-BIL+His+Asn+Lys; 0.777, 245.227, 1+ALB+AST+ALT+Asn+3MeHi s+Asp; 0.777, 244.079, 1+ALB+BUN+AST+Asn+3MeHis+Asp; 0.777, 248. 779, 1+ALB+Ca+AST+Asn+Arg+Ile; 0.777, 248.954, 1+ALB+ALT+T-BIL+His+Asn+Thr; 0.777, 251.973, 1+ALB+Asn+3MeHis+Arg+Tyr+Phe; 0.77 7, 246.617, 1+ALB+ALT+Asn+Asp+Lys+Trp; 0.777, 248.264, 1+ALB+AST+ALT+Glc+Asn+Thr; 0.777, 248.740, 1+ALB+ALT+gGT+Glc+Asn+Orn; 0. 777, 250.190, 1+ALB+BUN+NEFA+Asn+3MeHis+Tyr; 0.777, 246.505, 1+A LB+ALT+Asn+Asp+Val+Trp; 0.777, 246.688, 1+ALB+ALT+Asn+Asp+Orn+Trp; 0.777, 249.277, 1+ALB+ALT+NEFA+Asn+3MeHis+Trp; 0.777, 249.1 27, 1+ALB+ALT+NEFA+Asn+Orn+Trp; 0.777, 250.226, 1+ALB+AST+Glc+H is+Asn+Ile; 0.777, 247.937, 1+ALB+Ca+ALT+Asn+Arg+Thr; 0.777, 249. 754, 1+ALB+His+Asn+Arg+Thr+Orn; 0.777, 248.342, 1+ALB+ ALT+Glc+A sn+Arg+Orn; 0.777, 248.383, 1+ALB+ALT+ BHBA+Glc+Asn+Arg; 0.777, 2 48.671, 1+ALB+ALT+T-BIL+Glc+Asn+Orn; 0.777, 251.182, 1+ALB+gGT+NEFA+ His+Asn+Lys; 0.777, 248.731, 1+ALB+ALT+Asn+Arg+ Val+Phe; 0. 777, 251.850, 1+ALB+Ca+NEFA+Glc+Asn+ Ile; 0.777, 248.385, 1+ALB+C a+AST+ALT+Asn+Ile; 0.777, 251.251, 1+ALB+Ca+BHBA+Asn+Arg+Ile; 0. 777, 248.666, 1+ALB+ALT+Glc+Asn+Orn+Lys; 0.777, 249.063, 1+ALB+B UN+gGT+His+Asn+Thr; 0.777, 248.979, 1+ALB+ALT+Asn+3MeHis+Orn+T rp; 0.777, 249.908, 1+ALB+AST+NEFA+Asn+Thr+Orn; 0.777, 253.165, 1+ALB+NEFA+Asn+Orn+Lys+Tyr; 0.777, 248.754, 1+ALB+ALT+NEFA+Glc+Asn+Lys; 0.777, 249.775, 1+ALB+BUN+NEFA+Asn+Arg+Lys; 0.777, 250. 330, 1+ALB+BUN+Asn+Arg+Orn+Val; 0.777, 247.444, 1+ALB+BUN+Asn+A sp+Lys+Phe; 0.777, 248.364, 1+ALB+BUN+AST+Glc+Asn+Lys; 0.777, 25 0.001, 1+ALB+NEFA+His+Asn+Arg+Lys; 0.777, 245.718, 1+ALB+BUN+As n+3MeHis+Asp+Orn; 0.777, 249.264, 1+ALB+AST+gGT+His+Asn+Orn; 0. 777, 249.140, 1+ALB+ALT+gGT+BHBA+His+Asn; 0.777, 250.722, 1+ALB+T-BIL+His+Asn+Orn+Lys; 0.777, 249.260, 1+Ala+Phe+Tyr+ALT+ALB+B UN; 0.777, 249.457, 1+ALB+BUN+T-BIL+Asn+Arg+Thr; 0.777, 249.549, 1+ALB+ALT+gGT+NEFA+T-BIL+Asn; 0.777, 250.944, 1+ALB+gGT+BHBA+H is+Asn+Orn; 0.777, 252.064, 1+ALB+NEFA+T-BIL+Asn+Thr+Lys; 0.777, 250.345, 1+ALB+NEFA+BHBA+His+Asn+Arg; 0.777, 248.489, 1+ALB+BUN+ALT+Val+Phe+Trp; 0.777, 248.590, 1+Trp+ Phe+Tyr+ALT+ALB+BUN; 0. 777, 248.542, 1+ALB+ AST+ALT+Asn+Phe+Trp; 0.777, 252.517, 1+ALB+N EFA+BHBA+Asn+Thr+Lys; 0.777, 249.081, 1+ALB+ AST+ALT+BHBA+Asn+T hr; 0.777, 249.444, 1+ALB+ ALT+NEFA+T-BIL+BHBA+Asn; 0.777, 248.42 0, 1+ALB+AST+ALT+Asn+3MeHis+Trp; 0.777, 248.592, 1+ALB+AST+ALT+NEFA+Asn+Trp; 0.777, 247.464, 1+Trp+Phe+His+ALT+ALB+BUN; 0.777, 249.684, 1+ALB+BUN+Ca+NEFA+Asn+Thr; 0.777, 250.123, 1+ALB+ALT+N EFA+Asn+Tyr+Val; 0.777, 249.389, 1+ALB+BUN+NEFA+Asn+3MeHis+Ly s; 0.777, 249.426, 1+ALB+BUN+Asn+3MeHis+Arg+Lys; 0.777, 250.248, 1+ALB+BUN+NEFA+T-BIL+Asn+Orn; 0.777, 249.518, 1+ALB+BUN+Asn+3M eHis+Val+Phe; 0.777, 249.287, 1+ALB+BUN+AST+Asn+Tyr+Val; 0.777, 249.580, 1+Ala+Trp+Lys+His+ALB+BUN; 0.777, 248.862, 1+ALB+Ca+AL T+NEFA+His+Asn; 0.777, 248.724, 1+ALB+ALT+Asn+Arg+Orn+Val; 0.77 7, 249.108, 1+ALB+AST+ALT+T-BIL+Asn+Thr; 0.777, 251.876, 1+ALB+A sn+3MeHis+Arg+Lys+Tyr; 0.777, 249.818, 1+ALB+BUN+NEFA+T-BIL+Gl c+Asn; 0.777, 249.932, 1+ALB+BUN+Asn+Arg+Lys+Val; 0.777, 248.870, 1+ALB+BUN+AST+Asn+3MeHis+Val; 0.777, 250.939, 1+ALB+AST+NEFA+A sn+Thr+Ile; 0.777, 248.651, 1+ALB+BUN+Ca+T-BIL+His+Asn; 0.777, 2 49.324, 1+ALB+BUN+Asn+Arg+Thr+Orn; 0.777, 251.897, 1+ALB+NEFA+G lc+Asn+Thr+Orn; 0.777, 252.031, 1+ALB+Asn+3MeHis+Arg+Orn+Tyr; 0. 777, 250.497, 1+ALB+BUN+Asn+3MeHis+Tyr+Val; 0.777, 247.925, 1+AL B+BUN+AST+Asn+Arg+Thr; 0.777, 249.017, 1+ALB+ALT+Asn+Orn+Lys+V al; 0.777, 248.037, 1+Ala+ Phe+His+ALT+ALB+BUN; 0.777, 248.612, 1+ALB+ BUN+AST+Asn+Lys+Val; 0.777, 251.538, 1+ALB+gGT+ T-BIL+Asn+A rg+Ile; 0.777, 250.482, 1+ALB+AST+Asn+ 3MeHis+Tyr+Trp; 0.776, 253. 688, 1+ALB+Ca+NEFA+ BHBA+Asn+Ile; 0.776, 254.401, 1+ALB+NEFA+Asn+ Tyr+Val+Phe; 0.776, 250.844, 1+ALB+gGT+His+Asn+ Orn+Lys; 0.776, 246.697, 1+ALB+ALT+NEFA+Asn+Asp+ Trp; 0.776, 248.850, 1+ALB+BUN+T-BIL+BHBA+His+ Asn; 0.776, 249.195, 1+ALB+ALT+Asn+Lys+Tyr+Val; 0.776, 248.115, 1+ALB+Ca+ALT+Asn+Thr+Lys; 0.776, 253.027, 1+ALB+NEFA+His+Asn+Thr+Ile; 0.776, 253.821, 1+ALB+gGT+NEFA+BHBA+Asn+Ile; 0.776, 248.784, 1+ALB+BUN+gGT+T-BIL+His+Asn; 0.776, 249.395, 1+ALB+BUN+BHBA+Asn+Thr+Orn; 0.776, 250.889, 1+ALB+BHBA+His+Asn+Orn+Lys; 0.776, 248.678, 1+Ala+Trp+His+ALT+ALB+BUN; 0.776, 248. 854, 1+ALB+ALT+NEFA+Asn+Arg+Val; 0.776, 249.661, 1+ALB+BUN+NEFA+Asn+3MeHis+Arg; 0.776, 250.154, 1+ALB+BUN+NEFA+BHBA+Asn+Arg; 0. 776, 248.290, 1+ALB+AST+ALT+Asn+Orn+Tyr; 0.776, 248.488,

1+ALB+BUN+AST+Asn+3MeHis+Phe; 0.776, 248.806, 1+ALB+BUN+AST+Asn+3MeHis+Tyr; 0.776, 250.062, 1+ALB+BUN+gGT+T-BIL+Asn+Thr; 0.776, 252.470, 1+ALB+Asn+3MeHis+Orn+Val+Trp; 0.776, 247.300, 1+ALB+AST+ALT+Asn+Arg+Thr; 0.776, 249.022, 1+ALB+ALT+Asn+3MeHis+Orn+Lys; 0.776, 249.823, 1+ALB+BUN+Glc+Asn+Arg+Lys; 0.776, 251.511, 1+ALB+T-BIL+Asn+Arg+Thr+Ile; 0.776, 251.691, 1+Ala+BCAA+Trp+Phe+ALB+BUN; 0.776, 248.197, 1+ALB+BUN+AST+Asn+3MeHis+Lys; 0.776, 249.988, 1+ALB+BUN+NEFA+Asn+Arg+Phe; 0.776, 249.136, 1+ALB+ALT+gGT+T-BIL+His+Asn; 0.776, 250.048, 1+ALB+ALT+NEFA+Asn+3MeHis+Tyr; 0.776, 248.310, 1+ALB+ALT+T-BIL+Glc+Asn+Arg; 0.776, 249.649, 1+ALB+ALT+NEFA+Asn+Val+Phe; 0.776, 249.831, 1+ALB+BUN+Glc+Asn+Orn+Lys; 0.776, 250.135, 1+ALB+BUN+T-BIL+BHBA+Asn+Thr; 0.776, 250.314, 1+ALB+BUN+NEFA+Asn+3MeHis+Val; 0.776, 248.806, 1+ALB+ALT+Asn+Lys+Val+Trp; 0.776, 249.299, 1+ALB+ALT+NEFA+Asn+Phe+Trp; 0.776, 250.039, 1+ALB+BUN+NEFA+Asn+Orn+Phe; 0.776, 252.574, 1+ALB+Asn+3MeHis+Lys+Val+Trp; 0.776, 248.392, 1+Ala+Trp+Lys+ALT+ALB+BUN; 0.776, 247.991, 1+ALB+BUN+AST+NEFA+Glc+Asn; 0.776, 248.672, 1+ALB+BUN+AST+Asn+Orn+Val; 0.776, 245.392, 1+ALB+BUN+AST+NEFA+Asn+Asp; 0.776, 248.734, 1+ALB+Ca+ALT+Glc+Asn+Orn; 0.776, 249.582, 1+ALB+Ca+ALT+NEFA+Asn+Thr; 0.776, 247.459, 1+ALB+Ca+ALT+His+Asn+Lys; 0.776, 250.142, 1+ALB+Ca+His+Asn+Thr+Orn; 0.776, 248.342, 1+ALB+ALT+Glc+Asn+Arg+Lys; 0.776, 249.073, 1+ALB+AST+ALT+gGT+Asn+Thr; 0.776, 246.816, 1+ALB+ALT+Asn+Arg+Asp+Lys; 0.776, 249.033, 1+ALB+ALT+Asn+3MeHis+Phe+Trp; 0.776, 249.194, 1+Ala+Trp+ALT+ALB+BUN+TP; 0.776, 247.587, 1+ALB+BUN+Asn+Asp+Orn+Val; 0.776, 250.078, 1+ALB+AST+Glc+His+Asn+Lys; 0.776, 248.520, 1+ALB+BUN+AST+T-BIL+Asn+Lys; 0.776, 249.183, 1+ALB+Ca+AST+His+Asn+Orn; 0.776, 249.357, 1+ALB+BUN+Ca+Asn+Thr+Orn; 0.776, 247.841, 1+ALB+BUN+Ca+AST+His+Asn; 0.776, 253.686, 1+ALB+NEFA+Asn+Orn+Tyr+Val; 0.776, 248.739, 1+ALB+ALT+Asn+3MeHis+Lys+Val; 0.776, 249.556, 1+ALB+BUN+NEFA+Glc+Asn+Arg; 0.776, 248.659, 1+ALB+ALT+NEFA+Asn+Arg+Trp; 0.776, 249.475, 1+ALB+ALT+NEFA+BHBA+Asn+Orn; 0.776, 250.011, 1+ALB+BUN+NEFA+Asn+3MeHis+Orn; 0.776, 250.577, 1+ALB+AST+NEFA+Asn+Orn+Tyr; 0.776, 249.787, 1+ALB+BUN+Asn+3MeHis+Orn+Phe; 0.776, 246.896, 1+ALB+ALT+NEFA+Asn+Arg+Asp; 0.776, 249.853, 1+ALB+BUN+T-BIL+Glc+Asn+Orn; 0.776, 250.333, 1+ALB+BUN+NEFA+BHBA+Asn+Orn; 0.776, 251.284, 1+ALB+gGT+Asn+Arg+Thr+Ile; 0.776, 248.211, 1+ALB+AST+ALT+Asn+Orn+Trp; 0.776, 249.289, 1+ALB+Ca+ALT+NEFA+Glc+Asn; 0.776, 253.184, 1+ALB+NEFA+T-BIL+Asn+Thr+Ile; 0.776, 248.314, 1+ALB+ALT+Asn+3MeHis+Arg+Trp; 0.776, 248.351, 1+ALB+ALT+gGT+Glc+Asn+Arg; 0.776, 248.516, 1+ALB+AST+ALT+His+Asn+Thr; 0.776, 248.939, 1+ALB+ALT+Asn+3MeHis+Orn+Phe; 0.776, 250.102, 1+ALB+BUN+gGT+T-BIL+Asn+Lys; 0.776, 250.128, 1+ALB+BUN+T-BIL+BHBA+Asn+Lys; 0.776, 247.921, 1+ALB+Asn+3MeHis+Arg+Asp+Tyr; 0.776, 250.874, 1+Ala+BCAA+Trp+Lys+ALB+BUN; 0.776, 247.731, 1+ALB+BUN+AST+BHBA+His+Asn; 0.776, 249.024, 1+ALB+ALT+Asn+Orn+Phe+Trp; 0.776, 248.634, 1+ALB+AST+ALT+Asn+Lys+Tyr; 0.776, 248.381, 1+ALB+BUN+AST+NEFA+Asn+Phe; 0.776, 248.976, 1+ALB+BUN+Ca+His+Asn+Thr; 0.776, 252.578, 1+ALB+gGT+NEFA+Asn+Thr+Lys; 0.776, 252.941, 1+ALB+NEFA+Asn+3MeHis+Lys+Tyr; 0.776, 253.347, 1+ALB+gGT+NEFA+T-BIL+Asn+Ile; 0.776, 250.130, 1+ALB+BUN+T-BIL+Asn+Orn+Lys; 0.776, 250.418, 1+ALB+Glc+His+Asn+Arg+Lys; 0.776, 249.103, 1+Ala+Phe+ALT+ALB+BUN+NEFA; 0.776, 248.399, 1+ALB+AST+ALT+Asn+Lys+Trp; 0.776, 248.602, 1+ALB+BUN+ALT+Lys+Val+Phe; 0.776, 248.656, 1+ALB+BUN+AST+NEFA+Asn+Val; 0.776, 249.615, 1+ALB+Ca+ALT+T-BIL+Asn+Thr; 0.776, 249.104, 1+ALB+ALT+T-BIL+BHBA+His+Asn; 0.776, 249.476, 1+ALB+BUN+gGT+Glc+Asn+Thr; 0.776, 252.449, 1+ALB+NEFA+T-BIL+His+Asn+Ile; 0.776, 248.493, 1+ALB+ALT+Asn+3MeHis+Arg+Orn; 0.776, 246.907, 1+ALB+ALT+Asn+Arg+Asp+Orn; 0.776, 248.649, 1+ALB+ALT+Asn+Arg+Phe+Trp; 0.776, 250.037, 1+ALB+BUN+NEFA+T-BIL+Asn+Arg; 0.776, 252.199, 1+ALB+NEFA+Asn+Thr+Orn+Lys; 0.776, 252.758, 1+ALB+NEFA+T-BIL+His+Asn+Thr; 0.776, 247.303, 1+ALB+BUN+Asn+Asp+Orn+Lys; 0.776, 250.440, 1+ALB+Glc+His+Asn+Arg+Thr; 0.776, 251.325, 1+ALB+Asn+Asp+Orn+Tyr+Phe; 0.776, 252.304, 1+Ala+Trp+Phe+Tyr+ALB+BUN; 0.776, 250.635, 1+ALB+AST+NEFA+Glc+Asn+Thr; 0.776, 250.358, 1+ALB+T-BIL+His+Asn+Arg+Orn; 0.776, 248.916, 1+ALB+BUN+AST+Asn+Lys+Phe; 0.776, 248.436, 1+ALB+BUN+AST+Asn+3MeHis+Orn; 0.776, 249.598, 1+ALB+AST+NEFA+Asn+Arg+Tyr; 0.776, 247.528, 1+Lys+Phe+His+ALT+ALB+BUN; 0.776, 248.370, 1+ALB+Ca+ALT+Glc+Asn+Arg; 0.776, 250.744, 1+ALB+Ca+T-BIL+His+Asn+Orn; 0.776, 254.186, 1+ALB+Asn+Orn+Tyr+Val+Phe; 0.776, 249.999, 1+ALB+ALT+Asn+3MeHis+Tyr+Val; 0.776, 252.681, 1+ALB+NEFA+BHBA+Asn+Thr+Orn; 0.776, 248.939, 1+ALB+ALT+NEFA+Asn+Arg+Orn; 0.776, 250.141, 1+ALB+BUN+NEFA+Asn+Arg+Orn; 0.776, 247.828, 1+ALB+AST+ALT+Asn+Arg+Trp; 0.776, 248.530, 1+ALB+BUN+AST+NEFA+Asn+3MeHis; 0.776, 250.766, 1+ALB+AST+Glc+Asn+Thr+Ile; 0.776, 249.666, 1+ALB+Ca+ALT+BHBA+Asn+Thr; 0.776, 248.867, 1+ALB+Ca+ALT+His+Asn+Thr; 0.776, 250.855, 1+ALB+His+Asn+Arg+Thr+Lys; 0.776, 252.164, 1+ALB+NEFA+T-BIL+Asn+Thr+Orn; 0.776, 253.439, 1+ALB+Asn+Arg+Orn+Tyr+Phe; 0.776, 248.834, 1+ALB+ALT+NEFA+T-BIL+Asn+Lys; 0.776, 252.428, 1+ALB+T-BIL+BHBA+His+Asn+Lys; 0.776, 253.236, 1+ALB+Asn+3MeHis+Tyr+Val+Trp; 0.776, 248.471, 1+Ala+Lys+Phe+ALT+ALB+BUN; 0.776, 249.624, 1+ALB+BUN+Asn+3MeHis+Arg+Phe; 0.776, 249.843, 1+ALB+NEFA+T-BIL+His+Asn+Arg; 0.776, 245.859, 1+ALB+AST+ALT+Asn+Asp+Trp; 0.776, 249.174, 1+ALB+ALT+T-BIL+BHBA+Glc+Asn; 0.776, 249.441, 1+ALB+BUN+Asn+3MeHis+Arg+Val; 0.776, 249.534, 1+ALB+BUN+BHBA+Glc+Asn+Lys; 0.776, 250.520, 1+ALB+BUN+gGT+NEFA+T-BIL+Asn; 0.776, 248.700, 1+ALB+BUN+AST+gGT+Glc+Asn; 0.776, 252.820, 1+ALB+Ca+NEFA+His+Asn+Ile; 0.775, 253.509, 1+ALB+Asn+3MeHis+Lys+Tyr+Phe; 0.775, 248.785, 1+ALB+ALT+BHBA+Glc+Asn+Lys; 0.775, 249.303, 1+ALB+ALT+gGT+BHBA+Glc+Asn; 0.775, 254.158, 1+ALB+NEFA+Asn+Orn+Val+Phe; 0.775, 248.659, 1+ALB+ALT+Asn+Arg+Orn+Trp; 0.775, 249.357, 1+ALB+ALT+NEFA+Asn+Orn+Lys; 0.775, 253.211, 1+ALB+NEFA+Asn+3MeHis+Orn+Tyr; 0.775, 248.888, 1+ALB+ALT+Asn+3MeHis+Lys+Trp; 0.775, 248.952, 1+ALB+ALT+gGT+NEFA+Asn+Arg; 0.775, 249.896, 1+ALB+BUN+gGT+T-BIL+Glc+Asn; 0.775, 247.026, 1+ALB+ALT+NEFA+Asn+Asp+Orn; 0.775, 247.734, 1+ALB+BUN+Asn+Arg+Asp+Phe; 0.775, 250.567, 1+ALB+AST+NEFA+His+Asn+Ile; 0.775, 248.589, 1+ALB+BUN+AST+gGT+NEFA+Asn; 0.775, 250.098, 1+ALB+BUN+T-BIL+Asn+Arg+Lys; 0.775, 251.335, 1+ALB+gGT+Glc+His+Asn+Lys; 0.775, 246.815, 1+ALB+ALT+Asn+Arg+Asp+Val; 0.775, 248.868, 1+ALB+ALT+NEFA+BHBA+Asn+Arg; 0.775, 248.898, 1+ALB+BUN+BHBA+His+Asn+Thr; 0.775, 246.848, 1+ALB+ALT+NEFA+Asn+Asp+Lys; 0.775, 246.905, 1+ALB+ALT+Asn+Arg+Asp+Phe; 0.775, 247.564, 1+ALB+BUN+Asn+Asp+Val+Phe; 0.775, 248.159, 1+ALB+AST+ALT+NEFA+Asn+Arg; 0.775, 248.616, 1+ALB+BUN+AST+gGT+Asn+Thr; 0.775, 249.170, 1+ALB+ALT+NEFA+Asn+Lys+Trp; 0.775, 249.498, 1+ALB+ALT+gGT+BHBA+Asn+Orn; 0.775, 246.308, 1+ALB+AST+ALT+NEFA+Asn+Asp; 0.775, 247.758, 1+ALB+BUN+Asn+Asp+Orn+Phe; 0.775, 248.851, 1+ALB+BUN+AST+gGT+Asn+Lys; 0.775, 248.112, 1+Trp+Phe+ALT+ALB+BUN+TP; 0.775, 250.082, 1+ALB+AST+Glc+Asn+Thr+Orn; 0.775, 248.491, 1+ALB+BUN+Ca+AST+Asn+Thr; 0.775, 249.715, 1+ALB+BUN+gGT+NEFA+Glc+Asn; 0.775, 248.385, 1+ALB+ALT+Asn+3MeHis+Arg+Lys; 0.775, 248.980, 1+ALB+ALT+Asn+3MeHis+Lys+Phe; 0.775, 248.865, 1+Ala+Gly+Phe+ALT+ALB+BUN; 0.775, 248.462, 1+ALB+BUN+AST+Glc+Asn+Arg; 0.775, 248.868, 1+ALB+BUN+AST+Asn+Orn+Lys; 0.775, 253.028, 1+ALB+Asn+3MeHis+Orn+Lys+Tyr; 0.775, 249.568, 1+ALB+BUN+BHBA+Asn+Arg+Thr; 0.775, 249.746, 1+ALB+BUN+gGT+Glc+Asn+Lys; 0.775, 253.441, 1+ALB+NEFA+Asn+3MeHis+Orn+Val; 0.775, 250.297, 1+ALB+BUN+gGT+NEFA+Asn+Orn; 0.775, 252.422, 1+ALB+Ca+NEFA+Asn+Thr+Lys; 0.775, 249.725, 1+ALB+BUN+Ca+NEFA+Glc+Asn; 0.775, 249.010, 1+ALB+BUN+Ca+gGT+His+Asn; 0.775, 249.977, 1+ALB+BUN+Ca+T-BIL+Asn+Thr; 0.775, 250.785, 1+ALB+Ca+gGT+His+Asn+Orn; 0.775, 249.542, 1+ALB+BUN+gGT+Asn+Arg+Thr; 0.775, 253.168, 1+ALB+NEFA+BHBA+His+Asn+Thr; 0.775, 247.001, 1+ALB+ALT+Asn+Asp+Orn+Phe; 0.775, 249.284, 1+ALB+ALT+NEFA+Asn+3MeHis+Orn; 0.775, 250.460, 1+ALB+His+Asn+Arg+Orn+Lys; 0.775, 250.536, 1+ALB+BUN+NEFA+T-BIL+BHBA+Asn; 0.775, 249.048, 1+ALB+AST+ALT+NEFA+Asn+Phe; 0.775, 249.064, 1+ALB+ALT+Asn+Orn+Lys+Trp; 0.775, 248.139, 1+ALB+BUN+AST+Asn+3MeHis+Arg; 0.775, 248.434, 1+ALB+BUN+AST+NEFA+Asn+Orn; 0.775, 253.483, 1+ALB+Asn+3MeHis+Lys+Tyr+Val; 0.775, 249.165, 1+ALB+BUN+Glc+Asn+Arg+Thr; 0.775, 248.068, 1+ALB+ALT+NEFA+T-BIL+Asn+Arg; 0.775, 248.854, 1+ALB+ALT+T-BIL+Glc+Asn+Lys; 0.775, 251.678, 1+ALB+Ca+T-BIL+Asn+Arg+Ile; 0.775, 254.038, 1+ALB+gGT+NEFA+Asn+Thr+Ile; 0.775, 246.892, 1+ALB+ALT+Asn+Asp+Orn+Val; 0.775, 248.388, 1+ALB+ALT+Asn+3MeHis+Arg+Phe; 0.775, 250.375, 1+ALB+gGT+His+Asn+Arg+Orn; 0.775, 250.483, 1+ALB+BHBA+His+Asn+Arg+Orn; 0.775, 253.352, 1+ALB+NEFA+Asn+Orn+Val+Trp; 0.775, 251.252, 1+ALB+T-BIL+His+Asn+Arg+Lys; 0.775, 248.711, 1+ALB+BUN+AST+NEFA+T-BIL+Asn; 0.775, 248.658, 1+ALB+AST+Asn+Asp+Orn+Tyr; 0.775, 250.734, 1+ALB+Ca+His+Asn+Orn+Lys; 0.775, 249.368, 1+ALB+ALT+gGT+T-BIL+Glc+Asn; 0.775, 248.882, 1+ALB+ALT+BHBA+Asn+Arg+Orn; 0.775, 249.356, 1+ALB+ALT+BHBA+Asn+Orn+Lys; 0.775, 249.401, 1+ALB+AST+ALT+NEFA+Asn+Tyr; 0.775, 249.275, 1+ALB+ALT+NEFA+Asn+Lys+Val; 0.775, 249.381, 1+ALB+ALT+NEFA+Asn+Lys+Phe; 0.775, 249.678, 1+Ala+Trp+Glc+ALT+ALB+BUN; 0.775, 248.829, 1+ALB+BUN+AST+Asn+Arg+Lys; 0.775, 248.269, 1+ALB+BUN+AST+NEFA+Asn+Arg; 0.775, 251.621, 1+ALB+AST+Asn+Orn+Tyr+Phe; 0.775, 250.917, 1+ALB+Ca+NEFA+His+Asn+Lys; 0.775, 249.429, 1+ALB+Ca+ALT+NEFA+T-BIL+Asn; 0.775, 248.471, 1+ALB+ALT+NEFA+Asn+3MeHis+Arg; 0.775, 249.075, 1+ALB+Asn+3MeHis+Asp+Lys+Val; 0.775, 250.018, 1+ALB+BUN+Glc+Asn+Arg+Orn; 0.775, 251.574, 1+ALB+BHBA+His+Asn+Arg+Lys; 0.775, 248.645, 1+ALB+ALT+Asn+Arg+Lys+Trp; 0.775, 249.126, 1+ALB+ALT+Asn+Lys+Phe+Trp; 0.775, 249.223, 1+ALB+ALT+T-BIL+Asn+Orn+Lys; 0.775, 246.535, 1+ALB+BUN+ALT+Asp+Lys+Phe; 0.775, 250.035, 1+ALB+AST+His+Asn+Arg+Lys; 0.775, 248.246, 1+ALB+BUN+AST+T-BIL+Glc+Asn; 0.775, 248.974, 1+BCAA+Trp+Lys+ALT+ALB+BUN; 0.775, 250.850, 1+ALB+Ca+BHBA+His+Asn+Orn; 0.775, 248.733, 1+ALB+AST+ALT+T-BIL+His+Asn; 0.775, 247.683, 1+Ala+Trp+ALT+ALB+BUN; 0.775, 248.390, 1+ALB+BUN+AST+BHBA+Asn+Thr; 0.775, 249.712, 1+ALB+BUN+NEFA+BHBA+Glc+Asn; 0.775, 248.460, 1+ALB+AST+ALT+Asn+Orn+Val; 0.775, 249.656, 1+ALB+Ca+ALT+gGT+Asn+Thr; 0.775, 251.392, 1+ALB+Ca+Glc+His+Asn+Lys; 0.775, 250.913, 1+ALB+BHBA+Glc+His+Asn+Lys; 0.775, 253.056, 1+ALB+NEFA+T-BIL+Glc+A sn+Thr; 0.775, 253.079, 1+ALB+gGT+NEFA+His+Asn+Ile; 0.775, 249.467, 1+Ala+Trp+TG+ALT+ALB+BUN; 0.775, 251.197, 1+ALB+Asn+Asp+Orn+Lys+Tyr; 0.775, 245.515, 1+ALB+AST+ALT+Asn+Asp+Tyr; 0.775, 247.747, 1+ALB+BUN+Asn+Arg+Asp+Orn; 0.775, 251.444, 1+ALB+AST+NEFA+Asn+Lys+Val; 0.775, 250.070, 1+Ala+Trp+Phe+His+ALB+BUN; 0.775, 249.586, 1+ALB+BUN+Ca+Glc+Asn+Thr; 0.775, 249.766, 1+ALB+BUN+Asn+3MeHis+Arg+Orn; 0.775, 250.279, 1+ALB+BUN+BHBA+Asn+Orn+Lys; 0.775, 249.173, 1+ALB+NEFA+Asn+3MeHis+Asp+Tyr; 0.775, 249.035, 1+ALB+Ca+ALT+gGT+His+Asn; 0.775, 252.913, 1+ALB+Asn+3MeHis+Orn+Lys+Val; 0.775, 250.073, 1+ALB+ALT+NEFA+Asn+3MeHis+Val; 0.775, 253.724, 1+ALB+Asn+Arg+Lys+Tyr+Val; 0.775, 248.715, 1+ALB+AST+ALT+gGT+His+Asn; 0.775, 248.928, 1+ALB+ALT+gGT+Asn+Arg+Orn; 0.775, 249.628, 1+Ala+BCAA+Trp+ALT+ALB+BUN; 0.775, 250.095, 1+ALB+BUN+gGT+NEFA+Asn+Arg; 0.775, 248.256, 1+ALB+AST+ALT+gGT+Asn+Arg; 0.775, 251.064, 1+ALB+Asn+Arg+Asp+Lys+Tyr; 0.775, 249.756, 1+ALB+BUN+Ca+Glc+Asn+Lys; 0.775, 250.338, 1+ALB+BUN+Ca+NEFA+T-BIL+Asn; 0.775, 253.002, 1+ALB+Ca+NEFA+T-BIL+Asn+Ile; 0.774, 253.094, 1+ALB+NEFA+Asn+3MeHis+Lys+Val; 0.774, 246.880, 1+ALB+ALT+Asn+Asp+Orn+Lys; 0.774, 246.881, 1+ALB+ALT+Asn+Asp+Lys+Phe; 0.774, 247.047, 1+ALB+ALT+NEFA+Asn+Asp+Phe; 0.774, 248.652, 1+ALB+ALT+Asn+Arg+Lys+Val; 0.774, 248.753, 1+ALB+ALT+gGT+T-BIL+Asn+Arg; 0.774, 248.761, 1+ALB+ALT+T-BIL+BHBA+Asn+Arg; 0.774, 248.862, 1+ALB+ALT+gGT+Glc+Asn+Lys; 0.774, 249.643, 1+Ala+Trp+Thr+ALT+ALB+BUN; 0.774, 247.098, 1+ALB+ALT+NEFA+Asn+Asp+Val; 0.774, 250.950, 1+ALB+AST+gGT+Glc+Asn+Ile; 0.774, 247.648, 1+ALB+BUN+Asn+Arg+Asp+Val; 0.774, 245.919, 1+ALB+BUN+AST+Asn+Asp+Lys; 0.774, 251.683, 1+ALB+AST+Asn+Orn+Lys+Tyr; 0.774, 250.865, 1+ALB+AST+Asn+Arg+Orn+Tyr; 0.774, 252.216, 1+ALB+Ca+T-BIL+His+Asn+Lys; 0.774, 249.026, 1+ALB+Ca+ALT+BHBA+His+Asn; 0.774, 248.763, 1+ALB+Asn+3MeHis+Asp+Orn+Tyr; 0.774, 249.676, 1+Ala+Trp+ALT+ALB+BUN+NEFA; 0.774, 249.834, 1+ALB+BUN+T-BIL+Glc+Asn+Arg; 0.774, 250.568, 1+ALB+BUN+gGT+NEFA+BHBA+Asn; 0.774, 248.161,

1+ALB+AST+ALT+Asn+Arg+Val; 0.774, 248.767, 1+ALB+BUN+AST+BHBA+Asn+Lys; 0.774, 245.900, 1+ALB+BUN+AST+Asn+Asp+Val; 0.774, 249.372, 1+ALB+Ca+ALT+T-BIL+Glc+Asn; 0.774, 248.908, 1+ALB+ALT+gGT+BHBA+Asn+Arg; 0.774, 249.264, 1+Ala+Gly+Trp+ALT+ALB+BUN; 0.774, 249.548, 1+ALB+ALT+gGT+NEFA+Asn+Orn; 0.774, 247.734, 1+ALB+AST+ALT+Asn+3MeHis+Arg; 0.774, 248.903, 1+ALB+ALT+NEFA+Asn+Arg+Phe; 0.774, 249.475, 1+ALB+AST+ALT+NEFA+BHBA+Asn; 0.774, 249.611, 1+Ala+Trp+ALT+ALB+BUN+BHBA; 0.774, 253.472, 1+ALB+Asn+Arg+Orn+Lys+Tyr; 0.774, 248.266, 1+ALB+AST+ALT+Asn+Arg+Phe; 0.774, 250.337, 1+ALB+BUN+Asn+Orn+Lys+Phe; 0.774, 248.948, 1+ALB+BUN+AST+gGT+Asn+Orn; 0.774, 250.724, 1+ALB+AST+T-BIL+His+Asn+Lys; 0.774, 253.340, 1+ALB+Asn+3MeHis+Orn+Tyr+Val; 0.774, 252.570, 1+ALB+NEFA+Asn+Arg+Thr+Orn; 0.774, 253.762, 1+ALB+Asn+Arg+Lys+Tyr+Phe; 0.774, 249.934, 1+ALB+BUN+gGT+Glc+Asn+Orn; 0.774, 253.852, 1+ALB+NEFA+Asn+Orn+Lys+Val; 0.774, 249.140, 1+ALB+ALT+NEFA+Asn+3MeHis+Lys; 0.774, 249.261, 1+ALB+ALT+Asn+Orn+Lys+Phe; 0.774, 249.356, 1+Ala+Phe+Glc+ALT+ALB+BUN; 0.774, 249.675, 1+Ala+Trp+ALT+gGT+ALB+BUN; 0.774, 248.275, 1+ALB+AST+ALT+BHBA+Asn+Arg; 0.774, 248.557, 1+ALB+AST+ALT+NEFA+Glc+Asn; 0.774, 250.590, 1+ALB+BUN+T-BIL+BHBA+Asn+Orn; 0.774, 248.501, 1+ALB+AST+ALT+Asn+3MeHis+Lys; 0.774, 250.807, 1+ALB+AST+NEFA+His+Asn+Thr; 0.774, 251.425, 1+ALB+Ca+gGT+Asn+Arg+Ile; 0.774, 250.373, 1+ALB+Ca+His+Asn+Arg+Orn; 0.774, 249.324, 1+ALB+ALT+gGT+T-BIL+Asn+Orn; 0.774, 250.330, 1+ALB+BUN+gGT+Asn+Orn+Lys; 0.774, 252.181, 1+ALB+T-BIL+Glc+His+Asn+Thr; 0.774, 252.250, 1+ALB+Asn+3MeHis+Arg+Tyr+Val; 0.774, 249.414, 1+Ala+Phe+ALT+gGT+ALB+BUN; 0.774, 248.197, 1+ALB+AST+ALT+Asn+Arg+Orn; 0.774, 249.431, 1+ALB+BUN+ALT+Orn+Tyr+Phe; 0.774, 249.488, 1+ALB+AST+ALT+NEFA+Asn+Val; 0.774, 249.765, 1+BCAA+Phe+ALT+ALB+BUN+NEFA; 0.774, 248.797, 1+Trp+Phe+ALT+gGT+ALB+BUN; 0.774, 249.771, 1+ALB+AST+His+Asn+Arg+Thr; 0.774, 246.062, 1+ALB+BUN+AST+Asn+Arg+Asp; 0.774, 248.719, 1+ALB+BUN+AST+NEFA+BHBA+Asn; 0.774, 248.863, 1+ALB+BUN+AST+Asn+Arg+Val; 0.774, 250.398, 1+ALB+BUN+Ca+NEFA+BHBA+Asn; 0.774, 250.252, 1+ALB+BUN+gGT+BHBA+Asn+Lys; 0.774, 250.248, 1+ALB+ALT+gGT+NEFA+BHBA+Asn; 0.774, 250.463, 1+ALB+gGT+NEFA+His+Asn+Arg; 0.774, 246.449, 1+ALB+AST+ALT+Asn+Asp+Phe; 0.774, 250.785, 1+ALB+AST+Asn+3MeHis+Orn+Val; 0.774, 249.722, 1+ALB+AST+Asn+3MeHis+Arg+Tyr; 0.774, 250.827, 1+ALB+AST+Asn+3MeHis+Orn+Tyr; 0.774, 249.037, 1+ALB+Ca+ALT+T-BIL+His+Asn; 0.774, 249.572, 1+ALB+BUN+Ca+Asn+Arg+Thr; 0.774, 253.497, 1+ALB+Asn+Orn+Lys+Val+Trp; 0.774, 254.139, 1+ALB+Asn+Orn+Lys+Tyr+Phe; 0.774, 249.196, 1+ALB+BUN+BHBA+Glc+Asn+Thr; 0.774, 250.190, 1+ALB+T-BIL+Glc+His+Asn+Arg; 0.774, 248.698, 1+ALB+AST+ALT+BHBA+His+Asn; 0.774, 248.728, 1+ALB+ALT+T-BIL+Asn+Arg+Lys; 0.774, 249.680, 1+Ala+Trp+Tyr+ALT+ALB+BUN; 0.774, 250.487, 1+ALB+BUN+T-BIL+BHBA+Asn+Arg; 0.774, 252.415, 1+ALB+gGT+T-BIL+His+Asn+Lys; 0.774, 253.845, 1+ALB+Asn+Arg+Tyr+Val+Phe; 0.774, 249.094, 1+ALB+BUN+AST+Asn+Val+Phe; 0.774, 250.424, 1+ALB+AST+T-BIL+Glc+His+Asn; 0.774, 250.442, 1+ALB+BUN+T-BIL+Asn+Arg+Orn; 0.774, 251.108, 1+ALB+Asn+Arg+Asp+Orn+Tyr; 0.774, 251.077, 1+ALB+AST+NEFA+Asn+Orn+Val; 0.774, 249.303, 1+ALB+Ca+ALT+BHBA+Glc+Asn; 0.774, 249.360, 1+ALB+Ca+ALT+gGT+Glc+Asn; 0.774, 248.229, 1+ALB+AST+ALT+T-BIL+Asn+Arg; 0.774, 248.890, 1+ALB+ALT+Asn+Arg+Orn+Phe; 0.774, 249.016, 1+ALB+BUN+gGT+BHBA+His+Asn; 0.774, 250.242, 1+ALB+BUN+BHBA+Asn+Arg+Lys; 0.774, 250.304, 1+ALB+AST+T-BIL+Glc+Asn+Ile; 0.774, 248.632, 1+Trp+Phe+TG+ALT+ALB+BUN; 0.774, 248.809, 1+Gly+Trp+Phe+ALT+ALB+BUN; 0.774, 248.942, 1+ALB+BUN+AST+Asn+Orn+Phe; 0.774, 251.427, 1+ALB+Ca+Asn+Arg+Thr+Ile; 0.774, 248.708, 1+ALB+ALT+T-BIL+Asn+Arg+Orn; 0.774, 249.290, 1+ALB+ALT+NEFA+Asn+Orn+Phe; 0.774, 249.312, 1+ALB+ALT+T-BIL+BHBA+Asn+Orn; 0.774, 249.471, 1+ALB+ALT+NEFA+BHBA+Asn+Lys; 0.774, 250.556, 1+ALB+AST+Asn+Thr+Orn+Lys; 0.774, 251.484, 1+ALB+Ca+His+Asn+Arg+Lys; 0.774, 249.967, 1+ALB+BUN+Ca+T-BIL+Glc+Asn; 0.774, 255.140, 1+ALB+Asn+Lys+Tyr+Val+Phe; 0.774, 250.363, 1+ALB+BUN+Asn+Arg+Val+Phe; 0.774, 249.178, 1+ALB+AST+Glc+His+Asn+Arg; 0.774, 251.398, 1+ALB+AST+gGT+His+Asn+Lys; 0.774, 246.073, 1+ALB+BUN+AST+Asn+Asp+Orn; 0.774, 251.342, 1+ALB+AST+NEFA+T-BIL+Asn+Thr; 0.774, 251.510, 1+ALB+AST+Asn+Lys+Val+Trp; 0.774, 249.631, 1+ALB+BUN+Ca+NEFA+Asn+Lys; 0.774, 253.184, 1+ALB+gGT+NEFA+His+Asn+Thr; 0.774, 249.307, 1+Arg+Phe+Tyr+ALT+ALB+BUN; 0.774, 248.934, 1+ALB+AST+ALT+NEFA+T-BIL+Asn; 0.774, 246.200, 1+ALB+AST+ALT+Asn+Arg+Asp; 0.774, 248.262, 1+ALB+BUN+AST+BHBA+Glc+Asn; 0.774, 248.612, 1+ALB+AST+ALT+Asn+Orn+Phe; 0.774, 248.208, 1+Arg+Phe+His+ALT+ALB+BUN; 0.774, 248.743, 1+ALB+AST+ALT+NEFA+Asn+Lys; 0.774, 249.448, 1+ALB+Ca+ALT+BHBA+Asn+Orn; 0.774, 249.960, 1+ALB+BUN+Ca+T-BIL+Asn+Lys; 0.774, 250.341, 1+ALB+BUN+Ca+gGT+NEFA+Asn; 0.774, 250.001, 1+ALB+BUN+Ca+Glc+Asn+Orn; 0.774, 249.296, 1+Ala+Phe+ALT+ALB+BUN+TP; 0.774, 253.597, 1+ALB+Asn+Orn+Val+Phe+Trp; 0.774, 249.850, 1+ALB+BUN+BHBA+Glc+Asn+Arg; 0.774, 249.198, 1+ALB+BUN+ALT+Orn+Val+Phe; 0.774, 249.376, 1+ALB+ALT+gGT+Asn+Orn+Lys; 0.774, 246.298, 1+ALB+AST+ALT+Asn+Asp+Orn; 0.774, 251.879, 1+ALB+gGT+Glc+His+Asn+Ile; 0.774, 252.253, 1+ALB+NEFA+Asn+Arg+Thr+Lys; 0.774, 249.019, 1+Ala+Phe+ALT+ALB+BUN+BHBA; 0.774, 249.537, 1+ALB+AST+ALT+Asn+Tyr+Val; 0.774, 250.528, 1+ALB+BUN+gGT+T-BIL+Asn+Orn; 0.774, 252.170, 1+ALB+Glc+His+Asn+Thr+Ile; 0.774, 249.415, 1+ALB+AST+ALT+gGT+NEFA+Asn; 0.774, 248.967, 1+ALB+BUN+AST+gGT+Asn+Arg; 0.774, 249.345, 1+Ala+Trp+TCHO+ALT+ALB+BUN; 0.773, 252.832, 1+ALB+gGT+NEFA+Asn+Thr+Orn; 0.773, 248.895, 1+ALB+ALT+Asn+Arg+Orn+Lys; 0.773, 249.222, 1+ALB+ALT+Asn+Lys+Val+Phe; 0.773, 254.202, 1+ALB+Asn+Orn+Lys+Tyr+Val; 0.773, 248.932, 1+Ala+Trp+Arg+ALT+ALB+BUN; 0.773, 249.942, 1+ALB+BUN+T-BIL+BHBA+Glc+Asn; 0.773, 250.312, 1+ALB+BUN+Asn+Arg+Lys+Phe; 0.773, 250.541, 1+ALB+BUN+BHBA+Asn+Arg+Orn; 0.773, 246.228, 1+ALB+AST+ALT+Asn+Asp+Lys; 0.773, 248.405, 1+ALB+BUN+AST+Glc+Asn+Orn; 0.773, 248.973, 1+ALB+BUN+AST+Asn+Arg+Phe; 0.773, 251.135, 1+ALB+AST+NEFA+Asn+Val+Trp; 0.773, 251.076, 1+ALB+AST+gGT+NEFA+Asn+Ile; 0.773, 253.845, 1+ALB+Ca+NEFA+Asn+Thr+Ile; 0.773, 250.443, 1+ALB+Ca+NEFA+His+Asn+Arg; 0.773, 247.421, 1+Ala+Phe+ALT+ALB+BUN; 0.773, 250.323,

1+ALB+BUN+Asn+Arg+Orn+Lys; 0.773, 246.658, 1+ALB+ALT+Asn+Asp+Lys+Val; 0.773, 250.610, 1+Ala+Trp+Arg+His+ALB+BUN; 0.773, 250.146, 1+ALB+BUN+Ca+gGT+Asn+Thr; 0.773, 248.759, 1+ALB+BUN+Ca+AST+Asn+Lys; 0.773, 250.431, 1+ALB+BUN+Ca+T-BIL+Asn+Orn; 0.773, 250.184, 1+ALB+BUN+gGT+BHBA+Asn+Thr; 0.773, 253.161, 1+ALB+Asn+3MeHis+Orn+Val+Phe; 0.773, 246.337, 1+ALB+BUN+ALT+Asp+Phe+Trp; 0.773, 248.612, 1+Trp+Arg+Phe+ALT+ALB+BUN; 0.773, 250.157, 1+ALB+AST+NEFA+Asn+Arg+Thr; 0.773, 251.124, 1+ALB+AST+T-BIL+Asn+Thr+Lys; 0.773, 246.072, 1+ALB+BUN+AST+Asn+Asp+Phe; 0.773, 248.499, 1+ALB+BUN+ALT+3MeHis+Phe+Trp; 0.773, 250.159, 1+ALB+BUN+Ca+NEFA+Asn+Orn; 0.773, 248.882, 1+ALB+ALT+NEFA+Asn+Arg+Lys; 0.773, 250.270, 1+ALB+BUN+gGT+Asn+Arg+Lys; 0.773, 247.763, 1+ALB+AST+ALT+Glc+Asn+Arg; 0.773, 251.801, 1+BCAA+Trp+Lys+Phe+ALB+BUN; 0.773, 248.829, 1+ALB+AST+ALT+Asn+Lys+Val; 0.773, 249.503, 1+ALB+ALT+gGT+T-BIL+Asn+Lys; 0.773, 248.918, 1+ALB+BUN+AST+BHBA+Asn+Orn; 0.773, 249.625, 1+Ala+Trp+ALT+ALB+BUN+Ca; 0.773, 251.672, 1+ALB+T-BIL+BHBA+His+Asn+Arg; 0.773, 248.804, 1+ALB+AST+ALT+gGT+Glc+Asn; 0.773, 248.883, 1+ALB+ALT+Asn+Arg+Lys+Phe; 0.773, 249.256, 1+Ala+Phe+TG+ALT+ALB+BUN; 0.773, 249.466, 1+ALB+ALT+T-BIL+BHBA+Asn+Lys; 0.773, 249.834, 1+ALB+BUN+BHBA+Glc+Asn+Orn; 0.773, 251.115, 1+ALB+AST+NEFA+BHBA+His+Asn; 0.773, 245.699, 1+ALB+BUN+ALT+3MeHis+Asp+Phe; 0.773, 248.930, 1+ALB+Ca+ALT+NEFA+Asn+Arg; 0.773, 248.621, 1+ALB+BUN+Ca+AST+Glc+Asn; 0.773, 250.041, 1+ALB+BUN+Ca+BHBA+Asn+Thr; 0.773, 249.480, 1+ALB+Ca+ALT+gGT+Asn+Orn; 0.773, 249.264, 1+ALB+Ca+ALT+T-BIL+Asn+Orn; 0.773, 249.499, 1+ALB+ALT+gGT+NEFA+Asn+Lys; 0.773, 248.040, 1+ALB+AST+ALT+Glc+Asn+Orn; 0.773, 249.578, 1+ALB+Asn+3MeHis+Asp+Val+Trp; 0.773, 251.476, 1+ALB+AST+Asn+3MeHis+Lys+Tyr; 0.773, 251.050, 1+ALB+AST+Asn+Arg+Val+Trp; 0.773, 250.207, 1+ALB+BUN+Ca+Asn+Orn+Lys; 0.773, 248.842, 1+ALB+Ca+ALT+Glc+Asn+Lys; 0.773, 248.869, 1+ALB+ALT+BHBA+Asn+Arg+Lys; 0.773, 253.536, 1+ALB+Asn+Arg+Orn+Tyr+Val; 0.773, 249.301, 1+ALB+AST+ALT+Asn+Val+Phe; 0.773, 249.312, 1+ALB+AST+ALT+NEFA+Asn+3MeHis; 0.773, 251.274, 1+ALB+AST+BHBA+His+Asn+Lys; 0.773, 251.693, 1+ALB+AST+Asn+Orn+Tyr+Val; 0.773, 249.481, 1+ALB+Ca+ALT+NEFA+Asn+Orn; 0.773, 252.948, 1+ALB+NEFA+T-BIL+BHBA+His+Asn; 0.773, 249.169, 1+BCAA+Arg+Phe+ALT+ALB+BUN; 0.773, 251.399, 1+ALB+Asn+Arg+Asp+Tyr+Phe; 0.773, 248.666, 1+ALB+AST+ALT+NEFA+Asn+Orn; 0.773, 248.749, 1+ALB+BUN+AST+T-BIL+Asn+Orn; 0.773, 248.788, 1+ALB+BUN+Ca+BHBA+His+Asn; 0.773, 252.640, 1+ALB+T-BIL+Glc+Asn+Thr+Lys; 0.773, 249.569, 1+ALB+ALT+gGT+BHBA+Asn+Lys; 0.773, 252.242, 1+ALB+T-BIL+BHBA+Glc+His+Asn; 0.773, 248.648, 1+ALB+AST+ALT+Asn+Orn+Lys; 0.773, 249.288, 1+ALB+BUN+ALT+Lys+Val+Trp; 0.773, 248.671, 1+ALB+BUN+AST+T-BIL+Asn+Arg; 0.773, 248.902, 1+ALB+Ca+ALT+BHBA+Asn+Arg; 0.773, 253.238, 1+ALB+gGT+NEFA+Glc+Asn+Thr; 0.773, 252.100, 1+Ala+Trp+Lys+Tyr+ALB+BUN; 0.773, 252.876, 1+ALB+Asn+3MeHis+Arg+Orn+Val; 0.773, 253.593, 1+ALB+Asn+3MeHis+Lys+Val+Phe; 0.773, 248.892, 1+ALB+ALT+gGT+Asn+Arg+Lys; 0.773, 248.886, 1+Lys+Phe+Tyr+ALT+ALB+BUN; 0.773, 248.902, 1+Trp+Phe+ALT+ALB+BUN+NEFA; 0.773, 250.613, 1+ALB+AST+gGT+Asn+Thr+Orn; 0.773, 250.910, 1+ALB+Ca+AST+NEFA+Asn+Ile; 0.773, 248.740, 1+ALB+Ca+ALT+T-BIL+Asn+Arg; 0.773, 250.394, 1+ALB+gGT+Glc+His+Asn+Arg; 0.773, 253.531, 1+ALB+T-BIL+BHBA+Asn+Thr+Lys; 0.773, 249.008, 1+Ala+Arg+Phe+ALT+ALB+BUN; 0.773, 252.422, 1+ALB+T-BIL+Glc+Asn+Thr+Orn; 0.773, 253.487, 1+ALB+NEFA+Asn+Lys+Val+Trp; 0.773, 248.898, 1+Trp+Thr+Phe+ALT+ALB+BUN; 0.773, 250.573, 1+ALB+AST+T-BIL+Asn+Thr+Orn; 0.773, 251.382, 1+ALB+AST+NEFA+T-BIL+Asn+Lys; 0.773, 250.171, 1+ALB+Ca+ALT+NEFA+BHBA+Asn; 0.773, 250.029, 1+ALB+BUN+Ca+Glc+Asn+Arg; 0.773, 251.358, 1+ALB+T-BIL+His+Asn+Arg+Thr; 0.773, 252.246, 1+ALB+NEFA+Glc+Asn+Arg+Thr; 0.773, 253.320, 1+ALB+gGT+NEFA+BHBA+His+Asn; 0.773, 250.081, 1+BCAA+Phe+ALT+gGT+ALB+BUN; 0.773, 246.902, 1+Trp+Phe+ALT+ALB+BUN; 0.773, 249.293, 1+ALB+BUN+ALT+3MeHis+Val+Phe; 0.773, 249.434, 1+ALB+BUN+ALT+3MeHis+Tyr+Phe; 0.773, 248.378, 1+Trp+Lys+Phe+ALT+ALB+BUN; 0.773, 248.899, 1+ALB+BUN+AST+Asn+Arg+Orn; 0.773, 251.183, 1+ALB+AST+NEFA+Asn+Lys+Trp; 0.773, 249.023, 1+ALB+Ca+AST+ALT+Asn+Thr; 0.773, 248.857, 1+ALB+AST+ALT+Asn+3MeHis+Phe; 0.773, 252.926, 1+ALB+gGT+NEFA+T-BIL+His+Asn; 0.773, 246.453, 1+ALB+AST+ALT+Asn+Asp+Val; 0.773, 248.225, 1+ALB+AST+ALT+Asn+Arg+Lys; 0.773, 248.627, 1+ALB+AST+Asn+Arg+Asp+Tyr; 0.773, 248.562, 1+Trp+Phe+TCHO+ALT+ALB+BUN; 0.773, 249.910, 1+ALB+BUN+gGT+Glc+Asn+Arg; 0.773, 252.897, 1+ALB+NEFA+BHBA+Asn+Arg+Thr; 0.773, 253.368, 1+ALB+NEFA+BHBA+Glc+Asn+Thr; 0.773, 253.455, 1+ALB+Asn+Arg+Orn+Val+Trp; 0.773, 247.022, 1+ALB+ALT+Asn+Asp+Val+Phe; 0.773, 250.032, 1+ALB+Asn+3MeHis+Asp+Orn+Val; 0.773, 250.614, 1+ALB+BUN+gGT+BHBA+Asn+Orn; 0.773, 251.428, 1+ALB+Asn+Asp+Orn+Tyr+Val; 0.773, 251.943, 1+Ala+Gly+Trp+Phe+ALB+BUN; 0.773, 249.067, 1+ALB+BUN+AST+T-BIL+BHBA+Asn; 0.773, 247.831, 1+ALB+AST+NEFA+Asn+Asp+Tyr; 0.773, 250.492, 1+ALB+BUN+Ca+BHBA+Asn+Orn; 0.773, 254.028, 1+ALB+gGT+NEFA+T-BIL+Asn+Thr; 0.773, 250.829, 1+ALB+BUN+gGT+T-BIL+BHBA+Asn; 0.773, 248.967, 1+ALB+AST+ALT+T-BIL+Asn+Lys; 0.773, 249.373, 1+ALB+AST+ALT+Asn+3MeHis+Val; 0.773, 250.500, 1+ALB+BUN+Asn+Arg+Orn+Phe; 0.773, 251.634, 1+Ala+Gly+Trp+Lys+ALB+BUN; 0.773, 250.071, 1+BCAA+Phe+Glc+ALT+ALB+BUN; 0.773, 248.453, 1+ALB+AST+ALT+Asn+3MeHis+Orn; 0.773, 248.891, 1+Trp+Phe+Glc+ALT+ALB+BUN; 0.773, 250.015, 1+Gly+Phe+ALT+gGT+ALB+BUN; 0.773, 248.993, 1+ALB+BUN+AST+gGT+T-BIL+Asn; 0.773, 252.304, 1+ALB+Ca+T-BIL+Glc+His+Asn; 0.773, 250.170, 1+ALB+BUN+Ca+gGT+Asn+Lys; 0.772, 252.250, 1+ALB+Glc+Asn+Thr+Orn+Lys; 0.772, 247.188, 1+ALB+BUN+ALT+Asp+Tyr+Phe; 0.772, 248.813, 1+ALB+AST+ALT+T-BIL+Glc+Asn; 0.772, 249.340, 1+Ala+Thr+Phe+ALT+ALB+BUN; 0.772, 250.387, 1+ALB+BUN+gGT+T-BIL+Asn+Arg; 0.772, 251.705, 1+ALB+AST+NEFA+BHBA+Asn+Thr; 0.772, 254.977, 1+ALB+T-BIL+BHBA+Asn+Thr+Ile; 0.772, 252.833, 1+ALB+T-BIL+Glc+Asn+Thr+Ile; 0.772, 246.540, 1+ALB+BUN+ALT+Asp+Lys+Trp; 0.772, 248.732, 1+Trp+Phe+ALT+ALB+BUN+BHBA; 0.772, 248.737, 1+ALB+AST+ALT+BHBA+Asn+Orn; 0.772, 249.448, 1+Trp+Lys+ALT+gGT+ALB+BUN; 0.772, 250.697, 1+ALB+AST+BHBA+Asn+Thr+Orn; 0.772, 250.992, 1+ALB+AST+gGT+NEFA+His+Asn; 0.772, 248.881, 1+ALB+BUN+AST+BHBA+Asn+Arg; 0.772, 250.515, 1+Ala+Gly+Trp+His+ALB+BUN; 0.772, 249.155, 1+Ala+Phe+TCHO+ALT+ALB+BUN; 0.772, 249.361, 1+Ala+Phe+ALT+ALB+BUN+Ca; 0.772, 248.922, 1+ALB+Ca+ALT+gGT+Asn+Arg; 0.772, 252.763, 1+ALB+Ca+NEFA+Asn+Thr+Orn; 0.772, 252.124, 1+ALB+Ca+Glc+His+Asn+Ile; 0.772, 254.051, 1+ALB+NEFA+T-BIL+BHBA+Asn+Thr; 0.772, 250.516, 1+ALB+AST+Asn+Arg+Thr+Orn; 0.772, 250.919, 1+ALB+AST+NEFA+Asn+Orn+Trp; 0.772, 248.905, 1+ALB+Ca+ALT+Asn+Arg+Orn; 0.772, 250.064, 1+ALB+BUN+Ca+BHBA+Asn+Lys; 0.772, 250.832, 1+ALB+NEFA+Asn+Asp+Tyr+Val; 0.772, 248.737, 1+ALB+BUN+ALT+Orn+Phe+Trp; 0.772, 253.142, 1+ALB+Ca+NEFA+BHBA+His+Asn; 0.772, 249.304, 1+ALB+Ca+ALT+Asn+Orn+Lys; 0.772, 248.957, 1+ALB+AST+ALT+BHBA+Asn+Lys; 0.772, 249.299, 1+ALB+Asn+3MeHis+Asp+Tyr+Val; 0.772, 250.983, 1+ALB+AST+Glc+His+Asn+Thr; 0.772, 251.440, 1+ALB+AST+Asn+Arg+Tyr+Phe; 0.772, 250.042, 1+BCAA+Phe+ALT+ALB+BUN+Ca; 0.772, 250.195, 1+ALB+Ca+ALT+gGT+NEFA+Asn; 0.772, 254.542, 1+ALB+gGT+NEFA+BHBA+Asn+Thr; 0.772, 253.021, 1+ALB+T-BIL+BHBA+Glc+Asn+Ile; 0.772, 251.470, 1+ALB+gGT+His+Asn+Arg+Lys; 0.772, 251.556, 1+ALB+Asn+Asp+Lys+Tyr+Phe; 0.772, 248.309, 1+ALB+AST+ALT+Glc+Asn+Lys; 0.772, 248.686, 1+ALB+AST+ALT+T-BIL+Asn+Orn; 0.772, 249.229, 1+ALB+BUN+AST+gGT+BHBA+Asn; 0.772, 249.776, 1+ALB+AST+T-BIL+His+Asn+Arg; 0.772, 251.048, 1+ALB+AST+NEFA+T-BIL+Asn+Orn; 0.772, 248.619, 1+ALB+Ca+AST+ALT+His+Asn; 0.772, 250.618, 1+ALB+BUN+Ca+gGT+T-BIL+Asn; 0.772, 250.017, 1+ALB+BUN+Ca+NEFA+Asn+Arg; 0.772, 249.800, 1+ALB+Asn+3MeHis+Asp+Lys+Trp; 0.772, 250.811, 1+ALB+AST+NEFA+T-BIL+His+Asn; 0.772, 251.320, 1+ALB+AST+Asn+Arg+Lys+Tyr; 0.772, 248.643, 1+ALB+AST+ALT+BHBA+Glc+Asn; 0.772, 252.096, 1+Ala+Gly+Trp+Arg+ALB+BUN; 0.772, 250.579, 1+ALB+AST+BHBA+Glc+His+Asn; 0.772, 251.537, 1+ALB+AST+gGT+Asn+Thr+Lys; 0.772, 252.137, 1+Ala+Gly+Lys+His+ALB+BUN; 0.772, 248.311, 1+Lys+Phe+ALT+ALB+BUN+TP; 0.772, 248.912, 1+Phe+His+ALT+ALB+BUN+TP; 0.772, 249.049, 1+ALB+AST+Asn+Asp+Lys+Tyr; 0.772, 248.859, 1+ALB+BUN+Ca+AST+Asn+Orn; 0.772, 250.247, 1+ALB+Ca+ALT+gGT+BHBA+Asn; 0.772, 250.448, 1+ALB+BUN+Ca+Asn+Arg+Orn; 0.772, 250.095, 1+ALB+BUN+Ca+gGT+Glc+Asn; 0.772, 250.482, 1+ALB+BUN+gGT+Asn+Arg+Orn; 0.772, 251.779, 1+ALB+Asn+Asp+Orn+Val+Trp; 0.772, 254.002, 1+ALB+NEFA+Asn+Arg+Orn+Val; 0.772, 249.844, 1+Gly+BCAA+Phe+ALT+ALB+BUN; 0.772, 251.481, 1+ALB+AST+BHBA+Asn+Thr+Lys; 0.772, 248.494, 1+ALB+BUN+Ca+AST+NEFA+Asn; 0.772, 249.350, 1+ALB+AST+ALT+Asn+3MeHis+Tyr; 0.772, 249.855, 1+ALB+BUN+gGT+BHBA+Glc+Asn; 0.772, 249.961, 1+Phe+Tyr+ALT+ALB+BUN+NEFA; 0.772, 251.262, 1+ALB+AST+gGT+Glc+His+Asn; 0.772, 252.158, 1+ALB+AST+T-BIL+Asn+Thr+Ile; 0.772, 251.064, 1+ALB+AST+Asn+Arg+Phe+Trp; 0.772, 250.861, 1+ALB+Ca+AST+Glc+Asn+Ile; 0.772, 250.178, 1+ALB+BUN+Ca+Asn+Arg+Lys; 0.772, 250.483, 1+ALB+BUN+Ca+gGT+Asn+Orn; 0.772, 252.637, 1+ALB+Asn+3MeHis+Arg+Lys+Val; 0.772, 251.942, 1+ALB+NEFA+Asn+Asp+Lys+Val; 0.772, 251.309, 1+ALB+AST+Asn+Arg+Orn+Trp; 0.772, 252.397, 1+Ala+Gly+Trp+TG+ALB+BUN; 0.772, 252.407, 1+ALB+AST+T-BIL+BHBA+Asn+Ile; 0.772, 250.703, 1+ALB+BUN+Ca+T-BIL+BHBA+Asn; 0.772, 249.408, 1+ALB+Ca+ALT+NEFA+Asn+Lys; 0.772, 251.824, 1+ALB+BHBA+Glc+His+Asn+Ile; 0.772, 252.251, 1+Ala+Trp+Lys+Thr+ALB+BUN; 0.772, 249.247, 1+Ala+Phe+ALT+AST+ALB+BUN; 0.772, 252.338, 1+ALB+Asn+3MeHis+Arg+Val+Trp; 0.772, 253.256, 1+ALB+NEFA+Asn+3MeHis+Lys+Trp; 0.772, 249.060, 1+Ala+Trp+ALT+AST+ALB+BUN; 0.772, 249.549, 1+BCAA+Thr+Phe+ALT+ALB+BUN; 0.772, 249.821, 1+BCAA+Phe+ALT+ALB+BUN+TP; 0.772, 248.615, 1+Trp+Lys+His+ALT+ALB+BUN; 0.772, 249.000, 1+Phe+His+ALT+ALB+BUN+NEFA; 0.772, 250.820, 1+ALB+AST+NEFA+Asn+Arg+Trp; 0.772, 254.207, 1+ALB+T-BIL+BHBA+His+Asn+Ile; 0.772, 252.867, 1+Ala+Trp+Thr+Phe+ALB+BUN; 0.772, 251.354, 1+ALB+AST+NEFA+Asn+Phe+Trp; 0.772, 249.238, 1+Trp+Lys+His+ALB+BUN+TP; 0.772, 249.421, 1+ALB+Ca+ALT+T-BIL+Asn+Lys; 0.772, 252.935, 1+ALB+gGT+Glc+Asn+Thr+Lys; 0.772, 251.406, 1+ALB+gGT+His+Asn+Arg+Thr; 0.772, 253.324, 1+ALB+Asn+3MeHis+Lys+Phe+Trp; 0.772, 250.194, 1+Phe+Tyr+ALT+gGT+ALB+BUN; 0.772, 250.247, 1+ALB+AST+gGT+His+Asn+Arg; 0.772, 250.709, 1+ALB+AST+BHBA+Glc+Asn+Ile; 0.772, 251.362, 1+ALB+AST+Asn+Arg+Tyr+Val; 0.772, 251.249, 1+ALB+Ca+AST+His+Asn+Lys; 0.772, 250.691, 1+ALB+Ca+Glc+His+Asn+Arg; 0.771, 251.604, 1+ALB+BHBA+His+Asn+Arg+Thr; 0.771, 251.546, 1+ALB+gGT+T-BIL+His+Asn+Arg; 0.771, 252.824, 1+Ala+Trp+Arg+Tyr+ALB+BUN; 0.771, 252.832, 1+ALB+gGT+BHBA+His+Asn+Lys; 0.771, 248.917, 1+ALB+AST+ALT+Asn+Lys+Phe; 0.771, 248.237, 1+ALB+Ca+AST+ALT+Asn+Arg; 0.771, 251.641, 1+ALB+Ca+T-BIL+His+Asn+Arg; 0.771, 252.117, 1+ALB+gGT+T-BIL+Glc+His+Asn; 0.771, 250.497, 1+ALB+BUN+gGT+BHBA+Asn+Arg; 0.771, 248.127, 1+BCAA+Phe+ALT+ALB+BUN; 0.771, 248.668, 1+ALB+AST+ALT+gGT+Asn+Orn; 0.771, 251.731, 1+ALB+AST+Asn+Val+Phe+Trp; 0.771, 249.853, 1+BCAA+Phe+TCHO+ALT+ALB+BUN; 0.771, 249.230, 1+ALB+BUN+Ca+AST+gGT+Asn; 0.771, 252.871, 1+ALB+T-BIL+Asn+Thr+Orn+Lys; 0.771, 254.275, 1+ALB+NEFA+Asn+Lys+Val+Phe; 0.771, 250.033, 1+ALB+Asn+3MeHis+Asp+Orn+Lys; 0.771, 253.451, 1+Ala+Gly+BCAA+Lys+ALB+BUN; 0.771, 248.892, 1+ALB+AST+ALT+gGT+Asn+Lys; 0.771, 248.993, 1+Lys+Phe+ALT+gGT+ALB+BUN; 0.771, 252.524, 1+ALB+AST+BHBA+Asn+Thr+Ile; 0.771, 249.244, 1+Phe+His+TG+ALT+ALB+BUN; 0.771, 251.671, 1+Lys+Phe+His+ALB+BUN+TP; 0.771, 250.355, 1+ALB+BUN+Ca+T-BIL+Asn+Arg; 0.771, 252.925, 1+ALB+gGT+Glc+Asn+Thr+Ile; 0.771, 254.043, 1+ALB+Asn+Lys+Val+Phe+Trp; 0.771, 249.653, 1+ALB+AST+ALT+gGT+BHBA+Asn; 0.771, 250.041, 1+Gly+Phe+Tyr+ALT+ALB+BUN; 0.771, 251.475, 1+ALB+AST+Asn+3MeHis+Lys+Val; 0.771, 252.218, 1+ALB+AST+His+Asn+Thr+Ile; 0.771, 248.862, 1+ALB+BUN+Ca+AST+T-BIL+Asn; 0.771, 254.759, 1+ALB+Asn+3MeHis+Tyr+Val+Phe; 0.771, 252.841, 1+ALB+Asn+Arg+Thr+Orn+Lys; 0.771, 250.126, 1+BCAA+Phe+Tyr+ALT+ALB+BUN; 0.771, 248.274, 1+ALB+BUN+ALT+3MeHis+Lys+Phe; 0.771, 249.455, 1+ALB+BUN+ALT+NEFA+3MeHis+Phe; 0.771, 248.070, 1+Trp+Lys+ALT+ALB+BUN+TP; 0.771, 248.848, 1+Trp+Phe+ALT+ALB+BUN+Ca; 0.771, 252.689, 1+ALB+Ca+gGT+His+Asn+Lys; 0.771, 249.485, 1+ALB+Ca+ALT+BHBA+Asn+Lys; 0.771, 249.657, 1+ALB+AST+ALT+gGT+T-BIL+Asn; 0.771, 250.947, 1+ALB+AST+Glc+Asn+Thr+Lys; 0.771, 249.977, 1+BCAA+Phe+TG+ALT+ALB+BUN; 0.771, 248.789, 1+ALB+Ca+AST+ALT+Glc+Asn; 0.771, 252.647,

1+ALB+Ca+NEFA+T-BIL+His+Asn; 0.771, 253.104, 1+ALB+NEFA+T-BIL+Glc+Asn+Lys; 0.771, 249.928, 1+ALB+Asn+3MeHis+Asp+Lys+Phe; 0.771, 248.672, 1+Ala+Lys+His+ALT+ALB+BUN; 0.771, 250.033, 1+ALB+Asn+3MeHis+Asp+Phe+Trp; 0.771, 252.133, 1+ALB+AST+Asn+Orn+Lys+Val; 0.771, 251.189, 1+ALB+AST+NEFA+Asn+3MeHis+Lys; 0.771, 249.321, 1+ALB+AST+NEFA+Asn+Asp+Lys; 0.771, 251.896, 1+ALB+Asn+Asp+Lys+Val+Trp; 0.771, 251.097, 1+ALB+Asn+Arg+Asp+Tyr+Val; 0.771, 251.459, 1+ALB+Asn+Asp+Lys+Tyr+Val; 0.771, 250.595, 1+Ala+Gly+Trp+ALB+BUN; 0.771, 250.601, 1+ALB+AST+Asn+3MeHis+Orn+Trp; 0.771, 252.575, 1+ALB+Ca+BHBA+His+Asn+Lys; 0.771, 252.943, 1+ALB+BHBA+Asn+Thr+Orn+Lys; 0.771, 252.433, 1+Ala+Trp+Lys+Phe+ALB+BUN; 0.771, 253.592, 1+ALB+Asn+3MeHis+Val+Phe+Trp; 0.771, 251.754, 1+ALB+AST+NEFA+BHBA+Asn+Lys; 0.771, 251.527, 1+ALB+Ca+AST+Asn+Thr+Lys; 0.771, 254.165, 1+ALB+T-BIL+His+Asn+Thr+Ile; 0.771, 253.695, 1+ALB+NEFA+T-BIL+BHBA+Asn+Orn; 0.771, 253.492, 1+ALB+NEFA+Asn+Arg+Val+Trp; 0.771, 249.988, 1+ALB+NEFA+Asn+3MeHis+Asp+Lys; 0.771, 248.860, 1+ALB+Ca+ALT+Asn+Arg+Lys; 0.771, 249.901, 1+ALB+BUN+Ca+BHBA+Glc+Asn; 0.771, 253.258, 1+ALB+NEFA+Asn+3MeHis+Orn+Trp; 0.771, 254.257, 1+ALB+NEFA+Asn+Val+Phe+Trp; 0.771, 248.961, 1+Gly+Lys+Phe+ALT+ALB+BUN; 0.771, 249.993, 1+ALB+BUN+ALT+NEFA+Val+Phe; 0.771, 252.575, 1+Ala+Gly+Trp+ALB+BUN+NEFA; 0.771, 251.882, 1+ALB+AST+T-BIL+His+Asn+Ile; 0.771, 252.900, 1+ALB+AST+Asn+Lys+Tyr+Phe; 0.771, 250.854, 1+ALB+Ca+AST+NEFA+His+Asn; 0.771, 252.983, 1+ALB+Ca+NEFA+His+Asn+Thr; 0.771, 248.868, 1+ALB+BUN+Ca+AST+Asn+Arg; 0.771, 250.447, 1+ALB+BUN+Ca+BHBA+Asn+Arg; 0.771, 252.736, 1+ALB+gGT+T-BIL+Glc+Asn+Ile; 0.771, 252.594, 1+Ala+Gly+Trp+Glc+ALB+BUN; 0.771, 249.485, 1+ALB+Ca+ALT+gGT+Asn+Lys; 0.771, 252.957, 1+ALB+NEFA+T-BIL+Glc+Asn+Orn; 0.771, 253.276, 1+ALB+Asn+3MeHis+Orn+Phe+Trp; 0.771, 250.024, 1+ALB+Asn+3MeHis+Arg+Asp+Lys; 0.771, 251.066, 1+ALB+AST+Asn+Arg+Thr+Lys; 0.771, 250.171, 1+ALB+AST+BHBA+His+Asn+Arg; 0.771, 250.155, 1+ALB+Ca+ALT+gGT+T-BIL+Asn; 0.771, 252.561, 1+ALB+gGT+Glc+His+Asn+Thr; 0.771, 252.908, 1+ALB+gGT+Asn+Thr+Orn+Lys; 0.771, 253.307, 1+ALB+T-BIL+BHBA+Asn+Thr+Orn; 0.771, 253.337, 1+ALB+NEFA+Glc+Asn+Orn+Lys; 0.771, 254.755, 1+ALB+NEFA+Asn+3MeHis+Tyr+Val; 0.771, 249.536, 1+ALB+BUN+ALT+Arg+Val+Phe; 0.771, 251.028, 1+Ala+Trp+Phe+ALB+BUN; 0.771, 249.982, 1+ALB+Asn+3MeHis+Arg+Asp+Trp; 0.771, 248.888, 1+ALB+AST+NEFA+Asn+Asp+Trp; 0.771, 252.476, 1+ALB+Ca+Glc+Asn+Thr+Orn; 0.771, 249.663, 1+ALB+AST+ALT+T-BIL+BHBA+Asn; 0.771, 253.509, 1+ALB+gGT+T-BIL+Asn+Thr+Lys; 0.771, 250.478, 1+ALB+NEFA+Asn+3MeHis+Asp+Val; 0.771, 253.637, 1+ALB+NEFA+Asn+3MeHis+Val+Trp; 0.771, 249.949, 1+Thr+Phe+Tyr+ALT+ALB+BUN; 0.771, 252.575, 1+Ala+Gly+Trp+Thr+ALB+BUN; 0.771, 251.440, 1+ALB+AST+NEFA+BHBA+Asn+Orn; 0.771, 249.189, 1+Gly+Phe+His+ALT+ALB+BUN; 0.771, 251.464, 1+ALB+AST+NEFA+Asn+Orn+Lys; 0.770, 252.852, 1+ALB+NEFA+T-BIL+Glc+Asn+Arg; 0.770, 250.168, 1+Phe+Glc+ALT+gGT+ALB+BUN; 0.770, 246.670, 1+ALB+AST+Asn+3MeHis+Asp+Tyr; 0.770, 251.385, 1+ALB+AST+Asn+Orn+Lys+Trp; 0.770, 250.400, 1+ALB+BUN+Ca+gGT+Asn+Arg; 0.770, 250.040, 1+ALB+Asn+3MeHis+Arg+Asp+Val; 0.770, 252.936, 1+Ala+Trp+Arg+Phe+ALB+BUN; 0.770, 253.005, 1+Ala+Trp+Phe+gGT+ALB+BUN; 0.770, 249.066, 1+ALB+BUN+ALT+Orn+Lys+Phe; 0.770, 251.765, 1+ALB+NEFA+Asn+Asp+Val+Trp; 0.770, 252.322, 1+ALB+NEFA+Asn+Asp+Orn+Val; 0.770, 252.893, 1+ALB+AST+Asn+Lys+Tyr+Val; 0.770, 247.370, 1+ALB+AST+Asn+3MeHis+Asp+Trp; 0.770, 249.799, 1+Gly+Phe+TCHO+ALT+ALB+BUN; 0.770, 253.121, 1+ALB+Ca+gGT+NEFA+His+Asn; 0.770, 253.310, 1+ALB+Ca+NEFA+Glc+Asn+Thr; 0.770, 252.382, 1+ALB+gGT+Glc+Asn+Thr+Orn; 0.770, 245.671, 1+ALB+BUN+ALT+3MeHis+Asp+Lys; 0.770, 248.086, 1+Gly+Phe+ALT+ALB+BUN; 0.770, 249.566, 1+Trp+Lys+Tyr+ALT+ALB+BUN; 0.770, 249.566, 1+ALB+BUN+ALT+Orn+Lys+Trp; 0.770, 250.934, 1+ALB+AST+Asn+3MeHis+Lys+Trp; 0.770, 249.936, 1+Phe+Tyr+TCHO+ALT+ALB+BUN; 0.770, 250.207, 1+Phe+Tyr+Glc+ALT+ALB+BUN; 0.770, 253.004, 1+Ala+Trp+Phe+TG+ALB+BUN; 0.770, 253.015, 1+Ala+Trp+Phe+Glc+ALB+BUN; 0.770, 251.970, 1+ALB+AST+T-BIL+His+Asn+Thr; 0.770, 247.566, 1+Trp+Lys+ALT+ALB+BUN; 0.770, 250.682, 1+ALB+AST+NEFA+Glc+Asn+Orn; 0.770, 252.478, 1+ALB+AST+gGT+T-BIL+Asn+Ile; 0.770, 248.624, 1+Trp+Phe+ALT+AST+ALB+BUN; 0.770, 249.369, 1+ALB+Ca+AST+ALT+NEFA+Asn; 0.770, 252.957, 1+ALB+Ca+T-BIL+Glc+Asn+Ile; 0.770, 250.422, 1+ALB+BHBA+Glc+His+Asn+Arg; 0.770, 252.247, 1+ALB+NEFA+T-BIL+Asn+Arg+Thr; 0.770, 253.103, 1+ALB+NEFA+Asn+3MeHis+Arg+Val; 0.770, 249.485, 1+ALB+BUN+ALT+NEFA+Arg+Phe; 0.770, 248.956, 1+ALB+BUN+ALT+NEFA+Lys+Phe; 0.770, 252.194, 1+ALB+AST+Asn+Orn+Val+Phe; 0.770, 249.565, 1+Trp+Lys+Thr+ALT+ALB+BUN; 0.770, 250.958, 1+ALB+AST+NEFA+Asn+3MeHis+Trp; 0.770, 252.971, 1+ALB+Ca+Glc+Asn+Thr+Lys; 0.770, 252.710, 1+ALB+BHBA+Glc+Asn+Thr+Lys; 0.770, 253.540, 1+ALB+NEFA+BHBA+Glc+Asn+Lys; 0.770, 251.773, 1+ALB+gGT+BHBA+His+Asn+Arg; 0.770, 251.192, 1+ALB+AST+T-BIL+Asn+Arg+Thr; 0.770, 249.537, 1+Gly+Trp+Lys+ALT+ALB+BUN; 0.770, 254.049, 1+ALB+Ca+gGT+NEFA+Asn+Ile; 0.770, 252.835, 1+ALB+Asn+3MeHis+Arg+Lys+Trp; 0.770, 253.775, 1+ALB+NEFA+Asn+3MeHis+Phe+Trp; 0.770, 251.547, 1+ALB+AST+T-BIL+Glc+Asn+Thr; 0.770, 252.384, 1+ALB+AST+gGT+His+Asn+Ile; 0.770, 249.565, 1+Trp+Lys+Glc+ALT+ALB+BUN; 0.770, 250.904, 1+Ala+Trp+Lys+AST+ALB+BUN; 0.770, 249.003, 1+ALB+BUN+Ca+AST+BHBA+Asn; 0.770, 252.389, 1+ALB+Glc+Asn+Arg+Thr+Orn; 0.770, 252.420, 1+ALB+BHBA+Glc+Asn+Thr+Orn; 0.770, 254.106, 1+ALB+NEFA+BHBA+Asn+Orn+Lys; 0.770, 248.869, 1+ALB+BUN+AST+ALT+Lys+Phe; 0.770, 249.321, 1+ALB+BUN+AST+ALT+3MeHis+Phe; 0.770, 251.358, 1+Ala+Trp+Lys+ALB+BUN+TP; 0.770, 249.563, 1+Trp+Lys+ALT+ALB+BUN+NEFA; 0.770, 251.551, 1+ALB+AST+gGT+NEFA+Asn+Thr; 0.770, 251.622, 1+ALB+AST+Asn+Lys+Phe+Trp; 0.770, 250.116, 1+ALB+Ca+ALT+T-BIL+BHBA+Asn; 0.770, 250.639, 1+ALB+Ca+AST+Asn+Thr+Orn; 0.770, 253.493, 1+ALB+NEFA+Asn+3MeHis+Orn+Lys; 0.770, 253.753, 1+ALB+Asn+Arg+Lys+Val+Trp; 0.770, 253.291, 1+ALB+NEFA+Glc+Asn+Arg+Orn; 0.770, 250.347, 1+ALB+NEFA+Asn+3MeHis+Arg+Asp; 0.770, 251.497, 1+ALB+Ca+AST+NEFA+Asn+Thr; 0.770, 248.874, 1+ALB+Ca+AST+ALT+Asn+Lys; 0.770, 253.406, 1+ALB+Ca+T-BIL+Asn+Thr+Lys; 0.770, 252.695, 1+ALB+Glc+Asn+Arg+Thr+Lys; 0.770, 253.674, 1+ALB+gGT+NEFA+T-BIL+

Asn+Orn; 0.770, 248.955, 1+ALB+BUN+ALT+3MeHis+Orn+Phe; 0.770, 252.585, 1+Ala+Gly+Trp+gGT+ALB+BUN; 0.770, 247.717, 1+ALB+BUN+ALT+Arg+Asp+Trp; 0.770, 249.209, 1+ALB+AST+Asn+Asp+Val+Trp; 0.770, 254.311, 1+ALB+T-BIL+BHBA+His+Asn+Thr; 0.770, 253.103, 1+ALB+T-BIL+Asn+Arg+Thr+Orn; 0.770, 252.525, 1+Ala+Trp+Lys+Glc+ALB+BUN; 0.770, 253.292, 1+ALB+NEFA+Glc+Asn+Arg+Lys; 0.770, 250.244, 1+ALB+BUN+ALT+Tyr+Val+Phe; 0.770, 250.051, 1+ALB+Asn+3MeHis+Asp+Orn+Trp; 0.770, 250.076, 1+ALB+NEFA+Asn+3MeHis+Asp+Trp; 0.770, 250.808, 1+ALB+AST+NEFA+T-BIL+Asn+Arg; 0.770, 250.850, 1+ALB+AST+Asn+3MeHis+Val+Trp; 0.770, 252.522, 1+Ala+Trp+Arg+Lys+ALB+BUN; 0.770, 253.433, 1+ALB+NEFA+BHBA+Glc+Asn+Arg; 0.770, 253.848, 1+ALB+NEFA+Asn+Orn+Lys+Trp; 0.770, 253.935, 1+ALB+NEFA+Asn+Lys+Phe+Trp; 0.770, 249.579, 1+ALB+BUN+ALT+NEFA+Orn+Phe; 0.770, 251.859, 1+ALB+AST+Asn+3MeHis+Lys+Phe; 0.770, 248.664, 1+ALB+Ca+AST+ALT+Asn+Orn; 0.770, 254.461, 1+ALB+BHBA+His+Asn+Thr+Ile; 0.770, 253.791, 1+ALB+Asn+Arg+Val+Phe+Trp; 0.770, 247.408, 1+ALB+BUN+ALT+NEFA+Asp+Phe; 0.770, 251.802, 1+ALB+AST+NEFA+Asn+Lys+Phe; 0.770, 249.435, 1+Trp+Lys+ALT+ALB+BUN+BHBA; 0.770, 251.047, 1+ALB+AST+NEFA+Asn+3MeHis+Orn; 0.770, 251.196, 1+ALB+AST+Asn+Orn+Phe+Trp; 0.770, 252.314, 1+ALB+Ca+AST+Asn+Thr+Ile; 0.770, 251.535, 1+ALB+Ca+His+Asn+Arg+Thr; 0.770, 253.167, 1+ALB+Asn+3MeHis+Orn+Lys+Trp; 0.770, 253.530, 1+ALB+NEFA+T-BIL+Asn+Orn+Lys; 0.770, 253.684, 1+ALB+NEFA+Asn+3MeHis+Lys+Phe; 0.770, 254.006, 1+ALB+Asn+Orn+Lys+Phe+Trp; 0.770, 250.481, 1+ALB+Asn+3MeHis+Asp+Val+Phe; 0.770, 249.564, 1+ALB+AST+Asn+Asp+Lys+Trp; 0.769, 250.220, 1+ALB+ALT+gGT+T-BIL+BHBA+Asn; 0.769, 253.255, 1+ALB+Asn+3MeHis+Arg+Val+Phe; 0.769, 253.850, 1+ALB+NEFA+Asn+Arg+Lys+Val; 0.769, 252.864, 1+ALB+Asn+3MeHis+Arg+Orn+Trp; 0.769, 253.078, 1+ALB+NEFA+Asn+3MeHis+Arg+Lys; 0.769, 247.398, 1+ALB+BUN+ALT+Asp+Orn+Phe; 0.769, 250.321, 1+ALB+AST+Asn+3MeHis+Arg+Trp; 0.769, 251.959, 1+ALB+AST+Asn+Arg+Orn+Val; 0.769, 253.248, 1+ALB+NEFA+Asn+3MeHis+Arg+Orn; 0.769, 253.738, 1+ALB+NEFA+Asn+Arg+Lys+Trp; 0.769, 252.249, 1+ALB+Ca+AST+T-BIL+Asn+Ile; 0.769, 253.158, 1+ALB+Ca+Glc+Asn+Thr+Ile; 0.769, 252.782, 1+ALB+Ca+Glc+His+Asn+Thr; 0.769, 253.269, 1+ALB+Ca+BHBA+Asn+Thr+Orn; 0.769, 252.512, 1+Ala+Trp+Lys+TG+ALB+BUN; 0.769, 253.895, 1+ALB+NEFA+Asn+Orn+Phe+Trp; 0.769, 250.352, 1+ALB+Asn+3MeHis+Arg+Asp+Phe; 0.769, 251.840, 1+Ala+Gly+Trp+ALB+BUN+TP; 0.769, 249.474, 1+ALB+AST+Asn+Asp+Orn+Trp; 0.769, 249.550, 1+ALB+AST+Asn+Arg+Asp+Trp; 0.769, 254.228, 1+ALB+Ca+His+Asn+Thr+Ile; 0.769, 253.821, 1+ALB+Ca+NEFA+T-BIL+Asn+Thr; 0.769, 250.366, 1+ALB+Asn+3MeHis+Arg+Asp+Orn; 0.769, 253.965, 1+Ala+Gly+Lys+TG+ALB+BUN; 0.769, 247.457, 1+ALB+BUN+ALT+Arg+Asp+Phe; 0.769, 252.529, 1+ALB+AST+gGT+Asn+Thr+Ile; 0.769, 252.348, 1+ALB+AST+BHBA+His+Asn+Ile; 0.769, 251.477, 1+ALB+AST+Asn+Arg+Lys+Trp; 0.769, 252.521, 1+Ala+Gly+Trp+ALB+BUN+Ca; 0.769, 253.055, 1+ALB+BHBA+Glc+Asn+Thr+Ile; 0.769, 253.109, 1+ALB+BHBA+Asn+Arg+Thr+Orn; 0.769, 252.868, 1+ALB+Asn+3MeHis+Arg+Phe+Trp; 0.769, 251.547, 1+ALB+AST+NEFA+Asn+Orn+Phe; 0.769, 250.953, 1+ALB+AST+NEFA+Glc+Asn+Lys; 0.769, 250.155, 1+ALB+Ca+AST+His+Asn+Arg; 0.769, 250.697, 1+ALB+BUN+Ca+gGT+BHBA+Asn; 0.769, 254.453, 1+ALB+Ca+NEFA+BHBA+Asn+Thr; 0.769, 251.196, 1+ALB+Ca+AST+Glc+His+Asn; 0.769, 252.969, 1+ALB+gGT+BHBA+Glc+Asn+Ile; 0.769, 253.278, 1+ALB+gGT+BHBA+Asn+Thr+Orn; 0.769, 253.201, 1+Ala+Trp+Arg+TG+ALB+BUN; 0.769, 254.324, 1+ALB+gGT+His+Asn+Thr+Ile; 0.769, 254.800, 1+ALB+Asn+Orn+Lys+Val+Phe; 0.769, 250.530, 1+Ala+Trp+Lys+ALB+BUN; 0.769, 251.222, 1+ALB+AST+NEFA+T-BIL+Glc+Asn; 0.769, 251.786, 1+ALB+Asn+Asp+Lys+Phe+Trp; 0.769, 252.525, 1+Ala+Gly+Trp+ALB+BUN+BHBA; 0.769, 251.977, 1+ALB+AST+NEFA+Asn+3MeHis+Tyr; 0.769, 252.853, 1+ALB+AST+gGT+BHBA+Asn+Ile; 0.769, 251.227, 1+ALB+AST+NEFA+Asn+Arg+Val; 0.769, 251.327, 1+ALB+AST+Asn+3MeHis+Orn+Lys; 0.769, 252.089, 1+ALB+AST+NEFA+T-BIL+BHBA+Asn; 0.769, 249.026, 1+ALB+AST+Asn+Asp+Phe+Trp; 0.769, 249.056, 1+Trp+Lys+TCHO+ALT+ALB+BUN; 0.769, 253.256, 1+ALB+Ca+T-BIL+Asn+Thr+Orn; 0.769, 252.253, 1+ALB+BHBA+Glc+His+Asn+Thr; 0.769, 255.088, 1+ALB+gGT+BHBA+Asn+Thr+Ile; 0.769, 253.238, 1+ALB+Asn+3MeHis+Arg+Orn+Lys; 0.769, 249.969, 1+ALB+BUN+ALT+Thr+Lys+Ile; 0.769, 249.506, 1+Trp+Lys+ALT+ALB+BUN+Ca; 0.769, 249.824, 1+Trp+Arg+TG+ALT+ALB+BUN; 0.769, 253.022, 1+ALB+gGT+NEFA+Asn+Arg+Thr; 0.769, 253.059, 1+ALB+T-BIL+Glc+Asn+Arg+Thr; 0.769, 253.273, 1+ALB+gGT+T-BIL+Asn+Thr+Orn; 0.769, 253.763, 1+ALB+NEFA+Asn+3MeHis+Orn+Phe; 0.769, 254.335, 1+ALB+NEFA+Asn+Orn+Lys+Phe; 0.769, 253.725, 1+ALB+NEFA+Asn+Arg+Orn+Trp; 0.769, 254.764, 1+ALB+gGT+NEFA+T-BIL+BHBA+Asn; 0.769, 253.274, 1+ALB+NEFA+T-BIL+Asn+Arg+Orn; 0.769, 251.240, 1+ALB+AST+NEFA+Asn+Arg+Orn; 0.769, 254.885, 1+ALB+Ca+T-BIL+Asn+Thr+Ile; 0.769, 252.854, 1+ALB+Ca+Asn+Thr+Orn+Lys; 0.769, 251.665, 1+ALB+Ca+gGT+His+Asn+Arg; 0.769, 254.960, 1+ALB+gGT+T-BIL+Asn+Thr+Ile; 0.769, 255.089, 1+ALB+gGT+T-BIL+BHBA+Asn+Ile; 0.769, 252.349, 1+ALB+AST+T-BIL+BHBA+His+Asn; 0.769, 252.699, 1+ALB+BUN+3MeHis+Lys+Val+Phe; 0.769, 252.540, 1+ALB+AST+gGT+His+Asn+Thr; 0.769, 250.887, 1+ALB+AST+Glc+Asn+Arg+Thr; 0.769, 250.620, 1+ALB+AST+NEFA+Asn+3MeHis+Arg; 0.769, 251.137, 1+ALB+AST+Asn+3MeHis+Phe+Trp; 0.769, 252.200, 1+Ala+Trp+Lys+TCHO+ALB+BUN; 0.769, 253.471, 1+ALB+gGT+NEFA+Glc+Asn+Lys; 0.769, 254.368, 1+ALB+gGT+NEFA+BHBA+Asn+Lys; 0.769, 252.135, 1+Ala+Trp+Lys+ALB+BUN+NEFA; 0.769, 253.804, 1+ALB+NEFA+T-BIL+BHBA+Asn+Lys; 0.769, 247.519, 1+ALB+BUN+ALT+Asp+Val+Phe; 0.769, 247.518, 1+ALB+BUN+ALT+Asp+Lys+Val; 0.769, 252.199, 1+Gly+Trp+Lys+AST+ALB+TP; 0.769, 249.577, 1+ALB+Ca+AST+ALT+BHBA+Asn; 0.769, 255.077, 1+ALB+Ca+T-BIL+BHBA+Asn+Ile; 0.769, 253.465, 1+ALB+Ca+NEFA+Glc+Asn+Lys; 0.769, 253.700, 1+ALB+Asn+3MeHis+Orn+Lys+Phe; 0.769, 253.716, 1+ALB+gGT+NEFA+T-BIL+Glc+Asn; 0.769, 253.809, 1+ALB+gGT+NEFA+T-BIL+Asn+Lys; 0.769, 253.443, 1+ALB+NEFA+BHBA+Glc+Asn+Orn; 0.769, 252.297, 1+ALB+NEFA+Asn+Arg+Asp+Lys; 0.769, 253.980, 1+Ala+Gly+Lys+Glc+ALB+BUN; 0.769, 249.236, 1+Trp+Arg+Lys+ALT+ALB+BUN; 0.769, 251.430, 1+ALB+AST+BHBA+Asn+Arg+Thr; 0.769, 250.037, 1+Trp+Lys+AST+ALB+BUN+TP; 0.769, 249.570, 1+Ala+Lys+ALT+ALB+BUN+NEFA; 0.769, 252.008, 1+Ala+Gly+Lys+ALB+BUN; 0.769, 252.586, 1+Ala+BCAA+Trp+Arg+ALB+BUN; 0.769, 253.220, 1+Ala+Trp+Arg+Thr+ALB+BUN;

0.769, 249.469, 1+ALB+BUN+ALT+Arg+Orn+Phe; 0.769, 252.294, 1+ALB+NEFA+Asn+Asp+Orn+Lys; 0.769, 252.884, 1+ALB+NEFA+Asn+3Me His+Arg+Trp; 0.769, 251.849, 1+ALB+NEFA+Asn+Asp+Phe+Trp; 0.769, 249.586, 1+ALB+Ca+AST+ALT+T-BIL+Asn; 0.768, 254.454, 1+ALB+gGT+BHBA+His+Asn+Ile; 0.768, 253.013, 1+ALB+gGT+Asn+Arg+Thr+Orn; 0. 768, 254.372, 1+ALB+NEFA+Asn+Arg+Val+Phe; 0.768, 253.718, 1+ALB+NEFA+Asn+Arg+Phe+Trp; 0.768, 249.561, 1+ALB+Ca+AST+ALT+gGT+As n; 0.768, 253.361, 1+ALB+Asn+3MeHis+Arg+Orn+Phe; 0.768, 253.706, 1+ALB+gGT+BHBA+Asn+Thr+Lys; 0.768, 249.407, 1+Ala+Gly+Lys+ALT+ALB+BUN; 0.768, 247.415, 1+ALB+BUN+ALT+Asp+Orn+Lys; 0.768, 247.4 89, 1+ALB+BUN+ALT+NEFA+Asp+Lys; 0.768, 247.540, 1+ALB+BUN+ALT+A sp+Lys+Tyr; 0.768, 249.126, 1+Trp+Lys+ALT+AST+ALB+BUN; 0.768, 24 9.126, 1+ALB+BUN+AST+ALT+Lys+Trp; 0.768, 252.574, 1+ALB+Ca+AST+BHBA+Asn+Ile; 0.768, 255.022, 1+ALB+Ca+BHBA+Asn+Thr+Ile; 0.768, 251.876, 1+ALB+NEFA+Asn+Asp+Lys+Trp; 0.768, 251.950, 1+ALB+NEFA+Asn+Asp+Orn+Trp; 0.768, 251.355, 1+ALB+AST+gGT+NEFA+Asn+Orn; 0. 768, 252.177, 1+ALB+AST+NEFA+Asn+Tyr+Val; 0.768, 249.783, 1+ALB+AST+Asn+Asp+Tyr+Phe; 0.768, 250.420, 1+Ala+ Gly+Trp+AST+ALB+BU N; 0.768, 253.005, 1+ALB+Ca+ gGT+Glc+Asn+Ile; 0.768, 252.129, 1+Al a+Gly+Trp+ TCHO+ALB+BUN; 0.768, 251.874, 1+ALB+Ca+BHBA+ His+Asn+Arg; 0.768, 254.192, 1+ALB+gGT+T-BIL+His+ Asn+Thr; 0.768, 253.837, 1+ALB+Asn+Arg+Lys+Phe+ Trp; 0.768, 251.558, 1+ALB+AST+gGT+NEFA+Asn+Lys; 0.768, 253.064, 1+Ala+Gly+Trp+Lys+AST+ALB; 0.768, 254.3 07, 1+ALB+Ca+BHBA+His+Asn+Ile; 0.768, 254.589, 1+ALB+NEFA+Asn+3 MeHis+Val+Phe; 0.768, 252.963, 1+BCAA+Trp+Lys+gGT+ALB+BUN; 0.76 8, 253.997, 1+Ala+Gly+Lys+Thr+ALB+BUN; 0.768, 251.310, 1+ALB+AST+NEFA+Asn+Arg+Lys; 0.768, 253.572, 1+ALB+Ca+BHBA+Asn+Thr+Lys; 0. 768, 252.362, 1+Ala+Trp+Lys+ALB+BUN+BHBA; 0.768, 249.454, 1+Ala+Arg+Lys+ALT+ALB+BUN; 0.768, 248.678, 1+ALB+BUN+ALT+3MeHis+Arg+Phe; 0.768, 247.687, 1+ALB+AST+Asn+3MeHis+Asp+Lys; 0.768, 252.36 6, 1+Ala+Gly+Trp+Arg+AST+ALB; 0.768, 254.139, 1+ALB+NEFA+Asn+Ar g+Orn+Lys; 0.768, 252.081, 1+ALB+Asn+Arg+Asp+Val+Trp; 0.768, 252. 493, 1+ALB+NEFA+Asn+Asp+Orn+Phe; 0.768, 250.469, 1+ALB+NEFA+Asn+3MeHis+Asp+Orn; 0.768, 250.491, 1+ALB+Asn+3MeHis+Asp+Orn+Phe; 0.768, 252.101, 1+ALB+AST+gGT+Glc+Asn+Thr; 0.768, 249.419, 1+Trp+ Lys+TG+ALT+ALB+BUN; 0.768, 250.061, 1+BCAA+ Trp+Arg+ALT+ALB+BU N; 0.768, 250.173, 1+ALB+ BUN+ALT+Arg+Tyr+Trp; 0.768, 250.333, 1+B CAA+Lys+ Thr+ALT+ALB+BUN; 0.768, 251.359, 1+ALB+AST+ gGT+NEFA+Gl c+Asn; 0.768, 250.556, 1+BCAA+Trp+ Lys+ALB+BUN+TP; 0.768, 252.309, 1+ALB+AST+gGT+ T-BIL+His+Asn; 0.768, 251.409, 1+ALB+AST+Asn+3Me His+Orn+Phe; 0.768, 253.305, 1+ALB+BHBA+Asn+Arg+ Thr+Lys; 0.768, 253.963, 1+ALB+gGT+T-BIL+Glc+Asn+ Thr; 0.768, 250.606, 1+ALB+NEF A+Asn+3MeHis+Asp+ Phe; 0.768, 253.418, 1+ALB+NEFA+T-BIL+BHBA+As n+Arg; 0.768, 252.137, 1+ALB+NEFA+Asn+Asp+Lys+ Phe; 0.768, 249.21 2, 1+ALB+BUN+ALT+3MeHis+Lys+ Trp; 0.768, 252.458, 1+Ala+Trp+Lys+ALB+BUN+Ca; 0.768, 251.066, 1+Ala+Arg+Glc+ALT+ALB+BUN; 0.768, 25 3.350, 1+ALB+NEFA+Asn+3MeHis+Arg+Phe; 0.768, 253.670, 1+Ala+Gly+Lys+ALB+BUN+BHBA; 0.768, 253.919, 1+ALB+NEFA+BHBA+Asn+Arg+Or n; 0.768, 252.252, 1+ALB+BUN+3MeHis+Lys+Val+Trp; 0.768, 252.936, 1+BCAA+Trp+Lys+Thr+ALB+BUN; 0.768, 252.431, 1+ALB+AST+Asn+3MeH is+Tyr+Phe; 0.768, 253.158, 1+ALB+T-BIL+Asn+Arg+Thr+Lys; 0.768, 254.467, 1+ALB+gGT+BHBA+His+Asn+Thr; 0.768, 254.610, 1+Ala+Gly+BCAA+Trp+Lys+ALB; 0.768, 251.915, 1+ALB+Asn+Asp+Orn+Phe+Trp; 0. 768, 252.526, 1+ALB+NEFA+Asn+Arg+Asp+Val; 0.768, 254.042, 1+ALB+Ca+T-BIL+His+Asn+Ile; 0.768, 254.234, 1+ALB+Ca+NEFA+BHBA+Asn+L ys; 0.768, 253.673, 1+ALB+NEFA+T-BIL+BHBA+Glc+Asn; 0.768, 253.81 1, 1+ALB+Asn+Arg+Orn+Phe+Trp; 0.768, 251.250, 1+Ala+ Trp+Arg+ALB+BUN; 0.768, 253.234, 1+ALB+Asn+3Me- His+Arg+Lys+Phe; 0.768, 254.0 11, 1+ALB+Asn+Arg+ Orn+Lys+Trp; 0.768, 250.453, 1+Ala+Arg+Thr+AL T+ALB+BUN; 0.768, 249.809, 1+ALB+BUN+AST+ALT+ NEFA+Phe; 0.768, 24 7.535, 1+ALB+BUN+ALT+Arg+ Asp+Lys; 0.768, 250.867, 1+ALB+AST+Asn+3MeHis+ Arg+Orn; 0.768, 253.050, 1+ALB+Ca+Asn+Arg+Thr+Orn; 0.76 8, 248.018, 1+ALB+BUN+ALT+Asp+Orn+Trp; 0.768, 253.686, 1+Ala+Gly+Arg+Lys+ALB+BUN; 0.768, 254.177, 1+ALB+gGT+T-BIL+His+Asn+Ile; 0.768, 250.150, 1+ALB+BUN+ALT+NEFA+Arg+Trp; 0.768, 250.150, 1+Tr p+Arg+ALT+ALB+BUN+NEFA; 0.768, 250.714, 1+ALB+AST+Asn+3MeHis+A rg+Val; 0.768, 251.474, 1+BCAA+Trp+Lys+AST+ALB+BUN; 0.768, 252.6 73, 1+ALB+Ca+gGT+Glc+His+Asn; 0.768, 254.632, 1+ALB+Asn+Arg+Orn+Lys+Val; 0.768, 248.187, 1+Trp+ Arg+ALT+ALB+BUN; 0.768, 250.168, 1+Trp+Arg+ALT+ gGT+ALB+BUN; 0.768, 248.156, 1+ALB+BUN+ALT+ Asp+V al+Trp; 0.767, 253.187, 1+ALB+Ca+BHBA+Glc+ Asn+Ile; 0.767, 253.18 8, 1+ALB+Ca+gGT+Asn+Thr+Orn; 0.767, 253.899, 1+ALB+T-BIL+BHBA+A sn+Arg+Thr; 0.767, 252.990, 1+Ala+Trp+Arg+ALB+BUN+NEFA; 0.767, 2 50.176, 1+Trp+Arg+ALT+ALB+BUN+BHBA; 0.767, 250.673, 1+ALB+AST+N EFA+Glc+Asn+Arg; 0.767, 252.365, 1+ALB+AST+BHBA+His+Asn+Thr; 0. 767, 249.764, 1+ALB+BUN+ALT+His+Thr+Lys; 0.767, 253.342, 1+ALB+g GT+NEFA+Glc+Asn+Orn; 0.767, 248.962, 1+ALB+BUN+ALT+Arg+Lys+Ph e; 0.767, 250.093, 1+ALB+BUN+AST+ALT+Tyr+Phe; 0.767, 247.358, 1+A LB+BUN+AST+ALT+Asp+Phe; 0.767, 254.351, 1+ALB+Ca+T-BIL+BHBA+Hi s+Asn; 0.767, 253.507, 1+ALB+Ca+NEFA+T-BIL+Asn+Orn; 0.767, 252.2 52, 1+ALB+Asn+Asp+Orn+Lys+Trp; 0.767, 252.525, 1+Ala+Trp+Arg+AL B+BUN+TP; 0.767, 252.996, 1+ALB+BUN+Lys+Val+Phe+Trp; 0.767, 249. 260, 1+Trp+ Arg+ALT+ALB+BUN+TP; 0.767, 249.812, 1+ALB+BUN+ ALT+3M eHis+Arg+Trp; 0.767, 251.209, 1+ALB+ALT+ Arg+Tyr+Phe+Trp; 0.767, 250.949, 1+ALB+AST+Asn+ 3MeHis+Arg+Lys; 0.767, 251.436, 1+ALB+AS T+NEFA+ BHBA+Glc+Asn; 0.767, 247.798, 1+ALB+AST+Asn+ 3MeHis+Arg+Asp; 0.767, 252.874, 1+Ala+Trp+Arg+ TCHO+ALB+BUN; 0.767, 249.806, 1+Trp+Arg+TCHO+ ALT+ALB+BUN; 0.767, 253.044, 1+ALB+Ca+NEFA+ Asn+Arg+Thr; 0.767, 252.200, 1+ALB+gGT+BHBA+Glc+ His+Asn; 0.767, 253. 242, 1+ALB+gGT+Asn+Arg+Thr+ Lys; 0.767, 253.268, 1+ALB+NEFA+T-BI L+Asn+Arg+ Lys; 0.767, 252.498, 1+ALB+NEFA+Asn+Arg+Asp+Orn; 0.76 7, 250.178, 1+ALB+BUN+ALT+Arg+Val+Trp; 0.767, 252.202, 1+Ala+Gly+Lys+AST+ALB+BUN; 0.767, 253.034, 1+Ala+BCAA+Trp+TCHO+ALB+BUN; 0.767, 254.175, 1+ALB+Ca+NEFA+BHBA+Asn+Orn; 0.767, 254.254, 1+AL B+NEFA+Asn+Arg+Orn+Phe; 0.767, 252.259, 1+ALB+Asn+Arg+Asp+Orn+Trp; 0.767, 251.978, 1+ALB+NEFA+Asn+Arg+Asp+Trp; 0.767, 250.710, 1+ALB+AST+Asn+Arg+Asp+Lys; 0.767, 250.247,

1+ALB+AST+Asn+Asp+Orn+Val; 0.767, 249.393, 1+ALB+AST+NEFA+Asn+Asp+Orn; 0.767, 249.4 31, 1+ALB+AST+NEFA+Asn+Arg+Asp; 0.767, 253.709, 1+ALB+Ca+NEFA+T-BIL+Glc+Asn; 0.767, 254.445, 1+ALB+Ca+gGT+NEFA+Asn+Thr; 0.767, 253.989, 1+Ala+Gly+Lys+gGT+ALB+BUN; 0.767, 254.303, 1+ALB+gGT+N EFA+Asn+Orn+Lys; 0.767, 251.344, 1+Ala+BCAA+Trp+ALB+BUN; 0.767, 250.133, 1+ALB+BUN+ALT+His+Orn+Lys; 0.767, 250.141, 1+ALB+BUN+A LT+Arg+Orn+Trp; 0.767, 249.351, 1+ALB+BUN+ALT+His+Arg+Lys; 0.76 7, 251.402, 1+ALB+AST+NEFA+Asn+Arg+Phe; 0.767, 254.448, 1+ALB+T-BIL+BHBA+Glc+Asn+Lys; 0.767, 253.286, 1+ALB+gGT+NEFA+Glc+Asn+A rg; 0.767, 254.430, 1+ALB+gGT+T-BIL+BHBA+His+Asn; 0.767, 249.717, 1+Ala+Lys+Thr+ALT+ALB+BUN; 0.767, 252.526, 1+BCAA+Trp+Lys+ALB+BUN+NEFA; 0.767, 253.237, 1+Ala+Trp+Arg+Glc+ALB+BUN; 0.767, 250. 378, 1+ALB+BUN+ALT+T-BIL+Lys+Ile; 0.767, 252.433, 1+ALB+AST+NEF A+Asn+Val+Phe; 0.767, 247.847, 1+ALB+AST+NEFA+Asn+3MeHis+Asp; 0. 767, 253.159, 1+Ala+Trp+Arg+ALB+BUN+Ca; 0.767, 253.417, 1+ALB+Ca+NEFA+Glc+Asn+Arg; 0.767, 250.947, 1+Ala+Arg+TG+AST+ALT+ALB+BUN; 0. 767, 249.403, 1+ALB+BUN+AST+ALT+Arg+Phe; 0.767, 250.990, 1+BCAA+Trp+Lys+ALB+BUN; 0.767, 251.930, 1+ALB+Asn+Arg+Asp+Phe+Trp; 0.7 67, 252.989, 1+BCAA+Trp+Lys+Glc+ALB+BUN; 0.767, 253.259, 1+Ala+B CAA+Trp+ALB+BUN+BHBA; 0.767, 249.230, 1+ALB+BUN+3MeHis+Asp+Lys+Phe; 0.767, 252.296, 1+ALB+Asn+Arg+Asp+Lys+Trp; 0.767, 252.990, 1+BCAA+Trp+Lys+TG+ALB+BUN; 0.767, 251.469, 1+ALB+AST+gGT+Asn+A rg+Thr; 0.767, 251.610, 1+ALB+AST+BHBA+Glc+Asn+Thr; 0.767, 252.0 09, 1+Ala+Gly+BCAA+Trp+ALB+BUN; 0.767, 249.398, 1+ALB+BUN+AST+A LT+Orn+Phe; 0.767, 250.073, 1+Gly+Trp+Arg+ALT+ALB+BUN; 0.767, 25 1.345, 1+Ala+Trp+Arg+AST+ALB+BUN; 0.767, 253.145, 1+Ala+Gly+Trp+AST+ALB+TP; 0.767, 253.246, 1+Ala+Trp+Thr+TCHO+ALB+BUN; 0.767, 253.303, 1+Ala+BCAA+Trp+Thr+ALB+BUN; 0.767, 251.980, 1+ALB+Asn+Asp+Val+Phe+Trp; 0.767, 252.335, 1+ALB+AST+T-BIL+Asn+Orn+Lys; 0. 767, 253.124, 1+ALB+BHBA+Glc+Asn+Arg+Thr; 0.767, 251.608, 1+Ala+Trp+Thr+ALB+BUN; 0.767, 247.874, 1+ALB+AST+Asn+3MeHis+Asp+Val; 0.767, 251.636, 1+Ala+Trp+TG+AST+ALB+BUN; 0.767, 251.418, 1+ALB+Ca+AST+Asn+Arg+Thr; 0.767, 254.834, 1+ALB+Ca+gGT+Asn+Thr+Ile; 0. 767, 252.586, 1+ALB+Ca+AST+gGT+Asn+Ile; 0.767, 254.726, 1+ALB+As n+Arg+Orn+Val+Phe; 0.767, 249.716, 1+Ala+Lys+TG+ALT+ALB+BUN; 0. 767, 253.922, 1+ALB+NEFA+BHBA+Asn+Arg+Lys; 0.767, 253.340, 1+Ala+BCAA+Trp+Glc+ALB+BUN; 0.767, 250.414, 1+ALB+BUN+ALT+NEFA+Lys+Ile; 0.767, 250.033, 1+BCAA+Arg+Lys+ALT+ALB+BUN; 0.767, 253.429, 1+Ala+Gly+Lys+TCHO+ALB+BUN; 0.767, 253.577, 1+ALB+Ca+NEFA+T-BI L+Asn+Lys; 0.767, 254.066, 1+ALB+T-BIL+Glc+Asn+Orn+Lys; 0.767, 2 54.119, 1+ALB+T-BIL+BHBA+Glc+Asn+Thr; 0.767, 250.401, 1+Ala+Gly+Arg+ALT+ALB+BUN; 0.767, 252.024, 1+ALB+Asn+Asp+Tyr+Val+Phe; 0. 767, 253.097, 1+Ala+BCAA+Trp+ALB+BUN+NEFA; 0.767, 254.137, 1+ALB+NEFA+Asn+Arg+Lys+Phe; 0.767, 250.910, 1+Ala+Trp+ALB+BUN+TP; 0. 767, 253.330, 1+Ala+BCAA+Trp+TG+ALB+BUN; 0.767, 250.303, 1+ALB+B UN+ALT+gGT+His+Lys; 0.767, 249.531, 1+ALB+AST+NEFA+Asn+Asp+Va l; 0.767, 254.103, 1+ALB+Ca+T-BIL+His+Asn+Thr; 0.767, 249.750, 1+Ala+Lys+Glc+ALT+ALB+BUN; 0.767, 251.382, 1+Ala+Trp+ALB+BUN+NEF A; 0.767, 249.453, 1+ALB+BUN+ALT+Arg+Lys+Ile; 0.766, 252.122, 1+A LB+Ca+AST+His+Asn+Ile; 0.766, 253.627, 1+ALB+Ca+gGT+Asn+Thr+Ly s; 0.766, 252.363, 1+ALB+Ca+BHBA+Glc+His+Asn; 0.766, 252.581, 1+G ly+BCAA+Trp+Lys+ALB+BUN; 0.766, 253.382, 1+Ala+Trp+Glc+ALB+BUN+NEFA; 0.766, 250.109, 1+ALB+BUN+AST+ALT+Val+Phe; 0.766, 250.166, 1+ALB+BUN+ALT+NEFA+His+Lys; 0.766, 253.270, 1+ALB+AST+Asn+Lys+Val+Phe; 0.766, 252.136, 1+ALB+AST+T-BIL+Asn+Arg+Orn; 0.766, 254. 048, 1+ALB+Ca+NEFA+Asn+Arg+Lys; 0.766, 255.466, 1+ALB+gGT+T-BIL+BHBA+Asn+Thr; 0.766, 254.971, 1+ALB+T-BIL+BHBA+Asn+Orn+Lys; 0. 766, 251.293, 1+Ala+Gly+Trp+Arg+ALT+ALB; 0.766, 250.560, 1+ALB+B UN+ALT+NEFA+Thr+Lys; 0.766, 250.809, 1+Ala+Trp+AST+ALB+BUN+TP; 0.766, 248.193, 1+ALB+BUN+ALT+Asp+Tyr+Trp; 0.766, 247.916, 1+ALB+AST+Asn+3MeHis+Asp+Orn; 0.766, 249.616, 1+ALB+BUN+AST+Asp+Lys+Trp; 0.766, 254.143, 1+ALB+Ca+T-BIL+Glc+Asn+Thr; 0.766, 251.590, 1+Ala+Trp+TG+ALB+BUN; 0.766, 248.773, 1+ALB+BUN+3MeHis+Asp+Lys+Trp; 0.766, 251.724, 1+ALB+ALT+Orn+Val+Phe+Trp; 0.766, 252.670, 1+BCAA+Trp+Arg+Lys+ALB+BUN; 0.766, 252.758, 1+ALB+NEFA+Asn+Asp+Val+Phe; 0.766, 249.972, 1+ALB+BUN+ALT+BHBA+His+Lys; 0.766, 249. 770, 1+Ala+Lys+ALT+gGT+ALB+BUN; 0.766, 250.763, 1+ALB+BUN+Asp+L ys+Tyr+Trp; 0.766, 250.150, 1+ALB+BUN+ALT+3MeHis+Orn+Lys; 0.766, 250.169, 1+Trp+Arg+Glc+ALT+ALB+BUN; 0.766, 250.074, 1+ALB+BUN+A LT+T-BIL+His+Lys; 0.766, 251.397, 1+Ala+BCAA+Trp+AST+ALB+BUN; 0. 766, 251.709, 1+Ala+Trp+Thr+AST+ALB+BUN; 0.766, 254.320, 1+ALB+g GT+T-BIL+Glc+Asn+Lys; 0.766, 255.407, 1+ALB+gGT+T-BIL+BHBA+Asn+Lys; 0.766, 253.204, 1+Ala+Trp+Arg+gGT+ALB+BUN; 0.766, 253.483, 1+Ala+Trp+Glc+ALB+BUN+BHBA; 0.766, 252.902, 1+Ala+Trp+TG+ALB+B UN+TP; 0.766, 247.295, 1+ALB+BUN+ALT+3MeHis+Asp+Trp; 0.766, 250. 680, 1+ALB+AST+Asn+Asp+Lys+Val; 0.766, 251.827, 1+ALB+Ca+AST+NE FA+T-BIL+Asn; 0.766, 254.082, 1+ALB+gGT+NEFA+BHBA+Glc+Asn; 0.76 6, 253.278, 1+ALB+BUN+Lys+Tyr+Phe+Trp; 0.766, 249.614, 1+Ala+Trp+ALB+BUN; 0.766, 251.487, 1+Ala+Trp+ALB+BUN+BHBA; 0.766, 250.584, 1+ALB+BUN+ALT+gGT+Thr+Lys; 0.766, 252.851, 1+ALB+AST+gGT+T-BIL+Asn+Lys; 0.766, 253.234, 1+Ala+Trp+TCHO+TG+ALB+BUN; 0.766, 253. 402, 1+ALB+Ca+NEFA+Glc+Asn+Orn; 0.766, 254.226, 1+ALB+gGT+NEFA+BHBA+Asn+Orn; 0.766, 252.545, 1+ALB+NEFA+Asn+Arg+Asp+Phe; 0.766, 252.698, 1+Ala+BCAA+Trp+ALB+BUN+TP; 0.766, 252.907, 1+Ala+Trp+G lc+ALB+BUN+TP; 0.766, 252.794, 1+ALB+AST+T-BIL+BHBA+Asn+Thr; 0. 766, 251.011, 1+ALB+AST+Asn+3MeHis+Arg+Phe; 0.766, 251.297, 1+AL B+AST+gGT+NEFA+Asn+Arg; 0.766, 251.358, 1+ALB+Ca+AST+NEFA+Glc+Asn; 0.766, 252.116, 1+ALB+Ca+AST+T-BIL+His+Asn; 0.766, 253.156, 1+ALB+Asn+Arg+Asp+Lys+Val; 0.766, 253.362, 1+Ala+Trp+gGT+ALB+B UN+NEFA; 0.766, 250.512, 1+ALB+BUN+ALT+gGT+Lys+Ile; 0.766, 251.9 03, 1+ALB+AST+gGT+NEFA+T-BIL+Asn; 0.766, 252.499, 1+ALB+AST+BHB A+Asn+Orn+Lys; 0.766, 250.400, 1+ALB+BUN+ALT+Arg+Thr+Ile; 0.766, 251.371, 1+ALB+Ca+AST+NEFA+Asn+Orn; 0.766, 253.219, 1+ALB+Ca+Gl c+Asn+Arg+Thr; 0.766, 251.864, 1+ALB+ALT+Orn+Tyr+Phe+Trp; 0.766, 248.153, 1+ALB+BUN+ALT+NEFA+Asp+Trp; 0.766, 251.283, 1+ALB+AST+NEFA+BHBA+Asn+Arg; 0.766, 252.357, 1+ALB+Ca+AST+His+Asn+Thr; 0. 766, 255.341, 1+ALB+Ca+T-BIL+BHBA+Asn+Lys; 0.766, 253.586, 1+Ala+Trp+Glc+TG+ALB+BUN; 0.766, 250.198, 1+ALB+BUN+ALT+T-BIL+Arg+Lys; 0.766, 251.760, 1+ALB+AST+Glc+Asn+Orn+Lys; 0.766, 249.718, 1+Ala+Trp+AST+ALB+BUN; 0.766, 250.547, 1+ALB+BUN+ALT+T-BIL+Thr+Lys; 0.766, 251.712, 1+Ala+Trp+Glc+AST+ALB+BUN; 0.766, 252.325, 1+ALB+AST+T-BIL+BHBA+Asn+Orn; 0.766, 254.336, 1+ALB+Ca+BHBA+His+Asn+Thr; 0.766, 254.167, 1+ALB+Ca+NEFA+Asn+Orn+Lys; 0.766, 254.856, 1+ALB+T-BIL+Asn+Arg+Orn+Lys; 0.766, 252.896, 1+ALB+Asn+Asp+Orn+Lys+Val; 0.766, 250.664, 1+ALB+BUN+ALT+gGT+NEFA+Lys; 0.766, 251.570, 1+Ala+Trp+AST+gGT+ALB+BUN; 0.766, 252.447, 1+ALB+AST+Asn+Arg+Lys+Phe; 0.766, 251.584, 1+ALB+Ca+AST+NEFA+Asn+Lys; 0.766, 252.609, 1+ALB+Ca+AST+T-BIL+Asn+Thr; 0.766, 253.253, 1+Ala+BCAA+Trp+ALB+BUN+Ca; 0.766, 253.305, 1+Ala+BCAA+Trp+gGT+ALB+BUN; 0.766, 252.642, 1+Ala+Trp+ALB+BUN+TP+BHBA; 0.766, 249.406, 1+ALB+BUN+ALT+3MeHis+Arg+Lys; 0.766, 252.940, 1+ALB+AST+T-BIL+BHBA+Asn+Lys; 0.766, 249.272, 1+ALB+BUN+3MeHis+Asp+Orn+Lys; 0.766, 252.595, 1+ALB+AST+Asn+Arg+Lys+Val; 0.766, 253.271, 1+ALB+Ca+NEFA+T-BIL+Asn+Arg; 0.766, 253.143, 1+Ala+Trp+TCHO+ALB+BUN+BHBA; 0.766, 254.763, 1+ALB+Asn+Arg+Orn+Lys+Phe; 0.766, 254.123, 1+ALB+gGT+NEFA+Asn+Arg+Lys; 0.766, 251.359, 1+ALB+ALT+3MeHis+Orn+Val+Phe; 0.766, 253.447, 1+Ala+Trp+TG+ALB+BUN+BHBA; 0.766, 248.952, 1+ALB+BUN+3MeHis+Asp+Lys+Val; 0.766, 250.735, 1+Trp+ALT+ALB+BUN+TP+BHBA; 0.766, 251.477, 1+Ala+Trp+AST+ALB+BUN+BHBA; 0.766, 253.887, 1+Ala+Gly+Trp+TG+AST+ALB; 0.766, 254.289, 1+ALB+Ca+gGT+His+Asn+Thr; 0.766, 251.258, 1+Ala+Trp+TCHO+ALB+BUN; 0.766, 255.127, 1+ALB+Ca+gGT+BHBA+Asn+Ile; 0.766, 253.997, 1+ALB+T-BIL+Glc+Asn+Arg+Orn; 0.766, 254.862, 1+ALB+BHBA+Asn+Arg+Orn+Lys; 0.766, 252.981, 1+ALB+gGT+Glc+Asn+Arg+Thr; 0.766, 253.355, 1+Ala+Trp+ALB+BUN+NEFA+BHBA; 0.766, 250.645, 1+ALB+BUN+ALT+gGT+T-BIL+Lys; 0.766, 250.160, 1+ALB+BUN+ALT+NEFA+3MeHis+Lys; 0.766, 250.375, 1+ALB+BUN+ALT+Glc+His+Lys; 0.766, 250.766, 1+ALB+AST+Asn+Arg+Asp+Val; 0.765, 252.052, 1+ALB+Ca+AST+Glc+Asn+Thr; 0.765, 253.462, 1+Ala+Trp+gGT+ALB+BUN+BHBA; 0.765, 253.231, 1+Ala+Trp+TG+ALB+BUN+NEFA; 0.765, 250.021, 1+ALB+BUN+ALT+3MeHis+Lys+Tyr; 0.765, 250.626, 1+ALB+BUN+ALT+Thr+Orn+Lys; 0.765, 252.150, 1+ALB+AST+NEFA+Asn+3MeHis+Val; 0.765, 252.439, 1+ALB+AST+gGT+Asn+Orn+Lys; 0.765, 249.579, 1+ALB+BUN+AST+ALT+Arg+Trp; 0.765, 250.313, 1+ALB+BUN+ALT+His+Lys+Ile; 0.765, 250.509, 1+ALB+AST+Asn+Arg+Asp+Orn; 0.765, 253.503, 1+Ala+Trp+TG+ALB+BUN+Ca; 0.765, 252.494, 1+Ala+Trp+TCHO+ALB+BUN+TP; 0.765, 253.258, 1+Ala+Trp+Glc+TCHO+ALB+BUN; 0.765, 254.410, 1+ALB+Ca+T-BIL+Glc+Asn+Lys; 0.765, 253.361, 1+ALB+gGT+NEFA+T-BIL+Asn+Arg; 0.765, 249.409, 1+ALB+BUN+3MeHis+Asp+Lys+Tyr; 0.765, 249.848, 1+ALB+BUN+AST+ALT+3MeHis+Lys; 0.765, 248.070, 1+ALB+AST+Asn+3MeHis+Asp+Phe; 0.765, 252.254, 1+ALB+AST+gGT+Asn+Arg+Orn; 0.765, 250.284, 1+ALB+BUN+Ca+ALT+His+Lys; 0.765, 254.160, 1+ALB+Ca+gGT+His+Asn+Ile; 0.765, 253.244, 1+Ala+Trp+TCHO+gGT+ALB+BUN; 0.765, 250.845, 1+ALB+BUN+Asp+Lys+Val+Trp; 0.765, 247.227, 1+ALB+BUN+AST+ALT+Asp+Lys; 0.765, 252.435, 1+ALB+AST+gGT+BHBA+Asn+Orn; 0.765, 252.449, 1+ALB+AST+Asn+Orn+Lys+Phe; 0.765, 254.946, 1+ALB+gGT+T-BIL+BHBA+Asn+Orn; 0.765, 253.551, 1+Ala+Trp+TG+gGT+ALB+BUN; 0.765, 250.430, 1+ALB+BUN+ALT+BHBA+Thr+Lys; 0.765, 250.640, 1+ALB+BUN+ALT+Glc+Thr+Lys; 0.765, 252.297, 1+ALB+AST+Asn+Arg+Orn+Lys; 0.765, 253.242, 1+ALB+Ca+Asn+Arg+Thr+Lys; 0.765, 253.525, 1+ALB+BUN+Orn+Lys+Val+Trp; 0.765, 250.857, 1+BCAA+Trp+ALT+ALB+BUN+TP; 0.765, 253.203, 1+ALB+AST+gGT+BHBA+Asn+Lys; 0.765, 254.899, 1+ALB+Ca+T-BIL+Asn+Orn+Lys; 0.765, 254.114, 1+ALB+BHBA+Glc+Asn+Orn+Lys; 0.765, 254.960, 1+ALB+gGT+BHBA+Asn+Orn+Lys; 0.765, 254.160, 1+ALB+gGT+NEFA+Asn+Arg+Orn; 0.765, 251.584, 1+Ala+Trp+gGT+ALB+BUN; 0.765, 251.610, 1+Ala+Trp+Glc+ALB+BUN; 0.765, 250.188, 1+ALB+BUN+ALT+NEFA+Arg+Lys; 0.765, 250.508, 1+ALB+AST+Asn+Asp+Orn+Lys; 0.765, 254.133, 1+ALB+Ca+NEFA+Asn+Arg+Orn; 0.765, 254.106, 1+ALB+T-BIL+BHBA+Glc+Asn+Orn; 0.765, 254.993, 1+ALB+T-BIL+BHBA+Asn+Arg+Lys; 0.765, 252.683, 1+Ala+Trp+ALB+BUN+TP+NEFA; 0.765, 250.734, 1+ALB+BUN+ALT+NEFA+Orn+Lys; 0.765, 251.659, 1+ALB+AST+Glc+Asn+Arg+Orn; 0.765, 252.294, 1+ALB+AST+BHBA+Asn+Arg+Orn; 0.765, 247.658, 1+ALB+BUN+AST+ALT+Asp+Trp; 0.765, 249.442, 1+ALB+AST+Asn+Asp+Tyr+Val; 0.765, 253.301, 1+Ala+Trp+ALB+BUN+Ca+NEFA; 0.765, 255.459, 1+ALB+Ca+T-BIL+BHBA+Asn+Thr; 0.765, 254.487, 1+ALB+Ca+gGT+NEFA+T-BIL+Asn; 0.765, 254.186, 1+ALB+T-BIL+Glc+Asn+Arg+Lys; 0.765, 253.756, 1+ALB+gGT+T-BIL+Asn+Arg+Thr; 0.765, 253.638, 1+ALB+BUN+NEFA+Lys+Val+Phe; 0.765, 248.945, 1+Trp+ALT+ALB+BUN+TP; 0.765, 250.052, 1+ALB+BUN+ALT+3MeHis+Lys+Val; 0.765, 250.252, 1+ALB+BUN+ALT+Arg+Orn+Lys; 0.765, 250.234, 1+ALB+BUN+ALT+Glc+Arg+Lys; 0.765, 250.700, 1+ALB+BUN+ALT+T-BIL+Orn+Lys; 0.765, 251.271, 1+Ala+Trp+AST+ALB+BUN+NEFA; 0.765, 251.730, 1+ALB+AST+gGT+Glc+Asn+Orn; 0.765, 251.476, 1+ALB+AST+T-BIL+Glc+Asn+Orn; 0.765, 251.940, 1+ALB+AST+NEFA+Asn+3MeHis+Phe; 0.765, 249.588, 1+ALB+AST+NEFA+Asn+Asp+Phe; 0.765, 251.491, 1+Ala+Trp+TCHO+AST+ALB+BUN; 0.765, 252.947, 1+Ala+Trp+TCHO+ALB+BUN+NEFA; 0.765, 254.798, 1+ALB+T-BIL+BHBA+Asn+Arg+Orn; 0.765, 250.229, 1+ALB+BUN+ALT+Arg+Lys+Val; 0.765, 253.582, 1+Ala+Trp+Glc+gGT+ALB+BUN; 0.765, 250.264, 1+ALB+BUN+ALT+Arg+Lys+Tyr; 0.765, 253.400, 1+Ala+Trp+ALB+BUN+Ca+BHBA; 0.765, 254.088, 1+ALB+Glc+Asn+Arg+Orn+Lys; 0.765, 254.048, 1+ALB+BHBA+Glc+Asn+Arg+Orn; 0.765, 252.929, 1+ALB+Asn+Asp+Lys+Val+Phe; 0.765, 250.728, 1+ALB+BUN+ALT+NEFA+Lys+Val; 0.765, 250.742, 1+ALB+BUN+ALT+NEFA+Glc+Lys; 0.765, 252.272, 1+ALB+AST+gGT+T-BIL+Asn+Orn; 0.765, 254.326, 1+ALB+Ca+gGT+NEFA+Asn+Lys; 0.765, 252.834, 1+ALB+Asn+Asp+Orn+Lys+Phe; 0.765, 252.867, 1+ALB+Asn+Arg+Asp+Lys+Phe; 0.765, 250.710, 1+ALB+BUN+ALT+NEFA+T-BIL+Lys; 0.765, 251.124, 1+ALB+BUN+Asp+Orn+Lys+Trp; 0.765, 252.728, 1+ALB+AST+gGT+T-BIL+Asn+Thr; 0.765, 254.959, 1+ALB+Ca+T-BIL+BHBA+Asn+Orn; 0.765, 251.434, 1+ALB+BUN+Asp+Tyr+Phe+Trp; 0.765, 250.944, 1+Trp+ALT+gGT+ALB+BUN+TP; 0.765, 250.321, 1+ALB+BUN+AST+ALT+Lys+Ile; 0.765, 252.153, 1+ALB+AST+Asn+Arg+Orn+Phe; 0.765, 252.070, 1+Ala+Gly+Trp+AST+ALB; 0.765, 254.770, 1+ALB+Ca+Asn+Arg+Orn+Lys; 0.765, 253.119, 1+ALB+Asn+Arg+Asp+Orn+Lys; 0.765, 254.946, 1+ALB+gGT+T-BIL+Asn+Orn+Lys; 0.765, 253.820, 1+ALB+gGT+BHBA+Asn+Arg+Thr; 0.765, 250.241, 1+ALB+BUN+ALT+gGT+Arg+Lys; 0.765, 251.595, 1+ALB+AST+BHBA+Glc+Asn+Orn; 0.765, 252.066, 1+ALB+BUN+AST+Lys+Val+Trp; 0.765, 254.033, 1+Ala+Gly+Trp+AST+ALB+BHBA; 0.765, 251.528, 1+Ala+Trp+ALB+BUN+Ca; 0.765, 254.333, 1+ALB+Ca+gGT+NEFA+Asn+Orn; 0.764, 253.993, 1+ALB+gGT+NEFA+BHBA+Asn+Arg; 0.764, 249.592, 1+ALB+BUN+3MeHis+Arg+Asp+Lys; 0.764, 250.841, 1+Trp+TG+ALT+ALB+BUN+TP; 0.764, 250.101, 1+ALB+BUN+ALT+BHBA+Arg+Lys; 0.764, 252.690, 1+ALB+Ca+AST+gGT+His+Asn; 0.764, 251.932, 1+ALB+ALT+3MeHis+Orn+Tyr+Phe; 0.764, 250.633, 1+ALB+BUN+ALT+NEFA+Lys+Tyr; 0.764, 250.384, 1+ALB+AST+Asn+Asp+Lys+Phe; 0.764, 251.661, 1+Ala+Trp+AST+ALB+BUN+Ca; 0.764, 253.172, 1+Ala+Trp+TCHO+ALB+BUN+Ca; 0.764, 253.846, 1+ALB+BUN+3MeHis+Orn+Val+Phe; 0.764, 250.788, 1+ALB+BUN+ALT+gGT+Glc+Lys; 0.764, 252.744, 1+ALB+AST+gGT+BHBA+His+Asn; 0.764, 250.710, 1+ALB+BUN+ALT+T-BIL+Glc+Lys; 0.764, 250.995, 1+ALB+ALT+3MeHis+Arg+Tyr+Phe; 0.764, 248.170, 1+ALB+BUN+AST+3MeHis+Asp+Lys; 0.764, 252.373, 1+ALB+Ca+AST+Asn+Orn+Lys; 0.764, 253.500, 1+Ala+Trp+gGT+ALB+BUN+Ca; 0.764, 254.202, 1+ALB+Ca+gGT+Glc+Asn+Thr; 0.764, 250.940, 1+Trp+Glc+ALT+ALB+BUN+TP; 0.764, 250.269, 1+ALB+BUN+AST+ALT+T-BIL+Lys; 0.764, 253.873, 1+ALB+Ca+T-BIL+Asn+Arg+Thr; 0.764, 248.074, 1+ALB+BUN+ALT+3MeHis+Arg+Asp; 0.764, 253.248, 1+Ala+Gly+Trp+TG+ALT+ALB; 0.764, 250.318, 1+ALB+BUN+AST+ALT+NEFA+Lys; 0.764, 252.831, 1+ALB+Ca+AST+BHBA+Asn+Thr; 0.764, 253.524, 1+Ala+Trp+Glc+ALB+BUN+Ca; 0.764, 254.161, 1+ALB+Ca+NEFA+BHBA+Glc+Asn; 0.764, 255.035, 1+ALB+Ca+gGT+T-BIL+Asn+Ile; 0.764, 253.019, 1+ALB+Asn+Asp+Orn+Val+Phe; 0.764, 253.459, 1+ALB+BUN+Arg+Lys+Val+Trp; 0.764, 252.259, 1+ALB+BUN+AST+3MeHis+Lys+Phe; 0.764, 250.631, 1+Trp+TCHO+ALT+ALB+BUN+TP; 0.764, 253.956, 1+ALB+gGT+BHBA+Glc+Asn+Thr; 0.764, 250.498, 1+ALB+BUN+ALT+gGT+BHBA+Lys; 0.764, 252.101, 1+ALB+ALT+Arg+Orn+Tyr+Phe; 0.764, 250.326, 1+ALB+BUN+AST+ALT+gGT+Lys; 0.764, 253.597, 1+ALB+AST+Asn+Tyr+Val+Phe; 0.764, 251.441, 1+ALB+BUN+AST+3MeHis+Lys+Trp; 0.764, 251.698, 1+ALB+AST+T-BIL+Glc+Asn+Arg; 0.764, 254.061, 1+Ala+Gly+Trp+AST+ALB+NEFA; 0.764, 253.815, 1+Ala+Gly+Trp+AST+gGT+ALB; 0.764, 252.807, 1+Ala+Trp+ALB+BUN+TP+Ca; 0.764, 254.503, 1+ALB+Ca+NEFA+T-BIL+BHBA+Asn; 0.764, 253.139, 1+ALB+BUN+NEFA+Lys+Val+Trp; 0.764, 253.487, 1+ALB+BUN+3MeHis+Lys+Tyr+Phe; 0.764, 250.469, 1+ALB+BUN+ALT+Orn+Lys+Ile; 0.764, 252.444, 1+ALB+BUN+3MeHis+Lys+Phe+Trp; 0.764, 249.768, 1+ALB+BUN+3MeHis+Asp+Phe+Trp; 0.764, 250.097, 1+ALB+BUN+ALT+Arg+Thr+Lys; 0.764, 249.920, 1+ALB+BUN+ALT+His+Arg+Thr; 0.764, 253.026, 1+ALB+AST+gGT+BHBA+Asn+Thr; 0.764, 251.903, 1+Ala+Gly+Trp+ALT+AST+ALB; 0.764, 251.608, 1+Trp+TCHO+ALT+gGT+ALB+BUN; 0.764, 254.786, 1+ALB+Ca+BHBA+Asn+Arg+Orn; 0.764, 254.012, 1+ALB+gGT+Glc+Asn+Orn+Lys; 0.764, 253.054, 1+ALB+Asn+Arg+Asp+Orn+Val; 0.764, 252.411, 1+ALB+AST+T-BIL+Asn+Arg+Lys; 0.764, 252.667, 1+ALB+AST+gGT+Asn+Arg+Lys; 0.764, 250.927, 1+ALB+ALT+Arg+Thr+Lys+Ile; 0.764, 254.197, 1+ALB+Ca+gGT+T-BIL+His+Asn; 0.764, 251.211, 1+ALB+BUN+Arg+Asp+Lys+Trp; 0.764, 250.384, 1+ALB+BUN+ALT+BHBA+Lys+Ile; 0.764, 253.559, 1+ALB+BUN+Orn+Val+Phe+Trp; 0.764, 250.762, 1+ALB+BUN+ALT+gGT+Orn+Lys; 0.764, 250.517, 1+ALB+BUN+Ca+ALT+Lys+Ile; 0.764, 254.786, 1+ALB+Ca+T-BIL+Asn+Arg+Orn; 0.764, 254.028, 1+ALB+Ca+NEFA+BHBA+Asn+Arg; 0.764, 254.066, 1+ALB+Ca+T-BIL+Glc+Asn+Orn; 0.764, 254.923, 1+ALB+Asn+Arg+Lys+Val+Phe; 0.764, 250.578, 1+ALB+BUN+ALT+T-BIL+BHBA+Lys; 0.764, 250.608, 1+ALB+BUN+ALT+Lys+Tyr+Val; 0.764, 252.665, 1+ALB+AST+BHBA+Asn+Arg+Lys; 0.764, 251.712, 1+ALB+Ca+AST+Glc+Asn+Orn; 0.764, 254.285, 1+ALB+BHBA+Glc+Asn+Arg+Lys; 0.764, 254.324, 1+ALB+T-BIL+BHBA+Glc+Asn+Arg; 0.764, 250.993, 1+ALB+BUN+NEFA+Asp+Lys+Trp; 0.764, 252.373, 1+ALB+AST+gGT+NEFA+BHBA+Asn; 0.764, 250.784, 1+Trp+ALT+ALB+BUN+TP+Ca; 0.764, 254.930, 1+ALB+Ca+BHBA+Asn+Orn+Lys; 0.764, 252.934, 1+ALB+BUN+3MeHis+Lys+Tyr+Trp; 0.764, 249.496, 1+ALB+BUN+NEFA+3MeHis+Asp+Lys; 0.764, 250.958, 1+ALB+BUN+ALT+NEFA+Orn+Trp; 0.764, 251.043, 1+ALB+BUN+ALT+Orn+Val+Trp; 0.764, 251.223, 1+ALB+BUN+Asp+Lys+Phe+Trp; 0.764, 251.797, 1+ALB+ALT+Arg+Val+Phe+Trp; 0.764, 252.729, 1+ALB+AST+Asn+3MeHis+Tyr+Val; 0.763, 253.894, 1+ALB+BUN+NEFA+Lys+Tyr+Phe; 0.763, 250.598, 1+ALB+BUN+ALT+Glc+Lys+Ile; 0.763, 252.495, 1+ALB+AST+gGT+Glc+Asn+Lys; 0.763, 250.106, 1+Trp+ALT+AST+ALB+BUN+TP; 0.763, 252.218, 1+ALB+Ca+AST+T-BIL+Asn+Orn; 0.763, 252.355, 1+ALB+Ca+AST+BHBA+Asn+Orn; 0.763, 250.132, 1+ALB+BUN+Ca+ALT+Arg+Lys; 0.763, 254.738, 1+ALB+gGT+Asn+Arg+Orn+Lys; 0.763, 251.910, 1+Trp+TG+ALT+gGT+ALB+BUN; 0.763, 252.029, 1+ALB+ALT+NEFA+Arg+Tyr+Phe; 0.763, 255.142, 1+ALB+Ca+gGT+NEFA+BHBA+Asn; 0.763, 254.405, 1+ALB+gGT+BHBA+Glc+Asn+Lys; 0.763, 253.628, 1+ALB+BUN+Lys+Tyr+Val+Trp; 0.763, 250.899, 1+Trp+ALT+ALB+BUN+TP+NEFA; 0.763, 252.649, 1+ALB+ALT+NEFA+Orn+Tyr+Phe; 0.763, 251.380, 1+ALB+ALT+3MeHis+Lys+Val+Phe; 0.763, 251.115, 1+ALB+BUN+ALT+Arg+Thr+Orn; 0.763, 254.036, 1+Ala+Gly+Trp+Glc+AST+ALB; 0.763, 254.824, 1+ALB+Ca+gGT+Asn+Orn+Lys; 0.763, 253.807, 1+ALB+BUN+Arg+Tyr+Phe+Trp; 0.763, 250.565, 1+ALB+BUN+ALT+NEFA+BHBA+Lys; 0.763, 252.796, 1+Ala+Trp+gGT+ALB+BUN+TP; 0.763, 250.174, 1+ALB+BUN+AST+ALT+His+Lys; 0.763, 251.143, 1+ALB+BUN+ALT+NEFA+Arg+Thr; 0.763, 250.583, 1+ALB+BUN+Ca+ALT+Thr+Lys; 0.763, 254.124, 1+ALB+Ca+BHBA+Glc+Asn+Thr; 0.763, 253.946, 1+ALB+Ca+BHBA+Asn+Arg+Thr; 0.763, 251.163, 1+ALB+BUN+ALT+Glc+Arg+Thr; 0.763, 253.441, 1+ALB+BUN+NEFA+His+Thr+Lys; 0.763, 250.483, 1+ALB+AST+Asn+Arg+Asp+Phe; 0.763, 252.193, 1+ALB+Ca+AST+Asn+Arg+Orn; 0.763, 254.048, 1+ALB+Ca+Glc+Asn+Arg+Orn; 0.763, 254.000, 1+ALB+Ca+gGT+NEFA+Glc+Asn; 0.763, 253.993, 1+ALB+BUN+NEFA+Val+Phe+Trp; 0.763, 253.930, 1+ALB+gGT+T-BIL+Glc+Asn+Orn; 0.763, 251.067, 1+ALB+ALT+Asp+Orn+Tyr+Phe; 0.763, 253.213, 1+ALB+BUN+NEFA+Lys+Phe+Trp; 0.763, 250.928, 1+ALB+BUN+ALT+3MeHis+Orn+Trp; 0.763, 249.894, 1+ALB+BUN+AST+ALT+Arg+Lys; 0.763, 253.933, 1+ALB+BUN+gGT+NEFA+His+Lys; 0.763, 250.372, 1+ALB+ALT+Arg+Asp+Phe+Trp; 0.763, 250.047, 1+Trp+ALT+gGT+ALB+BUN; 0.763, 251.907, 1+BCAA+Trp+ALT+gGT+ALB+BUN; 0.763, 253.910, 1+ALB+BUN+NEFA+Tyr+Phe+Trp; 0.763, 250.280, 1+ALB+AST+Asn+Asp+Orn+Phe; 0.763, 253.641, 1+ALB+BUN+T-BIL+His+Thr+Lys; 0.763, 254.720,

1+ALB+gGT+BHBA+Asn+Arg+Orn; 0.763, 254.738, 1+ALB+gGT+T-BIL+Asn+Arg+Orn; 0.763, 250.683, 1+ALB+BUN+ALT+Orn+Lys+Tyr; 0.763, 252.460, 1+ALB+AST+T-BIL+BHBA+Asn+Ar g; 0.763, 251.542, 1+Trp+TCHO+TG+ALT+ALB+BUN; 0.763, 252.319, 1+A LB+Ca+AST+gGT+Asn+Orn; 0.763, 251.162, 1+ALB+ BUN+ALT+T-BIL+Arg+Thr; 0.763, 253.723, 1+Ala+Gly+ Trp+TCHO+AST+ALB; 0.763, 253.024, 1+ALB+Asn+ Arg+Asp+Orn+Phe; 0.763, 252.039, 1+Trp+Glc+ALT+ gGT+A LB+BUN; 0.763, 253.647, 1+ALB+BUN+Arg+ Lys+Tyr+Trp; 0.763, 251.75 1, 1+ALB+ALT+Arg+Orn+ Phe+Trp; 0.763, 252.139, 1+ALB+ALT+Lys+Tyr+Phe+Trp; 0.763, 252.593, 1+ALB+AST+Asn+Arg+Val+Phe; 0.763, 252. 300, 1+ALB+Ca+AST+NEFA+BHBA+Asn; 0.763, 255.262, 1+ALB+Ca+gGT+T-BIL+Asn+Lys; 0.763, 250.817, 1+ALB+BUN+ALT+Glc+Orn+Lys; 0.763, 253.842, 1+Ala+Gly+BCAA+Trp+AST+ALB; 0.763, 250.712, 1+ALB+BUN+Ca+ALT+gGT+Lys; 0.763, 252.454, 1+ALB+Ca+AST+BHBA+His+Asn; 0.76 3, 252.095, 1+ALB+AST+gGT+Glc+Asn+Arg; 0.763, 252.102, 1+ALB+BUN+AST+Lys+Phe+Trp; 0.763, 253.736, 1+ALB+Ca+gGT+Asn+Arg+Thr; 0.7 63, 253.144, 1+ALB+BUN+3MeHis+Orn+Phe+Trp; 0.763, 253.172, 1+ALB+BUN+3MeHis+Val+Phe+Trp; 0.763, 250.813, 1+ALB+BUN+ALT+Orn+Lys+Val; 0.763, 254.430, 1+ALB+Ca+gGT+BHBA+His+Asn; 0.763, 254.332, 1+ALB+Ca+Glc+Asn+Arg+Lys; 0.763, 254.135, 1+ALB+ Ca+Glc+Asn+Orn+Lys; 0.762, 250.592, 1+ALB+BUN+ ALT+BHBA+Glc+Lys; 0.762, 250.315, 1+ALB+BUN+ AST+ALT+Thr+Lys; 0.762, 250.547, 1+ALB+BUN+AST+ ALT+G lc+Lys; 0.762, 251.162, 1+ALB+BUN+ALT+gGT+ Arg+Thr; 0.762, 251.84 6, 1+ALB+ALT+3MeHis+Lys+ Tyr+Phe; 0.762, 252.061, 1+ALB+AST+Glc+Asn+Arg+ Lys; 0.762, 251.139, 1+ALB+BUN+ALT+BHBA+Arg+ Thr; 0.762, 251.282, 1+ALB+Ca+AST+NEFA+Asn+Arg; 0.762, 254.191, 1+ALB+BUN+3 MeHis+Lys+Tyr+Val; 0.762, 252.024, 1+ALB+ALT+Orn+Lys+Phe+Trp; 0. 762, 252.228, 1+ALB+ALT+NEFA+Orn+Phe+Trp; 0.762, 255.292, 1+ALB+Ca+gGT+T-BIL+Asn+Thr; 0.762, 254.880, 1+ALB+Ca+gGT+BHBA+Asn+Or n; 0.762, 253.773, 1+ALB+BUN+Orn+Tyr+Phe+Trp; 0.762, 248.581, 1+A LB+ALT+3MeHis+Asp+Lys+Phe; 0.762, 252.409, 1+ALB+ALT+Orn+Lys+V al+Phe; 0.762, 250.471, 1+ALB+ALT+Asp+Orn+Phe+Trp; 0.762, 251.87 7, 1+ALB+ALT+NEFA+Arg+Phe+Trp; 0.762, 252.219, 1+ALB+ALT+Arg+Th r+Orn+Ile; 0.762, 253.012, 1+ALB+ Ca+AST+gGT+Asn+Thr; 0.762, 254. 879, 1+ALB+Ca+ gGT+T-BIL+Asn+Orn; 0.762, 252.665, 1+ALB+BUN+ 3MeH is+Arg+Lys+Trp; 0.762, 251.128, 1+ALB+AST+ ALT+Arg+Phe+Trp; 0.76 2, 252.286, 1+ALB+BUN+AST+ Orn+Lys+Trp; 0.762, 253.209, 1+ALB+BUN+AST+ 3MeHis+Lys+Val; 0.762, 251.471, 1+ALB+AST+ALT+ Arg+Tyr+Tr p; 0.762, 251.859, 1+ALB+BUN+AST+ NEFA+Lys+Trp; 0.762, 254.763, 1+ALB+AST+NEFA+ Orn+Lys+Ile; 0.762, 250.932, 1+ALB+AST+ALT+Arg+Ly s+Ile; 0.762, 250.638, 1+ALB+BUN+Ca+ALT+T-BIL+Lys; 0.762, 252.05 6, 1+ALB+Ca+AST+Glc+Asn+Arg; 0.762, 253.623, 1+ALB+BUN+Orn+Lys+Phe+Trp; 0.762, 252.169, 1+ALB+BUN+AST+Arg+Lys+Trp; 0.762, 252.3 48, 1+ALB+ALT+BHBA+Arg+Thr+Ile; 0.762, 253.861, 1+ALB+BUN+Orn+L ys+Tyr+Trp; 0.762, 252.624, 1+ALB+ALT+NEFA+Orn+Val+Phe; 0.762, 2 49.895, 1+ALB+BUN+ALT+NEFA+Arg+Asp; 0.762, 249.773, 1+ALB+BUN+A LT+Arg+Asp+Orn; 0.762, 250.241, 1+ALB+BUN+AST+ALT+BHBA+Lys; 0.7 62, 250.389, 1+ALB+BUN+AST+Asp+Phe+Trp; 0.762, 253.057, 1+ALB+Ca+AST+BHBA+Asn+Lys; 0.762, 254.522, 1+ALB+Ca+gGT+Glc+Asn+Lys; 0. 762, 255.024, 1+ALB+ Ca+BHBA+Asn+Arg+Lys; 0.762, 253.077, 1+ALB+B UN+NEFA+3MeHis+Lys+Phe; 0.762, 250.584, 1+ALB+ BUN+ALT+BHBA+Orn+Lys; 0.762, 252.060, 1+ALB+ ALT+Lys+Val+Phe+Trp; 0.762, 253.960, 1+ALB+gGT+ BHBA+Glc+Asn+Orn; 0.762, 254.916, 1+ALB+gGT+T- BIL+As n+Arg+Lys; 0.762, 251.984, 1+ALB+AST+T-BIL+ Glc+Asn+Lys; 0.762, 2 52.489, 1+ALB+BUN+AST+ NEFA+Lys+Phe; 0.762, 252.469, 1+ALB+AST+g GT+T- BIL+Asn+Arg; 0.762, 250.676, 1+ALB+BUN+Ca+ALT+ NEFA+Lys; 0. 762, 254.949, 1+ALB+Ca+T-BIL+Asn+ Arg+Lys; 0.762, 253.604, 1+ALB+BUN+Arg+Lys+Phe+ Trp; 0.762, 251.085, 1+ALB+BUN+3MeHis+Asp+Orn+ Phe; 0.762, 253.030, 1+ALB+ALT+NEFA+Tyr+Phe+Trp; 0.762, 255.087, 1+ALB+Ca+T-BIL+BHBA+Asn+Arg; 0.762, 255.383, 1+ALB+Ca+gGT+BHBA+Asn+Lys; 0.762, 253.668, 1+ALB+BUN+T-BIL+His+Orn+Lys; 0.762, 25 1.619, 1+ALB+ALT+3MeHis+Orn+Phe+Trp; 0.762, 252.195, 1+ALB+AST+BHBA+Glc+Asn+Lys; 0.762, 254.777, 1+ALB+BUN+His+Thr+Lys+Ile; 0. 762, 249.542, 1+ALB+AST+ALT+Asp+Lys+Trp; 0.762, 253.874, 1+ALB+g GT+Glc+Asn+Arg+Orn; 0.762, 254.820, 1+ALB+gGT+T-BIL+BHBA+Glc+A sn; 0.762, 252.459, 1+ALB+BUN+AST+3MeHis+Arg+Lys; 0.762, 253.590, 1+ALB+BUN+NEFA+His+Orn+Lys; 0.762, 253.852, 1+ALB+BUN+NEFA+BHB A+His+Lys; 0.762, 253.039, 1+ALB+BUN+AST+3MeHis+Orn+Phe; 0.762, 249.882, 1+ALB+AST+ALT+Arg+Asp+Trp; 0.762, 254.949, 1+ALB+gGT+T-BIL+BHBA+Asn+Arg; 0.762, 254.972, 1+ALB+gGT+BHBA+Asn+Arg+Lys; 0.762, 252.025, 1+Gly+Trp+ALT+gGT+ALB+BUN; 0.762, 253.618, 1+ALB+BUN+NEFA+Orn+Lys+Trp; 0.762, 249.331, 1+ALB+ALT+3MeHis+Asp+Ph e+Trp; 0.762, 250.489, 1+ALB+ALT+Asp+Tyr+Phe+Trp; 0.762, 251.965, 1+Trp+ Glc+TG+ALT+ALB+BUN; 0.762, 252.884, 1+ALB+ BUN+NEFA+3MeHi s+Lys+Trp; 0.762, 252.431, 1+ALB+ AST+gGT+T-BIL+Glc+Asn; 0.762, 2 52.511, 1+ALB+ ALT+NEFA+Arg+Thr+Ile; 0.762, 253.710, 1+ALB+ AST+N EFA+Arg+Lys+Ile; 0.762, 250.740, 1+ALB+BUN+ Ca+ALT+Orn+Lys; 0.76 2, 252.457, 1+ALB+Ca+AST+ Glc+Asn+Lys; 0.762, 254.485, 1+ALB+Ca+B HBA+Glc+ Asn+Lys; 0.762, 252.022, 1+ALB+BUN+Asp+Val+Phe+ Trp; 0.7 62, 252.319, 1+ALB+BUN+AST+Lys+Tyr+Trp; 0.762, 250.364, 1+ALB+BU N+AST+NEFA+Asp+Lys; 0.762, 253.649, 1+ALB+BUN+AST+His+Orn+Lys; 0.762, 249.655, 1+Trp+TCHO+ALT+ALB+BUN; 0.762, 255.398, 1+ALB+Ca+gGT+BHBA+Asn+Thr; 0.761, 252.795, 1+ALB+BUN+Asp+Lys+Tyr+Phe; 0. 761, 252.947, 1+ALB+BUN+3MeHis+Orn+Lys+Trp; 0.761, 253.259, 1+AL B+Asn+Arg+Asp+Val+Phe; 0.761, 253.466, 1+Ala+ Gly+BCAA+Trp+ALT+ALB; 0.761, 253.847, 1+ALB+ BUN+NEFA+T-BIL+His+Lys; 0.761, 252.53 5, 1+ALB+ ALT+gGT+Arg+Thr+Ile; 0.761, 253.130, 1+ALB+Ca+ AST+gGT+Asn+Lys; 0.761, 251.025, 1+ALB+BUN+Ca+ ALT+Arg+Thr; 0.761, 254.28 1, 1+ALB+Ca+T-BIL+Glc+ Asn+Arg; 0.761, 253.900, 1+ALB+BUN+NEFA+3 MeHis+ Lys+Val; 0.761, 254.306, 1+ALB+BUN+3MeHis+Orn+ Lys+Val; 0. 761, 250.377, 1+ALB+BUN+AST+ALT+Lys+ Tyr; 0.761, 251.629, 1+ALB+A LT+Arg+Lys+Phe+Trp; 0.761, 252.679, 1+ALB+AST+Asn+3MeHis+Val+P he; 0.761, 251.685, 1+ALB+AST+ALT+Arg+Thr+Ile; 0.761, 254.180, 1+ALB+Ca+gGT+NEFA+Asn+Arg; 0.761, 251.468, 1+Ala+Gly+Trp+ALT+AL B; 0.761, 251.939, 1+ALB+BUN+NEFA+Asp+Lys+Phe; 0.761, 248.742, 1+ALB+ALT+3MeHis+Asp+Lys+Trp; 0.761, 251.829, 1+ALB+BUN+ALT+3MeH is+Val+Trp; 0.761, 250.646, 1+ALB+ALT+Arg+Asp+Tyr+Trp; 0.761, 25 0.960,

1+ALB+BUN+ALT+Orn+Tyr+Trp; 0.761, 251.898, 1+ALB+AST+BHB A+Glc+Asn+Arg; 0.761, 250.473, 1+ALB+BUN+AST+ALT+Orn+Lys; 0.761, 250.559, 1+ALB+BUN+AST+ALT+Lys+Val; 0.761, 252.683, 1+ALB+BUN+A ST+T-BIL+His+Lys; 0.761, 253.507, 1+ALB+BUN+3MeHis+Orn+Lys+Ph e; 0.761, 253.528, 1+ALB+BUN+NEFA+Lys+Tyr+Trp; 0.761, 257.397, 1+Ala+Gly+Trp+Glc+TG+ALB; 0.761, 253.893, 1+ALB+BUN+NEFA+His+Lys+Ile; 0.761, 251.630, 1+ALB+ALT+3MeHis+Orn+Lys+Phe; 0.761, 254.6 35, 1+ALB+Ca+gGT+Asn+Arg+Orn; 0.761, 253.467, 1+Ala+Gly+Trp+ALT+gGT+ALB; 0.761, 249.968, 1+Trp+TG+ALT+ALB+BUN; 0.761, 252.120, 1+ALB+ALT+NEFA+3MeHis+Orn+Phe; 0.761, 252.196, 1+ALB+ALT+NEFA+L ys+Phe+Trp; 0.761, 251.374, 1+ALB+ALT+NEFA+Arg+Lys+Ile; 0.761, 2 52.960, 1+ALB+BUN+AST+NEFA+Lys+Ile; 0.761, 252.772, 1+ALB+Ca+AS T+T-BIL+Asn+Lys; 0.761, 254.093, 1+ALB+Ca+BHBA+Glc+Asn+Orn; 0.7 61, 253.910, 1+ALB+BUN+NEFA+Orn+Phe+Trp; 0.761, 252.572, 1+ALB+A LT+Orn+Lys+Tyr+Phe; 0.761, 254.254, 1+ALB+BUN+His+Thr+Orn+Lys; 0.761, 253.097, 1+ALB+AST+Asp+Lys+Tyr+Trp; 0.761, 252.585, 1+ALB+Ca+AST+Asn+Arg+Lys; 0.761, 252.075, 1+ALB+BUN+Asp+Orn+Phe+Tr p; 0.761, 252.345, 1+ALB+AST+ALT+Orn+Lys+Ile; 0.761, 254.042, 1+A LB+gGT+T-BIL+Glc+Asn+Arg; 0.761, 253.413, 1+Ala+Gly+Trp+Glc+AL T+ALB; 0.761, 253.819, 1+ALB+BUN+Arg+Orn+Lys+Trp; 0.761, 249.536, 1+ALB+BUN+ALT+Arg+Asp+Val; 0.761, 251.238, 1+ALB+BUN+ALT+His+A rg+Orn; 0.761, 251.984, 1+ALB+ALT+Arg+Lys+Tyr+Phe; 0.761, 252.71 1, 1+ALB+AST+gGT+BHBA+Asn+Arg; 0.761, 252.544, 1+ALB+AST+ALT+Ty r+Phe+Trp; 0.761, 251.647, 1+Trp+Glc+TCHO+ALT+ALB+BUN; 0.761, 25 1.410, 1+ALB+AST+ALT+Orn+Phe+Trp; 0.761, 253.067, 1+ALB+BUN+Arg+Asp+Lys+Phe; 0.761, 254.260, 1+ALB+BUN+NEFA+Thr+Lys+Ile; 0.761, 251.533, 1+ALB+AST+ALT+NEFA+Arg+Trp; 0.761, 253.976, 1+ALB+BUN+NEFA+Glc+His+Lys; 0.761, 251.284, 1+ALB+BUN+ALT+His+Thr+Orn; 0. 761, 251.516, 1+BCAA+Trp+TCHO+ALT+ALB+BUN; 0.761, 251.294, 1+ALB+ALT+3MeHis+Arg+Val+Phe; 0.761, 252.070, 1+ALB+AST+ALT+NEFA+Or n+Phe; 0.761, 255.405, 1+ALB+BUN+Thr+Orn+Lys+Ile; 0.761, 251.850, 1+ALB+BUN+NEFA+Asp+Phe+Trp; 0.761, 253.665, 1+ALB+BUN+3MeHis+A rg+Lys+Val; 0.761, 254.035, 1+ALB+BUN+T-BIL+His+Lys+Ile; 0.761, 252.605, 1+ALB+BUN+AST+NEFA+His+Lys; 0.761, 250.138, 1+ALB+ALT+Asp+Lys+Phe+Trp; 0.761, 252.501, 1+ALB+ALT+3MeHis+Tyr+Phe+Trp; 0.761, 252.626, 1+ALB+ALT+NEFA+Arg+Val+Phe; 0.761, 252.551, 1+AL B+BUN+AST+NEFA+3MeHis+Lys; 0.761, 255.802, 1+ALB+AST+T-BIL+Orn+Lys+Ile; 0.761, 251.356, 1+ALB+AST+ALT+Arg+Orn+Trp; 0.761, 253. 035, 1+ALB+BUN+3MeHis+Arg+Phe+Trp; 0.761, 251.898, 1+ALB+BUN+AL T+NEFA+3MeHis+Trp; 0.761, 253.533, 1+ALB+BUN+NEFA+3MeHis+Phe+T rp; 0.761, 254.803, 1+ALB+BUN+His+Orn+Lys+Ile; 0.761, 252.311, 1+ALB+AST+ALT+Orn+Tyr+Phe; 0.761, 252.389, 1+ALB+AST+T-BIL+BHBA+Glc+Asn; 0.761, 251.493, 1+ALB+AST+ALT+3MeHis+Orn+Phe; 0.761, 25 2.649, 1+ALB+ALT+Thr+Orn+Lys+Ile; 0.761, 250.785, 1+ALB+BUN+Ca+ALT+Glc+Lys; 0.761, 252.746, 1+Ala+Gly+BCAA+ALT+ALB+BUN; 0.761, 252.167, 1+ALB+BUN+NEFA+Asp+Orn+Lys; 0.761, 251.831, 1+ALB+ALT+NEFA+3MeHis+Lys+Phe; 0.761, 251.899, 1+ALB+BUN+ALT+Glc+Arg+Or n; 0.761, 251.319, 1+ALB+ALT+3MeHis+Arg+Lys+Val; 0.761, 250.640, 1+ALB+BUN+AST+Asp+Orn+Trp; 0.761, 251.570, 1+ALB+ALT+Arg+Orn+L ys+Ile; 0.761, 251.034, 1+ALB+ALT+Arg+Asp+Tyr+Phe; 0.761, 252.12 6, 1+ALB+BUN+NEFA+Asp+Lys+Tyr; 0.761, 251.588, 1+ALB+AST+ALT+Ar g+Val+Trp; 0.761, 251.987, 1+BCAA+Trp+Glc+ALT+ALB+BUN; 0.761, 25 2.151, 1+ALB+BUN+Arg+Asp+Phe+Trp; 0.761, 249.503, 1+ALB+ALT+3Me His+Asp+Orn+Phe; 0.761, 251.476, 1+ALB+ALT+3MeHis+Lys+Phe+Trp; 0.761, 252.473, 1+ALB+ALT+3MeHis+Val+Phe+Trp; 0.761, 252.894, 1+ALB+BUN+AST+gGT+NEFA+Lys; 0.761, 253.493, 1+ALB+Ca+AST+T-BIL+B HBA+Asn; 0.761, 253.310, 1+ALB+BUN+3MeHis+Arg+Lys+Phe; 0.761, 25 4.139, 1+ALB+BUN+NEFA+3MeHis+Lys+Tyr; 0.761, 251.983, 1+Gly+BCA A+Trp+ALT+ALB+BUN; 0.761, 254.688, 1+ALB+BUN+gGT+NEFA+Lys+Ile; 0.761, 248.779, 1+ALB+ALT+3MeHis+Arg+Asp+Lys; 0.761, 251.916, 1+Gly+Trp+TG+ALT+ALB+BUN; 0.761, 252.579, 1+ALB+ALT+NEFA+Lys+Tyr+Phe; 0.761, 253.641, 1+ALB+AST+gGT+T-BIL+BHBA+Asn; 0.761, 252.4 83, 1+ALB+ALT+Glc+Arg+Thr+Ile; 0.760, 249.181, 1+ALB+ALT+3MeHis+Arg+Asp+Phe; 0.760, 251.791, 1+BCAA+Trp+TG+ALT+ALB+BUN; 0.760, 254.575, 1+ALB+BUN+BHBA+His+Thr+Lys; 0.760, 250.332, 1+ALB+BUN+AST+ALT+Orn+Trp; 0.760, 251.619, 1+ALB+AST+ALT+Lys+Phe+Trp; 0.7 60, 252.842, 1+ALB+ALT+Orn+Tyr+Val+Phe; 0.760, 249.991, 1+BCAA+T rp+ALT+ALB+BUN; 0.760, 251.931, 1+ALB+BUN+ALT+NEFA+Arg+Orn; 0.7 60, 252.230, 1+ALB+ALT+Arg+Lys+Val+Phe; 0.760, 254.075, 1+ALB+BU N+gGT+T-BIL+His+Lys; 0.760, 254.140, 1+ALB+gGT+Glc+Asn+Arg+Ly s; 0.760, 251.729, 1+ALB+ALT+Arg+Lys+Tyr+Trp; 0.760, 254.976, 1+A LB+BUN+gGT+His+Thr+Lys; 0.760, 255.019, 1+ALB+AST+T-BIL+His+Or n+Lys; 0.760, 250.542, 1+ALB+BUN+Ca+ALT+BHBA+Lys; 0.760, 251.292, 1+ALB+BUN+ALT+3MeHis+Arg+Val; 0.760, 251.923, 1+ALB+BUN+ALT+BH BA+Arg+Orn; 0.760, 249.038, 1+ALB+BUN+AST+3MeHis+Asp+Trp; 0.760, 250.690, 1+ALB+BUN+AST+Arg+Asp+Trp; 0.760, 251.639, 1+ALB+ALT+B HBA+Arg+Lys+Ile; 0.760, 251.640, 1+ALB+ALT+Glc+Arg+Lys+Ile; 0.7 60, 251.646, 1+Gly+Trp+TCHO+ALT+ALB+BUN; 0.760, 254.360, 1+ALB+C a+BHBA+Glc+Asn+Arg; 0.760, 253.057, 1+Ala+Gly+Trp+TCHO+ALT+AL B; 0.760, 250.857, 1+ALB+ALT+NEFA+Asp+Phe+Trp; 0.760, 252.163, 1+ALB+BUN+NEFA+Asp+Lys+Val; 0.760, 252.367, 1+ALB+ALT+NEFA+Arg+O rn+Phe; 0.760, 253.502, 1+ALB+BUN+NEFA+Arg+Lys+Trp; 0.760, 251.2 89, 1+ALB+BUN+ALT+3MeHis+Arg+Tyr; 0.760, 251.792, 1+ALB+BUN+ALT+NEFA+Val+Trp; 0.760, 250.700, 1+ALB+ALT+Asp+Lys+Tyr+Phe; 0.760, 251.946, 1+ALB+BUN+ALT+T-BIL+Arg+Orn; 0.760, 253.186, 1+ALB+ALT+Tyr+Val+Phe+Trp; 0.760, 254.320, 1+ALB+BUN+AST+Orn+Lys+Ile; 0. 760, 249.860, 1+ALB+BUN+AST+3MeHis+Asp+Phe; 0.760, 250.709, 1+AL B+BUN+AST+ALT+Arg+Thr; 0.760, 252.193, 1+ALB+AST+ALT+NEFA+3MeH is+Lys; 0.760, 251.631, 1+ALB+ALT+T-BIL+Arg+Lys+Ile; 0.760, 253. 082, 1+ALB+BUN+AST+3MeHis+Orn+Lys; 0.760, 254.866, 1+ALB+BUN+Gl c+His+Orn+Lys; 0.760, 251.408, 1+ALB+AST+ALT+3MeHis+Lys+Trp; 0. 760, 252.440, 1+ALB+AST+ALT+NEFA+His+Lys; 0.760, 256.013, 1+ALB+AST+His+Orn+Lys+Ile; 0.760, 252.448, 1+ALB+AST+ALT+NEFA+Lys+Il e; 0.760, 253.876, 1+ALB+BUN+Ca+NEFA+His+Lys; 0.760, 254.425, 1+A LB+BUN+Tyr+Val+Phe+Trp; 0.760, 254.128, 1+ALB+BUN+NEFA+3MeHis+Orn+Lys; 0.760, 254.279, 1+ALB+BUN+NEFA+Orn+Lys+Phe; 0.760, 251. 197, 1+ALB+ALT+NEFA+Arg+Asp+Phe; 0.760, 254.792, 1+ALB+BUN+Arg+Thr+Lys+Ile; 0.760, 252.531, 1+ALB+ALT+

NEFA+Lys+Val+Phe; 0.760, 251.050, 1+ALB+AST+ALT+ Arg+Lys+Trp; 0.760, 251.077, 1+ALB+ALT+His+Arg+ Lys+Ile; 0.760, 252.387, 1+ALB+Ca+AST+T-BIL+Glc+ Asn; 0.760, 250.487, 1+ALB+BUN+Ca+AST+ALT+Lys; 0.760, 255.763, 1+ALB+BUN+gGT+Thr+Lys+Ile; 0.760, 252.591, 1+ALB+ALT+Arg+Tyr+Val+Phe; 0.760, 252.306, 1+ALB+ALT+Arg+Orn+Tyr+Trp; 0.760, 253.205, 1+ALB+BUN+AST+T-BIL+Lys+Ile; 0.760, 254.691, 1+ALB+AST+Arg+Orn+Tyr+Trp; 0.760, 251.464, 1+ALB+Ca+ALT+Arg+Lys+Ile; 0.760, 250.124, 1+Trp+Glc+ALT+ALB+BUN; 0.760, 251.389, 1+ALB+BUN+ALT+NEFA+3MeHis+Arg; 0.760, 251.853, 1+ALB+BUN+ALT+Arg+Orn+Tyr; 0.760, 252.501, 1+ALB+ALT+NEFA+Arg+Tyr+Trp; 0.760, 254.866, 1+ALB+BUN+gGT+His+Orn+Lys; 0.760, 250.248, 1+ALB+ALT+Asp+Lys+Tyr+Trp; 0.760, 251.141, 1+Trp+ALT+AST+gGT+ALB+BUN; 0.760, 252.419, 1+ALB+BUN+AST+Orn+Phe+Trp; 0.760, 251.642, 1+ALB+ALT+gGT+Arg+Lys+Ile; 0.760, 254.210, 1+ALB+AST+NEFA+His+Orn+Lys; 0.760, 253.971, 1+ALB+Ca+gGT+Glc+Asn+Orn; 0.760, 252.211, 1+ALB+AST+ALT+Orn+Val+Phe; 0.760, 250.517, 1+ALB+BUN+3MeHis+Arg+Asp+Trp; 0.760, 249.528, 1+ALB+ALT+3MeHis+Arg+Asp+Trp; 0.760, 251.866, 1+ALB+BUN+ALT+Arg+Orn+Ile; 0.760, 251.906, 1+ALB+BUN+ALT+NEFA+His+Arg; 0.760, 251.959, 1+ALB+BUN+ALT+gGT+Arg+Orn; 0.760, 254.071, 1+ALB+BUN+T-BIL+Glc+His+Lys; 0.760, 254.072, 1+ALB+BUN+T-BIL+BHBA+His+Lys; 0.760, 254.945, 1+ALB+BUN+Glc+His+Thr+Lys; 0.760, 252.393, 1+ALB+Ca+AST+T-BIL+Asn+Arg; 0.760, 252.440, 1+ALB+Ca+ALT+Arg+Thr+Ile; 0.760, 254.116, 1+ALB+BUN+Arg+Val+Phe+Trp; 0.760, 255.037, 1+ALB+BUN+NEFA+Orn+Val+Phe; 0.760, 254.673, 1+ALB+BUN+T-BIL+Thr+Lys+Ile; 0.760, 255.475, 1+Ala+Gly+Trp+TG+ALB; 0.760, 249.041, 1+ALB+BUN+ALT+3MeHis+Asp+Orn; 0.760, 250.821, 1+ALB+ALT+NEFA+Arg+Asp+Lys; 0.760, 252.111, 1+ALB+AST+ALT+Arg+Tyr+Phe; 0.760, 252.026, 1+ALB+BUN+AST+3MeHis+Phe+Trp; 0.760, 254.308, 1+ALB+BUN+AST+Thr+Lys+Ile; 0.760, 251.650, 1+ALB+BUN+Ca+ALT+Arg+Orn; 0.760, 254.854, 1+ALB+Ca+gGT+Asn+Arg+Lys; 0.760, 253.452, 1+ALB+BUN+3MeHis+Tyr+Phe+Trp; 0.760, 251.177, 1+ALB+BUN+NEFA+3MeHis+Asp+Phe; 0.760, 252.485, 1+ALB+ALT+NEFA+Orn+Lys+Phe; 0.760, 250.612, 1+ALB+ALT+NEFA+Asp+Lys+Phe; 0.760, 252.455, 1+ALB+ALT+Arg+Tyr+Val+Trp; 0.760, 250.871, 1+ALB+AST+Asn+Asp+Val+Phe; 0.760, 251.402, 1+ALB+AST+ALT+3MeHis+Lys+Phe; 0.760, 252.005, 1+ALB+AST+ALT+3MeHis+Orn+Lys; 0.760, 255.103, 1+ALB+AST+NEFA+His+Lys+Ile; 0.760, 249.878, 1+ALB+ALT+3MeHis+Asp+Tyr+Phe; 0.760, 250.814, 1+ALB+ALT+Arg+Asp+Orn+Trp; 0.760, 251.920, 1+ALB+ALT+NEFA+Arg+Lys+Trp; 0.760, 253.287, 1+ALB+BUN+AST+NEFA+Lys+Val; 0.760, 254.792, 1+ALB+Ca+gGT+T-BIL+Glc+Asn; 0.760, 251.150, 1+ALB+BUN+3MeHis+Arg+Asp+Phe; 0.760, 251.164, 1+ALB+BUN+ALT+3MeHis+Arg+Orn; 0.760, 251.808, 1+ALB+ALT+Arg+Lys+Val+Trp; 0.760, 254.597, 1+ALB+BUN+His+Arg+Lys+Ile; 0.760, 254.887, 1+ALB+AST+NEFA+Orn+Val+Trp; 0.760, 251.477, 1+ALB+ALT+His+Arg+Thr+Ile; 0.760, 252.608, 1+ALB+Ca+AST+BHBA+Asn+Arg; 0.759, 255.457, 1+Ala+Gly+Trp+Glc+ALB; 0.759, 250.911, 1+ALB+ALT+Asp+Val+Phe+Trp; 0.759, 250.837, 1+ALB+ALT+Asp+Orn+Lys+Phe; 0.759, 253.425, 1+ALB+BUN+T-BIL+His+Arg+Lys; 0.759, 255.008, 1+ALB+Ca+T-BIL+BHBA+Glc+Asn; 0.759, 254.926, 1+ALB+Ca+gGT+T-BIL+Asn+Arg; 0.759, 254.893, 1+ALB+BUN+T-BIL+Orn+Lys+Ile; 0.759, 255.091, 1+ALB+BUN+NEFA+Orn+Tyr+Phe; 0.759, 249.915, 1+ALB+BUN+ALT+Arg+Asp+Tyr; 0.759, 250.688, 1+ALB+ALT+Arg+Asp+Lys+Phe; 0.759, 250.898, 1+ALB+BUN+AST+ALT+3MeHis+Arg; 0.759, 253.285, 1+ALB+BUN+AST+NEFA+T-BIL+Lys; 0.759, 254.836, 1+ALB+AST+Orn+Lys+Val+Trp; 0.759, 252.636, 1+ALB+Ca+AST+gGT+Asn+Arg; 0.759, 254.116, 1+ALB+gGT+BHBA+Glc+Asn+Arg; 0.759, 254.228, 1+ALB+BUN+NEFA+Arg+Lys+Phe; 0.759, 248.130, 1+Trp+ALT+ALB+BUN; 0.759, 251.247, 1+ALB+ALT+NEFA+Asp+Orn+Phe; 0.759, 251.424, 1+ALB+BUN+ALT+3MeHis+Tyr+Trp; 0.759, 251.929, 1+ALB+ALT+Arg+Orn+Lys+Trp; 0.759, 250.250, 1+ALB+AST+ALT+Asp+Orn+Trp; 0.759, 252.491, 1+ALB+ALT+T-BIL+Arg+Thr+Ile; 0.759, 255.414, 1+ALB+AST+NEFA+Orn+Lys+Val; 0.759, 256.120, 1+ALB+Ca+gGT+T-BIL+BHBA+Asn; 0.759, 251.476, 1+ALB+ALT+3MeHis+Arg+Lys+Tyr; 0.759, 252.234, 1+ALB+ALT+Arg+Orn+Lys+Phe; 0.759, 252.239, 1+ALB+BUN+ALT+T-BIL+Glc+Arg; 0.759, 252.466, 1+ALB+ALT+NEFA+His+Orn+Lys; 0.759, 252.565, 1+ALB+ALT+NEFA+3MeHis+Phe+Trp; 0.759, 252.591, 1+ALB+AST+gGT+BHBA+Glc+Asn; 0.759, 253.145, 1+ALB+ALT+Lys+Tyr+Val+Phe; 0.759, 252.357, 1+ALB+AST+ALT+NEFA+Phe+Trp; 0.759, 253.284, 1+ALB+BUN+AST+NEFA+Orn+Lys; 0.759, 255.843, 1+ALB+AST+Arg+Orn+Lys+Ile; 0.759, 251.581, 1+ALB+BUN+Ca+AST+ALT+Arg; 0.759, 252.900, 1+ALB+Ca+AST+gGT+Glc+Asn; 0.759, 251.842, 1+ALB+BUN+ALT+Arg+Orn+Val; 0.759, 254.733, 1+ALB+BUN+NEFA+Glc+Lys+Ile; 0.759, 252.108, 1+Gly+Trp+Glc+ALT+ALB+BUN; 0.759, 250.956, 1+ALB+ALT+3MeHis+Arg+Lys+Phe; 0.759, 252.236, 1+ALB+BUN+ALT+BHBA+Glc+Arg; 0.759, 251.203, 1+ALB+ALT+His+Arg+Thr+Lys; 0.759, 251.490, 1+ALB+ALT+His+Arg+Orn+Lys; 0.759, 251.630, 1+ALB+ALT+BHBA+His+Arg+Lys; 0.759, 253.368, 1+ALB+BUN+AST+NEFA+Glc+Lys; 0.759, 252.058, 1+ALB+AST+ALT+Lys+Tyr+Trp; 0.759, 252.581, 1+ALB+AST+ALT+Val+Phe+Trp; 0.759, 254.770, 1+ALB+AST+NEFA+3MeHis+Lys+Val; 0.759, 252.183, 1+ALB+Ca+AST+gGT+NEFA+Asn; 0.759, 253.037, 1+ALB+BUN+Asp+Lys+Val+Phe; 0.759, 251.142, 1+ALB+BUN+3MeHis+Asp+Tyr+Phe; 0.759, 257.428, 1+Ala+Gly+Trp+TG+gGT+ALB; 0.759, 250.175, 1+ALB+BUN+ALT+Asp+Orn+Tyr; 0.759, 251.344, 1+ALB+ALT+Asp+Tyr+Trp; 0.759, 250.155, 1+ALB+ALT+Arg+Asp+Lys+Trp; 0.759, 252.430, 1+ALB+BUN+AST+NEFA+Phe+Trp; 0.759, 252.923, 1+ALB+BUN+AST+NEFA+Arg+Lys; 0.759, 255.599, 1+ALB+BUN+Lys+Tyr+Val+Phe; 0.759, 252.397, 1+ALB+ALT+Arg+Orn+Val+Phe; 0.759, 253.105, 1+ALB+BUN+Asp+Orn+Lys+Phe; 0.759, 254.406, 1+Ala+Trp+Glc+TG+ALT+ALB; 0.759, 254.695, 1+ALB+BUN+NEFA+T-BIL+Lys+Ile; 0.759, 251.015, 1+ALB+ALT+3MeHis+Arg+Phe+Trp; 0.759, 253.138, 1+ALB+ALT+NEFA+Val+Phe+Trp; 0.759, 254.962, 1+ALB+Ca+gGT+BHBA+Asn+Arg; 0.759, 250.807, 1+ALB+AST+ALT+3MeHis+Arg+Lys; 0.759, 253.125, 1+ALB+BUN+NEFA+His+Arg+Lys; 0.759, 253.245, 1+ALB+BUN+AST+T-BIL+Arg+Lys; 0.759, 255.131, 1+ALB+AST+3MeHis+Orn+Val+Phe; 0.759, 252.775, 1+ALB+BUN+AST+ALT+gGT+Orn; 0.759, 253.987, 1+ALB+AST+3MeHis+Lys+Val+Trp; 0.759, 256.361, 1+ALB+AST+Thr+Orn+Lys+Ile; 0.759, 250.874, 1+Trp+TCHO+ALT+AST+ALB+BUN; 0.759, 254.871, 1+ALB+BUN+Ca+His+Thr+Lys; 0.759, 250.881, 1+ALB+AST+ALT+3MeHis+Arg+Trp; 0.759, 255.321, 1+ALB+BUN+Orn+Lys+Val+Phe; 0.759, 253.079, 1+Ala+BCAA+Glc+ALT+ALB+BUN;

0.759, 255.446, 1+ALB+BUN+Orn+Lys+Tyr+Phe; 0.759, 250.182, 1+ALB+AST+ALT+Asp+Phe+Trp; 0.759, 252.298, 1+ALB+BUN+ALT+T-BIL+BHBA+Arg; 0.759, 251.315, 1+ALB+BUN+3MeHis+Asp+Val+Phe; 0.759, 251.331, 1+ALB+ALT+NEFA+His+Arg+Lys; 0.759, 251.410, 1+ALB+BUN+AST+ALT+Arg+Orn; 0.759, 252.393, 1+ALB+AST+ALT+3MeHis+Lys+Val; 0.759, 254.122, 1+ALB+BUN+AST+Lys+Val+Phe; 0.759, 252.004, 1+ALB+AST+ALT+Lys+Val+Trp; 0.759, 255.751, 1+ALB+BUN+Glc+Thr+Lys+Ile; 0.759, 253.158, 1+ALB+BUN+AST+3MeHis+Lys+Tyr; 0.759, 251.459, 1+ALB+BUN+ALT+NEFA+Tyr+Trp; 0.759, 251.562, 1+ALB+BUN+ALT+Tyr+Val+Trp; 0.759, 252.261, 1+ALB+BUN+ALT+gGT+Glc+Arg; 0.759, 251.543, 1+ALB+ALT+His+Arg+Thr+Orn; 0.759, 251.925, 1+ALB+AST+ALT+3MeHis+Phe+Trp; 0.759, 252.178, 1+ALB+AST+ALT+His+Orn+Lys; 0.759, 255.426, 1+ALB+AST+NEFA+Lys+Tyr+Phe; 0.759, 256.569, 1+Ala+Gly+Trp+TCHO+TG+ALB; 0.759, 253.041, 1+Ala+BCAA+TG+ALT+ALB+BUN; 0.759, 250.113, 1+Gly+Trp+ALT+ALB+BUN; 0.759, 251.015, 1+ALB+ALT+Arg+Asp+Lys+Val; 0.759, 252.016, 1+ALB+ALT+3MeHis+Lys+Val+Trp; 0.759, 251.817, 1+ALB+ALT+3MeHis+Arg+Tyr+Trp; 0.759, 252.838, 1+ALB+BUN+AST+Tyr+Phe+Trp; 0.759, 252.521, 1+ALB+AST+ALT+Arg+Orn+Ile; 0.759, 252.923, 1+ALB+ALT+NEFA+Thr+Lys+Ile; 0.759, 253.366, 1+ALB+BUN+AST+NEFA+Lys+Tyr; 0.759, 253.886, 1+ALB+BUN+AST+His+Thr+Lys; 0.759, 252.303, 1+ALB+BUN+NEFA+Arg+Asp+Lys; 0.759, 254.127, 1+ALB+BUN+Arg+Orn+Phe+Trp; 0.759, 255.921, 1+ALB+BUN+Glc+Orn+Lys+Ile; 0.759, 250.093, 1+ALB+ALT+NEFA+3MeHis+Asp+Phe; 0.759, 251.177, 1+ALB+ALT+Arg+Asp+Orn+Phe; 0.759, 251.325, 1+ALB+ALT+3MeHis+Arg+Orn+Phe; 0.759, 252.055, 1+ALB+ALT+NEFA+Arg+Lys+Phe; 0.759, 251.789, 1+ALB+BUN+AST+Asp+Lys+Tyr; 0.759, 250.994, 1+ALB+BUN+AST+ALT+Tyr+Trp; 0.759, 251.627, 1+ALB+BUN+Ca+ALT+His+Arg; 0.759, 254.726, 1+ALB+BUN+NEFA+BHBA+Lys+Ile; 0.759, 250.760, 1+ALB+BUN+3MeHis+Asp+Orn+Trp; 0.759, 252.121, 1+ALB+BUN+ALT+NEFA+Arg+Tyr; 0.759, 250.761, 1+ALB+AST+ALT+Asp+Orn+Phe; 0.759, 252.255, 1+ALB+BUN+ALT+Glc+Arg+Ile; 0.759, 248.369, 1+ALB+AST+ALT+3MeHis+Asp+Lys; 0.759, 252.738, 1+ALB+BUN+AST+Arg+Orn+Trp; 0.759, 253.442, 1+ALB+AST+NEFA+Asp+Orn+Lys; 0.759, 253.554, 1+ALB+BUN+AST+His+Arg+Lys; 0.759, 255.647, 1+ALB+AST+NEFA+Orn+Val+Phe; 0.759, 250.650, 1+ALB+BUN+AST+NEFA+Asp+Trp; 0.759, 255.669, 1+ALB+BUN+Ca+Thr+Lys+Ile; 0.759, 255.478, 1+ALB+BUN+Arg+Lys+Tyr+Phe; 0.759, 250.091, 1+ALB+ALT+3MeHis+Asp+Val+Phe; 0.759, 253.536, 1+Ala+Gly+Trp+ALB; 0.759, 251.955, 1+ALB+BUN+ALT+Glc+His+Arg; 0.759, 251.973, 1+ALB+BUN+ALT+T-BIL+His+Arg; 0.759, 251.710, 1+ALB+AST+ALT+Orn+Lys+Trp; 0.759, 253.464, 1+ALB+BUN+AST+T-BIL+Orn+Lys; 0.759, 251.880, 1+ALB+AST+ALT+NEFA+Lys+Trp; 0.759, 254.689, 1+ALB+BUN+Ca+His+Orn+Lys; 0.759, 250.333, 1+ALB+ALT+3MeHis+Asp+Orn+Trp; 0.759, 250.906, 1+ALB+ALT+Arg+Asp+Lys+Tyr; 0.759, 252.584, 1+ALB+ALT+NEFA+Arg+Val+Trp; 0.759, 252.207, 1+ALB+BUN+ALT+Thr+Orn+Ile; 0.759, 253.486, 1+ALB+BUN+AST+T-BIL+Thr+Lys; 0.759, 255.591, 1+ALB+AST+NEFA+Orn+Tyr+Phe; 0.759, 252.979, 1+ALB+BUN+AST+Orn+Val+Trp; 0.759, 250.951, 1+ALB+BUN+AST+Asp+Tyr+Trp; 0.758, 253.449, 1+ALB+Ca+AST+gGT+T-BIL+Asn; 0.758, 251.015, 1+ALB+ALT+Arg+Asp+Orn+Lys; 0.758, 251.117, 1+ALB+ALT+3MeHis+Arg+Lys+Trp; 0.758, 252.070, 1+ALB+BUN+ALT+His+Arg+Ile; 0.758, 252.319, 1+ALB+BUN+ALT+gGT+T-BIL+Arg; 0.758, 252.351, 1+ALB+AST+ALT+Orn+Val+Trp; 0.758, 253.305, 1+ALB+BUN+AST+NEFA+BHBA+Lys; 0.758, 254.161, 1+ALB+BUN+AST+Lys+Tyr+Phe; 0.758, 254.667, 1+ALB+BUN+AST+Orn+Val+Phe; 0.758, 251.298, 1+ALB+BUN+AST+ALT+Val+Trp; 0.758, 251.809, 1+ALB+BUN+AST+Arg+Asp+Lys; 0.758, 252.652, 1+ALB+AST+ALT+Lys+Tyr+Phe; 0.758, 254.092, 1+ALB+BUN+His+Arg+Thr+Lys; 0.758, 255.037, 1+ALB+AST+Orn+Lys+Tyr+Trp; 0.758, 255.201, 1+ALB+AST+T-BIL+Arg+Lys+Ile; 0.758, 251.082, 1+ALB+AST+3MeHis+Arg+Asp+Lys; 0.758, 251.434, 1+Gly+Trp+ALT+AST+ALB+BUN; 0.758, 254.011, 1+ALB+BUN+AST+BHBA+His+Lys; 0.758, 254.444, 1+Ala+Trp+TG+ALT+gGT+ALB; 0.758, 255.017, 1+ALB+BUN+gGT+T-BIL+Lys+Ile; 0.758, 253.954, 1+ALB+BUN+NEFA+Arg+Phe+Trp; 0.758, 252.931, 1+ALB+ALT+NEFA+3MeHis+Lys+Val; 0.758, 250.900, 1+ALB+ALT+NEFA+Arg+Asp+Trp; 0.758, 251.400, 1+BCAA+Trp+ALT+AST+ALB+BUN; 0.758, 254.841, 1+ALB+AST+Arg+Orn+Val+Trp; 0.758, 254.995, 1+ALB+AST+NEFA+Orn+Tyr+Trp; 0.758, 255.931, 1+ALB+BUN+gGT+Orn+Lys+Ile; 0.758, 251.841, 1+ALB+AST+ALT+Arg+Orn+Phe; 0.758, 255.098, 1+ALB+BUN+gGT+NEFA+Thr+Lys; 0.758, 252.484, 1+ALB+ALT+Orn+Lys+Val+Trp; 0.758, 251.296, 1+Ala+Trp+ALT+AST+ALB; 0.758, 251.543, 1+ALB+ALT+NEFA+3MeHis+Arg+Lys; 0.758, 251.720, 1+ALB+ALT+gGT+His+Arg+Lys; 0.758, 252.065, 1+ALB+AST+ALT+Orn+Lys+Phe; 0.758, 254.717, 1+ALB+BUN+AST+Orn+Tyr+Phe; 0.758, 251.236, 1+ALB+AST+ALT+His+Arg+Lys; 0.758, 251.917, 1+ALB+BUN+AST+ALT+Arg+Ile; 0.758, 253.259, 1+ALB+BUN+AST+NEFA+Thr+Lys; 0.758, 250.848, 1+ALB+AST+NEFA+3MeHis+Asp+Lys; 0.758, 251.967, 1+ALB+BUN+AST+3MeHis+Arg+Trp; 0.758, 255.140, 1+ALB+AST+NEFA+Thr+Lys+Ile; 0.758, 251.964, 1+ALB+BUN+Ca+ALT+T-BIL+Arg; 0.758, 254.017, 1+Ala+Trp+TCHO+TG+ALT+ALB; 0.758, 254.611, 1+ALB+BUN+NEFA+Orn+Lys+Ile; 0.758, 255.070, 1+ALB+AST+3MeHis+Orn+Lys+Val; 0.758, 252.361, 1+ALB+BUN+ALT+gGT+Thr+Orn; 0.758, 251.812, 1+ALB+ALT+NEFA+Asp+Tyr+Phe; 0.758, 252.305, 1+ALB+BUN+ALT+BHBA+Arg+Ile; 0.758, 249.576, 1+ALB+BUN+AST+ALT+Arg+Asp; 0.758, 254.596, 1+ALB+BUN+AST+gGT+Lys+Ile; 0.758, 251.635, 1+ALB+ALT+T-BIL+His+Arg+Lys; 0.758, 251.796, 1+ALB+BUN+AST+ALT+Glc+Arg; 0.758, 251.812, 1+ALB+BUN+AST+Asp+Orn+Lys; 0.758, 252.632, 1+ALB+AST+ALT+Lys+Val+Phe; 0.758, 255.016, 1+ALB+AST+Orn+Val+Phe+Trp; 0.758, 251.316, 1+Trp+TG+ALT+AST+ALB+BUN; 0.758, 255.462, 1+ALB+AST+NEFA+T-BIL+Lys+Ile; 0.758, 252.705, 1+ALB+AST+ALT+Thr+Lys+Ile; 0.758, 257.419, 1+Ala+Gly+Trp+Glc+gGT+ALB; 0.758, 254.273, 1+ALB+BUN+NEFA+3MeHis+Orn+Phe; 0.758, 255.629, 1+ALB+BUN+gGT+His+Lys+Ile; 0.758, 252.602, 1+ALB+ALT+3MeHis+Orn+Lys+Val; 0.758, 252.653, 1+ALB+ALT+T-BIL+His+Orn+Lys; 0.758, 253.969, 1+ALB+BUN+NEFA+Arg+Lys+Ile; 0.758, 252.403, 1+ALB+ALT+Arg+Orn+Val+Trp; 0.758, 251.661, 1+ALB+AST+ALT+NEFA+Arg+Lys; 0.758, 256.835, 1+ALB+AST+Glc+Orn+Lys+Ile; 0.758, 254.678, 1+ALB+AST+Arg+Lys+Tyr+Trp; 0.758, 255.542, 1+ALB+AST+NEFA+Glc+Orn+Lys; 0.758, 253.442, 1+ALB+AST+Asp+Lys+Val+Trp; 0.758, 254.768, 1+ALB+AST+NEFA+Arg+

Ly s+Tyr; 0.758, 253.970, 1+ALB+BUN+Ca+T-BIL+His+Lys; 0.758, 251.971, 1+ALB+BUN+Ca+ALT+BHBA+Arg; 0.758, 252.446, 1+Ala+Trp+TG+ALT+ALB; 0.758, 254.437, 1+Ala+Trp+Glc+ALT+gGT+ALB; 0.758, 255.628, 1+ALB+BUN+Glc+His+Lys+Ile; 0.758, 250.389, 1+ALB+ALT+Asp+Orn+Ly s+Trp; 0.758, 252.191, 1+ALB+BUN+ALT+NEFA+Glc+Arg; 0.758, 248.877, 1+ALB+ALT+3MeHis+Asp+Lys+Val; 0.758, 251.891, 1+ALB+BUN+AST+ALT+gGT+Arg; 0.758, 250.203, 1+ALB+AST+ALT+NEFA+Asp+Lys; 0.758, 251.712, 1+ALB+BUN+AST+ALT+His+Arg; 0.758, 251.812, 1+ALB+BUN+A ST+Asp+Lys+Val; 0.758, 250.440, 1+ALB+AST+3MeHis+Asp+Lys+Trp; 0. 758, 255.521, 1+ALB+AST+NEFA+T-BIL+Orn+Lys; 0.758, 252.033, 1+AL B+AST+ALT+His+Arg+Orn; 0.758, 253.262, 1+ALB+AST+NEFA+Arg+Asp+Lys; 0.758, 249.606, 1+ALB+AST+ALT+3MeHis+Asp+Phe; 0.758, 251.80 7, 1+ALB+ALT+NEFA+3MeHis+Arg+Trp; 0.758, 255.152, 1+ALB+BUN+gGT+NEFA+T-BIL+Lys; 0.758, 252.273, 1+ALB+BUN+ALT+NEFA+T-BIL+Arg; 0.758, 252.318, 1+ALB+BUN+ALT+T-BIL+Arg+Ile; 0.758, 250.887, 1+A LB+ALT+Arg+Asp+Val+Trp; 0.758, 251.326, 1+ALB+AST+3MeHis+Asp+L ys+Phe; 0.758, 251.497, 1+Trp+Glc+ALT+AST+ALB+BUN; 0.758, 253.37 8, 1+ALB+AST+Arg+Asp+Lys+Trp; 0.758, 250.920, 1+ALB+AST+ALT+3Me His+Arg+Phe; 0.758, 253.417, 1+ALB+BUN+Arg+Asp+Orn+Lys; 0.758, 2 53.611, 1+ALB+BUN+NEFA+3MeHis+Arg+Lys; 0.758, 252.369, 1+ALB+BU N+ALT+gGT+Arg+Ile; 0.758, 252.517, 1+ALB+ALT+His+Orn+Lys+Ile; 0. 758, 252.725, 1+ALB+ALT+3MeHis+Lys+Tyr+Val; 0.758, 249.110, 1+AL B+ALT+NEFA+3MeHis+Asp+Lys; 0.758, 253.247, 1+ALB+BUN+AST+gGT+T-BIL+Lys; 0.758, 254.538, 1+ALB+AST+NEFA+3MeHis+Orn+Lys; 0.758, 251.704, 1+ALB+AST+ALT+Arg+Lys+Phe; 0.758, 251.956, 1+ALB+AST+A LT+NEFA+Lys+Phe; 0.758, 252.635, 1+ALB+AST+ALT+NEFA+Arg+Orn; 0. 758, 253.352, 1+ALB+BUN+AST+NEFA+Orn+Phe; 0.758, 254.608, 1+ALB+BUN+AST+gGT+Thr+Lys; 0.758, 253.326, 1+ALB+BUN+Ca+AST+NEFA+Ly s; 0.758, 252.032, 1+Ala+Trp+TCHO+ALT+ALB; 0.758, 251.930, 1+ALB+BUN+Ca+ALT+NEFA+Arg; 0.758, 252.438, 1+Ala+Trp+Glc+ALT+ALB; 0.7 58, 252.477, 1+Ala+Trp+ALT+gGT+ALB; 0.758, 251.950, 1+ALB+BUN+AL T+NEFA+Arg+Val; 0.758, 250.493, 1+ALB+BUN+ALT+NEFA+Asp+Orn; 0.7 58, 250.966, 1+ALB+BUN+3MeHis+Asp+Tyr+Trp; 0.758, 252.303, 1+ALB+BUN+ALT+gGT+BHBA+Arg; 0.758, 250.340, 1+ALB+ALT+Asp+Lys+Val+T rp; 0.758, 251.719, 1+ALB+ALT+Glc+His+Arg+Lys; 0.758, 252.415, 1+ALB+ALT+NEFA+Arg+Orn+Trp; 0.758, 250.348, 1+ALB+AST+ALT+Asp+Ly s+Phe; 0.758, 251.756, 1+ALB+BUN+AST+ALT+T-BIL+Arg; 0.758, 252.2 55, 1+ALB+AST+ALT+3MeHis+Lys+Tyr; 0.758, 252.941, 1+ALB+BUN+AST+Arg+Tyr+Trp; 0.758, 255.546, 1+ALB+AST+NEFA+BHBA+Orn+Lys; 0.75 8, 254.904, 1+ALB+AST+gGT+NEFA+Lys+Ile; 0.758, 256.520, 1+Ala+Gl y+Trp+Glc+TCHO+ALB; 0.758, 252.764, 1+Ala+Trp+TCHO+ALT+AST+AL B; 0.758, 251.997, 1+ALB+BUN+Ca+ALT+gGT+Arg; 0.758, 254.341, 1+Al a+BCAA+Trp+TG+ALT+ALB; 0.758, 255.006, 1+ALB+BUN+T-BIL+BHBA+Ly s+Ile; 0.758, 252.346, 1+ALB+BUN+ALT+BHBA+Thr+Orn; 0.758, 251.35 1, 1+ALB+ALT+NEFA+Asp+Orn+Trp; 0.758, 251.895, 1+ALB+ALT+3MeHis+Arg+Val+Trp; 0.758, 251.971, 1+ALB+BUN+ALT+BHBA+His+Arg; 0.758, 252.255, 1+ALB+BUN+ALT+NEFA+BHBA; 0.758, 252.274, 1+ALB+BUN+ALT+gGT+NEFA+Arg; 0.758, 251.540, 1+ALB+ALT+3MeHis+Arg+Orn+Ly s; 0.758, 252.390, 1+ALB+AST+ALT+NEFA+Orn+Trp; 0.758, 254.370, 1+ALB+AST+NEFA+Arg+Orn+Trp; 0.758, 254.811, 1+ALB+Ca+gGT+BHBA+Gl c+Asn; 0.758, 253.406, 1+ALB+BUN+Arg+Asp+Lys+Tyr; 0.758, 253.426, 1+ALB+BUN+Arg+Asp+Lys+Val; 0.758, 254.468, 1+ALB+BUN+3MeHis+Or n+Lys+Tyr; 0.758, 251.954, 1+ALB+BUN+ALT+Arg+Tyr+Val; 0.758, 251. 365, 1+ALB+ALT+Asp+Orn+Val+Trp; 0.758, 250.370, 1+ALB+ALT+NEFA+Asp+Lys+Trp; 0.758, 251.818, 1+ALB+ALT+3MeHis+Arg+Orn+Trp; 0.75 8, 252.021, 1+ALB+AST+ALT+Arg+Orn+Lys; 0.758, 252.265, 1+ALB+BUN+ALT+NEFA+Arg+Ile; 0.758, 253.045, 1+ALB+BUN+ALT+His+Orn+Ile; 0. 758, 253.552, 1+ALB+BUN+AST+T-BIL+Glc+Lys; 0.758, 253.554, 1+ALB+BUN+AST+T-BIL+BHBA+Lys; 0.758, 253.615, 1+ALB+BUN+AST+NEFA+3M eHis+Phe; 0.758, 251.807, 1+ALB+BUN+AST+ALT+BHBA+Arg; 0.758, 251. 822, 1+ALB+BUN+AST+ALT+Thr+Orn; 0.758, 252.871, 1+ALB+BUN+AST+V al+Phe+Trp; 0.758, 253.002, 1+ALB+AST+ALT+BHBA+His+Lys; 0.758, 2 53.254, 1+ALB+AST+NEFA+Asp+Lys+Tyr; 0.758, 255.110, 1+ALB+AST+O rn+Tyr+Phe+Trp; 0.758, 255.541, 1+ALB+AST+NEFA+Orn+Lys+Tyr; 0.7 58, 250.958, 1+ALB+BUN+AST+Asp+Val+Trp; 0.758, 251.802, 1+ALB+AS T+ALT+NEFA+Arg+Phe; 0.758, 254.525, 1+ALB+BUN+3MeHis+Orn+Tyr+P he; 0.758, 251.519, 1+ALB+BUN+AST+Asp+Lys+Phe; 0.758, 252.852, 1+ALB+AST+ALT+NEFA+T-BIL+Lys; 0.758, 253.112, 1+ALB+BUN+AST+Orn+Tyr+Trp; 0.758, 253.929, 1+ALB+BUN+AST+Arg+Lys+Ile; 0.758, 254.2 36, 1+ALB+AST+3MeHis+Arg+Lys+Val; 0.758, 256.163, 1+ALB+AST+Arg+Thr+Orn+Ile; 0.758, 256.404, 1+ALB+AST+NEFA+Thr+Orn+Ile; 0.758, 253.401, 1+ALB+BUN+Asp+Orn+Lys+Tyr; 0.758, 253.402, 1+ALB+BUN+A sp+Lys+Tyr+Val; 0.758, 253.957, 1+ALB+BUN+3MeHis+Arg+Lys+Tyr; 0. 758, 255.185, 1+ALB+BUN+gGT+NEFA+Glc+Lys; 0.758, 250.969, 1+ALB+BUN+3MeHis+Asp+Val+Trp; 0.758, 252.646, 1+ALB+ALT+Orn+Lys+Tyr+Trp; 0.758, 252.872, 1+ALB+ALT+NEFA+3MeHis+Lys+Tyr; 0.758, 251.1 66, 1+ALB+ALT+NEFA+Asp+Lys+Val; 0.758, 251.542, 1+ALB+BUN+AST+A LT+Arg+Val; 0.758, 252.572, 1+ALB+BUN+AST+Arg+Phe+Trp; 0.758, 25 1.378, 1+ALB+AST+3MeHis+Asp+Orn+Lys; 0.758, 252.939, 1+ALB+BUN+AST+ALT+Orn+Ile; 0.758, 254.273, 1+ALB+AST+3MeHis+Orn+Val+Trp; 0.758, 255.385, 1+ALB+AST+Orn+Tyr+Val+Trp; 0.758, 254.369, 1+ALB+AST+NEFA+Arg+Tyr+Trp; 0.758, 254.756, 1+ALB+BUN+Ca+AST+Lys+Il e; 0.758, 254.465, 1+ALB+BUN+T-BIL+Arg+Lys+Ile; 0.758, 252.569, 1+ALB+BUN+Arg+Asp+Orn+Trp; 0.758, 251.730, 1+ALB+BUN+AST+ALT+Ar g+Tyr; 0.758, 251.665, 1+ALB+BUN+AST+ALT+NEFA+Arg; 0.758, 252.54 0, 1+ALB+AST+ALT+NEFA+Orn+Lys; 0.758, 252.655, 1+ALB+ALT+His+Ar g+Orn+Ile; 0.758, 252.714, 1+ALB+BUN+AST+ALT+His+Orn; 0.758, 254. 768, 1+ALB+BUN+Glc+His+Arg+Lys; 0.758, 254.839, 1+ALB+BUN+AST+G lc+Lys+Ile; 0.758, 255.540, 1+ALB+AST+NEFA+Thr+Orn+Lys; 0.758, 2 52.420, 1+ALB+AST+NEFA+Asp+Lys+Trp; 0.757, 252.416, 1+ALB+Ca+AL T+His+Arg+Orn; 0.757, 251.964, 1+ALB+BUN+Ca+ALT+Glc+Arg; 0.757, 254.644, 1+ALB+BUN+Ca+NEFA+Lys+Ile; 0.757, 253.954, 1+ALB+BUN+A ST+Orn+Lys+Phe; 0.757, 253.416, 1+ALB+BUN+Asp+Orn+Lys+Val; 0.75 7, 255.105, 1+ALB+BUN+NEFA+Glc+Thr+Lys; 0.757, 250.913, 1+ALB+AL T+Asp+Lys+Val+Phe; 0.757, 252.374, 1+ALB+BUN+ALT+NEFA+Thr+Orn; 0.757, 252.883, 1+ALB+ALT+NEFA+Orn+Lys+Ile; 0.757, 253.107, 1+AL B+ALT+Glc+Orn+Lys+Ile; 0.757, 255.225, 1+ALB+AST+NEFA+Orn+Lys+Phe; 0.757, 250.282, 1+ALB+AST+ALT+Arg+Asp+Lys; 0.757, 253.269, 1+ALB+ALT+NEFA+T-BIL+Lys+Ile; 0.757, 256.797, 1+ALB+AST+BHBA+Or n+Lys+Ile; 0.757, 250.027, 1+ALB+BUN+AST+ALT+Asp+Orn; 0.757, 253. 452, 1+ALB+AST+NEFA+Asp+Lys+Val; 0.757, 255.286, 1+ALB+AST+NEFA+Arg+Thr+Ile; 0.757, 251.363, 1+ALB+ALT+Asp+Orn+Val+Phe; 0.757, 255.304, 1+ALB+BUN+NEFA+3MeHis+Val+Phe; 0.757, 255.505, 1+ALB+B UN+Glc+Arg+Lys+Ile; 0.757, 255.637, 1+ALB+BUN+gGT+Glc+His+Lys; 0.757, 250.119, 1+ALB+BUN+ALT+Asp+Orn+Val; 0.757, 252.374, 1+ALB+BUN+ALT+T-BIL+Thr+Orn; 0.757, 252.691, 1+ALB+ALT+3MeHis+Orn+L ys+Tyr; 0.757, 253.220, 1+ALB+ALT+Glc+Thr+Lys+Ile; 0.757, 253.26 7, 1+ALB+ALT+T-BIL+Thr+Lys+Ile; 0.757, 254.663, 1+ALB+AST+NEFA+Orn+Phe+Trp; 0.757, 255.456, 1+ALB+AST+NEFA+Glc+Lys+Ile; 0.757, 253.961, 1+ALB+BUN+3MeHis+Arg+Orn+Lys; 0.757, 252.657, 1+ALB+AL T+BHBA+His+Orn+Lys; 0.757, 254.381, 1+ALB+AST+NEFA+Orn+Lys+Tr p; 0.757, 251.240, 1+ALB+AST+3Me-His+Asp+Lys+Tyr; 0.757, 252.082, 1+ALB+BUN+ALT+gGT+His+Arg; 0.757, 254.425, 1+ALB+BUN+His+Arg+O rn+Lys; 0.757, 254.547, 1+ALB+BUN+AST+BHBA+Lys+Ile; 0.757, 251.3 81, 1+ALB+BUN+AST+ALT+3MeHis+Trp; 0.757, 252.871, 1+ALB+AST+ALT+NEFA+BHBA+Lys; 0.757, 252.610, 1+ALB+BUN+AST+NEFA+Arg+Trp; 0.7 57, 251.972, 1+ALB+BUN+Ca+ALT+Arg+Ile; 0.757, 253.502, 1+ALB+BUN+NEFA+Asp+Tyr+Phe; 0.757, 255.615, 1+ALB+BUN+BHBA+Thr+Lys+Ile; 0.757, 255.433, 1+ALB+BUN+Arg+Orn+Lys+Ile; 0.757, 252.757, 1+ALB+ALT+Arg+Orn+Lys+Tyr; 0.757, 252.717, 1+ALB+ALT+Glc+His+Arg+Or n; 0.757, 252.738, 1+ALB+ALT+Glc+His+Orn+Lys; 0.757, 255.710, 1+A LB+AST+Arg+Thr+Lys+Ile; 0.757, 255.450, 1+ALB+AST+NEFA+BHBA+Ly s+Ile; 0.757, 252.902, 1+ALB+BUN+AST+NEFA+Orn+Trp; 0.757, 254.25 4, 1+ALB+BUN+AST+gGT+His+Lys; 0.757, 255.712, 1+ALB+AST+NEFA+Ar g+Orn+Ile; 0.757, 251.575, 1+ALB+Ca+ALT+His+Arg+Lys; 0.757, 255. 019, 1+ALB+BUN+T-BIL+Glc+Lys+Ile; 0.757, 253.054, 1+ALB+3MeHis+Asp+Lys+Tyr+Phe; 0.757, 250.953, 1+ALB+BUN+NEFA+3MeHis+Asp+Tr p; 0.757, 253.111, 1+ALB+ALT+BHBA+Orn+Lys+Ile; 0.757, 254.537, 1+ALB+BUN+BHBA+His+Orn+Lys; 0.757, 252.072, 1+ALB+AST+ALT+Arg+Ly s+Tyr; 0.757, 252.855, 1+ALB+AST+ALT+T-BIL+His+Lys; 0.757, 255.5 02, 1+ALB+BUN+Arg+Lys+Val+Phe; 0.757, 254.288, 1+ALB+BUN+3MeHis+Arg+Orn+Phe; 0.757, 253.550, 1+ALB+BUN+ALT+gGT+Glc+Orn; 0.757, 249.040, 1+ALB+ALT+3MeHis+Asp+Lys+Tyr; 0.757, 252.741, 1+ALB+AL T+NEFA+3MeHis+Orn+Lys; 0.757, 253.084, 1+ALB+ALT+T-BIL+Orn+Lys+Ile; 0.757, 253.008, 1+ALB+ALT+NEFA+His+Lys+Ile; 0.757, 254.532, 1+ALB+BUN+AST+Thr+Orn+Lys; 0.757, 252.929, 1+ALB+AST+ALT+Glc+O rn+Lys; 0.757, 254.485, 1+ALB+BUN+AST+BHBA+Thr+Lys; 0.757, 254.5 98, 1+ALB+AST+NEFA+Lys+Tyr+Trp; 0.757, 254.455, 1+ALB+BUN+AST+H is+Lys+Ile; 0.757, 256.035, 1+ALB+AST+BHBA+His+Orn+Lys; 0.757, 2 51.510, 1+ALB+AST+3MeHis+Asp+Orn+Trp; 0.757, 254.144, 1+ALB+Ca+gGT+Glc+Asn+Arg; 0.757, 255.136, 1+ALB+BUN+gGT+NEFA+BHBA+Lys; 0. 757, 252.350, 1+ALB+BUN+ALT+Glc+Thr+Orn; 0.757, 255.082, 1+ALB+B UN+NEFA+T-BIL+Thr+Lys; 0.757, 255.351, 1+ALB+BUN+NEFA+3MeHis+T yr+Phe; 0.757, 252.230, 1+ALB+ALT+NEFA+3MeHis+Lys+Trp; 0.757, 25 4.033, 1+ALB+BUN+AST+Arg+Lys+Phe; 0.757, 252.720, 1+ALB+ALT+T-B IL+His+Arg+Orn; 0.757, 254.371, 1+ALB+BUN+AST+gGT+BHBA+Lys; 0.7 57, 251.499, 1+ALB+BUN+AST+NEFA+Trp; 0.757, 252.996, 1+ALB+B UN+AST+Arg+Val+Trp; 0.757, 253.502, 1+ALB+BUN+Ca+AST+T-BIL+Ly s; 0.757, 253.701, 1+ALB+Ca+AST+gGT+BHBA+Asn; 0.757, 254.824, 1+A LB+BUN+NEFA+Arg+Thr+Lys; 0.757, 255.157, 1+ALB+BUN+gGT+NEFA+Or n+Lys; 0.757, 253.026, 1+ALB+AST+ALT+NEFA+Arg+Ile; 0.757, 252.64 1, 1+ALB+ALT+NEFA+Orn+Lys+Trp; 0.757, 256.443, 1+ALB+AST+Glc+Ar g+Lys+Ile; 0.757, 249.100, 1+ALB+ALT+3MeHis+Asp+Orn+Lys; 0.757, 251.101, 1+ALB+AST+3MeHis+Asp+Lys+Val; 0.757, 254.795, 1+ALB+BU N+AST+Glc+Thr+Lys; 0.757, 254.043, 1+ALB+AST+NEFA+Arg+Lys+Trp; 0.757, 254.983, 1+ALB+AST+NEFA+Arg+Orn+Lys; 0.757, 256.750, 1+AL B+Ca+AST+Orn+Lys+Ile; 0.757, 255.917, 1+ALB+3MeHis+Lys+Val+Phe+Trp; 0.757, 250.336, 1+ALB+BUN+ALT+Asp+Tyr+Val; 0.757, 253.084, 1+ALB+ALT+gGT+Orn+Lys+Ile; 0.757, 253.231, 1+ALB+BUN+ALT+Glc+H is+Orn; 0.757, 250.894, 1+ALB+AST+ALT+Arg+Asp+Phe; 0.757, 252.60 2, 1+ALB+ALT+NEFA+His+Arg+Orn; 0.757, 252.722, 1+ALB+ALT+BHBA+H is+Arg+Orn; 0.757, 252.874, 1+ALB+AST+ALT+NEFA+Glc+Lys; 0.757, 2 52.956, 1+ALB+BUN+AST+ALT+Glc+Orn; 0.757, 254.378, 1+ALB+AST+3M eHis+Arg+Lys+Tyr; 0.757, 255.047, 1+ALB+AST+NEFA+Glc+Arg+Lys; 0. 757, 255.505, 1+ALB+BUN+Arg+Orn+Lys+Phe; 0.757, 253.552, 1+ALB+B UN+ALT+gGT+NEFA+Orn; 0.757, 253.792, 1+ALB+BUN+3MeHis+Arg+Orn+Trp; 0.757, 252.076, 1+ALB+ALT+3MeHis+Orn+Lys+Trp; 0.757, 253.30 0, 1+ALB+ALT+gGT+Thr+Lys+Ile; 0.757, 254.338, 1+ALB+BUN+AST+Arg+Thr+Lys; 0.757, 253.436, 1+ALB+AST+Arg+Asp+Tyr+Trp; 0.757, 253. 567, 1+ALB+AST+Arg+Asp+Orn+Trp; 0.757, 254.940, 1+ALB+AST+NEFA+3MeHis+Lys+Tyr; 0.757, 257.261, 1+ALB+AST+T-BIL+Thr+Orn+Ile; 0. 757, 253.311, 1+ALB+BUN+Ca+ALT+gGT+Orn; 0.757, 253.148, 1+ALB+AL T+NEFA+Glc+His+Lys; 0.757, 254.417, 1+ALB+BUN+AST+BHBA+Orn+Ly s; 0.757, 254.785, 1+ALB+BUN+AST+gGT+Glc+Lys; 0.757, 253.952, 1+A LB+AST+ALT+NEFA+His+Orn; 0.757, 252.675, 1+ALB+Ca+AST+ALT+Arg+Orn; 0.757, 255.777, 1+ALB+BUN+Ca+Orn+Lys+Ile; 0.757, 254.476, 1+ALB+AST+NEFA+Lys+Val+Trp; 0.757, 254.849, 1+ALB+BUN+NEFA+Arg+L ys+Tyr; 0.757, 252.561, 1+ALB+ALT+NEFA+Arg+Lys+Tyr; 0.757, 255.1 59, 1+ALB+BUN+gGT+BHBA+His+Lys; 0.757, 253.214, 1+ALB+BUN+ALT+g GT+His+Orn; 0.757, 254.670, 1+ALB+BUN+AST+Glc+Orn+Lys; 0.757, 25 2.859, 1+ALB+ALT+His+Thr+Lys+Ile; 0.757, 252.883, 1+ALB+AST+ALT+NEFA+Lys+Val; 0.757, 253.138, 1+ALB+AST+ALT+His+Lys+Ile; 0.757, 255.150, 1+ALB+AST+Arg+Tyr+Phe+Trp; 0.757, 252.916, 1+ALB+AST+A LT+T-BIL+Lys+Ile; 0.757, 253.589, 1+ALB+AST+NEFA+His+Arg+Lys; 0. 757, 256.366, 1+ALB+3MeHis+Orn+Lys+Val+Phe; 0.757, 255.142, 1+AL B+BUN+NEFA+T-BIL+BHBA+Lys; 0.757, 253.537, 1+ALB+BUN+ALT+gGT+T-BIL+Orn; 0.757, 252.445, 1+ALB+BUN+Arg+Asp+Tyr+Trp; 0.757, 252. 601, 1+ALB+ALT+NEFA+Arg+Lys+Val; 0.757, 253.657, 1+ALB+ALT+NEFA+3MeHis+Tyr+Phe; 0.757, 254.656, 1+ALB+BUN+AST+Arg+Orn+Phe; 0.7 57, 254.675, 1+ALB+BUN+AST+Orn+Lys+Val; 0.757, 254.779, 1+ALB+BU N+gGT+His+Arg+Lys; 0.757, 252.007, 1+ALB+AST+ALT+T-BIL+Arg+Ly s; 0.757, 252.381, 1+ALB+AST+ALT+Orn+Tyr+Trp; 0.757, 252.853, 1+A LB+AST+ALT+BHBA+Orn+Lys; 0.757, 253.467, 1+ALB+AST+Asp+Orn+Tyr+Trp; 0.757, 256.191, 1+ALB+AST+Glc+His+Orn+Lys; 0.757, 257.011, 1+ALB+AST+T-BIL+BHBA+His+Orn; 0.757, 255.251, 1+ALB+AST+NEFA+Glc+His+Lys; 0.757, 255.533, 1+ALB+Ca+AST+NEFA+Orn+Lys; 0.757, 255.102, 1+ALB+BUN+Ca+gGT+NEFA+Lys; 0.757, 250.992, 1+ALB+BUN+AST+3MeHis+Arg+Asp; 0.757, 251.151, 1+ALB+ALT+NEFA+Asp+Orn+Lys; 0.757, 252.850, 1+ALB+AST+ALT+T-BIL+Arg+Orn; 0.757, 252.918, 1+ALB+AST+ALT+Orn+Lys+Val; 0.757, 253.309, 1+ALB+ALT+BHBA+Thr+Lys+Ile; 0.757, 254.839, 1+ALB+AST+Arg+Orn+Lys+Trp; 0.757, 255.140, 1+ALB+AST+Orn+Lys+Phe+Trp; 0.757, 253.504, 1+ALB+AST+ALT+Thr+Orn+Ile; 0.757, 253.492, 1+ALB+AST+Asp+Lys+Phe+Trp; 0.756, 253.163, 1+ALB+Ca+ALT+Arg+Orn+Ile; 0.756, 255.064, 1+ALB+BUN+NEFA+Orn+Lys+Val; 0.756, 255.090, 1+ALB+BUN+NEFA+Lys+Tyr+Val; 0.756, 255.162, 1+ALB+BUN+NEFA+T-BIL+Glc+Lys; 0.756, 255.783, 1+ALB+BUN+BHBA+Orn+Lys+Ile; 0.756, 251.466, 1+ALB+ALT+Arg+Asp+Val+Phe; 0.756, 249.403, 1+ALB+BUN+ALT+3MeHis+Asp+Tyr; 0.756, 251.140, 1+ALB+ALT+NEFA+Asp+Lys+Tyr; 0.756, 252.599, 1+ALB+BUN+Asp+Orn+Val+Trp; 0.756, 252.833, 1+ALB+ALT+NEFA+Lys+Tyr+Trp; 0.756, 252.767, 1+ALB+ALT+NEFA+Lys+Val+Trp; 0.756, 254.618, 1+ALB+BUN+AST+Orn+Lys+Tyr; 0.756, 252.790, 1+ALB+AST+ALT+NEFA+Thr+Lys; 0.756, 253.123, 1+ALB+AST+ALT+BHBA+Lys+Ile; 0.756, 253.294, 1+ALB+AST+3MeHis+Arg+Lys+Trp; 0.756, 253.326, 1+ALB+AST+Asp+Orn+Lys+Trp; 0.756, 253.213, 1+ALB+Ca+AST+ALT+Lys+Ile; 0.756, 253.147, 1+ALB+BUN+ALT+NEFA+3MeHis+Orn; 0.756, 255.087, 1+ALB+BUN+NEFA+Thr+Orn+Lys; 0.756, 252.175, 1+ALB+3MeHis+Asp+Lys+Val+Trp; 0.756, 252.528, 1+ALB+BUN+Asp+Orn+Tyr+Trp; 0.756, 251.367, 1+ALB+ALT+Asp+Orn+Lys+Tyr; 0.756, 252.357, 1+ALB+AST+ALT+Arg+Val+Phe; 0.756, 253.658, 1+ALB+ALT+NEFA+3MeHis+Val+Phe; 0.756, 250.634, 1+ALB+AST+ALT+Asp+Orn+Lys; 0.756, 251.388, 1+ALB+AST+ALT+Arg+Asp+Orn; 0.756, 252.506, 1+ALB+BUN+AST+3MeHis+Orn+Trp; 0.756, 256.335, 1+ALB+NEFA+Arg+Thr+Lys+Ile; 0.756, 253.134, 1+ALB+AST+NEFA+Asp+Orn+Trp; 0.756, 255.285, 1+ALB+AST+NEFA+T-BIL+His+Lys; 0.756, 255.741, 1+ALB+AST+His+Thr+Orn+Lys; 0.756, 253.193, 1+ALB+Ca+AST+ALT+Arg+Ile; 0.756, 254.788, 1+ALB+BUN+Ca+NEFA+Arg+Lys; 0.756, 249.352, 1+ALB+BUN+ALT+3MeHis+Asp+Val; 0.756, 251.370, 1+ALB+ALT+Asp+Orn+Lys+Val; 0.756, 253.519, 1+ALB+BUN+ALT+Glc+Orn+Ile; 0.756, 254.483, 1+ALB+BUN+AST+Glc+Arg+Lys; 0.756, 252.092, 1+ALB+AST+ALT+Arg+Lys+Val; 0.756, 253.882, 1+ALB+AST+3MeHis+Orn+Lys+Trp; 0.756, 251.613, 1+ALB+AST+ALT+His+Arg+Thr; 0.756, 252.833, 1+ALB+AST+ALT+Thr+Orn+Lys; 0.756, 253.896, 1+ALB+AST+NEFA+3MeHis+Lys+Trp; 0.756, 251.156, 1+ALB+AST+3MeHis+Arg+Asp+Trp; 0.756, 252.874, 1+ALB+Ca+AST+ALT+Orn+Lys; 0.756, 252.952, 1+ALB+BUN+Ca+ALT+His+Orn; 0.756, 254.921, 1+ALB+BUN+Ca+T-BIL+Lys+Ile; 0.756, 254.887, 1+ALB+BUN+NEFA+Glc+Arg+Lys; 0.756, 255.542, 1+ALB+BUN+gGT+Arg+Lys+Ile; 0.756, 255.451, 1+ALB+AST+NEFA+Lys+Val+Phe; 0.756, 253.218, 1+ALB+BUN+ALT+NEFA+His+Orn; 0.756, 255.476, 1+ALB+BUN+Ca+His+Lys+Ile; 0.756, 253.871, 1+ALB+BUN+3MeHis+Arg+Tyr+Trp; 0.756, 250.408, 1+ALB+ALT+3MeHis+Arg+Asp+Val; 0.756, 253.122, 1+ALB+ALT+gGT+NEFA+His+Lys; 0.756, 254.515, 1+ALB+BUN+AST+Arg+Lys+Val; 0.756, 252.031, 1+ALB+AST+ALT+BHBA+Arg+Lys; 0.756, 249.595, 1+ALB+AST+ALT+3MeHis+Arg+Asp; 0.756, 252.707, 1+ALB+AST+ALT+NEFA+His+Arg; 0.756, 255.758, 1+ALB+AST+NEFA+Arg+Thr+Orn; 0.756, 256.032, 1+ALB+AST+gGT+His+Orn+Lys; 0.756, 253.088, 1+ALB+AST+NEFA+Arg+Asp+Trp; 0.756, 255.098, 1+ALB+AST+NEFA+His+Thr+Orn; 0.756, 255.284, 1+ALB+AST+NEFA+BHBA+His+Lys; 0.756, 256.722, 1+ALB+AST+T-BIL+BHBA+Lys+Ile; 0.756, 252.295, 1+ALB+BUN+Ca+ALT+Thr+Orn; 0.756, 253.025, 1+ALB+Ca+ALT+Orn+Lys+Ile; 0.756, 253.309, 1+ALB+BUN+Ca+ALT+Orn+Ile; 0.756, 253.430, 1+ALB+AST+ALT+T-BIL+Arg+Ile; 0.756, 255.152, 1+ALB+BUN+NEFA+BHBA+Glc+Lys; 0.756, 255.168, 1+ALB+BUN+NEFA+Glc+Orn+Lys; 0.756, 253.467, 1+ALB+ALT+NEFA+Thr+Orn+Lys; 0.756, 254.458, 1+ALB+BUN+AST+gGT+Orn+Lys; 0.756, 254.232, 1+ALB+BUN+AST+BHBA+Arg+Lys; 0.756, 254.413, 1+ALB+BUN+AST+Arg+Orn+Lys; 0.756, 252.090, 1+ALB+AST+ALT+Glc+Arg+Lys; 0.756, 254.862, 1+ALB+BUN+AST+Lys+Tyr+Val; 0.756, 252.490, 1+ALB+Ca+AST+BHBA+Glc+Asn; 0.756, 254.634, 1+ALB+AST+NEFA+Lys+Phe+Trp; 0.756, 255.315, 1+ALB+BUN+T-BIL+Thr+Orn+Lys; 0.756, 250.368, 1+ALB+ALT+3MeHis+Arg+Asp+Orn; 0.756, 255.169, 1+ALB+BUN+NEFA+Orn+Lys+Tyr; 0.756, 253.175, 1+ALB+BUN+ALT+T-BIL+His+Orn; 0.756, 252.140, 1+ALB+ALT+T-BIL+His+Arg+Thr; 0.756, 253.138, 1+ALB+ALT+NEFA+BHBA+His+Lys; 0.756, 253.082, 1+ALB+AST+ALT+NEFA+3MeHis+Phe; 0.756, 253.265, 1+ALB+AST+ALT+Glc+Lys+Ile; 0.756, 255.037, 1+ALB+AST+NEFA+Arg+Thr+Lys; 0.756, 255.910, 1+ALB+AST+His+Arg+Lys+Ile; 0.756, 254.365, 1+ALB+BUN+Ca+AST+His+Lys; 0.756, 251.998, 1+ALB+Ca+AST+ALT+Arg+Lys; 0.756, 255.169, 1+ALB+BUN+BHBA+His+Lys+Ile; 0.756, 255.371, 1+ALB+BUN+gGT+T-BIL+Orn+Lys; 0.756, 255.371, 1+ALB+BUN+T-BIL+BHBA+Orn+Lys; 0.756, 253.515, 1+ALB+BUN+ALT+gGT+Orn+Ile; 0.756, 254.894, 1+ALB+BUN+gGT+NEFA+Arg+Lys; 0.756, 250.447, 1+ALB+BUN+ALT+NEFA+Asp+Val; 0.756, 252.654, 1+ALB+BUN+Arg+Asp+Val+Trp; 0.756, 252.078, 1+ALB+AST+ALT+3MeHis+Orn+Trp; 0.756, 252.815, 1+ALB+AST+ALT+T-BIL+Orn+Lys; 0.756, 253.261, 1+ALB+AST+ALT+Glc+His+Lys; 0.756, 256.608, 1+ALB+AST+gGT+Orn+Lys+Ile; 0.756, 254.945, 1+ALB+AST+NEFA+Arg+Lys+Val; 0.756, 255.166, 1+ALB+BUN+NEFA+Arg+Tyr+Phe; 0.756, 254.662, 1+ALB+BUN+Arg+Orn+Val+Trp; 0.756, 252.225, 1+ALB+ALT+3MeHis+Lys+Tyr+Trp; 0.756, 251.945, 1+ALB+ALT+NEFA+His+Arg+Thr; 0.756, 252.139, 1+ALB+ALT+BHBA+His+Arg+Thr; 0.756, 252.447, 1+ALB+AST+ALT+Arg+Thr+Orn; 0.756, 254.402, 1+ALB+BUN+BHBA+His+Arg+Lys; 0.756, 251.990, 1+ALB+AST+ALT+Arg+Thr+Lys; 0.756, 255.295, 1+ALB+AST+Arg+Tyr+Val+Trp; 0.756, 255.485, 1+ALB+AST+3MeHis+Lys+Val+Phe; 0.756, 253.648, 1+ALB+AST+Asp+Orn+Val+Trp; 0.756, 254.327, 1+ALB+AST+3MeHis+Lys+Tyr+Trp; 0.756, 254.805, 1+ALB+AST+gGT+NEFA+His+Lys; 0.756, 255.485, 1+ALB+BUN+Ca+gGT+His+Lys; 0.756, 255.341, 1+ALB+BUN+T-BIL+BHBA+Thr+Lys; 0.756, 255.370, 1+ALB+BUN+T-BIL+Glc+Orn+Lys; 0.756, 253.503, 1+ALB+ALT+gGT+NEFA+Orn+Lys; 0.756, 253.715, 1+ALB+BUN+ALT+gGT+Thr+Ile; 0.756, 252.715, 1+ALB+ALT+gGT+His+Arg+Orn; 0.756, 253.423, 1+ALB+AST+NEFA+Asp+Lys+Phe; 0.756, 254.370,

1+ALB+BUN+AST+gGT+Arg+Lys; 0.756, 254.654, 1+ALB+BUN+AST+BHBA+Glc+Lys; 0.756, 256.326, 1+ALB+NEFA+BHBA+Arg+Lys+Ile; 0.756, 250.988, 1+ALB+AST+ALT+Asp+Val+Trp; 0.756, 253.123, 1+ALB+AST+ALT+gGT+His+Lys; 0.756, 254.995, 1+ALB+AST+Arg+Orn+Phe+Trp; 0.756, 254.421, 1+ALB+AST+NEFA+3MeHis+Orn+Trp; 0.756, 255.457, 1+ALB+Ca+AST+NEFA+Lys+Ile; 0.756, 254.731, 1+ALB+BUN+Ca+AST+Thr+Lys; 0.756, 254.557, 1+ALB+BUN+Ca+His+Arg+Lys; 0.756, 253.457, 1+ALB+AST+ALT+Glc+Arg+Ile; 0.756, 255.137, 1+ALB+BUN+NEFA+T-BIL+Orn+Lys; 0.756, 251.826, 1+ALB+AST+ALT+3MeHis+Arg+Orn; 0.756, 252.737, 1+ALB+BUN+ALT+Orn+Tyr+Val; 0.756, 255.070, 1+ALB+BUN+NEFA+BHBA+Thr+Lys; 0.756, 252.516, 1+ALB+BUN+NEFA+Asp+Orn+Trp; 0.756, 252.772, 1+ALB+ALT+Arg+Orn+Lys+Val; 0.756, 253.303, 1+ALB+ALT+NEFA+Arg+Thr+Orn; 0.756, 253.427, 1+ALB+ALT+NEFA+Arg+Orn+Ile; 0.756, 253.430, 1+ALB+ALT+BHBA+Arg+Orn+Ile; 0.756, 253.525, 1+ALB+BUN+ALT+NEFA+Orn+Ile; 0.756, 252.988, 1+ALB+AST+ALT+NEFA+T-BIL+Arg; 0.756, 253.140, 1+ALB+ALT+NEFA+T-BIL+His+Lys; 0.756, 254.512, 1+ALB+BUN+AST+Arg+Lys+Tyr; 0.756, 256.410, 1+ALB+AST+BHBA+Arg+Lys+Ile; 0.756, 255.021, 1+ALB+AST+NEFA+BHBA+Arg+Lys; 0.756, 255.487, 1+ALB+BUN+Ca+Glc+His+Lys; 0.756, 255.119, 1+ALB+BUN+Ca+NEFA+Glc+Lys; 0.756, 253.505, 1+ALB+AST+ALT+BHBA+Arg+Ile; 0.756, 255.160, 1+ALB+BUN+BHBA+Glc+His+Lys; 0.756, 255.330, 1+ALB+BUN+T-BIL+Glc+Thr+Lys; 0.756, 255.341, 1+ALB+BUN+gGT+T-BIL+Thr+Lys; 0.756, 252.918, 1+ALB+3MeHis+Arg+Asp+Lys+Tyr; 0.756, 253.546, 1+ALB+BUN+NEFA+Asp+Orn+Phe; 0.756, 254.676, 1+ALB+BUN+Arg+Orn+Tyr+Trp; 0.756, 253.132, 1+ALB+AST+ALT+NEFA+Glc+Arg; 0.756, 253.523, 1+ALB+ALT+NEFA+BHBA+Orn+Lys; 0.756, 252.726, 1+ALB+ALT+gGT+His+Orn+Lys; 0.756, 252.778, 1+ALB+ALT+Glc+Arg+Orn+Lys; 0.756, 252.860, 1+ALB+AST+ALT+Glc+Arg+Orn; 0.756, 252.868, 1+ALB+AST+ALT+BHBA+Arg+Orn; 0.756, 253.323, 1+ALB+ALT+gGT+Arg+Thr+Orn; 0.756, 253.351, 1+ALB+ALT+NEFA+BHBA+Lys+Ile; 0.756, 253.646, 1+ALB+BUN+ALT+gGT+BHBA+Thr; 0.756, 253.817, 1+ALB+ALT+3MeHis+Tyr+Val+Phe; 0.756, 252.298, 1+ALB+ALT+His+Thr+Orn+Lys; 0.756, 251.428, 1+ALB+AST+ALT+NEFA+Arg+Asp; 0.756, 252.881, 1+ALB+BUN+AST+ALT+NEFA+Orn; 0.756, 254.422, 1+ALB+BUN+AST+NEFA+Tyr+Phe; 0.756, 253.266, 1+ALB+AST+ALT+T-BIL+BHBA+Lys; 0.756, 255.130, 1+ALB+AST+gGT+NEFA+Orn+Lys; 0.756, 255.986, 1+ALB+AST+NEFA+T-BIL+Glc+Lys; 0.756, 254.391, 1+ALB+BUN+Ca+AST+Arg+Lys; 0.756, 255.324, 1+ALB+BUN+Ca+Arg+Lys+Ile; 0.756, 255.078, 1+ALB+BUN+Ca+NEFA+T-BIL+Lys; 0.756, 255.408, 1+ALB+BUN+gGT+T-BIL+BHBA+Lys; 0.756, 254.385, 1+ALB+BUN+3MeHis+Orn+Val+Trp; 0.756, 255.057, 1+ALB+BUN+Orn+Tyr+Val+Trp; 0.756, 252.619, 1+ALB+ALT+NEFA+Glc+Arg+Lys; 0.756, 252.739, 1+ALB+BUN+ALT+NEFA+Orn+Tyr; 0.756, 253.331, 1+ALB+ALT+NEFA+Glc+Lys+Ile; 0.756, 253.505, 1+ALB+BUN+ALT+T-BIL+Orn+Ile; 0.756, 253.615, 1+ALB+ALT+T-BIL+Thr+Orn+Lys; 0.756, 252.526, 1+ALB+BUN+AST+ALT+3MeHis+Orn; 0.756, 252.096, 1+ALB+AST+ALT+NEFA+Asp+Orn; 0.756, 252.457, 1+ALB+AST+ALT+NEFA+Arg+Thr; 0.756, 252.878, 1+ALB+BUN+AST+ALT+BHBA+Orn; 0.756, 253.189, 1+ALB+AST+ALT+T-BIL+Thr+Lys; 0.756, 253.325, 1+ALB+BUN+Ca+ALT+T-BIL+Orn; 0.756, 254.484, 1+ALB+BUN+Asp+Orn+Tyr+Phe; 0.756, 254.511, 1+ALB+BUN+3MeHis+Orn+Tyr+Trp; 0.756, 253.301, 1+ALB+BUN+ALT+NEFA+Orn+Val; 0.756, 253.569, 1+ALB+BUN+ALT+NEFA+Glc+Orn; 0.756, 251.425, 1+ALB+ALT+Asp+Lys+Tyr+Val; 0.756, 252.777, 1+ALB+ALT+T-BIL+Arg+Orn+Lys; 0.756, 252.777, 1+ALB+ALT+gGT+Arg+Orn+Lys; 0.756, 253.592, 1+ALB+BUN+ALT+BHBA+Thr+Ile; 0.756, 252.080, 1+ALB+ALT+Glc+His+Arg+Thr; 0.756, 252.754, 1+ALB+BUN+AST+ALT+Orn+Val; 0.756, 253.066, 1+ALB+ALT+NEFA+T-BIL+Arg+Thr; 0.756, 252.842, 1+ALB+BUN+AST+ALT+T-BIL+Orn; 0.756, 256.714, 1+ALB+AST+T-BIL+Arg+Orn+Ile; 0.756, 254.653, 1+ALB+BUN+AST+NEFA+Arg+Orn; 0.756, 255.381, 1+ALB+AST+His+Arg+Orn+Lys; 0.756, 255.032, 1+ALB+BUN+Ca+NEFA+Thr+Lys; 0.756, 253.347, 1+ALB+BUN+Ca+ALT+Glc+Orn; 0.756, 252.322, 1+ALB+3MeHis+Asp+Lys+Tyr+Trp; 0.756, 252.956, 1+ALB+3MeHis+Asp+Lys+Val+Phe; 0.756, 255.131, 1+ALB+BUN+NEFA+BHBA+Orn+Lys; 0.756, 253.837, 1+ALB+BUN+3MeHis+Arg+Val+Trp; 0.756, 254.877, 1+ALB+BUN+NEFA+BHBA+Arg+Lys; 0.756, 254.770, 1+ALB+BUN+NEFA+Arg+Lys+Val; 0.756, 253.385, 1+ALB+ALT+T-BIL+His+Lys+Ile; 0.756, 253.481, 1+ALB+ALT+T-BIL+Glc+His+Lys; 0.756, 253.598, 1+ALB+ALT+BHBA+Thr+Orn+Lys; 0.756, 253.612, 1+ALB+ALT+gGT+Thr+Orn+Lys; 0.756, 253.676, 1+ALB+BUN+ALT+Glc+Thr+Ile; 0.756, 255.692, 1+ALB+BUN+AST+Thr+Orn+Ile; 0.756, 256.027, 1+ALB+AST+NEFA+Arg+Orn+Tyr; 0.756, 256.617, 1+ALB+AST+T-BIL+Thr+Lys+Ile; 0.755, 256.105, 1+ALB+Ca+AST+His+Orn+Lys; 0.755, 255.137, 1+ALB+BUN+T-BIL+Arg+Thr+Lys; 0.755, 254.534, 1+ALB+BUN+NEFA+3MeHis+Orn+Trp; 0.755, 256.044, 1+ALB+BUN+gGT+BHBA+Lys+Ile; 0.755, 252.622, 1+ALB+ALT+gGT+NEFA+Arg+Lys; 0.755, 252.788, 1+ALB+ALT+Arg+Lys+Tyr+Val; 0.755, 252.816, 1+ALB+ALT+Lys+Tyr+Val+Trp; 0.755, 252.869, 1+ALB+AST+ALT+Arg+Orn+Tyr; 0.755, 253.685, 1+ALB+BUN+ALT+gGT+NEFA+Thr; 0.755, 250.758, 1+ALB+AST+ALT+Asp+Lys+Val; 0.755, 254.132, 1+ALB+AST+3MeHis+Orn+Phe+Trp; 0.755, 255.385, 1+ALB+AST+NEFA+Arg+Tyr+Phe; 0.755, 254.961, 1+ALB+AST+Arg+Lys+Val+Trp; 0.755, 255.995, 1+ALB+AST+NEFA+T-BIL+BHBA+Lys; 0.755, 252.668, 1+ALB+Ca+ALT+Arg+Orn+Lys; 0.755, 253.789, 1+ALB+Ca+ALT+NEFA+Arg+Ile; 0.755, 256.313, 1+ALB+Ca+AST+Arg+Lys+Ile; 0.755, 253.214, 1+ALB+Ca+AST+ALT+His+Lys; 0.755, 256.159, 1+ALB+3MeHis+Arg+Lys+Val+Phe; 0.755, 252.017, 1+ALB+ALT+NEFA+Asp+Val+Phe; 0.755, 254.524, 1+ALB+BUN+3MeHis+Arg+Val+Phe; 0.755, 252.100, 1+ALB+ALT+NEFA+Arg+Asp+Val; 0.755, 253.412, 1+ALB+ALT+NEFA+T-BIL+Orn+Lys; 0.755, 252.573, 1+ALB+ALT+NEFA+Arg+Thr+Lys; 0.755, 253.296, 1+ALB+ALT+gGT+NEFA+Lys+Ile; 0.755, 253.502, 1+ALB+ALT+NEFA+Orn+Lys+Val; 0.755, 253.649, 1+ALB+BUN+ALT+T-BIL+BHBA+Thr; 0.755, 253.712, 1+ALB+ALT+T-BIL+BHBA+Lys+Ile; 0.755, 252.102, 1+ALB+ALT+gGT+His+Arg+Thr; 0.755, 253.123, 1+ALB+AST+ALT+NEFA+BHBA+Arg; 0.755, 256.084, 1+ALB+AST+T-BIL+Arg+Orn+Lys; 0.755, 256.001, 1+ALB+AST+NEFA+BHBA+Glc+Lys; 0.755, 257.658, 1+ALB+AST+gGT+Thr+Orn+Ile; 0.755, 254.899, 1+ALB+AST+T-BIL+His+Arg+Lys; 0.755, 254.959, 1+ALB+AST+NEFA+T-BIL+Arg+Lys; 0.755, 253.287, 1+ALB+Ca+ALT+Thr+Lys+Ile; 0.755, 254.706, 1+ALB+BUN+Ca+AST+gGT+Lys; 0.755, 252.948, 1+ALB+Ca+AST+ALT+NEFA+Arg; 0.755, 255.157, 1+ALB+3MeHis+Arg+Lys+Val+Trp; 0.755, 250.447,

1+ALB+ALT+NEFA+3MeHis+Arg+Asp; 0.755, 253.506, 1+ALB+ALT+NEFA+Glc+Orn+Lys; 0.755, 254.891, 1+ALB+BUN+NEFA+Arg+Orn+Lys; 0.755, 255.420, 1+ALB+BUN+BHBA+Arg+Lys+Ile; 0.755, 253.335, 1+ALB+AST+ALT+BHBA+Glc+Lys; 0.755, 254.952, 1+ALB+AST+3MeHis+Orn+Lys+Phe; 0.755, 252.808, 1+ALB+AST+ALT+His+Thr+Lys; 0.755, 253.698, 1+ALB+AST+Asp+Orn+Phe+Trp; 0.755, 254.469, 1+ALB+BUN+AST+Glc+His+Lys; 0.755, 256.001, 1+ALB+AST+NEFA+Lys+Tyr+Val; 0.755, 256.501, 1+ALB+AST+NEFA+T-BIL+His+Orn; 0.755, 256.758, 1+ALB+AST+T-BIL+Glc+Lys+Ile; 0.755, 252.026, 1+ALB+Ca+ALT+His+Arg+Thr; 0.755, 254.600, 1+ALB+BUN+Ca+AST+BHBA+Lys; 0.755, 253.341, 1+ALB+BUN+Ca+ALT+NEFA+Orn; 0.755, 255.084, 1+ALB+BUN+Ca+NEFA+Orn+Lys; 0.755, 255.406, 1+ALB+BUN+T-BIL+BHBA+Glc+Lys; 0.755, 256.169, 1+ALB+BUN+Glc+Thr+Orn+Lys; 0.755, 250.441, 1+ALB+ALT+3MeHis+Arg+Asp+Tyr; 0.755, 253.509, 1+ALB+AST+ALT+gGT+Arg+Ile; 0.755, 253.564, 1+ALB+ALT+NEFA+Orn+Val+Trp; 0.755, 254.375, 1+ALB+AST+3MeHis+Arg+Orn+Lys; 0.755, 252.193, 1+ALB+ALT+NEFA+Arg+Asp+Orn; 0.755, 253.501, 1+ALB+BUN+ALT+gGT+BHBA+Orn; 0.755, 253.555, 1+ALB+BUN+ALT+T-BIL+Glc+Orn; 0.755, 252.619, 1+ALB+ALT+NEFA+Arg+Orn+Lys; 0.755, 252.721, 1+ALB+ALT+gGT+Arg+Thr+Lys; 0.755, 253.298, 1+ALB+ALT+T-BIL+Arg+Thr+Orn; 0.755, 254.405, 1+ALB+ALT+NEFA+Tyr+Val+Phe; 0.755, 254.512, 1+ALB+ALT+T-BIL+Thr+Orn+Ile; 0.755, 255.134, 1+ALB+BUN+NEFA+His+Thr+Orn; 0.755, 254.253, 1+ALB+AST+3MeHis+Lys+Phe+Trp; 0.755, 253.306, 1+ALB+Ca+ALT+NEFA+Lys+Ile; 0.755, 255.274, 1+ALB+BUN+Ca+T-BIL+Orn+Lys; 0.755, 253.256, 1+ALB+Ca+AST+ALT+T-BIL+Lys; 0.755, 252.744, 1+ALB+AST+ALT+BHBA+Arg+Thr; 0.755, 255.013, 1+ALB+BUN+NEFA+Orn+Val+Trp; 0.755, 253.673, 1+ALB+AST+NEFA+3MeHis+Arg+Lys; 0.755, 252.767, 1+ALB+ALT+BHBA+Arg+Orn+Lys; 0.755, 253.708, 1+ALB+ALT+NEFA+BHBA+Thr+Lys; 0.755, 253.640, 1+ALB+BUN+ALT+NEFA+BHBA+Thr; 0.755, 255.488, 1+ALB+AST+Arg+Asp+Lys+Tyr; 0.755, 254.946, 1+ALB+AST+NEFA+Arg+Lys+Phe; 0.755, 255.199, 1+ALB+BUN+AST+Arg+Thr+Ile; 0.755, 255.942, 1+ALB+AST+NEFA+T-BIL+Thr+Lys; 0.755, 256.147, 1+ALB+AST+gGT+NEFA+His+Orn; 0.755, 256.382, 1+ALB+AST+T-BIL+His+Lys+Ile; 0.755, 254.588, 1+ALB+BUN+Ca+AST+Orn+Lys; 0.755, 254.926, 1+ALB+BUN+Ca+AST+Glc+Lys; 0.755, 252.650, 1+ALB+Ca+AST+ALT+Arg+Thr; 0.755, 252.222, 1+ALB+AST+ALT+3MeHis+Arg+Tyr; 0.755, 251.290, 1+ALB+AST+ALT+NEFA+Asp+Phe; 0.755, 254.886, 1+ALB+BUN+NEFA+T-BIL+Arg+Lys; 0.755, 252.271, 1+ALB+ALT+Arg+Asp+Orn+Tyr; 0.755, 253.561, 1+ALB+BUN+ALT+NEFA+T-BIL+Orn; 0.755, 250.774, 1+ALB+AST+ALT+Asp+Lys+Tyr; 0.755, 252.804, 1+ALB+ALT+T-BIL+Glc+Arg+Lys; 0.755, 253.151, 1+ALB+BUN+ALT+BHBA+His+Orn; 0.755, 253.323, 1+ALB+ALT+BHBA+Arg+Thr+Orn; 0.755, 253.692, 1+ALB+BUN+ALT+gGT+Glc+Thr; 0.755, 250.131, 1+ALB+BUN+AST+ALT+Asp+Val; 0.755, 253.545, 1+ALB+BUN+AST+NEFA+Arg+Phe; 0.755, 254.483, 1+ALB+ALT+BHBA+Thr+Orn+Ile; 0.755, 253.268, 1+ALB+AST+ALT+T-BIL+Glc+Lys; 0.755, 253.371, 1+ALB+ALT+His+Thr+Orn+Ile; 0.755, 253.685, 1+ALB+AST+3MeHis+Arg+Tyr+Trp; 0.755, 255.751, 1+ALB+AST+Lys+Tyr+Phe+Trp; 0.755, 253.237, 1+ALB+AST+ALT+BHBA+Thr+Lys; 0.755, 255.497, 1+ALB+AST+T-BIL+His+Arg+Orn; 0.755, 255.937, 1+ALB+AST+NEFA+Glc+Thr+Lys; 0.755, 255.407, 1+ALB+BUN+gGT+T-BIL+Glc+Lys; 0.755, 253.285, 1+ALB+ALT+3MeHis+Orn+Val+Trp; 0.755, 256.050, 1+ALB+BUN+gGT+BHBA+Thr+Lys; 0.755, 256.301, 1+ALB+NEFA+3MeHis+Lys+Val+Phe; 0.755, 253.469, 1+ALB+ALT+gGT+Arg+Orn+Ile; 0.755, 253.090, 1+ALB+BUN+AST+3MeHis+Arg+Phe; 0.755, 253.658, 1+ALB+ALT+NEFA+Glc+Thr+Lys; 0.755, 253.670, 1+ALB+BUN+ALT+NEFA+Thr+Ile; 0.755, 253.691, 1+ALB+ALT+gGT+T-BIL+Lys+Ile; 0.755, 252.025, 1+ALB+AST+ALT+gGT+Arg+Lys; 0.755, 254.392, 1+ALB+AST+NEFA+Asp+Orn+Phe; 0.755, 255.448, 1+ALB+AST+NEFA+Arg+Orn+Phe; 0.755, 256.484, 1+ALB+AST+NEFA+BHBA+His+Orn; 0.755, 252.657, 1+ALB+Ca+ALT+His+Orn+Lys; 0.755, 255.019, 1+ALB+Ca+AST+NEFA+Arg+Lys; 0.755, 255.076, 1+ALB+BUN+Ca+NEFA+BHBA+Lys; 0.755, 256.495, 1+ALB+BUN+Orn+Tyr+Val+Phe; 0.755, 251.186, 1+ALB+AST+ALT+NEFA+Asp+Trp; 0.755, 252.979, 1+ALB+3MeHis+Arg+Asp+Lys+Val; 0.755, 253.140, 1+ALB+AST+ALT+NEFA+Arg+Tyr; 0.755, 253.475, 1+ALB+ALT+Glc+Arg+Orn+Ile; 0.755, 250.932, 1+ALB+ALT+3MeHis+Asp+Val+Trp; 0.755, 252.718, 1+ALB+ALT+Glc+Arg+Thr+Lys; 0.755, 252.723, 1+ALB+ALT+T-BIL+Arg+Thr+Lys; 0.755, 253.407, 1+ALB+ALT+NEFA+BHBA+Arg+Thr; 0.755, 252.860, 1+ALB+AST+ALT+Orn+Lys+Tyr; 0.755, 255.070, 1+ALB+BUN+Ca+BHBA+His+Lys; 0.755, 252.859, 1+ALB+Ca+AST+ALT+NEFA+Lys; 0.755, 253.543, 1+ALB+AST+ALT+BHBA+Glc+Arg; 0.755, 256.303, 1+ALB+BUN+gGT+Glc+Orn+Lys; 0.755, 253.920, 1+ALB+BUN+NEFA+3MeHis+Arg+Trp; 0.755, 255.949, 1+ALB+BUN+Arg+Thr+Orn+Lys; 0.755, 256.179, 1+ALB+NEFA+His+Orn+Lys+Ile; 0.755, 252.706, 1+ALB+ALT+Arg+Thr+Orn+Lys; 0.755, 252.803, 1+ALB+ALT+gGT+T-BIL+Arg+Lys; 0.755, 253.082, 1+ALB+AST+ALT+gGT+Lys+Ile; 0.755, 261.524, 1+BUN+ALT+His+Asn+Thr+Orn; 0.755, 252.714, 1+ALB+ALT+NEFA+3MeHis+Arg+Orn; 0.755, 256.306, 1+ALB+BUN+gGT+Glc+Lys+Ile; 0.755, 252.733, 1+ALB+ALT+3MeHis+Arg+Orn+Tyr; 0.755, 256.048, 1+ALB+BUN+BHBA+Glc+Lys+Ile; 0.755, 252.617, 1+ALB+ALT+NEFA+BHBA+Arg+Lys; 0.755, 253.233, 1+ALB+AST+ALT+Glc+His+Arg; 0.755, 253.676, 1+ALB+ALT+T-BIL+Glc+Orn+Lys; 0.755, 251.492, 1+ALB+BUN+AST+3MeHis+Asp+Orn; 0.755, 251.817, 1+ALB+BUN+AST+NEFA+Asp+Phe; 0.755, 253.466, 1+ALB+ALT+BHBA+His+Lys+Ile; 0.755, 253.479, 1+ALB+ALT+BHBA+Glc+His+Lys; 0.755, 253.571, 1+ALB+ALT+NEFA+T-BIL+Thr+Lys; 0.755, 253.682, 1+ALB+BUN+ALT+gGT+T-BIL+Thr; 0.755, 253.690, 1+ALB+ALT+T-BIL+Glc+Lys+Ile; 0.755, 252.821, 1+ALB+AST+ALT+gGT+Arg+Orn; 0.755, 252.824, 1+ALB+AST+ALT+Arg+Orn+Val; 0.755, 253.526, 1+ALB+BUN+ALT+gGT+His+Thr; 0.755, 252.771, 1+ALB+ALT+NEFA+His+Thr+Lys; 0.755, 255.765, 1+ALB+AST+Lys+Tyr+Val+Trp; 0.755, 255.980, 1+ALB+AST+NEFA+BHBA+Thr+Lys; 0.755, 254.652, 1+ALB+AST+NEFA+Arg+Asp+Orn; 0.755, 253.327, 1+ALB+Ca+AST+ALT+BHBA+Arg; 0.755, 252.180, 1+ALB+AST+ALT+NEFA+3MeHis+Arg; 0.755, 252.739, 1+ALB+AST+ALT+Glc+Arg+Thr; 0.755, 252.730, 1+ALB+ALT+3MeHis+Arg+Orn+Val; 0.755, 254.704, 1+ALB+BUN+NEFA+Arg+Tyr+Trp; 0.755, 253.532, 1+ALB+BUN+ALT+BHBA+Glc+Orn; 0.755, 253.539, 1+ALB+BUN+ALT+BHBA+Glc+Thr; 0.755, 252.717, 1+ALB+ALT+BHBA+Arg+Thr+Lys; 0.755, 252.752, 1+ALB+BUN+NEFA+Asp+Val+Trp; 0.755, 253.614,

1+ALB+ALT+NEFA+T-BIL+BHBA+Lys; 0.755, 256.317, 1+ALB+NEFA+Glc+His+Orn+Lys; 0.755, 253.468, 1+ALB+ALT+T-BIL+BHBA+His+Lys; 0.755, 252.827, 1+ALB+AST+ALT+NEFA+Lys+Tyr; 0.755, 254.096, 1+ALB+AST+ALT+T-BIL+His+Orn; 0.755, 256.069, 1+ALB+AST+NEFA+Glc+Arg+Orn; 0.755, 252.852, 1+ALB+BUN+AST+Asp+Orn+Phe; 0.755, 253.535, 1+ALB+ALT+Orn+Tyr+Val+Trp; 0.755, 253.589, 1+ALB+ALT+Glc+Thr+Orn+Lys; 0.755, 253.628, 1+ALB+ALT+Glc+His+Lys+Ile; 0.755, 253.631, 1+ALB+BUN+ALT+NEFA+Glc+Thr; 0.755, 250.700, 1+ALB+AST+ALT+3MeHis+Asp+Orn; 0.755, 256.357, 1+ALB+AST+gGT+Arg+Lys+Ile; 0.755, 253.600, 1+ALB+AST+3MeHis+Arg+Orn+Trp; 0.755, 254.909, 1+ALB+BUN+AST+NEFA+Thr+Orn; 0.755, 255.011, 1+ALB+BUN+AST+T-BIL+Arg+Orn; 0.755, 253.569, 1+ALB+Ca+ALT+Thr+Orn+Lys; 0.755, 253.321, 1+ALB+BUN+Ca+ALT+BHBA+Orn; 0.755, 254.086, 1+ALB+ALT+NEFA+Glc+Arg+Ile; 0.755, 253.775, 1+ALB+AST+ALT+NEFA+Tyr+Phe; 0.755, 253.014, 1+ALB+BUN+ALT+3MeHis+Orn+Val; 0.755, 253.241, 1+ALB+AST+ALT+BHBA+His+Arg; 0.755, 253.463, 1+ALB+ALT+T-BIL+Arg+Orn+Ile; 0.755, 253.487, 1+ALB+ALT+NEFA+Orn+Lys+Tyr; 0.755, 252.745, 1+ALB+BUN+NEFA+Asp+Tyr+Trp; 0.755, 253.319, 1+ALB+ALT+Glc+Arg+Thr+Orn; 0.755, 253.395, 1+ALB+BUN+ALT+BHBA+His+Thr; 0.755, 254.718, 1+ALB+AST+NEFA+Arg+Val+Trp; 0.755, 256.499, 1+ALB+AST+NEFA+Glc+His+Orn; 0.755, 257.693, 1+ALB+AST+Glc+Thr+Orn+Ile; 0.755, 254.461, 1+ALB+BUN+AST+His+Thr+Orn; 0.755, 255.257, 1+ALB+Ca+AST+NEFA+His+Lys; 0.755, 256.167, 1+ALB+BUN+gGT+Thr+Orn+Lys; 0.755, 252.737, 1+ALB+AST+ALT+T-BIL+Arg+Thr; 0.755, 254.211, 1+ALB+BUN+NEFA+3MeHis+Arg+Phe; 0.755, 255.954, 1+ALB+BUN+BHBA+Thr+Orn+Lys; 0.755, 253.163, 1+ALB+ALT+NEFA+3MeHis+Orn+Trp; 0.755, 253.187, 1+ALB+NEFA+3MeHis+Arg+Asp+Lys; 0.755, 255.972, 1+ALB+BUN+Glc+Arg+Thr+Lys; 0.755, 253.520, 1+ALB+ALT+NEFA+Orn+Tyr+Trp; 0.755, 253.757, 1+ALB+ALT+gGT+NEFA+Glc+Lys; 0.755, 252.807, 1+ALB+ALT+gGT+Glc+Arg+Lys; 0.755, 253.412, 1+ALB+BUN+ALT+His+Thr+Ile; 0.755, 253.504, 1+ALB+ALT+gGT+BHBA+His+Lys; 0.755, 253.689, 1+ALB+ALT+gGT+NEFA+Thr+Lys; 0.755, 253.497, 1+ALB+ALT+gGT+T-BIL+His+Lys; 0.755, 253.685, 1+ALB+BUN+ALT+NEFA+T-BIL+Thr; 0.755, 254.534, 1+ALB+AST+3MeHis+Orn+Tyr+Trp; 0.755, 254.832, 1+ALB+BUN+His+Arg+Thr+Orn; 0.755, 256.148, 1+ALB+BUN+AST+gGT+His+Orn; 0.755, 257.774, 1+ALB+AST+BHBA+Thr+Orn+Ile; 0.755, 257.390, 1+ALB+AST+Glc+Arg+Orn+Ile; 0.755, 255.843, 1+ALB+AST+T-BIL+His+Thr+Orn; 0.755, 252.767, 1+ALB+BUN+Ca+AST+ALT+Orn; 0.755, 253.913, 1+ALB+Ca+ALT+BHBA+Arg+Ile; 0.755, 253.472, 1+ALB+Ca+ALT+NEFA+Orn+Lys; 0.754, 252.736, 1+ALB+3MeHis+Arg+Asp+Lys+Trp; 0.754, 253.143, 1+ALB+AST+ALT+T-BIL+His+Arg; 0.754, 253.342, 1+ALB+3MeHis+Arg+Asp+Lys+Phe; 0.754, 254.924, 1+ALB+BUN+Arg+Tyr+Val+Trp; 0.754, 256.289, 1+ALB+AST+T-BIL+Glc+Arg+Lys; 0.754, 249.980, 1+ALB+AST+ALT+3MeHis+Asp+Trp; 0.754, 252.789, 1+ALB+ALT+T-BIL+BHBA+Arg+Lys; 0.754, 253.424, 1+ALB+BUN+ALT+T-BIL+His+Thr; 0.754, 253.941, 1+ALB+ALT+T-BIL+BHBA+Thr+Lys; 0.754, 252.764, 1+ALB+AST+ALT+gGT+Orn+Lys; 0.754, 256.913, 1+ALB+AST+Arg+Orn+Lys+Tyr; 0.754, 252.583, 1+ALB+AST+ALT+gGT+NEFA+Lys; 0.754, 256.739, 1+ALB+AST+NEFA+BHBA+Thr+Orn; 0.754, 253.113, 1+ALB+AST+ALT+gGT+T-BIL+Lys; 0.754, 256.361, 1+ALB+Ca+AST+NEFA+His+Orn; 0.754, 256.067, 1+ALB+BUN+BHBA+Glc+Orn+Lys; 0.754, 252.195, 1+ALB+ALT+Asp+Tyr+Val+Phe; 0.754, 253.437, 1+ALB+BUN+ALT+BHBA+Orn+Ile; 0.754, 252.209, 1+ALB+BUN+AST+ALT+Orn+Tyr; 0.754, 253.448, 1+ALB+ALT+gGT+NEFA+Arg+Thr; 0.754, 254.388, 1+ALB+AST+3MeHis+Arg+Lys+Phe; 0.754, 254.618, 1+ALB+AST+NEFA+His+Arg+Orn; 0.754, 254.997, 1+ALB+AST+NEFA+His+Thr+Lys; 0.754, 253.908, 1+ALB+Ca+ALT+gGT+Arg+Ile; 0.754, 253.651, 1+ALB+BUN+Ca+ALT+Thr+Ile; 0.754, 253.325, 1+ALB+Ca+AST+ALT+Glc+Arg; 0.754, 257.162, 1+ALB+Ca+AST+Arg+Orn+Ile; 0.754, 253.285, 1+ALB+AST+ALT+His+Arg+Ile; 0.754, 255.192, 1+ALB+BUN+T-BIL+BHBA+Arg+Lys; 0.754, 256.208, 1+ALB+BUN+Orn+Lys+Tyr+Val; 0.754, 253.688, 1+ALB+ALT+gGT+Glc+Orn+Lys; 0.754, 253.764, 1+ALB+ALT+NEFA+BHBA+Glc+Lys; 0.754, 253.767, 1+ALB+ALT+gGT+NEFA+BHBA+Lys; 0.754, 253.805, 1+ALB+AST+3MeHis+Arg+Phe+Trp; 0.754, 253.934, 1+ALB+ALT+gGT+BHBA+Thr+Lys; 0.754, 254.061, 1+ALB+BUN+AST+3MeHis+Arg+Orn; 0.754, 254.484, 1+ALB+AST+NEFA+3MeHis+Lys+Phe; 0.754, 254.608, 1+ALB+AST+NEFA+Arg+Phe+Trp; 0.754, 253.538, 1+ALB+Ca+ALT+gGT+Arg+Orn; 0.754, 253.678, 1+ALB+BUN+Ca+ALT+gGT+Thr; 0.754, 253.625, 1+ALB+Ca+ALT+gGT+Orn+Lys; 0.754, 256.945, 1+ALB+Ca+AST+T-BIL+His+Orn; 0.754, 253.503, 1+ALB+AST+ALT+gGT+T-BIL+Arg; 0.754, 253.516, 1+ALB+AST+ALT+T-BIL+BHBA+Arg; 0.754, 253.560, 1+ALB+AST+ALT+gGT+BHBA+Arg; 0.754, 256.035, 1+ALB+BUN+BHBA+Glc+Thr+Lys; 0.754, 256.067, 1+ALB+BUN+gGT+BHBA+Orn+Lys; 0.754, 256.089, 1+ALB+BUN+Arg+Orn+Lys+Val; 0.754, 253.656, 1+ALB+ALT+gGT+BHBA+Orn+Lys; 0.754, 253.679, 1+ALB+ALT+gGT+T-BIL+Orn+Lys; 0.754, 252.479, 1+ALB+BUN+NEFA+Arg+Asp+Trp; 0.754, 253.440, 1+ALB+BUN+ALT+NEFA+His+Thr; 0.754, 253.531, 1+ALB+ALT+BHBA+Glc+Arg+Thr; 0.754, 253.865, 1+ALB+ALT+BHBA+Glc+Thr+Lys; 0.754, 257.186, 1+ALB+AST+Orn+Lys+Val+Phe; 0.754, 253.494, 1+ALB+ALT+gGT+T-BIL+Arg+Thr; 0.754, 251.894, 1+ALB+AST+3MeHis+Asp+Phe+Trp; 0.754, 253.408, 1+ALB+AST+ALT+gGT+Glc+Lys; 0.754, 255.191, 1+ALB+BUN+AST+NEFA+His+Orn; 0.754, 255.975, 1+ALB+AST+NEFA+BHBA+Arg+Orn; 0.754, 256.066, 1+ALB+AST+NEFA+Arg+Orn+Val; 0.754, 252.536, 1+ALB+Ca+ALT+NEFA+Arg+Lys; 0.754, 253.625, 1+ALB+Ca+ALT+T-BIL+Orn+Lys; 0.754, 255.314, 1+ALB+BUN+Ca+T-BIL+BHBA+Lys; 0.754, 253.998, 1+ALB+Ca+AST+ALT+His+Orn; 0.754, 258.839, 1+ALB+NEFA+Orn+Tyr+Val+Phe; 0.754, 255.192, 1+ALB+BUN+T-BIL+Glc+Arg+Lys; 0.754, 253.668, 1+ALB+ALT+T-BIL+BHBA+Orn+Lys; 0.754, 256.064, 1+ALB+BUN+Glc+Arg+Orn+Lys; 0.754, 252.406, 1+ALB+ALT+NEFA+T-BIL+Arg+Lys; 0.754, 252.788, 1+ALB+ALT+BHBA+Glc+Arg+Lys; 0.754, 252.789, 1+ALB+ALT+gGT+BHBA+Arg+Lys; 0.754, 253.518, 1+ALB+ALT+T-BIL+Glc+Arg+Thr; 0.754, 253.611, 1+ALB+BUN+ALT+T-BIL+Glc+Thr; 0.754, 255.751, 1+ALB+AST+Lys+Val+Phe+Trp; 0.754, 253.695, 1+ALB+AST+ALT+NEFA+Thr+Orn; 0.754, 256.909, 1+ALB+AST+gGT+T-BIL+His+Orn; 0.754, 255.995, 1+ALB+Ca+AST+NEFA+BHBA+Lys; 0.754, 255.257, 1+ALB+BUN+Ca+T-BIL+Thr+Lys; 0.754, 253.497, 1+ALB+AST+ALT+T-BIL+Glc+Arg; 0.754, 257.210, 1+ALB+NEFA+Orn+Tyr+Phe+Trp; 0.754, 252.731, 1+ALB+AST+ALT+gGT+Arg+Thr; 0.754, 255.192,

1+ALB+BUN+T-BIL+Arg+Orn+Lys; 0.754, 253.678, 1+ALB+ALT+NEFA+BHBA+Arg+Orn; 0.754, 253.967, 1+ALB+ALT+gGT+T-BIL+Thr+Lys; 0.754, 252.910, 1+ALB+AST+ALT+NEFA+Arg+Val; 0.754, 253.528, 1+ALB+ALT+T-BIL+BHBA+Arg+Thr; 0.754, 253.241, 1+ALB+ALT+gGT+His+Thr+Lys; 0.754, 254.611, 1+ALB+BUN+AST+3MeHis+Val+Phe; 0.754, 255.388, 1+ALB+AST+Arg+Asp+Orn+Lys; 0.754, 254.936, 1+ALB+BUN+AST+His+Arg+Orn; 0.754, 252.698, 1+ALB+Ca+ALT+gGT+Arg+Lys; 0.754, 253.506, 1+ALB+Ca+ALT+NEFA+Arg+Orn; 0.754, 256.436, 1+ALB+BUN+Arg+Orn+Val+Phe; 0.754, 255.311, 1+ALB+AST+3MeHis+Orn+Lys+Tyr; 0.754, 254.616, 1+ALB+BUN+NEFA+Arg+Orn+Trp; 0.754, 252.831, 1+ALB+BUN+Asp+Tyr+Val+Trp; 0.754, 257.084, 1+ALB+T-BIL+His+Orn+Lys+Ile; 0.754, 253.835, 1+ALB+ALT+gGT+Glc+Lys+Ile; 0.754, 253.422, 1+ALB+AST+ALT+3MeHis+Val+Phe; 0.754, 254.810, 1+ALB+AST+3MeHis+Arg+Orn+Phe; 0.754, 257.222, 1+ALB+AST+Orn+Lys+Tyr+Phe; 0.754, 253.160, 1+ALB+ALT+Glc+His+Thr+Lys; 0.754, 255.839, 1+ALB+BUN+AST+NEFA+Glc+Orn; 0.754, 253.714, 1+ALB+AST+NEFA+3MeHis+Arg+Trp; 0.754, 252.697, 1+ALB+Ca+ALT+T-BIL+Arg+Lys; 0.754, 255.971, 1+ALB+Ca+AST+NEFA+T-BIL+Lys; 0.754, 256.221, 1+ALB+BUN+Ca+Glc+Thr+Lys; 0.754, 252.317, 1+ALB+BUN+ALT+3MeHis+Orn+Tyr; 0.754, 253.539, 1+ALB+AST+ALT+gGT+Glc+Arg; 0.754, 255.315, 1+ALB+BUN+NEFA+Arg+Orn+Phe; 0.754, 252.075, 1+ALB+ALT+Arg+Asp+Orn+Val; 0.754, 254.006, 1+ALB+ALT+NEFA+BHBA+Arg+Ile; 0.754, 253.660, 1+ALB+BUN+ALT+T-BIL+Thr+Ile; 0.754, 254.562, 1+ALB+ALT+gGT+Thr+Orn+Ile; 0.754, 251.443, 1+ALB+AST+ALT+Arg+Asp+Val; 0.754, 255.072, 1+ALB+AST+Arg+Lys+Phe+Trp; 0.754, 256.435, 1+ALB+AST+NEFA+His+Orn+Ile; 0.754, 256.480, 1+ALB+AST+T-BIL+Glc+Orn+Lys; 0.754, 255.256, 1+ALB+AST+NEFA+Asp+Orn+Val; 0.754, 256.465, 1+ALB+AST+T-BIL+BHBA+His+Lys; 0.754, 253.525, 1+ALB+Ca+ALT+T-BIL+Arg+Orn; 0.754, 255.314, 1+ALB+BUN+Ca+gGT+T-BIL+Lys; 0.754, 253.278, 1+ALB+Ca+AST+ALT+T-BIL+Arg; 0.754, 255.967, 1+ALB+Ca+AST+NEFA+Arg+Orn; 0.754, 253.503, 1+ALB+Ca+AST+ALT+Glc+Lys; 0.754, 256.061, 1+ALB+BUN+Ca+Thr+Orn+Lys; 0.754, 256.364, 1+ALB+BUN+Arg+Orn+Tyr+Phe; 0.754, 255.918, 1+ALB+3MeHis+Orn+Val+Phe+Trp; 0.754, 253.344, 1+ALB+3MeHis+Arg+Asp+Orn+Lys; 0.754, 256.085, 1+ALB+BUN+Arg+Orn+Lys+Tyr; 0.754, 252.807, 1+ALB+NEFA+3MeHis+Asp+Lys+Trp; 0.754, 253.534, 1+ALB+BUN+ALT+NEFA+BHBA+Orn; 0.754, 253.108, 1+ALB+ALT+BHBA+His+Thr+Lys; 0.754, 253.495, 1+ALB+ALT+gGT+Glc+Arg+Thr; 0.754, 257.368, 1+ALB+AST+NEFA+Glc+Orn+Ile; 0.754, 253.599, 1+ALB+BUN+Ca+ALT+BHBA+Thr; 0.754, 253.222, 1+ALB+Ca+ALT+Arg+Thr+Orn; 0.754, 253.565, 1+ALB+Ca+ALT+His+Lys+Ile; 0.754, 253.343, 1+ALB+Ca+AST+ALT+Thr+Lys; 0.754, 255.952, 1+ALB+BUN+Ca+BHBA+Lys+Ile; 0.754, 252.156, 1+ALB+AST+ALT+3MeHis+Arg+Val; 0.754, 256.323, 1+ALB+BUN+gGT+Glc+Thr+Lys; 0.754, 255.189, 1+ALB+BUN+gGT+T-BIL+Arg+Lys; 0.754, 253.471, 1+ALB+ALT+NEFA+T-BIL+Arg+Orn; 0.754, 253.533, 1+ALB+BUN+ALT+T-BIL+BHBA+Orn; 0.754, 253.719, 1+ALB+ALT+NEFA+Glc+Arg+Orn; 0.754, 256.895, 1+ALB+His+Arg+Orn+Lys+Ile; 0.754, 256.312, 1+ALB+BUN+AST+Glc+His+Orn; 0.754, 253.943, 1+ALB+Ca+ALT+T-BIL+Arg+Ile; 0.754, 252.694, 1+ALB+Ca+ALT+Glc+Arg+Lys; 0.754, 253.614, 1+ALB+Ca+ALT+BHBA+Orn+Lys; 0.754, 253.678, 1+ALB+Ca+ALT+NEFA+Thr+Lys; 0.754, 253.462, 1+ALB+Ca+ALT+T-BIL+His+Lys; 0.754, 252.959, 1+ALB+Ca+AST+ALT+His+Arg; 0.754, 256.372, 1+ALB+3MeHis+Arg+Orn+Lys+Val; 0.754, 256.015, 1+ALB+NEFA+3MeHis+Lys+Val+Trp; 0.754, 256.419, 1+ALB+NEFA+Arg+Lys+Tyr+Trp; 0.754, 253.440, 1+ALB+BUN+ALT+Glc+His+Thr; 0.754, 254.547, 1+ALB+ALT+NEFA+Thr+Orn+Ile; 0.754, 253.506, 1+ALB+ALT+gGT+BHBA+Arg+Thr; 0.754, 255.342, 1+ALB+NEFA+His+Arg+Lys+Ile; 0.754, 255.487, 1+ALB+AST+Asp+Orn+Lys+Phe; 0.754, 255.719, 1+ALB+AST+3MeHis+Lys+Tyr+Phe; 0.754, 255.339, 1+ALB+AST+NEFA+Asp+Orn+Tyr; 0.754, 255.963, 1+ALB+AST+NEFA+T-BIL+Arg+Orn; 0.754, 256.519, 1+ALB+AST+T-BIL+Thr+Orn+Lys; 0.754, 256.372, 1+ALB+AST+T-BIL+Glc+His+Lys; 0.754, 253.943, 1+ALB+Ca+ALT+Glc+Arg+Ile; 0.754, 252.693, 1+ALB+Ca+ALT+BHBA+Arg+Lys; 0.754, 253.521, 1+ALB+Ca+ALT+BHBA+Arg+Orn; 0.754, 253.341, 1+ALB+Ca+AST+ALT+BHBA+Lys; 0.754, 257.276, 1+ALB+Ca+AST+NEFA+Orn+Ile; 0.754, 256.396, 1+ALB+BUN+Ca+gGT+Glc+Lys; 0.754, 255.308, 1+ALB+BUN+Ca+T-BIL+Glc+Lys; 0.754, 253.125, 1+ALB+Ca+ALT+NEFA+His+Lys; 0.754, 257.505, 1+ALB+Orn+Lys+Tyr+Phe+Trp; 0.754, 256.391, 1+ALB+3MeHis+Lys+Tyr+Phe+Trp; 0.754, 252.848, 1+ALB+3MeHis+Asp+Orn+Lys+Trp; 0.754, 254.775, 1+ALB+BUN+NEFA+Arg+Val+Trp; 0.754, 255.770, 1+ALB+BUN+BHBA+Arg+Thr+Lys; 0.754, 253.582, 1+ALB+ALT+Orn+Lys+Tyr+Val; 0.754, 256.305, 1+ALB+AST+T-BIL+Arg+Thr+Lys; 0.754, 253.440, 1+ALB+ALT+NEFA+Glc+Arg+Thr; 0.754, 253.609, 1+ALB+ALT+gGT+His+Lys+Ile; 0.754, 256.749, 1+ALB+gGT+NEFA+Arg+Lys+Ile; 0.754, 255.214, 1+ALB+BUN+AST+Arg+Thr+Orn; 0.754, 254.202, 1+ALB+AST+ALT+Glc+His+Orn; 0.754, 254.504, 1+ALB+BUN+AST+NEFA+Val+Phe; 0.754, 257.313, 1+ALB+AST+NEFA+BHBA+Orn+Ile; 0.754, 255.479, 1+ALB+BUN+AST+gGT+NEFA+Orn; 0.754, 256.366, 1+ALB+AST+His+Arg+Orn+Ile; 0.754, 253.756, 1+ALB+Ca+ALT+NEFA+BHBA+Lys; 0.754, 253.657, 1+ALB+Ca+ALT+T-BIL+Lys+Ile; 0.754, 253.282, 1+ALB+Ca+ALT+NEFA+His+Arg; 0.754, 256.176, 1+ALB+BUN+Ca+gGT+Lys+Ile; 0.754, 251.231, 1+ALB+AST+ALT+Asp+Tyr+Trp; 0.754, 253.247, 1+ALB+ALT+3MeHis+Orn+Tyr+Trp; 0.754, 256.708, 1+ALB+NEFA+Glc+Arg+Lys+Ile; 0.754, 253.748, 1+ALB+ALT+gGT+BHBA+Lys+Ile; 0.754, 253.750, 1+ALB+ALT+BHBA+Glc+Lys+Ile; 0.754, 253.926, 1+ALB+AST+ALT+NEFA+3MeHis+Orn; 0.754, 253.179, 1+ALB+AST+ALT+gGT+BHBA+Lys; 0.754, 253.218, 1+ALB+BUN+AST+ALT+T-BIL+Thr; 0.754, 254.595, 1+ALB+BUN+AST+3MeHis+Tyr+Phe; 0.754, 257.079, 1+ALB+AST+T-BIL+Glc+His+Orn; 0.754, 257.324, 1+ALB+AST+BHBA+Glc+Orn+Lys; 0.754, 257.960, 1+ALB+AST+T-BIL+BHBA+Orn+Ile; 0.754, 253.914, 1+ALB+Ca+ALT+BHBA+Thr+Lys; 0.754, 257.719, 1+ALB+Ca+AST+Thr+Orn+Ile; 0.754, 253.937, 1+ALB+Ca+ALT+T-BIL+Thr+Lys; 0.754, 253.495, 1+ALB+Ca+ALT+BHBA+His+Lys; 0.754, 252.938, 1+ALB+ALT+3MeHis+Arg+Tyr+Val; 0.754, 254.714, 1+ALB+BUN+Arg+Asp+Orn+Phe; 0.754, 258.060, 1+ALB+NEFA+Arg+Orn+Tyr+Phe; 0.754, 253.704, 1+ALB+ALT+NEFA+T-BIL+Glc+Lys; 0.754, 253.762, 1+ALB+ALT+BHBA+Glc+Arg+Orn; 0.754, 250.953, 1+ALB+BUN+ALT+NEFA+Asp+Tyr; 0.754, 253.709, 1+ALB+ALT+gGT+NEFA+Arg+Orn; 0.754, 253.743, 1+ALB+AST+ALT+NEFA+Val+Phe; 0.754, 253.298, 1+ALB+BUN+AST+ALT+gGT+Thr; 0.754, 257.418, 1+ALB+AST+Orn+Lys+Tyr+Val; 0.754, 252.630, 1+ALB+AST+3MeHis+Asp+Orn+Phe; 0.754, 254.901, 1+ALB+AST+NEFA+3MeHis+Orn+Phe; 0.754, 255.476, 1+ALB+AST+Asp+Lys+Tyr; 0.754, 255.799, 1+ALB+BUN+AST+NEFA+T-BIL+Orn; 0.754, 256.812, 1+ALB+Ca+AST+T-BIL+Lys+Ile; 0.754, 252.639, 1+ALB+Ca+ALT+Arg+Thr+Lys; 0.754, 253.914, 1+ALB+Ca+ALT+gGT+NEFA+Arg; 0.754, 253.857, 1+ALB+Ca+ALT+NEFA+BHBA+Arg; 0.754, 254.496, 1+ALB+Ca+ALT+Thr+Orn+Ile; 0.754, 257.747, 1+ALB+Ca+AST+BHBA+His+Orn; 0.754, 255.844, 1+ALB+BUN+Ca+Arg+Thr+Lys; 0.754, 254.484, 1+ALB+BUN+3MeHis+Arg+Tyr+Phe; 0.754, 256.081, 1+ALB+BUN+gGT+Arg+Orn+Lys; 0.754, 253.632, 1+ALB+ALT+NEFA+Arg+Orn+Val; 0.754, 256.250, 1+ALB+AST+T-BIL+BHBA+Arg+Lys; 0.754, 255.881, 1+ALB+BUN+AST+ALT+NEFA+Thr; 0.754, 257.285, 1+ALB+AST+BHBA+Thr+Orn+Lys; 0.754, 257.422, 1+ALB+AST+BHBA+Arg+Orn+Ile; 0.754, 253.704, 1+ALB+AST+NEFA+Asp+Phe+Trp; 0.754, 255.512, 1+ALB+AST+gGT+NEFA+T-BIL+Lys; 0.754, 256.714, 1+ALB+AST+NEFA+T-BIL+Thr+Orn; 0.753, 254.039, 1+ALB+Ca+ALT+gGT+T-BIL+Arg; 0.753, 253.541, 1+ALB+Ca+ALT+Glc+Arg+Orn; 0.753, 255.974, 1+ALB+Ca+AST+NEFA+Glc+Lys; 0.753, 256.176, 1+ALB+BUN+Ca+Glc+Orn+Lys; 0.753, 254.707, 1+ALB+BUN+Asp+Orn+Val+Phe; 0.753, 256.762, 1+ALB+NEFA+3MeHis+Lys+Tyr+Phe; 0.753, 255.957, 1+ALB+BUN+gGT+Arg+Thr+Lys; 0.753, 252.505, 1+ALB+ALT+NEFA+Arg+Asp+Tyr; 0.753, 253.644, 1+ALB+ALT+BHBA+Glc+Orn+Lys; 0.753, 253.661, 1+ALB+ALT+gGT+NEFA+T-BIL+Lys; 0.753, 253.717, 1+ALB+ALT+NEFA+Arg+Orn+Tyr; 0.753, 253.859, 1+ALB+ALT+NEFA+T-BIL+Glc+Arg; 0.753, 256.012, 1+ALB+NEFA+His+Thr+Orn+Lys; 0.753, 251.908, 1+ALB+ALT+Asp+Tyr+Val+Trp; 0.753, 253.924, 1+ALB+ALT+T-BIL+Glc+Thr+Lys; 0.753, 254.167, 1+ALB+AST+ALT+BHBA+His+Orn; 0.753, 256.372, 1+ALB+AST+His+Thr+Orn+Ile; 0.753, 257.350, 1+ALB+AST+NEFA+T-BIL+Glc+Orn; 0.753, 255.923, 1+ALB+BUN+Ca+Arg+Orn+Lys; 0.753, 262.932, 1+BUN+AST+His+Asn+Thr+Orn; 0.753, 256.461, 1+ALB+BUN+NEFA+Tyr+Val+Phe; 0.753, 257.447, 1+ALB+NEFA+BHBA+Orn+Lys+Ile; 0.753, 256.134, 1+ALB+BUN+Arg+Lys+Tyr+Val; 0.753, 256.376, 1+ALB+NEFA+3MeHis+Lys+Tyr+Trp; 0.753, 252.029, 1+ALB+ALT+Arg+Asp+Tyr+Val; 0.753, 256.681, 1+ALB+NEFA+Arg+Orn+Lys+Ile; 0.753, 254.378, 1+ALB+ALT+Glc+Thr+Orn+Ile; 0.753, 252.103, 1+ALB+AST+ALT+Asp+Orn+Val; 0.753, 253.115, 1+ALB+ALT+T-BIL+His+Thr+Lys; 0.753, 253.854, 1+ALB+AST+ALT+T-BIL+Thr+Orn; 0.753, 255.953, 1+ALB+Ca+AST+NEFA+Thr+Lys; 0.753, 258.676, 1+ALB+Ca+AST+Glc+Orn+Ile; 0.753, 253.610, 1+ALB+BUN+Ca+ALT+Glc+Thr; 0.753, 255.074, 1+ALB+BUN+Ca+T-BIL+Arg+Lys; 0.753, 256.221, 1+ALB+BUN+Ca+gGT+Thr+Lys; 0.753, 253.631, 1+ALB+BUN+Ca+ALT+NEFA+Thr; 0.753, 253.666, 1+ALB+Ca+ALT+Glc+His+Lys; 0.753, 256.177, 1+ALB+BUN+Ca+gGT+Orn+Lys; 0.753, 254.063, 1+ALB+ALT+gGT+NEFA+Arg+Ile; 0.753, 255.709, 1+ALB+3MeHis+Orn+Lys+Val+Trp; 0.753, 257.118, 1+ALB+NEFA+Asp+Orn+Tyr+Phe; 0.753, 253.431, 1+ALB+3MeHis+Asp+Orn+Lys+Tyr; 0.753, 253.756, 1+ALB+ALT+T-BIL+Glc+Arg+Orn; 0.753, 256.291, 1+ALB+3MeHis+Arg+Lys+Tyr+Phe; 0.753, 251.057, 1+ALB+ALT+3MeHis+Asp+Tyr+Trp; 0.753, 253.980, 1+ALB+ALT+gGT+Glc+Thr+Lys; 0.753, 251.914, 1+ALB+AST+ALT+Arg+Asp+Tyr; 0.753, 256.943, 1+ALB+AST+Glc+Arg+Orn+Lys; 0.753, 255.238, 1+ALB+BUN+AST+T-BIL+His+Orn; 0.753, 255.848, 1+ALB+BUN+AST+NEFA+BHBA+Orn; 0.753, 256.730, 1+ALB+AST+NEFA+Glc+Thr+Orn; 0.753, 257.341, 1+ALB+AST+NEFA+T-BIL+Orn+Ile; 0.753, 256.468, 1+ALB+AST+T-BIL+BHBA+Orn+Lys; 0.753, 253.362, 1+ALB+Ca+AST+ALT+gGT+Lys; 0.753, 255.968, 1+ALB+BUN+Ca+BHBA+Thr+Lys; 0.753, 258.659, 1+ALB+Ca+AST+BHBA+Orn+Ile; 0.753, 253.769, 1+ALB+Ca+ALT+gGT+Lys+Ile; 0.753, 257.765, 1+ALB+Orn+Tyr+Val+Phe+Trp; 0.753, 257.256, 1+ALB+Arg+Orn+Tyr+Phe+Trp; 0.753, 252.840, 1+ALB+3MeHis+Asp+Lys+Phe+Trp; 0.753, 255.076, 1+ALB+BUN+NEFA+Orn+Tyr+Trp; 0.753, 253.087, 1+ALB+AST+ALT+gGT+NEFA+Arg; 0.753, 253.665, 1+ALB+ALT+Arg+Orn+Tyr+Val; 0.753, 254.038, 1+ALB+ALT+gGT+T-BIL+BHBA+Lys; 0.753, 256.372, 1+ALB+gGT+NEFA+His+Orn+Lys; 0.753, 254.029, 1+ALB+BUN+AST+NEFA+Val+Trp; 0.753, 254.263, 1+ALB+BUN+AST+NEFA+Arg+Thr; 0.753, 257.031, 1+ALB+AST+T-BIL+His+Orn+Ile; 0.753, 254.039, 1+ALB+Ca+ALT+gGT+Glc+Arg; 0.753, 253.527, 1+ALB+Ca+ALT+T-BIL+His+Arg; 0.753, 256.428, 1+ALB+3MeHis+Orn+Tyr+Phe+Trp; 0.753, 253.271, 1+ALB+3MeHis+Asp+Orn+Lys+Val; 0.753, 253.754, 1+ALB+BUN+ALT+NEFA+Tyr+Val; 0.753, 253.759, 1+ALB+ALT+gGT+Glc+Arg+Orn; 0.753, 256.757, 1+ALB+His+Arg+Thr+Lys+Ile; 0.753, 251.921, 1+ALB+ALT+NEFA+Asp+Val+Trp; 0.753, 256.349, 1+ALB+NEFA+T-BIL+His+Orn+Lys; 0.753, 257.245, 1+ALB+AST+Arg+Orn+Tyr+Phe; 0.753, 253.245, 1+ALB+BUN+AST+ALT+His+Thr; 0.753, 255.498, 1+ALB+NEFA+His+Arg+Orn+Lys; 0.753, 256.859, 1+ALB+AST+BHBA+Arg+Orn+Lys; 0.753, 256.942, 1+ALB+AST+Arg+Orn+Lys+Val; 0.753, 253.806, 1+ALB+BUN+AST+NEFA+3MeHis+Trp; 0.753, 255.142, 1+ALB+BUN+AST+T-BIL+Thr+Orn; 0.753, 255.840, 1+ALB+BUN+AST+NEFA+Orn+Ile; 0.753, 256.394, 1+ALB+AST+Glc+His+Arg+Orn; 0.753, 257.296, 1+ALB+Ca+AST+BHBA+Orn+Lys; 0.753, 253.318, 1+ALB+Ca+AST+ALT+gGT+Arg; 0.753, 254.216, 1+ALB+ALT+gGT+Glc+Arg+Ile; 0.753, 257.067, 1+ALB+NEFA+3MeHis+Orn+Val+Phe; 0.753, 253.572, 1+ALB+ALT+gGT+NEFA+His+Arg; 0.753, 254.800, 1+ALB+ALT+NEFA+BHBA+Thr+Orn; 0.753, 255.296, 1+ALB+Arg+Asp+Lys+Tyr+Trp; 0.753, 254.356, 1+ALB+AST+ALT+NEFA+T-BIL+Orn; 0.753, 253.250, 1+ALB+BUN+AST+ALT+BHBA+Thr; 0.753, 253.343, 1+ALB+AST+ALT+Glc+Thr+Lys; 0.753, 256.529, 1+ALB+AST+gGT+NEFA+Thr+Orn; 0.753, 253.979, 1+ALB+AST+Arg+Asp+Val+Trp; 0.753, 253.932, 1+ALB+Ca+ALT+NEFA+Glc+Arg; 0.753, 257.985, 1+ALB+Ca+AST+T-BIL+Orn+Ile; 0.753, 253.544, 1+ALB+Ca+ALT+Glc+His+Arg; 0.753, 253.965, 1+ALB+BUN+NEFA+Asp+Val+Phe; 0.753, 253.580, 1+ALB+ALT+NEFA+BHBA+His+Arg; 0.753, 253.256, 1+ALB+NEFA+3MeHis+Asp+Lys+Phe; 0.753, 256.303, 1+ALB+3MeHis+Lys+Tyr+Val+Trp; 0.753, 253.289, 1+ALB+AST+ALT+gGT+His+Arg; 0.753, 253.756, 1+ALB+ALT+gGT+BHBA+Arg+Orn; 0.753, 254.063, 1+ALB+ALT+gGT+T-BIL+Glc+Lys; 0.753, 253.724, 1+ALB+ALT+gGT+Glc+His+Lys; 0.753, 253.799, 1+ALB+ALT+NEFA+T-BIL+Arg+Ile; 0.753, 254.076, 1+ALB+BUN+AST+Arg+Asp+Orn; 0.753, 256.790, 1+ALB+NEFA+His+Thr+Lys+Ile; 0.753, 257.119, 1+ALB+T-BIL+Glc+His+Orn+Lys; 0.753, 253.351, 1+ALB+BUN+AST+ALT+Thr+Ile; 0.753, 253.526, 1+ALB+BUN+AST+3MeHis+Tyr+Trp; 0.753, 253.980, 1+ALB+AST+Arg+Asp+Phe+Trp; 0.753, 255.549, 1+ALB+AST+gGT+NEFA+Thr+Lys; 0.753, 256.493, 1+ALB+Ca+AST+T-BIL+Orn+Lys; 0.753, 253.973, 1+ALB+Ca+ALT+gGT+Thr+Lys; 0.753, 253.624, 1+ALB+BUN+Ca+ALT+T-BIL+Thr; 0.753, 257.786, 1+ALB+Ca+AST+Glc+His+Orn; 0.753, 253.779, 1+ALB+BUN+NEFA+Arg+Asp+Phe; 0.753, 255.451, 1+ALB+BUN+3MeHis+Tyr+Val+Trp; 0.753, 255.650, 1+ALB+BUN+NEFA+Arg+Val+Phe; 0.753, 255.822, 1+ALB+NEFA+Asp+Lys+Tyr+Phe; 0.753, 253.163, 1+ALB+AST+ALT+Arg+Tyr+Val; 0.753, 254.390, 1+ALB+AST+ALT+NEFA+BHBA+Orn; 0.753, 254.831, 1+ALB+ALT+gGT+NEFA+Thr+Orn; 0.753, 257.293, 1+ALB+AST+gGT+Glc+Orn+Lys; 0.753, 253.862, 1+ALB+AST+ALT+BHBA+Thr+Orn; 0.753, 256.151, 1+ALB+AST+BHBA+His+Arg+Lys; 0.753, 256.270, 1+ALB+AST+gGT+T-BIL+His+Lys; 0.753, 254.031, 1+ALB+Ca+ALT+gGT+BHBA+Arg; 0.753, 253.782, 1+ALB+Ca+ALT+Glc+Lys+Ile; 0.753, 252.936, 1+ALB+ALT+NEFA+3MeHis+Arg+Val; 0.753, 255.451, 1+ALB+BUN+NEFA+3MeHis+Tyr+Trp; 0.753, 257.025, 1+ALB+NEFA+Lys+Tyr+Phe+Trp; 0.753, 253.801, 1+ALB+ALT+NEFA+Arg+Tyr+Val; 0.753, 253.828, 1+ALB+ALT+gGT+Glc+His+Arg; 0.753, 255.330, 1+ALB+3MeHis+Arg+Lys+Tyr+Trp; 0.753, 256.102, 1+ALB+BUN+gGT+Glc+Arg+Lys; 0.753, 256.257, 1+ALB+NEFA+3MeHis+Lys+Phe+Trp; 0.753, 253.904, 1+ALB+AST+ALT+3MeHis+Orn+Val; 0.753, 256.099, 1+ALB+BUN+3MeHis+Tyr+Val+Phe; 0.753, 256.392, 1+ALB+NEFA+T-BIL+Arg+Lys+Ile; 0.753, 254.393, 1+ALB+AST+ALT+NEFA+Orn+Ile; 0.753, 257.331, 1+ALB+AST+NEFA+T-BIL+BHBA+Orn; 0.753, 258.244, 1+ALB+AST+Glc+His+Lys+Ile; 0.753, 253.650, 1+ALB+Ca+ALT+NEFA+T-BIL+Arg; 0.753, 253.545, 1+ALB+Ca+ALT+BHBA+His+Arg; 0.753, 254.241, 1+ALB+ALT+gGT+BHBA+Arg+Ile; 0.753, 252.940, 1+ALB+NEFA+3MeHis+Asp+Lys+Val; 0.753, 253.601, 1+ALB+ALT+NEFA+His+Arg+Ile; 0.753, 255.891, 1+ALB+BUN+BHBA+Glc+Arg+Lys; 0.753, 256.199, 1+ALB+BUN+gGT+BHBA+Glc+Lys; 0.753, 254.764, 1+ALB+NEFA+Asp+Lys+Tyr+Trp; 0.753, 254.950, 1+ALB+ALT+gGT+NEFA+His+Orn; 0.753, 253.029, 1+ALB+ALT+NEFA+3MeHis+Arg+Tyr; 0.753, 253.412, 1+ALB+ALT+NEFA+T-BIL+His+Arg; 0.753, 255.606, 1+ALB+AST+3MeHis+Orn+Tyr+Phe; 0.753, 257.793, 1+ALB+T-BIL+BHBA+Arg+Lys+Ile; 0.753, 252.196, 1+ALB+AST+ALT+Asp+Orn+Tyr; 0.753, 256.891, 1+ALB+AST+Arg+Orn+Lys+Phe; 0.753, 258.083, 1+ALB+AST+T-BIL+Glc+Orn+Ile; 0.753, 254.735, 1+ALB+AST+gGT+NEFA+Arg+Lys; 0.753, 256.013, 1+ALB+AST+NEFA+T-BIL+Arg+Thr; 0.753, 256.573, 1+ALB+AST+gGT+T-BIL+Lys+Ile; 0.753, 253.732, 1+ALB+Ca+ALT+gGT+NEFA+Lys; 0.753, 253.534, 1+ALB+Ca+ALT+His+Arg+Ile; 0.753, 255.963, 1+ALB+BUN+Ca+Glc+Arg+Lys; 0.753, 254.242, 1+ALB+ALT+gGT+T-BIL+Arg+Ile; 0.753, 254.248, 1+ALB+ALT+BHBA+Glc+Arg+Ile; 0.753, 254.262, 1+ALB+ALT+T-BIL+Glc+Arg+Ile; 0.753, 254.285, 1+ALB+ALT+T-BIL+BHBA+Arg+Ile; 0.753, 257.086, 1+ALB+His+Thr+Orn+Lys+Ile; 0.753, 252.901, 1+ALB+ALT+Asp+Orn+Tyr+Val; 0.753, 253.705, 1+ALB+ALT+NEFA+Lys+Tyr+Val; 0.753, 255.899, 1+ALB+BUN+His+Thr+Orn+Ile; 0.753, 256.562, 1+ALB+AST+NEFA+3MeHis+Orn+Val; 0.753, 253.239, 1+ALB+BUN+AST+NEFA+Asp+Orn; 0.753, 256.763, 1+ALB+AST+T-BIL+Arg+Thr+Orn; 0.753, 257.335, 1+ALB+AST+NEFA+BHBA+Glc+Orn; 0.753, 257.945, 1+ALB+AST+BHBA+His+Lys+Ile; 0.753, 256.110, 1+ALB+AST+NEFA+BHBA+Arg+Thr; 0.753, 256.177, 1+ALB+BUN+Ca+Glc+Lys+Ile; 0.753, 253.304, 1+ALB+3MeHis+Asp+Lys+Tyr+Val; 0.753, 257.505, 1+ALB+3MeHis+Lys+Tyr+Val+Phe; 0.753, 253.516, 1+ALB+3MeHis+Asp+Orn+Lys+Phe; 0.753, 253.903, 1+ALB+ALT+gGT+NEFA+T-BIL+Arg; 0.753, 253.813, 1+ALB+AST+3MeHis+Arg+Val+Trp; 0.753, 254.392, 1+ALB+AST+ALT+NEFA+Glc+Orn; 0.753, 255.640, 1+ALB+AST+Arg+Asp+Lys+Phe; 0.753, 255.730, 1+ALB+BUN+AST+gGT+T-BIL+Orn; 0.753, 255.984, 1+ALB+BUN+AST+T-BIL+Glc+Orn; 0.753, 254.556, 1+ALB+AST+Asp+Tyr+Phe+Trp; 0.753, 256.136, 1+ALB+BUN+AST+BHBA+His+Orn; 0.753, 256.889, 1+ALB+AST+T-BIL+BHBA+Arg+Orn; 0.753, 257.238, 1+ALB+AST+gGT+Thr+Orn+Lys; 0.753, 257.369, 1+ALB+AST+Glc+Thr+Orn+Lys; 0.753, 255.147, 1+ALB+AST+NEFA+Arg+Asp+Tyr; 0.753, 255.551, 1+ALB+AST+gGT+NEFA+Glc+Lys; 0.753, 253.732, 1+ALB+Ca+ALT+NEFA+Glc+Lys; 0.753, 257.277, 1+ALB+Ca+AST+NEFA+Glc+Orn; 0.753, 253.933, 1+ALB+Ca+ALT+Glc+Thr+Lys; 0.753, 254.263, 1+ALB+Ca+AST+ALT+NEFA+Orn; 0.753, 255.870, 1+ALB+BUN+BHBA+Arg+Orn+Lys; 0.753, 254.119, 1+ALB+ALT+NEFA+BHBA+Glc+Arg; 0.753, 253.764, 1+ALB+ALT+T-BIL+BHBA+Arg+Orn; 0.753, 251.532, 1+ALB+ALT+3MeHis+Asp+Orn+Tyr; 0.753, 256.849, 1+ALB+AST+gGT+Arg+Orn+Lys; 0.753, 253.240, 1+ALB+AST+ALT+gGT+Thr+Lys; 0.753, 253.753, 1+ALB+AST+ALT+gGT+Thr+Orn; 0.753, 254.156, 1+ALB+AST+ALT+His+Orn+Ile; 0.753, 258.000, 1+ALB+AST+T-BIL+BHBA+Glc+Orn; 0.753, 256.274, 1+ALB+AST+T-BIL+His+Thr+Lys; 0.753, 255.707, 1+ALB+BUN+Ca+AST+NEFA+Orn; 0.753, 254.116, 1+ALB+ALT+gGT+NEFA+BHBA+Arg; 0.753, 253.830, 1+ALB+ALT+gGT+T-BIL+His+Arg; 0.753, 253.315, 1+ALB+ALT+Glc+His+Thr+Orn; 0.753, 256.366, 1+ALB+NEFA+BHBA+His+Orn+Lys; 0.753, 255.212, 1+ALB+BUN+AST+NEFA+3MeHis+Orn; 0.753, 255.839, 1+ALB+NEFA+BHBA+His+Arg+Lys; 0.753, 255.886, 1+ALB+BUN+AST+Glc+Arg+Orn; 0.753, 255.960, 1+ALB+BUN+AST+T-BIL+BHBA+Orn; 0.753, 257.760, 1+ALB+AST+gGT+BHBA+His+Orn; 0.753, 253.864, 1+ALB+AST+ALT+3MeHis+Val+Trp; 0.753, 254.822, 1+ALB+AST+NEFA+3MeHis+Arg+Orn; 0.753, 257.918, 1+ALB+AST+BHBA+Glc+His+Orn; 0.753, 257.525, 1+ALB+AST+T-BIL+BHBA+Thr+Orn; 0.753, 253.507, 1+ALB+Ca+ALT+gGT+Glc+His+Arg; 0.753, 253.731, 1+ALB+Ca+ALT+BHBA+Lys+Ile; 0.752, 257.409, 1+ALB+NEFA+3MeHis+Orn+Tyr+Phe; 0.752, 253.065, 1+ALB+NEFA+3MeHis+Asp+Lys+Tyr; 0.752, 254.014, 1+ALB+ALT+gGT+BHBA+Glc+Lys; 0.752, 255.025, 1+ALB+ALT+gGT+BHBA+His+Orn; 0.752, 256.558, 1+ALB+BUN+Arg+Thr+Orn+Ile; 0.752, 257.173, 1+ALB+T-BIL+BHBA+His+Orn+Lys; 0.752, 257.777, 1+ALB+T-BIL+Arg+Thr+Lys+Ile; 0.752, 253.330, 1+ALB+BUN+AST+ALT+Glc+Thr; 0.752, 253.417, 1+ALB+AST+ALT+3MeHis+Tyr+Phe; 0.752, 255.850, 1+ALB+AST+Asp+Lys+Tyr+Val; 0.752, 257.836, 1+ALB+AST+Orn+Tyr+Val+Phe; 0.752, 257.153, 1+ALB+AST+gGT+BHBA+Orn+Lys; 0.752, 254.030, 1+ALB+AST+NEFA+Asp+Val+Trp; 0.752, 257.227, 1+ALB+Ca+AST+NEFA+BHBA+Orn; 0.752, 253.616, 1+ALB+Ca+ALT+Glc+Orn+Lys; 0.752, 256.049, 1+ALB+BUN+Ca+AST+His+Orn; 0.752, 256.901, 1+ALB+Ca+AST+T-BIL+Arg+Orn; 0.752, 255.972, 1+ALB+BUN+Ca+BHBA+Orn+Lys; 0.752, 254.151, 1+ALB+ALT+gGT+NEFA+Glc+Arg; 0.752, 254.862, 1+ALB+ALT+NEFA+His+Orn+Ile; 0.752, 254.952, 1+ALB+ALT+NEFA+Glc+His+Orn; 0.752, 258.223, 1+ALB+NEFA+Arg+Thr+Orn+Ile; 0.752, 257.381, 1+ALB+Ca+AST+Glc+Orn+Lys; 0.752, 254.012, 1+ALB+Ca+ALT+T-BIL+BHBA+Lys; 0.752, 253.666, 1+ALB+Ca+ALT+NEFA+T-BIL+Lys; 0.752, 256.778, 1+ALB+Ca+AST+NEFA+Thr+Orn; 0.752, 254.102, 1+ALB+Ca+ALT+gGT+Glc+Lys; 0.752, 253.467, 1+ALB+BUN+Ca+ALT+His+Thr; 0.752, 257.259, 1+ALB+Ca+AST+NEFA+T-BIL+Orn; 0.752, 256.139, 1+ALB+Ca+AST+His+Arg+Orn; 0.752, 257.904, 1+ALB+NEFA+Orn+Lys+Val+Phe; 0.752, 257.393, 1+ALB+NEFA+Thr+Orn+Lys+Ile; 0.752, 252.234, 1+ALB+ALT+NEFA+Asp+Tyr+Trp; 0.752, 254.606, 1+ALB+ALT+NEFA+T-BIL+Thr+Orn; 0.752, 254.956, 1+ALB+ALT+NEFA+BHBA+His+Orn; 0.752, 256.884, 1+ALB+AST+Arg+Thr+Orn+Lys; 0.752, 256.307, 1+ALB+AST+gGT+T-BIL+Orn+Lys; 0.752, 258.660, 1+ALB+Ca+AST+BHBA+Glc+Orn; 0.752, 253.365, 1+ALB+Ca+ALT+NEFA+Arg+Thr; 0.752, 255.980, 1+ALB+BUN+3MeHis+Arg+Orn+Tyr; 0.752, 251.875, 1+ALB+AST+ALT+Asp+Val+Phe; 0.752, 253.591, 1+ALB+ALT+NEFA+Glc+His+Arg; 0.752, 255.023, 1+ALB+ALT+gGT+T-BIL+His+Orn; 0.752, 255.932, 1+ALB+NEFA+3MeHis+Arg+Lys+Val; 0.752, 253.492, 1+ALB+BUN+ALT+3MeHis+Tyr+Val; 0.752, 254.550, 1+ALB+AST+ALT+T-BIL+BHBA+Orn; 0.752, 255.604, 1+ALB+AST+Arg+Asp+Lys+Val; 0.752, 253.791, 1+ALB+BUN+AST+3MeHis+Val+Trp; 0.752, 258.795, 1+ALB+AST+BHBA+Glc+Orn+Ile; 0.752, 254.707, 1+ALB+AST+Asp+Val+Phe+Trp; 0.752, 252.404, 1+ALB+AST+3MeHis+Asp+Val+Trp; 0.752, 254.030, 1+ALB+Ca+ALT+gGT+T-BIL+Lys; 0.752, 256.109, 1+ALB+BUN+Ca+gGT+BHBA+Lys; 0.752, 257.857, 1+ALB+Ca+AST+T-BIL+BHBA+Orn; 0.752, 256.655, 1+ALB+Ca+NEFA+Arg+Lys+Ile; 0.752, 262.825, 1+ALT+His+Asn+Thr+Orn+Ile; 0.752, 256.794, 1+ALB+NEFA+3MeHis+Orn+Lys+Val; 0.752, 253.874, 1+ALB+ALT+BHBA+Glc+His+Arg; 0.752, 253.896, 1+ALB+ALT+NEFA+T-BIL+BHBA+Arg; 0.752, 254.920, 1+ALB+ALT+BHBA+His+Orn+Ile; 0.752, 252.579, 1+ALB+AST+3MeHis+Arg+Asp+Phe; 0.752, 252.591, 1+ALB+AST+NEFA+3MeHis+Arg+Asp; 0.752, 254.173, 1+ALB+AST+ALT+gGT+NEFA+Orn; 0.752, 255.520, 1+ALB+AST+Asp+Orn+Lys+Val; 0.752, 254.061, 1+ALB+AST+ALT+gGT+His+Orn; 0.752, 254.131, 1+ALB+BUN+AST+NEFA+3MeHis+Arg; 0.752, 257.911, 1+ALB+AST+gGT+T-BIL+Orn+Ile; 0.752, 257.964, 1+ALB+AST+Glc+Thr+Lys+Ile; 0.752, 257.525, 1+ALB+AST+T-BIL+Glc+Thr+Orn; 0.752, 257.637, 1+ALB+AST+His+Thr+Lys+Ile; 0.752, 254.009, 1+ALB+Ca+ALT+T-BIL+Glc+Lys; 0.752, 253.665, 1+ALB+Ca+ALT+gGT+His+Lys; 0.752, 263.741, 1+ALT+Glc+His+Asn+Thr+Orn; 0.752, 256.563, 1+ALB+3MeHis+Arg+Orn+Lys+Tyr; 0.752, 253.509, 1+ALB+BUN+AST+Arg+Asp+Phe; 0.752, 253.850, 1+ALB+ALT+gGT+BHBA+His+Arg; 0.752, 251.603, 1+ALB+ALT+NEFA+3MeHis+Asp+Orn; 0.752, 252.885, 1+ALB+ALT+NEFA+Asp+Orn+Val; 0.752, 253.751, 1+ALB+ALT+gGT+T-BIL+Arg+Orn; 0.752, 254.015, 1+ALB+ALT+T-BIL+BHBA+Glc+Lys; 0.752, 254.032, 1+ALB+AST+ALT+NEFA+Val+Trp; 0.752, 255.848, 1+ALB+BUN+Glc+His+Thr+Orn; 0.752, 257.356, 1+ALB+AST+gGT+Arg+Orn+Ile; 0.752, 254.773, 1+ALB+BUN+AST+T-BIL+Arg+Thr; 0.752, 255.867, 1+ALB+AST+3MeHis+Lys+Tyr+Val; 0.752, 252.339, 1+ALB+AST+NEFA+3MeHis+Asp+Trp; 0.752, 257.651, 1+ALB+Ca+AST+gGT+His+Orn; 0.752, 255.207, 1+ALB+BUN+Arg+Asp+Tyr+Phe; 0.752, 253.884, 1+ALB+ALT+T-BIL+His+Arg+Ile; 0.752, 251.554, 1+ALB+ALT+3MeHis+Asp+Orn+Val; 0.752, 253.861, 1+ALB+ALT+gGT+His+Arg+Ile; 0.752, 253.875, 1+ALB+ALT+Glc+His+Arg+Ile; 0.752, 256.054, 1+ALB+NEFA+3MeHis+Arg+Lys+Tyr; 0.752, 254.846, 1+ALB+ALT+gGT+BHBA+Thr+Orn; 0.752, 255.965, 1+ALB+BUN+AST+T-BIL+Orn+Ile; 0.752, 252.683, 1+ALB+AST+3MeHis+Arg+Asp+Orn; 0.752, 253.338, 1+ALB+AST+ALT+Lys+Tyr+Val; 0.752, 253.431, 1+ALB+ALT+NEFA+His+Thr+Orn; 0.752, 256.463, 1+ALB+AST+gGT+His+Thr+Orn; 0.752, 257.022, 1+ALB+AST+gGT+NEFA+Orn+Ile; 0.752, 257.918, 1+ALB+AST+BHBA+Thr+Lys+Ile; 0.752, 255.569, 1+ALB+AST+gGT+NEFA+BHBA+Lys; 0.752, 254.071, 1+ALB+Ca+ALT+T-BIL+Glc+Arg; 0.752, 253.404, 1+ALB+Ca+ALT+T-BIL+Arg+Thr; 0.752, 257.211, 1+ALB+3MeHis+Orn+Lys+Tyr+Val; 0.752, 257.070, 1+ALB+3MeHis+Orn+Lys+Tyr+Phe; 0.752, 255.888, 1+ALB+BUN+gGT+BHBA+Arg+Lys; 0.752, 257.437, 1+ALB+NEFA+Orn+Val+Phe+Trp; 0.752, 254.263, 1+ALB+AST+ALT+NEFA+Orn+Val; 0.752, 254.604, 1+ALB+AST+ALT+Glc+Orn+Ile; 0.752, 256.507, 1+ALB+T-BIL+His+Arg+Orn+Lys; 0.752, 255.871, 1+ALB+BUN+AST+gGT+Arg+Orn; 0.752, 256.390, 1+ALB+AST+Glc+His+Arg+Lys; 0.752, 257.959, 1+ALB+Ca+AST+T-BIL+Glc+Orn; 0.752, 254.621, 1+ALB+3MeHis+Asp+Orn+Tyr+Phe; 0.752, 253.884, 1+ALB+ALT+T-BIL+BHBA+His+Arg; 0.752, 254.316, 1+ALB+ALT+gGT+T-BIL+BHBA+Arg; 0.752, 256.946, 1+ALB+NEFA+Glc+His+Thr+Lys; 0.752, 258.705, 1+ALB+AST+gGT+Glc+Orn+Ile; 0.752, 258.647, 1+ALB+AST+gGT+BHBA+Orn+Ile; 0.752, 255.472, 1+ALB+BUN+AST+NEFA+Orn+Tyr; 0.752, 256.185, 1+ALB+BUN+Ca+His+Arg+Orn; 0.752, 254.064, 1+ALB+Ca+ALT+BHBA+Glc+Arg; 0.752, 255.811, 1+ALB+BUN+Ca+His+Thr+Orn; 0.752, 253.218, 1+ALB+Ca+ALT+His+Thr+Lys; 0.752, 254.439, 1+ALB+Ca+AST+ALT+Orn+Ile; 0.752, 256.821, 1+ALB+T-BIL+His+Arg+Lys+Ile; 0.752, 257.825, 1+ALB+NEFA+Orn+Lys+Tyr+Phe; 0.752, 256.221, 1+ALB+NEFA+3MeHis+Orn+Lys+Trp; 0.752, 257.101, 1+ALB+NEFA+Orn+Lys+Tyr+Trp; 0.752, 254.722, 1+ALB+ALT+NEFA+Glc+Thr+Orn; 0.752, 255.026, 1+ALB+ALT+T-BIL+BHBA+His+Orn; 0.752, 255.031, 1+ALB+ALT+gGT+Glc+His+Orn; 0.752, 255.703, 1+ALB+3MeHis+Arg+Lys+Phe+Trp; 0.752, 254.935, 1+ALB+ALT+T-BIL+His+Orn+Ile; 0.752, 254.946, 1+ALB+ALT+gGT+His+Orn+Ile; 0.752, 255.509, 1+ALB+BUN+AST+Arg+Tyr+Phe; 0.752, 254.436, 1+ALB+AST+ALT+gGT+BHBA+Orn; 0.752, 254.550, 1+ALB+AST+ALT+T-BIL+Orn+Ile; 0.752, 255.309, 1+ALB+BUN+T-BIL+His+Thr+Orn; 0.752, 255.921, 1+ALB+BUN+gGT+His+Thr+Orn; 0.752, 257.312, 1+ALB+AST+Arg+Lys+Tyr+Val; 0.752, 258.240, 1+ALB+AST+BHBA+Glc+Lys+Ile; 0.752, 257.545, 1+ALB+AST+BHBA+Arg+Thr+Ile; 0.752, 256.269, 1+ALB+Ca+AST+T-BIL+Arg+Lys; 0.752, 253.410, 1+ALB+Ca+ALT+BHBA+Arg+Thr; 0.752, 253.048, 1+ALB+ALT+NEFA+Asp+Orn+Tyr; 0.752, 250.631, 1+ALB+BUN+ALT+NEFA+3MeHis+Asp; 0.752, 253.359, 1+ALB+NEFA+3MeHis+Asp+Orn+Lys; 0.752, 253.861, 1+ALB+ALT+T-BIL+Glc+His+Arg; 0.752, 255.648, 1+ALB+Asp+Lys+Tyr+Phe+Trp; 0.752, 255.022, 1+ALB+ALT+T-BIL+Glc+His+Orn; 0.752, 253.984, 1+ALB+AST+ALT+NEFA+Orn+Tyr; 0.752, 253.093, 1+ALB+BUN+AST+NEFA+Arg+Asp; 0.752, 252.432, 1+ALB+AST+3MeHis+Asp+Tyr+Trp; 0.752, 257.227, 1+ALB+Ca+AST+gGT+Orn+Lys; 0.752, 256.455, 1+ALB+Ca+AST+T-BIL+His+Lys; 0.752, 258.534, 1+ALB+Ca+AST+gGT+Orn+Ile; 0.752, 253.405, 1+ALB+Ca+ALT+gGT+Arg+Thr; 0.752, 255.695, 1+ALB+BUN+Ca+AST+Arg+Orn; 0.752, 255.963, 1+ALB+BUN+Ca+gGT+Arg+Lys; 0.752, 252.670, 1+ALB+BUN+3MeHis+Arg+Asp+Orn; 0.752, 256.037, 1+ALB+BUN+3MeHis+

Arg+Orn+Val; 0.752, 252.152, 1+ALB+AST+ALT+Asp+Tyr+Phe; 0.752, 254.125, 1+ALB+BUN+AST+Tyr+Val+Trp; 0.752, 253.287, 1+ALB+AST+NEFA+3MeHis+Asp+Orn; 0.752, 258.098, 1+ALB+AST+gGT+His+Lys+Ile; 0.752, 256.199, 1+ALB+AST+NEFA+Glc+Arg+Thr; 0.752, 252.794, 1+ALB+BUN+3MeHis+Arg+Asp+Val; 0.752, 263.903, 1+AST+NEFA+His+Asn+Orn+Ile; 0.752, 256.269, 1+ALB+3MeHis+Orn+Lys+Tyr+Trp; 0.752, 255.241, 1+ALB+NEFA+Asp+Lys+Val+Trp; 0.752, 257.230, 1+ALB+gGT+T-BIL+His+Orn+Lys; 0.752, 254.396, 1+ALB+AST+ALT+gGT+T-BIL+Orn; 0.752, 255.741, 1+ALB+BUN+His+Arg+Thr+Ile; 0.752, 253.866, 1+ALB+AST+ALT+Tyr+Val+Trp; 0.752, 254.651, 1+ALB+AST+NEFA+Arg+Asp+Phe; 0.752, 254.010, 1+ALB+Ca+ALT+gGT+BHBA+Lys; 0.752, 254.063, 1+ALB+Ca+ALT+T-BIL+BHBA+Arg; 0.752, 258.561, 1+ALB+Ca+AST+gGT+Glc+Orn; 0.752, 256.107, 1+ALB+BUN+Ca+BHBA+Glc+Lys; 0.752, 264.172, 1+ALT+NEFA+His+Asn+Thr+Orn; 0.752, 257.630, 1+ALB+3MeHis+Orn+Tyr+Val+Phe; 0.752, 254.297, 1+ALB+ALT+gGT+T-BIL+Glc+Arg; 0.752, 255.516, 1+ALB+Asp+Orn+Lys+Tyr+Trp; 0.752, 257.666, 1+ALB+gGT+NEFA+Orn+Lys+Ile; 0.752, 257.843, 1+ALB+Arg+Thr+Orn+Lys+Ile; 0.752, 257.918, 1+ALB+T-BIL+Arg+Orn+Lys+Ile; 0.752, 256.743, 1+ALB+BUN+AST+gGT+Glc+Orn; 0.752, 252.789, 1+ALB+AST+ALT+His+Thr+Orn; 0.752, 257.027, 1+ALB+AST+T-BIL+Glc+Arg+Orn; 0.752, 257.943, 1+ALB+AST+Glc+His+Orn+Ile; 0.752, 255.277, 1+ALB+AST+His+Arg+Thr+Orn; 0.752, 256.338, 1+ALB+AST+BHBA+His+Arg+Orn; 0.752, 258.199, 1+ALB+Ca+AST+His+Lys+Ile; 0.752, 253.813, 1+ALB+Ca+AST+ALT+Thr+Orn; 0.752, 255.829, 1+ALB+BUN+Ca+AST+T-BIL+Orn; 0.751, 254.338, 1+ALB+ALT+T-BIL+BHBA+Glc+Arg; 0.751, 254.735, 1+ALB+3MeHis+Asp+Orn+Val+Phe; 0.751, 255.853, 1+ALB+BUN+NEFA+3MeHis+Arg+Orn; 0.751, 258.461, 1+ALB+T-BIL+BHBA+Orn+Lys+Ile; 0.751, 257.873, 1+ALB+BHBA+His+Orn+Lys+Ile; 0.751, 254.946, 1+ALB+ALT+Glc+His+Orn+Ile; 0.751, 258.565, 1+ALB+T-BIL+Glc+His+Lys+Ile; 0.751, 254.548, 1+ALB+AST+ALT+T-BIL+Glc+Orn; 0.751, 254.587, 1+ALB+AST+ALT+BHBA+Glc+Orn; 0.751, 255.597, 1+ALB+BUN+AST+3MeHis+Orn+Val; 0.751, 255.765, 1+ALB+NEFA+T-BIL+His+Arg+Lys; 0.751, 258.651, 1+ALB+AST+gGT+BHBA+Glc+Orn; 0.751, 253.913, 1+ALB+BUN+AST+NEFA+Tyr+Trp; 0.751, 256.484, 1+ALB+AST+BHBA+His+Thr+Orn; 0.751, 257.329, 1+ALB+AST+BHBA+Arg+Thr+Orn; 0.751, 257.522, 1+ALB+AST+Glc+Arg+Thr+Ile; 0.751, 257.837, 1+ALB+AST+gGT+T-BIL+BHBA+Orn; 0.751, 254.621, 1+ALB+AST+Asp+Tyr+Val+Trp; 0.751, 258.230, 1+ALB+Ca+AST+Glc+His+Lys; 0.751, 256.187, 1+ALB+3MeHis+Orn+Lys+Phe+Trp; 0.751, 253.635, 1+ALB+AST+ALT+3MeHis+Tyr+Trp; 0.751, 256.496, 1+ALB+3MeHis+Arg+Lys+Tyr+Val; 0.751, 256.997, 1+ALB+NEFA+Orn+Lys+Val+Trp; 0.751, 257.212, 1+ALB+Arg+Lys+Tyr+Phe+Trp; 0.751, 258.174, 1+ALB+T-BIL+Glc+His+Thr+Lys; 0.751, 255.351, 1+ALB+AST+3MeHis+Arg+Orn+Tyr; 0.751, 257.374, 1+ALB+AST+Arg+Orn+Val+Phe; 0.751, 257.871, 1+ALB+AST+gGT+Glc+His+Orn; 0.751, 256.338, 1+ALB+AST+gGT+His+Arg+Lys; 0.751, 257.353, 1+ALB+AST+Glc+Arg+Thr+Orn; 0.751, 254.259, 1+ALB+BUN+AST+Asp+Orn+Tyr; 0.751, 253.979, 1+ALB+Ca+ALT+BHBA+Glc+Lys; 0.751, 257.589, 1+ALB+Ca+AST+T-BIL+Thr+Orn; 0.751, 256.311, 1+ALB+Ca+NEFA+His+Orn+Lys; 0.751, 256.515, 1+ALB+3MeHis+Arg+Orn+Lys+Phe; 0.751, 253.901, 1+ALB+ALT+BHBA+His+Arg+Ile; 0.751, 255.703, 1+ALB+Asp+Lys+Tyr+Val+Trp; 0.751, 253.495, 1+ALB+ALT+gGT+His+Thr+Orn; 0.751, 255.807, 1+ALB+BUN+AST+BHBA+Thr+Orn; 0.751, 256.188, 1+ALB+AST+gGT+T-BIL+Arg+Lys; 0.751, 257.164, 1+ALB+gGT+NEFA+His+Thr+Lys; 0.751, 257.197, 1+ALB+AST+BHBA+Arg+Thr+Lys; 0.751, 257.822, 1+ALB+AST+gGT+His+Orn+Ile; 0.751, 257.886, 1+ALB+AST+gGT+Thr+Lys+Ile; 0.751, 256.358, 1+ALB+AST+gGT+His+Arg+Orn; 0.751, 257.330, 1+ALB+Ca+AST+Thr+Orn+Lys; 0.751, 255.777, 1+ALB+BUN+Ca+BHBA+Arg+Lys; 0.751, 256.896, 1+ALB+3MeHis+Arg+Orn+Tyr+Phe; 0.751, 254.295, 1+ALB+ALT+gGT+BHBA+Glc+Arg; 0.751, 255.773, 1+ALB+3MeHis+Arg+Tyr+Phe+Trp; 0.751, 257.157, 1+ALB+NEFA+Lys+Val+Phe+Trp; 0.751, 257.122, 1+ALB+Arg+Orn+Lys+Tyr+Trp; 0.751, 257.905, 1+ALB+BHBA+Glc+His+Orn+Lys; 0.751, 254.759, 1+ALB+ALT+BHBA+Glc+Thr+Orn; 0.751, 253.495, 1+ALB+ALT+BHBA+His+Thr+Orn; 0.751, 253.495, 1+ALB+ALT+T-BIL+His+Thr+Orn; 0.751, 253.805, 1+ALB+AST+ALT+Glc+Thr+Orn; 0.751, 256.130, 1+ALB+BUN+AST+His+Orn+Ile; 0.751, 256.329, 1+ALB+AST+NEFA+3MeHis+Orn+Tyr; 0.751, 257.325, 1+ALB+AST+Glc+Arg+Thr+Lys; 0.751, 257.915, 1+ALB+AST+gGT+T-BIL+Glc+Orn; 0.751, 254.121, 1+ALB+AST+NEFA+Asp+Tyr+Trp; 0.751, 255.903, 1+ALB+AST+His+Arg+Thr+Lys; 0.751, 256.855, 1+ALB+Ca+AST+Arg+Orn+Lys; 0.751, 257.557, 1+ALB+Ca+AST+Glc+Arg+Orn; 0.751, 254.404, 1+ALB+Ca+AST+ALT+T-BIL+Orn; 0.751, 252.908, 1+ALB+BUN+3MeHis+Arg+Asp+Tyr; 0.751, 254.917, 1+ALB+ALT+NEFA+T-BIL+His+Orn; 0.751, 255.024, 1+ALB+ALT+BHBA+Glc+His+Orn; 0.751, 255.925, 1+ALB+NEFA+Arg+Asp+Lys+Tyr; 0.751, 250.676, 1+ALB+BUN+AST+ALT+Asp+Tyr; 0.751, 254.461, 1+ALB+AST+ALT+gGT+Orn+Ile; 0.751, 254.463, 1+ALB+AST+ALT+gGT+Glc+Orn; 0.751, 255.831, 1+ALB+BUN+AST+BHBA+Arg+Orn; 0.751, 255.798, 1+ALB+BUN+AST+gGT+Thr+Orn; 0.751, 258.320, 1+ALB+AST+gGT+Glc+Lys+Ile; 0.751, 257.005, 1+ALB+AST+gGT+NEFA+BHBA+Orn; 0.751, 257.041, 1+ALB+AST+gGT+NEFA+Glc+Orn; 0.751, 254.792, 1+ALB+Ca+ALT+gGT+His+Orn; 0.751, 253.387, 1+ALB+Ca+ALT+Glc+Arg+Thr; 0.751, 254.434, 1+ALB+Ca+AST+ALT+Glc+Orn; 0.751, 254.441, 1+ALB+Ca+AST+ALT+BHBA+Orn; 0.751, 255.710, 1+ALB+3MeHis+Arg+Orn+Lys+Trp; 0.751, 254.847, 1+ALB+ALT+NEFA+3MeHis+Orn+Val; 0.751, 254.598, 1+ALB+AST+NEFA+His+Arg+Thr; 0.751, 250.965, 1+ALB+ALT+NEFA+3MeHis+Asp+Trp; 0.751, 254.287, 1+ALB+BUN+AST+ALT+NEFA+Val; 0.751, 254.574, 1+ALB+ALT+3MeHis+Tyr+Val+Trp; 0.751, 250.292, 1+ALB+BUN+AST+ALT+3MeHis+Asp; 0.751, 253.037, 1+ALB+AST+3MeHis+Arg+Asp+Val; 0.751, 254.588, 1+ALB+AST+ALT+BHBA+Orn+Ile; 0.751, 255.805, 1+ALB+BUN+BHBA+His+Thr+Orn; 0.751, 257.291, 1+ALB+NEFA+Glc+His+Lys+Ile; 0.751, 254.126, 1+ALB+BUN+AST+Asp+Orn+Val; 0.751, 255.832, 1+ALB+NEFA+Glc+His+Arg+Lys; 0.751, 255.027, 1+ALB+BUN+AST+3MeHis+Orn+Tyr; 0.751, 255.755, 1+ALB+BUN+AST+NEFA+Orn+Val; 0.751, 257.490, 1+ALB+AST+gGT+T-BIL+Thr+Orn; 0.751, 258.522, 1+ALB+Ca+AST+gGT+BHBA+Orn; 0.751, 257.748, 1+ALB+Ca+AST+His+Orn+Ile; 0.751, 255.970, 1+ALB+Asp+Orn+Tyr+Phe+Trp; 0.751, 256.650, 1+ALB+NEFA+3MeHis+Orn+Lys+Phe; 0.751, 258.156, 1+ALB+Lys+Tyr+Val+Phe+Trp; 0.751, 254.582, 1+ALB+AST+NEFA+3MeHis+Arg+Phe; 0.751, 254.827, 1+ALB+ALT+gGT+T-BIL+Thr+Orn; 0.751, 257.349, 1+ALB+gGT+NEFA+His+

Lys+Ile; 0.751, 25 5.337, 1+ALB+AST+3MeHis+Arg+Orn+Val; 0.751, 255.499, 1+ALB+NEFA+His+Arg+Thr+Lys; 0.751, 255.839, 1+ALB+BUN+AST+Arg+Orn+Val; 0.751, 258.061, 1+ALB+AST+gGT+BHBA+Lys+Ile; 0.751, 256.828, 1+ALB+AST+T-BIL+Arg+Thr+Ile; 0.751, 254.737, 1+ALB+Ca+ALT+NEFA+His+Orn; 0.751, 254.826, 1+ALB+ALT+T-BIL+BHBA+Thr+Orn; 0.751, 254.526, 1+ALB+BUN+AST+His+Arg+Thr; 0.751, 254.766, 1+ALB+Ca+ALT+NEFA+Thr+Orn; 0.751, 263.574, 1+Ca+ALT+His+Asn+Thr+Orn; 0.751, 263.204, 1+AST+ALT+His+Asn+Thr+Orn; 0.751, 253.322, 1+ALB+BUN+3MeHis+Asp+Orn+Val; 0.751, 257.482, 1+ALB+Orn+Lys+Val+Phe+Trp; 0.751, 257.937, 1+ALB+gGT+His+Orn+Lys+Ile; 0.751, 254.440, 1+ALB+AST+ALT+Tyr+Val+Phe; 0.751, 257.421, 1+ALB+gGT+NEFA+Glc+His+Lys; 0.751, 253.041, 1+ALB+AST+3MeHis+Arg+Asp+Tyr; 0.751, 256.590, 1+ALB+BUN+AST+gGT+BHBA+Orn; 0.751, 257.331, 1+ALB+AST+Arg+Lys+Tyr+Phe; 0.751, 257.544, 1+ALB+AST+gGT+Arg+Thr+Ile; 0.751, 254.799, 1+ALB+Ca+ALT+BHBA+His+Orn; 0.751, 253.336, 1+ALB+BUN+Ca+AST+ALT+Thr; 0.751, 255.610, 1+ALB+NEFA+3MeHis+Arg+Lys+Trp; 0.751, 255.712, 1+ALB+BUN+NEFA+3MeHis+Val+Trp; 0.751, 256.888, 1+ALB+3MeHis+Arg+Orn+Val+Phe; 0.751, 259.035, 1+ALB+BHBA+Arg+Thr+Orn+Ile; 0.751, 254.759, 1+ALB+ALT+gGT+Glc+Thr+Orn; 0.751, 255.930, 1+ALB+AST+Asp+Lys+Val+Phe; 0.751, 262.703, 1+ALT+Glc+His+Asn+Orn+Ile; 0.751, 257.925, 1+ALB+Glc+His+Orn+Lys+Ile; 0.751, 255.953, 1+ALB+AST+Asp+Lys+Tyr+Phe; 0.751, 255.987, 1+ALB+AST+NEFA+Tyr+Phe+Trp; 0.751, 256.904, 1+ALB+BUN+AST+Glc+Orn+Ile; 0.751, 256.986, 1+ALB+AST+gGT+NEFA+T-BIL+Orn; 0.751, 254.794, 1+ALB+Ca+ALT+T-BIL+His+Orn; 0.751, 258.136, 1+ALB+Ca+AST+BHBA+Thr+Orn; 0.751, 261.255, 1+BUN+ALT+His+Asn+Orn+Ile; 0.751, 255.616, 1+ALB+BUN+ALT+gGT+T-BIL+Ile; 0.751, 258.629, 1+ALB+T-BIL+BHBA+Glc+His+Lys; 0.751, 255.577, 1+ALB+AST+Arg+Val+Phe+Trp; 0.751, 256.424, 1+ALB+AST+Glc+His+Thr+Orn; 0.751, 257.211, 1+ALB+AST+NEFA+Orn+Tyr+Val; 0.751, 257.694, 1+ALB+AST+BHBA+Glc+Arg+Orn; 0.751, 257.198, 1+ALB+AST+T-BIL+BHBA+Thr+Lys; 0.751, 257.818, 1+ALB+Ca+AST+gGT+T-BIL+Orn; 0.751, 253.728, 1+ALB+BUN+ALT+NEFA+3MeHis+Tyr; 0.751, 254.220, 1+ALB+BUN+AST+ALT+3MeHis+Val; 0.751, 258.052, 1+ALB+gGT+Glc+His+Orn+Lys; 0.751, 254.096, 1+ALB+AST+ALT+Orn+Tyr+Val; 0.751, 255.323, 1+ALB+BUN+AST+NEFA+T-BIL+Arg; 0.751, 255.845, 1+ALB+BUN+Ca+AST+Thr+Orn; 0.751, 255.733, 1+ALB+BUN+ALT+gGT+NEFA+Ile; 0.751, 253.986, 1+ALB+AST+ALT+NEFA+Tyr+Trp; 0.751, 254.665, 1+ALB+BUN+AST+3MeHis+Arg+Tyr; 0.751, 255.863, 1+ALB+BUN+AST+Arg+Orn+Tyr; 0.751, 255.868, 1+ALB+gGT+NEFA+His+Arg+Lys; 0.751, 256.800, 1+ALB+BUN+AST+BHBA+Glc+Orn; 0.751, 257.264, 1+ALB+AST+BHBA+Glc+Arg+Lys; 0.751, 257.889, 1+ALB+AST+BHBA+Glc+His+Lys; 0.751, 255.262, 1+ALB+BUN+AST+NEFA+Glc+Arg; 0.751, 254.989, 1+ALB+AST+NEFA+Arg+Asp+Val; 0.751, 256.897, 1+ALB+T-BIL+His+Thr+Orn+Lys; 0.751, 257.723, 1+ALB+NEFA+BHBA+Thr+Lys+Ile; 0.751, 255.553, 1+ALB+BUN+NEFA+His+Arg+Orn; 0.751, 255.758, 1+ALB+BUN+AST+Glc+Arg+Thr; 0.751, 255.379, 1+ALB+AST+NEFA+3MeHis+Phe+Trp; 0.751, 257.597, 1+ALB+AST+BHBA+His+Thr+Lys; 0.750, 258.002, 1+ALB+Ca+AST+Thr+Lys+Ile; 0.750, 254.295, 1+ALB+Ca+AST+ALT+gGT+Orn; 0.750, 255.322, 1+ALB+AST+3MeHis+Arg+Tyr+Phe; 0.750, 257.485, 1+ALB+NEFA+T-BIL+Orn+Lys+Ile; 0.750, 257.230, 1+ALB+NEFA+Orn+Lys+Phe+Trp; 0.750, 25 5.379, 1+ALB+NEFA+Arg+Asp+Lys+Trp; 0.750, 254.554, 1+ALB+ALT+NEFA+3MeHis+Tyr+Trp; 0.750, 256.010, 1+ALB+NEFA+His+Arg+Thr+Orn; 0.750, 258.219, 1+ALB+BHBA+Arg+Thr+Lys+Ile; 0.750, 255.737, 1+ALB+BUN+AST+gGT+Arg+Thr; 0.750, 255.917, 1+ALB+BUN+AST+Glc+Thr+Orn; 0.750, 256.236, 1+ALB+AST+Asp+Orn+Tyr+Phe; 0.750, 256.700, 1+ALB+AST+3MeHis+Orn+Tyr+Val; 0.750, 257.763, 1+ALB+AST+gGT+BHBA+His+Lys; 0.750, 256.953, 1+ALB+Ca+AST+gGT+NEFA+Orn; 0.750, 257.922, 1+ALB+Ca+AST+BHBA+His+Lys; 0.750, 257.604, 1+ALB+NEFA+Glc+Orn+Lys+Ile; 0.750, 255.577, 1+ALB+BUN+ALT+T-BIL+His+Ile; 0.750, 256.826, 1+ALB+NEFA+Arg+Tyr+Phe+Trp; 0.750, 257.285, 1+ALB+NEFA+Arg+Lys+Tyr+Phe; 0.750, 257.822, 1+ALB+NEFA+Arg+Orn+Lys+Tyr; 0.750, 258.271, 1+ALB+T-BIL+His+Thr+Lys+Ile; 0.750, 258.620, 1+ALB+gGT+T-BIL+Glc+His+Lys; 0.750, 258.079, 1+ALB+AST+gGT+BHBA+Thr+Orn; 0.750, 256.932, 1+ALB+AST+gGT+T-BIL+Arg+Orn; 0.750, 257.263, 1+ALB+Ca+AST+Arg+Thr+Orn; 0.750, 258.489, 1+ALB+T-BIL+Thr+Orn+Lys+Ile; 0.750, 258.737, 1+ALB+gGT+T-BIL+Orn+Lys+Ile; 0.750, 253.231, 1+ALB+BUN+3MeHis+Asp+Orn+Tyr; 0.750, 254.751, 1+ALB+ALT+T-BIL+Glc+Thr+Orn; 0.750, 257.316, 1+ALB+NEFA+Lys+Tyr+Val+Trp; 0.750, 253.405, 1+ALB+BUN+AST+ALT+Tyr+Val; 0.750, 257.352, 1+ALB+NEFA+BHBA+His+Lys+Ile; 0.750, 257.309, 1+ALB+AST+gGT+Arg+Thr+Orn; 0.750, 257.021, 1+ALB+AST+gGT+T-BIL+BHBA+Lys; 0.750, 253.435, 1+ALB+Ca+ALT+His+Thr+Orn; 0.750, 256.269, 1+ALB+Ca+AST+His+Arg+Lys; 0.750, 256.110, 1+ALB+NEFA+3MeHis+Arg+Lys+Phe; 0.750, 263.553, 1+AST+His+Asn+Thr+Orn+Ile; 0.750, 257.328, 1+ALB+NEFA+T-BIL+His+Lys+Ile; 0.750, 257.646, 1+ALB+AST+Arg+Orn+Tyr+Val; 0.750, 255.607, 1+ALB+BUN+Ca+AST+T-BIL+Arg; 0.750, 257.543, 1+ALB+Ca+AST+BHBA+Arg+Orn; 0.750, 252.781, 1+ALB+BUN+NEFA+3MeHis+Arg+Asp; 0.750, 257.332, 1+ALB+Arg+Orn+Lys+Val+Trp; 0.750, 257.106, 1+ALB+BUN+NEFA+Thr+Orn+Ile; 0.750, 255.431, 1+ALB+NEFA+Asp+Orn+Lys+Trp; 0.750, 256.400, 1+ALB+NEFA+Arg+Asp+Lys+Phe; 0.750, 257.962, 1+ALB+gGT+BHBA+His+Orn+Lys; 0.750, 258.662, 1+ALB+T-BIL+BHBA+His+Lys+Ile; 0.750, 253.454, 1+ALB+AST+ALT+3MeHis+Orn+Tyr; 0.750, 257.160, 1+ALB+NEFA+BHBA+His+Thr+Lys; 0.750, 255.328, 1+ALB+BUN+AST+NEFA+BHBA+Arg; 0.750, 256.518, 1+ALB+AST+NEFA+Arg+Tyr+Val; 0.750, 258.112, 1+ALB+Ca+AST+Glc+Thr+Orn; 0.750, 254.768, 1+ALB+Ca+ALT+Glc+His+Orn; 0.750, 254.785, 1+ALB+Ca+ALT+gGT+Thr+Orn; 0.750, 255.543, 1+ALB+Ca+AST+gGT+NEFA+Lys; 0.750, 254.575, 1+ALB+BUN+ALT+NEFA+3MeHis+Val; 0.750, 256.436, 1+ALB+NEFA+Asp+Lys+Val+Phe; 0.750, 258.133, 1+ALB+gGT+T-BIL+Arg+Lys+Ile; 0.750, 255.838, 1+ALB+BUN+AST+T-BIL+Glc+Arg; 0.750, 256.652, 1+ALB+AST+NEFA+BHBA+Arg+Ile; 0.750, 257.658, 1+ALB+AST+gGT+Glc+Arg+Orn; 0.750, 258.424, 1+ALB+AST+Lys+Tyr+Val+Phe; 0.750, 256.102, 1+ALB+AST+gGT+NEFA+Arg+Thr; 0.750, 255.449, 1+ALB+ALT+gGT+NEFA+T-BIL+Orn; 0.750, 254.796, 1+ALB+ALT+NEFA+Tyr+Val+Trp; 0.750, 257.096, 1+ALB+NEFA+T-BIL+His+Thr+Lys; 0.750, 257.492, 1+ALB+gGT+NEFA+BHBA+His+Lys; 0.750, 255.848, 1+ALB+AST+gGT+NEFA+Arg+Orn; 0.750, 257.964, 1+ALB+NEFA+BHBA+Arg+Thr+Ile; 0.750, 254.811, 1+ALB+BUN+AST+NEFA+His+Arg

[401. Formula (with Two Amino Acid Variables) with Improved Diagnostic Accuracy by Added Parity Term]
0.704, 268.286, 1+His+Orn

[402. Formula (with Three Amino Acid Variables) with Improved Diagnostic Accuracy by Added Parity Term]
0.717, 266.405, 1+His+Orn+Phe; 0.714, 268.558, 1+His+Orn+Cys

[403. Formula (with Four Amino Acid Variables) with Improved Diagnostic Accuracy by Added Parity Term]
0.730, 266.494, 1+His+Orn+Ile+Phe; 0.728, 266.975, 1+His+Orn+Leu+Phe; 0.725, 267.519, 1+His+Orn+Phe+BCAA; 0.724, 267.093, 1+His+S er+Orn+Phe; 0.723, 266.962, 1+His+Gly+Orn+Phe; 0.722, 267.869, 1+His+Cit+Orn+Phe; 0.722, 267.958, 1+His+Thr+Orn+Phe; 0.722, 266.3 68, 1+His+Orn+Cys+Phe; 0.721, 268.912, 1+His+Arg+Orn+Cys; 0.721, 266.891, 1+His+Asp+Orn+Phe; 0.720, 267.791, 1+His+Asp+Orn+Cys; 0. 720, 268.062, 1+His+Orn+Met+Phe; 0.719, 267.653, 1+His+Tau+Orn+P he; 0.719, 267.517, 1+His+3MeHis+Orn+Phe; 0.719, 268.074, 1+His+G ln+Orn+Phe; 0.719, 270.675, 1+His+Gly+Ala+Orn; 0.719, 268.356, 1+His+Ala+Orn+Phe; 0.719, 268.198, 1+His+Orn+Val+Phe; 0.718, 268.2 73, 1+His+Arg+Orn+Phe; 0.718, 270.048, 1+His+Cit+Orn+Cys; 0.717, 270.110, 1+His+Gln+Orn+Cys; 0.717, 268.357, 1+His+Glu+Orn+Phe; 0. 717, 268.402, 1+His+Pro+Orn+Phe; 0.717, 268.386, 1+His+Orn+Lys+P he; 0.717, 268.315, 1+His+Orn+Tyr+Phe; 0.716, 269.874, 1+His+Gly+Orn+Cys; 0.716, 268.095, 1+His+Orn+Phe+Trp; 0.715, 270.484, 1+His+Tau+Orn+Cys; 0.715, 268.315, 1+His+3MeHis+Asp+Orn; 0.715, 270.2 69, 1+His+3MeHis+Orn+Cys; 0.715, 270.342, 1+His+Glu+Orn+Cys; 0.7 14, 270.432, 1+His+Ser+Orn+Cys; 0.714, 270.237, 1+His+Pro+Orn+Cy s; 0.714, 269.104, 1+His+Orn+Cys+Lys; 0.714, 269.460, 1+His+Orn+C ys+Tyr; 0.714, 270.269, 1+His+Orn+Cys+Met; 0.714, 270.520, 1+His+Orn+Cys+Ile; 0.714, 270.550, 1+His+Orn+Cys+Leu; 0.713, 270.557, 1+His+Gln+Gly+Orn; 0.713, 270.944, 1+His+Gly+Pro+Orn; 0.713, 269. 956, 1+His+Asp+Ala+Orn; 0.713, 271.512, 1+His+Cit+Ala+Orn; 0.713, 270.535, 1+His+Orn+Cys+BCAA; 0.712, 269.440, 1+His+Tau+Asp+Orn; 0.712, 271.746, 1+His+Tau+Ala+Orn; 0.712, 270.505, 1+His+Thr+Orn+Cys; 0.712, 270.442, 1+His+Orn+Cys+Val; 0.711, 271.503, 1+His+Se r+Ala+Orn; 0.711, 271.025, 1+His+Arg+Ala+Orn; 0.710, 271.968, 1+H is+Glu+Ala+Orn; 0.710, 271.981, 1+His+Thr+Ala+Orn; 0.710, 271.82 8, 1+His+Ala+Orn+Ile; 0.710, 271.977, 1+His+Ala+Orn+BCAA; 0.709, 271.792, 1+His+Gln+Ala+Orn; 0.709, 271.895, 1+His+Ala+Pro+Orn; 0. 709, 271.213, 1+His+Ala+Orn+Tyr; 0.709, 271.954, 1+His+Ala+Orn+M et; 0.709, 271.979, 1+His+Ala+Orn+Leu; 0.709, 270.972, 1+His+Ala+Orn+Trp; 0.708, 271.878, 1+His+Ala+Orn+Val; 0.707, 270.984, 1+His+Orn+Tyr+Leu

[404. Formula (with Five Amino Acid Variables) with Improved Diagnostic Accuracy by Added Parity Term]
0.737, 266.646, 1+His+Gly+Orn+Leu+Phe; 0.735, 266.818, 1+His+Orn+Val+Phe+BCAA; 0.734, 265.821, 1+His+Ser+Asp+Orn+Phe

[405. Formula (with Six Amino Acid Variables) with Improved Diagnostic Accuracy by Added Parity Term]
0.749, 267.475, 1+His+Gly+Ala+Orn+Ile+Phe; 0.745, 266.628, 1+His+Gly+Asp+Orn+Leu+Phe; 0.745, 268.372, 1+His+Gly+Ala+Orn+Phe+BC AA; 0.745, 268.264, 1+His+Gly+Cit+Orn+Phe+BCAA; 0.745, 266.620, 1+His+Gly+Asp+Orn+Ile+Phe; 0.744, 266.408, 1+His+3MeHis+Asp+Orn+Ile+Phe; 0.743, 267.104, 1+His+Gly+Asp+Orn+Phe+BCAA; 0.743, 267. 667, 1+His+Gly+Cit+Orn+Leu+Phe; 0.743, 266.848, 1+His+Ser+Asp+C it+Orn+Phe; 0.742, 267.950, 1+His+Gln+Gly+Orn+Leu+Phe; 0.741, 26 6.815, 1+His+Ser+Asp+Orn+Ile+Phe; 0.741, 268.089, 1+His+Gln+Gly+Orn+Ile+Phe; 0.741, 266.997, 1+His+Ser+Asp+Orn+Leu+Phe; 0.741, 266.916, 1+His+Gly+Orn+Cys+Leu+Phe; 0.741, 267.926, 1+His+Gly+O rn+Val+Phe+BCAA; 0.740, 268.413, 1+His+Ser+Ala+Orn+Ile+Phe; 0.7 40, 268.592, 1+His+Gly+Thr+Orn+Leu+Phe; 0.740, 268.359, 1+His+Ta u+Gly+Orn+Leu+Phe; 0.740, 267.334, 1+His+Ser+Asp+Glu+Orn+Phe; 0. 740, 267.260, 1+His+Ser+Asp+Orn+Phe+BCAA; 0.739, 266.614, 1+His+3MeHis+Ser+Asp+Orn+Phe; 0.739, 268.644, 1+His+Ala+Orn+Val+Ile+Phe; 0.739, 268.596, 1+His+Gly+Glu+Orn+Leu+Phe; 0.739, 268.136, 1+His+Cit+Orn+Val+Phe+BCAA; 0.739, 268.638, 1+His+3MeHis+Cit+Or n+Phe+BCAA; 0.739, 268.416, 1+His+Gln+Gly+Orn+Phe+BCAA; 0.739, 2 67.678, 1+His+Ser+Asp+Thr+Orn+Phe; 0.739, 267.299, 1+His+Gly+Or n+Cys+Phe+BCAA; 0.739, 268.902, 1+His+Tau+Gly+Orn+Phe+BCAA; 0.7 39, 268.324, 1+His+3MeHis+Gly+Orn+Phe+BCAA; 0.738, 268.168, 1+Hi s+Arg+Orn+Val+Phe+BCAA; 0.738, 268.493, 1+His+Gly+Orn+Ile+Leu+Phe; 0.738, 269.472, 1+His+Gly+Ala+Orn+Val+Phe; 0.738, 268.293, 1+His+Gly+Orn+Val+Leu+Phe; 0.738, 266.133, 1+His+Tau+Ser+Asp+Or n+Phe; 0.738, 268.426, 1+His+Arg+Gly+Orn+Leu+Phe; 0.738, 267.626, 1+His+Ser+Asp+Orn+Val+Phe; 0.738, 268.676, 1+His+Ser+Cit+Orn+L eu+Phe; 0.738, 266.400, 1+His+Gly+Asp+Orn+Cys+Phe; 0.738, 268.50 1, 1+His+Gly+Orn+Lys+Leu+Phe; 0.738, 268.241, 1+His+Tau+3MeHis+Orn+Ile+Phe; 0.738, 267.332, 1+His+Ser+Arg+Asp+Orn+Phe; 0.738, 2 68.568, 1+His+Gly+Orn+Met+Leu+Phe; 0.738, 268.646, 1+His+Gly+Or n+Tyr+Leu+Phe; 0.737, 269.783, 1+His+Gly+Thr+Ala+Orn+Phe; 0.737, 267.469, 1+His+Ser+Gln+Asp+Orn+Phe; 0.737, 268.587, 1+His+Ser+G ly+Orn+Leu+Phe; 0.737, 267.852, 1+His+Gly+Pro+Orn+Leu+Phe; 0.73 7, 267.238, 1+His+3MeHis+Orn+Cys+Ile+Phe; 0.737, 268.557, 1+His+Gly+Orn+Leu+Phe+BCAA; 0.737, 268.213, 1+His+Gly+Orn+Leu+Phe+Tr p; 0.737, 267.530, 1+His+Ser+Asp+Ala+Orn+Phe; 0.736, 268.773, 1+H is+3MeHis+Ser+Orn+Phe+BCAA; 0.736, 267.406, 1+His+Ser+Gly+Asp+Orn+Phe; 0.736, 268.357, 1+His+Gly+Asp+Ala+Orn+Phe; 0.736, 268.6 11, 1+His+Orn+Lys+Val+Phe+BCAA; 0.735, 269.467, 1+His+Ser+Ala+O rn+Phe+BCAA; 0.735, 267.864, 1+His+Gln+Gly+Asp+Orn+Phe; 0.735, 2 67.351, 1+His+Tau+Gly+Asp+Orn+Phe; 0.735, 267.798, 1+His+Ser+As p+Orn+Met+Phe; 0.735, 265.580, 1+His+Ser+Asp+Orn+Cys+Phe; 0.735, 267.776, 1+His+Ser+Asp+Orn+Tyr+Phe; 0.735, 268.557, 1+His+Ser+O rn+Val+Phe+BCAA; 0.735, 268.812, 1+His+Orn+Ile+Leu+Phe+BCAA; 0. 735, 268.812, 1+His+Orn+Val+Leu+Phe+BCAA; 0.735, 268.812, 1+His+Orn+Val+Ile+Phe+BCAA; 0.735, 268.812, 1+His+Orn+Val+Ile+Leu+Ph e; 0.734, 268.817, 1+His+Orn+Met+Val+Phe+BCAA; 0.734, 269.283, 1+His+Asp+Glu+Orn+Leu+Phe; 0.734, 267.606, 1+His+Ser+Asp+Orn+Phe+Trp; 0.734, 268.773, 1+His+Glu+Orn+Val+Phe+BCAA; 0.734, 267.677, 1+His+Ser+Asp+Orn+Lys+Phe; 0.734, 267.677, 1+His+Ser+Asp+Pro+O rn+Phe; 0.734, 268.745, 1+His+Thr+Orn+Val+Phe+BCAA; 0.732, 269.3 86, 1+His+Ser+Gln+Orn+Leu+Phe; 0.732, 271.519, 1+His+Arg+Gly+Al a+Orn+Cys; 0.732, 269.570, 1+His+Ser+Orn+Tyr+Leu+Phe; 0.731, 269. 221, 1+His+Tau+Ser+Orn+Leu+Phe; 0.731, 269.569, 1+His+Gln+Gly+A la+Orn+Phe; 0.731, 269.031, 1+His+Tau+Gln+Gly+Orn+Phe

[406. Formula (with Two Biochemistry Variables) with Improved Diagnostic Accuracy by Added Parity Term]
0.729, 257.132, 1+ALB+BUN; 0.711, 262.141, 1+ALB+Ca; 0.729, 259.24 7, 1+ALB+AST; 0.731, 254.610, 1+ALB+

ALT; 0.716, 261.875, 1+ALB+gG T; 0.726, 259.148, 1+ALB+NEFA; 0.718, 260.087, 1+ALB+T-BIL; 0.713, 262.083, 1+ALB+BHBA; 0.707, 262.275, 1+ALB+Glc

[407. Formula (with Three Biochemistry Variables) with Improved Diagnostic Accuracy by Added Parity Term] 0.729, 259.071, 1+TP+ALB+BUN; 0.726, 261.158, 1+TP+ALB+AST; 0.731, 256.542, 1+TP+ALB+ALT; 0.715, 263.815, 1+TP+ALB+gGT; 0.726, 261.1 32, 1+TP+ALB+NEFA; 0.720, 262.041, 1+TP+ALB+T-BIL; 0.713, 263.996, 1+TP+ALB+BHBA; 0.726, 258.777, 1+ALB+BUN+Ca; 0.733, 256.798, 1+AL B+BUN+AST; 0.745, 252.538, 1+ALB+BUN+ALT; 0.728, 258.847, 1+ALB+B UN+gGT; 0.736, 257.014, 1+ALB+BUN+NEFA; 0.737, 256.558, 1+ALB+BUN+T-BIL; 0.730, 258.675, 1+ALB+BUN+BHBA; 0.729, 259.105, 1+ALB+BUN+Glc; 0.725, 258.830, 1+ALB+BUN+TG; 0.727, 257.797, 1+ALB+BUN+TCH O; 0.727, 261.073, 1+ALB+Ca+AST; 0.729, 256.345, 1+ALB+Ca+ALT; 0.7 16, 263.674, 1+ALB+Ca+gGT; 0.725, 261.017, 1+ALB+Ca+NEFA; 0.717, 2 61.935, 1+ALB+Ca+T-BIL; 0.735, 255.954, 1+ALB+AST+ALT; 0.729, 261. 235, 1+ALB+AST+gGT; 0.740, 257.408, 1+ALB+AST+NEFA; 0.735, 258.08 5, 1+ALB+AST+T-BIL; 0.732, 260.796, 1+ALB+AST+BHBA; 0.727, 261.14 8, 1+ALB+AST+Glc; 0.727, 260.914, 1+ALB+AST+TG; 0.728, 260.177, 1+ALB+AST+TCHO; 0.733, 256.535, 1+ALB+ALT+gGT; 0.734, 255.699, 1+AL B+ALT+NEFA; 0.733, 255.963, 1+ALB+ALT+T-BIL; 0.731, 256.426, 1+AL B+ALT+BHBA; 0.731, 256.577, 1+ALB+ALT+Glc; 0.731, 256.509, 1+ALB+ALT+TG; 0.731, 255.889, 1+ALB+ALT+TCHO; 0.726, 260.934, 1+ALB+gGT+NEFA; 0.723, 261.644, 1+ALB+gGT+T-BIL; 0.716, 263.612, 1+ALB+gGT+BHBA; 0.715, 263.714, 1+ALB+gGT+Glc; 0.715, 263.477, 1+ALB+gGT+T G; 0.727, 261.145, 1+ALB+NEFA+T-BIL; 0.727, 261.116, 1+ALB+NEFA+B HBA; 0.727, 260.951, 1+ALB+NEFA+Glc; 0.726, 261.147, 1+ALB+NEFA+T G; 0.722, 258.885, 1+ALB+NEFA+TCHO; 0.721, 261.876, 1+ALB+T-BIL+B HBA; 0.720, 261.639, 1+ALB+T-BIL+Glc; 0.719, 262.034, 1+ALB+T-BIL+TG; 0.720, 260.166, 1+ALB+T-BIL+TCHO

[408. Formula (with Four Biochemistry Variables) with Improved Diagnostic Accuracy by Added Parity Term] 0.731, 257.747, 1+ALB+ALT+TG+TCHO; 0.731, 257.800, 1+ALB+ALT+Glc+TCHO; 0.731, 258.482, 1+ALB+ALT+Glc+TG; 0.732, 258.357, 1+ALB+AL T+BHBA+TG; 0.733, 257.233, 1+ALB+ALT+T-BIL+TCHO; 0.733, 257.961, 1+ALB+ALT+T-BIL+TG; 0.733, 257.813, 1+ALB+ALT+T-BIL+Glc; 0.732, 257.952, 1+ALB+ALT+T-BIL+BHBA; 0.734, 256.855, 1+ALB+ALT+NEFA+T CHO; 0.735, 257.687, 1+ALB+ALT+NEFA+TG; 0.735, 257.623, 1+ALB+ALT+NEFA+Glc; 0.734, 257.698, 1+ALB+ALT+NEFA+BHBA; 0.734, 257.696, 1+ALB+ALT+NEFA+T-BIL; 0.734, 257.885, 1+ALB+ALT+gGT+T-BIL; 0.735, 257.669, 1+ALB+ALT+gGT+NEFA; 0.738, 259.180, 1+ALB+AST+T-BIL+TC HO; 0.736, 260.082, 1+ALB+AST+T-BIL+TG; 0.736, 259.699, 1+ALB+AST+T-BIL+Glc; 0.736, 259.946, 1+ALB+AST+T-BIL+BHBA; 0.740, 258.225, 1+ALB+AST+NEFA+TCHO; 0.740, 259.326, 1+ALB+AST+NEFA+TG; 0.739, 2 59.296, 1+ALB+AST+NEFA+Glc; 0.740, 259.408, 1+ALB+AST+NEFA+BHB A; 0.741, 259.308, 1+ALB+AST+NEFA+T-BIL; 0.735, 260.082, 1+ALB+AS T+gGT+T-BIL; 0.738, 259.326, 1+ALB+AST+gGT+NEFA; 0.735, 257.302, 1+ALB+AST+ALT+TCHO; 0.734, 257.866, 1+ALB+AST+ALT+TG; 0.735, 257. 924, 1+ALB+AST+ALT+Glc; 0.735, 257.672, 1+ALB+AST+ALT+BHBA; 0.73 6, 256.831, 1+ALB+AST+ALT+T-BIL; 0.739, 256.572, 1+ALB+AST+ALT+N EFA; 0.735, 257.953, 1+ALB+AST+ALT+gGT; 0.732, 257.771, 1+ALB+Ca+ALT+T-BIL; 0.734, 257.524, 1+ALB+Ca+ALT+NEFA; 0.735, 260.012, 1+A LB+Ca+AST+T-BIL; 0.739, 259.340, 1+ALB+Ca+AST+NEFA; 0.735, 257.7 23, 1+ALB+Ca+AST+ALT; 0.745, 254.046, 1+ALB+BUN+ALT+TCHO; 0.745, 254.527, 1+ALB+BUN+ALT+TG; 0.745, 254.536, 1+ALB+BUN+ALT+Glc; 0. 746, 254.194, 1+ALB+BUN+ALT+BHBA; 0.748, 253.736, 1+ALB+BUN+ALT+T-BIL; 0.749, 254.121, 1+ALB+BUN+ALT+NEFA; 0.744, 254.532, 1+ALB+BUN+ALT+gGT; 0.731, 258.768, 1+ALB+BUN+AST+Glc; 0.736, 258.290, 1+ALB+BUN+AST+BHBA; 0.741, 255.680, 1+ALB+BUN+AST+T-BIL; 0.740, 2 56.347, 1+ALB+BUN+AST+NEFA; 0.745, 254.166, 1+ALB+BUN+AST+ALT; 0. 746, 254.231, 1+ALB+BUN+Ca+ALT; 0.733, 258.560, 1+ALB+BUN+Ca+AS T; 0.731, 257.783, 1+TP+ALB+ALT+TCHO; 0.730, 258.457, 1+TP+ALB+AL T+TG; 0.731, 258.494, 1+TP+ALB+ALT+Glc; 0.731, 258.400, 1+TP+ALB+ALT+BHBA; 0.732, 257.938, 1+TP+ALB+ALT+T-BIL; 0.732, 258.495, 1+T P+ALB+ALT+gGT; 0.731, 262.773, 1+TP+ALB+AST+BHBA; 0.735, 260.080, 1+TP+ALB+AST+T-BIL; 0.740, 259.407, 1+TP+ALB+AST+NEFA; 0.734, 25 7.906, 1+TP+ALB+AST+ALT; 0.730, 258.306, 1+TP+ALB+Ca+ALT; 0.746, 254.520, 1+TP+ALB+BUN+ALT; 0.733, 258.772, 1+TP+ALB+BUN+AST

[409. Formula (with Five Biochemistry Variables) with Improved Diagnostic Accuracy by Added Parity Term] 0.730, 259.670, 1+ALB+ALT+Glc+TG+TCHO; 0.732, 259.612, 1+ALB+ALT+BHBA+TG+TCHO; 0.733, 259.224, 1+ALB+ALT+T-BIL+TG+TCHO; 0.735, 2 58.955, 1+ALB+ALT+T-BIL+Glc+TCHO; 0.733, 259.813, 1+ALB+ALT+T-B IL+Glc+TG; 0.733, 259.213, 1+ALB+ALT+T-BIL+BHBA+TCHO; 0.733, 259. 951, 1+ALB+ALT+T-BIL+BHBA+TG; 0.733, 259.813, 1+ALB+ALT+T-BIL+B HBA+Glc; 0.735, 258.846, 1+ALB+ALT+NEFA+TG+TCHO; 0.737, 258.666, 1+ALB+ALT+NEFA+Glc+TCHO; 0.735, 259.607, 1+ALB+ALT+NEFA+Glc+T G; 0.734, 258.853, 1+ALB+ALT+NEFA+BHBA+TCHO; 0.735, 259.687, 1+AL B+ALT+NEFA+BHBA+TG; 0.736, 259.610, 1+ALB+ALT+NEFA+BHBA+Glc; 0. 734, 258.855, 1+ALB+ALT+NEFA+T-BIL+TCHO; 0.735, 259.685, 1+ALB+A LT+NEFA+T-BIL+TG; 0.735, 259.605, 1+ALB+ALT+NEFA+T-BIL+Glc; 0.7 34, 259.696, 1+ALB+ALT+NEFA+T-BIL+BHBA; 0.733, 259.702, 1+ALB+AL T+gGT+TG+TCHO; 0.732, 259.724, 1+ALB+ALT+gGT+Glc+TCHO; 0.731, 26 0.424, 1+ALB+ALT+gGT+Glc+TG; 0.732, 259.660, 1+ALB+ALT+gGT+BHBA+TCHO; 0.732, 260.313, 1+ALB+ALT+gGT+BHBA+TG; 0.735, 259.165, 1+A LB+ALT+gGT+T-BIL+TCHO; 0.734, 259.885, 1+ALB+ALT+gGT+T-BIL+TG; 0.734, 259.720, 1+ALB+ALT+gGT+T-BIL+Glc; 0.734, 259.868, 1+ALB+A LT+gGT+T-BIL+BHBA; 0.735, 258.838, 1+ALB+ALT+gGT+NEFA+TCHO; 0.7 35, 259.653, 1+ALB+ALT+gGT+NEFA+TG; 0.736, 259.589, 1+ALB+ALT+gG T+NEFA+Glc; 0.735, 259.669, 1+ALB+ALT+gGT+NEFA+BHBA; 0.735, 259. 663, 1+ALB+ALT+gGT+NEFA+T-BIL; 0.738, 261.179, 1+ALB+AST+T-BIL+TG+TCHO; 0.736, 260.549, 1+ALB+AST+T-BIL+Glc+TCHO; 0.737, 261.68 2, 1+ALB+AST+T-BIL+Glc+TG; 0.735, 260.996, 1+ALB+AST+T-BIL+BHBA+TCHO; 0.737, 261.937, 1+ALB+AST+T-BIL+BHBA+TG; 0.736, 261.649, 1+ALB+AST+T-BIL+BHBA+Glc; 0.740, 260.133, 1+ALB+AST+NEFA+TG+TCH O; 0.737, 259.931, 1+ALB+AST+NEFA+Glc+TCHO; 0.739, 261.202, 1+ALB+AST+NEFA+Glc+TG; 0.739, 260.214, 1+ALB+AST+NEFA+BHBA+TCHO; 0.7 39, 261.326, 1+ALB+AST+NEFA+BHBA+TG; 0.739, 261.283, 1+ALB+AST+NEFA+BHBA+Glc; 0.740, 260.191, 1+ALB+AST+NEFA+T-BIL+TCHO; 0.740, 261.222, 1+ALB+AST+NEFA+T-BIL+TG; 0.739, 261.106, 1+ALB+AST+NEFA+T-BIL+Glc; 0.740, 261.270, 1+ALB+AST+NEFA+T-BIL+BHBA; 0.736, 262.080, 1+ALB+AST+gGT+T-BIL+TG; 0.736, 261.699, 1+ALB+AST+gGT+T-BIL+Glc; 0.736, 261.945, 1+ALB+AST+gGT+T-BIL+BHBA; 0.738, 260.111, 1+ALB+AST+gGT+NEFA+TCHO; 0.738, 261.256, 1+ALB+AST+gGT+NEFA+TG; 0.738, 261.224, 1+ALB+AST+gGT+NEFA+Glc; 0.738, 261.326, 1+ALB+AST+gGT+NEFA+BHBA; 0.738, 261.244, 1+ALB+AST+gGT+NEFA+T-BIL; 0.734, 259.172, 1+ALB+AST+ALT+TG+TCHO; 0.735, 259.235, 1+ALB+AST+ALT+Glc+TCHO; 0.734, 259.843, 1+ALB+AST+ALT+Glc+TG; 0.735, 259.029, 1+ALB+AST+ALT+BHBA+TCHO; 0.736, 259.618, 1+ALB+AST+ALT+BHBA+TG; 0.736, 259.569, 1+ALB+AST+ALT+BHBA+Glc; 0.736, 258.214, 1+ALB+AST+ALT+T-BIL+TCHO; 0.736, 258.824, 1+ALB+AST+ALT+T-BIL+TG; 0.736, 258.657, 1+ALB+AST+ALT+T-BIL+Glc; 0.736, 258.813, 1+ALB+AST+ALT+T-BIL+BHBA; 0.739, 257.855, 1+ALB+AST+ALT+NEFA+TCHO; 0.739, 258.511, 1+ALB+AST+ALT+NEFA+TG; 0.739, 258.511, 1+ALB+AST+ALT+NEFA+Glc; 0.739, 258.565, 1+ALB+AST+ALT+NEFA+BHBA; 0.738, 258.528, 1+ALB+AST+ALT+NEFA+T-BIL; 0.735, 259.301, 1+ALB+AST+ALT+gGT+TCHO; 0.734, 259.865, 1+ALB+AST+ALT+gGT+TG; 0.735, 259.923, 1+ALB+AST+ALT+gGT+Glc; 0.735, 259.669, 1+ALB+AST+ALT+gGT+BHBA; 0.735, 258.825, 1+ALB+AST+ALT+gGT+T-BIL; 0.738, 258.522, 1+ALB+AST+ALT+gGT+NEFA; 0.732, 259.065, 1+ALB+Ca+ALT+T-BIL+TCHO; 0.732, 259.768, 1+ALB+Ca+ALT+T-BIL+TG; 0.733, 259.527, 1+ALB+Ca+ALT+T-BIL+Glc; 0.732, 259.738, 1+ALB+Ca+ALT+T-BIL+BHBA; 0.733, 258.713, 1+ALB+Ca+ALT+NEFA+TCHO; 0.734, 259.516, 1+ALB+Ca+ALT+NEFA+TG; 0.736, 259.383, 1+ALB+Ca+ALT+NEFA+Glc; 0.734, 259.522, 1+ALB+Ca+ALT+NEFA+BHBA; 0.734, 259.523, 1+ALB+Ca+ALT+NEFA+T-BIL; 0.733, 259.711, 1+ALB+Ca+ALT+gGT+T-BIL; 0.734, 259.503, 1+ALB+Ca+ALT+gGT+NEFA; 0.736, 261.112, 1+ALB+Ca+AST+T-BIL+TCHO; 0.736, 262.010, 1+ALB+Ca+AST+T-BIL+TG; 0.736, 261.556, 1+ALB+Ca+AST+T-BIL+Glc; 0.734, 261.847, 1+ALB+Ca+AST+T-BIL+BHBA; 0.738, 260.164, 1+ALB+Ca+AST+NEFA+TCHO; 0.739, 261.261, 1+ALB+Ca+AST+NEFA+TG; 0.738, 261.197, 1+ALB+Ca+AST+NEFA+Glc; 0.739, 261.340, 1+ALB+Ca+AST+NEFA+BHBA; 0.740, 261.245, 1+ALB+Ca+AST+NEFA+T-BIL; 0.734, 262.008, 1+ALB+Ca+AST+gGT+T-BIL; 0.737, 261.255, 1+ALB+Ca+AST+gGT+NEFA; 0.734, 259.084, 1+ALB+Ca+AST+ALT+TCHO; 0.734, 259.635, 1+ALB+Ca+AST+ALT+TG; 0.734, 259.636, 1+ALB+Ca+AST+ALT+Glc; 0.735, 259.526, 1+ALB+Ca+AST+ALT+BHBA; 0.734, 258.699, 1+ALB+Ca+AST+ALT+T-BIL; 0.738, 258.452, 1+ALB+Ca+AST+ALT+NEFA; 0.735, 259.723, 1+ALB+Ca+AST+ALT+gGT; 0.745, 256.022, 1+ALB+BUN+ALT+TG+TCHO; 0.745, 256.031, 1+ALB+BUN+ALT+Glc+TCHO; 0.745, 256.526, 1+ALB+BUN+ALT+Glc+TG; 0.746, 255.716, 1+ALB+BUN+ALT+BHBA+TCHO; 0.747, 256.193, 1+ALB+BUN+ALT+BHBA+TG; 0.746, 256.160, 1+ALB+BUN+ALT+BHBA+Glc; 0.746, 255.246, 1+ALB+BUN+ALT+T-BIL+TCHO; 0.748, 255.688, 1+ALB+BUN+ALT+T-BIL+TG; 0.748, 255.694, 1+ALB+BUN+ALT+T-BIL+Glc; 0.748, 255.727, 1+ALB+BUN+ALT+T-BIL+BHBA; 0.748, 255.564, 1+ALB+BUN+ALT+NEFA+TCHO; 0.749, 256.087, 1+ALB+BUN+ALT+NEFA+TG; 0.749, 256.116, 1+ALB+BUN+ALT+NEFA+Glc; 0.747, 255.978, 1+ALB+BUN+ALT+NEFA+BHBA; 0.748, 255.714, 1+ALB+BUN+ALT+NEFA+T-BIL; 0.745, 256.039, 1+ALB+BUN+ALT+gGT+TCHO; 0.745, 256.523, 1+ALB+BUN+ALT+gGT+TG; 0.744, 256.529, 1+ALB+BUN+ALT+gGT+Glc; 0.746, 256.193, 1+ALB+BUN+ALT+gGT+BHBA; 0.747, 255.729, 1+ALB+BUN+ALT+gGT+T-BIL; 0.748, 256.120, 1+ALB+BUN+ALT+gGT+NEFA; 0.730, 259.988, 1+ALB+BUN+AST+Glc+TCHO; 0.730, 260.627, 1+ALB+BUN+AST+Glc+TG; 0.733, 259.646, 1+ALB+BUN+AST+BHBA+TCHO; 0.733, 260.173, 1+ALB+BUN+AST+BHBA+TG; 0.733, 260.211, 1+ALB+BUN+AST+BHBA+Glc; 0.740, 257.071, 1+ALB+BUN+AST+T-BIL+TCHO; 0.742, 257.608, 1+ALB+BUN+AST+T-BIL+TG; 0.741, 257.518, 1+ALB+BUN+AST+T-BIL+Glc; 0.741, 257.654, 1+ALB+BUN+AST+T-BIL+BHBA; 0.740, 257.480, 1+ALB+BUN+AST+NEFA+TCHO; 0.741, 258.252, 1+ALB+BUN+AST+NEFA+TG; 0.740, 258.323, 1+ALB+BUN+AST+NEFA+Glc; 0.740, 258.260, 1+ALB+BUN+AST+NEFA+BHBA; 0.742, 257.642, 1+ALB+BUN+AST+NEFA+T-BIL; 0.731, 260.768, 1+ALB+BUN+AST+gGT+Glc; 0.736, 260.276, 1+ALB+BUN+AST+gGT+BHBA; 0.741, 257.641, 1+ALB+BUN+AST+gGT+T-BIL; 0.741, 258.240, 1+ALB+BUN+AST+gGT+NEFA; 0.745, 255.699, 1+ALB+BUN+AST+ALT+TCHO; 0.745, 256.158, 1+ALB+BUN+AST+ALT+TG; 0.746, 256.163, 1+ALB+BUN+AST+ALT+Glc; 0.745, 255.768, 1+ALB+BUN+AST+ALT+BHBA; 0.748, 255.010, 1+ALB+BUN+AST+ALT+T-BIL; 0.747, 255.515, 1+ALB+BUN+AST+ALT+NEFA; 0.745, 256.148, 1+ALB+BUN+AST+ALT+gGT; 0.745, 255.756, 1+ALB+BUN+Ca+ALT+TCHO; 0.745, 256.218, 1+ALB+BUN+Ca+ALT+TG; 0.745, 256.201, 1+ALB+BUN+Ca+ALT+Glc; 0.745, 255.991, 1+ALB+BUN+Ca+ALT+BHBA; 0.748, 255.510, 1+ALB+BUN+Ca+ALT+T-BIL; 0.748, 255.876, 1+ALB+BUN+Ca+ALT+NEFA; 0.745, 256.229, 1+ALB+BUN+Ca+ALT+gGT; 0.730, 260.488, 1+ALB+BUN+Ca+AST+Glc; 0.735, 260.147, 1+ALB+BUN+Ca+AST+BHBA; 0.741, 257.566, 1+ALB+BUN+Ca+AST+T-BIL; 0.740, 258.224, 1+ALB+BUN+Ca+AST+NEFA; 0.733, 260.556, 1+ALB+BUN+Ca+AST+gGT; 0.745, 255.897, 1+ALB+BUN+Ca+AST+ALT; 0.732, 259.663, 1+TP+ALB+ALT+TG+TCHO; 0.731, 259.664, 1+TP+ALB+ALT+Glc+TCHO; 0.730, 260.417, 1+TP+ALB+ALT+Glc+TG; 0.731, 259.662, 1+TP+ALB+ALT+BHBA+TCHO; 0.732, 260.337, 1+TP+ALB+ALT+BHBA+TG; 0.734, 259.187, 1+TP+ALB+ALT+T-BIL+TCHO; 0.732, 259.937, 1+TP+ALB+ALT+T-BIL+TG; 0.734, 259.770, 1+TP+ALB+ALT+T-BIL+Glc; 0.733, 259.916, 1+TP+ALB+ALT+T-BIL+BHBA; 0.734, 258.835, 1+TP+ALB+ALT+NEFA+TCHO; 0.735, 259.603, 1+TP+ALB+ALT+NEFA+Glc; 0.732, 259.745, 1+TP+ALB+ALT+gGT+TCHO; 0.732, 260.424, 1+TP+ALB+ALT+gGT+TG; 0.731, 260.444, 1+TP+ALB+ALT+gGT+Glc; 0.732, 260.355, 1+TP+ALB+ALT+gGT+BHBA; 0.734, 259.877, 1+TP+ALB+ALT+gGT+T-BIL; 0.729, 264.563, 1+TP+ALB+AST+BHBA+Glc; 0.738, 261.170, 1+TP+ALB+AST+T-BIL+TCHO; 0.736, 262.077, 1+TP+ALB+AST+T-BIL+TG; 0.736, 261.678, 1+TP+ALB+AST+T-BIL+Glc; 0.736, 261.921, 1+TP+ALB+AST+T-BIL+BHBA; 0.740, 260.225, 1+TP+ALB+AST+NEFA+TCHO; 0.740, 261.326, 1+TP+ALB+AST+NEFA+TG; 0.739, 261.296, 1+TP+ALB+AST+NEFA+Glc; 0.740, 261.407, 1+TP+ALB+AST+NEFA+BHBA; 0.740, 261.307, 1+TP+ALB+AST+NEFA+T-BIL; 0.731, 264.773, 1+TP+ALB+AST+gGT+BHBA; 0.735, 262.074, 1+TP+ALB+AST+gGT+T-BIL; 0.738, 261.325, 1+TP+ALB+AST+gGT+

NEFA; 0.734, 259.216, 1+TP+ALB+AST+ALT+TCHO; 0.735, 259.831, 1+TP+ALB+AST+ALT+TG; 0.735, 25 9.865, 1+TP+ALB+AST+ALT+Glc; 0.735, 259.664, 1+TP+ALB+AST+ALT+BHBA; 0.735, 258.826, 1+TP+ALB+AST+ALT+T-BIL; 0.734, 259.904, 1+TP+ALB+AST+ALT+gGT; 0.731, 259.578, 1+TP+ALB+Ca+ALT+TCHO; 0.730, 260.269, 1+TP+ALB+Ca+ALT+gGT; 0.729, 264.678, 1+TP+ALB+Ca+AST+BHBA; 0.735, 262.010, 1+TP+ALB+Ca+AST+T-BIL; 0.739, 261.338, 1+TP+ALB+Ca+AST+NEFA; 0.733, 259.698, 1+TP+ALB+Ca+AST+ALT; 0.745, 256.011, 1+TP+ALB+BUN+ALT+TCHO; 0.745, 256.511, 1+TP+ALB+BUN+ALT+TG; 0.746, 256.516, 1+TP+ALB+BUN+ALT+Glc; 0.746, 256.194, 1+TP+ALB+BUN+ALT+BHBA; 0.749, 255.735, 1+TP+ALB+BUN+ALT+T-BIL; 0.748, 256.118, 1+TP+ALB+BUN+ALT+NEFA; 0.745, 256.517, 1+TP+ALB+BUN+ALT+gGT; 0.732, 260.735, 1+TP+ALB+BUN+AST+Glc; 0.736, 260.289, 1+TP+ALB+BUN+AST+BHBA; 0.741, 257.679, 1+TP+ALB+BUN+AST+T-BIL; 0.741, 258.345, 1+TP+ALB+BUN+AST+NEFA; 0.734, 260.766, 1+TP+ALB+BUN+AST+gGT; 0.745, 256.155, 1+TP+ALB+BUN+AST+ALT; 0.746, 256.227, 1+TP+ALB+BUN+Ca+ALT; 0.733, 260.549, 1+TP+ALB+BUN+Ca+AST

[410. Formula (with Six Biochemistry Variables) with Improved Diagnostic Accuracy by Added Parity Term]
0.733, 261.445, 1+ALB+ALT+BHBA+Glc+TG+TCHO; 0.735, 260.955, 1+ALB+ALT+T-BIL+Glc+TG+TCHO; 0.733, 261.207, 1+ALB+ALT+T-BIL+BHBA+TG+TCHO; 0.734, 260.954, 1+ALB+ALT+T-BIL+BHBA+Glc+TCHO; 0.733, 261.813, 1+ALB+ALT+T-BIL+BHBA+Glc+TG; 0.737, 260.645, 1+ALB+ALT+NEFA+Glc+TG+TCHO; 0.735, 260.843, 1+ALB+ALT+NEFA+BHBA+TG+TCHO; 0.737, 260.657, 1+ALB+ALT+NEFA+BHBA+Glc+TCHO; 0.735, 261.594, 1+ALB+ALT+NEFA+BHBA+Glc+TG; 0.734, 260.845, 1+ALB+ALT+NEFA+T-BIL+TG+TCHO; 0.737, 260.656, 1+ALB+ALT+NEFA+T-BIL+Glc+TCHO; 0.735, 261.587, 1+ALB+ALT+NEFA+T-BIL+Glc+TG; 0.734, 260.853, 1+ALB+ALT+NEFA+T-BIL+BHBA+TCHO; 0.734, 261.685, 1+ALB+ALT+NEFA+T-BIL+BHBA+TG; 0.735, 261.602, 1+ALB+ALT+NEFA+T-BIL+BHBA+Glc; 0.731, 261.619, 1+ALB+ALT+gGT+Glc+TG+TCHO; 0.733, 261.573, 1+ALB+ALT+gGT+BHBA+TG+TCHO; 0.733, 261.467, 1+ALB+ALT+gGT+BHBA+Glc+TCHO; 0.735, 261.162, 1+ALB+ALT+gGT+T-BIL+TG+TCHO; 0.734, 260.878, 1+ALB+ALT+gGT+T-BIL+Glc+TCHO; 0.734, 261.716, 1+ALB+ALT+gGT+T-BIL+Glc+TG; 0.735, 261.140, 1+ALB+ALT+gGT+T-BIL+BHBA+TCHO; 0.734, 261.867, 1+ALB+ALT+gGT+T-BIL+BHBA+TG; 0.734, 261.719, 1+ALB+ALT+gGT+T-BIL+BHBA+Glc; 0.735, 260.826, 1+ALB+ALT+gGT+NEFA+TG+TCHO; 0.735, 260.647, 1+ALB+ALT+gGT+NEFA+Glc+TCHO; 0.735, 261.566, 1+ALB+ALT+gGT+NEFA+Glc+TG; 0.735, 260.836, 1+ALB+ALT+gGT+NEFA+BHBA+TCHO; 0.734, 261.653, 1+ALB+ALT+gGT+NEFA+BHBA+TG; 0.736, 261.575, 1+ALB+ALT+gGT+NEFA+BHBA+Glc; 0.735, 260.838, 1+ALB+ALT+gGT+NEFA+T-BIL+TCHO; 0.734, 261.646, 1+ALB+ALT+gGT+NEFA+T-BIL+TG; 0.735, 261.559, 1+ALB+ALT+gGT+NEFA+T-BIL+Glc; 0.735, 261.662, 1+ALB+ALT+gGT+NEFA+T-BIL+BHBA; 0.736, 262.535, 1+ALB+AST+T-BIL+Glc+TG+TCHO; 0.736, 262.992, 1+ALB+AST+T-BIL+BHBA+TG+TCHO; 0.735, 262.490, 1+ALB+AST+T-BIL+BHBA+Glc+TCHO; 0.736, 263.626, 1+ALB+AST+T-BIL+BHBA+Glc+TG; 0.740, 261.810, 1+ALB+AST+NEFA+Glc+TG+TCHO; 0.740, 262.119, 1+ALB+AST+NEFA+BHBA+TG+TCHO; 0.738, 261.927, 1+ALB+AST+NEFA+BHBA+Glc+TCHO; 0.739, 263.189, 1+ALB+AST+NEFA+BHBA+Glc+TG; 0.740, 262.099, 1+ALB+AST+NEFA+T-BIL+TG+TCHO; 0.738, 261.808, 1+ALB+AST+NEFA+T-BIL+Glc+TCHO; 0.740, 262.998, 1+ALB+AST+NEFA+T-BIL+Glc+TG; 0.739, 262.136, 1+ALB+AST+NEFA+T-BIL+BHBA+TCHO; 0.740, 263.177, 1+ALB+AST+NEFA+T-BIL+BHBA+TG; 0.739, 263.095, 1+ALB+AST+NEFA+T-BIL+BHBA+Glc; 0.737, 263.682, 1+ALB+AST+gGT+T-BIL+Glc+TG; 0.737, 263.937, 1+ALB+AST+gGT+T-BIL+BHBA+TG; 0.736, 263.649, 1+ALB+AST+gGT+T-BIL+BHBA+Glc; 0.739, 262.032, 1+ALB+AST+gGT+NEFA+TG+TCHO; 0.737, 261.830, 1+ALB+AST+gGT+NEFA+Glc+TCHO; 0.738, 263.141, 1+ALB+AST+gGT+NEFA+Glc+TG; 0.737, 262.103, 1+ALB+AST+gGT+NEFA+BHBA+TCHO; 0.738, 263.256, 1+ALB+AST+gGT+NEFA+BHBA+TG; 0.738, 263.209, 1+ALB+AST+gGT+NEFA+BHBA+Glc; 0.737, 262.091, 1+ALB+AST+gGT+NEFA+T-BIL+TCHO; 0.739, 263.170, 1+ALB+AST+gGT+NEFA+T-BIL+TG; 0.738, 263.062, 1+ALB+AST+gGT+NEFA+T-BIL+Glc; 0.738, 263.218, 1+ALB+AST+gGT+NEFA+T-BIL+BHBA; 0.735, 261.117, 1+ALB+AST+ALT+Glc+TG+TCHO; 0.737, 260.939, 1+ALB+AST+ALT+BHBA+TG+TCHO; 0.735, 260.868, 1+ALB+AST+ALT+BHBA+Glc+TCHO; 0.736, 261.528, 1+ALB+AST+ALT+BHBA+Glc+TG; 0.736, 260.214, 1+ALB+AST+ALT+T-BIL+TG+TCHO; 0.737, 259.952, 1+ALB+AST+ALT+T-BIL+Glc+TCHO; 0.737, 260.636, 1+ALB+AST+ALT+T-BIL+Glc+TG; 0.736, 260.194, 1+ALB+AST+ALT+T-BIL+BHBA+TCHO; 0.736, 260.803, 1+ALB+AST+ALT+T-BIL+BHBA+TG; 0.736, 260.656, 1+ALB+AST+ALT+T-BIL+BHBA+Glc; 0.740, 259.811, 1+ALB+AST+ALT+NEFA+TG+TCHO; 0.741, 259.717, 1+ALB+AST+ALT+NEFA+Glc+TCHO; 0.740, 260.439, 1+ALB+AST+ALT+NEFA+Glc+TG; 0.738, 259.853, 1+ALB+AST+ALT+NEFA+BHBA+TCHO; 0.739, 260.506, 1+ALB+AST+ALT+NEFA+BHBA+TG; 0.739, 260.481, 1+ALB+AST+ALT+NEFA+BHBA+Glc; 0.738, 259.835, 1+ALB+AST+ALT+NEFA+T-BIL+TCHO; 0.739, 260.466, 1+ALB+AST+ALT+NEFA+T-BIL+TG; 0.738, 260.424, 1+ALB+AST+ALT+NEFA+T-BIL+Glc; 0.738, 260.527, 1+ALB+AST+ALT+NEFA+T-BIL+BHBA; 0.734, 261.172, 1+ALB+AST+ALT+gGT+TG+TCHO; 0.735, 261.233, 1+ALB+AST+ALT+gGT+Glc+TCHO; 0.734, 261.843, 1+ALB+AST+ALT+gGT+Glc+TG; 0.735, 261.028, 1+ALB+AST+ALT+gGT+BHBA+TCHO; 0.736, 261.611, 1+ALB+AST+ALT+gGT+BHBA+TG; 0.736, 261.568, 1+ALB+AST+ALT+gGT+BHBA+Glc; 0.736, 260.211, 1+ALB+AST+ALT+gGT+T-BIL+TCHO; 0.736, 260.820, 1+ALB+AST+ALT+gGT+T-BIL+TG; 0.736, 260.654, 1+ALB+AST+ALT+gGT+T-BIL+Glc; 0.735, 260.809, 1+ALB+AST+ALT+gGT+T-BIL+BHBA; 0.739, 259.806, 1+ALB+AST+ALT+gGT+NEFA+TCHO; 0.738, 260.468, 1+ALB+AST+ALT+gGT+NEFA+TG; 0.738, 260.465, 1+ALB+AST+ALT+gGT+NEFA+Glc; 0.737, 260.513, 1+ALB+AST+ALT+gGT+NEFA+BHBA; 0.738, 260.488, 1+ALB+AST+ALT+gGT+NEFA+T-BIL; 0.731, 261.053, 1+ALB+Ca+ALT+T-BIL+TG+TCHO; 0.733, 260.675, 1+ALB+Ca+ALT+T-BIL+Glc+TCHO; 0.731, 261.023, 1+ALB+Ca+ALT+T-BIL+BHBA+TCHO; 0.732, 261.737, 1+ALB+Ca+ALT+T-BIL+BHBA+TG; 0.733, 261.521, 1+ALB+Ca+ALT+T-BIL+BHBA+Glc; 0.733, 260.707, 1+ALB+Ca+ALT+NEFA+TG+TCHO; 0.735, 260.440, 1+ALB+Ca+ALT+NEFA+Glc+TCHO; 0.736, 261.369, 1+ALB+Ca+ALT+NEFA+Glc+TG; 0.732, 260.703, 1+ALB+Ca+ALT+NEFA+BHBA+TCHO; 0.734, 261.514, 1+ALB+Ca+ALT+NEFA+BHBA+TG; 0.736, 261.378, 1+ALB+Ca+ALT+

NEFA+BHBA+Glc; 0.733, 260.712, 1+ALB+Ca+ALT+NEFA+T-BIL+TCHO; 0.734, 261.514, 1+ALB+Ca+ALT+NEFA+T-BIL+TG; 0.736, 261.358, 1+ALB+Ca+ALT+NEFA+T-BIL+Glc; 0.734, 261.516, 1+ALB+Ca+ALT+NEFA+T-BIL+BHBA; 0.730, 261.475, 1+ALB+Ca+ALT+gGT+TG+TCHO; 0.731, 262.115, 1+ALB+Ca+ALT+gGT+Glc+TG; 0.733, 261.010, 1+ALB+Ca+ALT+gGT+T-BIL+TCHO; 0.733, 261.711, 1+ALB+Ca+ALT+gGT+T-BIL+TG; 0.734, 261.456, 1+ALB+Ca+ALT+gGT+T-BIL+Glc; 0.733, 261.671, 1+ALB+Ca+ALT+gGT+T-BIL+BHBA; 0.733, 260.700, 1+ALB+Ca+ALT+gGT+NEFA+TCHO; 0.735, 261.491, 1+ALB+Ca+ALT+gGT+NEFA+TG; 0.735, 261.359, 1+ALB+Ca+ALT+gGT+NEFA+Glc; 0.734, 261.501, 1+ALB+Ca+ALT+gGT+NEFA+BHBA; 0.734, 261.499, 1+ALB+Ca+ALT+gGT+NEFA+T-BIL; 0.736, 263.112, 1+ALB+Ca+AST+T-BIL+TG+TCHO; 0.734, 262.396, 1+ALB+Ca+AST+T-BIL+Glc+TCHO; 0.736, 263.538, 1+ALB+Ca+AST+T-BIL+Glc+TG; 0.735, 263.839, 1+ALB+Ca+AST+T-BIL+BHBA+TG; 0.734, 263.486, 1+ALB+Ca+AST+T-BIL+BHBA+Glc; 0.739, 262.074, 1+ALB+Ca+AST+NEFA+TG+TCHO; 0.737, 261.828, 1+ALB+Ca+AST+NEFA+Glc+TCHO; 0.737, 263.105, 1+ALB+Ca+AST+NEFA+Glc+TG; 0.737, 262.150, 1+ALB+Ca+AST+NEFA+BHBA+TCHO; 0.739, 263.260, 1+ALB+Ca+AST+NEFA+BHBA+TG; 0.737, 263.189, 1+ALB+Ca+AST+NEFA+BHBA+Glc; 0.738, 262.133, 1+ALB+Ca+AST+NEFA+T-BIL+TCHO; 0.739, 263.161, 1+ALB+Ca+AST+NEFA+T-BIL+TG; 0.738, 263.001, 1+ALB+Ca+AST+NEFA+T-BIL+Glc; 0.739, 263.197, 1+ALB+Ca+AST+NEFA+T-BIL+BHBA; 0.735, 264.006, 1+ALB+Ca+AST+gGT+T-BIL+TG; 0.736, 263.554, 1+ALB+Ca+AST+gGT+T-BIL+Glc; 0.734, 263.846, 1+ALB+Ca+AST+gGT+T-BIL+BHBA; 0.735, 262.048, 1+ALB+Ca+AST+gGT+NEFA+TCHO; 0.737, 263.187, 1+ALB+Ca+AST+gGT+NEFA+TG; 0.736, 263.121, 1+ALB+Ca+AST+gGT+NEFA+Glc; 0.737, 263.255, 1+ALB+Ca+AST+gGT+NEFA+BHBA; 0.736, 263.178, 1+ALB+Ca+AST+gGT+NEFA+T-BIL; 0.735, 260.952, 1+ALB+Ca+AST+ALT+TG+TCHO; 0.734, 260.942, 1+ALB+Ca+AST+ALT+Glc+TCHO; 0.735, 261.560, 1+ALB+Ca+AST+ALT+Glc+TG; 0.735, 260.889, 1+ALB+Ca+AST+ALT+BHBA+TCHO; 0.735, 261.467, 1+ALB+Ca+AST+ALT+BHBA+TG; 0.735, 261.368, 1+ALB+Ca+AST+ALT+BHBA+Glc; 0.736, 260.090, 1+ALB+Ca+AST+ALT+T-BIL+TCHO; 0.734, 260.694, 1+ALB+Ca+AST+ALT+T-BIL+TG; 0.738, 260.447, 1+ALB+Ca+AST+ALT+T-BIL+Glc; 0.735, 260.663, 1+ALB+Ca+AST+ALT+T-BIL+BHBA; 0.738, 259.749, 1+ALB+Ca+AST+ALT+NEFA+TCHO; 0.738, 260.399, 1+ALB+Ca+AST+ALT+NEFA+TG; 0.739, 260.344, 1+ALB+Ca+AST+ALT+NEFA+Glc; 0.738, 260.451, 1+ALB+Ca+AST+ALT+NEFA+BHBA; 0.737, 260.413, 1+ALB+Ca+AST+ALT+NEFA+T-BIL; 0.734, 261.084, 1+ALB+Ca+AST+ALT+gGT+TCHO; 0.734, 261.631, 1+ALB+Ca+AST+ALT+gGT+TG; 0.734, 261.636, 1+ALB+Ca+AST+ALT+gGT+Glc; 0.735, 261.521, 1+ALB+Ca+AST+ALT+gGT+BHBA; 0.735, 260.690, 1+ALB+Ca+AST+ALT+gGT+T-BIL; 0.736, 260.396, 1+ALB+Ca+AST+ALT+gGT+NEFA; 0.739, 262.357, 1+ALB+BUN+NEFA+T-BIL+Glc+TG; 0.739, 262.478, 1+ALB+BUN+NEFA+T-BIL+BHBA+TG; 0.739, 262.312, 1+ALB+BUN+gGT+NEFA+T-BIL+TG; 0.745, 258.010, 1+ALB+BUN+ALT+Glc+TG+TCHO; 0.746, 257.708, 1+ALB+BUN+ALT+BHBA+TG+TCHO; 0.745, 257.652, 1+ALB+BUN+ALT+BHBA+Glc+TCHO; 0.746, 258.160, 1+ALB+BUN+ALT+BHBA+Glc+TG; 0.746, 257.216, 1+ALB+BUN+ALT+T-BIL+TG+TCHO; 0.747, 257.153, 1+ALB+BUN+ALT+T-BIL+Glc+TCHO; 0.749, 257.631, 1+ALB+BUN+ALT+T-BIL+Glc+TG; 0.746, 257.242, 1+ALB+BUN+ALT+T-BIL+BHBA+TCHO; 0.748, 257.683, 1+ALB+BUN+ALT+T-BIL+BHBA+TG; 0.747, 257.672, 1+ALB+BUN+ALT+T-BIL+BHBA+Glc; 0.746, 257.537, 1+ALB+BUN+ALT+NEFA+TG+TCHO; 0.747, 257.531, 1+ALB+BUN+ALT+NEFA+Glc+TCHO; 0.749, 258.079, 1+ALB+BUN+ALT+NEFA+Glc+TG; 0.746, 257.456, 1+ALB+BUN+ALT+NEFA+BHBA+TCHO; 0.747, 257.950, 1+ALB+BUN+ALT+NEFA+BHBA+TG; 0.748, 257.947, 1+ALB+BUN+ALT+NEFA+BHBA+Glc; 0.746, 257.242, 1+ALB+BUN+ALT+NEFA+T-BIL+TCHO; 0.748, 257.679, 1+ALB+BUN+ALT+NEFA+T-BIL+TG; 0.747, 257.660, 1+ALB+BUN+ALT+NEFA+T-BIL+Glc; 0.748, 257.710, 1+ALB+BUN+ALT+NEFA+T-BIL+BHBA; 0.744, 258.017, 1+ALB+BUN+ALT+gGT+TG+TCHO; 0.745, 258.023, 1+ALB+BUN+ALT+gGT+Glc+TCHO; 0.745, 258.521, 1+ALB+BUN+ALT+gGT+Glc+TG; 0.746, 257.715, 1+ALB+BUN+ALT+gGT+BHBA+TCHO; 0.747, 258.192, 1+ALB+BUN+ALT+gGT+BHBA+TG; 0.746, 258.159, 1+ALB+BUN+ALT+gGT+BHBA+Glc; 0.745, 257.240, 1+ALB+BUN+ALT+gGT+T-BIL+TCHO; 0.747, 257.674, 1+ALB+BUN+ALT+gGT+T-BIL+TG; 0.746, 257.683, 1+ALB+BUN+ALT+gGT+T-BIL+Glc; 0.747, 257.721, 1+ALB+BUN+ALT+gGT+T-BIL+BHBA; 0.747, 257.564, 1+ALB+BUN+ALT+gGT+NEFA+TCHO; 0.748, 258.085, 1+ALB+BUN+ALT+gGT+NEFA+TG; 0.748, 258.115, 1+ALB+BUN+ALT+gGT+NEFA+Glc; 0.747, 257.978, 1+ALB+BUN+ALT+gGT+NEFA+BHBA; 0.747, 257.702, 1+ALB+BUN+ALT+gGT+NEFA+T-BIL; 0.731, 261.506, 1+ALB+BUN+AST+BHBA+TG+TCHO; 0.731, 261.475, 1+ALB+BUN+AST+BHBA+Glc+TCHO; 0.731, 262.111, 1+ALB+BUN+AST+BHBA+Glc+TG; 0.741, 259.014, 1+ALB+BUN+AST+T-BIL+TG+TCHO; 0.740, 258.775, 1+ALB+BUN+AST+T-BIL+Glc+TCHO; 0.742, 259.409, 1+ALB+BUN+AST+T-BIL+Glc+TG; 0.740, 259.025, 1+ALB+BUN+AST+T-BIL+BHBA+TCHO; 0.742, 259.573, 1+ALB+BUN+AST+T-BIL+BHBA+TG; 0.741, 259.514, 1+ALB+BUN+AST+T-BIL+BHBA+Glc; 0.743, 259.374, 1+ALB+BUN+AST+NEFA+TG+TCHO; 0.739, 259.373, 1+ALB+BUN+AST+NEFA+Glc+TCHO; 0.741, 260.220, 1+ALB+BUN+AST+NEFA+Glc+TG; 0.741, 259.442, 1+ALB+BUN+AST+NEFA+BHBA+TCHO; 0.741, 260.171, 1+ALB+BUN+AST+NEFA+BHBA+TG; 0.738, 260.205, 1+ALB+BUN+AST+NEFA+BHBA+Glc; 0.740, 258.975, 1+ALB+BUN+AST+NEFA+T-BIL+TCHO; 0.742, 259.535, 1+ALB+BUN+AST+NEFA+T-BIL+TG; 0.741, 259.504, 1+ALB+BUN+AST+NEFA+T-BIL+Glc; 0.742, 259.628, 1+ALB+BUN+AST+NEFA+T-BIL+BHBA; 0.731, 261.985, 1+ALB+BUN+AST+gGT+Glc+TCHO; 0.732, 261.625, 1+ALB+BUN+AST+gGT+BHBA+TCHO; 0.733, 262.146, 1+ALB+BUN+AST+gGT+BHBA+TG; 0.733, 262.201, 1+ALB+BUN+AST+gGT+BHBA+Glc; 0.741, 259.024, 1+ALB+BUN+AST+gGT+T-BIL+TCHO; 0.742, 259.581, 1+ALB+BUN+AST+gGT+T-BIL+TG; 0.740, 259.487, 1+ALB+BUN+AST+gGT+T-BIL+Glc; 0.741, 259.620, 1+ALB+BUN+AST+gGT+T-BIL+BHBA; 0.740, 259.344, 1+ALB+BUN+AST+gGT+NEFA+TCHO; 0.741, 260.160, 1+ALB+BUN+AST+gGT+NEFA+TG; 0.741, 260.222, 1+ALB+BUN+AST+gGT+NEFA+Glc; 0.741, 260.140, 1+ALB+BUN+AST+gGT+NEFA+BHBA; 0.741, 259.585, 1+ALB+BUN+AST+gGT+NEFA+T-BIL; 0.744, 257.678, 1+ALB+BUN+AST+ALT+TG+TCHO; 0.745, 257.687, 1+ALB+BUN+AST+ALT+Glc+TCHO; 0.745, 258.156, 1+ALB+BUN+AST+ALT+Glc+TG; 0.745, 257.304, 1+ALB+BUN+AST+ALT+BHBA+TCHO; 0.745, 257.768, 1+ALB+BUN+AST+ALT+BHBA+TG; 0.745, 257.732, 1+ALB+BUN+AST+ALT+BHBA+Glc; 0.747, 256.575, 1+ALB+BUN+AST+ALT+T-BIL+TCHO; 0.749, 256.912, 1+ALB+BUN+AST+ALT+T-BIL+TG; 0.747, 256.951, 1+ALB+BUN+AST+ALT+T-BIL+Glc; 0.747, 257.006, 1+ALB+BUN+AST+ALT+T-BIL+BHBA; 0.747, 257.008, 1+ALB+BUN+AST+ALT+NEFA+TCHO; 0.748, 257.434, 1+ALB+BUN+AST+ALT+NEFA+TG; 0.747, 257.509, 1+ALB+BUN+AST+ALT+NEFA+Glc; 0.747, 257.367, 1+ALB+BUN+AST+ALT+NEFA+BHBA; 0.748, 257.001, 1+ALB+BUN+AST+ALT+NEFA+T-BIL; 0.744, 257.687, 1+ALB+BUN+AST+ALT+gGT+TCHO; 0.745, 258.137, 1+ALB+BUN+AST+ALT+gGT+TG; 0.745, 258.146, 1+ALB+BUN+AST+ALT+gGT+Glc; 0.746, 257.723, 1+ALB+BUN+AST+ALT+gGT+BHBA; 0.747, 256.961, 1+ALB+BUN+AST+ALT+gGT+T-BIL; 0.747, 257.436, 1+ALB+BUN+AST+ALT+gGT+NEFA; 0.746, 257.729, 1+ALB+BUN+Ca+ALT+TG+TCHO; 0.744, 257.697, 1+ALB+BUN+Ca+ALT+Glc+TCHO; 0.745, 258.192, 1+ALB+BUN+Ca+ALT+Glc+TG; 0.745, 257.522, 1+ALB+BUN+Ca+ALT+BHBA+TCHO; 0.746, 257.988, 1+ALB+BUN+Ca+ALT+BHBA+TG; 0.744, 257.920, 1+ALB+BUN+Ca+ALT+BHBA+Glc; 0.745, 257.037, 1+ALB+BUN+Ca+ALT+T-BIL+TCHO; 0.747, 257.470, 1+ALB+BUN+Ca+ALT+T-BIL+TG; 0.748, 257.415, 1+ALB+BUN+Ca+ALT+T-BIL+Glc; 0.748, 257.509, 1+ALB+BUN+Ca+ALT+T-BIL+BHBA; 0.746, 257.347, 1+ALB+BUN+Ca+ALT+NEFA+TCHO; 0.747, 257.851, 1+ALB+BUN+Ca+ALT+NEFA+TG; 0.748, 257.844, 1+ALB+BUN+Ca+ALT+NEFA+Glc; 0.746, 257.784, 1+ALB+BUN+Ca+ALT+NEFA+BHBA; 0.747, 257.481, 1+ALB+BUN+Ca+ALT+NEFA+T-BIL; 0.745, 257.754, 1+ALB+BUN+Ca+ALT+gGT+TCHO; 0.745, 258.218, 1+ALB+BUN+Ca+ALT+gGT+TG; 0.745, 258.199, 1+ALB+BUN+Ca+ALT+gGT+Glc; 0.745, 257.991, 1+ALB+BUN+Ca+ALT+gGT+BHBA; 0.747, 257.507, 1+ALB+BUN+Ca+ALT+gGT+T-BIL; 0.749, 257.876, 1+ALB+BUN+Ca+ALT+gGT+NEFA; 0.729, 261.704, 1+ALB+BUN+Ca+AST+Glc+TCHO; 0.727, 262.354, 1+ALB+BUN+Ca+AST+Glc+TG; 0.732, 261.509, 1+ALB+BUN+Ca+AST+BHBA+TCHO; 0.731, 262.028, 1+ALB+BUN+Ca+AST+BHBA+TG; 0.732, 262.036, 1+ALB+BUN+Ca+AST+BHBA+Glc; 0.739, 258.965, 1+ALB+BUN+Ca+AST+T-BIL+TCHO; 0.741, 259.499, 1+ALB+BUN+Ca+AST+T-BIL+TG; 0.739, 259.356, 1+ALB+BUN+Ca+AST+T-BIL+Glc; 0.741, 259.527, 1+ALB+BUN+Ca+AST+T-BIL+BHBA; 0.738, 259.373, 1+ALB+BUN+Ca+AST+NEFA+TCHO; 0.740, 260.136, 1+ALB+BUN+Ca+AST+NEFA+TG; 0.739, 260.180, 1+ALB+BUN+Ca+AST+NEFA+Glc; 0.739, 260.157, 1+ALB+BUN+Ca+AST+NEFA+BHBA; 0.741, 259.533, 1+ALB+BUN+Ca+AST+NEFA+T-BIL; 0.731, 262.486, 1+ALB+BUN+Ca+AST+gGT+Glc; 0.734, 262.131, 1+ALB+BUN+Ca+AST+gGT+BHBA; 0.740, 259.522, 1+ALB+BUN+Ca+AST+gGT+T-BIL; 0.740, 260.111, 1+ALB+BUN+Ca+AST+gGT+NEFA; 0.745, 257.437, 1+ALB+BUN+Ca+AST+ALT+TCHO; 0.745, 257.887, 1+ALB+BUN+Ca+AST+ALT+TG; 0.745, 257.866, 1+ALB+BUN+Ca+AST+ALT+Glc; 0.746, 257.606, 1+ALB+BUN+Ca+AST+ALT+BHBA; 0.748, 256.846, 1+ALB+BUN+Ca+AST+ALT+T-BIL; 0.746, 257.330, 1+ALB+BUN+Ca+AST+ALT+NEFA; 0.745, 257.871, 1+ALB+BUN+Ca+AST+ALT+gGT; 0.732, 261.559, 1+TP+ALB+ALT+Glc+TG+TCHO; 0.732, 261.568, 1+TP+ALB+ALT+BHBA+TG+TCHO; 0.732, 261.457, 1+TP+ALB+ALT+BHBA+Glc+TCHO; 0.732, 262.239, 1+TP+ALB+ALT+BHBA+Glc+TG; 0.733, 261.180, 1+TP+ALB+ALT+T-BIL+TG+TCHO; 0.734, 260.876, 1+TP+ALB+ALT+T-BIL+Glc+TCHO; 0.734, 261.769, 1+TP+ALB+ALT+T-BIL+Glc+TG; 0.733, 261.151, 1+TP+ALB+ALT+T-BIL+BHBA+TCHO; 0.733, 261.916, 1+TP+ALB+ALT+T-BIL+BHBA+TG; 0.734, 261.766, 1+TP+ALB+ALT+T-BIL+BHBA+Glc; 0.735, 260.825, 1+TP+ALB+ALT+NEFA+TG+TCHO; 0.735, 260.626, 1+TP+ALB+ALT+NEFA+Glc+TCHO; 0.736, 261.585, 1+TP+ALB+ALT+NEFA+Glc+TG; 0.734, 260.829, 1+TP+ALB+ALT+NEFA+BHBA+TCHO; 0.736, 261.595, 1+TP+ALB+ALT+NEFA+BHBA+Glc; 0.734, 260.834, 1+TP+ALB+ALT+NEFA+T-BIL+TCHO; 0.735, 261.583, 1+TP+ALB+ALT+NEFA+T-BIL+Glc; 0.732, 261.639, 1+TP+ALB+ALT+gGT+TG+TCHO; 0.732, 261.625, 1+TP+ALB+ALT+gGT+Glc+TCHO; 0.731, 262.381, 1+TP+ALB+ALT+gGT+Glc+TG; 0.732, 261.625, 1+TP+ALB+ALT+gGT+BHBA+TCHO; 0.733, 262.304, 1+TP+ALB+ALT+gGT+BHBA+TG; 0.732, 262.240, 1+TP+ALB+ALT+gGT+BHBA+Glc; 0.735, 261.140, 1+TP+ALB+ALT+gGT+T-BIL+TCHO; 0.734, 261.877, 1+TP+ALB+ALT+gGT+T-BIL+TG; 0.735, 261.701, 1+TP+ALB+ALT+gGT+T-BIL+Glc; 0.733, 261.852, 1+TP+ALB+ALT+gGT+T-BIL+BHBA; 0.735, 260.824, 1+TP+ALB+ALT+gGT+NEFA+TCHO; 0.734, 261.578, 1+TP+ALB+ALT+gGT+NEFA+Glc; 0.737, 263.169, 1+TP+ALB+AST+T-BIL+TG+TCHO; 0.735, 262.506, 1+TP+ALB+AST+T-BIL+Glc+TCHO; 0.736, 263.657, 1+TP+ALB+AST+T-BIL+Glc+TG; 0.735, 262.957, 1+TP+ALB+AST+T-BIL+BHBA+TCHO; 0.736, 263.910, 1+TP+ALB+AST+T-BIL+BHBA+TG; 0.736, 263.610, 1+TP+ALB+AST+T-BIL+BHBA+Glc; 0.740, 262.133, 1+TP+ALB+AST+NEFA+TG+TCHO; 0.737, 261.927, 1+TP+ALB+AST+NEFA+Glc+TCHO; 0.739, 263.201, 1+TP+ALB+AST+NEFA+Glc+TG; 0.739, 262.214, 1+TP+ALB+AST+NEFA+BHBA+TCHO; 0.740, 263.326, 1+TP+ALB+AST+NEFA+BHBA+TG; 0.740, 263.283, 1+TP+ALB+AST+NEFA+BHBA+Glc; 0.740, 262.191, 1+TP+ALB+AST+NEFA+T-BIL+TCHO; 0.740, 263.221, 1+TP+ALB+AST+NEFA+T-BIL+TG; 0.739, 263.104, 1+TP+ALB+AST+NEFA+T-BIL+Glc; 0.740, 263.270, 1+TP+ALB+AST+NEFA+T-BIL+BHBA; 0.729, 266.562, 1+TP+ALB+AST+gGT+BHBA+Glc; 0.737, 263.155, 1+TP+ALB+AST+gGT+T-BIL+TCHO; 0.736, 264.072, 1+TP+ALB+AST+gGT+T-BIL+TG; 0.736, 263.673, 1+TP+ALB+AST+gGT+T-BIL+Glc; 0.735, 263.916, 1+TP+ALB+AST+gGT+T-BIL+BHBA; 0.737, 262.107, 1+TP+ALB+AST+gGT+NEFA+TCHO; 0.738, 263.254, 1+TP+ALB+AST+gGT+NEFA+TG; 0.737, 263.218, 1+TP+ALB+AST+gGT+NEFA+Glc; 0.738, 263.324, 1+TP+ALB+AST+gGT+NEFA+BHBA; 0.738, 263.244, 1+TP+ALB+AST+gGT+NEFA+T-BIL; 0.735, 261.104, 1+TP+ALB+AST+ALT+TG+TCHO; 0.734, 261.126, 1+TP+ALB+AST+ALT+Glc+TCHO; 0.736, 261.799, 1+TP+ALB+AST+ALT+Glc+TG; 0.735, 260.999, 1+TP+ALB+AST+ALT+BHBA+TCHO; 0.736, 261.613, 1+TP+ALB+AST+ALT+BHBA+TG; 0.735, 261.556, 1+TP+ALB+AST+ALT+BHBA+Glc; 0.736, 260.194, 1+TP+ALB+AST+ALT+T-BIL+TCHO; 0.736, 260.818, 1+TP+ALB+AST+ALT+T-BIL+TG; 0.737, 260.642, 1+TP+ALB+AST+ALT+T-BIL+Glc; 0.735, 260.801, 1+TP+ALB+AST+ALT+T-BIL+BHBA; 0.738, 259.850, 1+TP+ALB+AST+ALT+NEFA+TCHO; 0.734, 261.215, 1+TP+ALB+AST+ALT+gGT+TCHO; 0.734, 261.825, 1+TP+ALB+AST+ALT+gGT+TG; 0.734, 261.864, 1+TP+ALB+AST+ALT+gGT+Glc; 0.735, 261.658, 1+TP+ALB+AST+ALT+gGT+BHBA; 0.735, 260.816, 1+TP+ALB+AST+ALT+gGT+T-BIL; 0.731, 261.455, 1+TP+ALB+Ca+ALT+TG+TCHO; 0.732, 261.036, 1+TP+ALB+Ca+ALT+T-BIL+TCHO;

0.732, 261.503, 1+TP+ALB+Ca+ALT+T-BIL+Gl c; 0.734, 260.702, 1+TP+ALB+Ca+ALT+NEFA+TCHO; 0.732, 261.547, 1+T P+ALB+Ca+ALT+gGT+TCHO; 0.729, 262.153, 1+TP+ALB+Ca+ALT+gGT+Gl c; 0.728, 266.424, 1+TP+ALB+Ca+AST+BHBA+Glc; 0.736, 263.106, 1+TP+ALB+Ca+AST+T-BIL+TCHO; 0.735, 264.008, 1+TP+ALB+Ca+AST+T-BIL+TG; 0.736, 263.544, 1+TP+ALB+Ca+AST+T-BIL+Glc; 0.734, 263.830, 1+TP+ALB+Ca AST+T-BIL+BHBA; 0.738, 262.164, 1+TP+ALB+Ca+AST+NEFA+TCHO; 0.739, 263.260, 1+TP+ALB+Ca+AST+NEFA+TG; 0.738, 263.197, 1+TP+ALB+Ca+AST+NEFA+Glc; 0.738, 263.338, 1+TP+ALB+Ca+AST+NEFA+BHBA; 0.739, 263.243, 1+TP+ALB+Ca+AST+NEFA+T-BIL; 0.729, 266.678, 1+TP+ALB+Ca+AST+gGT+BHBA; 0.734, 264.004, 1+TP+ALB+Ca+AST+gGT+T-BIL; 0.737, 263.255, 1+TP+ALB+Ca+AST+gGT+NEFA; 0.734, 261.028, 1+TP+ALB+Ca+AST+ALT+TCHO; 0.734, 261.619, 1+TP+ALB+Ca+AST+ALT+TG; 0.734, 261.601, 1+TP+ALB+Ca+AST+ALT+Glc; 0.734, 260.698, 1+TP+ALB+Ca+AST+ALT+T-BIL; 0.734, 261.695, 1+TP+ALB+Ca+AST+ALT+gG T; 0.739, 262.502, 1+TP+ALB+BUN+NEFA+T-BIL+TG; 0.745, 257.991, 1+TP+ALB+BUN+ALT+TG+TCHO; 0.746, 257.990, 1+TP+ALB+BUN+ALT+Glc+T CHO; 0.745, 258.508, 1+TP+ALB+BUN+ALT+Glc+TG; 0.746, 257.712, 1+T P+ALB+BUN+ALT+BHBA+TCHO; 0.747, 258.193, 1+TP+ALB+BUN+ALT+BHBA+TG; 0.746, 258.160, 1+TP+ALB+BUN+ALT+BHBA+Glc; 0.746, 257.240, 1+TP+ALB+BUN+ALT+T-BIL+TCHO; 0.748, 257.685, 1+TP+ALB+BUN+ALT+T-BIL+TG; 0.748, 257.689, 1+TP+ALB+BUN+ALT+T-BIL+Glc; 0.747, 257. 727, 1+TP+ALB+BUN+ALT+T-BIL+BHBA; 0.747, 257.556, 1+TP+ALB+BUN+ALT+NEFA+TCHO; 0.749, 258.084, 1+TP+ALB+BUN+ALT+NEFA+TG; 0.748, 258.112, 1+TP+ALB+BUN+ALT+NEFA+Glc; 0.748, 257.712, 1+TP+ALB+BU N+ALT+NEFA+T-BIL; 0.745, 258.009, 1+TP+ALB+BUN+ALT+gGT+TCHO; 0. 745, 258.509, 1+TP+ALB+BUN+ALT+gGT+TG; 0.745, 258.513, 1+TP+ALB+BUN+ALT+gGT+Glc; 0.746, 258.193, 1+TP+ALB+BUN+ALT+gGT+BHBA; 0.7 47, 257.729, 1+TP+ALB+BUN+ALT+gGT+T-BIL; 0.748, 258.118, 1+TP+AL B+BUN+ALT+gGT+NEFA; 0.731, 261.938, 1+TP+ALB+BUN+AST+Glc+TCHO; 0.733, 261.643, 1+TP+ALB+BUN+AST+BHBA+TCHO; 0.733, 262.173, 1+TP+ALB+BUN+AST+BHBA+TG; 0.733, 262.209, 1+TP+ALB+BUN+AST+BHBA+Gl c; 0.740, 259.071, 1+TP+ALB+BUN+AST+T-BIL+TCHO; 0.742, 259.607, 1+TP+ALB+BUN+AST+T-BIL+TG; 0.741, 259.518, 1+TP+ALB+BUN+AST+T-B IL+Glc; 0.741, 259.654, 1+TP+ALB+BUN+AST+T-BIL+BHBA; 0.740, 259. 479, 1+TP+ALB+BUN+AST+NEFA+TCHO; 0.742, 260.251, 1+TP+ALB+BUN+A ST+NEFA+TG; 0.740, 260.322, 1+TP+ALB+BUN+AST+NEFA+Glc; 0.739, 26 0.249, 1+TP+ALB+BUN+AST+NEFA+BHBA; 0.741, 259.640, 1+TP+ALB+BUN+AST+NEFA+T-BIL; 0.732, 262.730, 1+TP+ALB+BUN+AST+gGT+Glc; 0.73 6, 262.274, 1+TP+ALB+BUN+AST+gGT+BHBA; 0.741, 259.640, 1+TP+ALB+BUN+AST+gGT+T-BIL; 0.741, 260.239, 1+TP+ALB+BUN+AST+gGT+NEFA; 0. 745, 257.672, 1+TP+ALB+BUN+AST+ALT+TCHO; 0.745, 258.148, 1+TP+AL B+BUN+AST+ALT+TG; 0.745, 258.150, 1+TP+ALB+BUN+AST+ALT+Glc; 0.7 46, 257.767, 1+TP+ALB+BUN+AST+ALT+BHBA; 0.747, 257.009, 1+TP+ALB+BUN+AST+ALT+T-BIL; 0.747, 257.515, 1+TP+ALB+BUN+AST+ALT+NEFA; 0.746, 258.129, 1+TP+ALB+BUN+AST+ALT+gGT; 0.746, 257.741, 1+TP+A LB+BUN+Ca+ALT+TCHO; 0.746, 258.215, 1+TP+ALB+BUN+Ca+ALT+TG; 0.7 45, 258.194, 1+TP+ALB+BUN+Ca+ALT+Glc; 0.745, 258.226, 1+TP+ALB+B UN+Ca+ALT+gGT; 0.730, 261.853, 1+TP+ALB+BUN+Ca+AST+TCHO; 0.731, 262.472, 1+TP+ALB+BUN+Ca+AST+Glc; 0.735, 262.146, 1+TP+ALB+BUN+Ca+AST+BHBA; 0.740, 259.562, 1+TP+ALB+BUN+Ca+AST+T-BIL; 0.740, 2 60.218, 1+TP+ALB+BUN+Ca+AST+NEFA; 0.734, 262.541, 1+TP+ALB+BUN+Ca+AST+gGT; 0.745, 257.895, 1+TP+ALB+BUN+Ca+AST+ALT

[411. Formula (with Two Amino Acid+Biochemistry Variables) with Improved Diagnostic Accuracy by Added Parity Term]

0.751, 250.928, 1+Lys+ALB; 0.748, 251.463, 1+Trp+ALB; 0.746, 251.9 28, 1+ALB+Orn; 0.743, 252.614, 1+Arg+ALB; 0.736, 256.166, 1+Phe+AL B; 0.733, 255.023, 1+ALB+Val; 0.731, 254.610, 1+ALB+ALT; 0.730, 257. 214, 1+Thr+ALB; 0.730, 256.539, 1+ALB+Cit; 0.729, 257.132, 1+ALB+B UN; 0.729, 259.247, 1+ALB+AST; 0.728, 256.102, 1+ALB+BCAA; 0.728, 2 57.315, 1+ALB+Pro; 0.726, 259.148, 1+ALB+NEFA; 0.726, 256.753, 1+A LB+Leu; 0.724, 257.277, 1+ALB+Tyr; 0.723, 258.818, 1+ALB+Met; 0.72 3, 259.905, 1+ALB+Gly; 0.722, 258.383, 1+ALB+Ile; 0.720, 259.937, 1+ALB+3MeHis; 0.718, 260.087, 1+ALB+T-BIL; 0.717, 256.888, 1+ALB+A sp; 0.716, 261.875, 1+ALB+gGT; 0.716, 261.000, 1+ALB+Gln; 0.714, 26 1.615, 1+ALB+His; 0.713, 261.534, 1+ALB+Ser; 0.713, 262.083, 1+ALB+BHBA; 0.711, 262.141, 1+ALB+Ca; 0.707, 262.275, 1+ALB+Glc

[412. Formula (with Three Amino Acid+Biochemistry Variables) with Improved Diagnostic Accuracy by Added Parity Term]

0.766, 248.802, 1+ALB+Cit+Trp; 0.765, 247.923, 1+Lys+ALB+BUN; 0.7 64, 248.646, 1+ALB+BUN+Trp; 0.759, 247.974, 1+Arg+ALT+ALB; 0.759, 247.457, 1+ALB+ALT+Lys; 0.757, 252.122, 1+ALB+Cys+Lys; 0.757, 250. 503, 1+ALB+Lys+Trp; 0.757, 250.672, 1+ALB+3MeHis+Lys; 0.756, 250. 224, 1+ALB+AST+Lys; 0.756, 249.022, 1+ALB+ALT+Orn; 0.756, 250.642, 1+ALB+AST+Orn; 0.756, 250.202, 1+Trp+AST+ALB; 0.756, 251.172, 1+A LB+BUN+Phe; 0.756, 252.160, 1+Gly+Trp+ALB; 0.755, 250.883, 1+ALB+Orn+Trp; 0.755, 251.288, 1+ALB+NEFA+Lys; 0.755, 251.184, 1+ALB+BU N+Orn; 0.754, 250.863, 1+ALB+Arg+Trp; 0.754, 251.609, 1+Lys+His+A LB; 0.754, 251.897, 1+ALB+Orn+Lys; 0.753, 255.172, 1+Gly+Phe+ALB; 0.752, 252.805, 1+ALB+Phe+Trp; 0.752, 251.356, 1+Lys+TCHO+ALB; 0. 752, 251.446, 1+ALB+AST+Arg; 0.752, 252.955, 1+Trp+Glc+ALB; 0.752, 252.970, 1+Ala+Trp+ALB; 0.752, 251.464, 1+ALB+BUN+Arg; 0.751, 252. 904, 1+Lys+ALB+TP; 0.751, 251.848, 1+Arg+Lys+ALB; 0.751, 253.077, 1+ALB+Orn+Phe; 0.751, 252.454, 1+Lys+Glc+ALB; 0.751, 252.751, 1+L ys+TG+ALB; 0.751, 252.928, 1+Lys+Tyr+ALB; 0.751, 252.928, 1+Ala+L ys+ALB; 0.751, 252.757, 1+Lys+gGT+ALB; 0.750, 250.939, 1+ALB+Asp+Lys; 0.750, 252.897, 1+ALB+Lys+Phe; 0.750, 252.905, 1+Lys+Thr+AL B; 0.750, 252.910, 1+BCAA+Lys+ALB; 0.750, 252.927, 1+Trp+His+ALB; 0.750, 252.528, 1+ALB+3MeHis+Orn; 0.750, 251.740, 1+ALB+3MeHis+A rg; 0.750, 252.842, 1+ALB+Lys+Val; 0.749, 250.838, 1+ALB+Asp+Trp; 0.749, 252.958, 1+ALB+Val+Trp; 0.749, 253.367, 1+Trp+ALB+TP; 0.74 9, 252.826, 1+Lys+ALB+Ca; 0.749, 252.335, 1+Trp+TCHO+ALB; 0.749, 2 52.885, 1+ALB+3MeHis+Trp; 0.749, 252.841, 1+Lys+ALB+BHBA; 0.749, 252.798, 1+ALB+Arg+Orn; 0.749, 253.298, 1+ALB+NEFA+Trp; 0.748, 25 3.430, 1+Trp+Thr+ALB; 0.748, 253.463, 1+Trp+ALB+BHBA; 0.748, 253. 312, 1+ALB+NEFA+Orn; 0.748, 253.176, 1+Arg+ALB+NEFA; 0.748, 253.3 94, 1+ALB+Tyr+Trp; 0.748, 253.359, 1+Trp+gGT+ALB; 0.747, 253.876, 1+Thr+ALB+BUN; 0.747, 253.425, 1+Trp+TG+ ALB; 0.746, 255.377, 1+Phe+ALB+NEFA; 0.746, 253.580, 1+Arg+His+ALB; 0.746, 253.369, 1+Trp+ALB+Ca; 0.746, 251.782, 1+BCAA+ALT+ALB; 0.746, 252.568, 1+Arg+ TCHO+ALB; 0.746, 253.940, 1+Arg+gGT+ALB; 0.745, 252.538, 1+ALB+BUN+ALT; 0.745, 255.200, 1+ALB+ 3MeHis+Phe; 0.744, 253.712, 1+ALB+Orn+Val; 0.744, 252.413, 1+ALB+Asp+Orn; 0.744, 253.841, 1+ALB+Orn+ Tyr; 0.744, 256.915, 1+Gly+Thr+ALB; 0.743, 253.271, 1+ALB+BUN+Val; 0.743, 254.502, 1+Arg+ALB+TP; 0.743, 254.187, 1+ALB+Arg+Phe; 0.743, 254.051, 1+Arg+ Thr+ALB; 0.743, 253.922, 1+BCAA+ALB+BUN; 0.743, 254.520, 1+Arg+Glc+ALB; 0.743, 254.614, 1+Arg+Tyr+ ALB; 0.743, 254.614, 1+Arg+ALB+BHBA; 0.742, 254.594, 1+Arg+TG+ALB; 0.742, 255.191, 1+Phe+AST+ ALB; 0.742, 254.525, 1+Ala+Arg+ALB; 0.742, 254.500, 1+Arg+ALB+Ca; 0.742, 253.589, 1+ALB+Arg+Val; 0.741, 254.230, 1+ALB+AST+Val; 0.741, 254.291, 1+Tyr+ALB+ BUN; 0.740, 253.554, 1+ALB+Arg+Asp; 0.740, 256.093, 1+Thr+AST+ALB; 0.740, 257.408, 1+ALB+AST+NEFA; 0.740, 254.253, 1+BCAA+Arg+ALB; 0.739, 255.195, 1+BCAA+AST+ALB; 0.738, 251.157, 1+ALB+ALT+Asp; 0.738, 258.458, 1+Gly+AST+ALB; 0.738, 256.311, 1+ALB+Val+Phe; 0.738, 257.677, 1+Phe+His+ALB; 0.737, 258.007, 1+Phe+Glc+ALB; 0.737, 253.422, 1+ALB+ BUN+Asp; 0.737, 256.736, 1+Gly+BCAA+ALB; 0.737, 256.229, 1+ALB+NEFA+Val; 0.736, 254.128, 1+ALB+ Asp+Val; 0.736, 257.476, 1+Thr+Phe+ALB; 0.736, 257.949, 1+Ala+Phe+ALB; 0.736, 257.933, 1+Phe+TG+ ALB; 0.736, 258.073, 1+Ala+Gly+ALB; 0.736, 256.025, 1+Phe+TCHO+ALB; 0.736, 257.014, 1+ALB+BUN+ NEFA; 0.736, 255.661, 1+His+ALT+ALB; 0.736, 257.427, 1+Thr+ALB+NEFA; 0.736, 257.231, 1+BCAA+Phe+ALB; 0.736, 256.252, 1+ALB+AST+Tyr; 0.735, 258.073, 1+Phe+ ALB+TP; 0.735, 257.415, 1+Gly+Tyr+ALB; 0.735, 256.239, 1+ALB+3MeHis+Val; 0.735, 257.963, 1+Phe+ ALB+BHBA; 0.735, 257.897, 1+ALB+Tyr+Phe; 0.735, 255.954, 1+ALB+AST+ALT; 0.734, 256.903, 1+BCAA+ ALB+NEFA; 0.734, 255.699, 1+ALB+ALT+NEFA; 0.734, 258.068, 1+Phe+ALB+Ca; 0.734, 255.791, 1+ALB+AST+ Asp; 0.734, 257.811, 1+Phe+gGT+ALB; 0.733, 255.498, 1+Gly+ALT+ALB; 0.733, 255.585, 1+ALB+Asp+Phe; 0.733, 257.163, 1+BCAA+His+ALB; 0.733, 257.942, 1+Gly+ALB+BUN; 0.733, 256.798, 1+ALB+BUN+AST; 0.732, 255.771, 1+ALB+ALT+3MeHis; 0.732, 258.521, 1+Thr+Glc+ALB; 0.731, 257.725, 1+ALB+BUN+3MeHis; 0.731, 256.871, 1+ALB+Tyr+Val; 0.731, 257.115, 1+ALB+ 3MeHis+Tyr; 0.731, 258.965, 1+ALB+AST+3MeHis; 0.731, 256.106, 1+BCAA+TCHO+ALB; 0.730, 258.780, 1+Thr+gGT+ALB; 0.730, 259.168, 1+Thr+ALB+BHBA; 0.730, 257.987, 1+ALB+NEFA+Tyr; 0.730, 259.915, 1+His+AST+ALB; 0.730, 257.870, 1+Thr+TCHO+ALB; 0.730, 258.898, 1+Thr+His+ALB; 0.730, 259.151, 1+Thr+ALB+ TP; 0.730, 258.553, 1+His+ALB+BUN; 0.730, 259.064, 1+Ala+AST+ALB; 0.730, 257.777, 1+BCAA+Thr+ALB; 0.730, 257.823, 1+BCAA+Glc+ALB; 0.729, 257.851, 1+Ala+BCAA+ALB; 0.729, 253.873, 1+ALB+3MeHis+ Asp; 0.728, 257.885, 1+BCAA+Tyr+ALB; 0.728, 259.108, 1+Thr+ALB+Ca; 0.728, 258.814, 1+Thr+TG+ALB; 0.728, 257.839, 1+BCAA+ALB+BHBA; 0.728, 258.192, 1+Thr+ Tyr+ALB; 0.728, 258.066, 1+BCAA+ALB+TP; 0.728, 256.142, 1+ALB+NEFA+Asp; 0.728, 257.847, 1+BCAA+ gGT+ALB; 0.727, 261.166, 1+Gly+His+ALB; 0.727, 258.024, 1+BCAA+ALB+Ca; 0.727, 257.975, 1+BCAA+TG+ ALB; 0.726, 260.773, 1+Gly+ALB+NEFA; 0.725, 259.215, 1+Tyr+Glc+ALB; 0.725, 259.030, 1+Ala+Tyr+ALB; 0.725, 260.931, 1+His+ALB+NEFA; 0.725, 260.412, 1+ALB+ NEFA+3MeHis; 0.725, 261.822, 1+Gly+ALB+TP; 0.724, 256.804, 1+Tyr+TCHO+ALB; 0.724, 261.763, 1+Gly+Glc+ ALB; 0.724, 259.212, 1+Tyr+ALB+TP; 0.724, 258.970, 1+Tyr+gGT+ALB; 0.724, 256.803, 1+ALB+Asp+Tyr; 0.724, 261.628, 1+Gly+gGT+ALB; 0.723, 259.063, 1+Tyr+ His+ALB; 0.723, 259.223, 1+Tyr+TG+ALB; 0.723, 261.768, 1+Gly+TG+ALB; 0.723, 261.705, 1+Gly+ALB+ BHBA; 0.722, 259.180, 1+Tyr+ALB+BHBA; 0.722, 259.183, 1+Tyr+ALB+Ca; 0.721, 261.715, 1+Gly+ALB+ Ca; 0.721, 259.584, 1+Gly+TCHO+ALB; 0.720, 263.048, 1+His+gGT+ALB; 0.719, 261.445, 1+Ala+gGT+ALB; 0.717, 261.466, 1+His+TCHO+ALB; 0.717, 260.175, 1+Ala+TCHO+ALB; 0.715, 263.435, 1+His+ALB+TP; 0.714, 263.507, 1+His+Glc+ALB; 0.714, 261.737, 1+Ala+ ALB+TP; 0.714, 263.206, 1+His+TG+ALB; 0.714, 263.439, 1+His+ALB+BHBA; 0.713, 263.421, 1+His+ALB+Ca

[413. Formula (with Four Amino Acid+Biochemistry Variables) with Improved Diagnostic Accuracy by Added Parity Term]

0.771, 247.738, 1+ALB+BUN+Lys+Trp; 0.770, 247.390, 1+ALB+BUN+ALT+Trp; 0.770, 248.325, 1+ALB+BUN+ His+Lys; 0.770, 249.074, 1+ALB+BUN+Lys+Ile; 0.769, 249.248, 1+ALB+BUN+Phe+Trp; 0.769, 249.244, 1+Ala+Trp+ALB+BUN; 0.768, 245.692, 1+ALB+BUN+ALT+ Lys; 0.768, 248.927, 1+Gly+Lys+ALB+BUN; 0.767, 247.744, 1+ALB+BUN+Asp+Trp; 0.767, 249.512, 1+ALB+BUN+Lys+Phe; 0.767, 248.133, 1+Trp+Arg+ ALT+ALB; 0.767, 248.133, 1+ALB+ALT+Arg+Trp; 0.767, 247.638, 1+ALB+BUN+Asp+Lys; 0.766, 248.645, 1+ALB+BUN+3MeHis+Lys; 0.766, 249.064, 1+ALB+B UN+NEFA+Lys; 0.766, 249.156, 1+ALB+BUN+Arg+Trp; 0.766, 249.030, 1+ALB+BUN+T-BIL+Lys; 0.766, 249.916, 1+ALB+BUN+Lys+Val; 0.766, 247.745, 1+ALB+BUN+ ALT+Arg; 0.766, 249.689, 1+Ala+Lys+ALB+BUN; 0.766, 248.949, 1+Lys+TCHO+ALB+BUN; 0.766, 249.982, 1+Trp+His+ALB+BUN; 0.766, 249.594, 1+Gly+Lys+ AST+ALB; 0.765, 249.087, 1+ALB+ALT+Orn+Trp; 0.765, 249.632, 1+ALB+BUN+Arg+Lys; 0.765, 249.760, 1+BCAA+Lys+ALB+BUN; 0.765, 250.424, 1+Trp+Glc+ALB+ BUN; 0.765, 250.181, 1+Gly+Trp+ALB+BUN; 0.765, 250.425, 1+Trp+ALB+BUN+TP; 0.765, 249.933, 1+Trp+ TCHO+ALB+BUN; 0.765, 249.919, 1+ALB+BUN+Lys+ Tyr; 0.765, 248.419, 1+Gly+Lys+ALT+ALB; 0.765, 249.803, 1+ALB+BUN+Orn+Lys; 0.765, 249.914, 1+ALB+BUN+Thr+Lys; 0.765, 248.448, 1+ALB+BUN+A ST+Trp; 0.764, 250.342, 1+Trp+Lys+His+ALB; 0.764, 249.738, 1+ALB+BUN+BHBA+Lys; 0.764, 250.600, 1+ALB+BUN+Tyr+Trp; 0.764, 250.298, 1+Gly+Phe+ ALT+ALB; 0.764, 250.641, 1+Trp+TG+ALB+BUN; 0.764, 248.598, 1+Gly+Arg+ALT+ALB; 0.764, 250.843, 1+Gly+ Trp+Lys+ALB; 0.764, 249.873, 1+Gly+Arg+AST+ALB; 0.764, 249.425, 1+ALB+BUN+Orn+Trp; 0.764, 250.593, 1+Trp+Thr+ALB+BUN; 0.764, 252.477, 1+Gly+BCAA+ Lys+ALB; 0.764, 248.178, 1+ALB+BUN+AST+Lys; 0.764, 248.243, 1+ALB+ALT+Lys+Trp; 0.764, 249.893, 1+Lys+ TG+ALB+BUN; 0.763, 251.074, 1+ALB+BUN+Orn+Phe; 0.763, 249.691, 1+ALB+BUN+Glc+Lys; 0.763, 249.867, 1+ALB+BUN+gGT+Lys; 0.763, 250.597, 1+Trp+ALB+ BUN+BHBA; 0.763, 249.812, 1+Lys+ALB+BUN+TP; 0.763, 250.636, 1+Trp+ALB+BUN+NEFA; 0.763, 249.834, 1+ALB+BUN+Ca+Lys; 0.763, 250.622, 1+Trp+ gGT+ALB+BUN; 0.763, 251.423, 1+Gly+Lys+His+ALB; 0.763, 250.443, 1+ALB+BUN+3MeHis+Trp; 0.763, 249.748, 1+ALB+ALT+Arg+Ile; 0.763, 250.633, 1+B CAA+Trp+ALB+BUN; 0.763, 251.750, 1+Gly+Phe+ALB+ BUN; 0.763, 250.549, 1+ALB+BUN+Val+Trp; 0.763, 250.553, 1+Trp+ALB+BUN+Ca; 0.763, 2 50.858, 1+Gly+Trp+Arg+ALB; 0.763, 250.898, 1+Trp+Glc+ALT+ALB; 0. 762, 248.594, 1+ALB+ALT+3MeHis+Lys; 0.762, 252.155, 1+Gly+Lys+Gl c+ALB; 0.762, 252.459, 1+Ala+Gly+Lys+ALB; 0.762, 250.499, 1+Trp+A rg+His+ALB; 0.762, 251.990, 1+Phe+His+ALB+BUN; 0.762, 249.709, 1+ALB+AST+Lys+Trp; 0.762, 248.185, 1+ALB+ALT+Arg+Lys; 0.762, 252.9 10, 1+Ala+Gly+Trp+ALB; 0.762, 249.674, 1+ALB+AST+Arg+Trp; 0.762, 249.051, 1+ALB+AST+ALT+Arg; 0.762, 250.619, 1+Gly+Trp+AST+ALB; 0. 762, 251.475, 1+ALB+BUN+3MeHis+Phe; 0.762, 248.983, 1+ALB+ALT+Ly s+Phe; 0.762, 252.579, 1+Gly+Lys+Phe+ALB; 0.762, 248.965, 1+ALB+A LT+Orn+Lys; 0.761, 248.678, 1+ALB+ALT+His+Lys; 0.761, 252.676, 1+Gly+Lys+Tyr+ALB; 0.761, 253.118, 1+Gly+Trp+Phe+ALB; 0.761, 249.2 93, 1+ALB+ALT+Arg+Orn; 0.761, 248.949, 1+ALB+ALT+3MeHis+Arg; 0.7 61, 250.201, 1+ALB+AST+NEFA+Lys; 0.761, 251.694, 1+ALB+BUN+NEFA+Phe; 0.761, 251.228, 1+Gly+Arg+Lys+ALB; 0.761, 248.604, 1+ALB+ALT+Lys+Ile; 0.761, 252.672, 1+Gly+Lys+Thr+ALB; 0.761, 249.586, 1+AL B+AST+Orn+Trp; 0.761, 251.821, 1+Arg+Phe+ALB+BUN; 0.761, 248.838, 1+ALB+BUN+ALT+Orn; 0.761, 249.165, 1+ALB+ALT+NEFA+Lys; 0.761, 25 1.084, 1+Trp+Thr+ALT+ALB; 0.760, 251.850, 1+BCAA+Trp+Lys+ALB; 0. 760, 252.129, 1+Trp+Lys+Tyr+ALB; 0.760, 250.813, 1+Gly+Lys+TCHO+ALB; 0.760, 251.265, 1+Trp+ALT+gGT+ALB; 0.760, 250.774, 1+ALB+ALT+Val+Trp; 0.760, 249.305, 1+Arg+TCHO+ALT+ALB; 0.760, 249.853, 1+A LB+ALT+NEFA+Arg; 0.760, 249.833, 1+ALB+ALT+gGT+Arg; 0.760, 252.6 16, 1+Gly+Lys+ALB+TP; 0.760, 249.970, 1+ALB+ALT+Arg+Tyr; 0.760, 2 50.967, 1+BCAA+Trp+ALT+ALB; 0.760, 248.783, 1+Lys+TCHO+ALT+ALB; 0.760, 250.636, 1+Gly+Trp+ALT+ALB; 0.760, 251.311, 1+ALB+3MeHis+Lys+Trp; 0.760, 249.137, 1+ALB+ALT+Glc+Lys; 0.760, 249.004, 1+ALB+3MeHis+Asp+Lys; 0.760, 249.952, 1+Arg+ALT+ALB+TP; 0.760, 251.24 8, 1+Trp+TG+ALT+ALB; 0.760, 251.867, 1+Trp+Lys+Thr+ALB; 0.760, 24 9.257, 1+ALB+ALT+His+Arg; 0.760, 251.260, 1+Trp+ALT+ALB+BHBA; 0. 760, 249.966, 1+ALB+ALT+BHBA+Arg; 0.760, 252.693, 1+Gly+Lys+TG+A LB; 0.760, 252.869, 1+Thr+Phe+ALB+BUN; 0.760, 247.164, 1+ALB+ALT+Asp+Lys; 0.759, 249.974, 1+ALB+ALT+T-BIL+Arg; 0.759, 251.933, 1+T rp+Lys+Glc+ALB; 0.759, 249.380, 1+ALB+ALT+T-BIL+Lys; 0.759, 251. 457, 1+ALB+AST+His+Lys; 0.759, 251.250, 1+Trp+ALT+ALB+NEFA; 0.75 9, 249.610, 1+ALB+ALT+Arg+Val; 0.759, 251.099, 1+Trp+His+ALT+AL B; 0.759, 250.021, 1+ALB+ALT+His+Orn; 0.759, 249.940, 1+Ala+Arg+A LT+ALB; 0.759, 253.626, 1+Gly+Trp+Glc+ALB; 0.759, 252.466, 1+ALB+AST+Orn+Ile; 0.759, 252.533, 1+Ala+Phe+ALB+BUN; 0.759, 250.984, 1+Trp+Tyr+ALT+ALB; 0.759, 252.658, 1+Gly+Lys+ALB+BHBA; 0.759, 251. 392, 1+Lys+His+ALB+NEFA; 0.759, 249.907, 1+ALB+ALT+Glc+Arg; 0.75 9, 251.568, 1+Arg+Lys+His+ALB; 0.759, 251.312, 1+ALB+AST+His+Or n; 0.759, 249.401, 1+ALB+ALT+BHBA+Lys; 0.759, 249.453, 1+Ala+Lys+ALT+ALB; 0.759, 249.941, 1+Trp+ALT+AST+ALB; 0.759, 251.470, 1+Trp+Arg+TCHO+ALB; 0.759, 248.170, 1+ALB+ALT+Asp+Trp; 0.759, 252.468, 1+Gly+Lys+ALB+NEFA; 0.759, 252.636, 1+Gly+Lys+gGT+ALB; 0.759, 24 9.450, 1+Lys+TG+ALT+ALB; 0.759, 249.453, 1+ALB+ALT+Lys+Val; 0.75 9, 248.647, 1+ALB+ALT+Arg+Asp; 0.759, 251.900, 1+Trp+Arg+Lys+AL B; 0.759, 251.832, 1+Phe+TCHO+ALB+BUN; 0.759, 251.024, 1+ALB+AST+Arg+Lys; 0.759, 250.694, 1+Trp+TCHO+ALT+ALB; 0.759, 249.446, 1+AL B+ALT+Lys+Tyr; 0.759, 249.879, 1+Arg+TG+ALT+ALB; 0.758, 249.866, 1+BCAA+Arg+ALT+ALB; 0.758, 249.456, 1+ALB+ALT+Thr+Lys; 0.758, 25 1.007, 1+ALB+AST+Orn+Lys; 0.758, 251.306, 1+ALB+3MeHis+Arg+Lys; 0.758, 252.346, 1+Trp+Lys+ALB+TP; 0.758, 251.429, 1+ALB+AST+Lys+Ile; 0.758, 252.892, 1+Ala+Gly+Arg+ALB; 0.758, 252.071, 1+ALB+AST+T-BIL+Orn; 0.758, 252.570, 1+Gly+Lys+ALB+Ca; 0.758, 254.027, 1+G ly+Trp+ALB+NEFA; 0.758, 249.452, 1+ALB+ALT+gGT+Lys; 0.758, 251.6 67, 1+ALB+AST+NEFA+Orn; 0.758, 248.626, 1+ALB+AST+ALT+Lys; 0.758, 251.316, 1+Trp+Lys+TCHO+ALB; 0.758, 249.867, 1+ALB+Ca+ALT+Arg; 0. 758, 251.228, 1+Trp+ALT+ALB+Ca; 0.758, 254.013, 1+Gly+Trp+ALB+T P; 0.758, 250.237, 1+ALB+AST+3MeHis+Lys; 0.758, 252.032, 1+Trp+Ly s+ALB+NEFA; 0.758, 250.984, 1+ALB+AST+T-BIL+Lys; 0.758, 249.417, 1+BCAA+Lys+ALT+ALB; 0.758, 251.655, 1+Ala+Trp+AST+ALB; 0.758, 25 1.746, 1+Trp+Glc+AST+ALB; 0.758, 252.053, 1+ALB+3MeHis+Orn+Lys; 0.758, 252.498, 1+Trp+Lys+ALB+BHBA; 0.758, 251.566, 1+ALB+AST+Ar g+Orn; 0.757, 251.215, 1+Phe+AST+ALB+BUN; 0.757, 252.483, 1+ALB+A ST+Thr+Orn; 0.757, 250.609, 1+ALB+ALT+3MeHis+Orn; 0.757, 252.968, 1+Gly+Arg+Phe+ALB; 0.757, 251.985, 1+Trp+AST+ALB+TP; 0.757, 253. 121, 1+Phe+Glc+ALB+BUN; 0.757, 253.245, 1+Lys+Phe+His+ALB; 0.757, 250.743, 1+ALB+BUN+AST+Orn; 0.757, 252.523, 1+Trp+Arg+Glc+ALB; 0. 757, 252.193, 1+ALB+AST+Lys+Phe; 0.757, 251.509, 1+Lys+TCHO+ALB+NEFA; 0.757, 252.542, 1+ALB+3MeHis+Lys+Phe; 0.757, 252.500, 1+Ala+Trp+Lys+ALB; 0.757, 252.135, 1+Lys+AST+ALB+TP; 0.757, 251.379, 1+Lys+TCHO+AST+ALB; 0.757, 256.297, 1+Ala+Gly+Phe+ALB; 0.757, 252. 392, 1+ALB+AST+Glc+Orn; 0.757, 252.478, 1+Trp+Lys+Phe+ALB; 0.757, 251.127, 1+Arg+AST+ALB+BUN; 0.757, 252.632, 1+ALB+AST+BHBA+Orn; 0.757, 251.462, 1+Arg+AST+ALB+NEFA; 0.756, 250.460, 1+ALB+BUN+AL T+Val; 0.756, 252.146, 1+Lys+TG+AST+ALB; 0.756, 251.980, 1+Trp+Hi s+AST+ALB; 0.756, 252.223, 1+Ala+Lys+AST+ALB; 0.756, 249.420, 1+A LB+Ca+ALT+Lys; 0.756, 254.085, 1+Gly+Trp+Thr+ALB; 0.756, 251.968, 1+ALB+AST+Orn+Phe; 0.756, 249.779, 1+ALB+AST+ALT+Orn; 0.756, 249. 011, 1+ALB+ALT+Asp+Orn; 0.756, 252.451, 1+Trp+Lys+TG+ALB; 0.756, 252.751, 1+Lys+Glc+ALB+NEFA; 0.756, 252.624, 1+ALB+AST+gGT+Orn; 0.756, 252.163, 1+Trp+AST+ALB+BHBA; 0.756, 253.134, 1+BCAA+Phe+A LB+BUN; 0.756, 254.154, 1+Gly+Trp+TG+ALB; 0.756, 253.049, 1+BCAA+Lys+ALB+NEFA; 0.756, 252.164, 1+ALB+AST+Lys+Val; 0.756, 253.168, 1+Phe+ALB+BUN+TP; 0.756, 250.751, 1+ALB+ALT+Thr+Orn; 0.756, 254. 082, 1+Gly+BCAA+Trp+ALB; 0.756, 254.153, 1+Gly+Trp+ALB+BHBA; 0.7 56, 253.487, 1+Lys+His+ALB+TP; 0.756, 253.536, 1+Lys+Thr+His+AL B; 0.756, 251.828, 1+Trp+AST+ALB+NEFA; 0.756, 251.451, 1+ALB+AST+3MeHis+Orn; 0.756, 252.199, 1+BCAA+Lys+AST+ALB; 0.756, 252.223, 1+Lys+Tyr+AST+ALB; 0.756, 253.151, 1+Phe+TG+ALB+BUN; 0.756, 252.4 38, 1+Trp+Lys+gGT+ALB; 0.756, 252.202, 1+Trp+TG+AST+ALB; 0.756, 2 51.178, 1+Gly+Arg+TCHO+ALB; 0.756, 254.506, 1+Ala+Trp+Glc+ALB; 0. 756, 251.725, 1+Trp+Phe+AST+ALB; 0.756, 253.809, 1+Ala+Trp+His+A LB; 0.756, 252.176, 1+Trp+Thr+AST+ALB; 0.756, 253.172, 1+Phe+Tyr+ALB+BUN; 0.756, 253.516, 1+Ala+Lys+His+ALB; 0.756, 253.773, 1+Gly+Phe+AST+ALB; 0.755, 252.208, 1+Lys+Thr+AST+ALB; 0.755, 253.276, 1+Lys+TG+ALB+NEFA; 0.755, 252.832, 1+Ala+Trp+Arg+ALB; 0.755, 253. 160, 1+Lys+ALB+TP+NEFA; 0.755, 252.068, 1+ALB+AST+BHBA+Lys; 0.75 5, 253.443, 1+BCAA+Lys+His+ALB; 0.755, 251.644, 1+Trp+

TCHO+AST+A LB; 0.755, 252.508, 1+Arg+Lys+ALB+NEFA; 0.755, 252.983, 1+Phe+gGT+ALB+BUN; 0.755, 252.500, 1+Arg+Thr+ALB+BUN; 0.755, 252.192, 1+Lys+AST+gGT+ALB; 0.755, 251.566, 1+Gly+Arg+ALB+BUN; 0.755, 253.238, 1+Lys+ALB+NEFA+BHBA; 0.755, 253.398, 1+Gly+Arg+TG+ALB; 0.755, 25 3.100, 1+Gly+Arg+Thr+ALB; 0.755, 252.920, 1+Lys+His+Glc+ALB; 0.755, 254.120, 1+Gly+Trp+gGT+ALB; 0.755, 252.709, 1+BCAA+Trp+Arg+A LB; 0.755, 251.729, 1+Lys+Glc+AST+ALB; 0.755, 252.154, 1+Trp+Tyr+AST+ALB; 0.755, 254.061, 1+Gly+Trp+ALB+Ca; 0.755, 250.151, 1+ALB+AST+Asp+Lys; 0.755, 252.086, 1+Trp+AST+gGT+ALB; 0.755, 250.631, 1+BCAA+ALT+ALB+BUN; 0.755, 254.618, 1+Ala+Trp+Phe+ALB; 0.755, 252. 770, 1+Trp+Arg+Thr+ALB; 0.755, 252.349, 1+Trp+Lys+ALB+Ca; 0.755, 252.612, 1+ALB+Ca+AST+Orn; 0.754, 252.841, 1+Trp+Arg+ALB+TP; 0.7 54, 252.107, 1+BCAA+Trp+AST+ALB; 0.754, 253.275, 1+Ala+Lys+ALB+N EFA; 0.754, 252.124, 1+Trp+AST+ALB+Ca; 0.754, 253.478, 1+Trp+Glc+TCHO+ALB; 0.754, 253.195, 1+Lys+Thr+ALB+NEFA; 0.754, 253.793, 1+A la+Trp+TCHO+ALB; 0.754, 252.044, 1+Arg+TCHO+ALB+BUN; 0.754, 252. 863, 1+Trp+Arg+TG+ALB; 0.754, 252.611, 1+Trp+Arg+gGT+ALB; 0.754, 252.435, 1+Lys+Glc+TCHO+ALB; 0.754, 252.817, 1+Ala+Arg+ALB+BUN; 0.754, 252.129, 1+Lys+AST+ALB+Ca; 0.754, 253.235, 1+Lys+gGT+ALB+NEFA; 0.754, 252.780, 1+Gly+Trp+TCHO+ALB; 0.753, 253.028, 1+Arg+g GT+ALB+BUN; 0.753, 253.140, 1+Gly+Arg+gGT+ALB; 0.753, 254.733, 1+Ala+Trp+ALB+NEFA; 0.753, 253.352, 1+Gly+Arg+Glc+ALB; 0.753, 253. 480, 1+Gly+BCAA+Arg+ALB; 0.753, 252.121, 1+Arg+Lys+TCHO+ALB; 0.7 53, 253.679, 1+BCAA+Arg+Lys+ALB; 0.753, 253.391, 1+Arg+AST+ALB+T P; 0.753, 252.396, 1+Arg+TCHO+AST+ALB; 0.753, 253.491, 1+Lys+His+gGT+ALB; 0.753, 253.420, 1+Arg+AST+gGT+ALB; 0.753, 254.803, 1+BCA A+Trp+Glc+ALB; 0.753, 253.445, 1+Arg+TG+AST+ALB; 0.752, 253.259, 1+Lys+Thr+TCHO+ALB; 0.752, 253.348, 1+BCAA+Lys+TCHO+ALB; 0.752, 253.402, 1+Arg+AST+ALB+BHBA; 0.752, 252.918, 1+Arg+Thr+AST+ALB; 0.752, 253.330, 1+Lys+TCHO+ALB+TP; 0.752, 253.539, 1+Arg+Lys+Glc+ALB; 0.752, 253.800, 1+Arg+Lys+Thr+ALB; 0.752, 254.762, 1+Trp+Gl c+ALB+NEFA; 0.752, 253.354, 1+Ala+Arg+AST+ALB; 0.752, 254.902, 1+Trp+Glc+ALB+TP; 0.752, 254.847, 1+Trp+Thr+Glc+ALB; 0.752, 254.96 9, 1+Ala+Trp+Tyr+ALB; 0.752, 254.694, 1+Lys+gGT+ALB+TP; 0.752, 25 4.936, 1+Ala+Trp+ALB+TP; 0.752, 253.453, 1+Arg+Glc+ALB+BUN; 0.75 2, 253.463, 1+Arg+TG+ALB+BUN; 0.752, 254.935, 1+Ala+BCAA+Trp+AL B; 0.752, 254.317, 1+Lys+Glc+TG+ALB; 0.752, 254.969, 1+Ala+Trp+AL B+BHBA; 0.752, 253.381, 1+Arg+Glc+AST+ALB; 0.752, 254.445, 1+Lys+Glc+ALB+TP; 0.752, 254.963, 1+Ala+Trp+Thr+ALB; 0.752, 253.355, 1+Ala+Lys+TCHO+ALB; 0.752, 254.627, 1+Lys+TG+gGT+ALB; 0.751, 254.8 79, 1+Lys+Phe+ALB+TP; 0.751, 254.717, 1+BCAA+Lys+TG+ALB; 0.751, 2 54.838, 1+BCAA+Lys+Phe+ALB; 0.751, 254.898, 1+Trp+Glc+ALB+BHBA; 0.751, 253.833, 1+Ala+Arg+Lys+ALB; 0.751, 254.904, 1+Lys+Tyr+ALB+TP; 0.751, 254.944, 1+Ala+Trp+TG+ALB; 0.751, 253.542, 1+Arg+Lys+gGT+ALB; 0.751, 254.867, 1+Gly+Thr+ALB+BUN; 0.751, 253.152, 1+Lys+ALB+Ca+NEFA; 0.751, 254.877, 1+Lys+Thr+ALB+TP; 0.751, 254.884, 1+BCAA+Lys+ALB+TP; 0.751, 254.903, 1+Ala+Lys+ALB+TP; 0.751, 254.7 17, 1+Lys+TG+ALB+TP; 0.751, 253.848, 1+Arg+Lys+ALB+TP; 0.751, 254. 736, 1+BCAA+Lys+gGT+ALB; 0.751, 254.432, 1+BCAA+Lys+Glc+ALB; 0.7 51, 253.305, 1+Lys+TCHO+gGT+ALB; 0.751, 254.453, 1+Lys+Thr+Glc+A LB; 0.751, 253.207, 1+BCAA+Arg+AST+ALB; 0.751, 254.928, 1+Ala+Lys+Tyr+ALB; 0.751, 254.851, 1+Ala+Trp+ALB+Ca; 0.751, 254.754, 1+Ala+Lys+gGT+ALB; 0.751, 254.229, 1+Lys+Glc+gGT+ALB; 0.751, 254.444, 1+Ala+Lys+Glc+ALB; 0.751, 254.055, 1+BCAA+Trp+TCHO+ALB; 0.751, 2 54.904, 1+Ala+Lys+Thr+ALB; 0.751, 254.924, 1+Trp+Glc+TG+ALB; 0.7 51, 254.751, 1+Ala+Lys+TG+ALB; 0.750, 254.910, 1+Ala+BCAA+Lys+AL B; 0.750, 253.172, 1+Lys+TCHO+TG+ALB; 0.750, 254.053, 1+Trp+TCHO+ALB+NEFA; 0.750, 254.237, 1+Trp+TCHO+ALB+TP; 0.750, 254.896, 1+Al a+Lys+Phe+ALB; 0.750, 254.791, 1+Lys+ALB+TP+BHBA; 0.750, 255.422, 1+Gly+Thr+AST+ALB; 0.750, 254.891, 1+Trp+Glc+ALB+Ca; 0.750, 253. 788, 1+Arg+Lys+TG+ALB; 0.750, 254.808, 1+Lys+ALB+TP+Ca; 0.750, 25 4.740, 1+Lys+Thr+gGT+ALB; 0.750, 254.809, 1+Ala+Trp+gGT+ALB; 0.7 50, 254.901, 1+BCAA+Lys+Thr+ALB; 0.750, 257.748, 1+Ala+Gly+Thr+A LB; 0.750, 254.733, 1+Lys+Thr+TG+ALB; 0.750, 255.257, 1+Trp+ALB+N EFA+BHBA; 0.749, 255.065, 1+Ala+Gly+ALB+BUN; 0.749, 254.844, 1+Th r+ALB+BUN+NEFA; 0.749, 254.803, 1+Trp+Glc+gGT+ALB; 0.749, 254.82 6, 1+Ala+Lys+ALB+Ca; 0.749, 254.333, 1+Trp+TCHO+ALB+BHBA; 0.749, 253.734, 1+Thr+AST+ALB+BUN; 0.749, 254.310, 1+Trp+TCHO+TG+ALB; 0. 749, 255.297, 1+Trp+TG+ALB+NEFA; 0.749, 255.319, 1+Trp+TG+ALB+T P; 0.749, 254.841, 1+Ala+Lys+ALB+BHBA; 0.748, 254.298, 1+Trp+TCHO+gGT+ALB; 0.748, 255.177, 1+Trp+ALB+TP+NEFA; 0.748, 255.472, 1+Th r+Glc+ALB+BUN; 0.748, 255.364, 1+Trp+ALB+TP+BHBA; 0.748, 254.220, 1+Trp+TCHO+ALB+Ca; 0.748, 255.286, 1+BCAA+Trp+Thr+ALB; 0.748, 25 5.282, 1+Trp+ALB+TP+Ca; 0.748, 255.213, 1+Trp+gGT+ALB+TP; 0.748, 255.201, 1+Trp+ALB+Ca+NEFA; 0.748, 255.130, 1+BCAA+Trp+ALB+NEF A; 0.748, 253.268, 1+Gly+BCAA+ALT+ALB; 0.748, 255.288, 1+BCAA+Trp+ALB+BHBA; 0.748, 255.217, 1+Trp+gGT+ALB+NEFA; 0.747, 255.208, 1+BCAA+Trp+ALB+TP; 0.747, 255.358, 1+Trp+gGT+ALB+BHBA; 0.747, 255. 194, 1+BCAA+Trp+gGT+ALB; 0.747, 253.665, 1+BCAA+ALT+ALB+NEFA; 0. 747, 255.201, 1+BCAA+Thr+ALB+BUN; 0.747, 253.626, 1+BCAA+Glc+ALT+ALB; 0.747, 255.262, 1+BCAA+Trp+TG+ALB; 0.747, 255.424, 1+Trp+TG+ALB+BHBA; 0.747, 255.337, 1+Trp+TG+gGT+ALB; 0.747, 252.952, 1+BC AA+TCHO+ALT+ALB; 0.746, 255.497, 1+Gly+BCAA+AST+ALB; 0.746, 253. 777, 1+BCAA+TG+ALT+ALB; 0.746, 253.636, 1+BCAA+ALT+ALB+BHBA; 0.7 46, 255.190, 1+BCAA+Trp+ALB+Ca; 0.746, 257.732, 1+Ala+Gly+BCAA+A LB; 0.746, 255.696, 1+Thr+TG+ALB+BUN; 0.746, 253.771, 1+BCAA+ALT+gGT+ALB; 0.746, 255.369, 1+Trp+ALB+Ca+BHBA; 0.746, 255.333, 1+Trp+TG+ALB+Ca; 0.746, 255.026, 1+Thr+TCHO+ALB+BUN; 0.746, 254.178, 1+Gly+ALT+ALB+BUN; 0.746, 253.043, 1+BCAA+ALT+AST+ALB; 0.746, 254. 904, 1+Ala+BCAA+ALB+BUN; 0.745, 255.260, 1+Trp+gGT+ALB+Ca; 0.745, 255.640, 1+Thr+gGT+ALB+BUN; 0.745, 256.539, 1+Ala+Gly+AST+ALB; 0. 744, 253.737, 1+BCAA+ALT+ALB+Ca; 0.744, 253.804, 1+BCAA+AST+ALB+BUN; 0.744, 255.352, 1+Gly+BCAA+ALB+BUN; 0.743, 255.276, 1+BCAA+A LB+BUN+NEFA; 0.743, 255.920, 1+BCAA+ALB+BUN+TP; 0.743, 255.599, 1+BCAA+AST+ALB+NEFA; 0.742, 257.751, 1+Ala+Thr+AST+ALB; 0.742, 25 5.511, 1+BCAA+ALB+BUN+BHBA; 0.742, 255.791, 1+BCAA+Glc+ALB+BUN; 0.741, 255.812, 1+BCAA+ALB+BUN+Ca; 0.741, 255.899, 1+BCAA+TG+ALB+BUN; 0.740, 257.366, 1+Gly+AST+ALB+BUN; 0.740, 258.435, 1+Gly+BCAA+Glc+ALB; 0.740, 257.299, 1+Ala+ALB+BUN+TP; 0.739, 256.927, 1+Ala+BCAA+AST+ALB; 0.739, 255.780, 1+BCAA+gGT+ALB+BUN; 0.739, 256. 295, 1+Ala+TCHO+ALB+BUN; 0.739, 259.044, 1+Gly+AST+ALB+NEFA; 0.7 39, 256.574, 1+Gly+ALT+AST+ALB; 0.739, 254.536, 1+BCAA+TCHO+ALB+BUN; 0.738, 260.144, 1+Gly+AST+ALB+BHBA; 0.738, 258.494, 1+Gly+BCAA+ALB+NEFA; 0.738, 257.192, 1+BCAA+AST+ALB+TP; 0.738, 256.807, 1+BCAA+AST+ALB+BHBA; 0.738, 257.184, 1+BCAA+AST+gGT+ALB; 0.738, 2 60.335, 1+Gly+Glc+AST+ALB; 0.738, 259.825, 1+Ala+Gly+ALB+TP; 0.7 38, 260.424, 1+Gly+TG+AST+ALB; 0.737, 260.437, 1+Gly+AST+gGT+AL B; 0.737, 260.432, 1+Gly+AST+ALB+TP; 0.737, 257.145, 1+BCAA+AST+A LB+Ca; 0.737, 258.727, 1+Gly+BCAA+TG+ALB; 0.737, 256.417, 1+Gly+B CAA+TCHO+ALB; 0.737, 259.970, 1+Ala+Gly+Glc+ALB; 0.737, 256.897, 1+BCAA+Glc+AST+ALB; 0.737, 256.097, 1+BCAA+TCHO+AST+ALB; 0.736, 258.724, 1+Gly+BCAA+ALB+TP; 0.736, 256.664, 1+BCAA+TCHO+ALB+NEF A; 0.736, 257.166, 1+BCAA+TG+AST+ALB; 0.736, 260.069, 1+Ala+Gly+T G+ALB; 0.736, 259.672, 1+Ala+Gly+gGT+ALB; 0.736, 258.613, 1+BCAA+Glc+ALB+NEFA; 0.735, 259.950, 1+Ala+Gly+ALB+BHBA; 0.735, 257.327, 1+Gly+ALT+ALB+NEFA; 0.735, 259.289, 1+Gly+TCHO+AST+ALB; 0.735, 2 57.592, 1+Ala+Gly+TCHO+ALB; 0.734, 258.588, 1+Gly+BCAA+gGT+ALB; 0.734, 257.380, 1+Gly+ALT+ALB+BHBA; 0.734, 259.996, 1+Ala+Gly+AL B+Ca; 0.734, 258.895, 1+BCAA+TG+ALB+NEFA; 0.734, 258.901, 1+BCAA+ALB+TP+NEFA; 0.734, 257.471, 1+Gly+ALT+gGT+ALB; 0.734, 258.897, 1+BCAA+ALB+NEFA+BHBA; 0.734, 257.446, 1+Gly+Glc+ALT+ALB; 0.734, 2 57.496, 1+Gly+TG+ALT+ALB; 0.733, 256.708, 1+Gly+TCHO+ALT+ALB; 0. 733, 257.465, 1+Gly+ALT+ALB+TP; 0.733, 258.828, 1+BCAA+ALB+Ca+NE FA; 0.732, 259.895, 1+Gly+Glc+ALB+BUN; 0.732, 258.696, 1+Ala+TCHO+ALB+NEFA; 0.732, 258.769, 1+BCAA+gGT+ALB+NEFA; 0.732, 257.429, 1+BCAA+Glc+TCHO+ALB; 0.732, 257.868, 1+Ala+BCAA+TCHO+ALB; 0.731, 258.004, 1+BCAA+TCHO+TG+ALB; 0.731, 260.516, 1+Ala+AST+ALB+BHB A; 0.731, 259.770, 1+Gly+gGT+ALB+BUN; 0.730, 259.861, 1+Gly+TG+AL B+BUN; 0.730, 261.003, 1+Ala+AST+gGT+ALB; 0.730, 259.768, 1+BCAA+Glc+ALB+TP; 0.730, 259.530, 1+Ala+BCAA+gGT+ALB; 0.730, 258.360, 1+Gly+TCHO+ALB+BUN; 0.730, 259.625, 1+Ala+BCAA+Glc+ALB; 0.729, 25 9.583, 1+Ala+BCAA+ALB+BHBA; 0.729, 259.733, 1+Ala+BCAA+TG+ALB; 0. 729, 261.009, 1+Ala+Glc+AST+ALB; 0.729, 258.017, 1+BCAA+TCHO+gGT+ALB; 0.729, 260.001, 1+Ala+TCHO+AST+ALB; 0.729, 260.847, 1+Ala+T G+AST+ALB; 0.729, 259.722, 1+BCAA+Glc+TG+ALB; 0.728, 260.770, 1+A la+AST+ALB+TP; 0.728, 260.988, 1+Ala+AST+ALB+Ca; 0.728, 259.515, 1+BCAA+Glc+gGT+ALB; 0.727, 259.769, 1+BCAA+TG+gGT+ALB; 0.727, 25 9.771, 1+Ala+BCAA+ALB+Ca; 0.724, 263.543, 1+Gly+TG+gGT+ALB; 0.72 3, 263.459, 1+Gly+Glc+gGT+ALB; 0.723, 263.639, 1+Gly+Glc+TG+ALB; 0.721, 261.509, 1+Gly+TCHO+gGT+ALB; 0.721, 261.126, 1+Gly+Glc+TC HO+ALB; 0.720, 263.217, 1+Ala+TG+gGT+ALB; 0.720, 261.797, 1+Ala+T CHO+gGT+ALB; 0.719, 263.334, 1+Ala+Glc+gGT+ALB; 0.718, 261.885, 1+Ala+Glc+TCHO+ALB; 0.717, 261.807, 1+Ala+TCHO+TG+ALB

[414. Formula (with Five Amino Acid+Biochemistry Variables) with Improved Diagnostic Accuracy by Added Parity Term]

0.780, 246.798, 1+ALB+BUN+ALT+Phe+Trp; 0.779, 247.356, 1+Trp+Lys+His+ALB+BUN; 0.778, 248.514, 1+BCAA+Trp+Lys+ALB+BUN; 0.777, 247. 960, 1+Gly+Phe+ALT+ALB+BUN; 0.775, 247.451, 1+ALB+BUN+ALT+Arg+T rp; 0.775, 249.117, 1+Trp+Phe+His+ALB+BUN; 0.775, 246.510, 1+ALB+BUN+ALT+Lys+Trp; 0.775, 249.162, 1+ALB+BUN+Lys+Val+Trp; 0.774, 2 47.602, 1+ALB+BUN+ALT+Orn+Phe; 0.774, 246.621, 1+ALB+BUN+ALT+Ly s+Phe; 0.774, 250.716, 1+ALB+BUN+Tyr+Phe+Trp; 0.774, 249.006, 1+L ys+Phe+His+ALB+BUN; 0.774, 250.656, 1+BCAA+Trp+Phe+ALB+BUN; 0.7 74, 247.568, 1+ALB+BUN+ALT+Arg+Phe; 0.774, 249.506, 1+Ala+Trp+Hi s+ALB+BUN; 0.773, 246.829, 1+ALB+BUN+ALT+Lys+Ile; 0.773, 249.411, 1+Ala+Trp+Lys+ALB+BUN; 0.773, 245.948, 1+ALB+BUN+ALT+Asp+Trp; 0. 773, 250.819, 1+BCAA+Lys+Phe+ALB+BUN; 0.773, 247.707, 1+ALB+BUN+Asp+Lys+Trp; 0.773, 249.227, 1+Trp+Lys+Thr+ALB+BUN; 0.773, 248.3 26, 1+ALB+BUN+ALT+Orn+Trp; 0.773, 250.577, 1+Ala+Trp+Phe+ALB+BU N; 0.773, 249.330, 1+ALB+BUN+Lys+Tyr+Trp; 0.773, 249.152, 1+ALB+B UN+NEFA+His+Lys; 0.773, 246.714, 1+ALB+BUN+ALT+His+Lys; 0.773, 2 50.523, 1+Gly+Trp+Phe+ALB+BUN; 0.773, 249.077, 1+Gly+Trp+Lys+AL B+BUN; 0.772, 249.168, 1+ALB+BUN+3MeHis+Lys+Trp; 0.772, 249.649, 1+ALB+BUN+Lys+Phe+Trp; 0.772, 248.932, 1+ALB+BUN+T-BIL+His+Ly s; 0.772, 250.546, 1+Ala+Trp+Arg+ALB+BUN; 0.772, 249.407, 1+Gly+L ys+His+ALB+BUN; 0.772, 249.454, 1+Trp+Lys+Glc+ALB+BUN; 0.772, 24 9.418, 1+Trp+Lys+ALB+BUN+TP; 0.772, 249.129, 1+Trp+His+ALT+ALB+BUN; 0.772, 249.255, 1+Trp+TG+ALT+ALB+BUN; 0.772, 249.865, 1+ALB+BUN+T-BIL+Lys+Ile; 0.772, 251.223, 1+ALB+BUN+Lys+Tyr+Phe; 0.772, 250.139, 1+Ala+Gly+Trp+ALB+BUN; 0.772, 247.250, 1+ALB+BUN+ALT+3 MeHis+Lys; 0.772, 249.670, 1+Ala+Lys+His+ALB+BUN; 0.772, 251.090, 1+Trp+Phe+Glc+ALB+BUN; 0.772, 250.287, 1+Ala+Gly+Lys+ALB+BUN; 0. 771, 251.930, 1+Phe+His+ALB+BUN+NEFA; 0.771, 250.408, 1+Gly+Lys+Phe+ALB+BUN; 0.771, 250.166, 1+ALB+BUN+Arg+Lys+Ile; 0.771, 249.7 37, 1+Trp+Lys+TG+ALB+BUN; 0.771, 249.651, 1+ALB+ALT+Arg+Tyr+Tr p; 0.771, 251.107, 1+Ala+BCAA+Trp+ALB+BUN; 0.771, 249.664, 1+Trp+Lys+ALB+BUN+BHBA; 0.771, 249.998, 1+Lys+His+ALB+BUN+TP; 0.771, 2 51.113, 1+Trp+Thr+Phe+ALB+BUN; 0.771, 249.612, 1+ALB+BUN+NEFA+L ys+Trp; 0.771, 247.348, 1+Gly+Lys+ALT+ALB+BUN; 0.771, 249.235, 1+Trp+Glc+ALT+ALB+BUN; 0.771, 250.202, 1+ALB+BUN+His+Thr+Lys; 0.7 71, 251.117, 1+Ala+Trp+Glc+ALB+BUN; 0.771, 249.738, 1+ALB+BUN+Or n+Lys+Trp; 0.771, 249.934, 1+ALB+BUN+Glc+His+Lys; 0.771, 248.543, 1+Trp+Arg+His+ALT+ALB; 0.771, 249.202, 1+Trp+Thr+ALT+ALB+BUN; 0. 771, 249.647, 1+ALB+BUN+Arg+Lys+Trp; 0.771, 250.739, 1+ALB+BUN+A rg+Tyr+Trp; 0.770, 249.373, 1+Trp+ALT+gGT+ALB+BUN; 0.770, 249.84 5, 1+ALB+BUN+NEFA+Lys+Ile; 0.770, 249.240, 1+ALB+BUN+ALT+NEFA+T rp; 0.770, 247.497, 1+BCAA+Lys+ALT+ALB+BUN; 0.770, 249.011, 1+Trp+Lys+TCHO+ALB+BUN; 0.770, 250.694, 1+ALB+BUN+3MeHis+Phe+Trp; 0. 770, 245.023, 1+ALB+BUN+ALT+Asp+Lys; 0.770, 249.730, 1+Trp+Lys+g GT+ALB+BUN; 0.770, 250.946, 1+ALB+BUN+Thr+Lys+Ile; 0.770, 250.07 9, 1+ALB+BUN+His+Lys+Ile; 0.770, 251.108, 1+ALB+BUN+Val+Phe+Tr p; 0.770, 251.107, 1+ALB+BUN+NEFA+Phe+Trp; 0.770, 250.741, 1+ALB+BUN+Arg+Phe+Trp; 0.770, 249.287, 1+Gly+Trp+Arg+AST+ALB; 0.770, 2 51.335, 1+Gly+BCAA+Lys+AST+ALB; 0.770, 250.658, 1+ALB+

BUN+Orn+Lys+Ile; 0.770, 247.220, 1+ALB+BUN+ALT+ Arg+Lys; 0.770, 247.521, 1+ALB+BUN+ALT+BHBA+ Lys; 0.770, 247.420, 1+Ala+Lys+ALT+ALB+BUN; 0. 770, 247.960, 1+ALB+BUN+AST+Lys+Trp; 0.770, 251.046, 1+ALB+BUN+gGT+Lys+Ile; 0.770, 249.483, 1+ALB+ BUN+His+Arg+Lys; 0.770, 247.67 2, 1+Lys+TG+ALT+ ALB+BUN; 0.770, 247.548, 1+ALB+BUN+ALT+T-BIL+ Ly s; 0.770, 249.131, 1+ALB+BUN+Asp+Phe+Trp; 0.770, 249.363, 1+Trp+A LT+ALB+BUN+BHBA; 0.770, 249.567, 1+ALB+BUN+His+Orn+Lys; 0.770, 2 48.960, 1+ALB+ BUN+AST+Arg+Trp; 0.770, 251.243, 1+Trp+Phe+TG+ ALB+BUN; 0.770, 251.148, 1+Ala+Trp+Tyr+ALB+BUN; 0.770, 251.096, 1+Tr p+Phe+ALB+BUN+TP; 0.770, 250.088, 1+ALB+BUN+3MeHis+Lys+Phe; 0.7 70, 246.858, 1+ALB+BUN+3MeHis+Asp+Lys; 0.769, 251.196, 1+Ala+Trp+Thr+ALB+BUN; 0.769, 249.380, 1+ALB+BUN+ALT+3MeHis+Trp; 0.769, 2 47.550, 1+Lys+ ALT+ALB+BUN+TP; 0.769, 251.170, 1+Ala+Trp+gGT+ ALB+BUN; 0.769, 249.208, 1+ALB+BUN+ALT+Tyr+Trp; 0.769, 249.247, 1+Gl y+Trp+ALT+ALB+BUN; 0.769, 247.684, 1+ALB+BUN+ALT+gGT+Lys; 0.769, 249.788, 1+ALB+ALT+Arg+Phe+Trp; 0.769, 250.986, 1+ALB+ BUN+BHBA+Lys+Ile; 0.769, 251.669, 1+Gly+BCAA+ Trp+Lys+ALB; 0.769, 251.364, 1+ALB+BUN+Lys+Val+ Phe; 0.769, 249.317, 1+ALB+BUN+AST+Phe+Trp; 0. 769, 248.988, 1+Trp+TCHO+ALT+ALB+BUN; 0.769, 250.563, 1+Gly+BCAA+Lys+ALB+BUN; 0.769, 250.256, 1+Gly+ Trp+Arg+ALB+BUN; 0.769, 248. 874, 1+Gly+Lys+AST+ ALB+BUN; 0.769, 250.920, 1+Gly+Lys+His+AST+A LB; 0.769, 250.792, 1+ALB+AST+Arg+Tyr+Trp; 0.769, 250.813, 1+ALB+ALT+Orn+Tyr+Phe; 0.769, 249.926, 1+Gly+Arg+Lys+AST+ALB; 0.769, 2 49.126, 1+Gly+Trp+ Arg+ALT+ALB; 0.769, 249.625, 1+Trp+Lys+ALB+BU N+Ca; 0.769, 250.512, 1+Ala+Trp+TCHO+ALB+BUN; 0.769, 251.230, 1+A la+Trp+TG+ALB+BUN; 0.769, 247.625, 1+ALB+BUN+ALT+NEFA+Lys; 0.76 9, 247.621, 1+ALB+BUN+ALT+Lys+Val; 0.769, 250.475, 1+Gly+Trp+ Phe+ALT+ALB; 0.769, 249.384, 1+ALB+BUN+AST+ Lys+Ile; 0.769, 249.743, 1+Gly+Lys+TCHO+ALB+BUN; 0.769, 251.175, 1+Ala+Trp+ALB+BUN+BHB A; 0.769, 250.768, 1+Gly+Lys+ALB+BUN+TP; 0.769, 249.331, 1+BCAA+T rp+ALT+ALB+BUN; 0.768, 249.285, 1+ALB+BUN+ALT+Val+Trp; 0.768, 24 9.068, 1+ALB+ BUN+ALT+Arg+Thr; 0.768, 249.213, 1+ALB+BUN+ ALT+His+Arg; 0.768, 249.131, 1+Ala+Trp+AST+ALB+ BUN; 0.768, 250.297, 1+AL B+BUN+gGT+His+Lys; 0.768, 248.171, 1+ALB+ALT+Arg+Lys+Ile; 0.768, 251.217, 1+Trp+Phe+gGT+ALB+BUN; 0.768, 250.684, 1+ALB+BUN+Orn+P he+Trp; 0.768, 249.335, 1+Trp+ ALT+ALB+BUN+Ca; 0.768, 249.425, 1+A rg+Phe+His+ ALT+ALB; 0.768, 249.039, 1+Gly+Arg+ALT+ALB+BUN; 0.76 8, 247.691, 1+ALB+BUN+ALT+Lys+Tyr; 0.768, 247.533, 1+ALB+BUN+ALT+Glc+Lys; 0.768, 248.918, 1+Trp+Lys+His+ALT+ALB; 0.768, 249.718, 1+Gly+Trp+ Lys+AST+ALB; 0.768, 252.249, 1+Trp+Glc+ALB+BUN+ TP; 0. 768, 251.180, 1+Ala+Trp+ALB+BUN+NEFA; 0.768, 247.692, 1+ALB+BUN+ALT+Thr+Lys; 0.768, 250.232, 1+ALB+BUN+Ca+His+Lys; 0.768, 247.23 1, 1+Lys+ TCHO+ALT+ALB+BUN; 0.768, 249.512, 1+ALB+BUN+ Asp+Lys+Ph e; 0.768, 249.058, 1+ALB+BUN+ALT+3Me- His+Arg; 0.768, 250.006, 1+BC AA+Trp+Arg+ALT+ALB; 0.768, 250.551, 1+ALB+BUN+3MeHis+Arg+Trp; 0. 768, 250.883, 1+ALB+BUN+NEFA+Lys+Val; 0.768, 247.671, 1+ALB+BUN+ALT+Orn+Lys; 0.768, 250.989, 1+ALB+ BUN+Ca+Lys+Ile; 0.768, 252.74 1, 1+Ala+Gly+Lys+His+ ALB; 0.768, 250.396, 1+ALB+BUN+3MeHis+Lys+Val; 0.768, 249.548, 1+Gly+Arg+Phe+ALT+ALB; 0.768, 251.698, 1+Gly+Phe+His+ALT+ALB; 0.768, 251.362, 1+Ala+Lys+Phe+ALB+BUN; 0.768, 252.612, 1+Ala+Gly+ Trp+Lys+ALB; 0.768, 250.922, 1+Gly+Lys+TG+AL B+BUN; 0.768, 250.011, 1+ALB+BUN+BHBA+His+Lys; 0.768, 250.778, 1+ALB+BUN+Glc+Lys+Ile; 0.768, 249.601, 1+ALB+BUN+Asp+Tyr+Trp; 0.7 68, 250.592, 1+ALB+BUN+NEFA+Lys+Phe; 0.768, 249.400, 1+ALB+ BUN+A rg+Asp+Trp; 0.768, 249.826, 1+Gly+Lys+Phe+ ALT+ALB; 0.768, 247.84 5, 1+ALB+BUN+ALT+Arg+ Asp; 0.768, 249.893, 1+Trp+Arg+Glc+ALT+AL B; 0.768, 250.615, 1+BCAA+Lys+ALB+BUN+NEFA; 0.768, 249.626, 1+Lys+Phe+His+ALT+ALB; 0.768, 251.586, 1+Gly+Arg+TG+AST+ALB; 0.768, 2 50.658, 1+Gly+Lys+ TCHO+AST+ALB; 0.768, 250.907, 1+Gly+Lys+gGT+A LB+BUN; 0.767, 250.395, 1+Gly+Arg+Lys+ALB+BUN; 0.767, 250.628, 1+Gly+Lys+Glc+ALB+BUN; 0.767, 249.221, 1+Gly+Arg+ALT+AST+ALB; 0.7 67, 250.438, 1+ALB+ALT+Arg+Tyr+Phe; 0.767, 252.489, 1+Ala+Gly+ Ph e+ALB+BUN; 0.767, 249.737, 1+ALB+BUN+Asp+ Val+Trp; 0.767, 248.869, 1+ALB+BUN+NEFA+Asp+Lys; 0.767, 250.292, 1+Ala+Gly+Arg+ALT+ALB; 0.767, 250.096, 1+Trp+Arg+ALT+gGT+ALB; 0.767, 248.587, 1+ALB+ALT+His+Arg+Lys; 0.767, 247.240, 1+ALB+ BUN+AST+ALT+Lys; 0.767, 251. 424, 1+ALB+BUN+ Orn+Lys+Phe; 0.767, 249.984, 1+Trp+Arg+TG+ALT+AL B; 0.767, 250.037, 1+ALB+ALT+Lys+Phe+Trp; 0.767, 251.384, 1+Gly+L ys+AST+ALB+TP; 0.767, 251.192, 1+Ala+Gly+Trp+AST+ALB; 0.767, 250. 116, 1+ALB+ ALT+NEFA+Arg+Trp; 0.767, 252.009, 1+Gly+Trp+ALB+ BUN+NEFA; 0.767, 251.324, 1+BCAA+Arg+Lys+ALB+ BUN; 0.767, 249.346, 1+A LB+ALT+Arg+Lys+Trp; 0.767, 251.280, 1+Ala+Gly+Lys+AST+ALB; 0.76 7, 251.928, 1+Gly+Trp+ALB+BUN+TP; 0.767, 251.050, 1+Trp+Arg+ ALB+BUN+TP; 0.767, 249.629, 1+ALB+BUN+Asp+Orn+ Lys; 0.767, 248.918, 1+ALB+AST+ALT+Arg+Trp; 0.767, 248.579, 1+ALB+BUN+AST+ALT+Trp; 0.7 67, 249.231, 1+Gly+Lys+ALT+AST+ALB; 0.767, 251.129, 1+Ala+Trp+ AL B+BUN+Ca; 0.767, 249.557, 1+Trp+Arg+TCHO+ ALT+ALB; 0.767, 251.447, 1+Ala+BCAA+Lys+ALB+ BUN; 0.767, 250.491, 1+ALB+ALT+Arg+Thr+Ile; 0.767, 251.931, 1+Gly+Trp+Glc+ALB+BUN; 0.767, 250.914, 1+Gly+Lys+Thr+ALB+BUN; 0.767, 250.188, 1+ALB+ ALT+Orn+Phe+Trp; 0.767, 250. 582, 1+ALB+BUN+3Me- His+Orn+Lys; 0.767, 247.649, 1+ALB+BUN+Ca+ALT+ Lys; 0.767, 249.696, 1+ALB+BUN+ALT+T-BIL+Arg; 0.767, 249.937, 1+ALB+ALT+Arg+Orn+Trp; 0.767, 250.119, 1+Trp+Arg+Thr+ALT+ALB; 0.7 67, 249.401, 1+Gly+Trp+Lys+ALT+ALB; 0.767, 247.602, 1+ALB+ BUN+AS T+Asp+Trp; 0.767, 251.026, 1+BCAA+Trp+ Lys+AST+ALB; 0.767, 251.39 8, 1+ALB+BUN+Arg+Lys+ Phe; 0.767, 249.274, 1+ALB+BUN+ALT+Arg+Or n; 0.767, 251.707, 1+Trp+TCHO+ALB+BUN+TP; 0.767, 251.504, 1+ALB+B UN+Arg+Lys+Tyr; 0.767, 251.124, 1+Trp+Arg+ TG+ALB+BUN; 0.767, 250. 124, 1+ALB+BUN+3MeHis+ Arg+Lys; 0.767, 249.714, 1+ALB+BUN+NEFA+A sp+Trp; 0.767, 249.636, 1+ALB+BUN+Arg+Asp+Lys; 0.767, 251.066, 1+ALB+ALT+Orn+Tyr+Trp; 0.767, 249.373, 1+ALB+BUN+Asp+Orn+Trp; 0.7 67, 249.716, 1+ALB+ ALT+His+Arg+Orn; 0.767, 250.115, 1+Trp+AST+AL B+BUN+TP; 0.767, 249.026, 1+ALB+BUN+AST+3Me- His+Lys; 0.767, 251.0 25, 1+Gly+Lys+Glc+AST+ALB; 0.766, 250.702, 1+Ala+Lys+ALB+BUN+NE FA; 0.766, 249.605, 1+ALB+BUN+Asp+Lys+Val; 0.766, 250.057, 1+Trp+Arg+ALT+ALB+BHBA; 0.766, 251.171, 1+Ala+ Gly+Arg+AST+ALB; 0.766, 249.815, 1+Trp+Lys+Glc+ ALT+ALB; 0.766, 251.095, 1+ALB+AST+Arg+L ys+Ile; 0.766, 251.316, 1+Lys+Phe+Glc+ALB+BUN; 0.766, 251.180, 1+Trp+Phe+Glc+ALT+ALB; 0.766, 251.019, 1+ALB+BUN+T-BIL+Orn+Lys; 0.766, 250.131, 1+ALB+ALT+Arg+Val+Trp; 0.766, 249.066, 1+ALB+BUN+AST+His+Lys; 0.766, 251.129, 1+ALB+BUN+Arg+Val+Trp; 0.766, 250.340, 1+ALB+BUN+NEFA+3MeHis+Lys; 0.766, 250.971, 1+ALB+BUN+NEFA+Lys+Tyr; 0.766, 249.738, 1+ALB+BUN+ALT+Glc+Arg; 0.766, 249.569, 1+Arg+TG+ALT+ALB+BUN; 0.766, 253.429, 1+Ala+Gly+Trp+His+ALB; 0.766, 252.415, 1+Trp+Glc+TG+ALB+BUN; 0.766, 252.093, 1+Ala+Trp+Lys+His+ALB; 0.766, 250.256, 1+Ala+Gly+Lys+ALT+ALB; 0.766, 249.791, 1+ALB+BUN+AST+Lys+Phe; 0.766, 250.689, 1+ALB+BUN+T-BIL+Glc+Lys; 0.766, 251.602, 1+ALB+BUN+Arg+Lys+Val; 0.766, 249.703, 1+ALB+ALT+3MeHis+Arg+Trp; 0.766, 248.521, 1+ALB+BUN+3MeHis+Asp+Trp; 0.766, 249.665, 1+ALB+BUN+ALT+Arg+Ile; 0.766, 249.790, 1+BCAA+Trp+Lys+ALT+ALB; 0.766, 251.585, 1+Gly+Lys+TG+AST+ALB; 0.766, 251.474, 1+Ala+Arg+Lys+ALB+BUN; 0.766, 249.737, 1+Arg+ALT+ALB+BUN+TP; 0.766, 250.946, 1+ALB+BUN+Arg+Orn+Trp; 0.766, 250.111, 1+Ala+Trp+Arg+ALT+ALB; 0.766, 252.126, 1+Gly+Trp+TG+ALB+BUN; 0.766, 250.956, 1+ALB+AST+NEFA+Lys+Ile; 0.766, 252.293, 1+Trp+Glc+ALB+BUN+BHBA; 0.766, 250.640, 1+ALB+BUN+3MeHis+Lys+Tyr; 0.766, 249.396, 1+ALB+BUN+Asp+Lys+Tyr; 0.766, 252.490, 1+Ala+Gly+Trp+Arg+ALB; 0.766, 254.107, 1+Ala+Gly+BCAA+Lys+ALB; 0.766, 251.355, 1+ALB+BUN+Orn+Tyr+Trp; 0.766, 248.965, 1+Gly+Arg+Lys+ALT+ALB; 0.766, 251.516, 1+Trp+Glc+TCHO+ALB+BUN; 0.766, 252.885, 1+ALB+BUN+NEFA+3MeHis+Phe; 0.766, 251.282, 1+Gly+Lys+AST+ALB+NEFA; 0.766, 251.578, 1+Gly+Lys+Thr+AST+ALB; 0.766, 249.625, 1+BCAA+Arg+ALT+ALB+BUN; 0.766, 251.111, 1+ALB+BUN+NEFA+Arg+Trp; 0.766, 249.180, 1+ALB+BUN+AST+ALT+Arg; 0.766, 251.877, 1+Trp+Lys+His+ALB+TP; 0.766, 251.405, 1+Trp+Lys+AST+ALB+TP; 0.766, 249.114, 1+ALB+BUN+AST+NEFA+Lys; 0.766, 249.770, 1+Gly+Trp+AST+ALB+BUN; 0.766, 250.714, 1+Ala+Lys+TCHO+ALB+BUN; 0.766, 251.014, 1+Lys+TG+ALB+BUN+NEFA; 0.766, 250.962, 1+ALB+BUN+NEFA+T-BIL+Lys; 0.766, 249.719, 1+ALB+BUN+ALT+BHBA+Arg; 0.766, 251.780, 1+ALB+BUN+Orn+Lys+Tyr; 0.766, 251.742, 1+BCAA+Lys+Thr+ALB+BUN; 0.766, 250.349, 1+Trp+AST+ALB+BUN+BHBA; 0.766, 252.775, 1+ALB+BUN+Orn+Tyr+Phe; 0.766, 251.915, 1+ALB+BUN+Lys+Tyr+Val; 0.766, 251.653, 1+Ala+Lys+Tyr+ALB+BUN; 0.766, 251.029, 1+ALB+BUN+T-BIL+BHBA+Lys; 0.766, 249.686, 1+ALB+BUN+ALT+NEFA+Arg; 0.766, 251.289, 1+ALB+BUN+Orn+Val+Trp; 0.766, 251.053, 1+ALB+BUN+gGT+NEFA+Lys; 0.766, 250.475, 1+ALB+ALT+Arg+Orn+Phe; 0.766, 251.628, 1+BCAA+Lys+ALB+BUN+TP; 0.766, 247.851, 1+ALB+BUN+AST+Asp+Lys; 0.766, 251.504, 1+Gly+Lys+AST+ALB+BHBA; 0.766, 252.411, 1+BCAA+Trp+Glc+ALB+BUN; 0.766, 252.599, 1+Gly+Trp+Lys+ALB+TP; 0.766, 249.213, 1+ALB+ALT+3MeHis+Arg+Lys; 0.766, 250.298, 1+Gly+Lys+ALT+ALB+TP; 0.766, 250.214, 1+Gly+Arg+TG+ALT+ALB; 0.766, 251.478, 1+ALB+AST+Orn+Lys+Ile; 0.765, 251.033, 1+ALB+BUN+NEFA+Thr+Lys; 0.765, 251.036, 1+ALB+BUN+NEFA+BHBA+Lys; 0.765, 250.991, 1+ALB+BUN+gGT+T-BIL+Lys; 0.765, 250.842, 1+ALB+BUN+NEFA+Glc+Lys; 0.765, 249.136, 1+ALB+BUN+AST+Orn+Trp; 0.765, 249.276, 1+Arg+TCHO+ALT+ALB+BUN; 0.765, 249.722, 1+ALB+BUN+ALT+Arg+Tyr; 0.765, 250.867, 1+ALB+BUN+T-BIL+Arg+Lys; 0.765, 251.002, 1+ALB+ALT+NEFA+Orn+Trp; 0.765, 250.871, 1+Lys+ALB+BUN+TP+NEFA; 0.765, 249.974, 1+Trp+Lys+Thr+ALT+ALB; 0.765, 251.046, 1+ALB+BUN+NEFA+Orn+Lys; 0.765, 252.416, 1+Trp+Glc+ALB+BUN+NEFA; 0.765, 249.610, 1+ALB+AST+ALT+Orn+Trp; 0.765, 248.751, 1+ALB+ALT+Arg+Asp+Trp; 0.765, 250.258, 1+Trp+AST+gGT+ALB+BUN; 0.765, 253.458, 1+ALB+BUN+NEFA+Tyr+Phe; 0.765, 251.037, 1+ALB+ALT+Orn+Val+Trp; 0.765, 249.446, 1+ALB+BUN+ALT+Arg+Val; 0.765, 252.605, 1+ALB+His+Orn+Lys+Ile; 0.765, 252.157, 1+Gly+Trp+ALB+BUN+BHBA; 0.765, 249.665, 1+Gly+Lys+TCHO+ALT+ALB; 0.765, 251.745, 1+ALB+BUN+Orn+Lys+Val; 0.765, 249.693, 1+ALB+BUN+ALT+gGT+Arg; 0.765, 252.199, 1+ALB+NEFA+Arg+Lys+Ile; 0.765, 250.241, 1+Gly+BCAA+Lys+ALT+ALB; 0.765, 249.433, 1+ALB+ALT+His+Orn+Lys; 0.765, 250.101, 1+Trp+Arg+ALT+ALB+Ca; 0.765, 250.392, 1+Gly+Lys+TG+ALT+ALB; 0.765, 251.584, 1+ALB+NEFA+His+Arg+Lys; 0.765, 252.380, 1+Trp+Glc+gGT+ALB+BUN; 0.765, 250.961, 1+ALB+BUN+T-BIL+Thr+Lys; 0.765, 249.150, 1+ALB+ALT+Asp+Orn+Trp; 0.765, 252.180, 1+Gly+BCAA+Trp+ALB+BUN; 0.765, 251.926, 1+Trp+TCHO+TG+ALB+BUN; 0.765, 254.416, 1+Ala+Gly+Trp+Glc+ALB; 0.765, 250.025, 1+ALB+ALT+Arg+Lys+Phe; 0.765, 249.639, 1+ALB+ALT+Orn+Lys+Ile; 0.765, 251.353, 1+ALB+AST+Orn+Val+Trp; 0.765, 250.395, 1+Trp+TG+AST+ALB+BUN; 0.765, 251.428, 1+Gly+Lys+AST+gGT+ALB; 0.765, 251.634, 1+Ala+Lys+ALB+BUN+TP; 0.765, 250.123, 1+ALB+BUN+ALT+His+Orn; 0.765, 254.435, 1+Ala+Gly+Trp+Phe+ALB; 0.765, 252.325, 1+Trp+ALB+BUN+TP+BHBA; 0.765, 250.993, 1+ALB+BUN+AST+Orn+Phe; 0.765, 250.419, 1+Gly+Lys+ALT+gGT+ALB; 0.765, 250.384, 1+ALB+BUN+AST+NEFA+Trp; 0.765, 249.798, 1+ALB+BUN+AST+Arg+Lys; 0.765, 251.155, 1+Trp+Lys+Thr+AST+ALB; 0.765, 249.578, 1+ALB+BUN+Ca+ALT+Arg; 0.765, 252.306, 1+ALB+BUN+NEFA+Orn+Phe; 0.765, 252.423, 1+Trp+TG+ALB+BUN+TP; 0.765, 252.410, 1+Trp+ALB+BUN+TP+NEFA; 0.765, 251.187, 1+ALB+AST+NEFA+Arg+Trp; 0.765, 251.616, 1+ALB+BUN+Arg+Thr+Lys; 0.765, 251.141, 1+ALB+BUN+3MeHis+Orn+Trp; 0.765, 250.297, 1+Gly+Arg+Thr+ALT+ALB; 0.765, 249.876, 1+ALB+AST+Asp+Lys+Trp; 0.765, 250.006, 1+ALB+ALT+Orn+Lys+Trp; 0.765, 250.236, 1+ALB+BUN+AST+3MeHis+Trp; 0.765, 251.347, 1+ALB+AST+Lys+Tyr+Trp; 0.765, 251.890, 1+BCAA+Trp+TCHO+ALB+BUN; 0.765, 251.891, 1+Trp+TCHO+ALB+BUN+NEFA; 0.765, 251.666, 1+Ala+Lys+TG+ALB+BUN; 0.765, 253.996, 1+Ala+Gly+Lys+Glc+ALB; 0.765, 250.524, 1+ALB+AST+ALT+Phe+Trp; 0.765, 252.801, 1+ALB+AST+Arg+Orn+Ile; 0.765, 249.193, 1+ALB+AST+ALT+Lys+Trp; 0.765, 248.982, 1+ALB+BUN+AST+T-BIL+Lys; 0.765, 250.965, 1+ALB+BUN+Ca+NEFA+Lys; 0.765, 250.933, 1+ALB+BUN+Ca+T-BIL+Lys; 0.764, 251.731, 1+ALB+BUN+3MeHis+Orn+Phe; 0.764, 251.608, 1+Lys+Glc+ALB+BUN+TP; 0.764, 250.951, 1+ALB+ALT+3MeHis+Orn+Trp; 0.764, 250.636, 1+BCAA+Lys+Phe+ALT+ALB; 0.764, 250.415, 1+Gly+Lys+Thr+ALT+ALB; 0.764, 250.005, 1+Lys+AST+ALB+BUN+TP; 0.764, 249.638, 1+Trp+Lys+TCHO+ALT+ALB; 0.764, 254.362, 1+Ala+Gly+Lys+Tyr+ALB; 0.764, 251.624, 1+Arg+Lys+TG+ALB+BUN; 0.764, 251.613, 1+ALB+BUN+Arg+Orn+Lys; 0.764, 252.418, 1+BCAA+Trp+ALB+BUN+TP; 0.764, 249.811, 1+ALB+ALT+3MeHis+Lys+Trp; 0.764, 250.873, 1+ALB+ALT+Lys+Tyr+Phe; 0.764, 250.201, 1+Trp+Glc+AST+ALB+BUN; 0.764, 251.047, 1+ALB+AST+Arg+Orn+Trp; 0.764, 251.663, 1+ALB+BUN+BHBA+Orn+Lys; 0.764, 250.032, 1+Gly+Lys+Glc+ALT+ALB; 0.764, 251.660, 1+Ala+Lys+Thr+ALB+BUN; 0.764, 250.653, 1+ALB+ALT+Arg+Orn+Ile;

0.764, 250.526, 1+Gly+Arg+ALT+g GT+ALB; 0.764, 250.259, 1+ALB+AST+ALT+Orn+Phe; 0.764, 250.252, 1+ALB+BUN+ALT+Thr+Orn; 0.764, 252.308, 1+Gly+Trp+AST+ALB+TP; 0.76 4, 251.774, 1+Lys+TG+ALB+BUN+TP; 0.764, 250.016, 1+ALB+ALT+His+A rg+Thr; 0.764, 251.943, 1+ALB+NEFA+His+Orn+Lys; 0.764, 251.592, 1+Ala+Lys+ALB+BUN+Ca; 0.764, 251.465, 1+Ala+Lys+ALB+BUN+Glc+Arg+Lys; 0.7 64, 251.453, 1+Ala+Lys+ALB+BUN+BHBA; 0.764, 252.173, 1+Gly+Trp+g GT+ALB+BUN; 0.764, 250.993, 1+ALB+AST+Arg+Lys+Trp; 0.764, 250.38 7, 1+ALB+BUN+AST+Val+Trp; 0.764, 250.097, 1+ALB+ALT+Lys+Val+Tr p; 0.764, 251.902, 1+Trp+TCHO+ALB+BUN+BHBA; 0.764, 252.332, 1+Trp+Glc+ALB+BUN+Ca; 0.764, 252.401, 1+Ala+Trp+Glc+ALT+ALB; 0.764, 2 52.623, 1+Trp+TG+ALB+BUN+NEFA; 0.764, 252.386, 1+Trp+Thr+ALB+BU N+TP; 0.764, 250.817, 1+ALB+BUN+NEFA+Arg+Lys; 0.764, 251.697, 1+A LB+BUN+gGT+BHBA+Lys; 0.764, 251.423, 1+ALB+BUN+NEFA+Orn+Trp; 0. 764, 250.492, 1+ALB+ALT+Orn+Lys+Phe; 0.764, 249.969, 1+Ala+Lys+A ST+ALB+BUN; 0.764, 249.967, 1+ALB+BUN+AST+BHBA+Lys; 0.764, 250.4 20, 1+ALB+BUN+AST+Tyr+Trp; 0.764, 250.066, 1+Trp+TCHO+AST+ALB+B UN; 0.764, 249.631, 1+Lys+TCHO+AST+ALB+BUN; 0.764, 252.971, 1+ALB+BUN+Orn+Val+Phe; 0.764, 251.533, 1+Ala+Lys+Glc+ALB+BUN; 0.764, 252.093, 1+Gly+Trp+ALB+BUN+Ca; 0.764, 250.445, 1+BCAA+Trp+AST+A LB+BUN; 0.764, 250.139, 1+ALB+ALT+Lys+Tyr+Trp; 0.764, 250.991, 1+ALB+AST+NEFA+Lys+Trp; 0.764, 251.930, 1+Trp+TCHO+gGT+ALB+BUN; 0. 764, 251.501, 1+ALB+BUN+BHBA+Arg+Lys; 0.764, 250.808, 1+ALB+AST+ALT+Arg+Ile; 0.764, 250.232, 1+Ala+Trp+Lys+ALT+ALB; 0.764, 250.2 42, 1+Trp+Lys+ALT+gGT+ALB; 0.764, 252.139, 1+Gly+Trp+Glc+AST+AL B; 0.764, 252.331, 1+Trp+ALB+BUN+TP+Ca; 0.764, 251.780, 1+ALB+BUN+Thr+Orn+Lys; 0.764, 250.173, 1+Lys+TG+AST+ALB+BUN; 0.764, 250.1 69, 1+ALB+BUN+AST+Lys+Val; 0.764, 251.864, 1+ALB+AST+T-BIL+Lys+Ile; 0.764, 252.589, 1+Trp+TG+ALB+BUN+BHBA; 0.764, 251.861, 1+ALB+BUN+gGT+Thr+Lys; 0.764, 248.230, 1+ALB+BUN+ALT+Asp+Orn; 0.764, 250.171, 1+ALB+BUN+AST+Thr+Lys; 0.764, 250.018, 1+BCAA+Lys+AST+ALB+BUN; 0.764, 254.421, 1+Ala+Gly+Lys+ALB+TP; 0.764, 252.597, 1+Trp+ALB+BUN+NEFA+BHBA; 0.764, 251.070, 1+ALB+AST+Orn+Lys+Trp; 0. 764, 251.264, 1+ALB+AST+NEFA+Arg+Lys; 0.763, 251.691, 1+ALB+BUN+Glc+Thr+Lys; 0.763, 251.582, 1+ALB+BUN+Glc+Orn+Lys; 0.763, 252.6 27, 1+BCAA+Trp+TG+ALB+BUN; 0.763, 251.398, 1+ALB+BUN+BHBA+Glc+L ys; 0.763, 250.256, 1+ALB+AST+ALT+Arg+Phe; 0.763, 249.921, 1+ALB+ALT+Arg+Lys+Tyr; 0.763, 250.171, 1+ALB+BUN+AST+Lys+Tyr; 0.763, 2 51.558, 1+ALB+AST+Lys+Val+Trp; 0.763, 251.598, 1+ALB+BUN+Asp+Or n+Phe; 0.763, 254.389, 1+Ala+Gly+Lys+Phe+ALB; 0.763, 251.744, 1+A LB+BUN+gGT+Orn+Lys; 0.763, 251.556, 1+ALB+BUN+Ca+Arg+Lys; 0.763, 251.721, 1+ALB+BUN+BHBA+Thr+Lys; 0.763, 251.886, 1+Lys+Thr+TG+A LB+BUN; 0.763, 250.490, 1+Gly+Arg+Glc+ALT+ALB; 0.763, 251.748, 1+ALB+ALT+T-BIL+Arg+Ile; 0.763, 252.581, 1+Gly+Trp+AST+ALB+NEFA; 0.763, 252.350, 1+Gly+Trp+AST+gGT+ALB; 0.763, 252.547, 1+Trp+TG+ALB+BUN+Ca; 0.763, 251.828, 1+ALB+BUN+Ca+Thr+Lys; 0.763, 251.722, 1+ALB+BUN+Ca+Orn+Lys; 0.763, 251.601, 1+Ala+Lys+gGT+ALB+BUN; 0. 763, 252.578, 1+BCAA+Trp+ALB+BUN+BHBA; 0.763, 252.577, 1+Trp+gGT+ALB+BUN+BHBA; 0.763, 251.310, 1+ALB+AST+Orn+Tyr+Trp; 0.763, 250. 238, 1+Trp+Lys+TG+ALT+ALB; 0.763, 250.104, 1+ALB+BUN+AST+gGT+Ly s; 0.763, 250.528, 1+ALB+AST+ALT+His+Arg; 0.763, 251.116, 1+ALB+A ST+His+Orn+Lys; 0.763, 251.336, 1+Gly+Trp+TCHO+ALB+BUN; 0.763, 2 52.438, 1+ALB+BUN+NEFA+3MeHis+Trp; 0.763, 252.284, 1+Ala+Gly+Ar g+ALB+BUN; 0.763, 250.542, 1+ALB+ALT+3MeHis+Arg+Orn; 0.763, 252. 614, 1+Trp+TG+gGT+ALB+BUN; 0.763, 252.546, 1+ALB+BUN+Tyr+Val+Tr p; 0.763, 250.227, 1+ALB+ALT+NEFA+Lys+Trp; 0.763, 251.914, 1+Lys+AST+ALB+TP+NEFA; 0.763, 250.151, 1+ALB+ALT+NEFA+His+Lys; 0.763, 252.878, 1+Trp+Glc+ALT+ALB+BHBA; 0.763, 252.605, 1+Gly+Trp+AST+ALB+BHBA; 0.763, 252.526, 1+Gly+Trp+TG+AST+ALB; 0.763, 250.131, 1+ALB+ALT+NEFA+Lys+Ile; 0.763, 252.378, 1+ALB+BUN+3MeHis+Val+Tr p; 0.763, 252.359, 1+ALB+BUN+3MeHis+Tyr+Trp; 0.763, 251.798, 1+Ly s+Thr+ALB+BUN+TP; 0.763, 251.531, 1+ALB+BUN+gGT+Arg+Lys; 0.763, 251.497, 1+ALB+BUN+AST+NEFA+Phe; 0.763, 249.897, 1+ALB+BUN+AST+Glc+Lys; 0.763, 249.968, 1+ALB+BUN+AST+Orn+Lys; 0.763, 251.760, 1+ALB+BUN+AST+Arg+Phe; 0.763, 251.607, 1+ALB+BUN+gGT+Glc+Lys; 0. 763, 250.271, 1+ALB+3MeHis+Asp+Lys+Trp; 0.763, 248.133, 1+ALB+AL T+Asp+Lys+Trp; 0.763, 250.522, 1+ALB+AST+3Me-His+Arg+Trp; 0.763, 249.287, 1+ALB+AST+ALT+Arg+Lys; 0.763, 251.556, 1+Lys+ALB+BUN+T P+BHBA; 0.763, 254.857, 1+Ala+Gly+Trp+TG+ALB; 0.763, 250.591, 1+A LB+ALT+3MeHis+Lys+Tyr; 0.763, 250.630, 1+Arg+Thr+ALT+AST+ALB; 0. 763, 251.647, 1+ALB+AST+His+Arg+Orn; 0.763, 250.439, 1+ALB+ALT+T-BIL+Lys+Ile; 0.763, 252.820, 1+Trp+Glc+ALT+ALB+TP; 0.763, 254.3 89, 1+Ala+Gly+Lys+Thr+ALB; 0.763, 252.893, 1+Trp+Glc+ALT+gGT+AL B; 0.763, 254.692, 1+Ala+Gly+Trp+ALB+NEFA; 0.763, 252.610, 1+BCAA+Trp+gGT+ALB+BUN; 0.763, 252.242, 1+Gly+Trp+Glc+ALT+ALB; 0.763, 250.051, 1+ALB+ALT+NEFA+Arg+Lys; 0.763, 254.865, 1+Ala+Gly+Trp+ALB+TP; 0.763, 251.590, 1+ALB+ALT+gGT+Arg+Ile; 0.763, 251.622, 1+Ala+Trp+Arg+AST+ALB; 0.763, 250.471, 1+ALB+AST+Arg+Asp+Trp; 0.7 63, 251.364, 1+ALB+AST+NEFA+3MeHis+Lys; 0.763, 250.379, 1+Trp+AS T+ALB+BUN+Ca; 0.763, 252.589, 1+ALB+BUN+NEFA+Arg+Phe; 0.763, 252. 615, 1+Trp+gGT+ALB+BUN+NEFA; 0.763, 252.545, 1+ALB+BUN+NEFA+Val+Trp; 0.763, 252.624, 1+BCAA+Trp+ALB+BUN+NEFA; 0.763, 251.695, 1+ALB+BUN+AST+3MeHis+Phe; 0.763, 250.274, 1+ALB+ALT+3MeHis+Orn+L ys; 0.763, 251.691, 1+Ala+Trp+Lys+AST+ALB; 0.762, 251.803, 1+ALB+BUN+3Me-His+Arg+Phe; 0.762, 254.459, 1+Ala+Gly+Lys+TG+ALB; 0.762, 252.362, 1+Trp+gGT+ALB+BUN+TP; 0.762, 250.504, 1+ALB+ALT+3MeHis+Lys+Val; 0.762, 251.675, 1+ALB+AST+NEFA+Orn+Lys; 0.762, 252.590, 1+Gly+BCAA+Trp+AST+ALB; 0.762, 250.164, 1+ALB+AST+Asp+Orn+Trp; 0.762, 250.272, 1+ALB+ALT+Glc+His+Lys; 0.762, 250.642, 1+ALB+ALT+Glc+Orn+Lys; 0.762, 248.746, 1+ALB+ALT+Arg+Asp+Lys; 0.762, 254. 887, 1+Ala+Gly+Trp+ALB+BHBA; 0.762, 251.592, 1+Trp+Glc+ALT+AST+ALB; 0.762, 250.680, 1+ALB+AST+3Me-His+Lys+Trp; 0.762, 250.759, 1+ALB+3MeHis+Arg+Asp+Lys; 0.762, 249.982, 1+ALB+ALT+Glc+Arg+Lys; 0.762, 250.748, 1+ALB+AST+3MeHis+Arg+Lys; 0.762, 252.901, 1+ALB+BUN+Arg+Orn+Phe; 0.762, 252.874, 1+Trp+Glc+TG+ALT+ALB; 0.762, 25 0.668, 1+ALB+AST+ALT+NEFA+Arg; 0.762, 248.548, 1+ALB+AST+3MeHis+Asp+Lys; 0.762, 251.443, 1+ALB+AST+His+Arg+Lys; 0.762, 251.071, 1+ALB+AST+NEFA+His+Lys; 0.762, 251.616, 1+ALB+BUN+Ca+BHBA+Lys; 0.762, 252.195, 1+Trp+

Glc+TCHO+ALT+ALB; 0.762, 251.693, 1+ALB+ALT+Glc+Arg+Ile; 0.762, 250.599, 1+ALB+BUN+ALT+3MeHis+Orn; 0.762, 251.707, 1+ALB+ALT+BHBA+Arg+Ile; 0.762, 251.598, 1+ALB+ALT+NEFA+Arg+Ile; 0.762, 250.184, 1+ALB+ALT+BHBA+Arg+Lys; 0.762, 250.146, 1+ALB+ALT+gGT+Arg+Lys; 0.762, 251.666, 1+ALB+AST+Arg+Val+Trp; 0. 762, 251.376, 1+ALB+AST+NEFA+Orn+Trp; 0.762, 252.890, 1+Trp+Glc+ALT+ALB+NEFA; 0.762, 250.734, 1+ALB+BUN+ALT+Glc+Orn; 0.762, 254. 888, 1+Ala+Gly+Trp+Thr+ALB; 0.762, 254.880, 1+Ala+Gly+BCAA+Trp+ALB; 0.762, 250.183, 1+ALB+ALT+T-BIL+Arg+Lys; 0.762, 250.144, 1+ALB+ALT+Arg+Orn+Lys; 0.762, 250.544, 1+ALB+ALT+NEFA+3MeHis+Lys; 0.762, 250.158, 1+ALB+ALT+Arg+Lys+Val; 0.762, 250.046, 1+ALB+BUN+AST+ALT+Orn; 0.762, 253.142, 1+ALB+NEFA+Orn+Lys+Ile; 0.762, 254.841, 1+Ala+Gly+Trp+Tyr+ALB; 0.762, 253.086, 1+Ala+Gly+Arg+Lys+ALB; 0.762, 250.176, 1+Ala+Arg+Lys+ALT+ALB; 0.762, 250.187, 1+ALB+AST+ALT+Arg+Orn; 0.762, 251.043, 1+ALB+AST+ALT+Arg+Tyr; 0.762, 251.674, 1+ALB+AST+Lys+Phe+Trp; 0.762, 250.435, 1+ALB+ALT+Thr+Lys+Ile; 0.762, 251.987, 1+Gly+Trp+TCHO+AST+ALB; 0.762, 252.358, 1+ALB+BUN+Arg+Asp+Phe; 0.762, 251.234, 1+ALB+ALT+Arg+Orn+Tyr; 0.762, 252.441, 1+ALB+3MeHis+Arg+Lys+Trp; 0.762, 252.049, 1+ALB+AST+NEFA+Lys+Tyr; 0.762, 251.004, 1+Ala+Arg+ALT+AST+ALB; 0.762, 250. 977, 1+Ala+Lys+Phe+ALT+ALB; 0.762, 252.926, 1+ALB+NEFA+His+Lys+Ile; 0.762, 251.592, 1+ALB+Ca+ALT+Arg+Ile; 0.762, 254.312, 1+Ala+Gly+Lys+ALB+Ca; 0.762, 251.186, 1+ALB+ALT+Arg+Thr+Orn; 0.762, 25 0.717, 1+ALB+AST+ALT+Arg+Val; 0.762, 250.646, 1+ALB+ALT+NEFA+Lys+Phe; 0.762, 252.566, 1+ALB+AST+T-BIL+His+Orn; 0.762, 252.427, 1+ALB+AST+NEFA+Arg+Orn; 0.762, 251.776, 1+ALB+BUN+Ca+gGT+Lys; 0. 762, 251.618, 1+ALB+BUN+Ca+Glc+Lys; 0.762, 250.983, 1+ALB+ALT+NEFA+His+Arg; 0.762, 252.621, 1+BCAA+Trp+Glc+ALT+ALB; 0.762, 250.9 31, 1+ALB+ALT+Lys+Val+Phe; 0.762, 251.048, 1+ALB+AST+ALT+gGT+Arg; 0.762, 249.921, 1+BCAA+Arg+Lys+ALT+ALB; 0.762, 251.150, 1+ALB+ALT+Glc+Arg+Orn; 0.762, 250.982, 1+Lys+Phe+ALT+gGT+ALB; 0.762, 2 50.537, 1+ALB+ALT+BHBA+His+Lys; 0.762, 252.102, 1+ALB+AST+NEFA+Lys+Phe; 0.762, 252.500, 1+Ala+Gly+Lys+TCHO+ALB; 0.762, 254.419, 1+Ala+Gly+Lys+ALB+BHBA; 0.762, 253.469, 1+ALB+BUN+3MeHis+Val+Phe; 0.762, 250.458, 1+ALB+BUN+ALT+Orn+Tyr; 0.762, 251.669, 1+ALB+AST+Arg+Phe+Trp; 0.762, 251.024, 1+ALB+AST+3MeHis+Orn+Trp; 0.76 2, 250.414, 1+ALB+ALT+T-BIL+His+Lys; 0.762, 248.961, 1+ALB+AST+ALT+Asp+Trp; 0.762, 252.540, 1+BCAA+Trp+ALB+BUN+Ca; 0.762, 253.46 8, 1+ALB+BUN+3MeHis+Tyr+Phe; 0.762, 252.198, 1+ALB+AST+NEFA+T-BIL+Lys; 0.762, 250.344, 1+Lys+Phe+TCHO+ALT+ALB; 0.761, 251.048, 1+ALB+AST+ALT+BHBA+Arg; 0.761, 250.946, 1+ALB+ALT+NEFA+3MeHis+Arg; 0.761, 250.917, 1+ALB+ALT+3MeHis+Arg+Tyr; 0.761, 251.219, 1+ALB+ALT+T-BIL+His+Arg; 0.761, 250.836, 1+ALB+BUN+ALT+Orn+Ile; 0.761, 251.224, 1+ALB+ALT+His+Arg+Ile; 0.761, 250.271, 1+ALB+ALT+His+Lys+Ile; 0.761, 250.677, 1+ALB+ALT+gGT+His+Lys; 0.761, 249.73 3, 1+ALB+AST+ALT+3MeHis+Lys; 0.761, 252.154, 1+Ala+Lys+AST+ALB+NEFA; 0.761, 252.544, 1+Trp+ALB+BUN+Ca+NEFA; 0.761, 251.105, 1+ALB+ALT+gGT+His+Arg; 0.761, 252.234, 1+ALB+BUN+His+Thr+Orn; 0.761, 250.573, 1+ALB+ALT+His+Thr+Lys; 0.761, 250.527, 1+Arg+TCHO+ALT+AST+ALB; 0.761, 251.015, 1+Gly+Trp+ALT+AST+ALB; 0.761, 250.169, 1+ALB+ALT+Arg+Thr+Lys; 0.761, 249.947, 1+ALB+AST+ALT+3MeHis+Arg; 0.761, 252.195, 1+ALB+AST+NEFA+BHBA+Lys; 0.761, 254.022, 1+ALB+Orn+Tyr+Phe+Trp; 0.761, 252.528, 1+Gly+Trp+TG+ALT+ALB; 0.761, 2 53.228, 1+ALB+T-BIL+Glc+His+Lys; 0.761, 251.097, 1+ALB+ALT+NEFA+T-BIL+Lys; 0.761, 252.530, 1+Trp+gGT+ALB+BUN+Ca; 0.761, 253.691, 1+ALB+BUN+NEFA+Val+Phe; 0.761, 252.129, 1+ALB+AST+NEFA+Lys+Val; 0.761, 250.966, 1+ALB+AST+ALT+T-BIL+Arg; 0.761, 251.256, 1+ALB+ALT+Arg+Orn+Val; 0.761, 252.820, 1+ALB+3MeHis+Arg+Lys+Tyr; 0.7 61, 250.957, 1+ALB+ALT+Orn+Lys+Tyr; 0.761, 250.837, 1+ALB+BUN+ALT+gGT+Orn; 0.761, 251.744, 1+ALB+BUN+AST+Arg+Orn; 0.761, 251.152, 1+Ala+Lys+ALT+ALB+NEFA; 0.761, 250.588, 1+ALB+ALT+BHBA+Lys+Ile; 0.761, 250.210, 1+ALB+ALT+Glc+Lys+Ile; 0.761, 251.256, 1+ALB+ALT+BHBA+Arg+Orn; 0.761, 250.837, 1+ALB+BUN+ALT+NEFA+Orn; 0.761, 252.094, 1+Gly+Trp+ALT+ALB+NEFA; 0.761, 250.957, 1+ALB+ALT+T-BIL+Orn+Lys; 0.761, 253.495, 1+ALB+AST+NEFA+Orn+Ile; 0.761, 250.10 1, 1+ALB+BUN+Ca+AST+Lys; 0.761, 251.272, 1+ALB+ALT+T-BIL+Arg+Orn; 0.761, 250.942, 1+ALB+ALT+Thr+Orn+Lys; 0.761, 250.848, 1+ALB+ALT+NEFA+Orn+Lys; 0.761, 250.818, 1+ALB+BUN+ALT+BHBA+Orn; 0.761, 253.068, 1+Ala+Lys+His+ALB+NEFA; 0.761, 250.979, 1+ALB+ALT+T-BIL+Glc+Lys; 0.761, 251.533, 1+ALB+AST+Orn+Phe+Trp; 0.761, 250.219, 1+ALB+AST+NEFA+Asp+Lys; 0.761, 254.753, 1+Ala+Gly+Trp+ALB+Ca; 0. 761, 254.274, 1+Ala+Gly+Lys+ALB+NEFA; 0.761, 250.801, 1+ALB+ALT+NEFA+Glc+Lys; 0.761, 251.270, 1+ALB+ALT+NEFA+Arg+Orn; 0.761, 251. 201, 1+ALB+ALT+Glc+His+Arg; 0.761, 255.560, 1+Gly+BCAA+Trp+Glc+ALB; 0.761, 251.165, 1+ALB+ALT+NEFA+BHBA+Lys; 0.761, 251.006, 1+ALB+AST+ALT+Glc+Arg; 0.761, 250.604, 1+ALB+ALT+gGT+Lys+Ile; 0.76 1, 253.870, 1+ALB+AST+Thr+Orn+Ile; 0.761, 249.805, 1+ALB+AST+ALT+Lys+Ile; 0.761, 253.478, 1+ALB+Orn+Lys+Tyr+Trp; 0.761, 253.055, 1+ALB+3MeHis+Lys+Tyr+Trp; 0.761, 252.933, 1+BCAA+Trp+TG+ALT+ALB; 0.761, 252.284, 1+ALB+BUN+AST+Arg+Thr; 0.761, 251.165, 1+ALB+ALT+gGT+NEFA+Lys; 0.761, 251.686, 1+ALB+BUN+AST+NEFA+Arg; 0.761, 250.158, 1+ALB+Ca+ALT+Arg+Lys; 0.761, 250.967, 1+ALB+Ca+AST+ALT+Arg; 0.761, 250.870, 1+ALB+ALT+3MeHis+Arg+Val; 0.761, 250.814, 1+ALB+BUN+ALT+T-BIL+Orn; 0.761, 252.618, 1+Gly+Trp+ALT+ALB+BHBA; 0.761, 252.470, 1+ALB+T-BIL+His+Orn+Lys; 0.761, 250.960, 1+ALB+ALT+BHBA+Orn+Lys; 0.761, 251.565, 1+ALB+AST+ALT+Val+Trp; 0.761, 253.929, 1+ALB+AST+Arg+Thr+Ile; 0.761, 253.504, 1+ALB+NEFA+Lys+Tyr+Trp; 0.761, 254.369, 1+Ala+Gly+Lys+gGT+ALB; 0.761, 252.438, 1+Gly+BCAA+Trp+ALT+ALB; 0.761, 251.462, 1+ALB+ALT+gGT+Arg+Thr; 0. 761, 250.254, 1+ALB+AST+ALT+Lys+Phe; 0.761, 249.966, 1+ALB+AST+ALT+Orn+Lys; 0.760, 253.907, 1+ALB+T-BIL+Orn+Lys+Ile; 0.760, 252. 576, 1+ALB+Glc+His+Orn+Lys; 0.760, 250.826, 1+ALB+BUN+AST+Asp+Orn; 0.760, 250.048, 1+ALB+AST+ALT+NEFA+Lys; 0.760, 253.352, 1+Ala+Gly+Trp+TCHO+ALB; 0.760, 252.682, 1+ALB+BUN+Asp+Tyr+Phe; 0.760, 251.212, 1+ALB+ALT+gGT+Arg+Orn; 0.760, 251.000, 1+ALB+3MeHis+Asp+Lys+Phe; 0.760, 253.247, 1+Lys+His+AST+ALB+TP; 0.760, 251.272, 1+Ala+Arg+TCHO+ALT+ALB; 0.760, 250.836, 1+ALB+NEFA+3MeHis+Asp+Lys; 0.760, 253.244, 1+Trp+TG+ALT+ALB+BHBA; 0.760, 251.830, 1+ALB+ALT+NEFA+Arg+Tyr; 0.760, 250.900, 1+ALB+ALT+Orn+Lys+Val; 0.760, 252.010, 1+Gly+Trp+TCHO+ALT+ALB; 0.760, 251.162, 1+ALB+ALT+NEFA+Lys+Tyr; 0.760, 250.959, 1+ALB+ALT+gGT+Orn+Lys; 0.760, 252.560, 1+ALB+AST+Arg+Orn+Lys; 0.760, 252.141, 1+ALB+AST+NEFA+Thr+Lys; 0.760, 251.658, 1+ALB+BUN+AST+His+Orn; 0.760, 250.056, 1+ALB+AST+ALT+His+Lys; 0.760, 253.336, 1+ALB+AST+Thr+Lys+Ile; 0.760, 251. 783, 1+ALB+AST+T-BIL+His+Lys; 0.760, 253.681, 1+ALB+3MeHis+Orn+Lys+Val; 0.760, 252.993, 1+ALB+3MeHis+Orn+Lys+Trp; 0.760, 250.54 5, 1+ALB+3MeHis+Asp+Lys+Tyr; 0.760, 252.734, 1+ALB+ALT+NEFA+Val+Trp; 0.760, 252.634, 1+Gly+Trp+ALT+gGT+ALB; 0.760, 248.944, 1+AL B+ALT+NEFA+Asp+Lys; 0.760, 251.466, 1+ALB+BUN+NEFA+Asp+Phe; 0.7 60, 250.702, 1+ALB+BUN+ALT+Orn+Val; 0.760, 251.833, 1+ALB+ALT+gG T+T-BIL+Arg; 0.760, 251.712, 1+ALB+Asp+Lys+Tyr+Trp; 0.760, 251.1 53, 1+ALB+ALT+NEFA+Thr+Lys; 0.760, 251.150, 1+ALB+ALT+NEFA+Lys+Val; 0.760, 252.262, 1+ALB+AST+T-BIL+Orn+Lys; 0.760, 252.102, 1+A LB+AST+T-BIL+Arg+Lys; 0.760, 253.145, 1+ALB+BHBA+His+Orn+Lys; 0. 760, 254.094, 1+ALB+Lys+Tyr+Phe+Trp; 0.760, 253.307, 1+ALB+3MeHi s+Lys+Phe+Trp; 0.760, 252.947, 1+BCAA+Trp+ALT+ALB+NEFA; 0.760, 2 53.813, 1+Ala+BCAA+Trp+Lys+ALB; 0.760, 251.787, 1+Ala+Arg+ALT+g GT+ALB; 0.760, 251.734, 1+ALB+ALT+Glc+His+Orn; 0.760, 251.223, 1+ALB+Ca+ALT+Arg+Orn; 0.760, 250.743, 1+ALB+BUN+Ca+ALT+Orn; 0.760, 252.337, 1+BCAA+Trp+TCHO+ALT+ALB; 0.760, 252.677, 1+ALB+BUN+3Me His+Arg+Orn; 0.760, 252.967, 1+BCAA+Trp+ALT+ALB+BHBA; 0.760, 251. 137, 1+Ala+Lys+Glc+ALT+ALB; 0.760, 252.305, 1+ALB+AST+NEFA+His+Orn; 0.760, 250.998, 1+ALB+AST+ALT+His+Orn; 0.760, 252.967, 1+BCAA+Trp+ALT+gGT+ALB; 0.760, 251.380, 1+ALB+ALT+Glc+Arg+Thr; 0.760, 251.821, 1+ALB+ALT+gGT+BHBA+Arg; 0.760, 253.446, 1+ALB+AST+Arg+Orn+Tyr; 0.760, 251.931, 1+Trp+ALT+AST+ALB+BHBA; 0.760, 255.496, 1+ALB+NEFA+Orn+Tyr+Phe; 0.760, 253.259, 1+Trp+ALT+gGT+ALB+BHB A; 0.760, 253.195, 1+ALB+NEFA+3MeHis+Lys+Trp; 0.760, 251.769, 1+A LB+ALT+NEFA+BHBA+Arg; 0.760, 250.094, 1+ALB+ALT+Arg+Asp+Orn; 0. 760, 250.782, 1+Ala+Lys+TCHO+ALT+ALB; 0.760, 250.936, 1+ALB+Ca+A LT+Orn+Lys; 0.760, 251.256, 1+ALB+ALT+BHBA+His+Arg; 0.760, 253.2 41, 1+Trp+TG+ALT+ALB+NEFA; 0.760, 249.044, 1+ALB+ALT+Asp+Orn+Ly s; 0.760, 251.106, 1+ALB+Ca+ALT+His+Arg; 0.760, 251.134, 1+ALB+AS T+NEFA+Asp+Trp; 0.760, 250.644, 1+ALB+3MeHis+Asp+Lys+Val; 0.760, 250.953, 1+ALB+ALT+BHBA+Glc+Lys; 0.760, 252.010, 1+ALB+ALT+T-BI L+His+Orn; 0.760, 251.923, 1+ALB+AST+ALT+NEFA+Trp; 0.760, 253.24 6, 1+Trp+TG+ALT+gGT+ALB; 0.760, 251.958, 1+ALB+ALT+T-BIL+BHBA+A rg; 0.760, 253.002, 1+ALB+3MeHis+Arg+Lys+Val; 0.760, 250.981, 1+A LB+3MeHis+Asp+Orn+Lys; 0.760, 254.829, 1+Ala+Gly+Trp+gGT+ALB; 0. 760, 253.352, 1+ALB+NEFA+His+Thr+Lys; 0.759, 252.721, 1+ALB+ALT+3MeHis+Val+Trp; 0.759, 251.747, 1+ALB+ALT+gGT+Glc+Arg; 0.759, 25 1.566, 1+ALB+ALT+NEFA+Arg+Val; 0.759, 251.625, 1+ALB+ALT+NEFA+T-BIL+Arg; 0.759, 252.915, 1+ALB+AST+Orn+Lys+Tyr; 0.759, 250.639, 1+ALB+Ca+ALT+His+Lys; 0.759, 249.820, 1+ALB+AST+3MeHis+Asp+Tr p; 0.759, 251.751, 1+ALB+ALT+NEFA+Glc+Arg; 0.759, 255.617, 1+Gly+Trp+Glc+TG+ALB; 0.759, 252.743, 1+ALB+ALT+Tyr+Val+Trp; 0.759, 25 2.020, 1+ALB+ALT+BHBA+His+Orn; 0.759, 250.349, 1+ALB+AST+ALT+T-BIL+Lys; 0.759, 254.725, 1+Ala+Gly+Arg+TG+ALB; 0.759, 253.247, 1+ALB+3MeHis+Arg+Orn+Lys; 0.759, 249.164, 1+ALB+ALT+Asp+Lys+Val; 0.759, 253.019, 1+ALB+AST+T-BIL+Arg+Orn; 0.759, 253.884, 1+ALB+A ST+T-BIL+Orn+Ile; 0.759, 252.642, 1+ALB+AST+Arg+Lys+Tyr; 0.759, 253.006, 1+Trp+Glc+TCHO+AST+ALB; 0.759, 251.410, 1+Trp+TCHO+ALT+AST+ALB; 0.759, 251.738, 1+ALB+ALT+gGT+NEFA+Arg; 0.759, 252.553, 1+ALB+AST+His+Thr+Orn; 0.759, 252.155, 1+ALB+AST+3MeHis+Lys+Va l; 0.759, 252.850, 1+ALB+3MeHis+Lys+Val+Trp; 0.759, 251.849, 1+Al a+BCAA+Arg+ALT+ALB; 0.759, 251.843, 1+Ala+Arg+TG+ALT+ALB; 0.759, 251.129, 1+ALB+ALT+Glc+Thr+Lys; 0.759, 248.334, 1+ALB+AST+ALT+A sp+Lys; 0.759, 253.311, 1+ALB+AST+His+Orn+Ile; 0.759, 251.454, 1+ALB+AST+3MeHis+Orn+Lys; 0.759, 250.512, 1+Lys+ALT+AST+ALB+TP; 0. 759, 251.907, 1+ALB+ALT+BHBA+Glc+Arg; 0.759, 251.900, 1+ALB+ALT+T-BIL+Glc+Arg; 0.759, 251.407, 1+ALB+ALT+Arg+Tyr+Val; 0.759, 252. 616, 1+ALB+AST+Glc+Orn+Lys; 0.759, 254.466, 1+ALB+AST+BHBA+Orn+Ile; 0.759, 251.374, 1+ALB+ALT+T-BIL+BHBA+Lys; 0.759, 251.737, 1+ALB+AST+NEFA+Glc+Lys; 0.759, 253.249, 1+Trp+ALT+ALB+NEFA+BHBA; 0.759, 253.249, 1+Trp+ALT+gGT+ALB+NEFA; 0.759, 250.609, 1+ALB+AL T+Arg+Asp+Tyr; 0.759, 251.398, 1+ALB+ALT+gGT+BHBA+Lys; 0.759, 25 1.371, 1+ALB+ALT+T-BIL+Thr+Lys; 0.759, 252.947, 1+ALB+AST+Orn+L ys+Val; 0.759, 249.741, 1+ALB+AST+ALT+Arg+Asp; 0.759, 252.686, 1+Trp+TCHO+TG+ALT+ALB; 0.759, 250.162, 1+ALB+ALT+NEFA+Asp+Trp; 0. 759, 251.973, 1+ALB+ALT+NEFA+His+Orn; 0.759, 251.126, 1+ALB+ALT+gGT+Glc+Lys; 0.759, 251.625, 1+ALB+AST+ALT+NEFA+Orn; 0.759, 251. 447, 1+Ala+Lys+TG+ALT+ALB; 0.759, 251.904, 1+Trp+TG+ALT+AST+AL B; 0.759, 251.745, 1+BCAA+Trp+ALT+AST+ALB; 0.759, 253.548, 1+Ala+Trp+AST+ALB+TP; 0.759, 250.514, 1+ALB+AST+ALT+BHBA+Lys; 0.759, 2 50.486, 1+ALB+AST+3MeHis+Arg+Asp; 0.759, 252.687, 1+Trp+TCHO+AL T+ALB+BHBA; 0.759, 250.571, 1+ALB+Ca+ALT+Lys+Ile; 0.759, 250.017, 1+Lys+TCHO+ALT+AST+ALB; 0.759, 252.940, 1+ALB+AST+Thr+Orn+Lys; 0.759, 252.018, 1+ALB+ALT+His+Orn+Ile; 0.759, 253.290, 1+ALB+AST+gGT+His+Orn; 0.759, 253.283, 1+ALB+AST+BHBA+His+Orn; 0.759, 250. 167, 1+ALB+ALT+Asp+Tyr+Trp; 0.759, 249.068, 1+ALB+ALT+Asp+Lys+T yr; 0.759, 252.980, 1+ALB+AST+Orn+Lys+Phe; 0.759, 251.335, 1+ALB+AST+ALT+3MeHis+Orn; 0.759, 250.298, 1+ALB+AST+ALT+Glc+Lys; 0.75 9, 253.381, 1+ALB+gGT+NEFA+His+Lys; 0.759, 251.743, 1+ALB+Ca+ALT+gGT+Arg; 0.759, 251.820, 1+ALB+AST+3MeHis+Arg+Orn; 0.759, 251.4 47, 1+Ala+Lys+ALT+gGT+ALB; 0.759, 252.957, 1+ALB+AST+BHBA+Arg+L ys; 0.759, 252.965, 1+ALB+AST+BHBA+Orn+Lys; 0.759, 250.579, 1+BCA A+Lys+ALT+AST+ALB; 0.759, 251.747, 1+ALB+Ca+ALT+Glc+Arg; 0.759, 254.461, 1+ALB+3MeHis+Lys+Tyr+Phe; 0.759, 251.451, 1+Ala+Lys+Th r+ALT+ALB; 0.759, 251.446, 1+ALB+ALT+Lys+Tyr+Val; 0.759, 251.375, 1+ALB+ALT+gGT+T-BIL+Lys; 0.759, 252.687, 1+Trp+TCHO+ALT+ALB+NE FA; 0.759, 253.989, 1+ALB+3MeHis+Orn+Lys+Tyr; 0.759, 254.310, 1+A LB+3MeHis+Lys+Val+Phe; 0.759, 251.114, 1+ALB+ALT+His+Thr+Orn; 0. 759, 251.397, 1+ALB+ALT+BHBA+Thr+Lys; 0.759, 251.341, 1+BCAA+Lys+ALT+ALB+TP; 0.759, 253.260, 1+Ala+Trp+Glc+AST+ALB; 0.758, 251.1 19, 1+ALB+Ca+ALT+NEFA+Lys; 0.758, 252.597, 1+Gly+Trp+ALT+ALB+C a; 0.758, 251.763, 1+ALB+Ca+ALT+NEFA+Arg; 0.758, 253.004, 1+ALB+A ST+Arg+Lys+Phe; 0.758, 251.955, 1+ALB+BUN+AST+T-BIL+Orn; 0.758, 254.029, 1+ALB+AST+ gGT+T-BIL+Orn; 0.758, 251.988, 1+ALB+AST+gGT+ NEFA+Lys; 0.758, 252.057, 1+ALB+Ca+AST+NEFA+Lys; 0.758, 252.693, 1+Trp+TCHO+ALT+gGT+ALB; 0.758, 252.258, 1+ALB+AST+NEFA+Arg+As p; 0.758, 251.799, 1+Trp+ALT+AST+gGT+ALB; 0.758, 251.671, 1+ALB+A ST+ALT+Orn+Ile; 0.758, 250.620, 1+Ala+Lys+ALT+ AST+ALB; 0.758, 25 1.107, 1+ALB+Ca+ALT+Glc+Lys; 0.758, 251.876, 1+Ala+Arg+Glc+ALT+ALB; 0.758, 253.762, 1+ALB+AST+Orn+Tyr+Phe; 0.758, 253.548, 1+Trp+AST+ALB+TP+NEFA; 0.758, 252.128, 1+ALB+ AST+3MeHis+Lys+Phe; 0.7 58, 252.595, 1+ALB+ALT+ NEFA+3MeHis+Orn; 0.758, 254.403, 1+ALB+BU N+Thr+ Orn+Ile; 0.758, 252.006, 1+ALB+ALT+gGT+His+Orn; 0.758, 251. 452, 1+ALB+ALT+gGT+Thr+Lys; 0.758, 251.755, 1+ALB+AST+Arg+Asp+L ys; 0.758, 254.431, 1+ALB+Ca+AST+Orn+Ile; 0.758, 252.928, 1+BCAA+ Trp+ALT+ALB+Ca; 0.758, 254.442, 1+ALB+AST+gGT+ Orn+Ile; 0.758, 25 1.410, 1+Ala+BCAA+Lys+ALT+ALB; 0.758, 253.137, 1+Ala+Trp+AST+AL B+NEFA; 0.758, 251.736, 1+ALB+AST+ALT+Tyr+Trp; 0.758, 251.526, 1+ALB+AST+ALT+Thr+Orn; 0.758, 253.654, 1+Ala+Trp+ TG+AST+ALB; 0.75 8, 250.624, 1+ALB+AST+ALT+Lys+ Val; 0.758, 250.623, 1+Lys+TG+ALT+AST+ALB; 0.758, 255.557, 1+Gly+Trp+Glc+gGT+ALB; 0.758, 252.989, 1+ALB+AST+Arg+Thr+Lys; 0.758, 250.568, 1+ALB+ AST+ALT+gGT+Lys; 0. 758, 253.661, 1+ALB+AST+ NEFA+Orn+Tyr; 0.758, 251.458, 1+ALB+AST+Asp+Val+ Trp; 0.758, 252.667, 1+ALB+AST+NEFA+Orn+Phe; 0.758, 252. 044, 1+ALB+BUN+AST+NEFA+Orn; 0.758, 250.626, 1+ALB+AST+ALT+Thr+Lys; 0.758, 253.103, 1+ALB+ AST+His+Lys+Ile; 0.758, 254.220, 1+ALB+AST+Glc+ Orn+Ile; 0.758, 252.999, 1+ALB+AST+Glc+His+Orn; 0.758, 253.652, 1+Ala+BCAA+Trp+AST+ALB; 0.758, 250.619, 1+ALB+AST+ALT+Lys+Tyr; 0.758, 251.867, 1+ALB+Ca+ALT+T-BIL+Arg; 0.758, 253.270, 1+ALB+ Ca+AST+His+Orn; 0.758, 251.492, 1+ALB+AST+Asp+ Phe+Trp; 0. 758, 253.962, 1+ALB+NEFA+3MeHis+Lys+ Phe; 0.758, 253.511, 1+ALB+A ST+Arg+Thr+Orn; 0.758, 252.973, 1+ALB+AST+gGT+Orn+Lys; 0.758, 25 3.612, 1+Ala+Trp+AST+ALB+BHBA; 0.758, 251.904, 1+ALB+ BUN+AST+3M eHis+Orn; 0.758, 252.254, 1+ALB+AST+ T-BIL+Glc+Lys; 0.758, 253.74 3, 1+Trp+Glc+TG+AST+ ALB; 0.758, 252.234, 1+ALB+AST+3MeHis+Lys+T yr; 0.758, 254.850, 1+ALB+3MeHis+Orn+Val+Phe; 0.758, 253.973, 1+A LB+AST+T-BIL+Thr+Orn; 0.758, 252.341, 1+ALB+ALT+Thr+Orn+Ile; 0. 758, 253.600, 1+ALB+ AST+NEFA+BHBA+Orn; 0.758, 253.513, 1+ALB+AST+ NEFA+Thr+Orn; 0.758, 253.376, 1+ALB+AST+gGT+Lys+ Ile; 0.757, 253. 915, 1+ALB+AST+T-BIL+BHBA+Orn; 0.757, 253.553, 1+ALB+AST+gGT+NE FA+Orn; 0.757, 251.905, 1+Trp+ALT+AST+ALB+Ca; 0.757, 253.095, 1+A la+Trp+TCHO+AST+ALB; 0.757, 251.846, 1+ALB+Ca+ ALT+BHBA+Arg; 0.7 57, 252.568, 1+ALB+ALT+3Me-His+Orn+Val; 0.757, 253.563, 1+ALB+AST+BHBA+Arg+ Orn; 0.757, 252.787, 1+ALB+AST+Glc+His+Lys; 0.757, 253. 235, 1+ALB+AST+BHBA+His+Lys; 0.757, 253.092, 1+ALB+AST+NEFA+3Me His+Orn; 0.757, 252.076, 1+ALB+AST+NEFA+Asp+Orn; 0.757, 249.920, 1+ALB+ AST+ALT+Asp+Orn; 0.757, 253.985, 1+Trp+TG+AST+ ALB+TP; 0.7 57, 252.867, 1+ALB+AST+T-BIL+Thr+Lys; 0.757, 253.663, 1+ALB+AST+NEFA+T-BIL+Orn; 0.757, 251.571, 1+ALB+AST+Asp+Orn+Lys; 0.757, 25 3.652, 1+ALB+AST+NEFA+Orn+Val; 0.757, 252.931, 1+ALB+ AST+T-BIL+BHBA+Lys; 0.757, 251.340, 1+ALB+Ca+ ALT+T-BIL+Lys; 0.757, 253.634, 1+ALB+AST+T-BIL+ Glc+Orn; 0.757, 254.468, 1+ALB+AST+gGT+Thr+Or n; 0.757, 253.588, 1+Ala+Trp+AST+gGT+ALB; 0.757, 252.654, 1+Trp+T CHO+ALT+ALB+Ca; 0.757, 252.338, 1+ALB+ALT+Glc+Thr+Orn; 0.757, 25 2.742, 1+ALB+ ALT+NEFA+Thr+Orn; 0.757, 251.725, 1+ALB+AST+ ALT+T-BIL+Orn; 0.757, 253.464, 1+Trp+TCHO+AST+ ALB+TP; 0.757, 251.944, 1+ALB+Ca+ALT+His+Orn; 0.757, 254.991, 1+Ala+Trp+Glc+TCHO+ALB; 0. 757, 253.383, 1+ALB+AST+Arg+Orn+Phe; 0.757, 252.342, 1+ALB+BUN+A ST+Thr+Orn; 0.757, 253.359, 1+ALB+ AST+BHBA+Lys+Ile; 0.757, 253.8 91, 1+Trp+AST+ALB+ TP+BHBA; 0.757, 250.770, 1+ALB+AST+3MeHis+Asp+ Orn; 0.757, 252.673, 1+ALB+BUN+AST+BHBA+Orn; 0.757, 254.476, 1+A LB+AST+BHBA+Thr+Orn; 0.757, 251.353, 1+ALB+Ca+ALT+BHBA+Lys; 0.7 57, 252.723, 1+ALB+ALT+BHBA+Thr+Orn; 0.757, 252.446, 1+ALB+ AST+3 MeHis+Orn+Phe; 0.757, 253.588, 1+Trp+Glc+ AST+ALB+TP; 0.757, 253. 373, 1+ALB+AST+NEFA+ Glc+Orn; 0.757, 253.904, 1+BCAA+Trp+AST+ALB+TP; 0.757, 253.533, 1+ALB+Ca+AST+Arg+Orn; 0.757, 253.162, 1+ALB+AST+NEFA+Arg+Thr; 0.757, 254.044, 1+ALB+Ca+AST+T-BIL+Orn; 0.757, 253.938, 1+ALB+ AST+Orn+Val+Phe; 0.757, 251.778, 1+ALB+AST+ALT+B HBA+Orn; 0.757, 253.829, 1+Gly+Trp+Glc+TCHO+ALB; 0.757, 251.567, 1+ALB+AST+ALT+Glc+Orn; 0.757, 251.718, 1+ALB+AST+ALT+Orn+Val; 0. 756, 253.539, 1+Ala+Trp+AST+ALB+Ca; 0.756, 252.861, 1+ALB+ AST+Gl c+Lys+Ile; 0.756, 256.041, 1+ALB+NEFA+Orn+ Val+Phe; 0.756, 251.73 4, 1+ALB+AST+ALT+gGT+Orn; 0.756, 256.218, 1+Ala+Trp+Glc+ALB+NEF A; 0.756, 253.640, 1+ALB+Ca+AST+NEFA+Orn; 0.756, 252.460, 1+ALB+B UN+ALT+NEFA+Val; 0.756, 250.986, 1+ALB+ ALT+NEFA+Asp+Orn; 0.756, 252.607, 1+ALB+BUN+ AST+Glc+Orn; 0.756, 254.610, 1+ALB+AST+gGT+B HBA+Orn; 0.756, 253.410, 1+ALB+AST+Glc+Arg+Orn; 0.756, 253.667, 1+Trp+Glc+AST+gGT+ALB; 0.756, 253.922, 1+Trp+AST+gGT+ALB+TP; 0.7 56, 252.734, 1+ALB+AST+Glc+Arg+Lys; 0.756, 251.415, 1+ALB+Ca+ ALT+gGT+Lys; 0.756, 251.420, 1+ALB+Ca+ALT+Thr+ Lys; 0.756, 251.986, 1+ALB+BUN+AST+ALT+Val; 0.756, 256.074, 1+Gly+BCAA+Trp+TG+ALB; 0. 756, 254.383, 1+ALB+AST+gGT+Glc+Orn; 0.756, 251.646, 1+ALB+ AST+A LT+Orn+Tyr; 0.756, 253.451, 1+ALB+AST+3Me-His+Orn+Val; 0.756, 250. 587, 1+ALB+Ca+AST+ALT+ Lys; 0.756, 252.946, 1+ALB+Ca+AST+Orn+Ly s; 0.756, 253.652, 1+BCAA+Trp+Glc+AST+ALB; 0.756, 253.644, 1+Trp+TCHO+TG+AST+ALB; 0.756, 253.362, 1+ALB+ Ca+AST+His+Lys; 0.756, 25 2.045, 1+BCAA+TCHO+ ALT+ALB+BUN; 0.756, 250.993, 1+ALB+ALT+Asp+O rn+Tyr; 0.755, 253.504, 1+BCAA+Trp+TCHO+AST+ALB; 0.755, 251.742, 1+ALB+Ca+AST+ALT+Orn; 0.755, 252.567, 1+BCAA+TG+ALT+ALB+BUN; 0. 755, 254.328, 1+ALB+AST+BHBA+Glc+Orn; 0.755, 254.043, 1+ALB+ AST+BHBA+Thr+Lys; 0.755, 253.924, 1+Trp+AST+ ALB+TP+Ca; 0.755, 252.72 7, 1+ALB+ALT+T-BIL+Thr+ Orn; 0.755, 252.723, 1+ALB+ALT+gGT+Thr+O rn; 0.755, 250.837, 1+ALB+ALT+Asp+Orn+Val; 0.755, 252.621, 1+BCAA+ALT+ALB+BUN+NEFA; 0.755, 252.564, 1+BCAA+Glc+ALT+ALB+BUN; 0.75 5, 253.572, 1+ALB+BUN+ALT+T-BIL+Ile; 0.755, 252.514, 1+Gly+ BCAA+ALT+ALB+BUN; 0.755, 256.043, 1+Gly+BCAA+ Trp+gGT+ALB; 0.755, 251. 948, 1+ALB+AST+Asp+Lys+ Tyr; 0.755, 252.718, 1+ALB+Ca+ALT+Thr+Or n; 0.755, 256.480, 1+Ala+BCAA+Trp+Glc+ALB; 0.755, 254.106, 1+BCAA+Trp+TG+AST+ALB; 0.755, 254.602, 1+ALB+ Ca+AST+BHBA+Orn; 0.755, 2 52.631, 1+BCAA+ALT+ gGT+ALB+BUN; 0.755, 256.109, 1+Gly+Trp+TG+gG T+ALB; 0.755, 252.334, 1+BCAA+ALT+ALB+BUN+ BHBA; 0.755, 254.085, 1+Trp+TG+AST+gGT+ALB;

0.755, 254.450, 1+ALB+Ca+AST+Thr+Orn; 0.75 5, 254.109, 1+ALB+AST+Glc+Thr+Orn; 0.755, 256.483, 1+Ala+Trp+Glc+TG+ALB; 0.755, 254.334, 1+ALB+Ca+AST+Glc+Orn; 0.754, 252.123, 1+ALB+AST+Asp+Lys+Val; 0.754, 255.204, 1+BCAA+Trp+Glc+TCHO+ALB; 0. 754, 253.524, 1+Trp+TCHO+AST+gGT+ALB; 0.754, 254.594, 1+ALB+Ca+A ST+gGT+Orn; 0.754, 255.411, 1+Ala+Trp+TCHO+ALB+NEFA; 0.754, 255. 536, 1+Ala+Gly+BCAA+ALB+BUN; 0.754, 253.988, 1+BCAA+Trp+AST+gGT+ALB; 0.754, 256.295, 1+Ala+Trp+Glc+gGT+ALB; 0.753, 255.778, 1+Al a+Trp+TCHO+TG+ALB; 0.753, 252.181, 1+BCAA+ALT+AST+ALB+BUN; 0.75 3, 254.617, 1+Gly+BCAA+Trp+TCHO+ALB; 0.753, 256.731, 1+Ala+Trp+T G+ALB+NEFA; 0.753, 254.746, 1+Gly+Trp+TCHO+TG+ALB; 0.753, 254.77 9, 1+Gly+Trp+TCHO+gGT+ALB; 0.753, 255.708, 1+Ala+BCAA+Trp+TCHO+ALB; 0.753, 256.706, 1+Ala+BCAA+Trp+ALB+NEFA; 0.752, 255.725, 1+A la+Trp+TCHO+gGT+ALB; 0.751, 256.912, 1+Ala+BCAA+Trp+TG+ALB; 0.7 51, 254.297, 1+Gly+BCAA+ALT+AST+ALB; 0.750, 256.799, 1+Ala+Trp+T G+gGT+ALB; 0.750, 254.642, 1+Ala+Gly+AST+ALB+BUN; 0.750, 256.784, 1+Ala+BCAA+Trp+gGT+ALB; 0.750, 256.660, 1+BCAA+Trp+Glc+gGT+AL B; 0.749, 257.065, 1+Ala+Gly+TG+ALB+BUN; 0.749, 256.040, 1+BCAA+T rp+TCHO+TG+ALB; 0.749, 254.857, 1+Ala+BCAA+AST+ALB+BUN; 0.749, 2 54.655, 1+BCAA+Glc+TCHO+ALT+ALB; 0.748, 255.212, 1+Gly+BCAA+TG+ALT+ALB; 0.748, 255.092, 1+Gly+BCAA+Glc+ALT+ALB; 0.748, 259.526, 1+Ala+Gly+BCAA+Glc+ALB; 0.748, 255.433, 1+Ala+Gly+TCHO+ALB+BU N; 0.748, 254.368, 1+Gly+BCAA+TCHO+ALT+ALB; 0.748, 256.783, 1+Ala+Gly+gGT+ALB+BUN; 0.748, 255.616, 1+BCAA+Glc+TG+ALT+ALB; 0.748, 257.176, 1+Gly+BCAA+Glc+AST+ALB; 0.748, 255.265, 1+Gly+BCAA+ALT+gGT+ALB; 0.747, 257.484, 1+Gly+BCAA+TG+AST+ALB; 0.747, 254.308, 1+BCAA+TCHO+ALT+AST+ALB; 0.747, 257.414, 1+Gly+BCAA+AST+gGT+AL B; 0.746, 256.171, 1+Gly+Glc+ALT+ALB+BUN; 0.746, 254.952, 1+BCAA+TCHO+TG+ALT+ALB; 0.746, 255.764, 1+BCAA+TG+ALT+gGT+ALB; 0.746, 2 56.284, 1+Gly+BCAA+TCHO+AST+ALB; 0.746, 255.609, 1+BCAA+Glc+ALT+gGT+ALB; 0.746, 255.009, 1+BCAA+ALT+AST+gGT+ALB; 0.746, 259.731, 1+Ala+Gly+BCAA+TG+ALB; 0.746, 255.033, 1+BCAA+TG+ALT+AST+ALB; 0. 746, 254.944, 1+BCAA+TCHO+ALT+gGT+ALB; 0.746, 256.864, 1+Ala+BCA A+Glc+ALB+BUN; 0.746, 256.177, 1+Gly+ALT+gGT+ALB+BUN; 0.746, 254. 995, 1+Gly+BCAA+AST+ALB+BUN; 0.745, 256.882, 1+Ala+BCAA+TG+ALB+BUN; 0.745, 258.532, 1+Ala+Gly+TG+AST+ALB; 0.745, 254.880, 1+BCAA+Glc+ALT+AST+ALB; 0.745, 259.507, 1+Ala+Gly+BCAA+gGT+ALB; 0.745, 258.539, 1+Ala+Gly+AST+gGT+ALB; 0.745, 255.582, 1+Ala+BCAA+TCHO+ALB+BUN; 0.744, 255.771, 1+BCAA+AST+gGT+ALB+BUN; 0.744, 255.804, 1+BCAA+TG+AST+ALB+BUN; 0.744, 258.470, 1+Ala+Gly+Glc+AST+ALB; 0. 743, 257.325, 1+Ala+Gly+BCAA+TCHO+ALB; 0.743, 255.656, 1+Gly+TCH O+ALT+ALB+BUN; 0.743, 255.636, 1+BCAA+Glc+AST+ALB+BUN; 0.743, 25 6.662, 1+Ala+BCAA+gGT+ALB+BUN; 0.742, 257.330, 1+Ala+Gly+TCHO+A ST+ALB; 0.741, 256.790, 1+Ala+TCHO+AST+ALB+BUN; 0.740, 257.447, 1+Ala+AST+gGT+ALB+BUN; 0.739, 258.925, 1+Ala+BCAA+AST+gGT+ALB; 0. 738, 257.394, 1+Ala+TG+AST+ALB+BUN; 0.738, 258.898, 1+Ala+BCAA+T G+AST+ALB; 0.738, 258.252, 1+Ala+Glc+TCHO+ALB+BUN; 0.737, 258.69 3, 1+Ala+BCAA+Glc+AST+ALB

[415. Formula (with Six Amino Acid+Biochemistry Variables) with Improved Diagnostic Accuracy by Added Parity Term]

0.786, 247.898, 1+BCAA+Trp+Phe+ALT+ALB+BUN; 0.786, 248.158, 1+AL B+BUN+ALT+Tyr+Phe+Trp; 0.783, 247.116, 1+Trp+Phe+His+ALT+ALB+B UN; 0.783, 249.774, 1+BCAA+Trp+Lys+Phe+ALB+BUN; 0.783, 249.719, 1+Ala+Trp+Phe+His+ALB+BUN; 0.783, 248.348, 1+ALB+BUN+ALT+Val+Ph e+Trp; 0.782, 248.330, 1+Ala+Trp+Lys+His+ALB+BUN; 0.782, 246.647, 1+Lys+Phe+His+ALT+ALB+BUN; 0.782, 247.427, 1+BCAA+Lys+Phe+ALT+ALB+BUN; 0.782, 248.542, 1+Trp+Lys+His+ALB+BUN+TP; 0.781, 249.09 8, 1+ALB+BUN+ALT+Orn+Tyr+Phe; 0.781, 248.138, 1+Lys+Phe+Tyr+ALT+ALB+BUN; 0.781, 247.887, 1+ALB+BUN+ALT+Lys+Phe+Trp; 0.781, 248. 679, 1+Trp+Thr+Phe+ALT+ALB+BUN; 0.781, 248.901, 1+ALB+BUN+ALT+A rg+Tyr+Phe; 0.781, 247.859, 1+Arg+Phe+His+ALT+ALB+BUN; 0.780, 24 8.772, 1+Trp+Phe+ALT+gGT+ALB+BUN; 0.780, 246.798, 1+Trp+Phe+ALT+ALB+BUN; 0.780, 248.715, 1+Trp+Phe+Glc+ALT+ALB+BUN; 0.780, 248. 606, 1+Trp+Phe+TG+ALT+ALB+BUN; 0.780, 248.788, 1+ALB+BUN+ALT+NE FA+Phe+Trp; 0.780, 249.831, 1+Ala+BCAA+Trp+Lys+ALB+BUN; 0.780, 2 49.482, 1+Gly+BCAA+Trp+Lys+ALB+BUN; 0.780, 248.515, 1+Gly+Trp+P he+ALT+ALB+BUN; 0.779, 248.731, 1+Trp+Phe+ALT+ALB+BUN+Ca; 0.779, 249.720, 1+Gly+BCAA+Phe+ALT+ALB+BUN; 0.779, 247.579, 1+BCAA+Trp+Lys+ALT+ALB+BUN; 0.779, 248.460, 1+Trp+Phe+TCHO+ALT+ALB+BUN; 0. 779, 248.701, 1+Trp+Phe+ALT+ALB+BUN+BHBA; 0.779, 248.020, 1+ALB+BUN+ALT+Lys+Val+Phe; 0.779, 250.509, 1+BCAA+Trp+Lys+TG+ALB+BU N; 0.779, 246.967, 1+Trp+Lys+His+ALT+ALB+BUN; 0.779, 250.212, 1+B CAA+Trp+Lys+Glc+ALB+BUN; 0.779, 250.273, 1+BCAA+Trp+Lys+ALB+BU N+NEFA; 0.779, 250.815, 1+ALB+BUN+Lys+Val+Phe+Trp; 0.779, 250.24 2, 1+BCAA+Trp+Arg+Lys+ALB+BUN; 0.779, 251.505, 1+ALB+BUN+Arg+Ty r+Phe+Trp; 0.779, 251.625, 1+Ala+Trp+Phe+Tyr+ALB+BUN; 0.778, 251. 598, 1+Ala+BCAA+Trp+Phe+ALB+BUN; 0.778, 248.871, 1+Gly+Phe+His+ALT+ALB+BUN; 0.778, 250.695, 1+Ala+Trp+Lys+Tyr+ALB+BUN; 0.778, 2 48.374, 1+ALB+BUN+ALT+Arg+Phe+Trp; 0.778, 248.556, 1+ALB+BUN+AL T+Orn+Phe+Trp; 0.778, 247.930, 1+ALB+BUN+ALT+Lys+Val+Trp; 0.778, 249.770, 1+Gly+Phe+Tyr+ALT+ALB+BUN; 0.778, 248.164, 1+Ala+Trp+L ys+ALT+ALB+BUN; 0.778, 249.080, 1+ALB+BUN+ALT+Orn+Val+Phe; 0.77 8, 249.178, 1+ALB+BUN+ALT+Arg+Tyr+Trp; 0.778, 248.111, 1+ALB+BUN+ALT+3Me-His+Lys+Phe; 0.778, 250.705, 1+Lys+Phe+His+ALB+BUN+TP; 0.778, 249.947, 1+Gly+Phe+ALT+gGT+ALB+BUN; 0.778, 248.514, 1+BCA A+Trp+Lys+ALB+BUN; 0.778, 249.992, 1+BCAA+Trp+Lys+ALB+BUN+TP; 0. 778, 248.347, 1+Trp+Lys+Tyr+ALT+ALB+BUN; 0.778, 248.347, 1+ALB+B UN+ALT+Lys+Tyr+Trp; 0.778, 250.752, 1+ALB+BUN+Lys+Tyr+Phe+Trp; 0.778, 249.790, 1+Ala+Trp+Arg+His+ALB+BUN; 0.778, 250.512, 1+BCA A+Trp+Lys+gGT+ALB+BUN; 0.778, 246.442, 1+ALB+BUN+ALT+Asp+Lys+P he; 0.778, 250.503, 1+ALB+ALT+Arg+Tyr+Phe+Trp; 0.777, 249.852, 1+ALB+BUN+Asp+Tyr+Phe+Trp; 0.777, 250.176, 1+ALB+BUN+3MeHis+Lys+Val+Trp; 0.777, 248.223, 1+Gly+Lys+Phe+ALT+ALB+BUN; 0.777, 248.2 95, 1+Trp+Lys+Glc+ALT+ALB+BUN; 0.777, 250.108, 1+Ala+Gly+Lys+Hi s+ALB+BUN; 0.777, 249.244, 1+BCAA+Trp+Arg+ALT+ALB+BUN; 0.777, 24 7.960, 1+Gly+Phe+ALT+ALB+BUN; 0.777, 248.785, 1+BCAA+Trp+Lys+AS

T+ALB+BUN; 0.777, 251.159, 1+ALB+BUN+3MeHis+ Lys+Val+Phe; 0.777, 246.045, 1+ALB+BUN+ALT+Asp+ Lys+Trp; 0.777, 250.189, 1+Ala+Gly+Trp+His+ALB+ BUN; 0.777, 248.265, 1+Gly+Trp+Lys+ALT+ALB+BUN; 0.77 7, 248.280, 1+Trp+Lys+Thr+ALT+ALB+BUN; 0.776, 250.393, 1+Ala+Gly+Trp+Lys+ALB+BUN; 0.776, 251.023, 1+ALB+BUN+Lys+Tyr+Val+Trp; 0. 776, 251.082, 1+ALB+BUN+Orn+Lys+Val+Trp; 0.776, 248.481, 1+Trp+L ys+ALT+gGT+ALB+BUN; 0.776, 249.550, 1+Gly+Phe+TCHO+ALT+ALB+BU N; 0.776, 251.771, 1+Ala+Trp+Arg+Tyr+ALB+BUN; 0.776, 248.377, 1+A LB+BUN+AST+ALT+Phe+Trp; 0.776, 249.027, 1+ALB+BUN+Asp+Lys+Val+Trp; 0.776, 250.804, 1+ALB+BUN+His+Arg+Lys+Ile; 0.776, 249.395, 1+ALB+BUN+ALT+Arg+Val+Trp; 0.776, 248.095, 1+Ala+ Lys+His+ALT+AL B+BUN; 0.776, 250.433, 1+BCAA+ Trp+Lys+Thr+ALB+BUN; 0.776, 249.28 4, 1+ALB+BUN+ ALT+3MeHis+Arg+Trp; 0.776, 248.253, 1+ALB+BUN+ ALT+Arg+Lys+Trp; 0.776, 248.492, 1+ALB+BUN+ALT+ Arg+Lys+Phe; 0.776, 2 48.546, 1+ALB+BUN+ALT+ NEFA+Lys+Phe; 0.776, 249.168, 1+Trp+Arg+T G+ALT+ ALB+BUN; 0.776, 247.435, 1+ALB+BUN+ALT+Arg+ Asp+Trp; 0.776, 251.380, 1+Ala+Gly+Trp+Phe+ALB+ BUN; 0.776, 249.485, 1+ALB+BUN+A LT+Arg+Val+Phe; 0.776, 251.019, 1+ALB+BUN+Arg+Lys+Val+Trp; 0.77 6, 248.442, 1+Trp+Lys+ALT+ALB+BUN+BHBA; 0.776, 251.743, 1+ALB+BU N+His+Thr+Lys+Ile; 0.776, 249.352, 1+ALB+BUN+ALT+NEFA+Arg+Trp; 0.776, 248.420, 1+Trp+Lys+TG+ALT+ALB+BUN; 0.775, 249.403, 1+ALB+BUN+ALT+Arg+Orn+Trp; 0.775, 250.879, 1+ALB+BUN+NEFA+Lys+Val+Tr p; 0.775, 249.076, 1+Gly+Trp+Arg+ALT+ALB+BUN; 0.775, 250.874, 1+A LB+BUN+Arg+Lys+Tyr+Trp; 0.775, 252.372, 1+ALB+ BUN+NEFA+Tyr+Phe+Trp; 0.775, 248.607, 1+Lys+Phe+ ALT+gGT+ALB+BUN; 0.775, 248.040, 1+ALB+BUN+ 3MeHis+Asp+Lys+Trp; 0.775, 247.451, 1+Trp+Arg+ALT+ AL B+BUN; 0.775, 249.451, 1+Trp+Arg+ALT+ALB+ BUN+BHBA; 0.775, 248.34 2, 1+ALB+BUN+ALT+ 3MeHis+Lys+Trp; 0.775, 248.355, 1+ALB+BUN+ALT+T- BIL+His+Lys; 0.775, 249.467, 1+ALB+BUN+ALT+ NEFA+Arg+Phe; 0.77 5, 249.451, 1+Trp+Arg+ALT+gGT+ ALB+BUN; 0.775, 249.560, 1+ALB+BUN+ALT+NEFA+ Orn+Phe; 0.775, 250.678, 1+Ala+Trp+Lys+Thr+ALB+ BUN; 0. 775, 248.503, 1+ALB+BUN+ALT+Orn+Lys+Trp; 0.775, 249.393, 1+ALB+B UN+AST+Lys+Val+Trp; 0.775, 249.355, 1+Trp+Arg+Glc+ALT+ALB+BUN; 0.775, 250.723, 1+ALB+BUN+NEFA+His+Lys+Ile; 0.775, 247.723, 1+AL B+BUN+ALT+Asp+Orn+Trp; 0.775, 247.581, 1+ALB+BUN+ALT+Arg+Lys+I le; 0.775, 251.758, 1+ALB+BUN+NEFA+Lys+Tyr+Phe; 0.775, 248.616, 1+ALB+BUN+ALT+Orn+Lys+Phe; 0.775, 246.510, 1+Trp+Lys+ALT+ALB+BU N; 0.775, 247.731, 1+ALB+BUN+ALT+His+Arg+Lys; 0.775, 248.089, 1+T rp+Lys+TCHO+ALT+ALB+BUN; 0.775, 249.353, 1+ALB+BUN+ALT+Arg+Orn+Phe; 0.775, 250.082, 1+ALB+BUN+AST+ALT+Tyr+Phe; 0.775, 248.528, 1+ALB+BUN+Asp+Lys+Tyr+Trp; 0.775, 251.747, 1+ALB+BUN+Orn+Tyr+P he+Trp; 0.775, 252.246, 1+Ala+ Trp+Trp+Thr+Phe+ALB+BUN; 0.775, 248.48 8, 1+ALB+BUN+ ALT+NEFA+Lys+Trp; 0.775, 251.213, 1+Ala+Gly+Trp+Ar g+ALB+BUN; 0.775, 251.210, 1+Ala+Trp+Lys+Glc+ ALB+BUN; 0.775, 250. 853, 1+ALB+BUN+3MeHis+Lys+ Tyr+Trp; 0.775, 251.963, 1+ALB+BUN+Or n+Val+Phe+ Trp; 0.774, 251.911, 1+Ala+Gly+Trp+ALB+BUN+NEFA; 0.77 4, 250.539, 1+ALB+BUN+T-BIL+His+Lys+Ile; 0.774, 251.201, 1+Ala+T rp+Lys+ALB+BUN+TP; 0.774, 247.908, 1+ALB+BUN+ALT+Asp+Tyr+Trp; 0. 774, 248.332, 1+ALB+BUN+ALT+His+Lys+Ile; 0.774, 248.624, 1+ALB+B UN+ALT+Thr+Lys+Ile; 0.774, 248.804, 1+ALB+BUN+ALT+gGT+Lys+Ile; 0.774, 249.054, 1+Trp+ Arg+TCHO+ALT+ALB+BUN; 0.774, 251.407, 1+Al a+Trp+Lys+TG+ALB+BUN; 0.774, 251.733, 1+ALB+ BUN+3MeHis+Lys+Tyr+Phe; 0.774, 249.550, 1+ALB+ BUN+Asp+Orn+Lys+Trp; 0.774, 251.934, 1+ALB+BUN+ Arg+Thr+Lys+Ile; 0.774, 251.185, 1+ALB+BUN+T-BIL+ Arg+Lys+Ile; 0.774, 252.690, 1+ALB+BUN+Tyr+Val+ Phe+Trp; 0.774, 251. 883, 1+ALB+BUN+NEFA+Lys+Val+ Phe; 0.774, 247.826, 1+ALB+BUN+ALT+NEFA+Asp+Trp; 0.774, 253.101, 1+Ala+Gly+BCAA+Trp+Lys+ALB; 0.774, 248.477, 1+ALB+BUN+ALT+Glc+His+Lys; 0.774, 250.779, 1+ALB+BUN+A sp+Lys+Tyr+Phe; 0.774, 249.236, 1+ALB+BUN+AST+ALT+Arg+Phe; 0.77 4, 250.684, 1+Ala+Trp+Lys+TCHO+ALB+BUN; 0.774, 251.627, 1+Ala+Gl y+BCAA+Lys+ALB+BUN; 0.774, 248.540, 1+ALB+BUN+ALT+NEFA+His+Ly s; 0.774, 251.371, 1+Ala+Trp+Lys+Phe+ALB+BUN; 0.774, 248.699, 1+A LB+BUN+3MeHis+Asp+Lys+Phe; 0.774, 250.400, 1+ALB+BUN+T-BIL+Glc+His+Lys; 0.774, 250.948, 1+ALB+BUN+NEFA+Arg+Lys+Ile; 0.774, 248. 412, 1+ALB+BUN+ALT+BHBA+His+Lys; 0.774, 248.837, 1+Ala+Gly+Lys+ALT+ALB+BUN; 0.774, 248.701, 1+ALB+BUN+ALT+gGT+His+Lys; 0.773, 2 50.801, 1+ALB+BUN+AST+Tyr+Phe+Trp; 0.773, 251.312, 1+ALB+BUN+Or n+Lys+Tyr+Trp; 0.773, 248.573, 1+ALB+BUN+ALT+His+Thr+Lys; 0.773, 250.219, 1+ALB+BUN+ALT+Orn+Val+Trp; 0.773, 251.134, 1+ALB+BUN+N EFA+Lys+Tyr+Trp; 0.773, 248.639, 1+ALB+BUN+ALT+Orn+Lys+Ile; 0.7 73, 251.973, 1+Ala+ Gly+Trp+TG+ALB+BUN; 0.773, 250.177, 1+ALB+BUN+ ALT+Arg+Thr+Ile; 0.773, 249.411, 1+Ala+Trp+Lys+ALB+ BUN; 0.773, 252.302, 1+ALB+BUN+3MeHis+Val+Phe+ Trp; 0.773, 251.445, 1+ALB+AL T+Orn+Tyr+Phe+Trp; 0.773, 252.447, 1+Ala+Trp+Arg+Glc+ALB+BUN; 0. 773, 247.942, 1+ALB+BUN+ALT+Asp+Val+Trp; 0.773, 250.581, 1+ALB+A LT+Arg+Lys+Tyr+Trp; 0.773, 248.453, 1+Trp+Lys+ALT+ALB+BUN+Ca; 0. 773, 252.854, 1+ALB+BUN+NEFA+Val+Phe+Trp; 0.773, 248.285, 1+ALB+BUN+AST+ALT+Lys+Phe; 0.773, 248.548, 1+ALB+BUN+ALT+T-BIL+Lys+I le; 0.773, 249.211, 1+ALB+BUN+AST+ALT+Orn+Phe; 0.773, 251.319, 1+Ala+Trp+Lys+ALB+BUN+BHBA; 0.773, 252.215, 1+ALB+BUN+3MeHis+Tyr+Phe+Trp; 0.773, 251.078, 1+Trp+Glc+TG+ALT+ALB+BUN; 0.773, 247.9 16, 1+ALB+BUN+AST+ALT+Lys+Trp; 0.773, 250.442, 1+ALB+BUN+AST+Ar g+Tyr+Trp; 0.773, 248.652, 1+ALB+BUN+ALT+NEFA+Lys+Ile; 0.773, 24 9.585, 1+ALB+BUN+NEFA+Asp+Lys+Trp; 0.773, 252.566, 1+Ala+Trp+Ph e+TG+ALB+BUN; 0.773, 250.325, 1+ALB+BUN+ALT+Orn+Tyr+Trp; 0.773, 248.618, 1+ALB+BUN+ALT+Glc+Lys+Ile; 0.773, 249.550, 1+ALB+BUN+A ST+Lys+Tyr+Trp; 0.773, 251.053, 1+ALB+BUN+NEFA+His+Thr+Lys; 0.7 73, 249.705, 1+ALB+BUN+Asp+Lys+Phe+Trp; 0.773, 250.980, 1+ALB+BU N+Asp+Val+Phe+Trp; 0.773, 252.479, 1+Ala+ Trp+Phe+Glc+ALB+BUN; 0. 773, 252.508, 1+Ala+Trp+ Arg+TG+ALB+BUN; 0.773, 250.577, 1+Ala+Tr p+Phe+ ALB+BUN; 0.773, 251.152, 1+ALB+BUN+gGT+NEFA+ His+Lys; 0.77 3, 250.130, 1+ALB+BUN+ALT+NEFA+ Orn+Trp; 0.773, 250.887, 1+ALB+BU N+T-BIL+His+Thr+ Lys; 0.773, 250.297, 1+ALB+BUN+ALT+3MeHis+Orn+ Trp; 0.773, 248.072, 1+ALB+BUN+3MeHis+Asp+Lys+ Val; 0.773, 251.15 1, 1+ALB+BUN+NEFA+3MeHis+Lys+ Trp; 0.773, 251.982, 1+Ala+Gly+Trp+Glc+ALB+BUN; 0.773, 252.069, 1+Ala+Gly+Trp+Thr+ALB+BUN; 0.773, 249.645, 1+ALB+BUN+Arg+Asp+Lys+Trp; 0.773, 250.707, 1+ALB+BUN+Arg+Asp+Tyr+Trp; 0.773, 252.504, 1+ALB+BUN+Arg+Val+Phe+Trp; 0.773, 248.684, 1+ALB+BUN+AST+ALT+Arg+Trp; 0.773, 251.112, 1+ALB+BUN+His+Orn+Lys+Ile; 0.773, 251.267, 1+Gly+Trp+Lys+AST+ALB+TP; 0.773, 251.385, 1+Ala+Trp+Lys+gGT+ALB+BUN; 0.773, 248.416, 1+ALB+BUN+ALT+His+Orn+Lys; 0.773, 249.630, 1+Ala+Trp+Lys+AST+ALB+BUN; 0.773, 250.883, 1+ALB+BUN+NEFA+T-BIL+His+Lys; 0.773, 250.412, 1+Ala+Trp+Arg+AST+ALB+BUN; 0.772, 252.031, 1+Ala+BCAA+Trp+Arg+ALB+BUN; 0.772, 251.241, 1+Ala+Trp+Lys+ALB+BUN+NEFA; 0.772, 252.261, 1+Ala+Gly+Lys+TG+ALB+BUN; 0.772, 252.986, 1+Ala+BCAA+Trp+Glc+ALB+BUN; 0.772, 251.374, 1+Ala+Trp+Arg+Lys+ALB+BUN; 0.772, 252.292, 1+Ala+Trp+Arg+Phe+ALB+BUN; 0.772, 250.958, 1+ALB+BUN+3MeHis+Arg+Lys+Trp; 0.772, 246.891, 1+ALB+BUN+ALT+Asp+Lys+Val; 0.772, 251.682, 1+ALB+BUN+Glc+His+Thr+Lys; 0.772, 251.600, 1+ALB+BUN+Arg+Lys+Phe+Trp; 0.772, 252.510, 1+Ala+Trp+Phe+gGT+ALB+BUN; 0.772, 251.649, 1+ALB+BUN+Orn+Lys+Phe+Trp; 0.772, 250.324, 1+ALB+AST+ALT+Arg+Tyr+Trp; 0.772, 251.360, 1+Ala+Gly+Trp+Lys+AST+ALB; 0.772, 251.778, 1+ALB+ALT+NEFA+Arg+Tyr+Phe; 0.772, 251.390, 1+ALB+ALT+Arg+Orn+Tyr+Trp; 0.772, 249.446, 1+ALB+BUN+AST+3MeHis+Lys+Trp; 0.772, 252.541, 1+ALB+AST+Arg+Tyr+Phe+Trp; 0.772, 252.496, 1+Ala+Trp+Arg+ALB+BUN+TP; 0.772, 250.260, 1+ALB+BUN+T-BIL+His+Arg+Lys; 0.772, 252.058, 1+ALB+BUN+Arg+Orn+Lys+Ile; 0.772, 250.283, 1+ALB+BUN+NEFA+His+Arg+Lys; 0.772, 250.804, 1+ALB+BUN+NEFA+Glc+His+Lys; 0.772, 251.168, 1+ALB+BUN+3MeHis+Orn+Lys+Trp; 0.772, 248.744, 1+ALB+BUN+ALT+BHBA+Lys+Ile; 0.772, 250.800, 1+Ala+Gly+Trp+Arg+AST+ALB; 0.772, 250.930, 1+ALB+BUN+T-BIL+BHBA+His+Lys; 0.772, 250.546, 1+Ala+Trp+Arg+ALB+BUN; 0.772, 248.663, 1+ALB+BUN+ALT+3MeHis+Arg+Lys; 0.772, 251.339, 1+ALB+BUN+His+Arg+Thr+Lys; 0.772, 251.712, 1+ALB+BUN+T-BIL+Orn+Lys+Ile; 0.772, 250.509, 1+ALB+BUN+T-BIL+His+Orn+Lys; 0.772, 252.908, 1+ALB+BUN+Arg+Lys+Tyr+Phe; 0.772, 250.979, 1+ALB+BUN+3MeHis+Lys+Phe+Trp; 0.772, 253.098, 1+Ala+BCAA+Trp+TG+ALB+BUN; 0.772, 251.216, 1+ALB+BUN+Glc+His+Arg+Lys; 0.772, 251.749, 1+ALB+BUN+T-BIL+BHBA+Lys+Ile; 0.772, 251.888, 1+Ala+Gly+Arg+Lys+ALB+BUN; 0.772, 249.255, 1+Trp+TG+ALT+ALB+BUN; 0.772, 251.178, 1+BCAA+Trp+TG+ALT+ALB+BUN; 0.772, 251.759, 1+Ala+Gly+BCAA+Trp+ALB+BUN; 0.772, 248.970, 1+ALB+BUN+ALT+3MeHis+Lys+Val; 0.772, 249.243, 1+ALB+BUN+ALT+3MeHis+Orn+Lys; 0.772, 251.730, 1+ALB+BUN+NEFA+Thr+Lys+Ile; 0.772, 252.410, 1+Ala+Trp+Arg+Thr+ALB+BUN; 0.772, 251.247, 1+Trp+TG+ALT+gGT+ALB+BUN; 0.772, 251.477, 1+ALB+BUN+NEFA+Lys+Phe+Trp; 0.772, 252.545, 1+ALB+BUN+Thr+Orn+Lys+Ile; 0.772, 249.250, 1+ALB+BUN+ALT+3MeHis+Lys+Tyr; 0.772, 247.886, 1+ALB+BUN+AST+Asp+Lys+Trp; 0.772, 249.525, 1+Trp+Lys+AST+ALB+BUN+TP; 0.772, 248.788, 1+ALB+BUN+Ca+ALT+Lys+Ile; 0.772, 253.177, 1+ALB+BUN+Lys+Tyr+Val+Phe; 0.772, 251.227, 1+Trp+Glc+ALT+gGT+ALB+BUN; 0.772, 250.139, 1+Ala+Gly+Trp+ALB+BUN; 0.772, 251.179, 1+ALB+BUN+ALT+NEFA+3MeHis+Trp; 0.772, 246.840, 1+ALB+BUN+ALT+Asp+Lys+Tyr; 0.772, 250.701, 1+ALB+BUN+NEFA+His+Orn+Lys; 0.772, 251.047, 1+Ala+Gly+Lys+TCHO+ALB+BUN; 0.772, 248.412, 1+ALB+BUN+AST+ALT+Lys+Ile; 0.772, 252.527, 1+ALB+BUN+Glc+Thr+Lys+Ile; 0.772, 246.905, 1+ALB+BUN+ALT+Asp+Orn+Lys; 0.772, 249.631, 1+ALB+BUN+ALT+His+Arg+Thr; 0.772, 251.820, 1+ALB+BUN+T-BIL+Thr+Lys+Ile; 0.772, 251.670, 1+ALB+BUN+Glc+His+Lys+Ile; 0.772, 251.056, 1+ALB+BUN+NEFA+BHBA+His+Lys; 0.772, 250.287, 1+Ala+Gly+Lys+ALB+BUN; 0.772, 249.580, 1+ALB+BUN+3MeHis+Asp+Phe+Trp; 0.772, 250.000, 1+ALB+ALT+Arg+Asp+Tyr+Trp; 0.772, 250.092, 1+ALB+BUN+ALT+His+Arg+Orn; 0.772, 251.366, 1+ALB+BUN+T-BIL+Glc+Lys+Ile; 0.772, 247.276, 1+ALB+BUN+AST+ALT+Asp+Trp; 0.771, 253.106, 1+Ala+BCAA+Trp+Thr+ALB+BUN; 0.771, 249.248, 1+ALB+BUN+ALT+NEFA+3MeHis+Lys; 0.771, 249.829, 1+ALB+BUN+AST+T-BIL+Lys+Ile; 0.771, 251.281, 1+Ala+Trp+Lys+ALB+BUN+Ca; 0.771, 249.393, 1+Ala+Lys+TG+ALT+ALB+BUN; 0.771, 251.586, 1+ALB+ALT+Arg+Tyr+Val+Trp; 0.771, 251.648, 1+ALB+ALT+NEFA+Arg+Tyr+Trp; 0.771, 251.852, 1+ALB+BUN+gGT+T-BIL+Lys+Ile; 0.771, 250.919, 1+ALB+BUN+gGT+T-BIL+His+Lys; 0.771, 249.061, 1+Ala+Arg+Lys+ALT+ALB+BUN; 0.771, 253.100, 1+Ala+Trp+Glc+TG+ALB+BUN; 0.771, 249.313, 1+Ala+Lys+ALT+ALB+BUN+NEFA; 0.771, 250.907, 1+Ala+Gly+Trp+Arg+ALT+ALB; 0.771, 249.733, 1+Ala+Gly+Trp+AST+ALB+BUN; 0.771, 249.955, 1+ALB+BUN+AST+NEFA+Lys+Ile; 0.771, 252.466, 1+Ala+Trp+Arg+ALB+BUN+NEFA; 0.771, 249.069, 1+ALB+BUN+ALT+Arg+Lys+Val; 0.771, 249.097, 1+ALB+BUN+ALT+Arg+Lys+Tyr; 0.771, 251.467, 1+ALB+BUN+His+Thr+Orn+Lys; 0.771, 252.169, 1+ALB+AST+NEFA+Arg+Tyr+Trp; 0.771, 251.702, 1+Ala+Trp+Arg+TCHO+ALB+BUN; 0.771, 253.060, 1+Ala+BCAA+Trp+ALB+BUN+BHBA; 0.771, 250.777, 1+Trp+Glc+TCHO+ALT+ALB+BUN; 0.771, 248.669, 1+ALB+BUN+Ca+ALT+His+Lys; 0.771, 248.351, 1+ALB+BUN+3MeHis+Asp+Lys+Tyr; 0.771, 248.619, 1+ALB+BUN+3MeHis+Asp+Orn+Lys; 0.771, 251.011, 1+ALB+BUN+NEFA+Asp+Phe+Trp; 0.771, 247.016, 1+ALB+BUN+ALT+Arg+Asp+Lys; 0.771, 249.347, 1+ALB+BUN+ALT+T-BIL+Glc+Lys; 0.771, 248.817, 1+BCAA+Arg+Lys+ALT+ALB+BUN; 0.771, 249.429, 1+BCAA+Lys+Thr+ALT+ALB+BUN; 0.771, 251.194, 1+ALB+BUN+Glc+His+Orn+Lys; 0.771, 252.155, 1+ALB+BUN+BHBA+Arg+Lys+Ile; 0.771, 251.107, 1+Ala+BCAA+Trp+ALB+BUN; 0.771, 251.733, 1+ALB+BUN+NEFA+T-BIL+Lys+Ile; 0.771, 252.997, 1+ALB+BUN+3MeHis+Orn+Val+Phe; 0.771, 252.725, 1+ALB+BUN+Arg+Tyr+Val+Trp; 0.771, 251.532, 1+ALB+BUN+NEFA+Glc+Lys+Ile; 0.771, 251.671, 1+ALB+BUN+NEFA+Orn+Lys+Ile; 0.771, 252.039, 1+ALB+AST+Arg+Orn+Tyr+Trp; 0.771, 252.127, 1+ALB+BUN+3MeHis+Orn+Phe+Trp; 0.771, 252.112, 1+Ala+Gly+Trp+ALB+BUN+BHBA; 0.771, 250.521, 1+ALB+BUN+AST+3MeHis+Lys+Phe; 0.771, 250.832, 1+ALB+BUN+Ca+T-BIL+His+Lys; 0.771, 251.978, 1+ALB+BUN+3MeHis+Arg+Phe+Trp; 0.771, 249.235, 1+Trp+Glc+ALT+ALB+BUN; 0.771, 249.324, 1+Ala+Lys+Glc+ALT+ALB+BUN; 0.771, 250.222, 1+Ala+Gly+Lys+AST+ALB+BUN; 0.771, 251.656, 1+ALB+BUN+3MeHis+Arg+Lys+Val; 0.771, 251.902, 1+ALB+BUN+BHBA+His+Thr+Lys; 0.771, 252.226, 1+Ala+Trp+Glc+TCHO+ALB+BUN; 0.771, 251.117, 1+Ala+Trp+Glc+ALB+BUN; 0.771, 251.636, 1+ALB+BUN+Arg+Orn+Lys+Trp; 0.771, 251.223, 1+Gly+Trp+ALT+gGT+ALB+BUN; 0.771, 251.987, 1+ALB+BUN+Glc+Arg+Lys+Ile; 0.771, 249.895, 1+ALB+BUN+AST+Lys+Phe+Trp; 0.771, 249.940, 1+ALB+ALT+NEFA+Arg+Lys+Ile; 0.771, 251.060, 1+Ala+Trp+TG+AST+ALB+BUN; 0.771, 251.174, 1+BCAA+Trp+Glc+ALT+ALB+BUN; 0.771, 246.991, 1+ALB+BUN+ALT+NEFA+Asp+Lys; 0.771, 251.841, 1+ALB+BUN+NEFA+BHBA+Lys+Ile; 0.771, 250. 713, 1+ALB+BUN+AST+Arg+Phe+Trp; 0.771, 252.085, 1+ALB+BUN+gGT+A rg+Lys+Ile; 0.771, 248.421, 1+ALB+BUN+AST+ALT+His+Lys; 0.771, 25 1.054, 1+ALB+BUN+Ca+NEFA+His+Lys; 0.771, 251.601, 1+ALB+ALT+Orn+Val+Phe+Trp; 0.771, 251.767, 1+ALB+BUN+NEFA+3MeHis+Lys+Phe; 0. 771, 250.882, 1+Trp+TCHO+TG+ALT+ALB+BUN; 0.771, 252.430, 1+Ala+Trp+Thr+TCHO+ALB+BUN; 0.771, 252.010, 1+Ala+Gly+Trp+ALB+BUN+Ca; 0.771, 252.153, 1+ALB+BUN+3Me-His+Arg+Tyr+Trp; 0.771, 249.197, 1+ALB+BUN+ALT+Arg+Orn+Lys; 0.771, 251.128, 1+ALB+BUN+His+Arg+Orn+Lys; 0.771, 249.935, 1+ALB+BUN+AST+Orn+Lys+Trp; 0.771, 251.464, 1+ALB+BUN+BHBA+Glc+His+Lys; 0.771, 253.472, 1+ALB+NEFA+BHBA+Ar g+Lys+Ile; 0.771, 252.515, 1+ALB+ALT+NEFA+Orn+Tyr+Phe; 0.771, 25 2.672, 1+ALB+BUN+NEFA+3MeHis+Phe+Trp; 0.771, 247.257, 1+ALB+BUN+AST+3MeHis+Asp+Lys; 0.771, 252.059, 1+ALB+BUN+gGT+His+Lys+Il e; 0.770, 249.119, 1+ALB+BUN+ALT+Glc+Arg+Lys; 0.770, 249.373, 1+T rp+ALT+gGT+ALB+BUN; 0.770, 250.703, 1+ALB+BUN+NEFA+Asp+Lys+Ph e; 0.770, 250.969, 1+ALB+BUN+Asp+Orn+Phe+Trp; 0.770, 251.517, 1+A LB+BUN+NEFA+Arg+Lys+Trp; 0.770, 253.026, 1+Ala+BCAA+Trp+gGT+AL B+BUN; 0.770, 251.610, 1+ALB+BUN+NEFA+Orn+Lys+Trp; 0.770, 251.84 5, 1+ALB+BUN+gGT+NEFA+Lys+Ile; 0.770, 249.810, 1+ALB+BUN+AST+Ar g+Lys+Trp; 0.770, 249.903, 1+ALB+ALT+Arg+Thr+Lys+Ile; 0.770, 250. 307, 1+ALB+BUN+AST+Arg+Lys+Ile; 0.770, 250.169, 1+ALB+BUN+AST+H is+Arg+Lys; 0.770, 252.459, 1+Ala+Trp+Arg+ALB+BUN+Ca; 0.770, 252. 605, 1+ALB+BUN+NEFA+Arg+Phe+Trp; 0.770, 249.153, 1+ALB+BUN+ALT+T-BIL+Arg+Lys; 0.770, 249.542, 1+ALB+BUN+ALT+gGT+T-BIL+Lys; 0.7 70, 251.860, 1+ALB+BUN+BHBA+His+Lys+Ile; 0.770, 252.220, 1+Ala+G ly+Lys+Thr+ALB+BUN; 0.770, 251.031, 1+Gly+Trp+TG+ALT+ALB+BUN; 0. 770, 251.245, 1+ALB+BUN+BHBA+His+Arg+Lys; 0.770, 251.723, 1+ALB+AST+Arg+Lys+Tyr+Trp; 0.770, 250.974, 1+Trp+TCHO+ALT+gGT+ALB+BU N; 0.770, 252.963, 1+Ala+Trp+Glc+ALB+BUN+BHBA; 0.770, 252.160, 1+ALB+BUN+3MeHis+Orn+Lys+Val; 0.770, 249.490, 1+ALB+BUN+ALT+NEFA+Lys+Val; 0.770, 251.075, 1+Gly+Trp+Glc+ALT+ALB+BUN; 0.770, 252. 101, 1+Ala+Gly+Trp+gGT+ALB+BUN; 0.770, 251.949, 1+ALB+AST+NEFA+Orn+Lys+Ile; 0.770, 251.666, 1+ALB+ALT+Arg+Orn+Tyr+Phe; 0.770, 2 52.116, 1+Ala+Gly+Lys+Glc+ALB+BUN; 0.770, 248.801, 1+ALB+BUN+NE FA+3MeHis+Asp+Lys; 0.770, 249.179, 1+ALB+BUN+ALT+NEFA+Arg+Lys; 0.770, 251.235, 1+ALB+ALT+3MeHis+Arg+Tyr+Trp; 0.770, 250.048, 1+ALB+ALT+Arg+Orn+Lys+Ile; 0.770, 252.434, 1+Ala+BCAA+Trp+TCHO+A LB+BUN; 0.770, 250.226, 1+Ala+Gly+Arg+ALT+ALB+BUN; 0.770, 249.42 0, 1+Ala+Lys+ALT+gGT+ALB+BUN; 0.770, 248.778, 1+ALB+BUN+AST+ALT+3MeHis+Lys; 0.770, 251.180, 1+ALB+AST+Arg+Asp+Tyr+Trp; 0.770, 2 52.168, 1+ALB+BUN+gGT+His+Thr+Lys; 0.770, 251.774, 1+ALB+BUN+Ca+T-BIL+Lys+Ile; 0.770, 251.187, 1+Ala+Gly+Trp+TCHO+ALB+BUN; 0.7 70, 252.098, 1+ALB+BUN+Ca+Arg+Lys+Ile; 0.770, 249.127, 1+ALB+BUN+ALT+BHBA+Arg+Lys; 0.770, 251.313, 1+BCAA+Trp+ALT+gGT+ALB+BUN; 0.770, 252.238, 1+Ala+Gly+Lys+gGT+ALB+BUN; 0.770, 253.034, 1+Ala+BCAA+Trp+ALB+BUN+NEFA; 0.770, 247.390, 1+Trp+ALT+ALB+BUN; 0.77 0, 251.173, 1+ALB+BUN+AST+Val+Phe+Trp; 0.770, 249.789, 1+ALB+BUN+AST+NEFA+His+Lys; 0.770, 252.109, 1+Ala+Gly+Lys+ALB+BUN+BHBA; 0.770, 249.506, 1+ALB+BUN+ALT+gGT+BHBA+Lys; 0.770, 251.104, 1+AL B+BUN+ALT+NEFA+Val+Trp; 0.770, 249.518, 1+ALB+BUN+ALT+BHBA+Orn+Lys; 0.770, 249.613, 1+ALB+BUN+ALT+gGT+NEFA+Lys; 0.770, 250.899, 1+ALB+BUN+AST+Arg+Val+Trp; 0.770, 253.047, 1+Ala+Trp+Glc+ALB+B UN+NEFA; 0.770, 249.220, 1+ALB+BUN+ALT+gGT+Arg+Lys; 0.770, 249.5 43, 1+ALB+BUN+ALT+NEFA+T-BIL+Lys; 0.770, 250.221, 1+ALB+ALT+NEF A+His+Arg+Lys; 0.770, 250.899, 1+ALB+AST+NEFA+Arg+Lys+Ile; 0.77 0, 252.093, 1+ALB+BUN+Ca+His+Thr+Lys; 0.770, 253.037, 1+ALB+BUN+Orn+Lys+Tyr+Phe; 0.770, 253.126, 1+ALB+BUN+Orn+Lys+Val+Phe; 0.7 70, 251.072, 1+ALB+BUN+Arg+Asp+Phe+Trp; 0.770, 252.549, 1+ALB+BU N+Arg+Orn+Phe+Trp; 0.770, 249.218, 1+ALB+BUN+ALT+Arg+Thr+Lys; 0. 770, 251.486, 1+ALB+BUN+Arg+Asp+Lys+Phe; 0.770, 252.476, 1+ALB+B UN+Arg+Orn+Tyr+Trp; 0.770, 251.902, 1+ALB+BUN+NEFA+3MeHis+Lys+Val; 0.770, 252.888, 1+ALB+BUN+BHBA+Thr+Lys+Ile; 0.770, 251.074, 1+Ala+Trp+Thr+AST+ALB+BUN; 0.770, 252.475, 1+ALB+NEFA+His+Arg+Lys+Ile; 0.770, 253.550, 1+ALB+BUN+NEFA+Orn+Tyr+Phe; 0.770, 249. 463, 1+ALB+BUN+ALT+NEFA+Glc+Lys; 0.770, 251.624, 1+ALB+ALT+Lys+Tyr+Phe+Trp; 0.770, 249.415, 1+Ala+Lys+Thr+ALT+ALB+BUN; 0.770, 2 51.035, 1+Ala+Trp+AST+gGT+ALB+BUN; 0.770, 252.915, 1+ALB+BUN+gG T+Thr+Lys+Ile; 0.770, 251.263, 1+ALB+BUN+AST+Thr+Lys+Ile; 0.770, 250.011, 1+ALB+BUN+3MeHis+Arg+Asp+Trp; 0.770, 252.636, 1+ALB+BU N+BHBA+Orn+Lys+Ile; 0.770, 249.254, 1+ALB+BUN+ALT+BHBA+Glc+Ly s; 0.770, 249.518, 1+ALB+BUN+ALT+BHBA+Thr+Lys; 0.770, 252.653, 1+ALB+BUN+NEFA+Arg+Tyr+Trp; 0.770, 249.487, 1+ALB+BUN+ALT+T-BIL+BHBA+Lys; 0.770, 249.546, 1+ALB+BUN+ALT+T-BIL+Orn+Lys; 0.770, 25 0.961, 1+Ala+BCAA+Trp+AST+ALB+BUN; 0.770, 249.380, 1+ALB+ALT+Hi s+Arg+Lys+Ile; 0.770, 250.150, 1+ALB+ALT+gGT+Arg+Lys+Ile; 0.770, 252.374, 1+ALB+BUN+Glc+Orn+Lys+Ile; 0.770, 249.506, 1+ALB+BUN+A LT+NEFA+BHBA+Lys; 0.770, 246.604, 1+ALB+BUN+AST+ALT+Asp+Lys; 0. 770, 249.734, 1+ALB+BUN+AST+NEFA+Lys+Trp; 0.770, 251.705, 1+ALB+AST+3MeHis+Arg+Tyr+Trp; 0.769, 248.857, 1+ALB+BUN+3MeHis+Arg+A sp+Lys; 0.769, 253.020, 1+Ala+Trp+Glc+gGT+ALB+BUN; 0.769, 251.19 6, 1+Ala+Trp+Thr+ALB+BUN; 0.769, 250.987, 1+Ala+Trp+Glc+AST+ALB+BUN; 0.769, 249.542, 1+ALB+BUN+ALT+T-BIL+Thr+Lys; 0.769, 250.36 2, 1+ALB+BUN+AST+3MeHis+Arg+Trp; 0.769, 251.397, 1+ALB+BUN+gGT+His+Arg+Lys; 0.769, 251.170, 1+Ala+Trp+gGT+ALB+BUN; 0.769, 251.0 54, 1+ALB+BUN+ALT+NEFA+Arg+Thr; 0.769, 251.195, 1+ALB+BUN+ALT+T yr+Val+Trp; 0.769, 249.247, 1+Gly+Trp+ALT+ALB+BUN; 0.769, 249.14 3, 1+ALB+BUN+AST+Asp+Phe+Trp; 0.769, 249.684, 1+ALB+BUN+ALT+gGT+Thr+Lys; 0.769, 251.540, 1+ALB+BUN+gGT+His+Orn+Lys; 0.769, 250. 270, 1+ALB+BUN+AST+His+Orn+Lys; 0.769, 253.517, 1+ALB+BUN+NEFA+Arg+Tyr+Phe; 0.769, 250.328, 1+ALB+BUN+NEFA+Asp+Lys+Tyr; 0.769, 252.347, 1+ALB+BUN+3MeHis+Lys+Tyr+Val; 0.769, 251.848, 1+ALB+BU N+Ca+Glc+His+Lys; 0.769, 252.598, 1+ALB+BUN+NEFA+Orn+Phe+Trp; 0. 769, 250.614, 1+ALB+BUN+NEFA+Asp+Lys+Val; 0.769, 252.632, 1+ALB+BUN+gGT+Orn+Lys+Ile; 0.769, 249.396, 1+ALB+BUN+AST+ALT+Orn+Tr p; 0.769, 251.753, 1+ALB+BUN+Ca+NEFA+Lys+Ile; 0.769, 252.494, 1+A la+Trp+TCHO+TG+

ALB+BUN; 0.769, 253.121, 1+Ala+Trp+TG+ALB+BUN+NEFA; 0.769, 251.206, 1+Gly+BCAA+Trp+ALT+ALB+BUN; 0.769, 250.355, 1+Trp+ALT+AST+gGT+ALB+BUN; 0.769, 250.158, 1+ALB+ALT+T-BIL+Arg+Lys+Ile; 0.769, 250.773, 1+ALB+BUN+AST+His+Lys+Ile; 0.769, 251.951, 1+ALB+AST+T-BIL+Arg+Lys+Ile; 0.769, 250.976, 1+ALB+BUN+Asp+Orn+Tyr+Trp; 0.769, 251.675, 1+ALB+ALT+Arg+Val+Phe+Trp; 0.769, 251.346, 1+ALB+ALT+Arg+Lys+Tyr+Phe; 0.769, 249.546, 1+ALB+BUN+ALT+Orn+Lys+Val; 0.769, 252.693, 1+ALB+AST+Arg+Tyr+Val+Trp; 0.769, 252.335, 1+ALB+AST+His+Arg+Lys+Ile; 0.769, 248.988, 1+Trp+TCHO+ALT+ALB+BUN; 0.769, 251.060, 1+ALB+BUN+ALT+BHBA+Arg+Thr; 0.769, 251.185, 1+ALB+BUN+ALT+3MeHis+Tyr+Trp; 0.769, 251.282, 1+ALB+BUN+ALT+3MeHis+Val+Trp; 0.769, 250.826, 1+ALB+BUN+AST+3MeHis+Phe+Trp; 0.769, 251.881, 1+ALB+BUN+gGT+Glc+His+Lys; 0.769, 249.480, 1+ALB+BUN+AST+T-BIL+His+Lys; 0.769, 250.763, 1+Ala+Trp+TCHO+AST+ALB+BUN; 0.769, 251.594, 1+ALB+ALT+Arg+Orn+Phe+Trp; 0.769, 250.926, 1+ALB+BUN+ALT+Arg+Thr+Orn; 0.769, 251.026, 1+ALB+BUN+ALT+NEFA+Tyr+Trp; 0.769, 248.724, 1+ALB+BUN+AST+ALT+Arg+Lys; 0.769, 249.231, 1+ALB+BUN+AST+Arg+Asp+Trp; 0.769, 251.787, 1+ALB+ALT+NEFA+Arg+Phe+Trp; 0.769, 249.623, 1+ALB+BUN+ALT+NEFA+Lys+Tyr; 0.769, 250.640, 1+ALB+BUN+AST+Orn+Phe+Trp; 0.769, 249.256, 1+ALB+AST+ALT+Arg+Lys+Ile; 0.769, 249.503, 1+ALB+BUN+Ca+ALT+T-BIL+Lys; 0.769, 252.699, 1+ALB+ALT+Orn+Tyr+Val+Phe; 0.769, 251.063, 1+ALB+BUN+ALT+T-BIL+Arg+Thr; 0.769, 249.530, 1+ALB+BUN+ALT+gGT+Glc+Lys; 0.769, 249.589, 1+ALB+BUN+ALT+Lys+Tyr+Val; 0.769, 249.624, 1+ALB+BUN+ALT+NEFA+Thr+Lys; 0.769, 251.365, 1+ALB+BUN+BHBA+His+Orn+Lys; 0.769, 252.436, 1+ALB+ALT+NEFA+Arg+Thr+Ile; 0.769, 252.995, 1+Ala+BCAA+Trp+ALB+BUN+Ca; 0.769, 251.986, 1+ALB+BUN+Ca+His+Lys+Ile; 0.769, 250.909, 1+BCAA+Trp+TCHO+ALT+ALB+BUN; 0.769, 250.983, 1+ALB+BUN+3MeHis+Asp+Orn+Phe; 0.769, 252.053, 1+ALB+BUN+3MeHis+Orn+Lys+Phe; 0.769, 253.153, 1+Ala+Trp+TG+ALB+BUN+BHBA; 0.769, 250.665, 1+ALB+BUN+AST+NEFA+Lys+Phe; 0.769, 251.879, 1+ALB+ALT+Arg+Thr+Orn+Ile; 0.769, 253.633, 1+ALB+AST+NEFA+Arg+Orn+Ile; 0.769, 251.439, 1+ALB+AST+ALT+Arg+Thr+Ile; 0.769, 250.512, 1+Ala+Trp+TCHO+ALB+BUN; 0.769, 253.025, 1+Ala+Trp+Glc+ALB+BUN+Ca; 0.769, 250.485, 1+ALB+ALT+Asp+Tyr+Phe+Trp; 0.769, 249.244, 1+Ala+Trp+ALB+BUN; 0.769, 251.501, 1+ALB+BUN+Asp+Orn+Lys+Phe; 0.769, 251.083, 1+ALB+BUN+3MeHis+Asp+Tyr+Phe; 0.769, 251.230, 1+Ala+Trp+TG+ALB+BUN; 0.769, 253.145, 1+Ala+Trp+TG+gGT+ALB+BUN; 0.769, 249.512, 1+ALB+BUN+ALT+Glc+Orn+Lys; 0.769, 251.075, 1+ALB+BUN+ALT+T-BIL+His+Arg; 0.769, 250.461, 1+ALB+ALT+His+Arg+Thr+Lys; 0.769, 252.163, 1+ALB+ALT+BHBA+Arg+Thr+Ile; 0.769, 250.235, 1+ALB+ALT+His+Arg+Orn+Lys; 0.769, 251.208, 1+ALB+BUN+ALT+Glc+His+Arg; 0.769, 252.097, 1+ALB+ALT+Glc+Arg+Thr+Ile; 0.769, 250.284, 1+Gly+Trp+ALT+AST+ALB+BUN; 0.769, 250.806, 1+ALB+BUN+AST+Orn+Lys+Ile; 0.769, 251.274, 1+ALB+BUN+AST+gGT+Lys+Ile; 0.769, 251.405, 1+ALB+BUN+Ca+His+Arg+Lys; 0.769, 253.379, 1+ALB+BUN+3MeHis+Orn+Tyr+Phe; 0.769, 251.175, 1+Ala+Trp+ALB+BUN+BHBA; 0.769, 252.429, 1+Ala+Trp+Arg+gGT+ALB+BUN; 0.769, 249.331, 1+BCAA+Trp+ALT+ALB+BUN; 0.769, 251.061, 1+ALB+BUN+ALT+NEFA+His+Arg; 0.769, 250.831, 1+Gly+Trp+TCHO+ALT+ALB+BUN; 0.769, 252.437, 1+Ala+Trp+TCHO+ALB+BUN+TP; 0.768, 250.760, 1+ALB+BUN+ALT+3MeHis+Arg+Orn; 0.768, 253.117, 1+Ala+Trp+gGT+ALB+BUN+NEFA; 0.768, 250.770, 1+ALB+BUN+NEFA+Asp+Orn+Lys; 0.768, 252.628, 1+ALB+BUN+AST+Orn+Tyr+Phe; 0.768, 252.730, 1+ALB+BUN+gGT+Glc+Lys+Ile; 0.768, 249.525, 1+ALB+BUN+ALT+Glc+Thr+Lys; 0.768, 249.131, 1+Ala+Trp+AST+ALB+BUN; 0.768, 250.979, 1+Ala+Trp+AST+ALB+BUN+BHBA; 0.768, 250.344, 1+ALB+ALT+Glc+His+Arg+Lys; 0.768, 250.989, 1+ALB+BUN+Ca+ALT+His+Arg; 0.768, 253.150, 1+Ala+Trp+ALB+BUN+NEFA+BHBA; 0.768, 251.716, 1+ALB+AST+ALT+Arg+Tyr+Phe; 0.768, 252.615, 1+ALB+BUN+BHBA+Glc+Lys+Ile; 0.768, 251.212, 1+ALB+BUN+ALT+His+Arg+Ile; 0.768, 250.501, 1+ALB+BUN+AST+ALT+Arg+Thr; 0.768, 252.589, 1+ALB+BUN+Ca+Orn+Lys+Ile; 0.768, 251.492, 1+ALB+BUN+Ca+His+Orn+Lys; 0.768, 249.182, 1+ALB+BUN+Ca+ALT+Arg+Lys; 0.768, 249.617, 1+ALB+BUN+ALT+NEFA+Orn+Lys; 0.768, 250.553, 1+ALB+ALT+gGT+His+Arg+Lys; 0.768, 251.074, 1+ALB+BUN+AST+NEFA+Phe+Trp; 0.768, 250.698, 1+ALB+BUN+AST+Arg+Orn+Trp; 0.768, 250.646, 1+ALB+BUN+AST+Glc+His+Lys; 0.768, 252.844, 1+ALB+BUN+Ca+Thr+Lys+Ile; 0.768, 251.180, 1+Ala+Trp+ALB+BUN+NEFA; 0.768, 250.403, 1+ALB+BUN+AST+3MeHis+Arg+Lys; 0.768, 250.956, 1+Ala+Trp+AST+ALB+BUN+NEFA; 0.768, 251.484, 1+ALB+ALT+His+Arg+Orn+Ile; 0.768, 253.387, 1+ALB+His+Arg+Orn+Lys+Ile; 0.768, 251.379, 1+ALB+BUN+Asp+Lys+Val+Phe; 0.768, 250.224, 1+ALB+BUN+3MeHis+Asp+Orn+Trp; 0.768, 251.836, 1+ALB+BUN+3MeHis+Arg+Lys+Phe; 0.768, 252.585, 1+ALB+BUN+NEFA+Orn+Lys+Phe; 0.768, 251.033, 1+ALB+BUN+ALT+gGT+Arg+Thr; 0.768, 249.671, 1+ALB+BUN+ALT+Orn+Lys+Tyr; 0.768, 250.951, 1+ALB+BUN+ALT+Arg+Orn+Ile; 0.768, 251.081, 1+ALB+ALT+Arg+Lys+Val+Trp; 0.768, 250.102, 1+ALB+ALT+BHBA+Arg+Lys+Ile; 0.768, 251.892, 1+ALB+BUN+3MeHis+Arg+Lys+Tyr; 0.768, 251.381, 1+ALB+BUN+Arg+Asp+Val+Trp; 0.768, 250.781, 1+ALB+ALT+3MeHis+Arg+Lys+Trp; 0.768, 248.400, 1+ALB+BUN+AST+3MeHis+Asp+Trp; 0.768, 250.805, 1+ALB+BUN+AST+NEFA+Arg+Trp; 0.768, 253.245, 1+ALB+BUN+Arg+Lys+Val+Phe; 0.768, 249.537, 1+ALB+BUN+ALT+Arg+Asp+Orn; 0.768, 249.783, 1+ALB+BUN+ALT+NEFA+Arg+Asp; 0.768, 251.560, 1+ALB+BUN+NEFA+Asp+Tyr+Trp; 0.768, 252.965, 1+ALB+BUN+gGT+BHBA+Lys+Ile; 0.768, 249.037, 1+ALB+BUN+AST+ALT+BHBA+Lys; 0.768, 249.175, 1+ALB+BUN+AST+ALT+Lys+Val; 0.768, 253.063, 1+Ala+Gly+Trp+AST+ALB+TP; 0.768, 251.057, 1+ALB+BUN+ALT+3MeHis+Arg+Tyr; 0.768, 249.844, 1+ALB+BUN+ALT+Arg+Asp+Tyr; 0.768, 251.286, 1+ALB+ALT+Arg+Lys+Phe+Trp; 0.768, 251.724, 1+ALB+ALT+Lys+Val+Phe+Trp; 0.768, 250.761, 1+ALB+BUN+AST+ALT+His+Arg; 0.768, 253.393, 1+ALB+AST+His+Arg+Orn+Ile; 0.768, 252.852, 1+ALB+AST+Arg+Thr+Lys+Ile; 0.768, 252.287, 1+ALB+ALT+Arg+Tyr+Val+Phe; 0.768, 251.051, 1+ALB+BUN+ALT+NEFA+3MeHis+Arg; 0.768, 252.779, 1+ALB+BUN+Arg+Orn+Val+Trp; 0.768, 250.478, 1+ALB+ALT+T-BIL+His+Arg+Lys; 0.768, 251.477, 1+ALB+BUN+AST+Lys+Tyr+Phe; 0.768, 249.059, 1+ALB+BUN+AST+ALT+Glc+Lys; 0.768, 249.981, 1+ALB+AST+ALT+His+Arg+Lys; 0.768, 252.572, 1+ALB+AST+T-BIL+Orn+Lys+Ile; 0.768, 252.960, 1+ALB+BUN+Ca+gGT+Lys+Ile; 0.768, 249.462, 1+ALB+BUN+Ca+ALT+BHBA+Lys; 0.768, 249.580,

1+ALB+BUN+Ca+ALT+NEFA+Lys; 0.768, 252.143, 1+ALB+ALT+Orn+Lys+Tyr+Phe; 0.768, 253.018, 1+ALB+BUN+Asp+Orn+Tyr+Phe; 0.768, 253.108, 1+Ala+Trp+gGT+ALB+BUN+BHBA; 0.768, 251.494, 1+ALB+BUN+Asp+Tyr+Val+Trp; 0.768, 249.928, 1+ALB+ALT+Glc+Arg+Lys+Ile; 0.768, 252.402, 1+ALB+AST+His+Orn+Lys+Ile; 0.768, 250.412, 1+Trp+TG+ALT+AST+ALB+BUN; 0.768, 252.354, 1+ALB+ALT+gGT+Arg+Thr+Ile; 0.768, 253.885, 1+ALB+BUN+NEFA+Orn+Val+Phe; 0.768, 250.970, 1+ALB+BUN+ALT+Glc+Arg+Thr; 0.768, 251.277, 1+ALB+BUN+Asp+Orn+Val+Trp; 0.768, 251.289, 1+ALB+BUN+Arg+Asp+Orn+Trp; 0.768, 251.854, 1+ALB+ALT+Arg+Orn+Val+Trp; 0.768, 250.786, 1+ALB+BUN+AST+3MeHis+Lys+Val; 0.768, 249.130, 1+ALB+BUN+AST+ALT+gGT+Lys; 0.768, 251.444, 1+ALB+ALT+3MeHis+Lys+Val+Trp; 0.768, 250.898, 1+ALB+AST+ALT+Arg+Val+Trp; 0.768, 252.465, 1+Ala+Trp+TCHO+ALB+BUN+BHBA; 0.768, 249.664, 1+ALB+BUN+ALT+gGT+Orn+Lys; 0.768, 249.642, 1+ALB+BUN+Ca+ALT+gGT+Lys; 0.768, 251.032, 1+ALB+ALT+Asp+Orn+Tyr+Phe; 0.768, 251.353, 1+ALB+BUN+NEFA+Arg+Asp+Trp; 0.768, 252.510, 1+ALB+BUN+NEFA+Arg+Lys+Phe; 0.768, 250.404, 1+ALB+BUN+3MeHis+Asp+Tyr+Trp; 0.768, 249.671, 1+ALB+BUN+ALT+Thr+Orn+Lys; 0.768, 250.582, 1+ALB+BUN+AST+ALT+Arg+Orn; 0.768, 251.768, 1+ALB+ALT+Orn+Lys+Phe+Trp; 0.768, 250.429, 1+ALB+BUN+AST+ALT+3MeHis+Arg; 0.768, 252.546, 1+ALB+BUN+NEFA+3MeHis+Arg+Trp; 0.768, 251.248, 1+ALB+ALT+His+Arg+Thr+Ile; 0.768, 251.637, 1+ALB+BUN+AST+Lys+Val+Phe; 0.768, 250.553, 1+ALB+BUN+AST+ALT+3MeHis+Trp; 0.768, 251.022, 1+Ala+Trp+AST+ALB+BUN+Ca; 0.768, 253.114, 1+Ala+Trp+TG+ALB+BUN+Ca; 0.768, 248.942, 1+ALB+BUN+AST+ALT+T-BIL+Lys; 0.768, 251.340, 1+ALB+ALT+Arg+Orn+Lys+Trp; 0.768, 250.405, 1+Trp+Glc+ALT+AST+ALB+BUN; 0.768, 254.069, 1+ALB+His+Arg+Thr+Lys+Ile; 0.768, 252.380, 1+ALB+AST+Arg+Orn+Lys+Ile; 0.768, 251.233, 1+ALB+AST+NEFA+His+Arg+Lys; 0.767, 251.998, 1+ALB+BUN+gGT+BHBA+His+Lys; 0.767, 254.546, 1+ALB+T-BIL+BHBA+Arg+Lys+Ile; 0.767, 252.880, 1+ALB+BUN+Ca+BHBA+Lys+Ile; 0.767, 250.135, 1+ALB+Ca+ALT+Arg+Lys+Ile; 0.767, 250.979, 1+ALB+BUN+ALT+3MeHis+Arg+Val; 0.767, 252.426, 1+ALB+BUN+3MeHis+Arg+Val+Trp; 0.767, 252.867, 1+ALB+BUN+NEFA+Lys+Tyr+Val; 0.767, 250.865, 1+ALB+BUN+NEFA+Arg+Asp+Lys; 0.767, 251.910, 1+ALB+BUN+NEFA+3MeHis+Arg+Lys; 0.767, 249.412, 1+ALB+BUN+AST+Asp+Tyr+Trp; 0.767, 252.563, 1+ALB+BUN+3MeHis+Orn+Lys+Tyr; 0.767, 249.581, 1+ALB+ALT+Asp+Lys+Tyr+Trp; 0.767, 250.544, 1+ALB+ALT+BHBA+His+Arg+Lys; 0.767, 248.857, 1+ALB+BUN+AST+NEFA+Asp+Lys; 0.767, 249.067, 1+ALB+BUN+AST+ALT+NEFA+Lys; 0.767, 250.897, 1+ALB+BUN+AST+3MeHis+Orn+Lys; 0.767, 251.049, 1+ALB+BUN+AST+Glc+Lys+Ile; 0.767, 253.520, 1+ALB+NEFA+BHBA+His+Arg+Lys; 0.767, 250.981, 1+ALB+BUN+AST+His+Thr+Lys; 0.767, 252.486, 1+ALB+AST+NEFA+His+Lys+Ile; 0.767, 252.378, 1+Ala+Trp+TCHO+ALB+BUN+Ca; 0.767, 252.486, 1+Ala+Trp+TCHO+gGT+ALB+BUN; 0.767, 252.383, 1+Ala+Trp+TCHO+ALB+BUN+NEFA; 0.767, 251.266, 1+ALB+BUN+ALT+T-BIL+Arg+Orn; 0.767, 251.629, 1+ALB+ALT+NEFA+His+Arg+Orn; 0.767, 251.151, 1+ALB+BUN+ALT+gGT+His+Arg; 0.767, 252.279, 1+ALB+ALT+NEFA+Lys+Tyr+Phe; 0.767, 251.017, 1+ALB+ALT+Glc+His+Orn+Lys; 0.767, 250.762, 1+ALB+ALT+His+Orn+Lys+Ile; 0.767, 250.786, 1+ALB+AST+Asp+Lys+Tyr+Trp; 0.767, 253.624, 1+ALB+T-BIL+His+Arg+Lys+Ile; 0.767, 250.761, 1+ALB+BUN+AST+BHBA+His+Lys; 0.767, 250.991, 1+ALB+BUN+AST+gGT+His+Lys; 0.767, 253.386, 1+ALB+AST+Thr+Orn+Lys+Ile; 0.767, 251.111, 1+ALB+BUN+3MeHis+Arg+Asp+Phe; 0.767, 251.925, 1+ALB+AST+ALT+Orn+Tyr+Phe; 0.767, 250.747, 1+ALB+AST+ALT+Arg+Phe+Trp; 0.767, 249.556, 1+ALB+AST+ALT+Arg+Asp+Trp; 0.767, 249.240, 1+ALB+BUN+AST+ALT+Thr+Lys; 0.767, 253.368, 1+ALB+BUN+Arg+Orn+Lys+Phe; 0.767, 251.897, 1+ALB+ALT+NEFA+Arg+Orn+Trp; 0.767, 252.440, 1+ALB+BUN+NEFA+Arg+Lys+Tyr; 0.767, 251.644, 1+ALB+ALT+Orn+Lys+Val+Trp; 0.767, 251.847, 1+ALB+BUN+AST+3MeHis+Orn+Phe; 0.767, 254.101, 1+ALB+NEFA+Arg+Thr+Lys+Ile; 0.767, 249.240, 1+ALB+BUN+AST+ALT+Lys+Tyr; 0.767, 252.771, 1+ALB+AST+Arg+Orn+Val+Trp; 0.767, 251.192, 1+Ala+Gly+Trp+AST+ALB; 0.767, 252.343, 1+ALB+ALT+Arg+Orn+Val+Phe; 0.767, 251.269, 1+ALB+BUN+ALT+BHBA+Arg+Orn; 0.767, 251.605, 1+ALB+BUN+Arg+Asp+Lys+Val; 0.767, 250.915, 1+ALB+ALT+Asp+Orn+Tyr+Trp; 0.767, 251.064, 1+ALB+ALT+His+Arg+Thr+Orn; 0.767, 251.345, 1+ALB+ALT+NEFA+Arg+Lys+Trp; 0.767, 249.179, 1+ALB+BUN+AST+Asp+Orn+Trp; 0.767, 249.490, 1+ALB+BUN+AST+NEFA+Asp+Trp; 0.767, 250.861, 1+ALB+BUN+ALT+His+Thr+Orn; 0.767, 250.898, 1+ALB+AST+ALT+NEFA+Arg+Trp; 0.767, 252.520, 1+ALB+AST+Orn+Lys+Val+Trp; 0.767, 253.182, 1+Ala+Gly+Trp+AST+ALB+BHBA; 0.767, 251.030, 1+ALB+ALT+Arg+Asp+Tyr+Phe; 0.767, 251.267, 1+ALB+BUN+ALT+NEFA+Arg+Orn; 0.767, 251.274, 1+ALB+BUN+ALT+Arg+Orn+Tyr; 0.767, 251.629, 1+ALB+BUN+Arg+Asp+Orn+Lys; 0.767, 251.711, 1+ALB+ALT+BHBA+His+Arg+Orn; 0.767, 250.541, 1+ALB+BUN+AST+ALT+NEFA+Trp; 0.767, 250.598, 1+ALB+AST+ALT+Orn+Lys+Ile; 0.767, 250.876, 1+ALB+BUN+AST+Orn+Val+Trp; 0.767, 252.482, 1+ALB+AST+Orn+Lys+Tyr+Trp; 0.767, 252.725, 1+ALB+AST+NEFA+Arg+Orn+Trp; 0.767, 254.053, 1+ALB+AST+NEFA+Arg+Thr+Ile; 0.767, 252.705, 1+ALB+BUN+Ca+Glc+Lys+Ile; 0.767, 251.614, 1+ALB+Ca+ALT+His+Arg+Orn; 0.767, 253.051, 1+Ala+Trp+gGT+ALB+BUN+Ca; 0.767, 251.129, 1+Ala+Trp+ALB+BUN+Ca; 0.767, 249.649, 1+ALB+BUN+Ca+ALT+Thr+Lys; 0.767, 249.096, 1+ALB+AST+ALT+Asp+Lys+Trp; 0.767, 249.630, 1+ALB+BUN+Ca+ALT+Orn+Lys; 0.767, 251.711, 1+ALB+BUN+NEFA+Asp+Val+Trp; 0.767, 252.187, 1+ALB+ALT+NEFA+Orn+Phe+Trp; 0.767, 252.697, 1+ALB+BUN+NEFA+Asp+Tyr+Phe; 0.767, 250.460, 1+ALB+BUN+NEFA+3MeHis+Asp+Trp; 0.767, 251.711, 1+ALB+ALT+T-BIL+His+Arg+Orn; 0.767, 251.840, 1+ALB+ALT+3MeHis+Lys+Tyr+Phe; 0.767, 252.564, 1+ALB+BUN+NEFA+Arg+Lys+Val; 0.767, 251.650, 1+ALB+ALT+gGT+His+Arg+Orn; 0.767, 249.776, 1+ALB+BUN+AST+3MeHis+Asp+Phe; 0.767, 250.255, 1+ALB+AST+ALT+Arg+Lys+Trp; 0.767, 250.997, 1+ALB+BUN+Ca+ALT+Arg+Thr; 0.767, 251.363, 1+ALB+BUN+Arg+Asp+Lys+Tyr; 0.767, 252.911, 1+ALB+BUN+3MeHis+Orn+Val+Trp; 0.767, 253.016, 1+ALB+BUN+T-BIL+BHBA+Orn+Lys; 0.767, 250.446, 1+ALB+BUN+AST+ALT+Tyr+Trp; 0.767, 251.328, 1+ALB+ALT+T-BIL+His+Orn+Lys; 0.767, 252.388, 1+ALB+AST+NEFA+His+Arg+Orn; 0.767, 252.424, 1+ALB+ALT+T-BIL+Arg+Thr+Ile; 0.767, 253.031, 1+ALB+NEFA+Glc+His+Arg+Lys; 0.767, 253.094, 1+ALB+AST+BHBA+Arg+Lys+Ile; 0.767, 254.063,

1+ALB+AST+Arg+Thr+Orn+Ile; 0.767, 253.062, 1+Ala+Trp+ALB+BUN+Ca+NEFA; 0.767, 253.0 43, 1+Ala+Trp+ALB+BUN+Ca+BHBA; 0.767, 251.230, 1+ALB+BUN+ALT+Ar g+Orn+Val; 0.767, 251.524, 1+ALB+ALT+Thr+Orn+Lys+Ile; 0.767, 252. 115, 1+ALB+ALT+NEFA+Arg+Val+Trp; 0.767, 252.287, 1+ALB+BUN+NEFA+3MeHis+Lys+Tyr; 0.767, 252.824, 1+ALB+BUN+AST+Orn+Val+Phe; 0.7 67, 251.150, 1+ALB+BUN+ALT+BHBA+His+Arg; 0.767, 249.601, 1+ALB+B UN+AST+Asp+Val+Trp; 0.767, 251.281, 1+ALB+BUN+AST+BHBA+Lys+Il e; 0.767, 254.744, 1+ALB+BUN+Orn+Tyr+Val+Phe; 0.767, 251.696, 1+A LB+BUN+ALT+T-BIL+BHBA+Arg; 0.767, 252.410, 1+ALB+BUN+3MeHis+Ar g+Orn+Trp; 0.767, 253.504, 1+ALB+BUN+Arg+Lys+Tyr+Val; 0.767, 251. 092, 1+ALB+BUN+AST+ALT+Arg+Ile; 0.767, 249.183, 1+ALB+BUN+AST+A LT+Orn+Lys; 0.767, 251.443, 1+ALB+AST+ALT+Arg+Orn+Ile; 0.767, 25 1.089, 1+ALB+AST+ALT+Lys+Phe+Trp; 0.767, 252.854, 1+ALB+AST+NEF A+BHBA+Lys+Ile; 0.767, 252.202, 1+ALB+BUN+Ca+gGT+His+Lys; 0.767, 256.360, 1+Ala+Gly+Trp+Glc+TG+ALB; 0.767, 251.558, 1+ALB+ALT+Gl c+His+Arg+Orn; 0.767, 253.280, 1+ALB+NEFA+His+Orn+Lys+Ile; 0.76 7, 250.500, 1+ALB+BUN+AST+ALT+Val+Trp; 0.767, 254.122, 1+ALB+BUN+His+Arg+Thr+Ile; 0.767, 252.886, 1+ALB+AST+NEFA+Thr+Lys+Ile; 0. 766, 252.433, 1+ALB+Ca+ALT+Arg+Thr+Ile; 0.766, 253.075, 1+ALB+BU N+NEFA+Arg+Val+Trp; 0.766, 254.726, 1+ALB+BUN+NEFA+3MeHis+Tyr+Phe; 0.766, 251.995, 1+ALB+ALT+NEFA+Lys+Phe+Trp; 0.766, 253.616, 1+ALB+NEFA+Glc+Arg+Lys+Ile; 0.766, 250.441, 1+ALB+AST+ALT+3MeH is+Arg+Trp; 0.766, 250.545, 1+BCAA+Trp+ALT+AST+ALB+BUN; 0.766, 2 51.202, 1+ALB+ALT+NEFA+His+Orn+Lys; 0.766, 251.561, 1+ALB+ALT+N EFA+3MeHis+Arg+Trp; 0.766, 251.604, 1+ALB+BUN+Asp+Orn+Lys+Val; 0.766, 249.735, 1+ALB+BUN+AST+Asp+Lys+Phe; 0.766, 250.830, 1+ALB+ALT+3MeHis+Arg+Lys+Tyr; 0.766, 250.870, 1+ALB+AST+ALT+His+Arg+Orn; 0.766, 251.462, 1+ALB+ALT+NEFA+Orn+Lys+Ile; 0.766, 251.661, 1+ALB+BUN+ALT+Glc+Arg+Ile; 0.766, 254.060, 1+ALB+NEFA+Arg+Orn+Lys+Ile; 0.766, 251.018, 1+ALB+BUN+AST+3MeHis+Lys+Tyr; 0.766, 25 2.783, 1+Ala+Gly+Trp+Glc+AST+ALB; 0.766, 252.997, 1+Ala+Gly+Trp+TG+AST+ALB; 0.766, 251.871, 1+ALB+BUN+Ca+BHBA+His+Lys; 0.766, 2 50.174, 1+Trp+TCHO+ALT+AST+ALB+BUN; 0.766, 2 53.867, 1+ALB+T-BIL+His+Orn+Lys+Ile; 0.766, 251.390, 1+ALB+BUN+Asp+Lys+Tyr+Val; 0. 766, 251.570, 1+ALB+ALT+3MeHis+Arg+Orn+Trp; 0.766, 251.661, 1+AL B+ALT+3MeHis+Arg+Val+Trp; 0.766, 252.924, 1+ALB+BUN+His+Arg+Th r+Orn; 0.766, 251.697, 1+ALB+AST+NEFA+His+Orn+Lys; 0.766, 252.09 9, 1+ALB+AST+T-BIL+His+Orn+Lys; 0.766, 254.405, 1+ALB+BUN+Arg+O rn+Tyr+Phe; 0.766, 252.953, 1+ALB+BUN+NEFA+T-BIL+Orn+Lys; 0.766, 252.954, 1+ALB+ALT+NEFA+Orn+Val+Trp; 0.766, 250.507, 1+ALB+BUN+3MeHis+Asp+Val+Trp; 0.766, 251.215, 1+ALB+ALT+Glc+Orn+Lys+Ile; 0.766, 250.747, 1+ALB+BUN+AST+T-BIL+Arg+Lys; 0.766, 250.893, 1+A LB+BUN+AST+NEFA+Lys+Val; 0.766, 251.427, 1+ALB+AST+Asp+Orn+Tyr+Trp; 0.766, 250.696, 1+ALB+AST+ALT+His+Orn+Lys; 0.766, 251.312, 1+ALB+BUN+Ca+AST+Lys+Ile; 0.766, 249.490, 1+ALB+BUN+Ca+ALT+Glc+Lys; 0.766, 251.677, 1+ALB+BUN+ALT+T-BIL+Glc+Arg; 0.766, 252.65 9, 1+ALB+BUN+NEFA+T-BIL+Glc+Lys; 0.766, 252.65, 1+ALB+BUN+NEFA+Glc+Orn+Lys; 0.766, 251.588, 1+ALB+BUN+ALT+NEFA+Arg+Ile; 0.766, 252.323, 1+ALB+BUN+NEFA+3MeHis+Orn+Lys; 0.766, 251.250, 1+ALB+B UN+ALT+gGT+Arg+Orn; 0.766, 251.612, 1+ALB+ALT+T-BIL+Orn+Lys+Il e; 0.766, 251.631, 1+ALB+BUN+AST+Orn+Lys+Phe; 0.766, 252.820, 1+A LB+AST+Orn+Tyr+Phe+Trp; 0.766, 249.625, 1+ALB+AST+3MeHis+Asp+L ys+Trp; 0.766, 252.088, 1+ALB+AST+T-BIL+His+Arg+Lys; 0.766, 252. 675, 1+ALB+BUN+T-BIL+BHBA+Glc+Lys; 0.766, 251.358, 1+ALB+BUN+NE FA+Asp+Orn+Trp; 0.766, 251.396, 1+ALB+BUN+Asp+Orn+Lys+Tyr; 0.76 6, 252.787, 1+ALB+BUN+NEFA+Asp+Orn+Phe; 0.766, 252.863, 1+ALB+AL T+3MeHis+Orn+Val+Trp; 0.766, 254.994, 1+ALB+Arg+Orn+Tyr+Phe+Tr p; 0.766, 254.263, 1+ALB+His+Thr+Orn+Lys+Ile; 0.766, 251.069, 1+A LB+AST+ALT+Orn+Phe+Trp; 0.766, 250.596, 1+ALB+BUN+AST+T-BIL+Gl c+Lys; 0.766, 250.632, 1+ALB+AST+ALT+Arg+Orn+Trp; 0.766, 251.449, 1+ALB+AST+ALT+Orn+Val+Trp; 0.766, 252.368, 1+ALB+AST+NEFA+Arg+Lys+Tyr; 0.766, 252.955, 1+ALB+AST+NEFA+T-BIL+Lys+Ile; 0.766, 25 3.081, 1+ALB+AST+gGT+Arg+Lys+Ile; 0.766, 253.129, 1+Ala+Gly+Trp+AST+ALB+NEFA; 0.766, 253.267, 1+ALB+BUN+3MeHis+Arg+Tyr+Phe; 0. 766, 251.239, 1+ALB+BUN+ALT+Glc+Arg+Orn; 0.766, 251.612, 1+ALB+B UN+ALT+T-BIL+Arg+Ile; 0.766, 252.118, 1+ALB+BUN+3MeHis+Arg+Orn+Lys; 0.766, 250.626, 1+ALB+ALT+Arg+Asp+Orn+Trp; 0.766, 249.813, 1+ALB+BUN+AST+Asp+Lys+Val; 0.766, 251.010, 1+ALB+BUN+AST+Orn+T yr+Trp; 0.766, 252.475, 1+ALB+AST+NEFA+Lys+Tyr+Trp; 0.766, 253.6 04, 1+ALB+AST+NEFA+Arg+Tyr+Phe; 0.766, 251.682, 1+ALB+BUN+ALT+N EFA+BHBA+Arg; 0.766, 251.685, 1+ALB+BUN+ALT+NEFA+T-BIL+Arg; 0.7 66, 252.681, 1+ALB+BUN+T-BIL+Glc+Orn+Lys; 0.766, 253.495, 1+ALB+BUN+NEFA+3MeHis+Orn+Phe; 0.766, 252.924, 1+ALB+BUN+NEFA+Arg+Or n+Trp; 0.766, 251.174, 1+ALB+BUN+AST+ALT+Glc+Arg; 0.766, 251.726, 1+ALB+ALT+3MeHis+Lys+Tyr+Trp; 0.766, 253.024, 1+ALB+Arg+Asp+Ly s+Tyr+Trp; 0.766, 251.608, 1+ALB+BUN+ALT+gGT+Arg+Ile; 0.766, 251. 538, 1+ALB+AST+ALT+Orn+Tyr+Trp; 0.766, 252.811, 1+ALB+BUN+AST+H is+Arg+Thr; 0.766, 253.086, 1+Ala+Gly+BCAA+Trp+AST+ALB; 0.766, 2 53.008, 1+Ala+Gly+Trp+AST+gGT+ALB; 0.766, 252.932, 1+ALB+BUN+NE FA+Orn+Lys+Tyr; 0.766, 254.965, 1+ALB+NEFA+Arg+Tyr+Phe+Trp; 0.7 66, 249.488, 1+ALB+BUN+ALT+Arg+Asp+Val; 0.766, 251.416, 1+ALB+BU N+ALT+Arg+Tyr+Val; 0.766, 252.986, 1+ALB+ALT+NEFA+Orn+Tyr+Trp; 0.766, 253.478, 1+ALB+BUN+Arg+Orn+Lys+Tyr; 0.766, 251.656, 1+ALB+BUN+ALT+BHBA+Arg+Ile; 0.766, 249.849, 1+ALB+BUN+AST+Arg+Asp+L ys; 0.766, 250.434, 1+ALB+BUN+AST+3MeHis+Arg+Asp; 0.766, 250.860, 1+ALB+BUN+AST+3MeHis+Orn+Trp; 0.766, 253.404, 1+ALB+AST+gGT+Or n+Lys+Ile; 0.766, 253.216, 1+Ala+Gly+Trp+Glc+ALT+ALB; 0.766, 252. 360, 1+ALB+AST+ALT+Tyr+Phe+Trp; 0.766, 249.851, 1+ALB+BUN+AST+A sp+Orn+Lys; 0.766, 250.999, 1+ALB+BUN+AST+ALT+T-BIL+Arg; 0.766, 251.613, 1+ALB+BUN+AST+Arg+Lys+Phe; 0.766, 252.322, 1+ALB+AST+N EFA+Arg+Lys+Trp; 0.766, 251.046, 1+ALB+BUN+Ca+AST+ALT+Arg; 0.76 6, 251.700, 1+ALB+BUN+ALT+BHBA+Glc+Arg; 0.766, 252.800, 1+ALB+BU N+NEFA+Orn+Lys+Val; 0.766, 253.273, 1+ALB+BUN+Orn+Tyr+Val+Trp; 0.766, 250.755, 1+ALB+BUN+AST+NEFA+Arg+Lys; 0.766, 251.616, 1+AL B+BUN+AST+Arg+Lys+Tyr; 0.766, 253.318, 1+ALB+AST+Lys+Tyr+Val+T rp; 0.766, 250.557, 1+ALB+Ca+ALT+His+Arg+Lys; 0.766, 253.332, 1+A LB+BUN+3MeHis+Arg+Orn+Phe; 0.766, 251.673, 1+ALB+BUN+

ALT+NEFA+Glc+Arg; 0.766, 252.639, 1+ALB+BUN+ NEFA+Glc+Arg+Lys; 0.766, 252. 863, 1+ALB+BUN+T-BIL+Arg+Orn+Lys; 0.766, 251.122, 1+ALB+BUN+AST+ ALT+BHBA+Arg; 0.766, 252.788, 1+ALB+BUN+AST+ Arg+Orn+Phe; 0.766, 251.370, 1+ALB+AST+ALT+His+ Arg+Thr; 0.766, 250.909, 1+ALB+BUN+A ST+T-BIL+ Thr+Lys; 0.766, 253.062, 1+ALB+Ca+AST+Arg+Lys+Ile; 0.7 66, 251.094, 1+ALB+ALT+NEFA+Asp+Orn+Trp; 0.766, 252.006, 1+ALB+A ST+ALT+Orn+Val+Phe; 0.766, 252.127, 1+ALB+ALT+Orn+Lys+Val+Phe; 0.766, 252.413, 1+ALB+ALT+NEFA+Lys+Val+Phe; 0.766, 253.033, 1+AL B+ALT+Orn+Tyr+Val+Trp; 0.766, 253.352, 1+ALB+ BUN+NEFA+Orn+Tyr+Trp; 0.766, 251.179, 1+ALB+ BUN+AST+ALT+gGT+Arg; 0.766, 251.213, 1+ALB+ ALT+NEFA+3MeHis+Arg+Lys; 0.766, 251.213, 1+ALB+ ALT+3MeHis+Arg+Orn+Lys; 0.766, 251.812, 1+ALB+ ALT+Orn+Lys+Tyr+Trp; 0.766, 250.557, 1+ALB+BUN+ AST+NEFA+3MeHis+Lys; 0.766, 250.743, 1+ALB+A ST+ALT+3MeHis+Lys+Trp; 0.766, 249.199, 1+ALB+ BUN+Ca+AST+ALT+Ly s; 0.766, 251.677, 1+ALB+BUN+ ALT+NEFA+Arg+Tyr; 0.766, 254.252, 1+ALB+3MeHis+ Arg+Tyr+Phe+Trp; 0.766, 251.954, 1+ALB+ALT+Arg+ Orn+Lys+Phe; 0.766, 253.283, 1+ALB+BUN+NEFA+Orn+ Val+Trp; 0.766, 252. 257, 1+ALB+BUN+AST+NEFA+ Arg+Phe; 0.766, 249.964, 1+ALB+ALT+Asp+Lys+Val+ Trp; 0.766, 250.979, 1+ALB+BUN+AST+ALT+NEFA+ Arg; 0.766, 251.396, 1+ALB+ALT+BHBA+His+Orn+Lys; 0.766, 252.061, 1+ALB+ALT+Lys+Tyr+Val+Trp; 0.766, 251.071, 1+ALB+BUN+AST+NEFA+BHBA+Lys; 0. 766, 253.529, 1+ALB+NEFA+His+Arg+Thr+Lys; 0.766, 254.253, 1+ALB+AST+T-BIL+Arg+Orn+Ile; 0.765, 251.154, 1+ALB+BUN+Ca+ALT+Arg+Or n; 0.765, 251.569, 1+ALB+BUN+Ca+ALT+BHBA+Arg; 0.765, 252.962, 1+A LB+BUN+NEFA+T-BIL+BHBA+Lys; 0.765, 253.006, 1+ALB+BUN+NEFA+Thr+Orn+Lys; 0.765, 253.104, 1+ALB+BUN+3MeHis+Orn+Tyr+Trp; 0.765, 2 53.700, 1+ALB+BUN+3MeHis+Arg+Val+Phe; 0.765, 251.929, 1+ALB+BUN+AST+3MeHis+Arg+Phe; 0.765, 254.849, 1+ALB+BUN+NEFA+3MeHis+Val+Phe; 0.765, 250.263, 1+ALB+AST+ALT+3MeHis+Arg+Lys; 0.765, 250.8 72, 1+ALB+BUN+AST+NEFA+Glc+Lys; 0.765, 253.045, 1+ALB+NEFA+His+Arg+Orn+Lys; 0.765, 254.115, 1+ALB+gGT+NEFA+Arg+Lys+Ile; 0.765, 251.779, 1+Ala+Gly+Trp+ALT+AST+ALB; 0.765, 253.320, 1+ALB+AST+L ys+Tyr+Phe+Trp; 0.765, 251.540, 1+ALB+BUN+Ca+ALT+gGT+Arg; 0.765, 252.939, 1+ALB+BUN+gGT+NEFA+T-BIL+Lys; 0.765, 250.738, 1+ALB+AL T+NEFA+Arg+Asp+Trp; 0.765, 251.667, 1+ALB+ALT+Glc+His+Arg+Thr; 0.765, 254.529, 1+ALB+gGT+His+Orn+Lys+Ile; 0.765, 249.571, 1+ALB+ BUN+AST+Asp+Lys+Tyr; 0.765, 253.916, 1+ALB+ NEFA+T-BIL+Arg+Lys+Ile; 0.765, 250.894, 1+ALB+ BUN+AST+gGT+NEFA+Lys; 0.765, 253.378, 1+ALB+ AST+NEFA+Orn+Lys+Val; 0.765, 252.904, 1+ALB+ BUN+NEFA+T-B IL+Thr+Lys; 0.765, 253.888, 1+ALB+ BUN+Arg+Asp+Tyr+Phe; 0.765, 25 2.663, 1+ALB+BUN+ T-BIL+Glc+Thr+Lys; 0.765, 253.742, 1+ALB+BUN+O rn+Lys+Tyr+Val; 0.765, 250.872, 1+ALB+ALT+3MeHis+ Arg+Lys+Val; 0. 765, 253.546, 1+ALB+T-BIL+Glc+His+ Orn+Lys; 0.765, 253.268, 1+ALB+NEFA+Glc+His+Orn+ Lys; 0.765, 253.104, 1+ALB+AST+Orn+Val+Phe+T rp; 0.765, 251.052, 1+ALB+BUN+AST+NEFA+Orn+Lys; 0.765, 251.659, 1+ALB+ALT+NEFA+His+Lys+Ile; 0.765, 252.304, 1+ALB+AST+His+Arg+O rn+Lys; 0.765, 252.414, 1+ALB+AST+3MeHis+Lys+Tyr+Trp; 0.765, 252. 886, 1+ALB+AST+T-BIL+His+Arg+Orn; 0.765, 251.646, 1+ALB+BUN+ALT+gGT+T-BIL+Arg; 0.765, 252.575,

1+ALB+BUN+T-BIL+Glc+Arg+Lys; 0. 765, 253.378, 1+ALB+BUN+AST+Arg+Tyr+Phe; 0.765, 250.751, 1+ALB+A LT+Arg+Asp+Val+Trp; 0.765, 251.436, 1+ALB+BUN+ALT+NEFA+Arg+Va 1; 0.765, 251.673, 1+ALB+BUN+ALT+gGT+BHBA+Arg; 0.765, 252.960, 1+ALB+BUN+T-BIL+BHBA+Thr+Lys; 0.765, 253.344, 1+ALB+3MeHis+Arg+L ys+Tyr+Trp; 0.765, 250.891, 1+ALB+BUN+AST+ALT+Arg+Val; 0.765, 25 4.691, 1+ALB+NEFA+BHBA+Orn+Lys+Ile; 0.765, 253.901, 1+ALB+NEFA+His+Thr+Orn+Lys; 0.765, 249.825, 1+ALB+AST+ALT+Asp+Orn+Trp; 0.7 65, 251.087, 1+ALB+BUN+AST+NEFA+Orn+Trp; 0.765, 251.355, 1+ALB+A LT+His+Thr+Orn+Lys; 0.765, 253.475, 1+ALB+AST+BHBA+Orn+Lys+Il e; 0.765, 252.161, 1+ALB+AST+3MeHis+Lys+Val+Trp; 0.765, 253.025, 1+ALB+BUN+gGT+NEFA+Thr+Lys; 0.765, 253.555, 1+ALB+BUN+Arg+Orn+Lys+Val; 0.765, 251.610, 1+ALB+AST+ALT+NEFA+Orn+Trp; 0.765, 253. 222, 1+ALB+AST+Orn+Tyr+Val+Trp; 0.765, 251.976, 1+ALB+ AST+ALT+N EFA+His+Arg; 0.765, 252.732, 1+ALB+ AST+Arg+Lys+Val+Trp; 0.765, 2 54.147, 1+ALB+NEFA+ Glc+His+Lys+Ile; 0.765, 251.013, 1+ALB+AST+A LT+Lys+Val+Trp; 0.765, 252.638, 1+ALB+AST+gGT+ NEFA+Lys+Ile; 0.7 65, 251.534, 1+ALB+BUN+Ca+ALT+ NEFA+Arg; 0.765, 252.835, 1+ALB+BU N+NEFA+Glc+ Thr+Lys; 0.765, 252.858, 1+ALB+BUN+T-BIL+BHBA+ Arg+L ys; 0.765, 251.572, 1+ALB+AST+ALT+Arg+Orn+ Phe; 0.765, 251.613, 1+ALB+ALT+BHBA+Orn+Lys+Ile; 0.765, 252.340, 1+ALB+ALT+NEFA+Orn+L ys+Phe; 0.765, 252.023, 1+ALB+BUN+AST+NEFA+Orn+Phe; 0.765, 251.6 95, 1+ALB+ALT+NEFA+Glc+His+Lys; 0.765, 251.071, 1+ALB+AST+ALT+N EFA+Lys+Trp; 0.765, 251.991, 1+ALB+BUN+ALT+Glc+His+Orn; 0.765, 2 51.681, 1+ALB+BUN+ALT+gGT+Glc+Arg; 0.765, 252.988, 1+ALB+BUN+gG T+T-BIL+BHBA+Lys; 0.765, 249.894, 1+ALB+ALT+Arg+Asp+Lys+Trp; 0. 765, 254.605, 1+ALB+BHBA+His+Orn+Lys+Ile; 0.765, 252.367, 1+ALB+AST+ALT+NEFA+Arg+Ile; 0.765, 252.978, 1+ALB+BUN+gGT+T-BIL+Orn+Lys; 0.765, 253.024, 1+ALB+BUN+NEFA+BHBA+Orn+Lys; 0.765, 251.919, 1+ALB+ALT+Arg+Lys+Val+Phe; 0.765, 253.205, 1+ALB+BUN+AST+NEFA+Tyr+Phe; 0.765, 252.154, 1+ALB+BUN+AST+His+Arg+Orn; 0.765, 251.9 78, 1+ALB+AST+Arg+Asp+Orn+Trp; 0.765, 252.123, 1+ALB+BUN+ALT+gG T+His+Orn; 0.765, 253.118, 1+ALB+BUN+NEFA+3MeHis+Orn+Trp; 0.765, 254.416, 1+Ala+Gly+Trp+Glc+ALB; 0.765, 254.097, 1+ALB+ NEFA+Arg+Lys+Tyr+Trp; 0.765, 249.343, 1+ALB+BUN+ AST+ALT+Arg+Asp; 0.765, 2 51.661, 1+ALB+ALT+ NEFA+Arg+Lys+Tyr; 0.765, 251.431, 1+ALB+ALT+g GT+His+Orn+Lys; 0.765, 250.939, 1+ALB+BUN+AST+T-BIL+Orn+Lys; 0. 765, 251.152, 1+ALB+AST+NEFA+ Asp+Lys+Trp; 0.765, 252.469, 1+ALB+AST+ALT+His+ Arg+Ile; 0.765, 253.152, 1+ALB+AST+NEFA+Arg+Val+ Tr p; 0.765, 253.851, 1+ALB+AST+T-BIL+Thr+Lys+Ile; 0.765, 251.546, 1+ALB+BUN+Ca+ALT+Glc+Arg; 0.765, 252.081, 1+ALB+BUN+ALT+His+Orn+Ile; 0.765, 253.026, 1+ALB+BUN+gGT+NEFA+BHBA+Lys; 0.765, 251.12 8, 1+ALB+ALT+Asp+Orn+Val+Trp; 0.765, 251.850, 1+ALB+ALT+NEFA+Ar g+Lys+Phe; 0.765, 250.510, 1+ALB+ALT+Asp+Lys+Tyr+Phe; 0.765, 251. 639, 1+ALB+ALT+gGT+Orn+Lys+Ile; 0.765, 254.770, 1+ALB+AST+BHBA+Arg+Orn+Ile; 0.765, 250.923, 1+ALB+BUN+AST+NEFA+T-BIL+Lys; 0.76 5, 251.542, 1+ALB+BUN+Ca+ALT+T-BIL+Arg; 0.765, 250.652, 1+ALB+AL T+Arg+Asp+Lys+Phe; 0.765, 251.644, 1+ALB+BUN+ALT+gGT+NEFA+Arg; 0.765, 251.976,

1+ALB+AST+ALT+NEFA+Orn+Phe; 0.765, 251.605,
1+ALB+BUN+AST+Glc+Arg+Lys; 0.765, 250.824,
1+ALB+AST+ALT+Orn+Lys+Trp; 0.765, 251.197,
1+ALB+AST+ALT+Arg+Lys+Phe; 0.765, 252.051,
1+ALB+ALT+NEFA+Lys+Val+Trp; 0.765, 251.686,
1+ALB+AST+Asp+Lys+Val+Trp; 0.765, 252.819,
1+ALB+BUN+gGT+NEFA+Glc+Lys; 0.765, 251.638,
1+ALB+ALT+3MeHis+Orn+Lys+Trp; 0.765, 251.806,
1+ALB+ALT+NEFA+3MeHis+Lys+Trp; 0.765, 252.015,
1+ALB+ALT+BHBA+His+Arg+Thr; 0.765, 255.306,
1+ALB+T-BIL+BHBA+Orn+Lys+Ile; 0.765, 251.759,
1+ALB+BUN+AST+gGT+Arg+Lys; 0.765, 250.986,
1+ALB+AST+ALT+Arg+Lys+Tyr; 0.765, 251.090,
1+ALB+BUN+AST+NEFA+Thr+Lys; 0.765, 251.975,
1+ALB+BUN+ALT+Thr+Orn+Ile; 0.765, 250.854,
1+ALB+BUN+AST+gGT+T-BIL+Lys; 0.765, 251.055,
1+ALB+AST+ALT+Lys+Tyr+Trp; 0.765, 252.925,
1+ALB+BUN+Ca+T-BIL+Orn+Lys; 0.765, 252.771,
1+ALB+BUN+NEFA+Arg+Thr+Lys; 0.765, 252.786,
1+ALB+BUN+T-BIL+Arg+Thr+Lys; 0.765, 252.999,
1+ALB+BUN+NEFA+BHBA+Thr+Lys; 0.765, 253.033,
1+ALB+BUN+gGT+NEFA+Orn+Lys; 0.765, 252.043,
1+ALB+BUN+ALT+T-BIL+His+Orn; 0.765, 252.759,
1+ALB+ALT+NEFA+3MeHis+Orn+Trp; 0.765, 250.026,
1+ALB+BUN+ALT+Asp+Orn+Val; 0.765, 251.166,
1+ALB+BUN+AST+ALT+Arg+Tyr; 0.765, 253.369,
1+ALB+BUN+AST+Arg+Orn+Ile; 0.765, 252.006,
1+ALB+ALT+NEFA+Orn+Lys+Trp; 0.765, 252.101,
1+ALB+ALT+NEFA+Lys+Tyr+Trp; 0.765, 253.044,
1+ALB+AST+Arg+Orn+Phe+Trp; 0.765, 251.710,
1+ALB+AST+3MeHis+Arg+Lys+Trp; 0.765, 252.387,
1+ALB+AST+3MeHis+Arg+Val+Trp; 0.765, 250.993,
1+ALB+BUN+Ca+AST+His+Lys; 0.765, 256.360,
1+ALB+NEFA+Arg+Orn+Tyr+Phe; 0.765, 252.745,
1+ALB+BUN+NEFA+BHBA+Glc+Lys; 0.765, 252.810,
1+ALB+BUN+NEFA+BHBA+Arg+Lys; 0.765, 252.940,
1+ALB+ALT+3MeHis+Orn+Tyr+Trp; 0.765, 252.200,
1+ALB+AST+3MeHis+Arg+Lys+Tyr; 0.765, 252.523,
1+ALB+AST+ALT+Val+Phe+Trp; 0.765, 254.505,
1+ALB+NEFA+Glc+His+Thr+Lys; 0.765, 252.400,
1+ALB+AST+NEFA+3MeHis+Lys+Trp; 0.765, 250.981,
1+ALB+BUN+AST+T-BIL+BHBA+Lys; 0.765, 253.532,
1+ALB+NEFA+T-BIL+His+Arg+Lys; 0.765, 250.993,
1+ALB+AST+ALT+NEFA+Lys+Ile; 0.765, 253.571,
1+ALB+AST+T-BIL+BHBA+Lys+Ile; 0.764, 252.623,
1+ALB+BUN+gGT+T-BIL+Glc+Lys; 0.764, 252.941,
1+ALB+BUN+T-BIL+Thr+Orn+Lys; 0.764, 250.075,
1+ALB+ALT+Asp+Lys+Phe+Trp; 0.764, 253.548,
1+ALB+AST+NEFA+Lys+Tyr+Phe; 0.764, 252.628,
1+ALB+AST+NEFA+Lys+Val+Trp; 0.764, 252.933,
1+ALB+BUN+Ca+T-BIL+BHBA+Lys; 0.764, 252.109,
1+ALB+BUN+ALT+NEFA+His+Orn; 0.764, 252.810,
1+ALB+BUN+NEFA+Arg+Orn+Lys; 0.764, 252.635,
1+ALB+ALT+NEFA+Arg+Orn+Ile; 0.764, 252.248,
1+ALB+BUN+ALT+T-BIL+Thr+Orn; 0.764, 251.745,
1+ALB+BUN+AST+Arg+Orn+Lys; 0.764, 251.950,
1+ALB+AST+NEFA+Arg+Asp+Trp; 0.764, 252.632,
1+ALB+AST+3MeHis+Orn+Val+Trp; 0.764, 252.621,
1+ALB+ALT+T-BIL+Arg+Orn+Ile; 0.764, 253.969,
1+ALB+Glc+His+Orn+Lys+Ile; 0.764, 251.757, 1+ALB+BUN+AST+Arg+Lys+Val; 0.764, 251.873, 1+ALB+BUN+AST+Orn+Lys+Val; 0.764, 252.979, 1+ALB+AST+3MeHis+Orn+Lys+Val; 0.764, 252.015, 1+ALB+ALT+NEFA+Thr+Lys+Ile; 0.764, 253.168, 1+ALB+AST+NEFA+Arg+Phe+Trp; 0.764, 252.002, 1+ALB+BUN+Ca+ALT+His+Orn; 0.764, 252.767, 1+ALB+BUN+NEFA+T-BIL+Arg+Lys; 0.764, 253.591, 1+ALB+BUN+Arg+Thr+Orn+Lys; 0.764, 251.474, 1+ALB+3MeHis+Asp+Lys+Val+Trp; 0.764, 252.797, 1+ALB+BUN+gGT+T-BIL+Arg+Lys; 0.764, 252.013, 1+ALB+ALT+T-BIL+His+Arg+Thr; 0.764, 251.895, 1+ALB+ALT+gGT+His+Arg+Thr; 0.764, 253.661, 1+ALB+BUN+Glc+His+Thr+Orn; 0.764, 250.911, 1+ALB+AST+ALT+NEFA+Arg+Lys; 0.764, 252.892, 1+ALB+BUN+AST+NEFA+3MeHis+Phe; 0.764, 252.252, 1+ALB+BUN+ALT+NEFA+Thr+Orn; 0.764, 254.799, 1+ALB+AST+gGT+Arg+Orn+Ile; 0.764, 250.458, 1+ALB+AST+3MeHis+Arg+Asp+Trp; 0.764, 251.706, 1+ALB+AST+Arg+Asp+Lys+Trp; 0.764, 252.389, 1+ALB+AST+3MeHis+Arg+Lys+Val; 0.764, 252.794, 1+ALB+AST+T-BIL+Glc+His+Lys; 0.764, 252.528, 1+Ala+Gly+Trp+TCHO+AST+ALB; 0.764, 252.623, 1+ALB+BUN+Ca+T-BIL+Glc+Lys; 0.764, 252.076, 1+ALB+BUN+ALT+BHBA+His+Orn; 0.764, 253.131, 1+ALB+BUN+NEFA+Arg+Asp+Phe; 0.764, 254.102, 1+ALB+BUN+NEFA+Arg+Orn+Phe; 0.764, 255.412, 1+ALB+BUN+NEFA+Tyr+Val+Phe; 0.764, 253.339, 1+ALB+BUN+BHBA+Glc+Orn+Lys; 0.764, 253.443, 1+ALB+BUN+Glc+Arg+Orn+Lys; 0.764, 253.574, 1+ALB+BUN+Asp+Orn+Val+Phe; 0.764, 253.618, 1+ALB+BUN+gGT+BHBA+Orn+Lys; 0.764, 252.461, 1+ALB+ALT+BHBA+Arg+Orn+Ile; 0.764, 252.507, 1+ALB+ALT+Glc+Arg+Orn+Ile; 0.764, 253.262, 1+ALB+BUN+NEFA+His+Arg+Orn; 0.764, 253.718, 1+ALB+T-BIL+His+Arg+Orn+Lys; 0.764, 252.084, 1+ALB+ALT+NEFA+BHBA+Lys+Ile; 0.764, 252.180, 1+ALB+BUN+AST+3MeHis+Tyr+Trp; 0.764, 252.202, 1+ALB+BUN+AST+3MeHis+Val+Trp; 0.764, 252.864, 1+ALB+BUN+AST+NEFA+His+Arg; 0.764, 253.508, 1+ALB+gGT+NEFA+His+Arg+Lys; 0.764, 251.464, 1+ALB+BUN+Ca+ALT+Arg+Ile; 0.764, 254.368, 1+Ala+Trp+Glc+TG+ALT+ALB; 0.764, 250.139, 1+ALB+BUN+ALT+Asp+Orn+Tyr; 0.764, 253.726, 1+ALB+BUN+gGT+Thr+Orn+Lys; 0.764, 252.571, 1+ALB+ALT+gGT+Arg+Orn+Ile; 0.764, 253.124, 1+ALB+AST+NEFA+Orn+Val+Trp; 0.764, 253.295, 1+ALB+AST+T-BIL+His+Lys+Ile; 0.764, 252.942, 1+ALB+BUN+Ca+NEFA+Thr+Lys; 0.764, 252.401, 1+Ala+Trp+Glc+ALT+ALB; 0.764, 253.466, 1+ALB+BUN+NEFA+3MeHis+Arg+Phe; 0.764, 252.927, 1+ALB+BUN+gGT+T-BIL+Thr+Lys; 0.764, 254.917, 1+ALB+3MeHis+Lys+Tyr+Phe+Trp; 0.764, 251.770, 1+ALB+AST+ALT+NEFA+Arg+Phe; 0.764, 251.864, 1+ALB+ALT+Arg+Orn+Lys+Tyr; 0.764, 253.925, 1+ALB+gGT+NEFA+His+Orn+Lys; 0.764, 252.251, 1+ALB+BUN+ALT+gGT+Thr+Orn; 0.764, 252.423, 1+ALB+BUN+AST+Arg+Asp+Orn; 0.764, 252.386, 1+ALB+BUN+AST+Tyr+Val+Trp; 0.764, 253.029, 1+ALB+AST+Glc+Orn+Lys+Ile; 0.764, 251.449, 1+ALB+BUN+AST+ALT+His+Orn; 0.764, 252.228, 1+ALB+BUN+AST+NEFA+3MeHis+Trp; 0.764, 252.829, 1+ALB+AST+Arg+Lys+Phe+Trp; 0.764, 255.153, 1+ALB+3MeHis+Orn+Tyr+Phe+Trp; 0.764, 251.202, 1+ALB+3MeHis+Asp+Lys+Tyr+Trp; 0.764, 255.154, 1+ALB+3MeHis+Orn+Lys+Val+Phe; 0.764, 251.583, 1+ALB+BUN+AST+BHBA+Glc+Lys; 0.764, 252.142, 1+ALB+3MeHis+Arg+Asp+Lys+Trp; 0.764, 251.006, 1+ALB+BUN+AST+NEFA+Lys+Tyr; 0.764, 251.783, 1+ALB+BUN+AST+Arg+Thr+Lys; 0.764, 252.336, 1+ALB+BUN+AST+NEFA+Val+Trp; 0.764, 250.708, 1+ALB+AST+3MeHis+Asp+Orn+Trp; 0.764, 253.553, 1+ALB+AST+Lys+Val+Phe+Trp; 0.764, 252.785, 1+ALB+BUN+Ca+T-BIL+Arg+Lys; 0.764, 252.266, 1+ALB+3MeHis+Asp+Lys+Tyr+Phe; 0.764, 250.225, 1+ALB+BUN+ALT+NEFA+Asp+Orn; 0.764, 251.799, 1+ALB+ALT+NEFA+Glc+Arg+Lys; 0.764, 253.891, 1+ALB+AST+NEFA+Orn+Tyr+Phe;

0.764, 251.287, 1+ALB+AST+ALT+3MeHis+Lys+Phe; 0.764, 252.506, 1+ALB+AST+3MeHis+Arg+Phe+Trp; 0.764, 253.081, 1+ALB+AST+NEFA+3MeHis+Lys+Val; 0.764, 252.889, 1+ALB+BUN+Ca+gGT+T-BIL+Lys; 0.764, 252.773, 1+ALB+BUN+Ca+NEFA+Glc+Lys; 0.764, 256.041, 1+ALB+NEFA+Orn+Lys+Tyr+Phe; 0.764, 252.445, 1+ALB+ALT+3MeHis+Arg+Orn+Tyr; 0.764, 254.576, 1+ALB+Arg+Orn+Lys+Tyr+Trp; 0.764, 250.828, 1+ALB+ALT+Asp+Orn+Lys+Phe; 0.764, 251.972, 1+ALB+ALT+NEFA+Arg+Lys+Val; 0.764, 252.009, 1+ALB+BUN+ALT+Glc+Thr+Orn; 0.764, 252.241, 1+ALB+BUN+ALT+BHBA+Thr+Orn; 0.764, 252.134, 1+ALB+AST+3MeHis+Arg+Orn+Trp; 0.764, 252.613, 1+ALB+AST+NEFA+Orn+Lys+Trp; 0.764, 252.710, 1+ALB+AST+ALT+T-BIL+Arg+Ile; 0.764, 254.351, 1+ALB+AST+NEFA+Orn+Val+Phe; 0.764, 252.991, 1+ALB+AST+NEFA+Lys+Phe+Trp; 0.764, 253.080, 1+ALB+AST+NEFA+Arg+Lys+Val; 0.764, 254.430, 1+Ala+Gly+Trp+Glc+TCHO+ALB; 0.764, 252.862, 1+ALB+BUN+Ca+NEFA+T-BIL+Lys; 0.764, 255.603, 1+ALB+NEFA+Orn+Tyr+Phe+Trp; 0.764, 253.463, 1+ALB+BUN+Glc+Arg+Thr+Lys; 0.764, 253.494, 1+ALB+BUN+BHBA+Arg+Orn+Lys; 0.764, 250.603, 1+ALB+ALT+NEFA+Arg+Asp+Lys; 0.764, 249.623, 1+ALB+BUN+AST+ALT+Asp+Orn; 0.764, 254.142, 1+ALB+AST+Arg+Orn+Lys+Tyr; 0.764, 251.928, 1+ALB+BUN+AST+Orn+Lys+Tyr; 0.764, 253.094, 1+ALB+AST+NEFA+Orn+Tyr+Trp; 0.764, 253.163, 1+ALB+AST+NEFA+Arg+Orn+Lys; 0.764, 255.246, 1+ALB+T-BIL+Arg+Thr+Lys+Ile; 0.764, 252.080, 1+ALB+ALT+NEFA+His+Thr+Lys; 0.764, 252.955, 1+Ala+Gly+Trp+TCHO+ALT+ALB; 0.764, 252.952, 1+ALB+BUN+Ca+gGT+NEFA+Lys; 0.764, 254.143, 1+ALB+Ca+NEFA+Arg+Lys+Ile; 0.764, 253.239, 1+ALB+BUN+BHBA+Glc+Arg+Lys; 0.764, 249.022, 1+ALB+ALT+3MeHis+Asp+Lys+Tyr; 0.764, 250.108, 1+ALB+ALT+Asp+Orn+Lys+Trp; 0.764, 253.938, 1+ALB+NEFA+T-BIL+His+Orn+Lys; 0.764, 251.648, 1+ALB+ALT+NEFA+Glc+Lys+Ile; 0.764, 252.360, 1+ALB+BUN+AST+NEFA+Tyr+Trp; 0.764, 252.803, 1+ALB+AST+ALT+gGT+Arg+Ile; 0.764, 253.687, 1+ALB+BUN+NEFA+His+Thr+Orn; 0.764, 253.588, 1+ALB+BUN+Arg+Asp+Orn+Phe; 0.764, 254.194, 1+ALB+Asp+Orn+Tyr+Phe+Trp; 0.764, 254.379, 1+Ala+Trp+Glc+ALT+gGT+ALB; 0.764, 255.340, 1+ALB+Orn+Lys+Tyr+Phe+Trp; 0.764, 251.927, 1+ALB+ALT+Glc+Arg+Orn+Lys; 0.764, 251.823, 1+ALB+ALT+NEFA+His+Arg+Thr; 0.764, 251.959, 1+ALB+ALT+3MeHis+Orn+Lys+Val; 0.764, 252.887, 1+ALB+BUN+AST+NEFA+Arg+Orn; 0.764, 254.419, 1+ALB+NEFA+His+Arg+Thr+Orn; 0.764, 251.863, 1+ALB+BUN+AST+gGT+BHBA+Lys; 0.764, 252.812, 1+ALB+AST+Glc+Arg+Lys+Ile; 0.764, 254.111, 1+ALB+AST+NEFA+Arg+Orn+Tyr; 0.764, 251.271, 1+ALB+AST+ALT+NEFA+His+Lys; 0.764, 252.373, 1+ALB+AST+NEFA+Glc+Lys+Ile; 0.764, 252.565, 1+ALB+AST+Glc+His+Orn+Lys; 0.764, 251.402, 1+ALB+Ca+ALT+His+Orn+Lys; 0.764, 252.951, 1+ALB+BUN+Ca+NEFA+Orn+Lys; 0.764, 254.562, 1+ALB+BUN+NEFA+Arg+Val+Phe; 0.764, 255.098, 1+ALB+gGT+T-BIL+Arg+Lys+Ile; 0.764, 252.606, 1+ALB+AST+ALT+NEFA+Arg+Tyr; 0.764, 251.187, 1+ALB+AST+ALT+Arg+Orn+Lys; 0.764, 251.272, 1+ALB+AST+ALT+3MeHis+Orn+Lys; 0.764, 251.641, 1+ALB+AST+Asp+Orn+Lys+Trp; 0.764, 251.847, 1+ALB+ALT+T-BIL+Glc+His+Lys; 0.764, 252.077, 1+ALB+ALT+NEFA+T-BIL+Lys+Ile; 0.764, 254.710, 1+ALB+NEFA+His+Thr+Lys+Ile; 0.764, 253.569, 1+ALB+BUN+AST+Arg+Thr+Ile; 0.763, 252.875, 1+ALB+BUN+Ca+T-BIL+Thr+Lys; 0.763, 252.923, 1+ALB+BUN+Ca+NEFA+BHBA+Lys; 0.763, 254.163, 1+ALB+3MeHis+Orn+Lys+Val+Trp; 0.763, 253.397, 1+ALB+BUN+BHBA+Glc+Thr+Lys; 0.763, 253.683, 1+ALB+BUN+gGT+BHBA+Thr+Lys; 0.763, 252.155, 1+ALB+AST+ALT+Lys+Tyr+Phe; 0.763, 251.439, 1+ALB+AST+ALT+3MeHis+Orn+Trp; 0.763, 251.814, 1+ALB+BUN+AST+BHBA+Orn+Lys; 0.763, 252.125, 1+ALB+ALT+gGT+NEFA+Lys+Ile; 0.763, 252.167, 1+ALB+BUN+AST+Lys+Tyr+Val; 0.763, 252.450, 1+ALB+AST+Arg+Asp+Phe+Trp; 0.763, 253.220, 1+ALB+AST+NEFA+Orn+Phe+Trp; 0.763, 253.045, 1+ALB+AST+BHBA+His+Orn+Lys; 0.763, 251.877, 1+ALB+ALT+NEFA+T-BIL+Arg+Lys; 0.763, 254.721, 1+ALB+3MeHis+Lys+Val+Phe+Trp; 0.763, 252.974, 1+ALB+BUN+AST+T-BIL+Arg+Orn; 0.763, 253.908, 1+ALB+NEFA+BHBA+His+Orn+Lys; 0.763, 254.843, 1+ALB+AST+Arg+Orn+Tyr+Phe; 0.763, 250.221, 1+ALB+AST+3MeHis+Arg+Asp+Lys; 0.763, 251.954, 1+ALB+BUN+AST+BHBA+Thr+Lys; 0.763, 252.806, 1+ALB+AST+ALT+BHBA+Arg+Ile; 0.763, 251.187, 1+ALB+AST+ALT+T-BIL+Arg+Lys; 0.763, 251.894, 1+ALB+BUN+AST+gGT+Orn+Lys; 0.763, 252.426, 1+ALB+AST+NEFA+3MeHis+Arg+Trp; 0.763, 252.519, 1+ALB+AST+ALT+gGT+His+Arg; 0.763, 253.053, 1+ALB+AST+Orn+Lys+Phe+Trp; 0.763, 254.426, 1+ALB+AST+T-BIL+BHBA+His+Orn; 0.763, 255.658, 1+ALB+BHBA+Arg+Thr+Lys+Ile; 0.763, 253.262, 1+ALB+AST+NEFA+Arg+Lys+Phe; 0.763, 253.072, 1+ALB+AST+His+Thr+Orn+Lys; 0.763, 252.737, 1+ALB+BUN+Ca+NEFA+Arg+Lys; 0.763, 252.527, 1+ALB+Ca+ALT+Arg+Orn+Ile; 0.763, 254.741, 1+ALB+Ca+AST+Arg+Orn+Ile; 0.763, 252.487, 1+ALB+ALT+NEFA+Glc+Orn+Lys; 0.763, 251.915, 1+ALB+ALT+Arg+Lys+Tyr+Val; 0.763, 251.952, 1+ALB+AST+NEFA+Arg+Asp+Lys; 0.763, 252.467, 1+ALB+AST+NEFA+Glc+His+Lys; 0.763, 251.629, 1+ALB+AST+ALT+Thr+Lys+Ile; 0.763, 253.539, 1+ALB+BUN+Ca+Arg+Orn+Lys; 0.763, 251.613, 1+ALB+Ca+ALT+Orn+Lys+Ile; 0.763, 254.831, 1+ALB+BUN+Arg+Orn+Val+Phe; 0.763, 253.066, 1+ALB+ALT+gGT+His+Arg+Ile; 0.763, 251.252, 1+ALB+AST+ALT+Arg+Lys+Val; 0.763, 251.986, 1+ALB+AST+Asp+Orn+Val+Trp; 0.763, 252.469, 1+ALB+AST+Arg+Asp+Val+Trp; 0.763, 251.711, 1+ALB+AST+Asp+Lys+Phe+Trp; 0.763, 252.148, 1+ALB+ALT+gGT+NEFA+His+Lys; 0.763, 252.933, 1+ALB+AST+T-BIL+Glc+Lys+Ile; 0.763, 253.543, 1+ALB+BUN+Ca+Arg+Thr+Lys; 0.763, 253.437, 1+ALB+Ca+AST+Orn+Lys+Ile; 0.763, 251.014, 1+ALB+BUN+Ca+AST+NEFA+Lys; 0.763, 252.871, 1+ALB+ALT+gGT+NEFA+His+Arg; 0.763, 254.670, 1+ALB+Arg+Lys+Tyr+Phe+Trp; 0.763, 252.079, 1+ALB+ALT+Arg+Orn+Lys+Val; 0.763, 253.390, 1+ALB+AST+NEFA+Orn+Lys+Tyr; 0.763, 253.450, 1+ALB+AST+Glc+His+Arg+Orn; 0.763, 254.682, 1+ALB+AST+Glc+Arg+Orn+Ile; 0.763, 254.972, 1+ALB+T-BIL+Arg+Orn+Lys+Ile; 0.763, 252.330, 1+ALB+ALT+T-BIL+Thr+Lys+Ile; 0.763, 253.215, 1+ALB+AST+NEFA+BHBA+Arg+Lys; 0.763, 253.750, 1+ALB+AST+gGT+T-BIL+Lys+Ile; 0.763, 252.948, 1+ALB+ALT+NEFA+His+Arg+Ile; 0.763, 252.029, 1+ALB+ALT+NEFA+BHBA+Arg+Lys; 0.763, 253.336, 1+ALB+BUN+gGT+Glc+Arg+Lys; 0.763, 253.578, 1+ALB+BUN+Glc+Thr+Orn+Lys; 0.763, 252.237, 1+ALB+AST+ALT+Arg+Val+Phe; 0.763, 252.256, 1+ALB+NEFA+3MeHis+Asp+Lys+Trp; 0.763, 252.428, 1+ALB+BUN+AST+3MeHis+Arg+Orn; 0.763, 254.945, 1+ALB+BUN+Arg+Thr+Orn+Ile; 0.763, 251.642, 1+ALB+BUN+AST+BHBA+Arg+Lys; 0.763, 251.897, 1+ALB+

BUN+AST+Glc+Thr+Lys; 0.763, 251.276, 1+ALB+AST+ALT+Arg+Thr+Lys; 0.763, 252.140, 1+ALB+ALT+NEFA+BHBA+His+Lys; 0.763, 253.847, 1+ALB+BUN+Ca+His+Arg+Orn; 0.763, 252.927, 1+ALB+ALT+NEFA+BHBA+His+Arg; 0.763, 253.476, 1+ALB+BUN+BHBA+Arg+Thr+Lys; 0.763, 253.731, 1+ALB+3MeHis+Arg+Lys+Val+Trp; 0.763, 253.937, 1+ALB+AST+3MeHis+Orn+Val+Phe; 0.763, 254.346, 1+ALB+BUN+NEFA+3MeHis+Tyr+Trp; 0.763, 250.125, 1+ALB+ALT+NEFA+Asp+Lys+Trp; 0.763, 252.858, 1+ALB+ALT+Lys+Tyr+Val+Phe; 0.763, 253.496, 1+ALB+BUN+AST+NEFA+Val+Phe; 0.763, 251.711, 1+ALB+BUN+AST+Glc+Orn+Lys; 0.763, 251.639, 1+ALB+AST+ALT+NEFA+Lys+Phe; 0.763, 252.846, 1+ALB+AST+3MeHis+Orn+Tyr+Trp; 0.763, 256.798, 1+ALB+NEFA+BHBA+Arg+Thr+Ile; 0.763, 253.077, 1+ALB+AST+gGT+His+Orn+Lys; 0.763, 252.540, 1+ALB+ALT+3MeHis+Arg+Orn+Val; 0.763, 252.783, 1+ALB+BUN+gGT+NEFA+Arg+Lys; 0.763, 253.496, 1+ALB+BUN+gGT+Glc+Orn+Lys; 0.763, 253.680, 1+ALB+BUN+AST+3MeHis+Tyr+Phe; 0.763, 254.369, 1+ALB+BUN+NEFA+3MeHis+Val+Trp; 0.763, 253.539, 1+ALB+ALT+gGT+BHBA+Arg+Ile; 0.763, 252.777, 1+ALB+AST+ALT+Glc+Arg+Ile; 0.763, 252.030, 1+ALB+ALT+Glc+His+Thr+Lys; 0.763, 252.759, 1+ALB+AST+Arg+Orn+Lys+Trp; 0.763, 253.570, 1+ALB+AST+NEFA+Thr+Orn+Lys; 0.763, 254.666, 1+ALB+gGT+NEFA+Glc+His+Lys; 0.763, 252.040, 1+ALB+ALT+NEFA+Arg+Orn+Lys; 0.763, 252.268, 1+ALB+ALT+NEFA+3MeHis+Orn+Lys; 0.763, 252.270, 1+ALB+3MeHis+Asp+Orn+Lys+Trp; 0.763, 251.843, 1+ALB+BUN+AST+gGT+Glc+Lys; 0.763, 250.135, 1+ALB+AST+NEFA+3MeHis+Asp+Lys; 0.763, 251.519, 1+ALB+BUN+AST+ALT+Thr+Orn; 0.763, 252.094, 1+ALB+BUN+AST+gGT+Thr+Lys; 0.763, 252.341, 1+ALB+AST+ALT+T-BIL+His+Arg; 0.763, 253.647, 1+ALB+AST+gGT+His+Arg+Orn; 0.763, 253.516, 1+ALB+BUN+gGT+Arg+Orn+Lys; 0.763, 253.470, 1+ALB+ALT+gGT+NEFA+Arg+Ile; 0.763, 252.630, 1+ALB+AST+ALT+BHBA+Arg+Thr; 0.763, 251.103, 1+ALB+AST+ALT+Glc+Arg+Lys; 0.763, 252.222, 1+ALB+AST+3MeHis+Orn+Lys+Trp; 0.763, 254.714, 1+ALB+AST+NEFA+Tyr+Phe+Trp; 0.763, 252.144, 1+ALB+ALT+NEFA+T-BIL+His+Lys; 0.763, 252.439, 1+ALB+ALT+gGT+T-BIL+Lys+Ile; 0.763, 253.685, 1+ALB+BUN+T-BIL+His+Thr+Orn; 0.763, 251.887, 1+ALB+ALT+T-BIL+Glc+Lys+Ile; 0.763, 254.851, 1+ALB+NEFA+BHBA+His+Lys+Ile; 0.763, 251.938, 1+ALB+ALT+His+Thr+Lys+Ile; 0.763, 251.371, 1+ALB+AST+ALT+T-BIL+Lys+Ile; 0.763, 253.099, 1+ALB+ALT+Arg+Orn+Tyr+Val; 0.763, 253.633, 1+ALB+BUN+BHBA+Thr+Orn+Lys; 0.763, 253.139, 1+ALB+ALT+BHBA+Arg+Thr+Orn; 0.763, 253.589, 1+ALB+ALT+gGT+T-BIL+Arg+Ile; 0.763, 254.857, 1+Ala+Gly+Trp+TG+ALB; 0.763, 251.262, 1+ALB+AST+ALT+BHBA+Arg+Lys; 0.763, 252.163, 1+ALB+AST+ALT+T-BIL+Arg+Orn; 0.763, 252.345, 1+ALB+AST+ALT+NEFA+Arg+Thr; 0.763, 252.176, 1+ALB+AST+NEFA+3MeHis+Arg+Lys; 0.763, 253.393, 1+ALB+BUN+Ca+Glc+Arg+Lys; 0.763, 255.906, 1+ALB+Orn+Tyr+Val+Phe+Trp; 0.763, 253.607, 1+ALB+BUN+gGT+Glc+Thr+Lys; 0.763, 252.630, 1+ALB+AST+ALT+gGT+Arg+Thr; 0.763, 252.085, 1+ALB+AST+NEFA+Asp+Orn+Lys; 0.763, 250.932, 1+ALB+AST+ALT+NEFA+Asp+Trp; 0.763, 255.095, 1+ALB+T-BIL+Glc+His+Thr+Lys; 0.763, 251.848, 1+ALB+ALT+Glc+Thr+Lys+Ile; 0.763, 253.534, 1+ALB+AST+NEFA+His+Thr+Orn; 0.763, 255.236, 1+ALB+AST+T-BIL+Arg+Thr+Ile; 0.763, 251.971, 1+ALB+Ca+ALT+His+Arg+Thr; 0.763, 252.830, 1+ALB+Ca+AST+NEFA+Lys+Ile; 0.763, 253.705, 1+ALB+BUN+Ca+Thr+Orn+Lys; 0.763, 251.860, 1+ALB+AST+ALT+Orn+Lys+Val; 0.763, 252.504, 1+ALB+3MeHis+Asp+Lys+Val+Phe; 0.763, 253.330, 1+ALB+BUN+gGT+BHBA+Glc+Lys; 0.763, 255.108, 1+ALB+NEFA+Thr+Orn+Lys+Ile; 0.763, 252.255, 1+ALB+3MeHis+Asp+Lys+Phe+Trp; 0.763, 253.189, 1+ALB+ALT+T-BIL+His+Arg+Ile; 0.763, 254.302, 1+ALB+NEFA+3MeHis+Arg+Lys+Tyr; 0.763, 252.088, 1+ALB+AST+ALT+Arg+Thr+Orn; 0.763, 254.122, 1+ALB+BUN+His+Thr+Orn+Ile; 0.763, 251.878, 1+ALB+AST+NEFA+Asp+Orn+Trp; 0.763, 253.864, 1+ALB+AST+T-BIL+Arg+Orn+Lys; 0.763, 251.973, 1+ALB+ALT+T-BIL+His+Lys+Ile; 0.763, 255.904, 1+ALB+AST+gGT+Arg+Thr+Ile; 0.763, 255.548, 1+ALB+NEFA+3MeHis+Lys+Tyr+Phe; 0.763, 252.564, 1+ALB+ALT+BHBA+Glc+Orn+Lys; 0.763, 253.168, 1+ALB+ALT+NEFA+Arg+Thr+Orn; 0.763, 252.578, 1+ALB+BUN+ALT+NEFA+3MeHis+Orn; 0.763, 252.016, 1+ALB+ALT+NEFA+Arg+Thr+Lys; 0.763, 252.262, 1+ALB+ALT+3MeHis+Orn+Lys+Tyr; 0.763, 252.603, 1+ALB+AST+ALT+T-BIL+Arg+Thr; 0.763, 249.866, 1+ALB+AST+ALT+Arg+Asp+Lys; 0.763, 250.547, 1+ALB+AST+3MeHis+Asp+Lys+Phe; 0.763, 251.966, 1+ALB+BUN+AST+ALT+gGT+Orn; 0.763, 253.586, 1+ALB+AST+NEFA+Orn+Lys+Phe; 0.763, 253.893, 1+ALB+AST+NEFA+Lys+Val+Phe; 0.763, 253.376, 1+ALB+AST+His+Arg+Thr+Lys; 0.762, 252.642, 1+ALB+ALT+Glc+Thr+Orn+Lys; 0.762, 253.519, 1+ALB+BUN+gGT+Arg+Thr+Lys; 0.762, 254.346, 1+ALB+BUN+3MeHis+Tyr+Val+Trp; 0.762, 251.930, 1+ALB+ALT+gGT+Glc+Arg+Lys; 0.762, 251.046, 1+ALB+AST+ALT+Arg+Asp+Orn; 0.762, 255.222, 1+ALB+Arg+Thr+Orn+Lys+Ile; 0.762, 251.271, 1+ALB+AST+ALT+gGT+Arg+Lys; 0.762, 253.648, 1+ALB+AST+NEFA+BHBA+Orn+Lys; 0.762, 252.402, 1+ALB+ALT+T-BIL+BHBA+Lys+Ile; 0.762, 252.453, 1+ALB+ALT+BHBA+His+Thr+Lys; 0.762, 252.734, 1+ALB+BUN+AST+T-BIL+His+Orn; 0.762, 255.432, 1+ALB+AST+T-BIL+Thr+Orn+Ile; 0.762, 253.556, 1+ALB+BUN+Ca+BHBA+Orn+Lys; 0.762, 251.741, 1+ALB+BUN+Ca+AST+Arg+Lys; 0.762, 253.684, 1+ALB+ALT+T-BIL+Glc+Arg+Ile; 0.762, 252.109, 1+ALB+ALT+gGT+Arg+Orn+Lys; 0.762, 253.506, 1+ALB+ALT+NEFA+Glc+Arg+Ile; 0.762, 250.730, 1+ALB+ALT+Arg+Asp+Lys+Val; 0.762, 252.009, 1+ALB+AST+ALT+NEFA+Arg+Orn; 0.762, 250.802, 1+ALB+AST+ALT+Asp+Val+Trp; 0.762, 251.834, 1+ALB+ALT+Glc+His+Lys+Ile; 0.762, 252.680, 1+ALB+AST+3MeHis+Lys+Phe+Trp; 0.762, 253.631, 1+ALB+AST+BHBA+His+Arg+Orn; 0.762, 252.276, 1+ALB+3MeHis+Arg+Asp+Lys+Val; 0.762, 252.118, 1+ALB+ALT+Arg+Thr+Orn+Lys; 0.762, 250.305, 1+ALB+ALT+Arg+Asp+Lys+Tyr; 0.762, 251.981, 1+ALB+ALT+Glc+Arg+Thr+Lys; 0.762, 251.648, 1+ALB+AST+ALT+NEFA+Orn+Lys; 0.762, 252.509, 1+ALB+AST+ALT+BHBA+His+Arg; 0.762, 253.667, 1+ALB+AST+NEFA+T-BIL+Orn+Lys; 0.762, 253.225, 1+ALB+AST+NEFA+T-BIL+Arg+Lys; 0.762, 253.264, 1+ALB+AST+NEFA+3MeHis+Lys+Tyr; 0.762, 251.937, 1+ALB+ALT+BHBA+Glc+His+Lys; 0.762, 253.149, 1+ALB+ALT+T-BIL+Arg+Thr+Orn; 0.762, 254.435, 1+ALB+NEFA+Glc+Orn+Lys+Ile; 0.762, 250.740, 1+ALB+ALT+Arg+Asp+Orn+Lys; 0.762, 251.938, 1+ALB+ALT+BHBA+Glc+Arg+Lys; 0.762, 251.951, 1+ALB+ALT+T-BIL+Glc+Arg+Lys; 0.762, 253.387, 1+ALB+ALT+NEFA+BHBA+Arg+Ile; 0.762, 253.678, 1+ALB+ALT+BHBA+Glc+Arg+Ile; 0.762, 251.412, 1+ALB+AST+ALT+Glc+Lys+Ile; 0.762, 251.513, 1+ALB+BUN+AST+Asp+Orn+Phe; 0.762, 252.618, 1+ALB+AST+ALT+NEFA+BHBA+Arg; 0.762, 252.162, 1+ALB+AST+Asp+Orn+Phe+Trp; 0.762, 252.488, 1+ALB+AST+ALT+Glc+His+Arg; 0.762, 252.748, 1+ALB+AST+3MeHis+Arg+Lys+Phe; 0.762, 251.565, 1+ALB+AST+ALT+T-BIL+His+Lys; 0.762, 253.071, 1+ALB+AST+NEFA+BHBA+His+Lys; 0.762, 252.513, 1+ALB+ALT+NEFA+3MeHis+Arg+Orn; 0.762, 255.253, 1+ALB+NEFA+Lys+Tyr+Phe+Trp; 0.762, 254.357, 1+ALB+T-BIL+BHBA+His+Orn+Lys; 0.762, 253.166, 1+ALB+AST+NEFA+Arg+Thr+Lys; 0.762, 253.854, 1+ALB+Ca+NEFA+His+Orn+Lys; 0.762, 253.407, 1+ALB+BUN+Ca+BHBA+Arg+Lys; 0.762, 253.022, 1+ALB+Ca+ALT+Glc+Arg+Orn; 0.762, 253.109, 1+ALB+ALT+NEFA+Glc+Arg+Orn; 0.762, 252.592, 1+ALB+ALT+T-BIL+Glc+Orn+Lys; 0.762, 252.723, 1+ALB+ALT+3MeHis+Arg+Tyr+Val; 0.762, 255.403, 1+ALB+NEFA+3MeHis+Lys+Val+Phe; 0.762, 252.144, 1+ALB+ALT+BHBA+Arg+Orn+Lys; 0.762, 252.538, 1+ALB+BUN+ALT+3MeHis+Orn+Val; 0.762, 252.731, 1+ALB+BUN+ALT+NEFA+Glc+Orn; 0.762, 252.027, 1+ALB+ALT+gGT+NEFA+Arg+Lys; 0.762, 253.067, 1+ALB+ALT+gGT+T-BIL+His+Arg; 0.762, 255.012, 1+ALB+NEFA+T-BIL+Orn+Lys+Ile; 0.762, 252.927, 1+ALB+AST+NEFA+Glc+Arg+Lys; 0.762, 253.605, 1+ALB+BUN+Ca+BHBA+Thr+Lys; 0.762, 253.184, 1+ALB+ALT+NEFA+BHBA+Arg+Orn; 0.762, 252.144, 1+ALB+ALT+T-BIL+Arg+Orn+Lys; 0.762, 252.183, 1+ALB+ALT+T-BIL+BHBA+Arg+Lys; 0.762, 253.420, 1+ALB+BUN+gGT+BHBA+Arg+Lys; 0.762, 252.146, 1+ALB+ALT+gGT+BHBA+Arg+Lys; 0.762, 251.944, 1+ALB+BUN+AST+Thr+Orn+Lys; 0.762, 252.910, 1+ALB+AST+NEFA+3MeHis+Orn+Lys; 0.762, 253.034, 1+ALB+AST+Glc+His+Arg+Lys; 0.762, 253.442, 1+ALB+AST+gGT+His+Arg+Lys; 0.762, 253.068, 1+ALB+Ca+AST+His+Orn+Lys; 0.762, 253.124, 1+ALB+ALT+T-BIL+Glc+His+Arg; 0.762, 254.821, 1+ALB+3MeHis+Arg+Orn+Lys+Val; 0.762, 252.754, 1+ALB+3MeHis+Arg+Asp+Orn+Lys; 0.762, 252.846, 1+ALB+ALT+NEFA+T-BIL+His+Arg; 0.762, 254.424, 1+ALB+3MeHis+Arg+Lys+Phe+Trp; 0.762, 255.453, 1+ALB+BUN+3MeHis+Tyr+Val+Phe; 0.762, 252.910, 1+Ala+Gly+Trp+ALB; 0.762, 253.031, 1+ALB+ALT+gGT+Glc+His+Arg; 0.762, 255.619, 1+ALB+NEFA+BHBA+Thr+Lys+Ile; 0.762, 252.066, 1+ALB+BUN+AST+NEFA+Arg+Asp; 0.762, 253.349, 1+ALB+BUN+AST+T-BIL+Arg+Thr; 0.762, 250.491, 1+ALB+AST+3MeHis+Asp+Orn+Lys; 0.762, 252.034, 1+ALB+BUN+AST+ALT+Orn+Ile; 0.762, 254.501, 1+ALB+AST+Arg+Orn+Lys+Val; 0.762, 254.565, 1+ALB+AST+T-BIL+His+Orn+Ile; 0.762, 255.900, 1+ALB+AST+BHBA+Arg+Thr+Ile; 0.762, 253.058, 1+ALB+AST+NEFA+T-BIL+His+Lys; 0.762, 252.205, 1+ALB+BUN+Ca+ALT+Thr+Orn; 0.762, 253.066, 1+ALB+ALT+NEFA+T-BIL+Arg+Orn; 0.762, 253.193, 1+ALB+ALT+NEFA+Arg+Orn+Tyr; 0.762, 254.609, 1+ALB+3MeHis+Arg+Lys+Tyr+Phe; 0.762, 252.219, 1+ALB+BUN+ALT+3MeHis+Orn+Tyr; 0.762, 252.756, 1+ALB+3MeHis+Arg+Asp+Lys+Phe; 0.762, 255.262, 1+ALB+NEFA+Arg+Lys+Tyr+Phe; 0.762, 252.144, 1+ALB+ALT+gGT+T-BIL+Arg+Lys; 0.762, 253.200, 1+ALB+ALT+T-BIL+BHBA+His+Arg; 0.762, 253.658, 1+ALB+ALT+T-BIL+BHBA+Arg+Ile; 0.762, 251.612, 1+ALB+AST+ALT+Orn+Lys+Phe; 0.762, 251.943, 1+ALB+BUN+AST+ALT+Glc+Orn; 0.762, 252.016, 1+ALB+BUN+AST+NEFA+Asp+Orn; 0.762, 251.608, 1+ALB+AST+ALT+His+Lys+Ile; 0.762, 253.927, 1+ALB+AST+T-BIL+His+Thr+Orn; 0.762, 253.348, 1+ALB+AST+NEFA+His+Arg+Thr; 0.762, 253.772, 1+ALB+BUN+Ca+gGT+Thr+Lys; 0.762, 253.513, 1+ALB+BUN+Ca+Glc+Orn+Lys; 0.762, 252.881, 1+ALB+ALT+NEFA+Glc+His+Arg; 0.762, 251.916, 1+ALB+ALT+NEFA+Asp+Val+Trp; 0.762, 252.687, 1+ALB+BUN+ALT+T-BIL+Glc+Orn; 0.762, 252.730, 1+ALB+BUN+ALT+Glc+Orn+Ile; 0.762, 252.185, 1+ALB+AST+ALT+BHBA+Arg+Orn; 0.762, 252.543, 1+ALB+ALT+NEFA+3MeHis+Lys+Tyr; 0.762, 252.637, 1+ALB+AST+3MeHis+Arg+Orn+Lys; 0.762, 253.517, 1+ALB+ALT+gGT+Glc+Arg+Ile; 0.762, 252.206, 1+ALB+ALT+BHBA+His+Lys+Ile; 0.762, 252.413, 1+ALB+ALT+NEFA+3MeHis+Lys+Val; 0.762, 252.537, 1+ALB+ALT+gGT+BHBA+His+Lys; 0.762, 252.661, 1+ALB+AST+ALT+gGT+NEFA+Arg; 0.762, 252.213, 1+ALB+AST+NEFA+Asp+Lys+Phe; 0.762, 253.121, 1+ALB+BUN+AST+NEFA+Arg+Thr; 0.762, 253.665, 1+ALB+AST+Arg+Val+Phe+Trp; 0.762, 255.743, 1+ALB+T-BIL+BHBA+His+Lys+Ile; 0.762, 253.138, 1+ALB+Ca+ALT+Arg+Thr+Orn; 0.762, 252.680, 1+ALB+Ca+AST+ALT+Arg+Ile; 0.762, 254.795, 1+ALB+3MeHis+Lys+Tyr+Val+Trp; 0.762, 250.943, 1+ALB+AST+ALT+Asp+Tyr+Trp; 0.762, 251.524, 1+ALB+AST+ALT+NEFA+3MeHis+Lys; 0.762, 252.434, 1+ALB+ALT+BHBA+Thr+Lys+Ile; 0.762, 252.556, 1+ALB+BUN+AST+His+Thr+Orn; 0.762, 254.929, 1+ALB+AST+NEFA+Thr+Orn+Ile; 0.762, 253.318, 1+ALB+AST+BHBA+His+Arg+Lys; 0.762, 253.592, 1+ALB+Ca+ALT+T-BIL+Arg+Ile; 0.762, 253.618, 1+ALB+BUN+Ca+Glc+Thr+Lys; 0.762, 250.883, 1+ALB+BUN+Ca+AST+T-BIL+Lys; 0.762, 252.636, 1+ALB+NEFA+3MeHis+Arg+Asp+Lys; 0.762, 253.104, 1+ALB+ALT+gGT+Arg+Thr+Orn; 0.762, 253.691, 1+ALB+BUN+AST+3MeHis+Val+Phe; 0.762, 254.419, 1+ALB+3MeHis+Arg+Orn+Lys+Trp; 0.762, 254.748, 1+ALB+3MeHis+Arg+Orn+Lys+Tyr; 0.762, 256.303, 1+Ala+Gly+Trp+Glc+gGT+ALB; 0.762, 251.907, 1+ALB+BUN+AST+ALT+T-BIL+Orn; 0.762, 254.915, 1+ALB+NEFA+T-BIL+His+Lys+Ile; 0.762, 254.922, 1+ALB+gGT+NEFA+His+Lys+Ile; 0.762, 253.050, 1+ALB+AST+NEFA+His+Thr+Lys; 0.762, 253.476, 1+ALB+Ca+ALT+Glc+Arg+Ile; 0.762, 251.849, 1+ALB+BUN+Ca+AST+Glc+Lys; 0.762, 255.092, 1+ALB+3MeHis+Orn+Val+Phe+Trp; 0.762, 252.961, 1+ALB+ALT+Glc+Arg+Thr+Orn; 0.762, 252.502, 1+ALB+AST+ALT+Arg+Tyr+Val; 0.762, 252.762, 1+ALB+ALT+NEFA+T-BIL+Orn+Lys; 0.762, 252.450, 1+ALB+ALT+3MeHis+Lys+Tyr+Val; 0.762, 253.223, 1+ALB+ALT+BHBA+His+Arg+Ile; 0.762, 252.754, 1+ALB+AST+ALT+Glc+His+Orn; 0.762, 254.426, 1+ALB+AST+NEFA+Arg+Orn+Val; 0.762, 252.356, 1+ALB+ALT+T-BIL+His+Thr+Lys; 0.762, 252.407, 1+ALB+ALT+T-BIL+BHBA+His+Lys; 0.762, 252.435, 1+ALB+ALT+gGT+Thr+Lys+Ile; 0.762, 253.998, 1+ALB+AST+T-BIL+BHBA+Arg+Lys; 0.762, 254.779, 1+ALB+T-BIL+Glc+His+Lys+Ile; 0.762, 253.571, 1+ALB+BUN+Ca+gGT+BHBA+Lys; 0.762, 253.456, 1+ALB+Ca+ALT+gGT+Arg+Ile; 0.762, 253.053, 1+ALB+Ca+ALT+His+Arg+Ile; 0.762, 252.989, 1+ALB+Ca+ALT+Glc+His+Arg; 0.762, 253.146, 1+ALB+ALT+BHBA+Glc+Arg+Orn; 0.762, 250.899, 1+ALB+ALT+NEFA+Asp+Orn+Lys; 0.762, 251.776, 1+ALB+3MeHis+Arg+Asp+Lys+Tyr; 0.762, 252.163, 1+ALB+ALT+T-BIL+Arg+Thr+Lys; 0.762, 252.277, 1+ALB+BUN+AST+Arg+Asp+Phe; 0.762, 252.460, 1+ALB+ALT+Glc+His+Thr+Orn; 0.762, 252.835, 1+ALB+BUN+ALT+NEFA+Orn+Ile; 0.762, 254.390, 1+ALB+NEFA+3MeHis+Arg+Lys+Trp; 0.762, 254.581, 1+ALB+NEFA+3MeHis+Arg+Lys+Val; 0.762, 254.091, 1+ALB+AST+T-BIL+Thr+Orn+Lys; 0.762, 252.210, 1+ALB+AST+ALT+Lys+Val+Phe; 0.762, 253.001, 1+ALB+AST+ALT+gGT+Glc+Arg; 0.762, 252.413, 1+ALB+ALT+gGT+T-BIL+His+Lys; 0.762, 252.571, 1+ALB+ALT+gGT+His+Thr+Lys; 0.762, 253.910, 1+ALB+AST+NEFA+Arg+Asp+Tyr; 0. 762, 253.102, 1+ALB+AST+His+Arg+Thr+Orn; 0.762, 252.595, 1+ALB+Ca+AST+ALT+Arg+Thr; 0.761, 253.148, 1+ALB+ALT+T-BIL+Glc+Arg+Or n; 0.761, 255.574, 1+ALB+3MeHis+Arg+Orn+Tyr+Phe; 0.761, 252.835, 1+ALB+BUN+ALT+gGT+Orn+Ile; 0.761, 253.736, 1+ALB+BUN+AST+Arg+O rn+Tyr; 0.761, 251.198, 1+ALB+BUN+AST+NEFA+Asp+Phe; 0.761, 252.5 64, 1+ALB+AST+ALT+NEFA+T-BIL+Arg; 0.761, 252.939, 1+ALB+AST+ALT+T-BIL+BHBA+Arg; 0.761, 254.296, 1+ALB+AST+NEFA+BHBA+Arg+Orn; 0. 761, 249.840, 1+ALB+AST+ALT+NEFA+Asp+Lys; 0.761, 251.961, 1+ALB+BUN+AST+ALT+Orn+Val; 0.761, 251.871, 1+ALB+AST+ALT+BHBA+His+Ly s; 0.761, 252.002, 1+ALB+AST+ALT+NEFA+Lys+Val; 0.761, 252.832, 1+ALB+AST+gGT+NEFA+His+Lys; 0.761, 253.662, 1+ALB+BUN+Ca+gGT+Orn+Lys; 0.761, 252.613, 1+ALB+Ca+AST+ALT+NEFA+Arg; 0.761, 252.407, 1+ALB+Ca+AST+ALT+His+Arg; 0.761, 252.266, 1+ALB+ALT+gGT+Glc+Hi s+Lys; 0.761, 254.588, 1+ALB+3MeHis+Orn+Lys+Tyr+Trp; 0.761, 252. 453, 1+ALB+BUN+ALT+Orn+Tyr+Val; 0.761, 253.172, 1+ALB+ALT+Glc+H is+Arg+Ile; 0.761, 254.390, 1+ALB+gGT+T-BIL+His+Orn+Lys; 0.761, 251.903, 1+ALB+AST+ALT+3MeHis+Arg+Tyr; 0.761, 252.179, 1+ALB+AS T+ALT+Arg+Orn+Val; 0.761, 252.180, 1+ALB+AST+ALT+gGT+Arg+Orn; 0. 761, 252.271, 1+ALB+ALT+gGT+His+Lys+Ile; 0.761, 252.965, 1+ALB+A ST+ALT+gGT+T-BIL+Arg; 0.761, 253.248, 1+ALB+AST+NEFA+Glc+Orn+L ys; 0.761, 252.628, 1+ALB+ALT+gGT+Glc+Orn+Lys; 0.761, 256.464, 1+ALB+NEFA+Orn+Lys+Val+Phe; 0.761, 256.075, 1+ALB+Lys+Tyr+Val+Ph e+Trp; 0.761, 253.736, 1+ALB+BUN+AST+gGT+Arg+Orn; 0.761, 257.180, 1+ALB+BHBA+Arg+Thr+Orn+Ile; 0.761, 254.064, 1+ALB+AST+NEFA+Arg+Orn+Phe; 0.761, 254.195, 1+ALB+AST+NEFA+T-BIL+BHBA+Lys; 0.761, 253.142, 1+ALB+AST+gGT+NEFA+Arg+Lys; 0.761, 251.842, 1+ALB+BUN+Ca+AST+BHBA+Lys; 0.761, 252.098, 1+ALB+Ca+ALT+NEFA+His+Lys; 0.7 61, 251.938, 1+ALB+Ca+ALT+Glc+Arg+Lys; 0.761, 251.711, 1+ALB+AST+3MeHis+Asp+Tyr+Trp; 0.761, 253.239, 1+ALB+ALT+NEFA+Arg+Orn+Va l; 0.761, 253.279, 1+ALB+ALT+NEFA+Glc+Arg+Thr; 0.761, 252.818, 1+ALB+BUN+ALT+NEFA+BHBA+Orn; 0.761, 253.105, 1+ALB+ALT+gGT+BHBA+His+Arg; 0.761, 254.752, 1+ALB+3MeHis+Arg+Lys+Tyr+Val; 0.761, 25 5.118, 1+ALB+gGT+NEFA+Orn+Lys+Ile; 0.761, 255.890, 1+ALB+T-BIL+Thr+Orn+Lys+Ile; 0.761, 250.888, 1+ALB+ALT+Asp+Orn+Lys+Tyr; 0.7 61, 251.689, 1+ALB+AST+ALT+Arg+Asp+Tyr; 0.761, 252.789, 1+ALB+AL T+NEFA+T-BIL+Glc+Lys; 0.761, 253.046, 1+ALB+AST+ALT+gGT+BHBA+A rg; 0.761, 253.067, 1+ALB+ALT+NEFA+T-BIL+BHBA+Lys; 0.761, 252.86 2, 1+ALB+AST+ALT+T-BIL+His+Orn; 0.761, 254.900, 1+ALB+AST+NEFA+BHBA+Arg+Ile; 0.761, 253.455, 1+ALB+BUN+Ca+gGT+Arg+Lys; 0.761, 2 52.859, 1+ALB+Ca+ALT+NEFA+His+Arg; 0.761, 252.587, 1+ALB+BUN+Ca+ALT+Glc+Orn; 0.761, 252.608, 1+ALB+Ca+ALT+Glc+Orn+Lys; 0.761, 2 54.848, 1+ALB+NEFA+3MeHis+Lys+Tyr+Trp; 0.761, 252.419, 1+ALB+AL T+NEFA+Arg+Asp+Tyr; 0.761, 253.231, 1+ALB+ALT+gGT+Glc+Arg+Thr; 0.761, 254.449, 1+ALB+T-BIL+His+Thr+Orn+Lys; 0.761, 251.898, 1+A LB+AST+ALT+NEFA+3MeHis+Arg; 0.761, 251.946, 1+ALB+AST+ALT+Orn+Lys+Tyr; 0.761, 252.099, 1+ALB+AST+ALT+Arg+Orn+Tyr; 0.761, 250.1 55, 1+ALB+AST+3MeHis+Asp+Lys+Val; 0.761, 250.196, 1+ALB+AST+ALT+Asp+Lys+Phe; 0.761, 252.836, 1+ALB+AST+3MeHis+Orn+Phe+Trp; 0.7 61, 253.643, 1+ALB+BUN+AST+NEFA+T-BIL+Arg; 0.761, 252.790, 1+ALB+AST+ALT+NEFA+His+Orn; 0.761, 253.492, 1+ALB+AST+gGT+NEFA+Orn+Lys; 0.761, 254.382, 1+ALB+AST+NEFA+Arg+Thr+Orn; 0.761, 253.509, 1+ALB+Ca+ALT+BHBA+Arg+Ile; 0.761, 252.024, 1+ALB+Ca+ALT+NEFA+A rg+Lys; 0.761, 252.870, 1+ALB+AST+NEFA+Asp+Phe+Trp; 0.761, 252.1 98, 1+ALB+BUN+3MeHis+Arg+Asp+Orn; 0.761, 252.916, 1+ALB+ALT+NEF A+3MeHis+Arg+Tyr; 0.761, 252.166, 1+ALB+ALT+BHBA+Arg+Thr+Lys; 0. 761, 252.462, 1+ALB+AST+ALT+Glc+Arg+Thr; 0.761, 252.928, 1+ALB+A ST+Asp+Tyr+Phe+Trp; 0.761, 252.752, 1+ALB+ALT+NEFA+BHBA+Glc+Ly s; 0.761, 252.976, 1+ALB+3MeHis+Asp+Orn+Lys+Phe; 0.761, 250.050, 1+ALB+AST+3MeHis+Asp+Lys+Tyr; 0.761, 251.778, 1+ALB+BUN+AST+AL T+3MeHis+Orn; 0.761, 253.096, 1+ALB+ALT+gGT+NEFA+T-BIL+Lys; 0.7 61, 252.929, 1+ALB+BUN+AST+NEFA+His+Orn; 0.761, 253.536, 1+ALB+B UN+Ca+gGT+Glc+Lys; 0.761, 251.904, 1+ALB+BUN+Ca+AST+Orn+Lys; 0. 761, 252.089, 1+ALB+Ca+ALT+NEFA+Lys+Ile; 0.761, 255.223, 1+Ala+G ly+Trp+TCHO+TG+ALB; 0.761, 252.966, 1+ALB+Ca+AST+ALT+gGT+Arg; 0. 761, 252.451, 1+ALB+BUN+3MeHis+Arg+Asp+Val; 0.761, 253.255, 1+AL B+ALT+T-BIL+BHBA+Arg+Orn; 0.761, 252.811, 1+ALB+BUN+ALT+T-BIL+BHBA+Orn; 0.761, 252.861, 1+ALB+ALT+NEFA+3MeHis+Arg+Val; 0.761, 252.810, 1+ALB+ALT+NEFA+Thr+Orn+Lys; 0.761, 253.676, 1+ALB+Asp+Lys+Tyr+Phe+Trp; 0.761, 251.407, 1+ALB+AST+ALT+3MeHis+Arg+Orn; 0.761, 253.227, 1+ALB+BUN+AST+3MeHis+Arg+Tyr; 0.761, 253.682, 1+ALB+BUN+AST+NEFA+BHBA+Arg; 0.761, 251.635, 1+ALB+AST+ALT+3MeHi s+Lys+Val; 0.761, 251.758, 1+ALB+AST+ALT+BHBA+Lys+Ile; 0.761, 25 1.895, 1+ALB+AST+3MeHis+Arg+Asp+Orn; 0.761, 251.945, 1+ALB+AST+ALT+Thr+Orn+Lys; 0.761, 252.214, 1+ALB+AST+3MeHis+Arg+Asp+Tyr; 0.761, 252.987, 1+ALB+AST+NEFA+3MeHis+Orn+Trp; 0.761, 254.380, 1+ALB+AST+NEFA+T-BIL+Arg+Orn; 0.761, 252.028, 1+ALB+AST+ALT+NEF A+Lys+Tyr; 0.761, 252.036, 1+ALB+AST+ALT+NEFA+T-BIL+Lys; 0.761, 253.957, 1+ALB+AST+T-BIL+Arg+Thr+Lys; 0.761, 254.242, 1+ALB+AST+His+Thr+Orn+Ile; 0.761, 252.896, 1+ALB+Ca+AST+ALT+T-BIL+Arg; 0. 761, 251.795, 1+ALB+ALT+Asp+Tyr+Val+Trp; 0.761, 252.732, 1+ALB+B UN+ALT+gGT+Glc+Orn; 0.761, 252.836, 1+ALB+BUN+ALT+gGT+NEFA+Or n; 0.761, 252.773, 1+ALB+BUN+AST+NEFA+3MeHis+Arg; 0.761, 252.957, 1+ALB+ALT+T-BIL+BHBA+Orn+Lys; 0.761, 253.696, 1+ALB+BUN+AST+BH BA+Arg+Orn; 0.761, 252.109, 1+ALB+ALT+BHBA+Glc+Lys+Ile; 0.761, 2 53.315, 1+ALB+BUN+Ca+BHBA+Glc+Lys; 0.761, 251.265, 1+ALB+Ca+AST+ALT+Arg+Lys; 0.761, 253.188, 1+ALB+ALT+BHBA+Glc+His+Arg; 0.761, 255.099, 1+ALB+NEFA+Orn+Lys+Tyr+Trp; 0.761, 252.673, 1+ALB+BUN+ALT+BHBA+Glc+Orn; 0.761, 252.818, 1+ALB+BUN+ALT+gGT+BHBA+Orn; 0. 761, 252.818, 1+ALB+BUN+ALT+BHBA+Orn+Ile; 0.761, 254.037, 1+ALB+AST+NEFA+Lys+Tyr+Val; 0.761, 254.282, 1+ALB+BUN+AST+gGT+Arg+Th r; 0.761, 253.094, 1+ALB+ALT+NEFA+T-BIL+Thr+Lys; 0.761, 252.588, 1+ALB+ALT+gGT+BHBA+Lys+Ile; 0.761, 253.009, 1+ALB+AST+ALT+Thr+Orn+Ile; 0.761, 253.217, 1+ALB+AST+NEFA+3MeHis+Lys+Phe; 0.761, 2 53.740,

1+ALB+AST+T-BIL+BHBA+His+Lys; 0.761, 253.177, 1+ALB+Ca+AST+NEFA+Arg+Lys; 0.761, 251.794, 1+ALB+ALT+Arg+Asp+Tyr+Val; 0.761, 252.502, 1+ALB+3MeHis+Asp+Orn+Lys+Val; 0.761, 250.726, 1+ALB+ALT+NEFA+Asp+Lys+Tyr; 0.761, 252.846, 1+ALB+ALT+gGT+NEFA+Orn+Lys; 0.761, 254.167, 1+ALB+AST+3MeHis+Orn+Tyr+Phe; 0.761, 252.482, 1+ALB+AST+ALT+NEFA+Arg+Val; 0.761, 251.639, 1+ALB+AST+ALT+Glc+His+Lys; 0.761, 251.749, 1+ALB+BUN+AST+ALT+Orn+Tyr; 0.761, 253.652, 1+ALB+BUN+AST+NEFA+Glc+Arg; 0.761, 254.164, 1+ALB+BUN+BHBA+His+Thr+Orn; 0.761, 255.225, 1+ALB+T-BIL+BHBA+Glc+His+Lys; 0.761, 251.981, 1+ALB+BUN+Ca+AST+ALT+Orn; 0.761, 253.465, 1+ALB+Ca+ALT+NEFA+Arg+Ile; 0.761, 253.204, 1+ALB+Ca+ALT+NEFA+Arg+Orn; 0.761, 252.097, 1+ALB+BUN+Ca+AST+Thr+Lys; 0.761, 255.631, 1+ALB+3MeHis+Orn+Lys+Tyr+Phe; 0.761, 252.341, 1+ALB+NEFA+3MeHis+Asp+Lys+Val; 0.761, 252.933, 1+ALB+ALT+BHBA+Thr+Orn+Lys; 0.761, 252.926, 1+ALB+ALT+T-BIL+Thr+Orn+Lys; 0.761, 255.676, 1+ALB+NEFA+Arg+Orn+Lys+Tyr; 0.761, 252.801, 1+ALB+ALT+NEFA+Glc+Thr+Lys; 0.761, 252.979, 1+ALB+ALT+T-BIL+Glc+Thr+Lys; 0.761, 253.510, 1+ALB+BUN+AST+Arg+Thr+Orn; 0.761, 253.524, 1+ALB+AST+3MeHis+Arg+Orn+Phe; 0.761, 251.327, 1+ALB+AST+ALT+NEFA+Arg+Asp; 0.761, 251.689, 1+ALB+AST+ALT+NEFA+Glc+Lys; 0.761, 251.732, 1+ALB+AST+ALT+3MeHis+Lys+Tyr; 0.761, 253.370, 1+ALB+AST+3MeHis+Orn+Lys+Tyr; 0.761, 253.477, 1+ALB+AST+ALT+3MeHis+Val+Trp; 0.761, 254.514, 1+ALB+AST+gGT+T-BIL+His+Orn; 0.761, 251.545, 1+ALB+AST+NEFA+Asp+Lys+Tyr; 0.761, 255.354, 1+ALB+AST+NEFA+BHBA+Orn+Ile; 0.761, 253.594, 1+ALB+Ca+AST+His+Arg+Orn; 0.761, 251.976, 1+ALB+ALT+Arg+Asp+Orn+Tyr; 0.761, 252.812, 1+ALB+BUN+ALT+T-BIL+Orn+Ile; 0.761, 255.281, 1+ALB+NEFA+3MeHis+Orn+Lys+Val; 0.761, 252.452, 1+ALB+BUN+ALT+NEFA+Orn+Tyr; 0.761, 252.817, 1+ALB+ALT+NEFA+Orn+Lys+Tyr; 0.761, 251.487, 1+ALB+AST+3MeHis+Asp+Phe+Trp; 0.761, 251.902, 1+ALB+AST+ALT+gGT+Orn+Lys; 0.761, 252.951, 1+ALB+ALT+gGT+T-BIL+Orn+Lys; 0.761, 250.219, 1+ALB+AST+ALT+Asp+Lys+Tyr; 0.761, 252.117, 1+ALB+Ca+ALT+Arg+Orn+Lys; 0.761, 252.976, 1+ALB+Ca+ALT+gGT+His+Arg; 0.761, 252.789, 1+ALB+BUN+ALT+NEFA+T-BIL+Orn; 0.761, 252.814, 1+ALB+BUN+ALT+gGT+T-BIL+Orn; 0.761, 252.075, 1+ALB+AST+ALT+Glc+Arg+Orn; 0.761, 252.736, 1+ALB+ALT+NEFA+Orn+Lys+Val; 0.761, 253.448, 1+ALB+ALT+gGT+T-BIL+Arg+Thr; 0.761, 251.936, 1+ALB+AST+ALT+BHBA+Orn+Lys; 0.761, 252.987, 1+ALB+AST+ALT+BHBA+Glc+Arg; 0.761, 254.864, 1+ALB+AST+Orn+Lys+Val+Phe; 0.761, 252.000, 1+ALB+BUN+AST+ALT+BHBA+Orn; 0.761, 253.423, 1+ALB+AST+NEFA+Arg+Asp+Orn; 0.761, 251.986, 1+ALB+BUN+AST+ALT+NEFA+Orn; 0.761, 252.111, 1+ALB+AST+NEFA+Asp+Lys+Val; 0.761, 254.132, 1+ALB+BUN+gGT+His+Thr+Orn; 0.761, 254.522, 1+ALB+AST+Arg+Lys+Tyr+Val; 0.761, 254.540, 1+ALB+AST+gGT+His+Thr+Orn; 0.761, 253.611, 1+ALB+BUN+AST+gGT+His+Orn; 0.761, 252.157, 1+ALB+Ca+ALT+BHBA+Arg+Lys; 0.761, 252.967, 1+ALB+Ca+AST+ALT+BHBA+Arg; 0.761, 252.917, 1+ALB+ALT+T-BIL+BHBA+Glc+Lys; 0.761, 251.846, 1+ALB+AST+ALT+T-BIL+Orn+Lys; 0.761, 253.165, 1+ALB+ALT+gGT+NEFA+BHBA+Lys; 0.761, 251.975, 1+ALB+AST+ALT+His+Thr+Lys; 0.761, 252.031, 1+ALB+BUN+Ca+AST+gGT+Lys; 0.761, 252.156, 1+ALB+Ca+ALT+T-BIL+Arg+Lys; 0.761, 252.935, 1+ALB+Ca+AST+NEFA+His+Lys; 0.761, 252.884, 1+ALB+Ca+AST+ALT+Glc+Arg; 0.761, 253.196, 1+ALB+ALT+gGT+NEFA+Arg+Orn; 0.761, 255.681, 1+ALB+3MeHis+Orn+Lys+Tyr+Val; 0.761, 253.430, 1+ALB+ALT+gGT+BHBA+Arg+Thr; 0.761, 253.695, 1+ALB+BUN+AST+Arg+Orn+Val; 0.761, 254.656, 1+ALB+NEFA+3MeHis+Lys+Val+Trp; 0.761, 252.583, 1+ALB+AST+ALT+NEFA+Glc+Arg; 0.761, 255.602, 1+ALB+AST+Glc+Arg+Thr+Ile; 0.760, 253.197, 1+ALB+Ca+ALT+T-BIL+Arg+Orn; 0.760, 253.169, 1+ALB+Ca+ALT+BHBA+Arg+Orn; 0.760, 252.120, 1+ALB+Ca+ALT+gGT+Arg+Lys; 0.760, 251.017, 1+ALB+ALT+Asp+Orn+Lys+Val; 0.760, 251.891, 1+ALB+AST+ALT+3MeHis+Arg+Val; 0.760, 252.799, 1+ALB+ALT+gGT+NEFA+Glc+Lys; 0.760, 254.489, 1+ALB+AST+Arg+Thr+Orn+Lys; 0.760, 251.891, 1+ALB+AST+ALT+gGT+NEFA+Lys; 0.760, 254.558, 1+ALB+AST+Arg+Orn+Lys+Phe; 0.760, 255.288, 1+ALB+AST+Arg+Orn+Tyr+Val; 0.760, 256.864, 1+ALB+NEFA+Arg+Thr+Orn+Ile; 0.760, 251.717, 1+ALB+AST+ALT+gGT+Lys+Ile; 0.760, 252.046, 1+ALB+AST+ALT+NEFA+BHBA+Lys; 0.760, 252.208, 1+ALB+ALT+gGT+Glc+Lys+Ile; 0.760, 253.409, 1+ALB+AST+NEFA+Asp+Orn+Phe; 0.760, 253.892, 1+ALB+AST+3MeHis+Lys+Val+Phe; 0.760, 253.963, 1+ALB+AST+NEFA+Glc+His+Orn; 0.760, 255.818, 1+ALB+T-BIL+His+Thr+Lys+Ile; 0.760, 253.078, 1+ALB+Ca+ALT+T-BIL+His+Arg; 0.760, 256.453, 1+ALB+NEFA+3MeHis+Orn+Tyr+Phe; 0.760, 251.658, 1+ALB+AST+ALT+Glc+Orn+Lys; 0.760, 254.050, 1+ALB+3MeHis+Asp+Orn+Tyr+Phe; 0.760, 254.699, 1+ALB+ALT+NEFA+Tyr+Val+Trp; 0.760, 253.675, 1+ALB+ALT+T-BIL+Glc+His+Orn; 0.760, 251.351, 1+ALB+AST+ALT+Arg+Asp+Val; 0.760, 250.135, 1+ALB+AST+ALT+Asp+Orn+Lys; 0.760, 253.360, 1+ALB+AST+3MeHis+Orn+Lys+Phe; 0.760, 253.563, 1+ALB+AST+ALT+NEFA+Val+Trp; 0.760, 252.035, 1+ALB+AST+ALT+NEFA+Thr+Lys; 0.760, 255.492, 1+ALB+AST+NEFA+T-BIL+Orn+Ile; 0.760, 257.465, 1+ALB+NEFA+Orn+Tyr+Val+Phe; 0.760, 252.843, 1+ALB+ALT+NEFA+BHBA+Orn+Lys; 0.760, 252.900, 1+ALB+ALT+Orn+Lys+Tyr+Val; 0.760, 252.954, 1+ALB+ALT+gGT+BHBA+Orn+Lys; 0.760, 252.132, 1+ALB+ALT+gGT+Arg+Thr+Lys; 0.760, 252.965, 1+ALB+ALT+gGT+T-BIL+Glc+Lys; 0.760, 253.339, 1+ALB+ALT+NEFA+T-BIL+Arg+Ile; 0.760, 256.754, 1+Ala+Gly+Trp+TG+gGT+ALB; 0.760, 254.369, 1+ALB+AST+gGT+NEFA+Arg+Orn; 0.760, 253.782, 1+ALB+AST+T-BIL+His+Thr+Lys; 0.760, 254.161, 1+ALB+BUN+Ca+His+Thr+Orn; 0.760, 252.833, 1+ALB+NEFA+3MeHis+Asp+Orn+Lys; 0.760, 254.899, 1+ALB+AST+Orn+Lys+Tyr+Val; 0.760, 252.996, 1+ALB+AST+ALT+His+Orn+Ile; 0.760, 253.635, 1+ALB+BUN+AST+His+Orn+Ile; 0.760, 253.958, 1+ALB+BUN+AST+Thr+Orn+Ile; 0.760, 255.578, 1+ALB+AST+T-BIL+BHBA+Orn+Ile; 0.760, 253.749, 1+ALB+Ca+AST+T-BIL+Lys+Ile; 0.760, 252.235, 1+ALB+Ca+ALT+His+Lys+Ile; 0.760, 252.390, 1+ALB+Ca+ALT+Thr+Lys+Ile; 0.760, 252.826, 1+ALB+NEFA+3MeHis+Asp+Lys+Phe; 0.760, 252.701, 1+ALB+BUN+ALT+NEFA+Orn+Val; 0.760, 255.400, 1+ALB+Arg+Orn+Lys+Val+Trp; 0.760, 253.412, 1+ALB+ALT+gGT+NEFA+Arg+Thr; 0.760, 250.757, 1+ALB+BUN+AST+3MeHis+Asp+Orn; 0.760, 252.954, 1+ALB+AST+ALT+gGT+His+Orn; 0.760, 254.139, 1+ALB+AST+NEFA+BHBA+Thr+Lys; 0.760, 254.045, 1+ALB+AST+3MeHis+Lys+Tyr+Phe; 0.760, 254.141, 1+ALB+AST+NEFA+T-BIL+Thr+Lys; 0.760, 253.552, 1+ALB+BUN+

AST+BHBA+His+Orn; 0.760, 255.846, 1+ALB+AST+ BHBA+Thr+Orn+Ile; 0.760, 252.739, 1+ALB+BUN+Ca+ ALT+Orn+Ile; 0.7 60, 252.367, 1+ALB+Ca+ALT+T-BIL+ His+Lys; 0.760, 254.982, 1+ALB+3 MeHis+Orn+Lys+Phe+ Trp; 0.760, 252.058, 1+ALB+ALT+NEFA+Arg+Asp+Orn; 0.760, 253.678, 1+ALB+BUN+AST+Glc+Arg+Orn; 0.760, 253.810, 1+ALB+ALT+gGT+T-BIL+BHBA+Arg; 0.760, 253.150, 1+ALB+ALT+NEFA+Ly s+Tyr+Val; 0.760, 253.631, 1+ALB+AST+3MeHis+Arg+Orn+Tyr; 0.760, 253.916, 1+ALB+BUN+AST+T-BIL+Orn+Ile; 0.760, 255.848, 1+ALB+AST+gGT+Thr+Orn+Ile; 0.760, 253.704, 1+ALB+AST+gGT+T-BIL+His+Lys; 0.760, 252.402, 1+ALB+Ca+ALT+T-BIL+Lys+Ile; 0.760, 254.947, 1+AL B+NEFA+3MeHis+Orn+Lys+Trp; 0.760, 252.936, 1+ALB+ALT+gGT+Thr+O rn+Lys; 0.760, 253.192, 1+ALB+ALT+gGT+T-BIL+Arg+Orn; 0.760, 254. 906, 1+ALB+3MeHis+Arg+Lys+Val+Phe; 0.760, 253.711, 1+ALB+Asp+Ly s+Tyr+Val+Trp; 0.760, 253.153, 1+ALB+ ALT+gGT+NEFA+Thr+Lys; 0.76 0, 253.013, 1+ALB+ AST+Asp+Tyr+Val+Trp; 0.760, 254.305, 1+ALB+AST+ NEFA+His+Orn+Ile; 0.760, 253.571, 1+ALB+Ca+AST+ NEFA+Orn+Lys; 0. 760, 256.051, 1+ALB+3MeHis+Arg+ Orn+Val+Phe; 0.760, 252.005, 1+AL B+ALT+Arg+Asp+ Orn+Val; 0.760, 253.170, 1+ALB+ALT+gGT+BHBA+ Arg+Orn; 0.760, 255.740, 1+ALB+NEFA+Lys+Val+Phe+ Trp; 0.760, 254.229, 1+ALB+NEFA+Arg+Asp+Lys+Trp; 0.760, 253.067, 1+ALB+ALT+NEFA+His+Thr+Orn; 0.760, 253.838, 1+ALB+AST+3MeHis+Arg+Tyr+Phe; 0.760, 2 52.874, 1+ALB+AST+ALT+T-BIL+Glc+Arg; 0.760, 253.471, 1+ALB+BUN+AST+Glc+His+Orn; 0.760, 254.031, 1+ALB+AST+T-BIL+Glc+His+Orn; 0. 760, 254.076, 1+ALB+AST+gGT+T-BIL+Arg+Lys; 0.760, 254.912, 1+ALB+AST+His+Thr+Lys+Ile; 0.760, 252.743, 1+ALB+BUN+Ca+ALT+NEFA+Or n; 0.760, 252.743, 1+ALB+BUN+Ca+ALT+gGT+Orn; 0.760, 254.537, 1+AL B+Ca+AST+T-BIL+His+Orn; 0.760, 253.399, 1+ALB+Ca+ AST+His+Arg+L ys; 0.760, 253.053, 1+ALB+ALT+gGT+ Glc+Arg+Orn; 0.760, 253.703, 1+ALB+ALT+BHBA+Glc+ His+Orn; 0.760, 253.733, 1+ALB+ALT+Glc+His+Or n+Ile; 0.760, 254.438, 1+ALB+gGT+Glc+His+Orn+Lys; 0.760, 252.654, 1+ALB+BUN+AST+Asp+Orn+Val; 0.760, 253.153, 1+ALB+ALT+NEFA+BHBA+Thr+Lys; 0.760, 253.546, 1+ALB+AST+ALT+Tyr+Val+Trp; 0.760, 254. 296, 1+ALB+AST+NEFA+T-BIL+His+Orn; 0.760, 252.734, 1+ALB+BUN+Ca+ALT+BHBA+Orn; 0.760, 253.150, 1+ALB+Ca+ALT+gGT+Arg+Orn; 0.760, 251.786, 1+ALB+AST+NEFA+3MeHis+Asp+Trp; 0.760, 252.179, 1+ALB+N EFA+3MeHis+Asp+Lys+Tyr; 0.760, 252.449, 1+ALB+3MeHis+Asp+Lys+T yr+Val; 0.760, 254.577, 1+ALB+BUN+NEFA+3MeHis+Arg+Orn; 0.760, 25 3.023, 1+ALB+NEFA+Asp+Lys+Tyr+Trp; 0.760, 253.380, 1+ALB+ALT+BH BA+Glc+Arg+Thr; 0.760, 253.441, 1+ALB+Asp+Orn+Lys+Tyr+Trp; 0.76 0, 253.776, 1+ALB+AST+3MeHis+Arg+Orn+Val; 0.760, 254.031, 1+ALB+NEFA+Asp+Lys+Val+Trp; 0.760, 252.988, 1+ALB+AST+ALT+BHBA+His+O rn; 0.760, 254.595, 1+ALB+AST+Arg+Lys+Tyr+Phe; 0.760, 255.302, 1+ALB+AST+Glc+Thr+Orn+Ile; 0.760, 252.724, 1+ALB+ BUN+Ca+ALT+T-BI L+Orn; 0.760, 253.049, 1+ALB+ AST+NEFA+Asp+Val+Trp; 0.760, 255.88 1, 1+ALB+ NEFA+Asp+Orn+Tyr+Phe; 0.760, 253.329, 1+ALB+ALT+ NEFA+A rg+Tyr+Val; 0.760, 253.620, 1+ALB+ALT+gGT+ NEFA+Glc+Arg; 0.760, 2 55.441, 1+ALB+NEFA+Lys+ Tyr+Val+Trp; 0.760, 255.193, 1+ALB+AST+N EFA+Glc+ Orn+Ile; 0.760, 252.236, 1+ALB+Ca+ALT+Glc+His+Lys; 0.76 0, 253.678, 1+ALB+BUN+Ca+AST+Arg+Orn; 0.760, 252.139, 1+ALB+Ca+A ST+ALT+Arg+Orn; 0.760, 254.399, 1+ALB+Ca+AST+NEFA+Arg+Orn; 0.76 0, 253.380, 1+ALB+ALT+T-BIL+Glc+Arg+Thr; 0.760, 253.738, 1+ALB+A LT+gGT+T-BIL+Glc+Arg; 0.760, 253.958, 1+ALB+ALT+NEFA+BHBA+His+Orn; 0.760, 254.734, 1+ALB+AST+Orn+Lys+Tyr+Phe; 0.760, 254.534, 1+ALB+AST+BHBA+Arg+Orn+Lys; 0.760, 254.549, 1+ALB+AST+gGT+Arg+O rn+Lys; 0.760, 255.435, 1+ALB+AST+T-BIL+Glc+Orn+Ile; 0.760, 252. 103, 1+ALB+AST+NEFA+3MeHis+Arg+Asp; 0.760, 252.205, 1+ALB+AST+A LT+His+Thr+Orn; 0.760, 252.510, 1+ALB+AST+ALT+BHBA+Thr+Lys; 0.7 60, 254.171, 1+ALB+AST+T-BIL+BHBA+Orn+Lys; 0.760, 254.144, 1+ALB+AST+3MeHis+Lys+Tyr+Val; 0.760, 252.950, 1+ALB+Ca+ALT+T-BIL+Gl c+Lys; 0.760, 252.944, 1+ALB+Ca+AST+ALT+His+Orn; 0.760, 256.718, 1+ALB+3MeHis+Orn+Tyr+Val+Phe; 0.760, 252.464, 1+ALB+3MeHis+Asp+Orn+Lys+Tyr; 0.760, 254.380, 1+ALB+NEFA+Asp+Lys+Tyr+Phe; 0.760, 252.479, 1+ALB+BUN+NEFA+3MeHis+Arg+Asp; 0.760, 252.535, 1+ALB+B UN+3MeHis+Arg+Asp+Tyr; 0.760, 252.808, 1+ALB+BUN+AST+Asp+Orn+T yr; 0.760, 252.901, 1+ALB+ALT+His+Thr+Orn+Ile; 0.760, 254.813, 1+ALB+ AST+T-BIL+BHBA+Arg+Orn; 0.760, 253.579, 1+ALB+ BUN+Ca+AST+H is+Orn; 0.760, 252.522, 1+ALB+Ca+ ALT+His+Thr+Lys; 0.760, 252.141, 1+ALB+Ca+ALT+ Arg+Thr+Lys; 0.760, 253.465, 1+ALB+BUN+NEFA+ Asp+V al+Phe; 0.760, 253.747, 1+ALB+ALT+gGT+ BHBA+Glc+Arg; 0.760, 252.9 50, 1+ALB+ALT+BHBA+ Glc+Thr+Lys; 0.760, 254.890, 1+ALB+AST+BHBA+Thr+ Orn+Lys; 0.760, 253.134, 1+ALB+AST+Arg+Asp+Lys+ Tyr; 0.760, 2 54.273, 1+ALB+AST+NEFA+BHBA+His+ Orn; 0.760, 252.001, 1+ALB+AST+ALT+gGT+His+Lys; 0.760, 255.288, 1+ALB+AST+BHBA+Thr+Lys+Ile; 0. 760, 253.105, 1+ALB+Ca+ALT+BHBA+His+Arg; 0.760, 253.563, 1+ALB+C a+ALT+Glc+His+Orn; 0.760, 253.288, 1+ALB+Ca+ALT+Glc+Arg+Thr; 0. 760, 253.810, 1+ALB+ BUN+Ca+AST+T-BIL+Arg; 0.759, 251.805, 1+ALB+ AST+3MeHis+Asp+Val+Trp; 0.759, 254.676, 1+ALB+ BUN+3MeHis+Arg+O rn+Val; 0.759, 253.656, 1+ALB+ ALT+gGT+NEFA+BHBA+Arg; 0.759, 253. 710, 1+ALB+ ALT+gGT+Glc+His+Orn; 0.759, 253.896, 1+ALB+ALT+T-BIL+BHBA+Glc+Arg; 0.759, 256.295, 1+ALB+3MeHis+ Lys+Tyr+Val+Phe; 0. 759, 251.040, 1+ALB+ALT+Asp+ Lys+Val+Trp; 0.759, 253.553, 1+ALB+A LT+gGT+NEFA+ T-BIL+Arg; 0.759, 254.165, 1+ALB+NEFA+Arg+Asp+ Lys+Tyr; 0.759, 255.238, 1+ALB+3MeHis+Arg+Orn+Lys+ Phe; 0.759, 254.00 7, 1+ALB+ALT+T-BIL+His+Orn+Ile; 0.759, 253.872, 1+ALB+BUN+AST+g GT+T-BIL+Orn; 0.759, 255.180, 1+ALB+NEFA+3MeHis+Lys+Phe+Trp; 0. 759, 250.918, 1+ALB+ALT+NEFA+Asp+Lys+Val; 0.759, 253.116, 1+ALB+ALT+gGT+Glc+Thr+Lys; 0.759, 254.393, 1+ALB+BHBA+Glc+His+Orn+Ly s; 0.759, 252.348, 1+ALB+AST+ALT+T-BIL+BHBA+Lys; 0.759, 253.479, 1+ALB+AST+NEFA+3MeHis+Arg+Orn; 0.759, 254.530, 1+ALB+AST+BHBA+His+Thr+Orn; 0.759, 255.344, 1+ALB+NEFA+BHBA+His+Thr+Lys; 0.759, 253.643, 1+ALB+AST+T-BIL+Glc+Orn+Lys; 0.759, 254.612, 1+ALB+AST+Glc+Thr+Lys+Ile; 0.759, 253.716, 1+ALB+ALT+NEFA+BHBA+Glc+Arg; 0.759, 253.660, 1+ALB+ALT+NEFA+Glc+His+Orn; 0.759, 251.737, 1+AL B+AST+ALT+NEFA+Asp+Orn; 0.759, 253.452, 1+ALB+ AST+Arg+Asp+Orn+Lys; 0.759, 254.000, 1+ALB+BUN+ AST+NEFA+Orn+Ile; 0.759, 254.219, 1+ALB+AST+ NEFA+Glc+Arg+Orn; 0.759, 253.913, 1+ALB+AST+ gGT+NEFA+Thr+Lys; 0.759, 254.178, 1+ALB+AST+ gGT+NEFA+His+Orn; 0.759, 255. 365, 1+ALB+AST+ gGT+NEFA+Orn+Ile; 0.759, 252.475, 1+ALB+Ca+ALT+B

HBA+His+Lys; 0.759, 252.926, 1+ALB+Ca+ALT+T-BIL+ Orn+Lys; 0.759, 255.807, 1+ALB+gGT+T-BIL+Orn+Lys+ Ile; 0.759, 253.624, 1+ALB+ALT+NEFA+T-BIL+BHBA+ Arg; 0.759, 253.699, 1+ALB+AST+NEFA+3MeHis+Arg+Phe; 0.759, 253.775, 1+ALB+BUN+AST+T-BIL+Glc+ Arg; 0.759, 253.9 22, 1+ALB+AST+NEFA+3MeHis+Orn+ Phe; 0.759, 252.436, 1+ALB+AST+AL T+gGT+BHBA+ Lys; 0.759, 253.653, 1+ALB+Ca+AST+T-BIL+His+Lys; 0.7 59, 252.173, 1+ALB+Ca+ALT+Glc+Lys+Ile; 0.759, 253.660, 1+ALB+Ca+ALT+gGT+NEFA+Arg; 0.759, 254.669, 1+ALB+BUN+3MeHis+Arg+Orn+Ty r; 0.759, 250.686, 1+ALB+AST+ALT+3MeHis+Asp+Orn; 0.759, 253.364, 1+ALB+ALT+T-BIL+BHBA+Thr+Lys; 0.759, 254.271, 1+ALB+AST+Glc+Ar g+Orn+Lys; 0.759, 254.194, 1+ALB+AST+gGT+T-BIL+Orn+Lys; 0.759, 2 55.009, 1+ALB+AST+gGT+T-BIL+Arg+Orn; 0.759, 253.051, 1+ALB+Ca+A LT+NEFA+T-BIL+Lys; 0.759, 255.470, 1+ALB+Ca+AST+NEFA+Orn+Ile; 0. 759, 253.720, 1+ALB+AST+NEFA+T-BIL+Glc+Lys; 0.759, 255.100, 1+AL B+gGT+T-BIL+Glc+His+Lys; 0.759, 252.149, 1+ALB+AST+3MeHis+Arg+Asp+Phe; 0.759, 251.892, 1+ALB+AST+ALT+T-BIL+Glc+Lys; 0.759, 253. 959, 1+ALB+ALT+NEFA+T-BIL+His+Orn; 0.759, 253.969, 1+ALB+ALT+NE FA+His+Orn+Ile; 0.759, 253.370, 1+ALB+ALT+gGT+T-BIL+BHBA+Lys; 0. 759, 256.253, 1+ALB+NEFA+Orn+Val+Phe+Trp; 0.759, 252.946, 1+ALB+ALT+gGT+BHBA+Glc+Lys; 0.759, 254.018, 1+ALB+ALT+BHBA+His+Orn+I le; 0.759, 252.089, 1+ALB+AST+3MeHis+Asp+Orn+Phe; 0.759, 253.998, 1+ALB+ALT+T-BIL+BHBA+His+Orn; 0.759, 253.728, 1+ALB+AST+NEFA+G lc+Thr+Lys; 0.759, 252.773, 1+ALB+Ca+ALT+NEFA+Glc+Lys; 0.759, 25 2.928, 1+ALB+Ca+ALT+BHBA+Orn+Lys; 0.759, 253.096, 1+ALB+ALT+gGT+His+Thr+Orn; 0.759, 250.334, 1+ALB+AST+ALT+Asp+Lys+Val; 0.759, 253.542, 1+ALB+AST+ALT+3MeHis+Tyr+Trp; 0.759, 253.613, 1+ALB+AS T+ALT+T-BIL+Orn+Ile; 0.759, 255.375, 1+ALB+gGT+NEFA+BHBA+His+L ys; 0.759, 255.254, 1+ALB+AST+gGT+BHBA+His+Orn; 0.759, 255.287, 1+ALB+AST+gGT+His+Orn+Ile; 0.759, 252.571, 1+ALB+ Ca+ALT+gGT+Lys+Ile; 0.759, 252.637, 1+ALB+Ca+ ALT+gGT+His+Lys; 0.759, 255.644, 1+ALB+Orn+Lys+ Val+Phe+Trp; 0.759, 253.572, 1+ALB+AST+T-BIL+Glc+ Arg+Lys; 0.759, 254.427, 1+ALB+AST+Glc+His+Lys+Ile; 0.759, 255.2 86, 1+ALB+AST+gGT+Thr+Lys+Ile; 0.759, 255.837, 1+ALB+Ca+AST+Thr+Orn+Ile; 0.759, 254.596, 1+ALB+AST+gGT+Glc+Orn+Lys; 0.759, 252. 272, 1+ALB+AST+ALT+gGT+T-BIL+Lys; 0.759, 254.147, 1+ALB+BUN+AST+Glc+Arg+Thr; 0.759, 253.653, 1+ALB+BUN+AST+T-BIL+Thr+Orn; 0.75 9, 252.929, 1+ALB+Ca+ALT+gGT+Orn+Lys; 0.759, 253.743, 1+ALB+Ca+A LT+gGT+T-BIL+Arg; 0.759, 251.937, 1+ALB+Ca+AST+ALT+Orn+Lys; 0.7 59, 252.914, 1+ALB+Ca+ALT+Thr+Orn+Lys; 0.759, 256.474, 1+ALB+ NEF A+3MeHis+Orn+Val+Phe; 0.759, 252.160, 1+ALB+ ALT+NEFA+Asp+Tyr+T rp; 0.759, 253.698, 1+ALB+ ALT+Glc+Thr+Orn+Ile; 0.759, 253.366, 1+ALB+ALT+ gGT+T-BIL+Thr+Lys; 0.759, 253.517, 1+ALB+AST+ ALT+NEFA+Orn+Ile; 0.759, 253.713, 1+ALB+AST+ NEFA+BHBA+Glc+Lys; 0.759, 252. 958, 1+ALB+AST+ NEFA+Asp+Tyr+Trp; 0.759, 255.288, 1+ALB+NEFA+ Orn+Lys+Val+Trp; 0.759, 254.181, 1+ALB+ALT+BHBA+ Thr+Orn+Ile; 0.759, 255.054, 1+ALB+gGT+BHBA+His+ Orn+Lys; 0.759, 253.306, 1+ALB+AST+ALT+NEFA+ 3MeHis+Orn; 0.759, 255.014, 1+ALB+AST+NEFA+ BHBA+Arg+T hr; 0.759, 255.832, 1+ALB+AST+gGT+T-BIL+Orn+Ile; 0.759, 254.054, 1+ALB+Ca+AST+NEFA+T-BIL+Lys; 0.759, 251.987, 1+ALB+Ca+AST+ALT+NEFA+ Lys; 0.759, 253.328, 1+ALB+AST+ALT+3MeHis+Orn+ Val; 0.759, 2 55.759, 1+ALB+AST+Orn+Tyr+Val+Phe; 0.759, 252.042, 1+ALB+AST+AL T+BHBA+Glc+Lys; 0.759, 254.662, 1+ALB+AST+NEFA+Arg+Tyr+Val; 0.7 59, 255.341, 1+ALB+NEFA+T-BIL+His+Thr+Lys; 0.759, 252.329, 1+ALB+AST+ALT+T-BIL+Thr+Lys; 0.759, 254.975, 1+ALB+AST+BHBA+His+Lys+Ile; 0.759, 254.338, 1+ALB+ALT+NEFA+Thr+Orn+Ile; 0.759, 254.922, 1+ALB+AST+gGT+BHBA+Orn+Lys; 0.759, 253.752, 1+ALB+AST+Arg+Asp+Lys+Val; 0.759, 253.975, 1+ALB+AST+gGT+NEFA+T-BIL+Lys; 0.758, 25 3.118, 1+ALB+Ca+ALT+NEFA+BHBA+Lys; 0.758, 253.746, 1+ALB+Ca+ALT+BHBA+Glc+Arg; 0.758, 254.056, 1+ALB+Ca+AST+NEFA+BHBA+Lys; 0.75 8, 253.719, 1+ALB+Ca+ALT+gGT+BHBA+Arg; 0.758, 252.812, 1+ALB+Ca+ALT+NEFA+Orn+Lys; 0.758, 253.700, 1+ALB+BUN+AST+T-BIL+Glc+Orn; 0.758, 253.963, 1+ALB+ALT+gGT+NEFA+His+Orn; 0.758, 256.441, 1+AL B+AST+gGT+BHBA+Orn+Ile; 0.758, 253.833, 1+ALB+AST+NEFA+Arg+Asp+Phe; 0.758, 253.906, 1+ALB+BUN+AST+T-BIL+BHBA+Orn; 0.758, 254.9 97, 1+ALB+AST+T-BIL+Arg+Thr+Orn; 0.758, 253.528, 1+ALB+Ca+ALT+N EFA+T-BIL+Arg; 0.758, 252.551, 1+ALB+Ca+ALT+BHBA+Lys+Ile; 0.758, 255.010, 1+ALB+NEFA+3MeHis+Arg+Lys+Phe; 0.758, 253.112, 1+ALB+A LT+BHBA+His+Thr+Orn; 0.758, 253.114, 1+ALB+ALT+T-BIL+His+Thr+O rn; 0.758, 254.599, 1+ALB+AST+Glc+Thr+Orn+Lys; 0.758, 253.500, 1+ALB+AST+ALT+T-BIL+Thr+Orn; 0.758, 253.526, 1+ALB+AST+ALT+BHBA+Thr+Orn; 0.758, 253.919, 1+ALB+BUN+AST+NEFA+T-BIL+Orn; 0.758, 25 5.339, 1+ALB+gGT+NEFA+His+Thr+Lys; 0.758, 252.288, 1+ALB+AST+AL T+Glc+Thr+Lys; 0.758, 253.985, 1+ALB+AST+gGT+NEFA+BHBA+Lys; 0.7 58, 253.119, 1+ALB+Ca+ALT+gGT+NEFA+Lys; 0.758, 253.741, 1+ALB+Ca+ALT+T-BIL+Glc+Arg; 0.758, 254.514, 1+ALB+Ca+AST+Arg+Orn+Lys; 0. 758, 255.953, 1+ALB+BUN+NEFA+Thr+Orn+Ile; 0.758, 254.017, 1+ALB+Ca+AST+NEFA+Thr+Lys; 0.758, 252.016, 1+ALB+Ca+AST+ALT+His+Lys; 0.758, 254.690, 1+ALB+ ALT+NEFA+BHBA+Thr+Orn; 0.758, 253.394, 1+A LB+ALT+gGT+BHBA+Thr+Lys; 0.758, 253.558, 1+ALB+ AST+gGT+NEFA+Gl c+Lys; 0.758, 253.700, 1+ALB+ AST+Arg+Asp+Lys+Phe; 0.758, 253.110, 1+ALB+Ca+ ALT+NEFA+Thr+Lys; 0.758, 256.431, 1+ALB+Ca+AST+ BHBA+O rn+Ile; 0.758, 254.025, 1+ALB+Ca+AST+T-BIL+Arg+Lys; 0.758, 251.7 71, 1+ALB+Ca+AST+ALT+ Lys+Ile; 0.758, 254.503, 1+ALB+3MeHis+Asp+Orn+Val+ Phe; 0.758, 255.606, 1+ALB+NEFA+3MeHis+Orn+Lys+ Phe; 0.7 58, 254.900, 1+ALB+AST+gGT+Thr+Orn+Lys; 0.758, 253.611, 1+ALB+AS T+ALT+NEFA+T-BIL+Orn; 0.758, 253.669, 1+ALB+AST+ALT+BHBA+Orn+I le; 0.758, 252.568, 1+ALB+AST+ALT+gGT+Thr+Lys; 0.758, 253.606, 1+ALB+Ca+ALT+gGT+Glc+Arg; 0.758, 252.925, 1+ALB+Ca+ALT+BHBA+Glc+Lys; 0.758, 255.246, 1+ALB+Ca+AST+gGT+His+Orn; 0.758, 252.256, 1+ALB+AST+ALT+gGT+Glc+Lys; 0.758, 253.703, 1+ALB+AST+ALT+T-BIL+B HBA+Orn; 0.758, 254.577, 1+ALB+AST+NEFA+3MeHis+Phe+Trp; 0.758, 2 54.999, 1+ALB+AST+Glc+His+Orn+Ile; 0.758, 253.908, 1+ALB+ BUN+AS T+gGT+NEFA+Orn; 0.758, 254.172, 1+ALB+ Ca+AST+T-BIL+Orn+Lys; 0.7 58, 255.228, 1+ALB+Ca+ AST+Thr+Lys+Ile; 0.758, 253.836, 1+ALB+Ca+ALT+T-BIL+BHBA+Arg; 0.758, 253.995, 1+ALB+ALT+gGT+T-BIL+His+Or n; 0.758, 254.005, 1+ALB+ALT+gGT+ BHBA+His+Orn; 0.758, 254.044, 1+ALB+BUN+AST+

NEFA+BHBA+Orn; 0.758, 254.270, 1+ALB+NEFA+Asp+ Orn+Lys+Trp; 0.758, 254.293, 1+ALB+ALT+T-BIL+Thr+ Orn+Ile; 0.758, 253. 387, 1+ALB+AST+ALT+NEFA+Thr+ Orn; 0.758, 252.619, 1+ALB+AST+ALT+Lys+Tyr+Val; 0.758, 253.665, 1+ALB+BUN+AST+NEFA+Thr+Orn; 0.758, 254.276, 1+ALB+Ca+AST+NEFA+His+Orn; 0.758, 253.333, 1+ALB+Ca+AL T+T-BIL+Thr+Lys; 0.758, 253.655, 1+ALB+Ca+ALT+NEFA+BHBA+Arg; 0. 758, 255.268, 1+ALB+Ca+AST+His+Orn+Ile; 0.758, 254.341, 1+ALB+AS T+Asp+Orn+Tyr+Phe; 0.758, 255.050, 1+ALB+AST+NEFA+T-BIL+Arg+Th r; 0.758, 253.099, 1+ALB+Ca+ALT+Glc+Thr+Lys; 0.758, 253.329, 1+AL B+Ca+ALT+T-BIL+BHBA+Lys; 0.758, 254.991, 1+ALB+ Ca+AST+T-BIL+Ar g+Orn; 0.758, 255.858, 1+ALB+Ca+ AST+T-BIL+Orn+Ile; 0.758, 253.59 6, 1+ALB+Ca+AST+ ALT+NEFA+Orn; 0.758, 254.313, 1+ALB+ALT+NEFA+ Gl c+Thr+Orn; 0.758, 253.607, 1+ALB+AST+ALT+ NEFA+BHBA+Orn; 0.758, 2 54.003, 1+ALB+ALT+gGT+ His+Orn+Ile; 0.758, 254.911, 1+ALB+AST+BH BA+Arg+ Thr+Lys; 0.758, 253.452, 1+ALB+AST+ALT+Glc+Orn+ Ile; 0.75 8, 253.540, 1+ALB+AST+ALT+gGT+NEFA+Orn; 0.758, 253.894, 1+ALB+BU N+AST+3MeHis+Orn+Val; 0.758, 254.618, 1+ALB+BUN+AST+gGT+BHBA+O rn; 0.758, 255.248, 1+ALB+Ca+AST+BHBA+His+Orn; 0.758, 253.591, 1+ALB+ALT+NEFA+T-BIL+Glc+Arg; 0.758, 253.619, 1+ALB+AST+ALT+gGT+Orn+Ile; 0.758, 252.428, 1+ALB+AST+3MeHis+Arg+Asp+Val; 0.758, 25 3.854, 1+ALB+AST+Glc+His+Thr+Orn; 0.758, 255.882, 1+ALB+AST+gGT+T-BIL+BHBA+Orn; 0.758, 255.821, 1+ALB+AST+T-BIL+BHBA+Thr+Orn; 0.758, 252.549, 1+ALB+AST+NEFA+3MeHis+Asp+Orn; 0.758, 253.386, 1+ALB+AST+ALT+NEFA+Glc+Orn; 0.758, 253.211, 1+ALB+AST+Asp+Orn+L ys+Tyr; 0.758, 253.569, 1+ALB+AST+Asp+Orn+Lys+Phe; 0.758, 253.73 0, 1+ALB+AST+ALT+NEFA+Tyr+Trp; 0.758, 253.631, 1+ALB+BUN+AST+NE FA+3MeHis+Orn; 0.758, 254.576, 1+ALB+BUN+AST+Glc+Orn+Ile; 0.758, 254.874, 1+ALB+AST+NEFA+Glc+Arg+Thr; 0.757, 253.713, 1+ALB+BUN+AST+3MeHis+Orn+Tyr; 0.757, 254.552, 1+ALB+ALT+NEFA+3MeHis+Orn+Val; 0.757, 254.023, 1+ALB+AST+NEFA+Asp+Orn+Tyr; 0.757, 254.319, 1+ALB+ALT+gGT+Thr+Orn+Ile; 0.757, 253.196, 1+ALB+AST+ALT+3MeHi s+Orn+Tyr; 0.757, 253.486, 1+ALB+AST+ALT+gGT+Thr+Orn; 0.757, 254. 049, 1+ALB+AST+NEFA+Asp+Orn+Val; 0.757, 253.170, 1+ALB+AST+ALT+Glc+Thr+Orn; 0.757, 254.817, 1+ALB+AST+T-BIL+BHBA+Thr+Lys; 0.75 7, 255.409, 1+ALB+AST+gGT+NEFA+Thr+Orn; 0.757, 255.054, 1+ALB+AS T+gGT+His+Lys+Ile; 0.757, 253.608, 1+ALB+Ca+ALT+NEFA+Glc+Arg; 0. 757, 254.587, 1+ALB+Ca+AST+Glc+Orn+Lys; 0.757, 255.091, 1+ALB+ AS T+NEFA+3MeHis+Orn+Val; 0.757, 255.377, 1+ALB+ AST+Arg+Orn+Val+P he; 0.757, 255.937, 1+ALB+AST+ gGT+T-BIL+Thr+Orn; 0.757, 255.509, 1+ALB+AST+ BHBA+Arg+Thr+Orn; 0.757, 255.511, 1+ALB+AST+ gGT+Arg+Thr+Orn; 0.757, 256.205, 1+ALB+AST+gGT+ Glc+Orn+Ile; 0.757, 253.9 40, 1+ALB+Ca+ALT+BHBA+ His+Orn; 0.757, 253.334, 1+ALB+Ca+ALT+gGT+T-BIL+ Lys; 0.757, 253.915, 1+ALB+BUN+Ca+AST+T-BIL+Orn; 0.757, 2 53.432, 1+ALB+AST+Asp+Val+Phe+Trp; 0.757, 255.760, 1+ALB+NEFA+O rn+Lys+Phe+Trp; 0.757, 254.987, 1+ALB+AST+gGT+Glc+His+Orn; 0.75 7, 253.957, 1+ALB+BUN+AST+NEFA+Orn+Tyr; 0.757, 254.013, 1+ALB+BU N+AST+NEFA+Orn+Val; 0.757, 255.593, 1+ALB+AST+NEFA+T-BIL+BHBA+Orn; 0.757, 255.492, 1+ALB+AST+NEFA+T-BIL+Thr+Orn; 0.757, 253.85 2, 1+ALB+Ca+AST+gGT+NEFA+Lys; 0.757,
252.276, 1+ALB+Ca+AST+ALT+Glc+Lys; 0.757, 253.448, 1+ALB+AST+ALT+T-BIL+Glc+Orn; 0.757, 254. 281, 1+ALB+BUN+AST+BHBA+Thr+Orn; 0.757, 254.576, 1+ALB+BUN+AST+gGT+Glc+Orn; 0.757, 255.367, 1+ALB+AST+NEFA+BHBA+Glc+Orn; 0.757, 255.541, 1+ALB+AST+gGT+NEFA+T-BIL+Orn; 0.757, 255.490, 1+ALB+AS T+gGT+NEFA+BHBA+Orn; 0.757, 254.868, 1+ALB+AST+gGT+T-BIL+BHBA+Lys; 0.757, 253.096, 1+ALB+Ca+ALT+gGT+Glc+Lys; 0.757, 252.452, 1+ALB+ Ca+AST+ALT+BHBA+Lys; 0.757, 251.820, 1+ALB+ AST+ALT+Asp+Orn+Val; 0.757, 251.914, 1+ALB+AST+ ALT+Asp+Orn+Tyr; 0.757, 253.672, 1+ALB+AST+ALT+ gGT+T-BIL+Orn; 0.757, 253.936, 1+ALB+Ca+ALT+T-BI L+His+Orn; 0.757, 256.405, 1+ALB+Ca+AST+gGT+Orn+ Ile; 0.757, 256. 142, 1+ALB+Ca+AST+Glc+Orn+Ile; 0.757, 252.855, 1+ALB+BUN+3MeHis+Asp+Orn+Tyr; 0.757, 254.338, 1+ALB+ALT+T-BIL+Glc+Thr+Orn; 0.75 7, 256.194, 1+ALB+AST+BHBA+Glc+Orn+Ile; 0.757, 255.606, 1+ALB+AS T+gGT+T-BIL+Glc+Orn; 0.757, 255.652, 1+ALB+AST+NEFA+Orn+Tyr+Va 1; 0.757, 255.433, 1+ALB+AST+NEFA+BHBA+Thr+Orn; 0.757, 253.541, 1+ALB+AST+Asp+Orn+Lys+Val; 0.757, 253.084, 1+ALB+Ca+ALT+His+Thr+Orn; 0.757, 253.624, 1+ALB+Ca+AST+ALT+Orn+Ile; 0.757, 254.334, 1+ALB+ ALT+BHBA+Glc+Thr+Orn; 0.757, 254.472, 1+ALB+ AST+BHBA+Glc+Orn+Lys; 0.757, 253.590, 1+ALB+ AST+ALT+NEFA+Orn+Val; 0.757, 254. 697, 1+ALB+ AST+T-BIL+Glc+Arg+Orn; 0.757, 255.069, 1+ALB+AST+ NEF A+3MeHis+Orn+Tyr; 0.757, 255.204, 1+ALB+AST+ BHBA+His+Thr+Lys; 0. 757, 252.848, 1+ALB+BUN+ 3MeHis+Asp+Orn+Val; 0.757, 255.279, 1+AL B+AST+ gGT+NEFA+Glc+Orn; 0.757, 254.825, 1+ALB+AST+ gGT+Glc+Lys+Ile; 0.757, 254.892, 1+ALB+Ca+AST+Thr+ Orn+Lys; 0.757, 253.901, 1+ALB+Ca+ALT+NEFA+His+ Orn; 0.757, 253.678, 1+ALB+Ca+AST+NEFA+Glc+Lys; 0.757, 256.003, 1+ALB+Ca+AST+gGT+T-BIL+Orn; 0.757, 254.595, 1+ALB+ALT+NEFA+T-BIL+Thr+Orn; 0.757, 253.732, 1+ALB+AST+ALT+gG T+BHBA+Orn; 0.757, 254.310, 1+ALB+BUN+AST+gGT+Thr+Orn; 0.757, 25 5.138, 1+ALB+AST+gGT+NEFA+Arg+Thr; 0.757, 255.177, 1+ALB+AST+gG T+BHBA+His+Lys; 0.757, 253.535, 1+ALB+AST+ALT+NEFA+Orn+Tyr; 0.7 57, 254.889, 1+ALB+AST+BHBA+Glc+His+Orn; 0.756, 254.004, 1+ALB+B UN+Ca+AST+NEFA+Orn; 0.756, 253.350, 1+ALB+Ca+ALT+gGT+BHBA+Lys; 0.756, 253.503, 1+ALB+Ca+AST+ALT+Thr+Orn; 0.756, 254.894, 1+ALB+Ca+AST+Glc+His+Orn; 0.756, 252.298, 1+ALB+Ca+AST+ALT+T-BIL+Ly s; 0.756, 253.533, 1+ALB+AST+ALT+BHBA+Glc+Orn; 0.756, 253.899, 1+ALB+BUN+AST+NEFA+Glc+Orn; 0.756, 255.586, 1+ALB+AST+T-BIL+BHBA+Glc+Orn; 0.756, 255.289, 1+ALB+AST+Glc+Arg+Thr+Orn; 0.756, 255. 365, 1+ALB+AST+NEFA+T-BIL+Glc+Orn; 0.756, 256.459, 1+ALB+AST+gG T+BHBA+Thr+Orn; 0.756, 255.588, 1+ALB+Ca+AST+T-BIL+Glc+Orn; 0.7 56, 254.293, 1+ALB+ALT+gGT+Glc+Thr+Orn; 0.756, 255.378, 1+ALB+AS T+BHBA+Glc+Arg+Orn; 0.756, 254.068, 1+ALB+BUN+AST+Glc+Thr+Orn; 0.756, 254.727, 1+ALB+AST+Glc+Arg+Thr+Lys; 0.756, 254.477, 1+ALB+BUN+AST+BHBA+Glc+Orn; 0.756, 254.372, 1+ALB+AST+BHBA+Glc+His+Lys; 0.756, 253.932, 1+ALB+Ca+ALT+gGT+His+Orn; 0.756, 254.310, 1+ALB+Ca+ALT+Thr+Orn+Ile; 0.756, 253.693, 1+ALB+ Ca+AST+ALT+T-BIL+Orn; 0.756, 252.824, 1+ALB+ALT+ NEFA+Asp+Orn+Val; 0.756, 255.410, 1+ALB+AST+gGT+ Glc+Arg+Orn; 0.756, 254.003, 1+ALB+AST+NEFA+Arg+ Asp+Val; 0.756, 253.415, 1+ALB+Ca+ALT+gGT+Thr+

Lys; 0.756, 254.43 3, 1+ALB+BUN+ALT+NEFA+ 3MeHis+Val; 0.756, 254.717, 1+ALB+ALT+gGT+NEFA+ Thr+Orn; 0.756, 255.080, 1+ALB+AST+NEFA+Glc+Thr+ Orn; 0.75 6, 255.411, 1+ALB+AST+T-BIL+Glc+Thr+Orn; 0.756, 255.292, 1+ALB+A ST+gGT+BHBA+Lys+Ile; 0.756, 253.351, 1+ALB+Ca+ALT+BHBA+Thr+Ly s; 0.756, 255.480, 1+ALB+Ca+AST+Arg+Thr+Orn; 0.756, 255.530, 1+AL B+Ca+AST+BHBA+Arg+Orn; 0.756, 254.720, 1+ALB+ALT+T-BIL+BHBA+Th r+Orn; 0.756, 253.962, 1+ALB+BUN+AST+ALT+NEFA+Val; 0.756, 254.56 2, 1+ALB+AST+BHBA+Glc+Arg+Lys; 0.756, 256.098, 1+ALB+AST+Lys+Ty r+Val+Phe; 0.756, 255.574, 1+ALB+Ca+AST+NEFA+BHBA+Orn; 0.756, 25 5.016, 1+ALB+Ca+AST+His+Lys+Ile; 0.756, 255.526, 1+ALB+ Ca+AST+g GT+NEFA+Orn; 0.756, 255.635, 1+ALB+Ca+ AST+NEFA+T-BIL+Orn; 0.756, 253.534, 1+ALB+AST+ ALT+gGT+Glc+Orn; 0.756, 252.587, 1+ALB+Ca+AS T+ALT+Thr+Lys; 0.756, 253.953, 1+ALB+BUN+AST+ ALT+3MeHis+Val; 0. 756, 253.891, 1+ALB+AST+Asp+ Lys+Tyr+Phe; 0.756, 255.888, 1+ALB+C a+AST+T-BIL+ BHBA+Orn; 0.756, 255.938, 1+ALB+Ca+AST+T-BIL+ Thr+O rn; 0.756, 252.974, 1+ALB+ALT+NEFA+Asp+Orn+ Tyr; 0.756, 255.369, 1+ALB+NEFA+Asp+Lys+Val+Phe; 0.756, 254.297, 1+ALB+BUN+Ca+AST+Th r+Orn; 0.756, 255.252, 1+ALB+NEFA+Arg+Asp+Lys+Phe; 0.756, 253.64 1, 1+ALB+AST+ALT+Orn+Tyr+Val; 0.755, 254.751, 1+ALB+Ca+AST+Glc+His+Lys; 0.755, 254.918, 1+ALB+ALT+gGT+NEFA+T-BIL+Orn; 0.755, 25 3.742, 1+ALB+Ca+AST+ALT+BHBA+Orn; 0.755, 255.352, 1+ALB+Ca+AST+Glc+Arg+Orn; 0.755, 254.694, 1+ALB+ ALT+gGT+BHBA+Thr+Orn; 0.755, 254.884, 1+ALB+Ca+ AST+BHBA+Orn+Lys; 0.755, 252.532, 1+ALB+Ca+AS T+ALT+gGT+Lys; 0.755, 254.914, 1+ALB+Ca+AST+ gGT+Orn+Lys; 0.755, 254.710, 1+ALB+Ca+ALT+NEFA+ Thr+Orn; 0.755, 255.471, 1+ALB+Ca+AS T+NEFA+Thr+ Orn; 0.755, 255.336, 1+ALB+Ca+AST+NEFA+Glc+Orn; 0.75 5, 255.073, 1+ALB+Ca+AST+BHBA+His+Lys; 0.755, 253.481, 1+ALB+Ca+AST+ALT+Glc+Orn; 0.755, 255.506, 1+ALB+BUN+ALT+T-BIL+His+Ile; 0. 755, 256.440, 1+ALB+Ca+AST+BHBA+Thr+Orn; 0.755, 252.827, 1+ALB+A LT+Asp+Orn+Tyr+Val; 0.755, 254.701, 1+ALB+ALT+gGT+T-BIL+Thr+Or n; 0.755, 254.691, 1+ALB+AST+BHBA+Glc+Lys+Ile; 0.755, 253.695, 1+ALB+Ca+AST+ALT+gGT+Orn; 0.755, 256.314, 1+ALB+AST+gGT+BHBA+Glc+Orn; 0.755, 256.581, 1+ALB+Ca+AST+gGT+BHBA+Orn; 0.755, 253.749, 1+ALB+AST+Asp+Lys+Tyr+Val; 0.754, 255.368, 1+ALB+AST+3MeHis+Or n+Tyr+Val; 0.754, 254.692, 1+ALB+Ca+ALT+gGT+Thr+Orn; 0.754, 254. 101, 1+ALB+AST+Asp+Lys+Val+Phe; 0.754, 255.562, 1+ALB+BUN+ALT+g GT+T-BIL+Ile; 0.754, 256.323, 1+ALB+Ca+AST+gGT+Glc+Orn; 0.754, 2 56.280, 1+ALB+Ca+AST+BHBA+Glc+Orn; 0.754, 255.732, 1+ALB+BUN+AL T+gGT+NEFA+Ile; 0.753, 256.071, 1+ALB+Ca+AST+Glc+Thr+Orn

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A feeding management method executed by a feeding management system for a free stall cow barn, wherein the feeding management system includes an evaluation-related information storage unit, an evaluating unit, a selecting unit, a transmission unit, a reading unit, a feed information acquiring unit, an association information storage unit, a device information acquiring unit, and a control information transmitting unit, and the free stall cow barn is provided with a plurality of feeding places, and an intrusion control device is provided in each of the feeding places to control the intrusion of a dairy cow to the feeding place, the feeding management method includes:

a step executed by the evaluating unit of evaluating a risk of developing a perinatal disease after parturition of a dairy cow by using evaluation information included in evaluation-related information stored in the evaluation-related information storage unit that stores the evaluation-related information, and storing an obtained evaluation result in the evaluation-related information, wherein the evaluation-related information stores (I) cow specifying information for specifying a dairy cow, (II) transmission-unit specifying information for specifying a transmission unit attached to the dairy cow, and (III) the evaluation information including at least one value selected from the group consisting of a concentration value of an amino acid in blood of the dairy cow before parturition and a measurement value of a blood chemistry parameter in blood of the dairy cow before parturition, and is capable of further storing (IV) an evaluation result about a risk of developing a perinatal disease after parturition of the dairy cow and (V) feed specifying information for specifying a feed effective in preventing the perinatal disease after parturition;

a step executed by the selecting unit of, when an obtained evaluation result indicates a presence of the risk of disease development, selecting a feed effective in preventing the perinatal disease after parturition according to a degree of the risk of disease, based on the evaluation result, and storing feed specifying information on the selected feed in the evaluation-related information;

a step executed by the transmission unit of transmitting the cow specifying information or the transmission-unit specifying information;

a step executed by the reading unit provided at a predetermined position in the cow barn of reading the transmitted information;

a step executed by the feed information acquiring unit of acquiring, from the evaluation-related information storage unit, the feed specifying information included in the evaluation-related information, which was specified by using the read information;

a step executed by the device information acquiring unit of acquiring, from the association information storage unit that stores a plurality of pieces of association information including (I) device specifying information, which is an identification code or an identification ID, for specifying the intrusion control device and (II) feed specifying information on a feed to be provided in the feeding place, the device specifying information included in the association information, which was specified by using the acquired feed specifying information; and a step executed by the control information transmitting unit of transmitting control information for controlling the intrusion control device to allow intrusion, the intrusion control device being specified based on the acquired device specifying information, which is an identification code or an identification ID, to a controller that controls the operation of the intrusion control device.

2. The feeding management method according to claim 1, wherein the amino acid is at least one of Ala, Arg, Asn, Asp, BCAA, Cit, Cys, Glu, Gln, Gly, His, Ile, Leu, Lys, Met, 3MeHis, Orn, Phe, Pro, Ser, Tau, Thr, Trp, Tyr, and Val in blood of the dairy cow before parturition and the blood chemistry parameter is at least one of ALB, ALT, AST, BHBA, BUN, Ca, gGTP, Glc, NEFA, T-Bil, TCHO, TG, and TP in blood of the dairy cow before parturition, and the perinatal disease is ketosis.

\* \* \* \* \*